US011352316B2

(12) United States Patent
Medina et al.

(10) Patent No.: US 11,352,316 B2
(45) Date of Patent: Jun. 7, 2022

(54) OPIOID RECEPTOR MODULATORS AND PRODUCTS AND METHODS RELATED THERETO

(71) Applicant: Epiodyne, Inc., San Francisco, CA (US)

(72) Inventors: Julio Cesar Medina, South San Francisco, CA (US); Lawrence R McGee, South San Francisco, CA (US); Zhi-Liang Wei, South San Francisco, CA (US); Corinne Sadlowski, South San Francisco, CA (US); Frederick Seidl, South San Francisco, CA (US); Ulhas Bhatt, South San Francisco, CA (US); Xiaodong Wang, South San Francisco, CA (US); Thomas Nguyen, South San Francisco, CA (US); David Sperandio, South San Francisco, CA (US); Pingyu Ding, South San Francisco, CA (US); Alok Nerurkar, South San Francisco, CA (US); Yihong Li, South San Francisco, CA (US); Jason Duquette, Union City, CA (US)

(73) Assignee: EPIODYNE, INC., San Francisco, CA (US)

( * ) Notice: Subject to any disclaimer, the term of this patent is extended or adjusted under 35 U.S.C. 154(b) by 0 days.

(21) Appl. No.: 16/926,536

(22) Filed: Jul. 10, 2020

(65) Prior Publication Data
US 2021/0163402 A1    Jun. 3, 2021

Related U.S. Application Data

(63) Continuation of application No. 16/691,377, filed on Nov. 21, 2019, now abandoned, which is a
(Continued)

(51) Int. Cl.
| C07C 233/78 | (2006.01) |
| A61P 23/00 | (2006.01) |
| C07C 233/62 | (2006.01) |
| C07C 233/63 | (2006.01) |
| C07C 235/60 | (2006.01) |
| C07C 237/42 | (2006.01) |
| C07D 207/16 | (2006.01) |
(Continued)

(52) U.S. Cl.
CPC ............ *C07C 233/78* (2013.01); *A61P 23/00* (2018.01); *C07C 233/62* (2013.01); *C07C 233/63* (2013.01); *C07C 235/60* (2013.01); *C07C 237/30* (2013.01); *C07C 237/38* (2013.01); *C07C 237/42* (2013.01); *C07C 237/48* (2013.01); *C07C 271/20* (2013.01); *C07C 275/24* (2013.01); *C07D 207/16* (2013.01); *C07D 209/14* (2013.01); *C07D 209/34* (2013.01); *C07D 213/40* (2013.01); *C07D 217/06* (2013.01); *C07D 217/14* (2013.01); *C07D 231/56* (2013.01); *C07D 241/24* (2013.01); *C07D 263/58* (2013.01); *C07D 295/13* (2013.01); *C07D 401/12* (2013.01); *C07D 403/06* (2013.01); *C07D 471/04* (2013.01)

(58) Field of Classification Search
CPC .................................................... C07C 233/78
See application file for complete search history.

(56) References Cited

U.S. PATENT DOCUMENTS

| 6,593,348 B2 | 7/2003 | Carroll et al. |
| 7,807,704 B2 | 10/2010 | Thomas et al. |
(Continued)

FOREIGN PATENT DOCUMENTS

| CN | 101823987 B | 6/2014 |
| EP | 0147211 B1 | 9/1990 |
(Continued)

OTHER PUBLICATIONS

Totah et al. Detection of aminium ion intermediates: N-cyclopropyl versus N-carboxymethyl groups as reporters. J Am Chem Soc 123(41):10107-8 (2001).
(Continued)

*Primary Examiner* — Golam M Shameem
(74) *Attorney, Agent, or Firm* — Wilson Sonsini Goodrich & Rosati

(57) ABSTRACT

Compounds are provided having the structure of Formula (I):

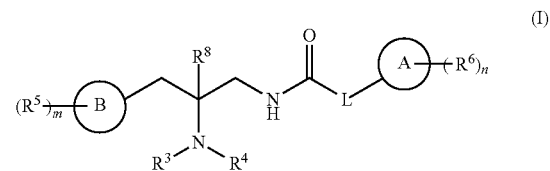

or a pharmaceutically acceptable isomer, racemate, hydrate, solvate, isotope, or salt thereof, wherein A, B, L, $R^3$, $R^4$, $R^5$, $R^6$, $R^8$, m and n are as defined herein. Such compounds modulate the opioid receptor, particulare the mu-opioid receptor (MOR) and/or the kappa-opioid receptor (KOR), and/or the delta-opioid receptor (DOR). Products containing such compounds, as well as methods for their use and preparation, are also provided.

20 Claims, 2 Drawing Sheets

Related U.S. Application Data continuation of application No. 16/375,811, filed on Apr. 4, 2019, now abandoned.

(60) Provisional application No. 62/792,754, filed on Jan. 15, 2019, provisional application No. 62/652,819, filed on Apr. 4, 2018.

(51) Int. Cl.

| | |
|---|---|
| *C07D 209/14* | (2006.01) |
| *C07D 217/06* | (2006.01) |
| *C07D 217/14* | (2006.01) |
| *C07D 231/56* | (2006.01) |
| *C07D 241/24* | (2006.01) |
| *C07D 263/58* | (2006.01) |
| *C07D 295/13* | (2006.01) |
| *C07D 403/06* | (2006.01) |
| *C07D 471/04* | (2006.01) |
| *C07C 237/30* | (2006.01) |
| *C07C 237/38* | (2006.01) |
| *C07C 237/48* | (2006.01) |
| *C07C 271/20* | (2006.01) |
| *C07C 275/24* | (2006.01) |
| *C07D 209/34* | (2006.01) |
| *C07D 213/40* | (2006.01) |
| *C07D 401/12* | (2006.01) |

(56) References Cited

U.S. PATENT DOCUMENTS

| | | | |
|---|---|---|---|
| 10,702,498 B2 * | 7/2020 | Shoichet | C07C 275/24 |
| 10,780,078 B2 | 9/2020 | Shoichet et al. | |
| 2005/0277674 A1 | 12/2005 | Hinze et al. | |
| 2007/0135402 A1 | 6/2007 | Habashita et al. | |
| 2007/0265301 A1 | 11/2007 | Edwards et al. | |
| 2014/0288077 A1 | 9/2014 | Fujii et al. | |
| 2016/0095854 A1 | 4/2016 | Carroll et al. | |
| 2020/0109126 A1 | 4/2020 | Shoichet et al. | |
| 2021/0052548 A1 | 2/2021 | Shoichet et al. | |
| 2021/0147343 A1 | 5/2021 | Medina et al. | |

FOREIGN PATENT DOCUMENTS

| | | |
|---|---|---|
| WO | WO-9310089 A1 | 5/1993 |
| WO | WO-9731940 A1 | 9/1997 |
| WO | WO-9817636 A1 | 4/1998 |
| WO | WO-2005009315 A1 | 2/2005 |
| WO | WO-2005120494 A1 | 12/2005 |
| WO | WO-2008093960 A1 | 8/2008 |
| WO | WO-2010013037 A1 | 2/2010 |
| WO | WO-2011054844 A1 | 5/2011 |
| WO | WO-2013033310 A1 | 3/2013 |
| WO | WO-2013068467 A1 | 5/2013 |
| WO | 2017/007695 A1 | 1/2017 |
| WO | WO-2017007695 A1 | 1/2017 |
| WO | WO-2017035366 A1 | 3/2017 |
| WO | 2018/129393 A1 | 7/2018 |
| WO | WO-2018129393 A1 | 7/2018 |
| WO | 2019/036678 A1 | 2/2019 |
| WO | WO-2019036678 A1 | 2/2019 |
| WO | WO-2019195634 A1 | 10/2019 |

OTHER PUBLICATIONS

U.S. Appl. No. 16/475,208 Office Action dated Nov. 10, 2020.
Anderson. The process of structure-based drug design. Chem Biol 10:787-797 (2003).
Andrews et al. Stabilised G protein-coupled receptors in structure-based drug design: a case study with adenosine A2A receptor. MedChemComm. 4(1):52-67 (2013).
Balter et al. Thermal sensitivity as a measure of spontaneous morphine withdrawal in mice. J Pharmacol Toxicol Methods 67:162-168 (2013).
Berge et al. Pharmaceutical Salts. Journal of Pharmaceutical Sciences 66(1):1-19 (Jan. 1977).
Bissantz C et al. Protein-based virtual screening of chemical databases. II. Are homology models of G-Protein Coupled Receptors suitable targets? Proteins 50(1):5-25 (2003).
Bohn et al. Enhanced morphine analgesia in mice lacking beta-arrestin 2. Science 286(5449):2495-2498 (1999).
Calvey et al. Chapter 3: Drug Action. Principles and Practice of Pharmacology for Anaesthetists (pp. 43-67) (2009).
Carlsson et al. Structure-based discovery of A2A adenosine receptor ligands. J Med Chem 53(9):3748-3755 (2010).
Carlsson et al. Ligand discovery from a dopamine D3 receptor homology model and crystal structure. Nat Chem Biol. 7(11):769-778 (2011).
Clougherty et al. Chronic social stress and susceptibility to concentrated ambient fine particles in rats. Environ Health Perspect. 18(6):769-75 (2010).
De Graaf et al. Crystal structure-based virtual screening for fragment-like ligands of the human histamine H(1) receptor. J Med Chem 54(23):8195-8206 (2011).
Deekonda et al. Design synthesis and structure-activity relationship of 5-substituted (tetrahydronaphthalen-2y1)methyl with N-phenyl-N-(piperidin-2-yl)propionamide derivatives as opioid ligands. Bioorg Med Chem 24(2):85-91 (Jan. 15, 2016, e-published Nov. 23, 2015).
Dewire et al. A G protein-biased ligand at the µ-opioid receptor is potently analgesic with reduced gastrointestinal and respiratory dysfunction compared with morphine. J Pharmacol Exp Ther 344(3):708-717 (2013).
Emerich et al. Central analgesic actions of loperamide following transient permeation of the blood brain barrier with Cereport (RMP-7). Brain Research 801(1-2):259-266 (1998).
Gaulton et al. ChEMBL: a large-scale bioactivity database for drug discovery. Nucleic Acids Res 40(D1):D1100-D1107 (2012).
Gomes et al. Identification of a µ-σ opioid receptor heteromer-biased agonist with antinociceptive activity. PNAS USA 110(29):12072-12077 (2013).
Gould et al. Salt Selection for Basic Drugs. Int J. Pharm. 33:201-217 (1986).
Granier et al. Structure of the σ-opioid receptor bound to naltrindole. Nature 485(7398):400-404 (2012).
Hermann et al. Metal impurities cause false positives in high-throughput screening campaigns. ACS Med Chem Lett 4(2):197-200 (2012).
Irwin et al. Automated docking screens: a feasibility study. J Med Chem 52(18):5712-5720 (2009).
Irwin et al. ZINC: a free tool to discover chemistry for biology. J Chem Inf Model 52(7):1757-1768 (2012).
Irwin et al. ZINC—a free database of commercially available compounds for virtual screening J Chem Inf Model 45(1):177-182 (2004).
Kalani et al. The predicted 3D structure of the human D2 dopamine receptor and the binding site and binding affinities for agonists and antagonists. PNAS USA 101(11):3815-3820 (2004).
Katritch et al. Structure-based discovery of novel chemotypes for adenosine A(2A) receptor antagonists.J Med Chem 53(4):1799-1809 (2010).
Kieffer. Drug discovery: Designing the ideal opioid. Nature 537(7619):170-171 (2016).
Kolb et al. Structure-based discovery of beta2-adrenergic receptor ligands. PNAS USA 106(16):6843-6848 (2009).
Kolb et al. The golden age of GPCR structural biology: any impact on drug design? Angew Chem Int Ed Engl. 50(49):11573-11575 (2011).
Kruse et al. Muscarinic receptors as model targets and antitargets for structure-based ligand discovery. Mol Pharmacol 84(4):528-540 (2013).
Laferriere et al. Ontogeny of respiratory sensitivity and tolerance to the mu-opioid agonist fentanyl in rat. Brain Res Dev Brain Res 156(2):210-217 (2005).

(56) References Cited

OTHER PUBLICATIONS

Langmead et al. Identification of novel adenosine A(2A) receptor antagonists by virtual screening. J Med Chem 55(5):1904-1909 (2012).

Link et al. G-Protein-Coupled Receptors: Sustained Signaling via Intracellular Megaplexes and Pathway-Specific Drugs. Angewandte Chemie, International Edition 55(52):15962-15964 (2016).

Lorber et al. Hierarchical docking of databases of multiple ligand conformations. Curr Top med Chem 5(8):739-749 (2005).

Manglik et al. Crystal structure of the μ-opioid receptor bound to a morphinan antagonist. Nature, 485(7398):321-326 (2012).

Manglik et al. Structure-based discovery of opioid analgesics with reduced side effects. Nature 537(7619):185-190 (2016).

Muchmore et al. Application of belief theory to similarity data fusion for use in analog searching and lead hopping. J Chem Inf Model 48(5):941-948 (2008).

Mysinger et al. Rapid context-dependent ligand desolvation in molecular docking. J Chem Inf Model 50(9):1561-1573 (2010).

Mysinger et al. Structure-based ligand discovery for the protein-protein interface of chemokine receptor CXCR4. PNAS USA 109(14):5517-5522 (2012).

Negri et al. Discovery of a novel selective kappa-opioid receptor agonist using crystal structure-based virtual screening. J Chem Inf Model 53(3):521-526 (2013).

Noel et al. Synthesis and SAR of tetrahydroisoquinolines as Rev-erbα agonists. Bioorg Med Chem Lett 22(11):3739-3742 (2012).

Oprea. Virtual Screening in Lead Discovery: A Viewpoint. Molecules 7(1):51-62 (2002).

Page et al. New scaffolds in the development of Mu opioid-receptor ligands. Bioorg Med Chem Lett 13(9):1585-1589 (2003).

PCT/US2016/040553 International Search Report and Written Opinion dated Dec. 12, 2016.

PCT/US2018/012683 International Search Report and Written Opinion dated May 2, 2018.

PCT/US2018/046983 International Search Report and Written Opinion dated Oct. 31, 2018.

PCT/US2019/025910 International Search Report and Written Opinion dated Jul. 15, 2019.

Philippe et al. Mu opioid receptor expression is increased in inflammatory bowel diseases: implications for homeostatic intestinal inflammation. Gut 55(6):815-823 (2006).

Powers et al. Structure-based discovery of a novel, noncovalent inhibitor of AmpC beta-lactamase. Structure 10(7):1013-1023.

PubChem CID 18589025, date created: Dec. 4, 2007, date accessed: Nov. 8, 2016.

PubChem CID 63120296, date created: Oct. 22, 2012, date accessed Nov. 8, 2016.

Sherrill et al. An Improved Synthesis and Resolution of 3-Amino-1,3-dihydro-5-phenyl-2H-1,4-benzodiazepin-2-ones. J. Org. Chem. 60:730-734 (1995).

Shi et al. Unpredictable stereochemical preferences for mu opioid receptor activity in an exhaustively stereodiversified library of 1,4-enediols. Organic Letters 5(5):633-636 (2003).

Spetea et al. The p opioid receptor and ligands acting at the p opioid receptor, as therapeutics and potential therapeutics. Curr Pharm Des 19(42):7415-7434 (2013).

Thiel. Structure-aided drug design's next generation. Nat Biotechnol 22(5):513-319 (2004).

Thompson et al. Structure-based discovery of a novel, noncovalent inhibitor of AmpC beta-lactamase. Nature 485(7398):395-399 (2012).

Tondi et al. Structure-based optimization of a non-beta-lactam lead results in inhibitors that do not up-regulate beta-lactamase expression in cell culture. J Am Chem Soc 127(13):4632-4639 (2005).

U.S. Appl. No. 15/743,079 Office Action dated Jul. 16, 2019.

U.S. Appl. No. 15/743,079 Office Action dated Nov. 27, 2019.

U.S. Appl. No. 16/104,803 Office Action dated Sep. 19, 2019.

Weiss et al. Conformation guides molecular efficacy in docking screens of activated β-2 adrenergic G protein coupled receptor. ACS Chemical Biol 8(5):1018-1026 (2013).

Wu et al. Structure of the human κ-opioid receptor in complex with JDTic. Nature 485(7398):327-332 (2012).

Co-pending U.S. Appl. No. 17/714,030, inventors Mendina; Julio Cesar et al., filed Apr. 5, 2022.

* cited by examiner

OPIOID RECEPTOR MODULATORS AND PRODUCTS AND METHODS RELATED THERETO

This application is a continuation of U.S. application Ser. No. 16/691,377, filed Nov. 21, 2019, which is a continuation of U.S. application Ser. No. 16/375,811, filed Apr. 4, 2019, which claims benefit of U.S. Provisional Application No. 62/792,754, filed Jan. 15, 2019, and U.S. Provisional Application No. 62/652,819, filed Apr. 4, 2018.

This application claims the benefit of priority to U.S. Provisional Application No. 62/652,819, filed Apr. 4, 2018, and U.S. Provisional Application No. 62/792,754, filed Jan. 15, 2019, which applications are hereby incorporated by reference in their entirety.

FIELD OF THE INVENTION

The invention relates to opioid receptor modulators, and particularly to compounds that modulate the mu-opioid receptor (MOR) and/or the kappa-opioid receptor (KOR), and/or the delta-opioid receptor (DOR), as well as to products containing the same and to methods of their use and preparation.

BACKGROUND

Opioid receptors are a group of inhibitory G protein-coupled receptors with opioids as ligands, which have long been used to treat pain. Opioids generally act on these receptors as agonists, antagonists, or partial agonists. There are three classical opioid receptors, originally named mu (after morphine, its most commonly recognized exogenous ligand), delta (after vas deferens, the tissue within which it was first isolated) and kappa (after the first ligand to act at this receptor, ketocyclazocine). These opioid receptors are distributed widely within the central nervous system and, to a lesser extent, throughout the periphery. Opioids, whether naturally occurring or synthetic, exhibit any number of problematic side effects, such as constipation, addiction and respiratory depression, and efforts to eliminate such attributes have been meet with only limited successes. Accordingly, there remains a need in the art for agents that can modulate opioid receptors in a manner that limit the side effects normally associated with such agents.

BRIEF SUMMARY

In one embodiment, compounds are provided having the structure of Formula (I):

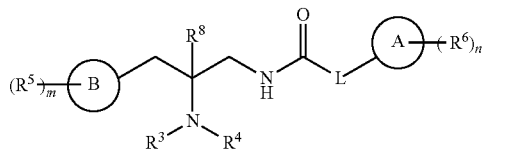

(I)

or a pharmaceutically acceptable isomer, racemate, hydrate, solvate, isotope, or salt thereof, wherein A, B, L, $R^3$, $R^4$, $R^5$, $R^6$, $R^8$, m and n are as defined below.

In more specific embodiments, compounds are provided having the structure of any one of Formulas (II) through (XI), or any one of the compounds listed in any one of Tables 1, 2 or 3. In further embodiments, compounds are provided of Formula (I), or any one of Formulas (II) through (XI), with the various applicable provisos provided below.

In another embodiment, a pharmaceutical composition is provided comprising a compound of any of the embodiments disclosed herein in combination with a pharmaceutically acceptable carrier, diluent, or excipient.

In another embodiment, a method is provided for modulating an opioid receptor comprising contacting the opioid receptor with an effective amount of a compound as provided herein, or a pharmaceutically acceptable isomer, racemate, hydrate, solvate, isotope, or salt thereof, or a pharmaceutical composition comprising the same. In more specific embodiments, the compound is a mu opioid receptor agonist and/or a kappa opioid receptor antagonist.

BRIEF DESCRIPTION OF THE DRAWINGS

FIG. 1 also illustrates that MOR antagonists Compound B-15 blocks in vivo the analgesic activity of the agonist Compound B-56 when co-dosed, but has no effect on its own.

DETAILED DESCRIPTION

Figure 1:
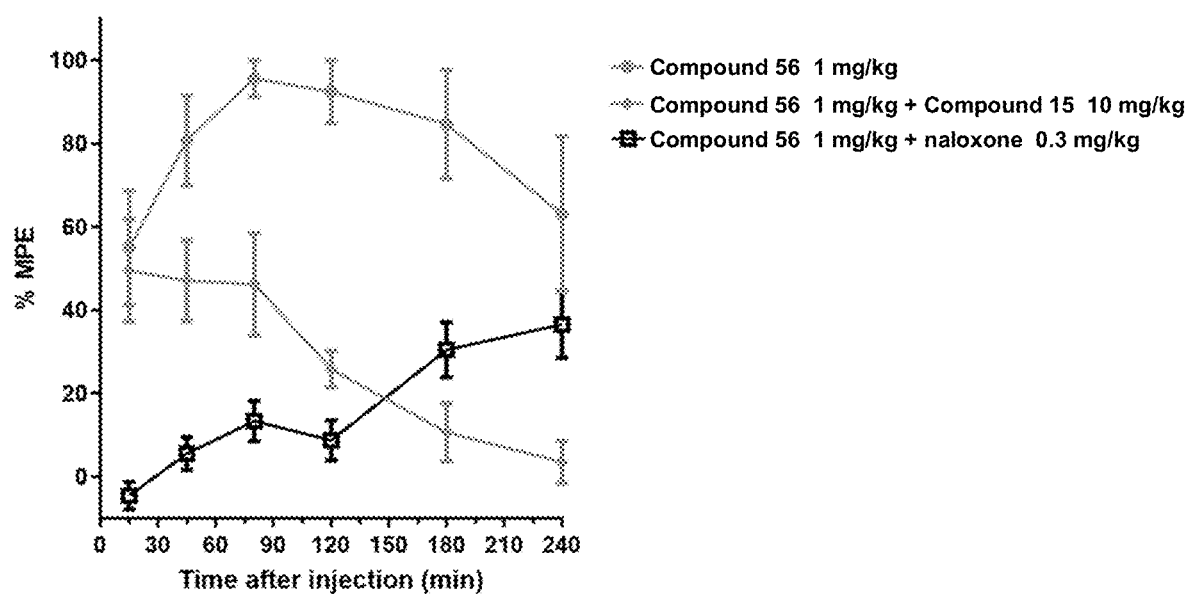
FIG. 1 illustrates that MOR agonist Compound B-56 is an analgesic in the hotplate test, increasing the time to exhibit a withdrawal response.

Unless specifically defined otherwise, the technical terms, as used herein, have their normal meaning as understood in the art. The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Thus the phrase "comprising A or B" means including A, B, or A and B.

As mentioned above, the invention relates to compounds that modulate one, two or three of the mu opioid receptor (MOR), the kappa opioid receptor (KOR) and/or the delta opioid receptor (DOR). As used herein, a "modulator" of MOR and/or KOR and/or DOR a compound which, when administered to a subject, provides the desired modulation of the target receptor. For example, the compound may function as a full or partial antagonist or agonist of the receptor, either by interacting directly or indirectly with the target receptor. In one embodiment, the compounds is a MOR agonist, a KOR antagonist, or both a MOR agonist and a KOR antagonist.

In one embodiment, compounds are provided having the structure of Formula (I):

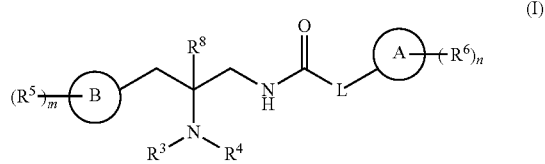

(I)

or a pharmaceutically acceptable isomer, racemate, hydrate, solvate, isotope, or salt thereof, wherein:

ring A is carbocycle or heterocycle;
ring B is carbocycle or heterocycle;
L is a bond, —$(CR^7_2)_q$-Q-$(CR^7_2)_r$—, or ring C;
Q is —$C(R^a)_2$—, —$NR^a$—, or —O—;
ring C is a $C_3$-$C_7$ cycloalkyl or 3-7 membered heterocycloalkyl, substituted with 0-5 $R^7$;
each $R^a$ is H or $(C_1$-$C_6)$alkyl;
$R^1$ and $R^2$ are each, independently, H, or $(C_1$-$C_6)$alkyl or $C_3$-$C_7$ cycloalkyl substituted with 0-5 halo;
$R^3$ and $R^4$ are each, independently, H, $(C_1$-$C_6)$alkyl, $(C_1$-$C_6)$haloalkyl, carbocycle, or carbocyclealkyl;
or $R^3$ and $R^4$, together with the N to which they are connected, form a 4-7 membered heterocycle;
$R^5$, $R^6$, and $R^7$ are each, independently, —$C(O)NR^1R^2$, —$NR^1C(O)R^2$, —$OC(O)R^1$, —$C(O)OR^1$, —$S(O)_tNR^1R^2$, —$NR^1S(O)_tR^2$, —OH, —CN, halo, oxo, $(C_1$-$C_6)$alkyl, $(C_1$-$C_6)$haloalkyl, $(C_1$-$C_6)$alkoxy, or carbocycle;
or $R^3$ and one $R^5$, together with the atoms to which they are connected, form a 5-7 membered heterocycle;
$R^8$ is H or $(C_1$-$C_6)$alkyl;
m is 0-5;
n is 0-5;
q is 0-5;
r is 0-5; and
t is 0-2.

As used herein, "alkyl" means a straight chain or branched saturated hydrocarbon group. "Lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 2 carbon atoms. Examples of straight chain lower alkyl groups include, but are not limited to, methyl, ethyl, n-propyl, n-butyl, n-pentyl, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

As used herein, "alkylene" means a divalent alkyl group. Examples of straight chain lower alkylene groups include, but are not limited to, methylene (i.e., —$CH_2$—), ethylene (i.e., —$CH_2CH_2$—), propylene (i.e., —$CH_2CH_2CH_2$—), and butylene (i.e., —$CH_2CH_2CH_2CH_2$—). As used herein, "heteroalkylene" is an alkylene group of which one or more carbon atoms is replaced with a heteroatom such as, but not limited to, N, O, S, or P.

"Alkoxy" refers to an alkyl as defined above joined by way of an oxygen atom (i.e., —O-alkyl). Examples of lower alkoxy groups include, but are not limited to, methoxy, ethoxy, n-propoxy, n-butoxy, isopropoxy, sec-butoxy, tert-butoxy, and the like.

The terms "carbocyclic" and "carbocycle" denote a ring structure wherein the atoms of the ring are carbon. Carbocycles may be monocyclic or polycyclic. Carbocycle encompasses both saturated and unsaturated rings. Carbocycle encompasses both cycloalkyl and aryl groups. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

"Cycloalkyl" groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-, 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

"Aryl" groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The terms "aryl" and "aryl groups" include fused rings wherein at least one ring, but not necessarily all rings, are aromatic, such as fused aromatic-aliphatic ring systems (e.g., indanyl, tetrahydronaphthyl, and the like).

As used herein, "heterocycle" or "heterocyclyl" groups include aromatic and non-aromatic ring compounds (heterocyclic rings) containing 3 or more ring members, of which one or more is a heteroatom such as, but not limited to, N, O, S, or P. A heterocyclyl group as defined herein can be a heteroaryl group or a partially or completely saturated cyclic group including at least one ring heteroatom. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-membered ring with two carbon atoms and three heteroatoms, a 6-membered ring with two carbon atoms and four heteroatoms and so forth. Likewise a $C_4$-heterocyclyl can be a 5-membered ring with one heteroatom, a 6-membered ring with two heteroatoms, and so forth. The number of carbon atoms plus the number of heteroatoms sums up to equal the total number of ring atoms. A saturated heterocyclic ring refers to a heterocyclic ring containing no unsaturated carbon atoms.

"Heteroaryl" groups are aromatic ring compounds containing 5 or more ring members, of which, one or more is a heteroatom such as, but not limited to, N, O, and S. A heteroaryl group designated as a C2-heteroaryl can be a 5-membered ring with two carbon atoms and three heteroatoms, a 6-membered ring with two carbon atoms and four heteroatoms and so forth. Likewise a C4-heteroaryl can be a 5-membered ring with one heteroatom, a 6-membered ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl.

"Halo" or "halogen" refers to fluorine, chlorine, bromine and iodine.

"Haloalkyl" refers to an alkyl as defined above with one or more hydrogen atoms replaced with halogen. Examples of lower haloalkyl groups include, but are not limited to, —CF$_3$, —CH$_2$CF$_3$, and the like.

As used herein, the term "optionally substituted" refers to a group (e.g., an alkyl, carbocycle, or heterocycle) having 0, 1, or more substituents, such as 0-25, 0-20, 0-10 or 0-5 substituents. Substituents include, but are not limited to, halo, cyano, —OR', —NR'R", —S(O)$_2$R' or —S(O)$_2$OR', wherein each R' and R" is, independently, H or alkyl.

In one embodiment, compounds are provided having the structure of Formula (I):

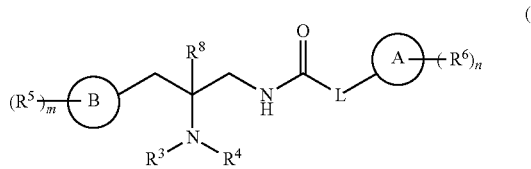

or a pharmaceutically acceptable isomer, racemate, hydrate, solvate, isotope, or salt thereof, wherein:
  ring A is carbocycle or heterocycle;
  ring B is carbocycle or heterocycle;
  L is a bond, —(CR$^7_2$)$_q$-Q-(CR$^7_2$)$_r$—, or ring C;
  Q is —C(R$^a$)$_2$—, —NR$^a$—, or —O—;
  ring C is a C$_3$-C$_7$ cycloalkyl or 3-7 membered heterocycloalkyl, substituted with 0-5 R$^7$;
  each R$^a$ is H or (C$_1$-C$_6$)alkyl;
  R$^1$ and R$^2$ are each, independently, H, or (C$_1$-C$_6$)alkyl or C$_3$-C$_7$ cycloalkyl substituted with 0-5 halo;
  R$^3$ and R$^4$ are each, independently, H, (C$_1$-C$_6$)alkyl, (C$_1$-C$_6$)haloalkyl, carbocycle, or carbocyclealkyl;
  or R$^3$ and R$^4$, together with the N to which they are connected, form a 4-7 membered heterocycle;
  R$^5$, R$^6$, and R$^7$ are each, independently, —C(O)NR$^1$R$^2$, —NR$^1$C(O)R$^2$, —OC(O)R$^1$, —C(O)OR$^1$, —S(O)$_t$NR$^1$R$^2$, —NR$^1$S(O)$_t$R$^2$, —OH, —CN, halo, oxo, (C$_1$-C$_6$)alkyl, (C$_1$-C$_6$)haloalkyl, (C$_1$-C$_6$)alkoxy, or carbocycle;
  or R$^3$ and one R$^5$, together with the atoms to which they are connected, form a 5-7 membered heterocycle;
  R$^8$ is H or (C$_1$-C$_6$)alkyl;
  m is 0-5;
  n is 0-5;
  q is 0-5;
  r is 0-5; and
  t is 0-2;
with the provisos that:
  when L is —(CR$^7_2$)$_q$-Q-(CR$^7_2$)$_r$—,
    m is not 0 and at least one R$^5$ is not —OH, halo, or alkoxy when ring B is an aromatic monocyclic carbocycle or heterocycle, or
    at least one R$^5$ is not halo when ring B is an aromatic monocyclic carbocycle or heterocycle and m is 2-5, or R$^3$ and R$^4$ are not both H and ring A is not thiophene when ring B is an aromatic polycyclic carbocycle or heterocyle;
  when L is ring C,
    m is not 0 when ring B is phenyl or pyrrolyl and R$^3$ is H, (C$_1$-C$_6$)alkyl, or forms a 5-7 membered heterocycle together with one R$^5$, or
    R$^5$ is not halo when R$^3$ and R$^4$, together with the N to which they are connected, form a 4-7 membered heterocycle, one R$^6$ is halo, and m is 1; and
  when L is a bond,
    m is not 0 when ring B is phenyl or pyrrolyl and R$^3$ is H or (C$_1$-C$_6$)alkyl, or
    m' is not 0 when R$^3$ and one R$^5$, together with the atoms to which they are connected, form a 5-7 membered heterocycle,
    R$^5$ is not halo or alkoxy when ring B is phenyl, R$^3$ and one R$^5$, together with the atoms to which they are connected, form a 5-7 membered heterocycle, and m' is 1, or
    R$^5$ is not —OH when ring B is a 7-membered carbocycle, R$^3$ and one R$^5$, together with the atoms to which they are connected, form a 5-7 membered heterocycle, and m' is 1, or
    m is not 0 when ring B is a monocyclic carbocycle or heterocycle and R$^3$ and R$^4$ are each, independently, H, (C$_1$-C$_6$)alkyl, (C$_1$-C$_6$)haloalkyl, carbocycle, or carbocyclealkyl or R$^3$ and R$^4$, together with the N to which they are connected, form a 4-7 membered heterocycle, or
    R$^5$ is not halo when ring B is phenyl and R$^3$ and R$^4$ are each H or R$^3$ and R$^4$, together with the N to which they are connected, form a 4-7 membered heterocycle, or
    n is not 0 when ring A is imidazolyl and ring B is phenyl.

Accordingly, in one embodiment compounds are provided having the structure of Formula (I), or a pharmaceutically acceptable isomer, racemate, hydrate, solvate, isotope, or salt thereof, wherein L is —(CR$^7_2$)$_q$-Q-(CR$^7_2$)$_r$— and with the provisos that:
  m is not 0 and at least one R$^5$ is not —OH, halo, or alkoxy when ring B is an aromatic monocyclic carbocycle or heterocycle, or
  at least one R$^5$ is not halo when ring B is an aromatic monocyclic carbocycle or heterocyle and m is 2-5, or
  R$^3$ and R$^4$ are not both H and ring A is not thiophene when ring B is an aromatic polycyclic carbocycle or heterocyle.

Accordingly, in another embodiment compounds are provided having the structure of Formula (I), or a pharmaceutically acceptable isomer, racemate, hydrate, solvate, isotope, or salt thereof, wherein L is ring C and with the provisos that:
  m is not 0 when ring B is phenyl or pyrrolyl and R$^3$ is H, (C$_1$-C$_6$)alkyl, or forms a 5-7 membered heterocycle together with one R$^5$, or
  R$^5$ is not halo when R$^3$ and R$^4$, together with the N to which they are connected, form a 4-7 membered heterocycle, one R$^6$ is halo, and m is 1.

Accordingly, in another embodiment compounds are provided having the structure of Formula (I), or a pharmaceutically acceptable isomer, racemate, hydrate, solvate, isotope, or salt thereof, wherein L is a bond and with the proviso that:
  m is not 0 when ring B is phenyl or pyrrolyl and R$^3$ is H or (C$_1$-C$_6$)alkyl, or m' is not 0 when R³ and one R⁵, together with the atoms to which they are connected, form a 5-7 membered heterocycle, R⁵ is not halo or alkoxy when ring B is phenyl, R³ and one R⁵, together with the atoms to which they are connected, form a 5-7 membered heterocycle, and m' is 1, or R⁵ is not —OH when ring B is a 7-membered carbocycle, R³ and one R⁵, together with the atoms to which they are connected, form a 5-7 membered heterocycle, and m' is 1, or m is not 0 when ring B is a monocyclic carbocycle or heterocyle and R³ and R⁴ are each, independently, H, (C₁-C₆)alkyl, (C₁-C₆)haloalkyl, carbocycle, or carbocyclealkyl or R³ and R⁴, together with the N to which they are connected, form a 4-7 membered heterocycle, or R⁵ is not halo when ring B is phenyl and R³ and R⁴ are each H or R³ and R⁴, together with the N to which they are connected, form a 4-7 membered heterocycle, or n is not 0 when ring A is imidazolyl and ring B is phenyl.

In one embodiment, compounds are provided having the structure of Formula (II):

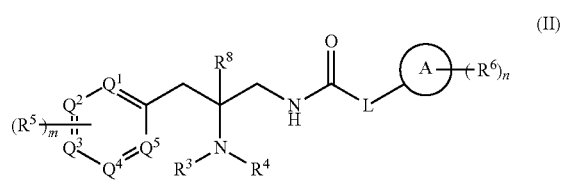

(II)

or a pharmaceutically acceptable isomer, racemate, hydrate, solvate, isotope, or salt thereof, wherein:

ring A is carbocycle or heterocycle;

L is a bond, —(CR⁷₂)$_q$-Q-(CR⁷₂)$_r$—, or ring C;

Q is —C(Rᵃ)₂—, —NRᵃ—, or —O—;

ring C is a C₃-C₇ cycloalkyl or 3-7 membered heterocyloalkyl, substituted with 0-5 R⁷;

each Rᵃ is H or (C₁-C₆)alkyl;

R¹ and R² are each, independently, H, or (C₁-C₆)alkyl or C₃-C₇ cycloalkyl substituted with 0-5 halo;

R³ and R⁴ are each, independently, H, (C₁-C₆)alkyl, (C₁-C₆)haloalkyl, carbocycle, or carbocyclealkyl;

or R³ and R⁴, together with the N to which they are connected, form a 4-7 membered heterocycle;

R⁵, R⁶, and R⁷ are each, independently, —C(O)NR¹R², —NR¹C(O)R², —OC(O)R¹, —C(O)OR¹, —S(O)$_t$NR¹R², —NR¹S(O)$_t$R², —OH, —CN, halo, oxo, (C₁-C₆)alkyl, (C₁-C₆)haloalkyl, (C₁-C₆)alkoxy, or carbocycle;

or R³ and one R⁵, together with the atoms to which they are connected, form a 5-7 membered heterocycle;

R⁸ is H or (C₁-C₆)alkyl;

Q¹, Q², Q³, Q⁴, and Q⁵ are each, independently, C or N; wherein 0, 1, or 2 of Q¹, Q², Q³, Q⁴, and Q⁵ is N;

m is 0-5;
n is 0-5;
q is 0-5;
r is 0-5; and
t is 0-2;

with the provisos that:
when L is —(CR⁷₂)$_q$-Q-(CR⁷₂)$_r$—,
m is not 0 and at least one R⁵ is not —OH, halo, or alkoxy, or
at least one R⁵ is not halo when m is 2-5; or
when L is ring C, m is not 0 when Q¹, Q², Q³, Q⁴, and Q⁵ are each, independently, C and R³ is H, (C₁-C₆)alkyl, or forms a 5-7 membered heterocycle together with one R⁵, or R⁵ is not halo when R³ and R⁴, together with the N to which they are connected, form a 4-7 membered heterocycle, one R⁶ is halo, and m is 1; and when L is a bond,
m is not 0 when Q¹, Q², Q³, Q⁴, and Q⁵ are each, independently, C and R³ is H or (C₁-C₆)alkyl, or m' is not 0 when R³ and one R⁵, together with the atoms to which they are connected, form a 5-7 membered heterocycle, R⁵ is not halo or alkoxy when Q¹, Q², Q³, Q⁴, and Q⁵ are each, independently, C and, R³ and one R⁵, together with the atoms to which they are connected, form a 5-7 membered heterocycle, and m' is 1, or m is not 0 when R³ and R⁴ are each, independently, H, (C₁-C₆)alkyl, (C₁-C₆)haloalkyl, carbocycle, or carbocyclealkyl or R³ and R⁴, together with the N to which they are connected, form a 4-7 membered heterocycle, or R⁵ is not halo when Q¹, Q², Q³, Q⁴, and Q⁵ are each, independently, C and R³ and R⁴ are each H or R³ and R⁴, together with the N to which they are connected, form a 4-7 membered heterocycle, or n is not 0 when ring A is imidazolyl and Q¹, Q², Q³, Q⁴, and Q⁵ are each, independently, C.

In one embodiment, compounds are provided having the structure of Formula (III):

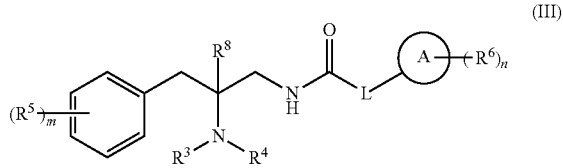

(III)

or a pharmaceutically acceptable isomer, racemate, hydrate, solvate, isotope, or salt thereof, wherein:

ring A is carbocycle or heterocycle;

L is a bond, —(CR⁷₂)$_q$-Q-(CR⁷₂)$_r$—, or ring C;

Q is —C(Rᵃ)₂—, —NRᵃ—, or —O—;

ring C is a C₃-C₇ cycloalkyl or 3-7 membered heterocyloalkyl, substituted with 0-5 R⁷;

each Rᵃ is H or (C₁-C₆)alkyl;

R¹ and R² are each, independently, H, or (C₁-C₆)alkyl or C₃-C₇ cycloalkyl substituted with 0-5 halo;

R³ and R⁴ are each, independently, H, (C₁-C₆)alkyl, (C₁-C₆)haloalkyl, carbocycle, or carbocyclealkyl;

or R³ and R⁴, together with the N to which they are connected, form a 4-7 membered heterocycle;

R⁵, R⁶, and R⁷ are each, independently, —C(O)NR¹R², —NR¹C(O)R², —OC(O)R¹, —C(O)OR¹, —S(O)$_t$NR¹R², —NR¹S(O)$_t$R², —OH, —CN, halo, oxo, (C₁-C₆)alkyl, (C₁-C₆)haloalkyl, (C₁-C₆)alkoxy, or carbocycle;

or R³ and one R⁵, together with the atoms to which they are connected, form a 5-7 membered heterocycle;

R⁸ is H or (C₁-C₆)alkyl;

m is 0-5;
n is 0-5;
q is 0-5;
r is 0-5; and
t is 0-2;

with the provisos that:
when L is —(CR⁷₂)$_q$-Q-(CR⁷₂)$_r$—, m is not 0 and at least one $R^5$ is not —OH, halo, or alkoxy, or at least one $R^5$ is not halo when m is 2-5; or when L is ring C, m is not 0 when $R^3$ is H, $(C_1-C_6)$alkyl, or forms a 5-7 membered heterocycle together with one $R^5$, or $R^5$ is not halo when $R^3$ and $R^4$, together with the N to which they are connected, form a 4-7 membered heterocycle, one $R^6$ is halo, and m is 1; and when L is a bond, m is not 0 when $R^3$ is H or $(C_1-C_6)$alkyl, or m' is not 0 when $R^3$ and one $R^5$, together with the atoms to which they are connected, form a 5-7 membered heterocycle, $R^5$ is not halo or alkoxy when $R^3$ and one $R^5$, together with the atoms to which they are connected, form a 5-7 membered heterocycle, and m' is 1, or m is not 0 when $R^3$ and $R^4$ are each, independently, H, $(C_1-C_6)$alkyl, $(C_1-C_6)$haloalkyl, carbocycle, or carbocyclealkyl or $R^3$ and $R^4$, together with the N to which they are connected, form a 4-7 membered heterocycle, or $R^5$ is not halo when $R^3$ and $R^4$ are each H or $R^3$ and $R^4$, together with the N to which they are connected, form a 4-7 membered heterocycle, or n is not 0 when ring A is imidazolyl.

In one embodiment, compounds are provided having the structure of Formula (IV):

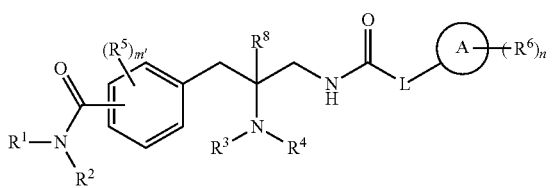

(IV)

or a pharmaceutically acceptable isomer, racemate, hydrate, solvate, isotope, or salt thereof, wherein:

ring A is carbocycle or heterocycle;

L is a bond, —$(CR^7{}_2)_q$-Q-$(CR^7{}_2)_r$—, or ring C;

Q is —$C(R^a)_2$—, —$NR^a$—, or —O—;

ring C is a $C_3-C_7$ cycloalkyl or 3-7 membered heterocycloalkyl, substituted with 0-5 $R^7$;

each $R^a$ is H or $(C_1-C_6)$alkyl;

$R^1$ and $R^2$ are each, independently, H, or $(C_1-C_6)$alkyl or $C_3-C_7$ cycloalkyl substituted with 0-5 halo;

$R^3$ and $R^4$ are each, independently, H, $(C_1-C_6)$alkyl, $(C_1-C_6)$haloalkyl, carbocycle, or carbocyclealkyl;

or $R^3$ and $R^4$, together with the N to which they are connected, form a 4-7 membered heterocycle;

$R^5$, $R^6$, and $R^7$ are each, independently, —$C(O)NR^1R^2$, —$NR^1C(O)R^2$, —$OC(O)R^1$, —$C(O)OR^1$, —$S(O)_tNR^1R^2$, —$NR^1S(O)_tR^2$, —CN, halo, oxo, $(C_1-C_6)$alkyl, $(C_1-C_6)$haloalkyl, $(C_1-C_6)$alkoxy, or carbocycle;

or $R^3$ and one $R^5$, together with the atoms to which they are connected, form a 5-7 membered heterocycle;

$R^8$ is H or $(C_1-C_6)$alkyl;

m' is 0-4;

n is 0-5;

q is 0-5;

r is 0-5; and t is 0-2.

In one embodiment, compounds are provided having the structure of Formula (V):

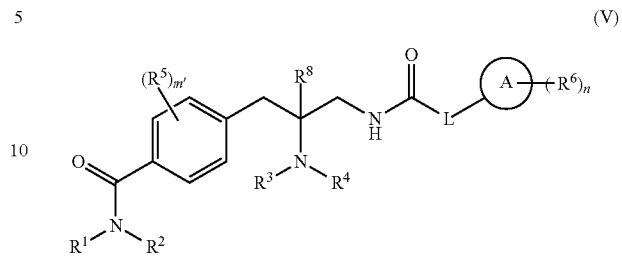

(V)

or a pharmaceutically acceptable isomer, racemate, hydrate, solvate, isotope, or salt thereof, wherein:

ring A is carbocycle or heterocycle;

L is a bond, —$(CR^7{}_2)_q$-Q-$(CR^7{}_2)_r$—, or ring C;

Q is —$C(R^a)_2$—, —$NR^a$—, or —O—;

ring C is a $C_3-C_7$ cycloalkyl or 3-7 membered heterocycloalkyl, substituted with 0-5 $R^7$;

each $R^a$ is H or $(C_1-C_6)$alkyl;

$R^1$ and $R^2$ are each, independently, H, or $(C_1-C_6)$alkyl or $C_3-C_7$ cycloalkyl substituted with 0-5 halo;

$R^3$ and $R^4$ are each, independently, H, $(C_1-C_6)$alkyl, $(C_1-C_6)$haloalkyl, carbocycle, or carbocyclealkyl;

or $R^3$ and $R^4$, together with the N to which they are connected, form a 4-7 membered heterocycle;

$R^5$, $R^6$, and $R^7$ are each, independently, —$C(O)NR^1R^2$, —$NR^1C(O)R^2$, —$OC(O)R^1$, —$C(O)OR^1$, —$S(O)_tNR^1R^2$, —$NR^1S(O)_tR^2$, —CN, halo, oxo, $(C_1-C_6)$alkyl, $(C_1-C_6)$haloalkyl, $(C_1-C_6)$alkoxy, or carbocycle;

or $R^3$ and one $R^5$, together with the atoms to which they are connected, form a 5-7 membered heterocycle;

$R^8$ is H or $(C_1-C_6)$alkyl;

m' is 0-4;

n is 0-5;

q is 0-5;

r is 0-5; and t is 0-2.

In one embodiment, compounds are provided having the structure of Formula (VI):

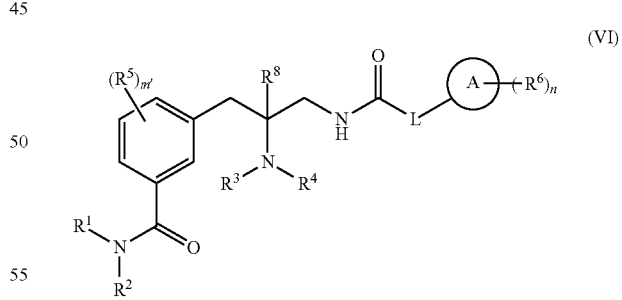

(VI)

or a pharmaceutically acceptable isomer, racemate, hydrate, solvate, isotope, or salt thereof, wherein:

ring A is carbocycle or heterocycle;

L is a bond, —$(CR^7{}_2)_q$-Q-$(CR^7{}_2)_r$—, or ring C;

Q is —$C(R^a)_2$—, —$NR^a$—, or —O—;

ring C is a $C_3-C_7$ cycloalkyl or 3-7 membered heterocycloalkyl, substituted with 0-5 $R^7$;

each $R^a$ is H or $(C_1-C_6)$alkyl;

$R^1$ and $R^2$ are each, independently, H, or $(C_1-C_6)$alkyl or $C_3-C_7$ cycloalkyl substituted with 0-5 halo;

$R^3$ and $R^4$ are each, independently, H, $(C_1-C_6)$alkyl, $(C_1-C_6)$haloalkyl, carbocycle, or carbocyclealkyl;

or $R^3$ and $R^4$, together with the N to which they are connected, form a 4-7 membered heterocycle;

$R^5$, $R^6$, and $R^7$ are each, independently, —C(O)NR$^1$R$^2$, —NR$^1$C(O)R$^2$, —OC(O)R$^1$, —C(O)OR$^1$, —S(O)$_t$NR$^1$R$^2$, —NR$^1$S(O)$_t$R$^2$, —OH, —CN, halo, oxo, $(C_1-C_6)$alkyl, $(C_1-C_6)$haloalkyl, $(C_1-C_6)$alkoxy, or carbocycle;

or $R^3$ and one $R^5$, together with the atoms to which they are connected, form a 5-7 membered heterocycle;

$R^8$ is H or $(C_1-C_6)$alkyl;

m' is 0-4;

n is 0-5;

q is 0-5;

r is 0-5; and t is 0-2.

In one embodiment, compounds are provided wherein $Q^1$, $Q^2$, $Q^3$, and $Q^4$ are each C, and $Q^5$ is N and having the structure of Formula (VII):

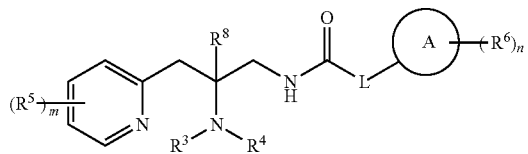

(VII)

or a pharmaceutically acceptable isomer, racemate, hydrate, solvate, isotope, or salt thereof, wherein:

ring A is carbocycle or heterocycle;

L is a bond, —(CR$^7_2$)$_q$-Q-(CR$^7_2$)$_r$—, or ring C;

Q is —C(R$^a$)$_2$—, —NR$^a$—, or —O—;

ring C is a $C_3-C_7$ cycloalkyl or 3-7 membered heterocycloalkyl, substituted with 0-5 $R^7$;

each $R^a$ is H or $(C_1-C_6)$alkyl;

$R^1$ and $R^2$ are each, independently, H, or $(C_1-C_6)$alkyl or $C_3-C_7$ cycloalkyl substituted with 0-5 halo;

$R^3$ and $R^4$ are each, independently, H, $(C_1-C_6)$alkyl, $(C_1-C_6)$haloalkyl, carbocycle, or carbocyclealkyl;

or $R^3$ and $R^4$, together with the N to which they are connected, form a 4-7 membered heterocycle;

$R^5$, $R^6$, and $R^7$ are each, independently, —C(O)NR$^1$R$^2$, —NR$^1$C(O)R$^2$, —OC(O)R$^1$, —C(O)OR$^1$, —S(O)$_t$NR$^1$R$^2$, —NR$^1$S(O)$_t$R$^2$, —OH, —CN, halo, oxo, $(C_1-C_6)$alkyl, $(C_1-C_6)$haloalkyl, $(C_1-C_6)$alkoxy, or carbocycle;

or $R^3$ and one $R^5$, together with the atoms to which they are connected, form a 5-7 membered heterocycle;

$R^8$ is H or $(C_1-C_6)$alkyl;

m is 0-5;

n is 0-5;

q is 0-5;

r is 0-5; and t is 0-2;

with the provisos that:

when L is —(CR$^7_2$)$_q$-Q-(CR$^7_2$)$_r$—, m is not 0 and at least one $R^5$ is not —OH, halo, or alkoxy, or at least one $R^5$ is not halo when m is 2-5; and when L is ring C, $R^5$ is not halo when $R^3$ and $R^4$, together with the N to which they are connected, form a 4-7 membered heterocycle, one $R^6$ is halo, and m is 1; and when L is a bond, m' is not 0 when $R^3$ and one $R^5$, together with the atoms to which they are connected, form a 5-7 membered heterocycle, or m is not 0 when ring B is a monocyclic carbocycle or heterocyle and $R^3$ and $R^4$ are each, independently, H, $(C_1-C_6)$alkyl, $(C_1-C_6)$haloalkyl, carbocycle, or carbocyclealkyl or $R^3$ and $R^4$, together with the N to which they are connected, form a 4-7 membered heterocycle.

In one embodiment, compounds are provided having the structure of Formula (VIII):

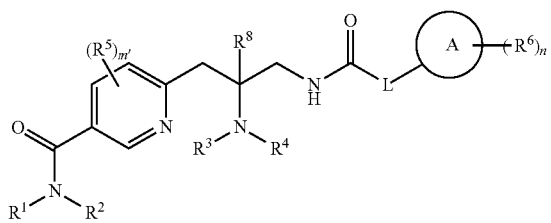

(VIII)

or a pharmaceutically acceptable isomer, racemate, hydrate, solvate, isotope, or salt thereof, wherein:

ring A is carbocycle or heterocycle;

L is a bond, —(CR$^7_2$)$_q$-Q-(CR$^7_2$)$_r$—, or ring C;

Q is —C(R$^a$)$_2$—, —NR$^a$—, or —O—;

ring C is a $C_3-C_7$ cycloalkyl or 3-7 membered heterocycloalkyl, substituted with 0-5 $R^7$;

each $R^a$ is H or $(C_1-C_6)$alkyl;

$R^1$ and $R^2$ are each, independently, H, or $(C_1-C_6)$alkyl or $C_3-C_7$ cycloalkyl substituted with 0-5 halo;

$R^3$ and $R^4$ are each, independently, H, $(C_1-C_6)$alkyl, $(C_1-C_6)$haloalkyl, carbocycle, or carbocyclealkyl;

or $R^3$ and $R^4$, together with the N to which they are connected, form a 4-7 membered heterocycle;

$R^5$, $R^6$, and $R^7$ are each, independently, —C(O)NR$^1$R$^2$, —NR$^1$C(O)R$^2$, —OC(O)R$^1$, —C(O)OR$^1$, —S(O)$_t$NR$^1$R$^2$, —NR$^1$S(O)$_t$R$^2$, —OH, —CN, halo, oxo, $(C_1-C_6)$alkyl, $(C_1-C_6)$haloalkyl, $(C_1-C_6)$alkoxy, or carbocycle;

or $R^3$ and one $R^5$, together with the atoms to which they are connected, form a 5-7 membered heterocycle;

$R^8$ is H or $(C_1-C_6)$alkyl;

m' is 0-4;

n is 0-5;

q is 0-5;

r is 0-5; and t is 0-2.

In one embodiment, compounds are provided having the structure of Formula (IX):

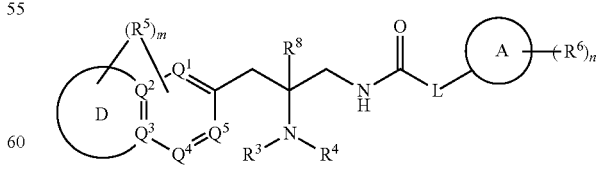

(IX)

or a pharmaceutically acceptable isomer, racemate, hydrate, solvate, isotope, or salt thereof, wherein:

ring A is carbocycle or heterocycle;

L is a bond, —(CR$^7_2$)$_q$-Q-(CR$^7_2$)$_r$—, or ring C;

Q is —C(R$^a$)$_2$—, —NR$^a$—, or —O—;

ring C is a $C_3$-$C_7$ cycloalkyl or 3-7 membered heterocycloalkyl, substituted with 0-5 $R^7$;

each $R^a$ is H or ($C_1$-$C_6$)alkyl;

$R^1$ and $R^2$ are each, independently, H, or ($C_1$-$C_6$)alkyl or $C_3$-$C_7$ cycloalkyl substituted with 0-5 halo;

$R^3$ and $R^4$ are each, independently, H, ($C_1$-$C_6$)alkyl, ($C_1$-$C_6$)haloalkyl, carbocycle, or carbocyclealkyl;

or $R^3$ and $R^4$, together with the N to which they are connected, form a 4-7 membered heterocycle;

$R^5$, $R^6$, and $R^7$ are each, independently, —C(O)N$R^1R^2$, —N$R^1$C(O)$R^2$, —OC(O)$R^1$, —C(O)O$R^1$, —S(O)$_t$N$R^1R^2$, —N$R^1$S(O)$_t$$R^2$, —OH, —CN, halo, oxo, ($C_1$-$C_6$)alkyl, ($C_1$-$C_6$)haloalkyl, ($C_1$-$C_6$)alkoxy, or carbocycle;

or $R^3$ and one $R^5$, together with the atoms to which they are connected, form a 5-7 membered heterocycle;

$R^8$ is H or ($C_1$-$C_6$)alkyl;

$Q^1$, $Q^4$, and $Q^5$ are each, independently, C or N;

$Q^2$ and $Q^3$ are each C;

ring D is a 5-6 membered carbocycle or heterocycle which forms, together with $Q^2$ and $Q^3$, a fused bicyclic ring B;

m is 0-5;
n is 0-5;
q is 0-5;
r is 0-5; and
t is 0-2;

with the proviso that:
when L is —(C$R^7_2$)$_q$-Q-(C$R^7_2$)$_r$—,
$R^3$ and $R^4$ are not both H, and ring A is not thiophene.

In one embodiment, compounds are provided having the structure of Formula (X):

(X)

or a pharmaceutically acceptable isomer, racemate, hydrate, solvate, isotope, or salt thereof, wherein:

ring A is carbocycle or heterocycle;

L is a bond, —(C$R^7_2$)$_q$-Q-(C$R^7_2$)$_r$—, or ring C;

Q is —C($R^a$)$_2$—, —N$R^a$—, or —O—;

ring C is a $C_3$-$C_7$ cycloalkyl or 3-7 membered heterocycloalkyl, substituted with 0-5 $R^7$;

each $R^a$ is H or ($C_1$-$C_6$)alkyl;

$R^1$ and $R^2$ are each, independently, H, or ($C_1$-$C_6$)alkyl or $C_3$-$C_7$ cycloalkyl substituted with 0-5 halo;

$R^3$ and $R^4$ are each, independently, H, ($C_1$-$C_6$)alkyl, ($C_1$-$C_6$)haloalkyl, carbocycle, or carbocyclealkyl;

or $R^3$ and $R^4$, together with the N to which they are connected, form a 4-7 membered heterocycle;

$R^5$, $R^6$, and $R^7$ are each, independently, —C(O)N$R^1R^2$, —N$R^1$C(O)$R^2$, —OC(O)$R^1$, —C(O)O$R^1$, —S(O)$_t$N$R^1R^2$, —N$R^1$S(O)$_t$$R^2$, —OH, —CN, halo, oxo, ($C_1$-$C_6$)alkyl, ($C_1$-$C_6$)haloalkyl, ($C_1$-$C_6$)alkoxy, or carbocycle;

or $R^3$ and one $R^5$, together with the atoms to which they are connected, form a 5-7 membered heterocycle;

$R^8$ is H or ($C_1$-$C_6$)alkyl;

$Q^1$, $Q^4$, and $Q^5$ are each, independently, C or N;

m is 0-5;
n is 0-5;
q is 0-5;
r is 0-5; and
t is 0-2.

In one embodiment, compounds are provided having the structure of Formula (XI):

(XI)

or a pharmaceutically acceptable isomer, racemate, hydrate, solvate, isotope, or salt thereof, wherein:

ring A is carbocycle or heterocycle;

L is a bond, —(C$R^7_2$)$_q$-Q-(C$R^7_2$)$_r$—, or ring C;

Q is —C($R^a$)$_2$—, —N$R^a$—, or —O—;

ring C is a $C_3$-$C_7$ cycloalkyl or 3-7 membered heterocycloalkyl, substituted with 0-5 $R^7$;

each $R^a$ is H or ($C_1$-$C_6$)alkyl;

$R^1$ and $R^2$ are each, independently, H, or ($C_1$-$C_6$)alkyl or $C_3$-$C_7$ cycloalkyl substituted with 0-5 halo;

$R^3$ and $R^4$ are each, independently, H, ($C_1$-$C_6$)alkyl, ($C_1$-$C_6$)haloalkyl, carbocycle, or carbocyclealkyl;

or $R^3$ and $R^4$, together with the N to which they are connected, form a 4-7 membered heterocycle;

$R^5$, $R^6$, and $R^7$ are each, independently, —C(O)N$R^1R^2$, —N$R^1$C(O)$R^2$, —OC(O)$R^1$, —C(O)O$R^1$, —S(O)$_t$N$R^1R^2$, —N$R^1$S(O)$_t$$R^2$, —OH, —CN, halo, oxo, ($C_1$-$C_6$)alkyl, ($C_1$-$C_6$)haloalkyl, ($C_1$-$C_6$)alkoxy, or carbocycle;

or $R^3$ and one $R^5$, together with the atoms to which they are connected, form a 5-7 membered heterocycle;

$R^8$ is H or ($C_1$-$C_6$)alkyl;

$Q^1$, $Q^4$, and $Q^5$ are each, independently, C or N;

m is 0-5;
n is 0-5;
q is 0-5;
r is 0-5; and
t is 0-2.

In one embodiment, a compound of any one of Formulas (I)-(XI) is provided, or a pharmaceutically acceptable isomer, racemate, hydrate, solvate, isotope, or salt thereof, wherein ring A is an aromatic carbocycle.

In one embodiment, a compound of any one of Formulas (I)-(XI) is provided, or a pharmaceutically acceptable isomer, racemate, hydrate, solvate, isotope, or salt thereof, wherein ring A is phenyl.

In one embodiment, a compound of any one of Formulas (I)-(XI) is provided, or a pharmaceutically acceptable isomer, racemate, hydrate, solvate, isotope, or salt thereof, wherein ring A is an aromatic heterocycle.

In one embodiment, a compound of any one of Formulas (I)-(XI) is provided, or a pharmaceutically acceptable isomer, racemate, hydrate, solvate, isotope, or salt thereof, wherein ring A is pyrrolyl, furanyl, pyrazolyl, imidazolyl, triazolyl, tetrazolyl, oxazolyl, isoxazolyl, thiazolyl, isothiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, quinazolinyl, tetrahydroquinolinyl, tetrahydroisoquinolinyl, 2,3-dihydro indolyl, benzoxazolone, or pyrazolopyridine.

In one embodiment, a compound of any one of Formulas (I)-(XI) is provided, or a pharmaceutically acceptable isomer, racemate, hydrate, solvate, isotope, or salt thereof, wherein ring B is pyrrolyl, furanyl, pyrazolyl, imidazolyl, triazolyl, tetrazolyl, oxazolyl, isoxazolyl, thiazolyl, isothiazolyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, quinazolinyl, tetrahydroquinolinyl, tetrahydroisoquinolinyl, 2,3-dihydro indolyl, benzoxazolone, or pyrazolopyridine.

In one embodiment, a compound of any one of Formulas (I)-(XI) is provided, or a pharmaceutically acceptable isomer, racemate, hydrate, solvate, isotope, or salt thereof, wherein L is —$(CR^7{}_2)_q$-Q-$(CR^7{}_2)_r$—.

In one embodiment, a compound of any one of Formulas (I)-(XI) is provided, or a pharmaceutically acceptable isomer, racemate, hydrate, solvate, isotope, or salt thereof, wherein q is 0.

In one embodiment, a compound of any one of Formulas (I)-(XI) is provided, or a pharmaceutically acceptable isomer, racemate, hydrate, solvate, isotope, or salt thereof, wherein Q is —O—.

In one embodiment, a compound of any one of Formulas (I)-(XI) is provided, or a pharmaceutically acceptable isomer, racemate, hydrate, solvate, isotope, or salt thereof, wherein Q is —$C(R^a)_2$—.

In one embodiment, a compound of any one of Formulas (I)-(XI) is provided, or a pharmaceutically acceptable isomer, racemate, hydrate, solvate, isotope, or salt thereof, wherein Q is —$NR^a$—.

In one embodiment, a compound of any one of Formulas (I)-(XI) is provided, or a pharmaceutically acceptable isomer, racemate, hydrate, solvate, isotope, or salt thereof, wherein L is ring C.

In one embodiment, a compound of any one of Formulas (I)-(XI) is provided, or a pharmaceutically acceptable isomer, racemate, hydrate, solvate, isotope, or salt thereof, wherein ring C is cyclopropyl.

In one embodiment, a compound of any one of Formulas (I)-(XI) is provided, or a pharmaceutically acceptable isomer, racemate, hydrate, solvate, isotope, or salt thereof, wherein ring C is pyrrolidinyl.

In one embodiment, a compound of any one of Formulas (I)-(XI) is provided, or a pharmaceutically acceptable isomer, racemate, hydrate, solvate, isotope, or salt thereof, wherein L is a bond.

In one embodiment, a compound of any one of Formulas (I)-(XI) is provided, or a pharmaceutically acceptable isomer, racemate, hydrate, solvate, isotope, or salt thereof, wherein $R^3$ and $R^4$ are each, independently, H, $(C_1-C_6)$alkyl, carbocycle, or carbocyclealkyl.

In one embodiment, a compound of any one of Formulas (I)-(XI) is provided, or a pharmaceutically acceptable isomer, racemate, hydrate, solvate, isotope, or salt thereof, wherein $R^3$ and $R^4$ are each methyl or ethyl.

In one embodiment, a compound of any one of Formulas (I)-(XI) is provided, or a pharmaceutically acceptable isomer, racemate, hydrate, solvate, isotope, or salt thereof, wherein $R^3$ and $R^4$ are each H.

In one embodiment, a compound of any one of Formulas (I)-(XI) is provided, or a pharmaceutically acceptable isomer, racemate, hydrate, solvate, isotope, or salt thereof, wherein $R^3$ is methyl and $R^4$ is cyclopropylmethyl.

In one embodiment, a compound of any one of Formulas (I)-(XI) is provided, or a pharmaceutically acceptable isomer, racemate, hydrate, solvate, isotope, or salt thereof, wherein $R^3$ and $R^4$, together with the N to which they are connected, form a 4-7 membered heterocycle.

In one embodiment, a compound of any one of Formulas (I)-(XI) is provided, or a pharmaceutically acceptable isomer, racemate, hydrate, solvate, isotope, or salt thereof, wherein $R^3$ and $R^4$, together with the N to which they are connected, form pyrrolidinyl or morpholinyl.

In one embodiment, a compound of any one of Formulas (I)-(XI) is provided, or a pharmaceutically acceptable isomer, racemate, hydrate, solvate, isotope, or salt thereof, wherein $R^3$ and one $R^5$, together with the atoms to which they are connected, form a 5-7 membered heterocycle.

In one embodiment, a compound of any one of Formulas (I)-(XI) is provided, or a pharmaceutically acceptable isomer, racemate, hydrate, solvate, isotope, or salt thereof, wherein at least one $R^5$ is —OH.

In one embodiment, a compound of any one of Formulas (I)-(XI) is provided, or a pharmaceutically acceptable isomer, racemate, hydrate, solvate, isotope, or salt thereof, wherein at least one $R^5$ is —$C(O)NR^1R^2$.

In one embodiment, a compound of any one of Formulas (I)-(XI) is provided, or a pharmaceutically acceptable isomer, racemate, hydrate, solvate, isotope, or salt thereof, wherein at least one $R^5$ is halo.

In one embodiment, a compound of any one of Formulas (I)-(XI) is provided, or a pharmaceutically acceptable isomer, racemate, hydrate, solvate, isotope, or salt thereof, wherein at least one $R^5$ is Cl or F.

In one embodiment, a compound of any one of Formulas (I)-(XI) is provided, or a pharmaceutically acceptable isomer, racemate, hydrate, solvate, isotope, or salt thereof, wherein at least one $R^5$ is $(C_1-C_6)$alkyl.

In one embodiment, a compound of any one of Formulas (I)-(XI) is provided, or a pharmaceutically acceptable isomer, racemate, hydrate, solvate, isotope, or salt thereof, wherein at least one $R^5$ is methyl.

In one embodiment, a compound of any one of Formulas (I)-(XI) is provided, or a pharmaceutically acceptable isomer, racemate, hydrate, solvate, isotope, or salt thereof, wherein at least one $R^5$ is —$OC(O)R^1$.

In one embodiment, a compound of any one of Formulas (I)-(XI) is provided, or a pharmaceutically acceptable isomer, racemate, hydrate, solvate, isotope, or salt thereof, wherein at least one $R^6$ is carbocycle.

In one embodiment, a compound of any one of Formulas (I)-(XI) is provided, or a pharmaceutically acceptable isomer, racemate, hydrate, solvate, isotope, or salt thereof, wherein at least one $R^6$ is cycloalkyl.

In one embodiment, a compound of any one of Formulas (I)-(XI) is provided, or a pharmaceutically acceptable isomer, racemate, hydrate, solvate, isotope, or salt thereof, wherein at least one $R^6$ is cyclopropyl.

In one embodiment, a compound of any one of Formulas (I)-(XI) is provided, or a pharmaceutically acceptable isomer, racemate, hydrate, solvate, isotope, or salt thereof, wherein at least one $R^6$ is an aromatic carbocycle.

In one embodiment, a compound of any one of Formulas (I)-(XI) is provided, or a pharmaceutically acceptable isomer, racemate, hydrate, solvate, isotope, or salt thereof, wherein at least one $R^6$ is phenyl.

In one embodiment, a compound of any one of Formulas (I)-(XI) is provided, or a pharmaceutically acceptable isomer, racemate, hydrate, solvate, isotope, or salt thereof, wherein at least one $R^6$ is halo.

In one embodiment, a compound of any one of Formulas (I)-(XI) is provided, or a pharmaceutically acceptable isomer, racemate, hydrate, solvate, isotope, or salt thereof, wherein at least one $R^6$ is Cl, F or Br.

In one embodiment, a compound of any one of Formulas (I)-(XI) is provided, or a pharmaceutically acceptable isomer, racemate, hydrate, solvate, isotope, or salt thereof, wherein at least one $R^6$ is $(C_1-C_6)$alkyl.

In one embodiment, a compound of any one of Formulas (I)-(XI) is provided, or a pharmaceutically acceptable isomer, racemate, hydrate, solvate, isotope, or salt thereof, wherein the at least one $R^6$ is methyl.

In one embodiment, a compound of any one of Formulas (I)-(XI) is provided, or a pharmaceutically acceptable isomer, racemate, hydrate, solvate, isotope, or salt thereof, wherein at least one $R^6$ is $(C_1-C_6)$alkoxy.

In one embodiment, a compound of any one of Formulas (I)-(XI) is provided, or a pharmaceutically acceptable isomer, racemate, hydrate, solvate, isotope, or salt thereof, wherein the at least one $R^6$ is methoxy.

In one embodiment, a compound of any one of Formulas (I)-(XI) is provided, or a pharmaceutically acceptable isomer, racemate, hydrate, solvate, isotope, or salt thereof, wherein at least one $R^7$ is $(C_1-C_6)$alkyl.

In one embodiment, a compound of any one of Formulas (I)-(XI) is provided, or a pharmaceutically acceptable isomer, racemate, hydrate, solvate, isotope, or salt thereof, wherein at least one $R^7$ is methyl, ethyl, isopropyl, or tert-butyl.

In one embodiment, a compound of any one of Formulas (I)-(XI) is provided, or a pharmaceutically acceptable isomer, racemate, hydrate, solvate, isotope, or salt thereof, wherein at least one $R^7$ is carbocycle.

In one embodiment, a compound of any one of Formulas (I)-(XI) is provided, or a pharmaceutically acceptable isomer, racemate, hydrate, solvate, isotope, or salt thereof, wherein at least one $R^7$ is cycloalkyl.

In one embodiment, a compound of any one of Formulas (I)-(XI) is provided, or a pharmaceutically acceptable isomer, racemate, hydrate, solvate, isotope, or salt thereof, wherein at least one $R^7$ is cyclopropyl.

In one embodiment, a compound of any one of Formulas (I)-(XI) is provided, or a pharmaceutically acceptable isomer, racemate, hydrate, solvate, isotope, or salt thereof, wherein $R^8$ is H.

In one embodiment, a compound of any one of Formulas (I)-(XI) is provided, or a pharmaceutically acceptable isomer, racemate, hydrate, solvate, isotope, or salt thereof, wherein $R^8$ is methyl.

In one embodiment, a compound of any one of Formulas (I)-(XI) is provided, or a pharmaceutically acceptable isomer, racemate, hydrate, solvate, isotope, or salt thereof, having the structure of any one of the compounds listed in Table 1.

In one embodiment, a compound of any one of Formulas (I)-(XI) is provided, or a pharmaceutically acceptable isomer, racemate, hydrate, solvate, isotope, or salt thereof, having the structure of any one of the compounds listed in Table 2.

In one embodiment, a compound of any one of Formulas (I)-(XI) is provided, or a pharmaceutically acceptable isomer, racemate, hydrate, solvate, isotope, or salt thereof, having the structure of any one of the compounds listed in Table 3.

Representative compounds of Formulas (I)-(XI) as applicable, include the compounds listed in Table 1 below, as well as pharmaceutically acceptable isomers, racemates, hydrates, solvates, homologs, and salts thereof.

TABLE 1

REPRESENTATIVE COMPOUNDS

| Structure | Compound No. |
|---|---|
| 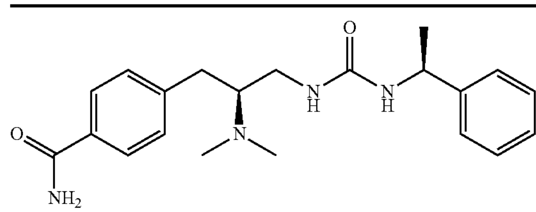 | A-1 |
| 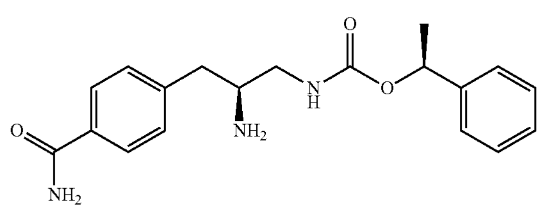 [SMILES: C[C@H](OC(=O)NC[C@@H](N)Cc1ccc(C(N)=O)cc1)c1ccccc1] | A-2 |
| 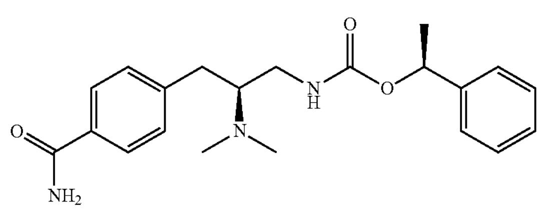 [SMILES: C[C@H](OC(=O)NC[C@H](Cc1ccc(C(N)=O)cc1)N(C)C)c1ccccc1] | A-3 |

TABLE 1-continued

REPRESENTATIVE COMPOUNDS

| Structure | Compound No. |
|---|---|
| 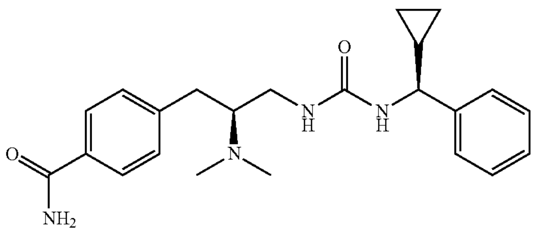 [SMILES: CN(C)[C@H](CNC(=O)N[C@H](c1ccccc1)C1CC1)Cc1ccc(C(N)=O)cc1] | A-4 |
| 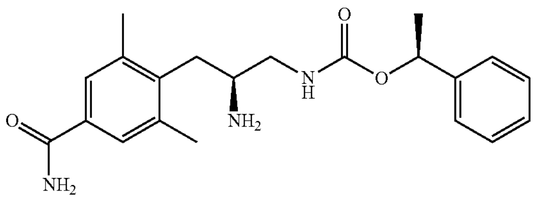 [SMILES: Cc1cc(C(N)=O)cc(C)c1C[C@H](N)CNC(=O)O[C@@H](C)c1ccccc1] | A-5 |
| 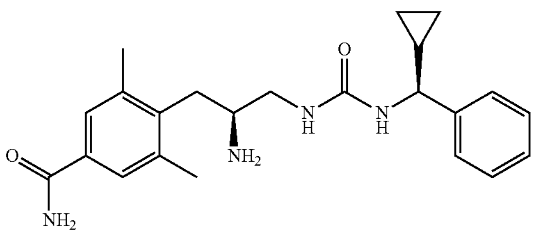 [SMILES: Cc1cc(C(N)=O)cc(C)c1C[C@H](N)CNC(=O)N[C@H](c1ccccc1)C1CC1] | A-6 |
| 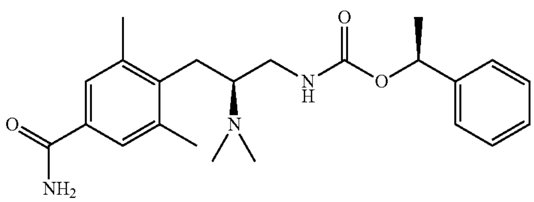 [SMILES: Cc1cc(C(N)=O)cc(C)c1C[C@@H](CNC(=O)O[C@@H](C)c1ccccc1)N(C)C] | A-7 |
| 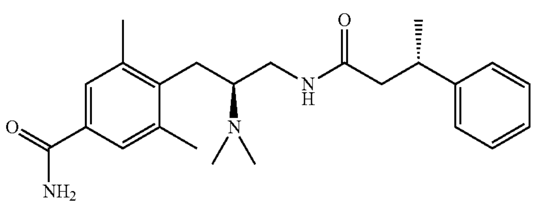 [SMILES: Cc1cc(C(N)=O)cc(C)c1C[C@@H](CNC(=O)C[C@H](C)c1ccccc1)N(C)C] | A-8 |
| 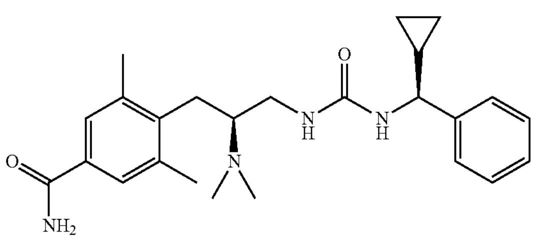 [SMILES: Cc1cc(C(N)=O)cc(C)c1C[C@@H](CNC(=O)N[C@H](c1ccccc1)C1CC1)N(C)C] | A-9 |
| 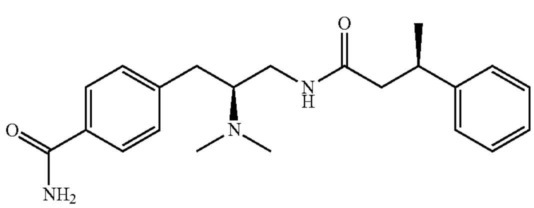 [SMILES: C[C@H](CC(=O)NC[C@H](Cc1ccc(C(N)=O)cc1)N(C)C)c1ccccc1] | A-10 |

TABLE 1-continued

REPRESENTATIVE COMPOUNDS

| Structure | Compound No. |
| --- | --- |
| 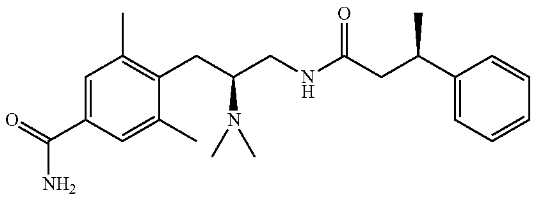 [SMILES: Cc1cc(C(N)=O)cc(C)c1C[C@@H](CNC(=O)C[C@@H](C)c1ccccc1)N(C)C] | A-11 |
| 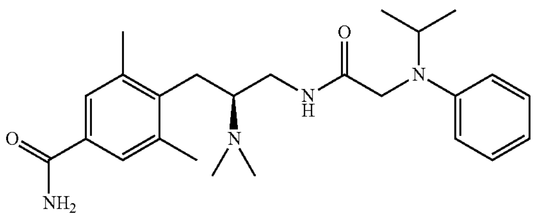 [SMILES: Cc1cc(C(N)=O)cc(C)c1C[C@@H](CNC(=O)CN(c1ccccc1)C(C)C)N(C)C] | A-12 |
| 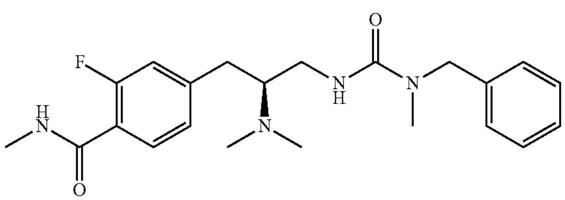 [SMILES: CNC(=O)c1ccc(C[C@@H](CNC(=O)N(C)Cc2ccccc2)N(C)C)cc1F] | A-13 |
| 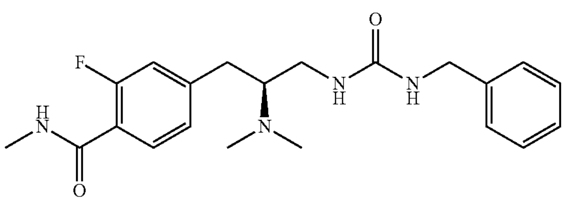 [SMILES: CNC(=O)c1ccc(C[C@@H](CNC(=O)NCc2ccccc2)N(C)C)cc1F] | A-14 |
| 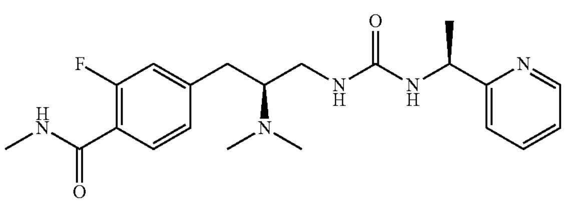 [SMILES: CNC(=O)c1ccc(C[C@@H](CNC(=O)N[C@@H](C)c2ccccn2)N(C)C)cc1F] | A-15 |
| 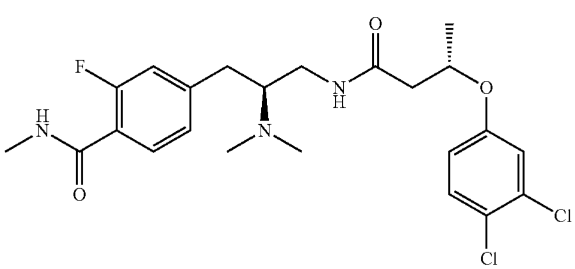 [SMILES: CNC(=O)c1ccc(C[C@@H](CNC(=O)C[C@H](C)Oc2ccc(Cl)c(Cl)c2)N(C)C)cc1F] | A-16 |
| 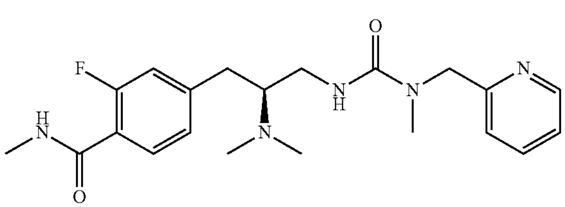 [SMILES: CNC(=O)c1ccc(C[C@@H](CNC(=O)N(C)Cc2ccccn2)N(C)C)cc1F] | A-17 |

TABLE 1-continued

REPRESENTATIVE COMPOUNDS

| Structure | Compound No. |
|---|---|
| 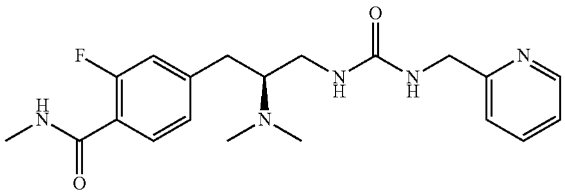 [SMILES: CNC(=O)c1ccc(C[C@@H](CNC(=O)NCc2ccccn2)N(C)C)cc1F] | A-18 |
| 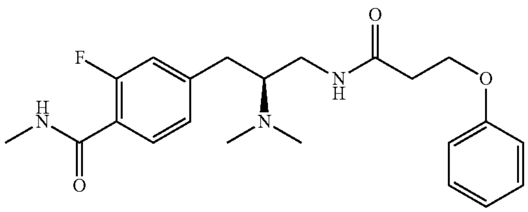 [SMILES: CNC(=O)c1ccc(C[C@@H](CNC(=O)CCOc2ccccc2)N(C)C)cc1F] | A-19 |
| 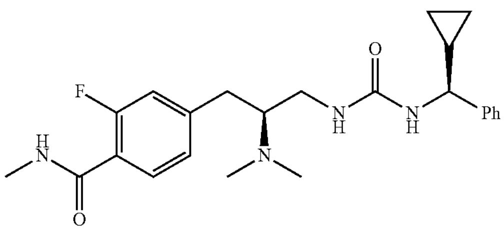 [SMILES: CNC(=O)c1ccc(C[C@@H](CNC(=O)N[C@H](c2ccccc2)C2CC2)N(C)C)cc1F] | A-20 |
| 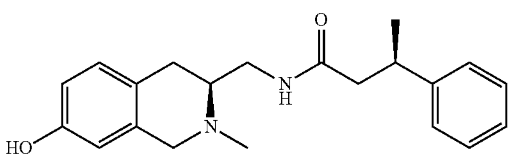 [SMILES: C[C@H](CC(=O)NC[C@@H]1Cc2ccc(O)cc2CN1C)c1ccccc1] | A-21 |
| 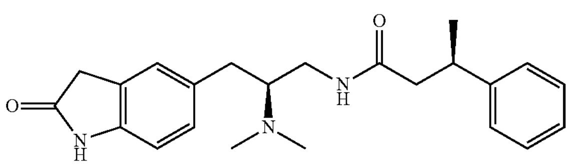 [SMILES: C[C@H](CC(=O)NC[C@H](Cc1ccc2c(c1)CC(=O)N2)N(C)C)c1ccccc1] | A-22 |
| 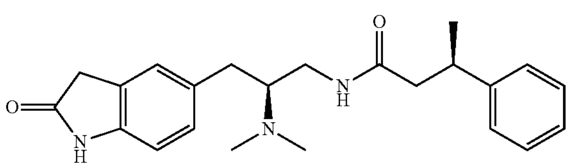 [SMILES: C[C@H](CC(=O)NC[C@H](Cc1ccc2c(c1)CC(=O)N2)N(C)C)c1ccccc1] | A-23 |

Representative compounds of Formulas (I)-(XI) as applicable, include the compounds listed in Table 2 below, as well as pharmaceutically acceptable isomers, racemates, hydrates, solvates, homologs, and salts thereof.

TABLE 2

REPRESENTATIVE COMPOUNDS

| Structure | Compound No. |
|---|---|
| 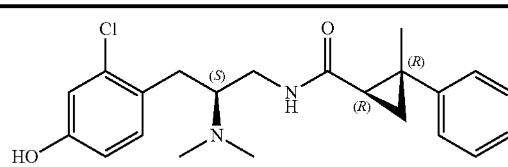 | B-1 |

TABLE 2-continued

REPRESENTATIVE COMPOUNDS

| Structure | Compound No. |
|---|---|
| 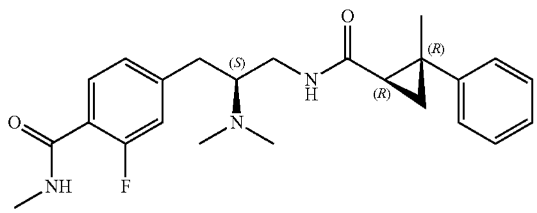 | B-2 |
| 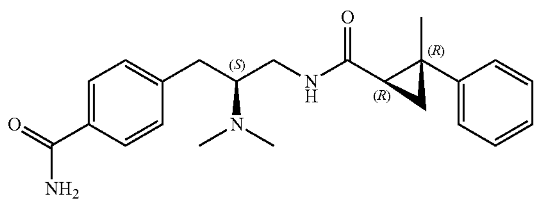 | B-3 |
| 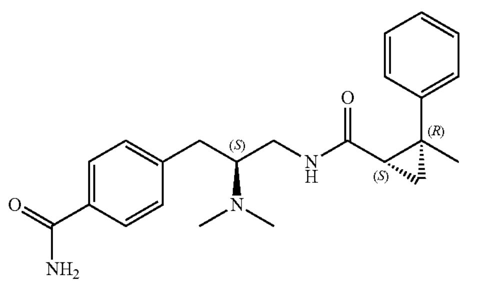 | B-4 |
| 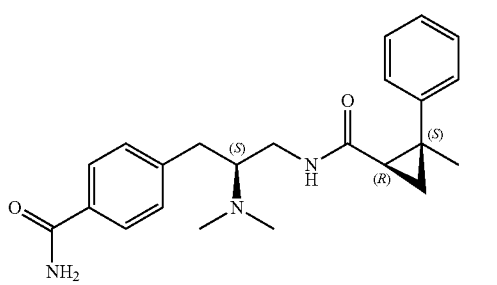 | B-5 |
| 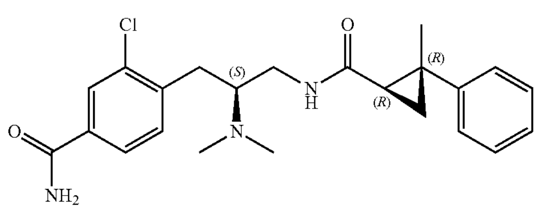 | B-6 |
| 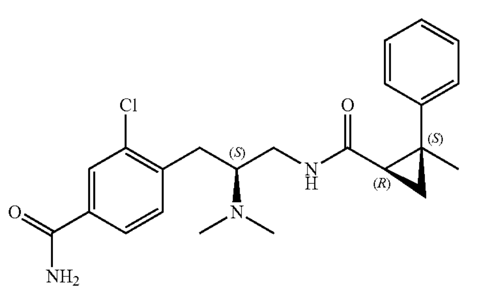 | B-7 |

TABLE 2-continued

REPRESENTATIVE COMPOUNDS

| Structure | Compound No. |
|---|---|
| 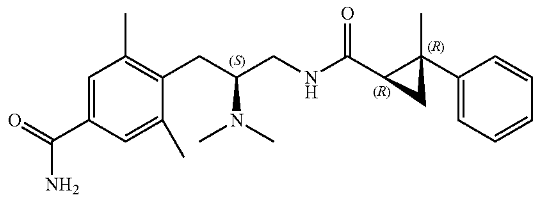 | B-8 |
| 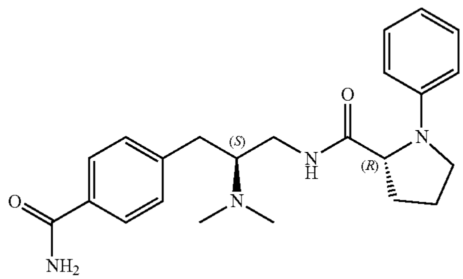 | B-9 |
| 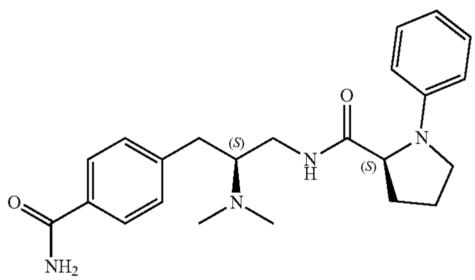 | B-10 |
| 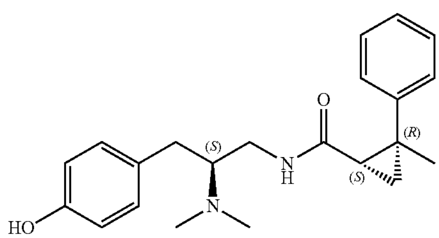 | B-11 |
| 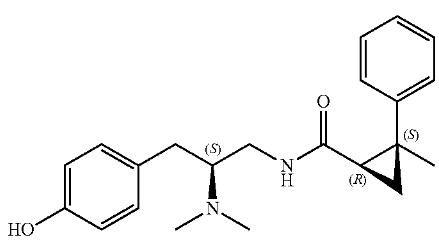 | B-12 |
| 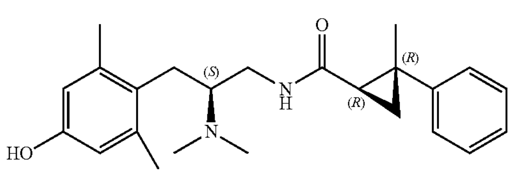 | B-13 |

TABLE 2-continued

REPRESENTATIVE COMPOUNDS

| Structure | Compound No. |
|---|---|
| 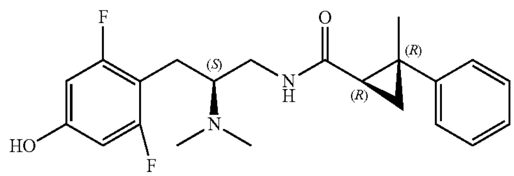 | B-14 |
| 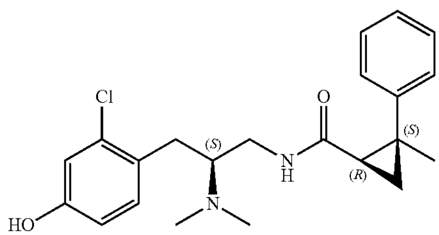 | B-15 |
| 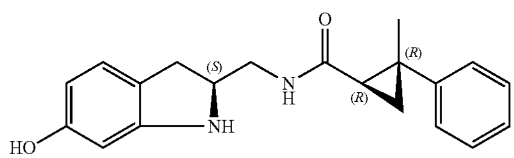 | B-16 |
| 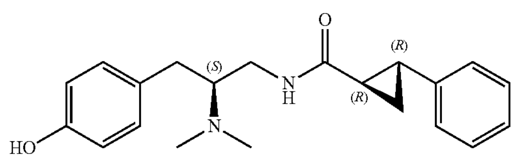 | B-17 |
| 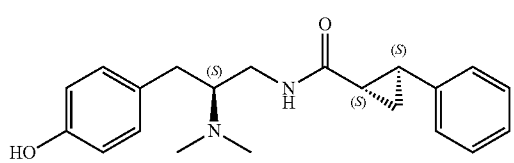 | B-18 |
| 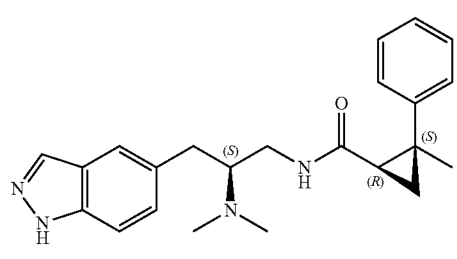 | B-19 |
| 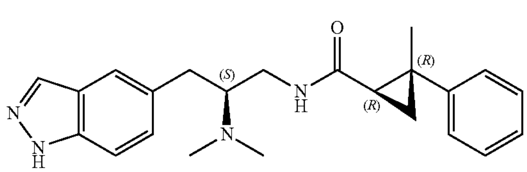 | B-20 |

TABLE 2-continued

REPRESENTATIVE COMPOUNDS

| Structure | Compound No. |
|---|---|
| 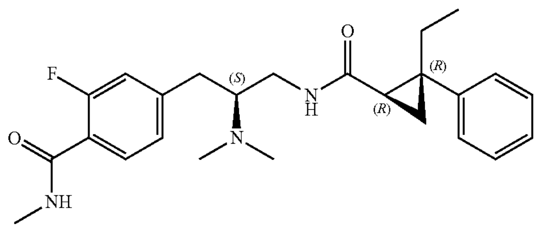 | B-21 |
| 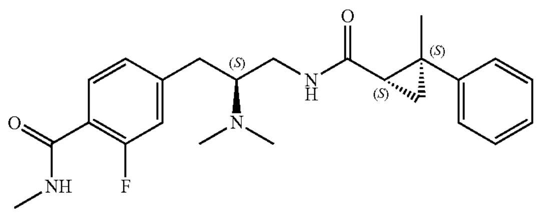 | B-22 |
| 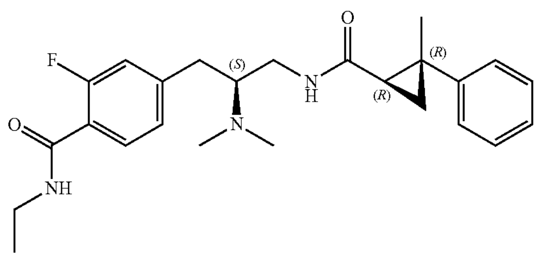 | B-23 |
| 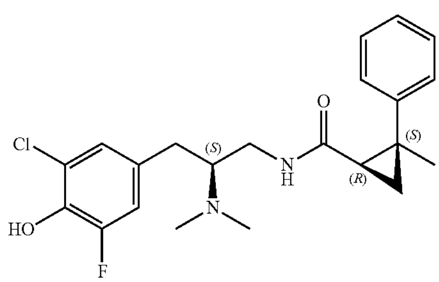 | B-24 |
| 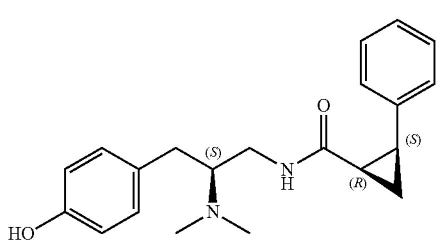 | B-25 |
| 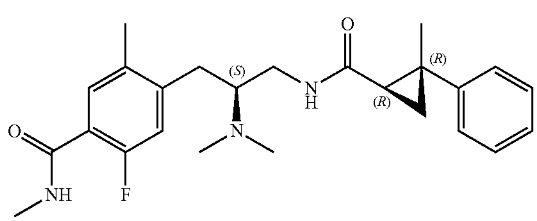 | B-26 |

TABLE 2-continued

REPRESENTATIVE COMPOUNDS

| Structure | Compound No. |
|---|---|
| 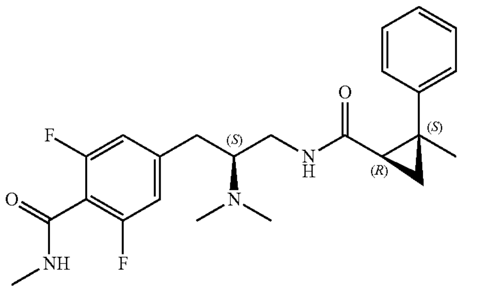 | B-27 |
| 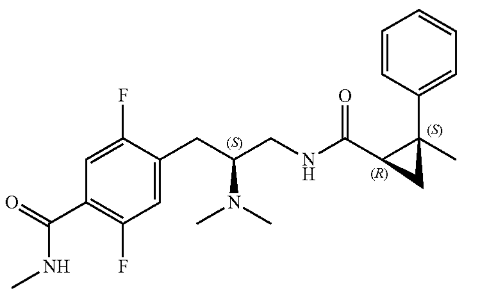 | B-28 |
| 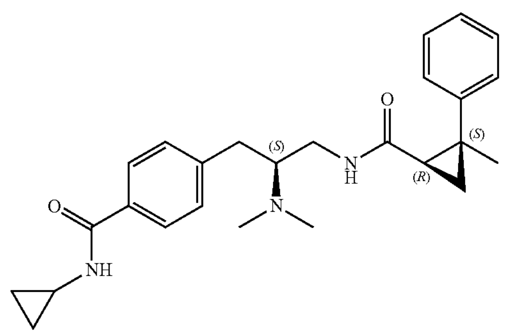 | B-29 |
| 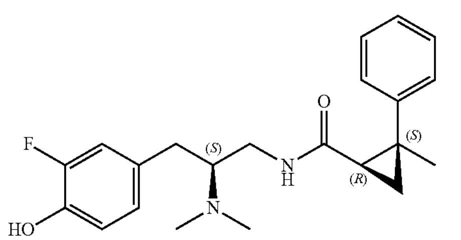 | B-30 |
| 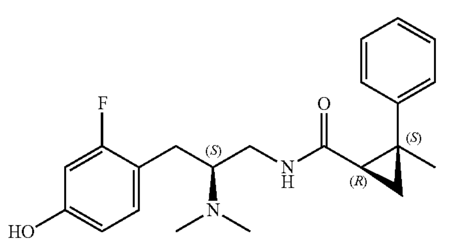 | B-31 |

TABLE 2-continued

REPRESENTATIVE COMPOUNDS

| Structure | Compound No. |
|---|---|
| 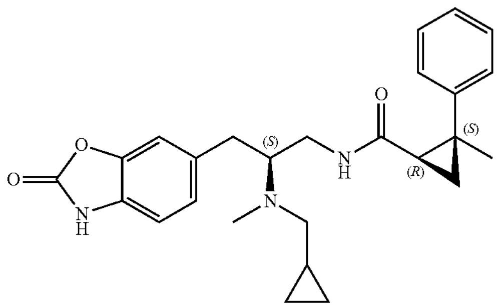 | B-32 |
| 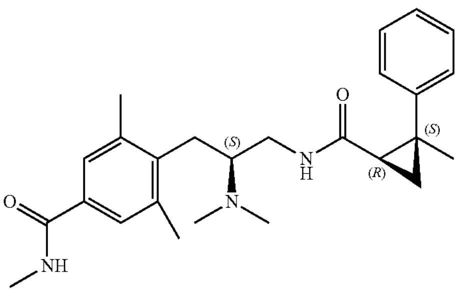 | B-33 |
| 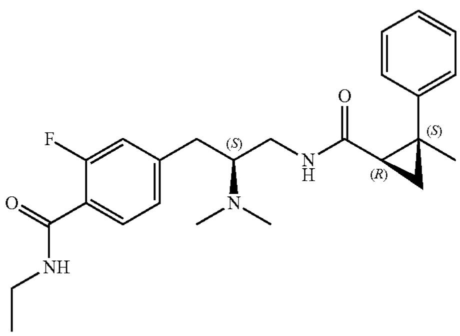 | B-34 |
| 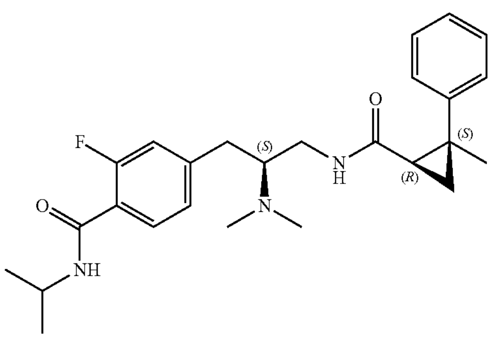 | B-35 |
| 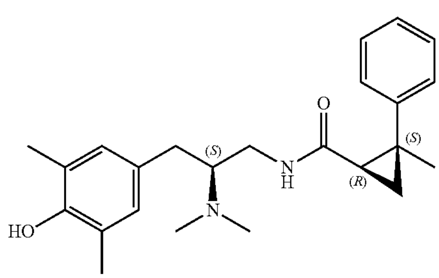 | B-36 |

TABLE 2-continued

REPRESENTATIVE COMPOUNDS

| Structure | Compound No. |
|---|---|
| 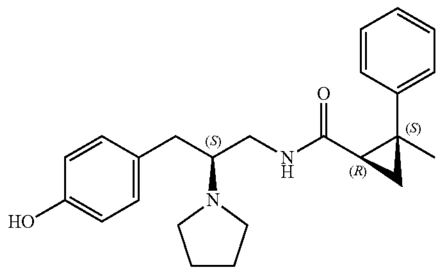 | B-37 |
| 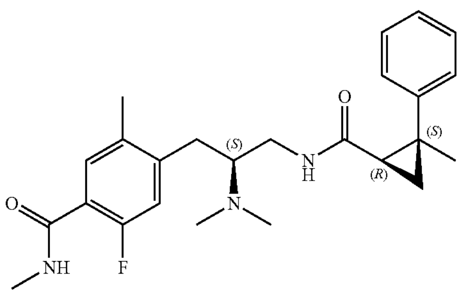 | B-38 |
| 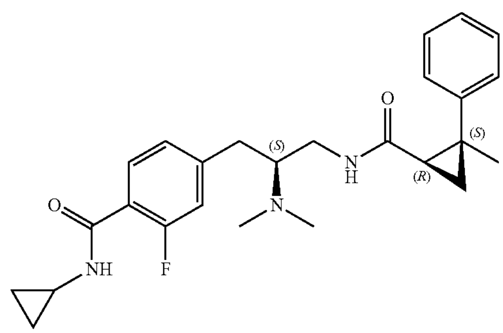 | B-39 |
| 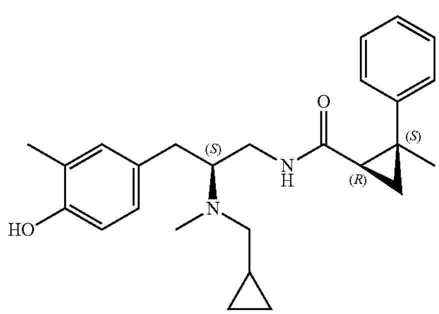 | B-40 |
| 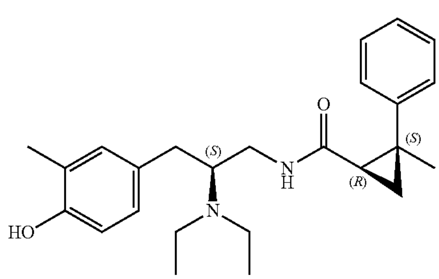 | B-41 |

TABLE 2-continued

REPRESENTATIVE COMPOUNDS

| Structure | Compound No. |
|---|---|
| 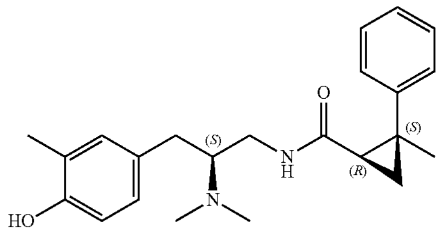 | B-42 |
| 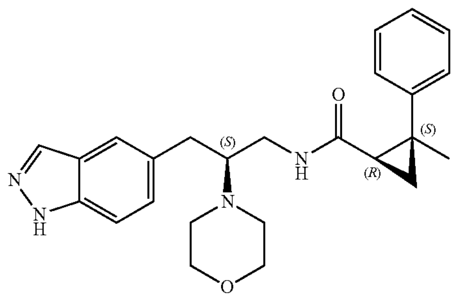 | B-43 |
| 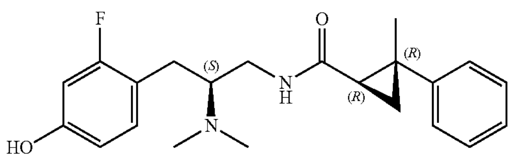 | B-44 |
| 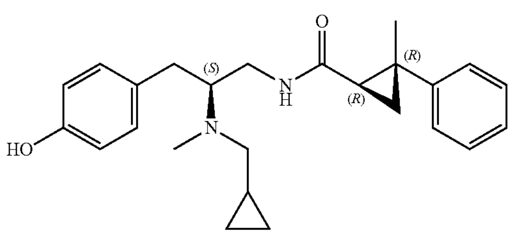 | B-45 |
| 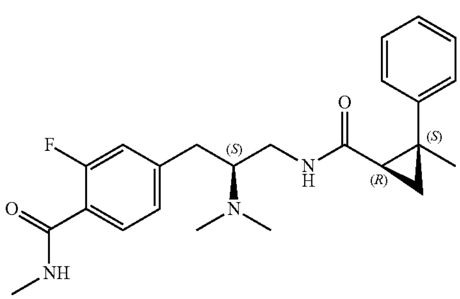 | B-46 |
| 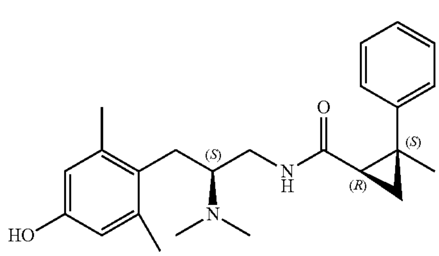 | B-47 |

TABLE 2-continued

REPRESENTATIVE COMPOUNDS

| Structure | Compound No. |
|---|---|
| 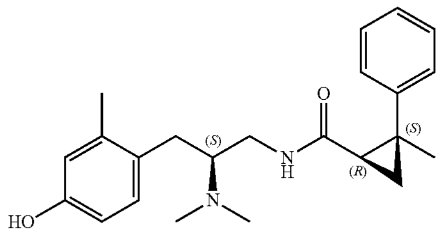 | B-48 |
| 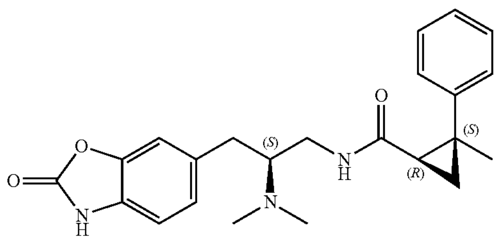 | B-49 |
| 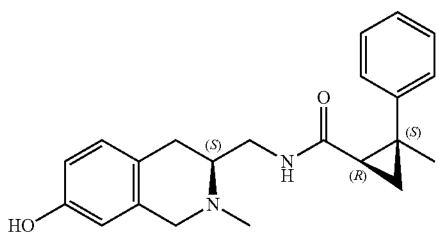 | B-50 |
| 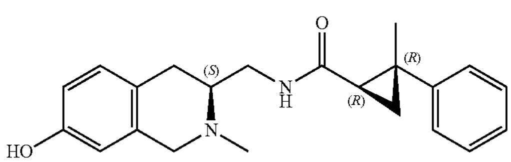 | B-51 |
| 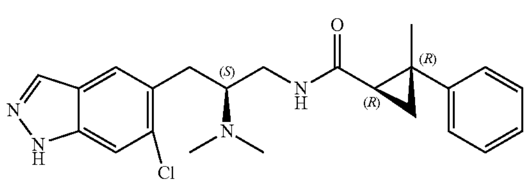 | B-52 |
| 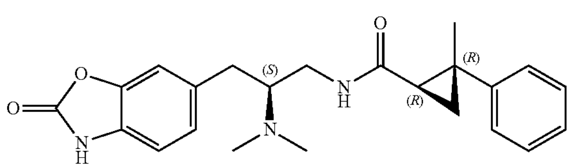 | B-53 |
| 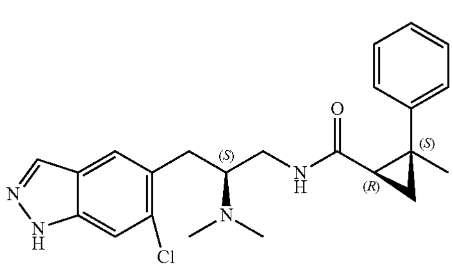 | B-54 |

TABLE 2-continued

REPRESENTATIVE COMPOUNDS

| Structure | Compound No. |
|---|---|
| 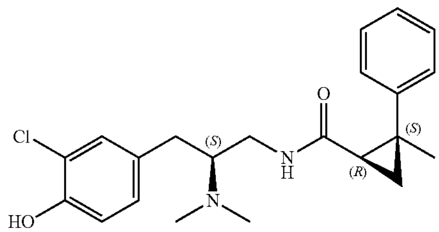 | B-55 |
| 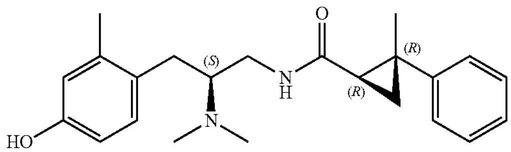 | B-56 |
| 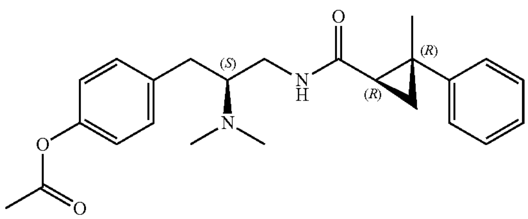 | B-57 |
| 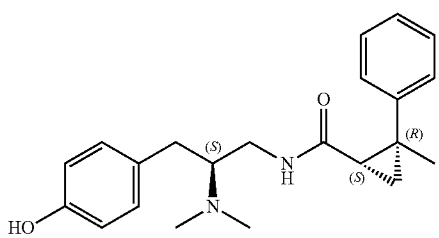 | B-58 |
| 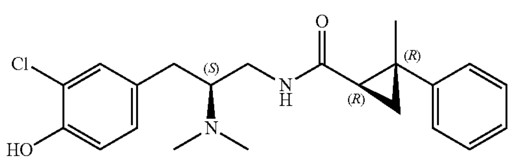 | B-59 |
| 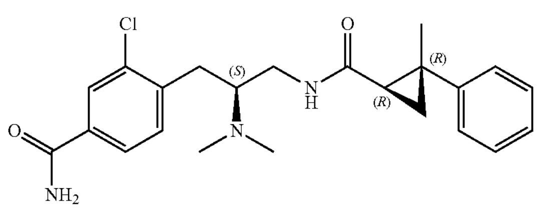 | B-60 |
| 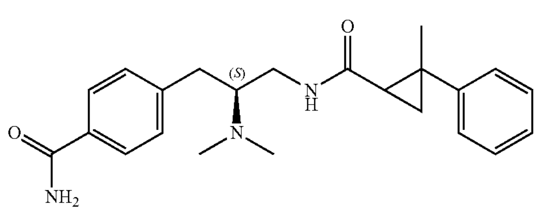 | B-61 |

TABLE 2-continued

REPRESENTATIVE COMPOUNDS

| Structure | Compound No. |
|---|---|
| 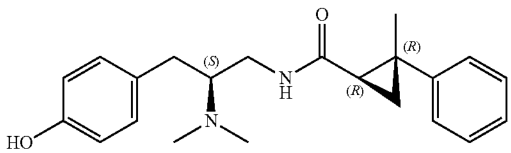 | B-62 |
| 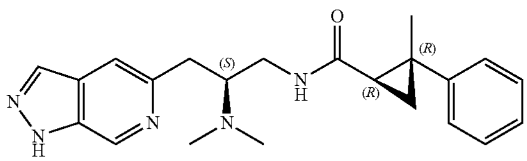 | B-63 |
| 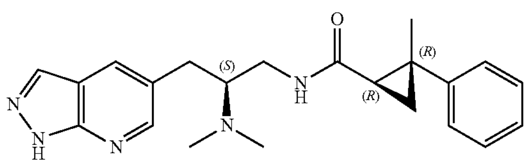 | B-64 |
| 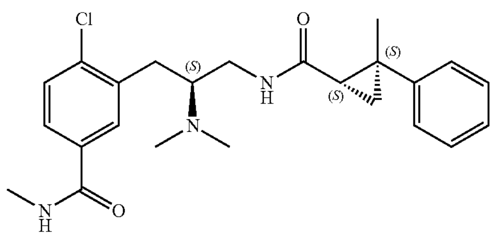 | B-65 |
| 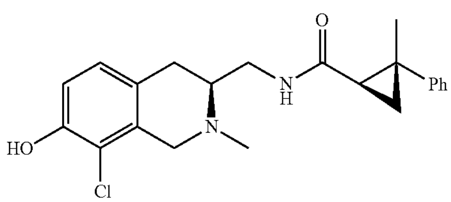 [SMILES: CN1Cc2c(ccc(O)c2Cl)C[C@H]1CNC(=O)[C@@H]1C[C@@]1(C)c1ccccc1] | B-66 |
| 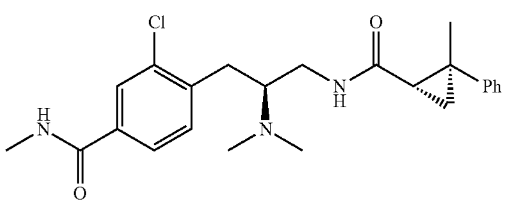 [SMILES: CNC(=O)c1ccc(C[C@@H](CNC(=O)[C@H]2C[C@]2(C)c2ccccc2)N(C)C)c(Cl)c1] | B-67 |
| 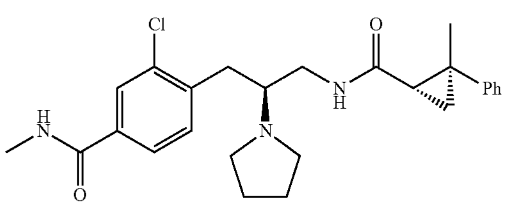 [SMILES: CNC(=O)c1ccc(C[C@@H](CNC(=O)[C@H]2C[C@]2(C)c2ccccc2)N2CCCC2)c(Cl)c1] | B-68 |
| 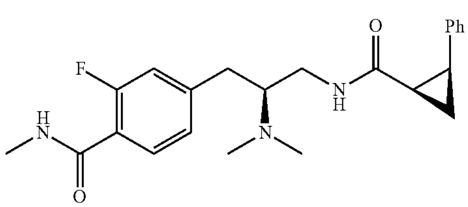 [SMILES: CNC(=O)c1ccc(C[C@@H](CNC(=O)[C@@H]2C[C@@H]2c2ccccc2)N(C)C)cc1F] | B-69 |

TABLE 2-continued

REPRESENTATIVE COMPOUNDS

| Structure | Compound No. |
|---|---|
| 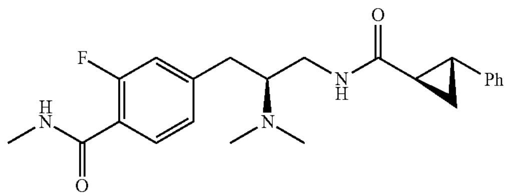 [SMILES: CNC(=O)c1ccc(C[C@@H](CNC(=O)[C@@H]2C[C@H]2c2ccccc2)N(C)C)cc1F] | B-70 |
| 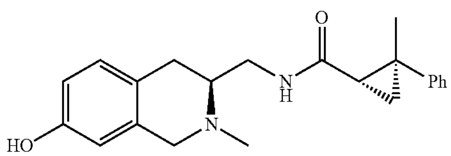 [SMILES: CN1Cc2cc(O)ccc2C[C@H]1CNC(=O)[C@H]1C[C@]1(C)c1ccccc1] | B-71 |
| 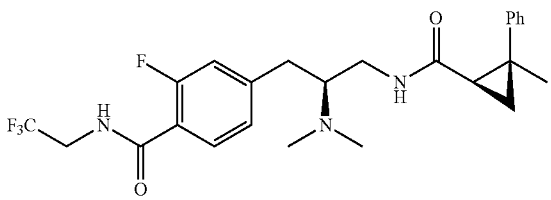 [SMILES: CN(C)[C@H](CNC(=O)[C@@H]1C[C@]1(C)c1ccccc1)Cc1ccc(C(=O)NCC(F)(F)F)c(F)c1] | B-72 |

Representative compounds of Formulas (I)-(XI) as applicable, include the compounds listed in Table 3 below, as well as pharmaceutically acceptable isomers, racemates, hydrates, solvates, homologs, and salts thereof.

TABLE 3

REPRESENTATIVE COMPOUNDS

| Structure | Compd. No. |
|---|---|
| 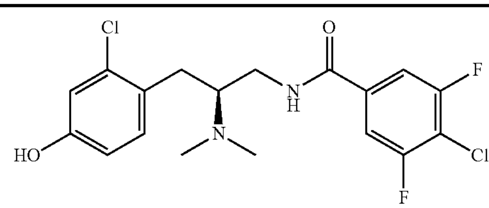 | C-1 |
| 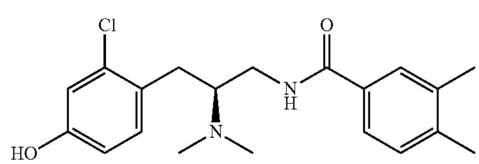 [SMILES: Cc1ccc(C(=O)NC[C@H](Cc2ccc(O)cc2Cl)N(C)C)cc1C] | C-2 |
| 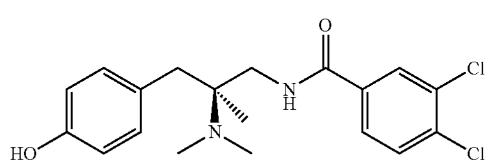 [SMILES: CN(C)[C@](C)(CNC(=O)c1ccc(Cl)c(Cl)c1)Cc1ccc(O)cc1] | C-3 |
| 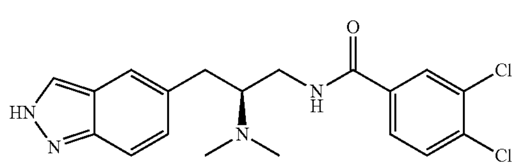 [SMILES: CN(C)[C@H](CNC(=O)c1ccc(Cl)c(Cl)c1)Cc1ccc2n[nH]cc2c1] | C-4 |

TABLE 3-continued

REPRESENTATIVE COMPOUNDS

| Structure | Compd. No. |
|---|---|
| 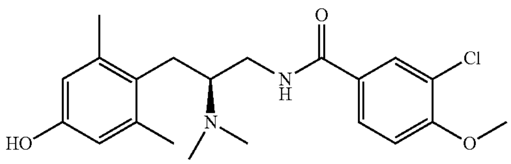 [SMILES: COc1ccc(C(=O)NC[C@H](Cc2c(C)cc(O)cc2C)N(C)C)cc1Cl] | C-5 |
| 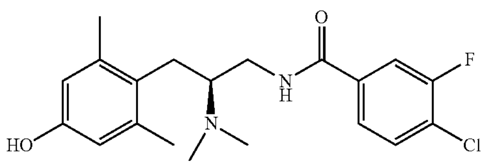 [SMILES: Cc1cc(O)cc(C)c1C[C@@H](CNC(=O)c1ccc(Cl)c(F)c1)N(C)C] | C-6 |
| 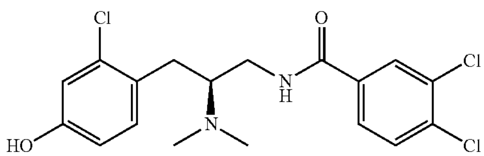 [SMILES: CN(C)[C@H](CNC(=O)c1ccc(Cl)c(Cl)c1)Cc1ccc(O)cc1Cl] | C-7 |
| 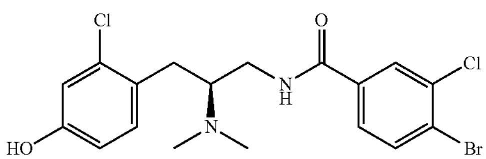 [SMILES: CN(C)[C@H](CNC(=O)c1ccc(Br)c(Cl)c1)Cc1ccc(O)cc1Cl] | C-8 |
| 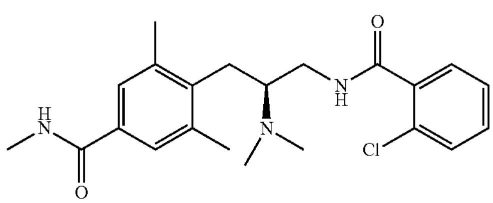 [SMILES: CNC(=O)c1cc(C)c(C[C@@H](CNC(=O)c2ccccc2Cl)N(C)C)c(C)c1] | C-10 |
| 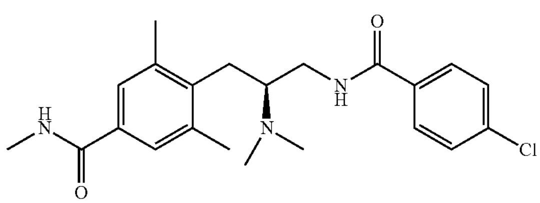 [SMILES: CNC(=O)c1cc(C)c(C[C@@H](CNC(=O)c2ccc(Cl)cc2)N(C)C)c(C)c1] | C-11 |
| 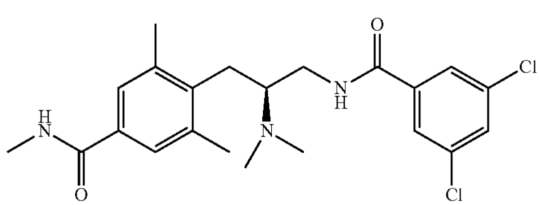 [SMILES: CNC(=O)c1cc(C)c(C[C@@H](CNC(=O)c2cc(Cl)cc(Cl)c2)N(C)C)c(C)c1] | C-12 |
| 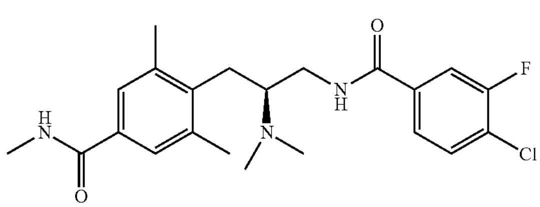 | C-13 |

TABLE 3-continued

REPRESENTATIVE COMPOUNDS

| Structure | Compd. No. |
|---|---|
| 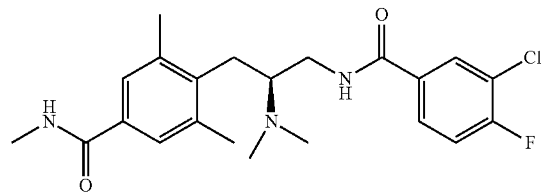 | C-14 |
| 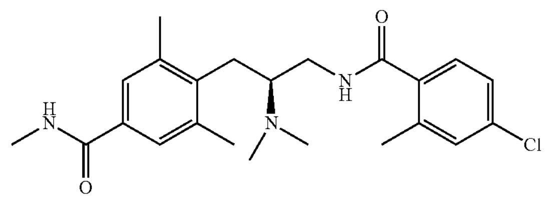 [SMILES: CNC(=O)c1cc(C)c(C[C@@H](CNC(=O)c2ccc(Cl)cc2C)N(C)C)c(C)c1] | C-15 |
| 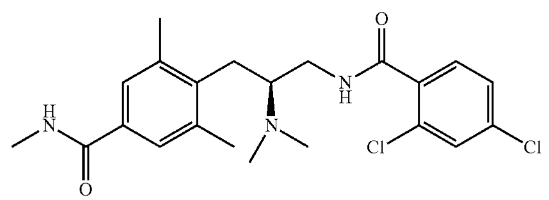 [SMILES: CNC(=O)c1cc(C)c(C[C@@H](CNC(=O)c2ccc(Cl)cc2Cl)N(C)C)c(C)c1] | C-16 |
| 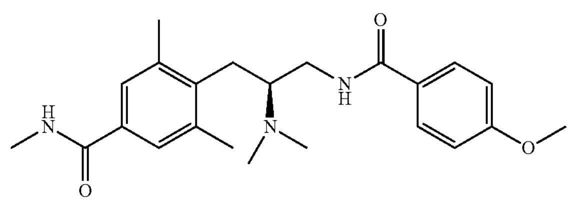 | C-17 |
| 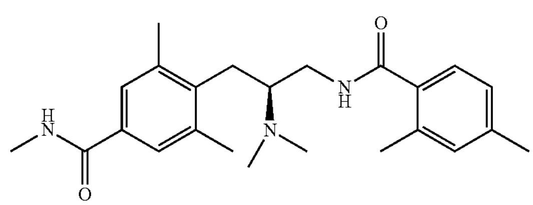 | C-18 |
| 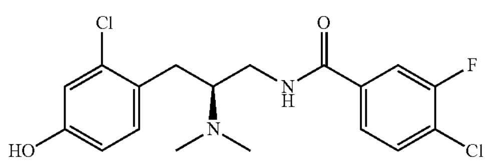 [SMILES: CN(C)[C@H](CNC(=O)c1ccc(Cl)c(F)c1)Cc1ccc(O)cc1Cl] | C-19 |
| 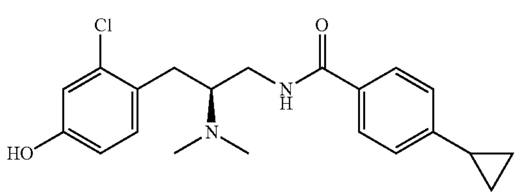 [SMILES: CN(C)[C@H](CNC(=O)c1ccc(C2CC2)cc1)Cc1ccc(O)cc1Cl] | C-20 |
| 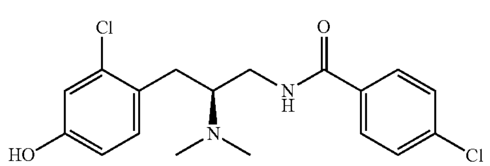 [SMILES: CN(C)[C@H](CNC(=O)c1ccc(Cl)cc1)Cc1ccc(O)cc1Cl] | C-21 |

TABLE 3-continued

REPRESENTATIVE COMPOUNDS

| Structure | Compd. No. |
|---|---|
| 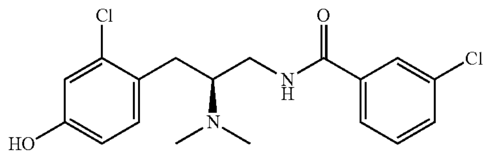 [SMILES: CN(C)[C@H](CNC(=O)c1cccc(Cl)c1)Cc1ccc(O)cc1Cl] | C-22 |
| 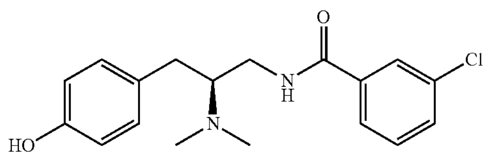 [SMILES: CN(C)[C@H](CNC(=O)c1cccc(Cl)c1)Cc1ccc(O)cc1] | C-23 |
| 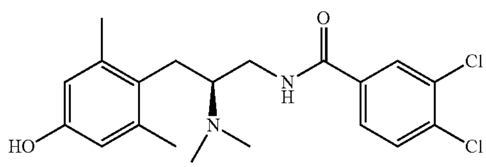 [SMILES: Cc1cc(O)cc(C)c1C[C@@H](CNC(=O)c1ccc(Cl)c(Cl)c1)N(C)C] | C-24 |
| 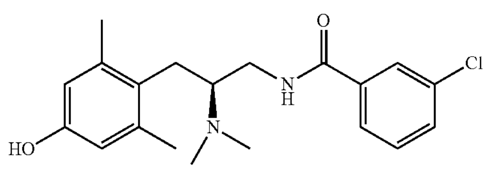 [SMILES: Cc1cc(O)cc(C)c1C[C@@H](CNC(=O)c1cccc(Cl)c1)N(C)C] | C-25 |
| 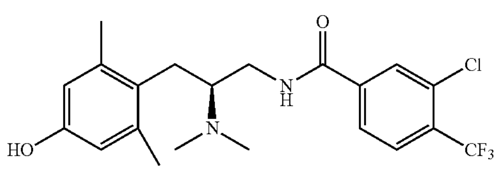 [SMILES: Cc1cc(O)cc(C)c1C[C@@H](CNC(=O)c1ccc(C(F)(F)F)c(Cl)c1)N(C)C] | C-26 |
| 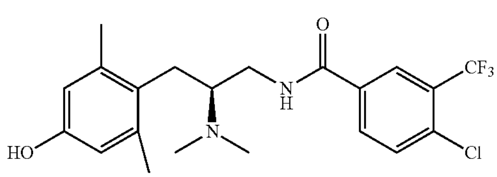 [SMILES: Cc1cc(O)cc(C)c1C[C@@H](CNC(=O)c1ccc(Cl)c(C(F)(F)F)c1)N(C)C] | C-27 |
| 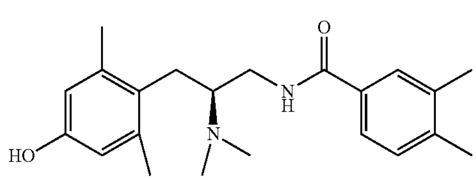 [SMILES: Cc1ccc(C(=O)NC[C@H](Cc2c(C)cc(O)cc2C)N(C)C)cc1C] | C-28 |
| 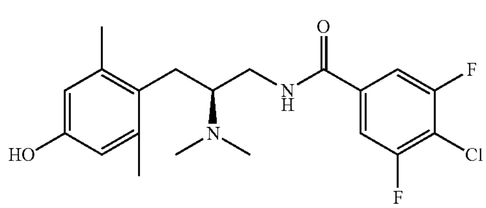 [SMILES: Cc1cc(O)cc(C)c1C[C@@H](CNC(=O)c1cc(F)c(Cl)c(F)c1)N(C)C] | C-29 |

TABLE 3-continued

REPRESENTATIVE COMPOUNDS

| Structure | Compd. No. |
|---|---|
| 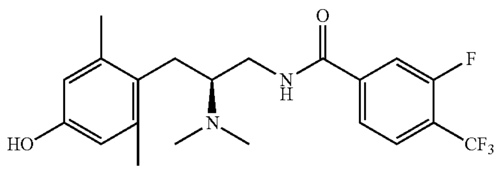 [SMILES: Cc1cc(O)cc(C)c1C[C@@H](CNC(=O)c1ccc(C(F)(F)F)c(F)c1)N(C)C] | C-30 |
| 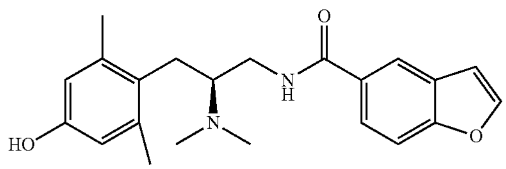 [SMILES: Cc1cc(O)cc(C)c1C[C@@H](CNC(=O)c1ccc2occc2c1)N(C)C] | C-31 |
| 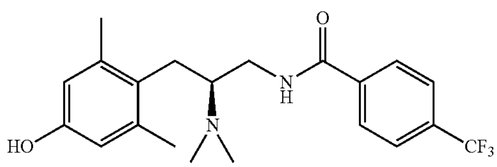 [SMILES: Cc1cc(O)cc(C)c1C[C@@H](CNC(=O)c1ccc(C(F)(F)F)cc1)N(C)C] | C-32 |
| 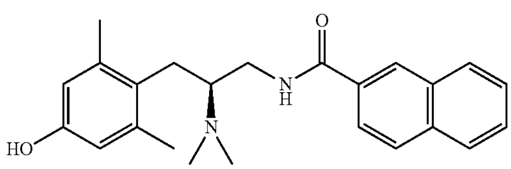 [SMILES: Cc1cc(O)cc(C)c1C[C@@H](CNC(=O)c1ccc2ccccc2c1)N(C)C] | C-33 |
| 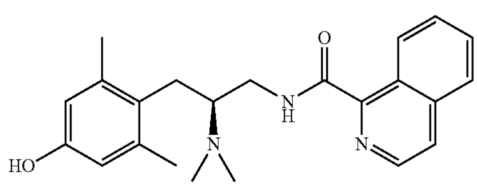 [SMILES: Cc1cc(O)cc(C)c1C[C@@H](CNC(=O)c1nccc2ccccc12)N(C)C] | C-34 |
| 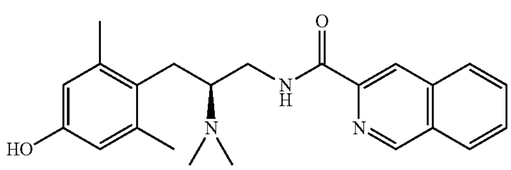 [SMILES: Cc1cc(O)cc(C)c1C[C@@H](CNC(=O)c1cc2ccccc2cn1)N(C)C] | C-35 |
| 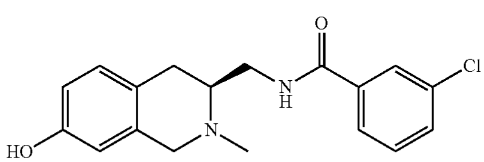 [SMILES: CN1Cc2cc(O)ccc2C[C@H]1CNC(=O)c1cccc(Cl)c1] | C-36 |
| 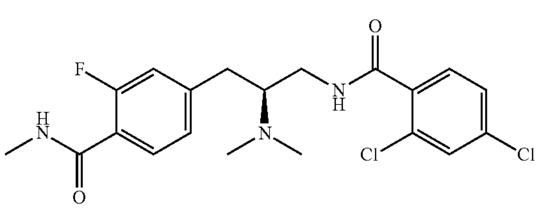 [SMILES: CNC(=O)c1ccc(C[C@@H](CNC(=O)c2ccc(Cl)cc2Cl)N(C)C)cc1F] | C-37 |

TABLE 3-continued

REPRESENTATIVE COMPOUNDS

| Structure | Compd. No. |
|---|---|
| 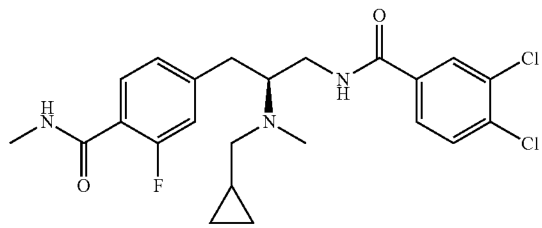 [SMILES: CNC(=O)c1ccc(C[C@@H](CNC(=O)c2ccc(Cl)c(Cl)c2)N(C)CC2CC2)cc1F] | C-38 |
| 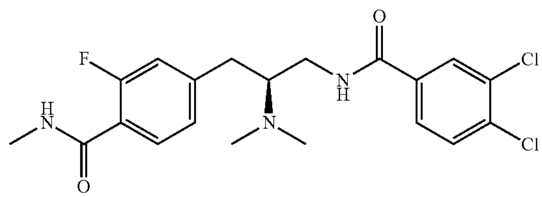 [SMILES: CNC(=O)c1ccc(C[C@@H](CNC(=O)c2ccc(Cl)c(Cl)c2)N(C)C)cc1F] | C-39 |
| 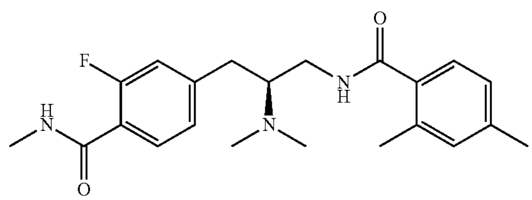 | C-40 |
| 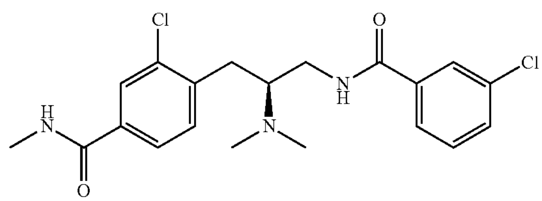 [SMILES: CNC(=O)c1ccc(C[C@@H](CNC(=O)c2cccc(Cl)c2)N(C)C)c(Cl)c1] | C-41 |
| 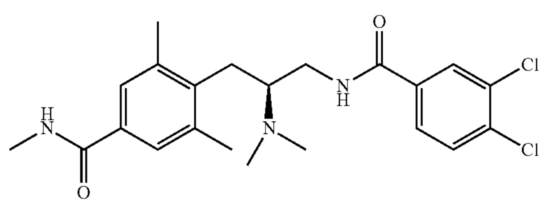 [SMILES: CNC(=O)c1cc(C)c(C[C@@H](CNC(=O)c2ccc(Cl)c(Cl)c2)N(C)C)c(C)c1] | C-42 |
| 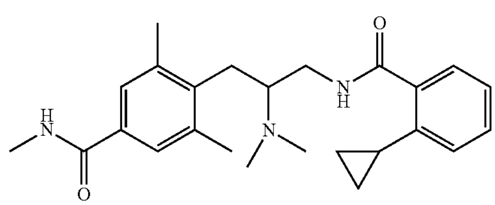 [SMILES: CNC(=O)c1cc(C)c(CC(CNC(=O)c2ccccc2C2CC2)N(C)C)c(C)c1] | C-43 |
| 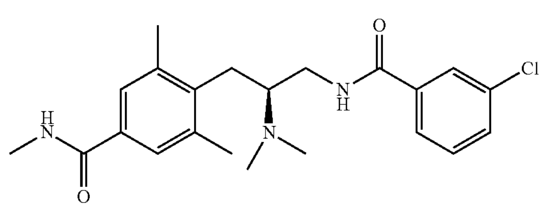 [SMILES: CNC(=O)c1cc(C)c(C[C@@H](CNC(=O)c2cccc(Cl)c2)N(C)C)c(C)c1] | C-44 |

TABLE 3-continued

REPRESENTATIVE COMPOUNDS

| Structure | Compd. No. |
|---|---|
| 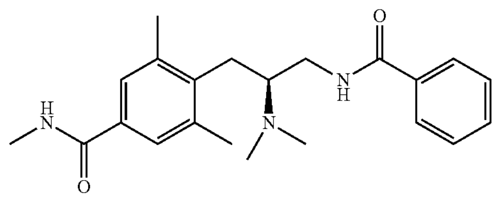 [SMILES: CNC(=O)c1cc(C)c(C[C@@H](CNC(=O)c2ccccc2)N(C)C)c(C)c1] | C-45 |
| 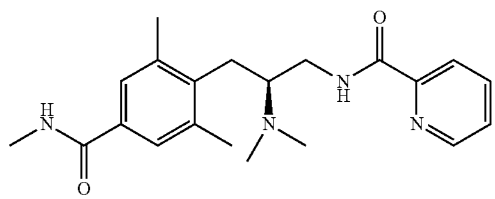 [SMILES: CNC(=O)c1cc(C)c(C[C@@H](CNC(=O)c2ccccn2)N(C)C)c(C)c1] | C-46 |
| 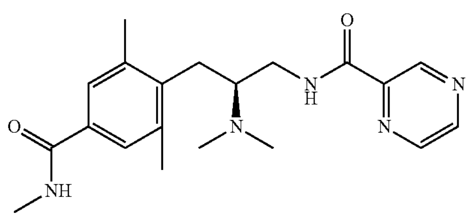 [SMILES: CNC(=O)c1cc(C)c(C[C@@H](CNC(=O)c2cnccn2)N(C)C)c(C)c1] | C-47 |
| 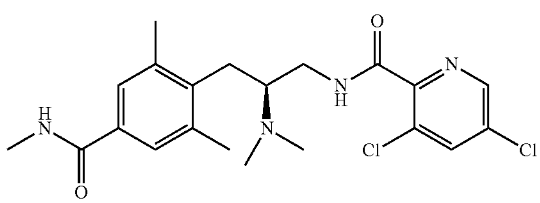 [SMILES: CNC(=O)c1cc(C)c(C[C@@H](CNC(=O)c2ncc(Cl)cc2Cl)N(C)C)c(C)c1] | C-48 |
| 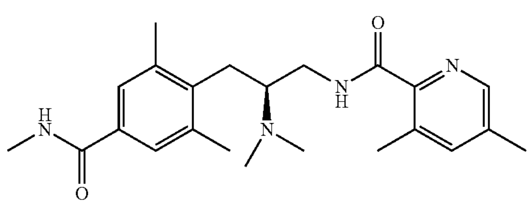 | C-49 |
| 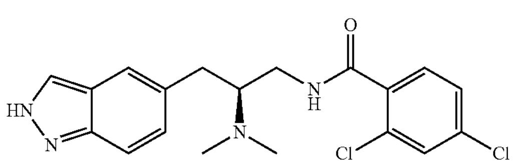 [SMILES: CN(C)[C@H](CNC(=O)c1ccc(Cl)cc1Cl)Cc1ccc2n[nH]cc2c1] | C-50 |
| 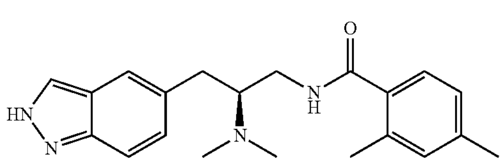 [SMILES: Cc1ccc(C(=O)NC[C@H](Cc2ccc3n[nH]cc3c2)N(C)C)c(C)c1] | C-51 |
| 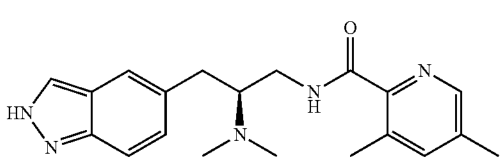 [SMILES: Cc1cnc(C(=O)NC[C@H](Cc2ccc3n[nH]cc3c2)N(C)C)c(C)c1] | C-52 |

TABLE 3-continued

REPRESENTATIVE COMPOUNDS

| Structure | Compd. No. |
|---|---|
| 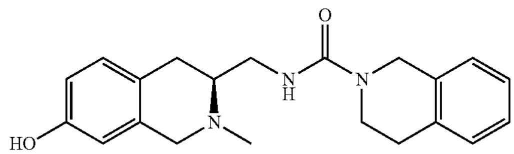 [SMILES: CN1Cc2cc(O)ccc2C[C@H]1CNC(=O)N1CCc2ccccc2C1] | C-53 |
| 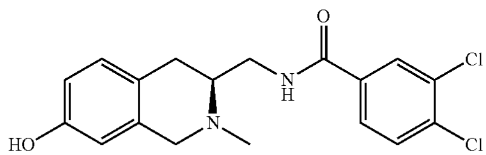 [SMILES: CN1Cc2cc(O)ccc2C[C@H]1CNC(=O)c1ccc(Cl)c(Cl)c1] | C-54 |
| 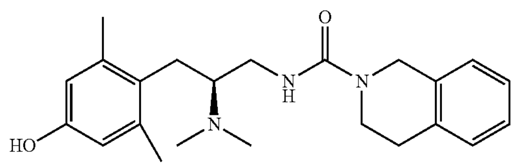 [SMILES: Cc1cc(O)cc(C)c1C[C@@H](CNC(=O)N1CCc2ccccc2C1)N(C)C] | C-55 |
| 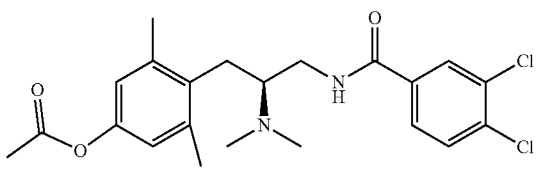 [SMILES: CC(=O)Oc1cc(C)c(C[C@@H](CNC(=O)c2ccc(Cl)c(Cl)c2)N(C)C)c(C)c1] | C-56 |
| 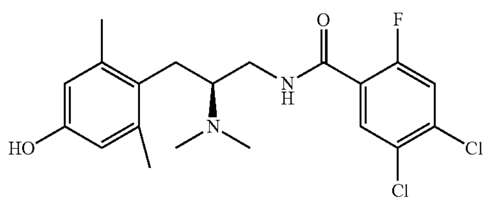 [SMILES: Cc1cc(O)cc(C)c1C[C@@H](CNC(=O)c1cc(Cl)c(Cl)cc1F)N(C)C] | C-57 |
| 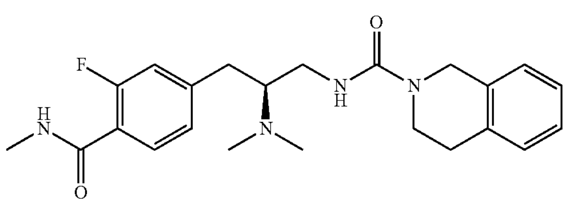 [SMILES: CNC(=O)c1ccc(C[C@@H](CNC(=O)N2CCc3ccccc3C2)N(C)C)cc1F] | C-58 |
| 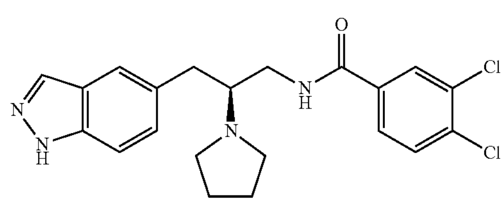 [SMILES: O=C(NC[C@H](Cc1ccc2[nH]ncc2c1)N1CCCC1)c1ccc(Cl)c(Cl)c1] | C-59 |
| 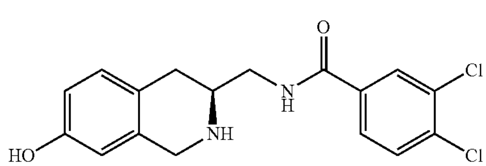 [SMILES: O=C(NC[C@@H]1Cc2ccc(O)cc2CN1)c1ccc(Cl)c(Cl)c1] | C-60 |

TABLE 3-continued

REPRESENTATIVE COMPOUNDS

| Structure | Compd. No. |
|---|---|
| 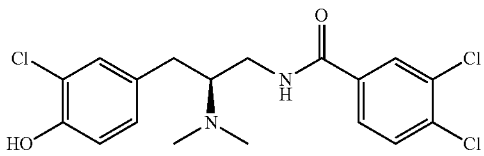 [SMILES: CN(C)[C@H](CNC(=O)c1ccc(Cl)c(Cl)c1)Cc1ccc(O)c(Cl)c1] | C-61 |
| 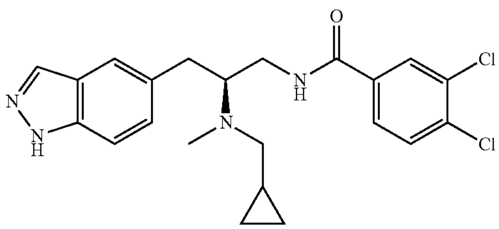 [SMILES: CN(CC1CC1)[C@H](CNC(=O)c1ccc(Cl)c(Cl)c1)Cc1ccc2[nH]ncc2c1] | C-62 |
| 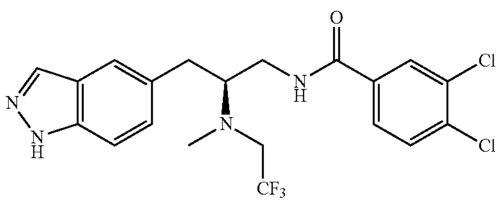 [SMILES: CN(CC(F)(F)F)[C@H](CNC(=O)c1ccc(Cl)c(Cl)c1)Cc1ccc2[nH]ncc2c1] | C-63 |
| 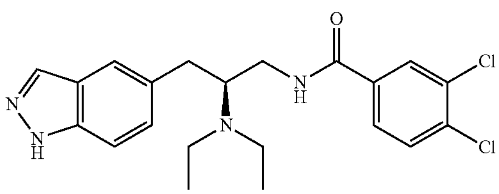 [SMILES: CCN(CC)[C@H](CNC(=O)c1ccc(Cl)c(Cl)c1)Cc1ccc2[nH]ncc2c1] | C-64 |
| 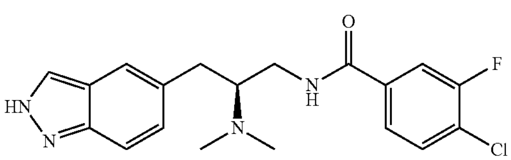 | C-65 |
| 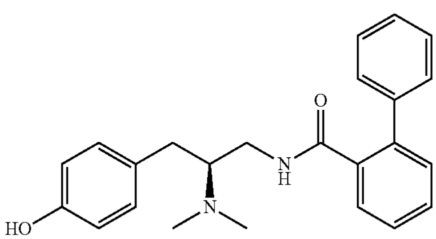 [SMILES: CN(C)[C@H](CNC(=O)c1ccccc1-c1ccccc1)Cc1ccc(O)cc1] | C-66 |
| 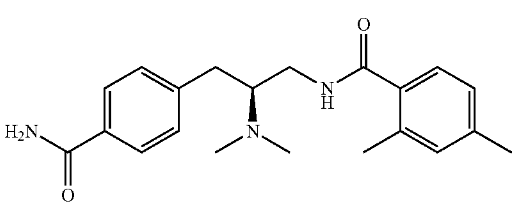 [SMILES: Cc1ccc(C(=O)NC[C@H](Cc2ccc(C(N)=O)cc2)N(C)C)c(C)c1] | C-67 |

TABLE 3-continued

REPRESENTATIVE COMPOUNDS

| Structure | Compd. No. |
|---|---|
| 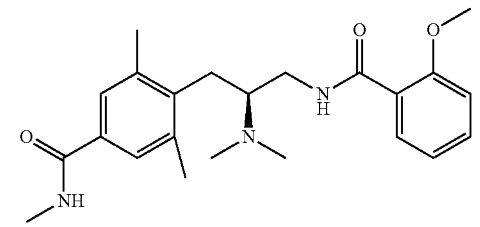 [SMILES: CNC(=O)c1cc(C)c(C[C@@H](CNC(=O)c2ccccc2OC)N(C)C)c(C)c1] | C-68 |
| 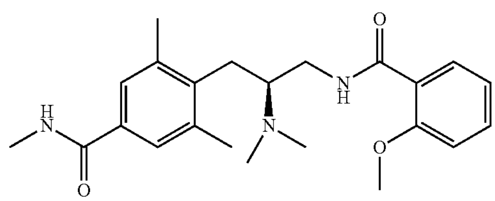 [SMILES: CNC(=O)c1cc(C)c(C[C@@H](CNC(=O)c2ccccc2OC)N(C)C)c(C)c1] | C-69 |

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the disclosure. The isomers resulting from the presence of a chiral center comprise a pair of non-superimposable isomers that are called "enantiomers." Single enantiomers of a pure compound are optically active (i.e., they are capable of rotating the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure. In other embodiments, the isolated isomer is at least 90% pure or at least 98% pure, or at least 99% pure by weight.

"Substantially enantiomerically or diasteromerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out).

A "hydrate" is a compound that exists in combination with water molecules. The combination can include water in stoichiometric quantities, such as a monohydrate or a dihydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of Formulas (I)-(X) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine 19 is longest-lived. Thus, an isotope of a compound having the structure of Formulas (I)-(X) includes, but not limited to, compounds of Formulas (I)-(X) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, *Int. J. Pharm.*, 33, 201-217, 1986) (incorporated by reference herein).

Pharmaceutically acceptable base addition salts of compounds of the disclosure include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N' dibenzylethylenediamine, chloroprocaine, choline, diethanolamine, ethylenediamine, meglumine (N-methylglucamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenyl acetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, βhydroxybutyric, salicylic, -galactaric, and galacturonic acid.

Although pharmaceutically unacceptable salts are not generally useful as medicaments, such salts may be useful, for example as intermediates in the synthesis of compounds having the structure of Formulas (I)-(XI), for example in their purification by recrystallization.

In certain embodiments, the disclosure provides a pharmaceutical composition comprising a compound of any one of Formulas (I)-(XI), or a pharmaceutically acceptable isomer, racemate, hydrate, solvate, isotope, or salt thereof, together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more of the compounds described herein, or a pharmaceutically acceptable isomer, racemate, hydrate, solvate, homolog or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in Remington: The Science and Practice of Pharmacy, 21$^{st}$ Ed., Gennaro, Ed., Lippencott Williams & Wilkins (2005) and in The United States Pharmacopeia: The National Formulary (USP 36 NF31), published in 2013.

In another embodiment, there are provided methods of making a composition of a compound described herein including formulating a compound of the disclosure with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

As used herein, the term "pharmaceutically acceptable carrier" refers to any ingredient other than the disclosed compounds, or a pharmaceutically acceptable isomer, racemate, hydrate, solvate, homolog or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the disclosure to the appropriate or desired site of action, such as oral, nasal, pulmonary, buccal, subdermal, intradermal, transdermal, or parenteral, e.g., rectal, depot, subcutaneous, intravenous, intraurethral, intramuscular, intranasal, ophthalmic solution, or an ointment, the oral route being preferred.

Dosage forms can be administered once a day, or more than once a day, such as twice or thrice daily. Alternatively, dosage forms can be administered less frequently than daily, such as every other day, or weekly, if found to be advisable by a prescribing physician. Dosing regimens include, for example, dose titration to the extent necessary or useful for the indication to be treated, thus allowing the patient's body to adapt to the treatment and/or to minimize or avoid unwanted side effects associated with the treatment. Other dosage forms include delayed or controlled-release forms. Suitable dosage regimens and/or forms include those set out, for example, in the latest edition of the *Physicians' Desk Reference*, incorporated herein by reference.

As used herein, the term "administering" or "administration" refers to providing a compound, a pharmaceutical composition comprising the same, to a subject by any acceptable means or route, including (for example) by oral, parenteral (e.g., intravenous), or topical administration.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the term "effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

In one embodiment, a method is provided of modulating an opioid receptor comprising contacting the opioid receptor with an effective amount of a compound having the structure of Formulas (I) through (XI), or a pharmaceutically acceptable isomer, racemate, hydrate, solvate, homolog, salt, or composition thereof. In another embodiment, the opioid receptor is the kappa opioid receptor (KOR), and in a further embodiment the compound is a KOR antagonist. In another embodiment, the opioid receptor is the mu opioid receptor (MOR), and in a further embodiment the compound is a MOR agonist. In another embodiment, the compound is both a KOR antagonist and a MOR agonist. In another embodiment, the method does not modulate arrestin function.

In one embodiment, a method is provided for treating pain, opioid overdose, addiction, a neuropsychiatric disorder, a sleep disorder, a gastrointestinal disorder, a skin disorder, dyspnea, autism spectrum disorder, Prader-Willi Syndrome, headache, or temporomandibular joint dysfunction, comprising administering to a subject in need thereof an effective amount of a compound of Formulas (I) through (XI), or a pharmaceutically acceptable isomer, racemate, hydrate, solvate, isotope, or salt thereof, or a pharmaceutical composition comprising the same.

In one embodiment, a method is provided of treating pain, comprising administering to a subject in need thereof an effective amount of a compound having the structure of Formulas (I) through (XI), or a pharmaceutically acceptable isomer, racemate, hydrate, solvate, homolog, salt, or composition thereof. In one embodiment, the method of treating pain does not increase the risk of respiratory depression or constipation in the subject. In one embodiment, the pain is acute pain. In one embodiment, the pain is chronic pain. In another embodiment, the pain is fibromyalgia, neuropathic pain, chronic low back pain, surgical pain, cancer pain, or severe pain.

In one embodiment, a method is provided of treating opioid overdose, comprising administering to a subject in need thereof an effective amount of a compound having the structure of Formulas (I) through (XI), or a pharmaceutically acceptable isomer, racemate, hydrate, solvate, homolog, salt, or composition thereof.

In one embodiment, a method is provided of treating addiction, comprising administering to a subject in need thereof an effective amount of a compound having the structure of Formulas (I) through (XI), or a pharmaceutically acceptable isomer, racemate, hydrate, solvate, homolog, salt, or composition thereof. In one embodiment, the addiction is opioid use disorder. In one embodiment, the method of treating addiction comprises maintenance of opioid use disorder.

In one embodiment, a method is provided of treating a neuropsychiatric disorder, comprising administering to a subject in need thereof an effective amount of a compound having the structure of Formulas (I) through (XI), or a pharmaceutically acceptable isomer, racemate, hydrate, solvate, homolog, salt, or composition thereof.

In one embodiment, the neuropsychiatric disorder is characterized by compulsive behavior. In one embodiment, the neuropsychiatric disorder characterized by compulsive behavior is obsessive compulsive disorder, trichotillomania, or skin picking. In one embodiment, the compulsive behavior is associated with a neurodegenerative disorder. In one embodiment, the neurodegenerative disorder is Huntington's disease or Parkinson's disease.

In one embodiment, the neuropsychiatric disorder is characterized by impulsive behavior. In one embodiment, the neuropsychiatric disorder characterized by impulsive behavior is addiction, pathological gambling, alcohol use disorder, nicotine addiction, sex addiction, Tourette syndrome, or kleptomania. In one embodiment, the impulsive behavior is associated with a neurodegenerative disorder. In one embodiment, the neurodegenerative disorder is frontotemporal dementia or Alzheimer's disorder.

In one embodiment, the neuropsychiatric disorder is characterized by depressive mood. In one embodiment, the neuropsychiatric disorder characterized by depressive mood is major depressive disorder, anxiety disorder, panic disorder, dysphoria, or anhedonia.

In one embodiment, the neuropsychiatric disorder is an eating disorder. In one embodiment, the eating disorder is anorexia nervosa, bulimia nervosa, binge eating disorder, or obesity.

In one embodiment, the neuropsychiatric disorder is Schizophrenia, psychosis, or bipolar disorder.

In one embodiment, a method is provided of treating a sleep disorder, comprising administering to a subject in need thereof an effective amount of a compound having the structure of Formulas (I) through (XI), or a pharmaceutically acceptable isomer, racemate, hydrate, solvate, homolog, salt, or composition thereof. In one embodiment, the sleep disorder is sleep disruption. In one embodiment, the sleep disruption is associated with a neurodegenerative disorder. In one embodiment, the neurodegenerative disorder is supranuclear palsy.

In one embodiment, a method is provided of treating a gastrointestinal disorder, comprising administering to a subject in need thereof an effective amount of a compound having the structure of Formulas (I) through (XI), or a pharmaceutically acceptable isomer, racemate, hydrate, solvate, homolog, salt, or composition thereof. In one embodiment, the gastrointestinal disorder is constipation, diarrhea, irritable bowel syndrome, inflammatory bowel disease, or Crohn's disease.

In one embodiment, a method is provided of treating a skin disorder, comprising administering to a subject in need thereof an effective amount of a compound having the structure of Formulas (I) through (XI), or a pharmaceutically acceptable isomer, racemate, hydrate, solvate, homolog, salt, or composition thereof. In one embodiment, the skin disorder is itching or urticaria.

In one embodiment, a method is provided of treating dyspnea, comprising administering to a subject in need thereof an effective amount of a compound having the structure of Formulas (I) through (XI), or a pharmaceutically acceptable isomer, racemate, hydrate, solvate, homolog, salt, or composition thereof.

In one embodiment, a method is provided of treating autism spectrum disorder, comprising administering to a subject in need thereof an effective amount of a compound having the structure of Formulas (I) through (XI), or a pharmaceutically acceptable isomer, racemate, hydrate, solvate, homolog, salt, or composition thereof.

In one embodiment, a method is provided of treating Prader-Willi Syndrome, comprising administering to a subject in need thereof an effective amount of a compound having the structure of Formulas (I) through (XI), or a pharmaceutically acceptable isomer, racemate, hydrate, solvate, homolog, salt, or composition thereof.

In one embodiment, a method is provided of treating headache, comprising administering to a subject in need thereof an effective amount of a compound having the structure of Formulas (I) through (XI), or a pharmaceutically acceptable isomer, racemate, hydrate, solvate, homolog, salt, or composition thereof. In one embodiment, the headache is migraine.

In one embodiment, a method is provided of treating temporomandibular joint dysfunction, comprising administering to a subject in need thereof an effective amount of a compound having the structure of Formulas (I) through (XI), or a pharmaceutically acceptable isomer, racemate, hydrate, solvate, homolog, salt, or composition thereof.

Compounds having the structure of Formulas (I) through (XI) can be synthesized using standard synthetic techniques known to those of skill in the art. For examples, compounds of the present disclosure can be synthesized using the general synthetic procedures set forth in Schemes 1-2.

To this end, the reactions, processes and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

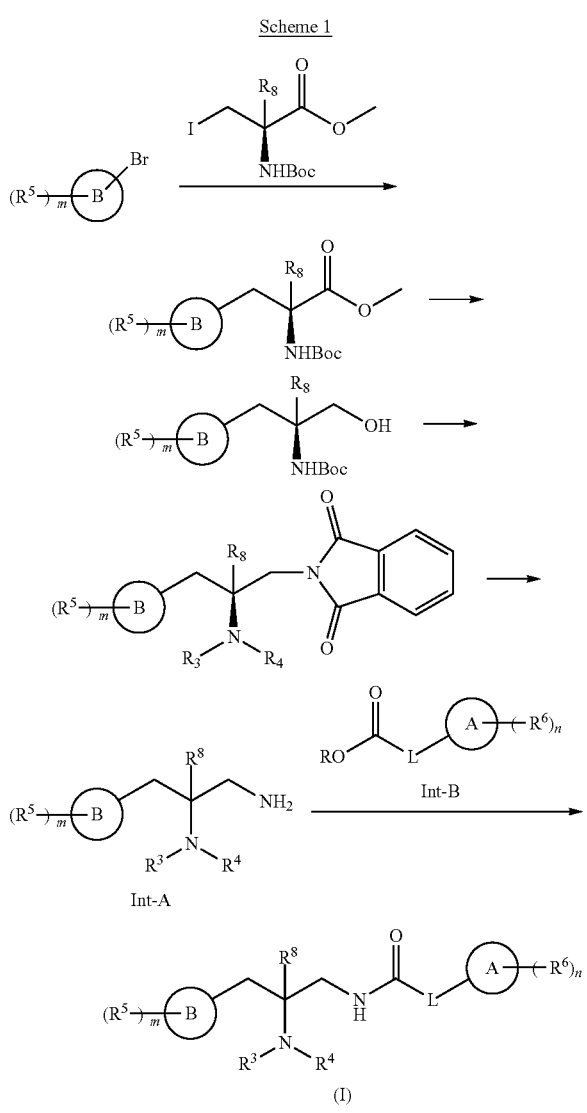

Scheme 1

Scheme 2

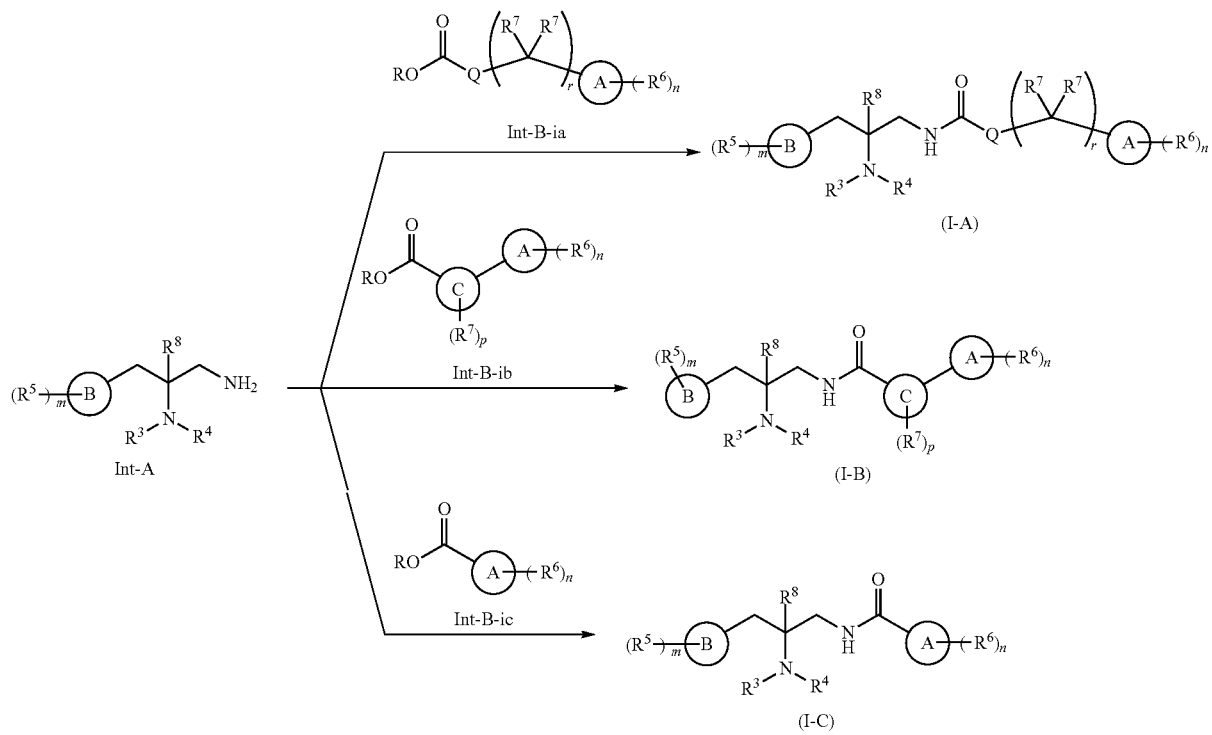

EXAMPLES

The invention is further illustrated by the following examples. The examples below are non-limiting are merely representative of various aspects of the invention. Solid and dotted wedges within the structures herein disclosed illustrate relative stereochemistry, with absolute stereochemistry depicted only when specifically stated or delineated.

General Methods

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to a person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography or reverse phase column chromatography, using prepacked silica gel cartridges. In some cases, the compounds may be purified by preparative HPLC using prepacked silica gel cartridges, e.g. RediSep® $R_f$ and eluents such as gradients of 0-100% ethyl acetate in hexanes or 0-100% of 10% MeOH in $CH_2Cl_2$.

Purification methods as described herein may provide compounds of the present disclosure which possess a sufficiently basic or acidic functionality in the form of a salt, such as, in the case of a compound of the present disclosure which is sufficiently basic, a trifluoroacetate or formate salt, or, in the case of a compound of the present disclosure which is sufficiently acidic, an ammonium salt. A salt of this type can either be transformed into its free base or free acid form, respectively, by various methods known to a person skilled in the art, or be used as salts in subsequent biological assays. It is to be understood that the specific form of a compound of the present disclosure as isolated and as described herein is not necessarily the only form in which said compound can be applied to a biological assay in order to quantify the specific biological activity.

All the starting materials and reagents are commercially available and were used as is. $^1$H Nuclear magnetic resonance (NMR) spectroscopy was carried out using a Bruker Avance III instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad. Preparative HPLC purification was performed by reverse phase HPLC using Agilent Technologies 1200 Infinity Series or an equivalent HPLC system such as Teledyne ISCO CombiFlash $R_f$.

Chemical names were generated using the ChemDraw naming software (Version 17.0.0.206) by PerkinElmer Informatics, Inc. In some cases, generally accepted names of commercially available reagents were used in place of names generated by the naming software.

Abbreviations

The following abbreviations are used in the examples, while other abbreviations have their customary meaning in the art:

BOC: tert-butoxycarbonyl protecting group
DIAD: Diisopropyl azodicarboxylate
EDCl: 1-ethyl-3-(3-dimethylaminopropyl)carbodiimide hydrochloride
EtOH: Ethanol
EtOC(O)Cl Ethyl chloroformate
h hour(s)
HOBt: Hydroxybenzotriazole
KO'Bu: Potassium t-butoxide
l: Liter
LCMS: liquid chromatography-mass spectrometry
M: Molar
MeOH: Methanol
min: Minute(s)
μl: Microliter
ml: Millliliter
$N_2$: Nitrogen
$N_2H_4$: Hydrazine monohydrate
$NaBH_4$: Sodium borohydride
$N_2CHCO_2Et$ ethyl diazoacetate
NMR: nuclear magnetic resonance spectroscopy
$Pd_2(dba)_3$: Tris(dibenzylideneacetone)dipalladium(0)
$PPh_3$: Triphenylphosphine
ppm: parts per million
$Rh_2(OAc)_4$ Rhodium (II) acetate dimer
rt: Room temperature
Rt: Retention time
sat.: Saturated
Sphos: 2-dicyclohexylphosphino-2',6'-dimethoxybiphenyl
TEA: Triethylamine
THF: Tetrahydrofuran Analytical LC-MS Methods Analytical Method A: Column: Eclipse Plus C18 4.6×3.5 μm; eluent A: 0.1% TFA in $H_2O$; eluent B: 0.1% TFA in $CH_3CN$; gradient: 20-100% over 4 minutes; flow: 1.5 mL/min; injection volume 1-5 μL; temperature: 23° C.; UV scan: 220 and 250 nm; signal settings—scan positive mode.

Preparative HPLC

Preparative Method A: Instrument: Agilent Technologies 1200 Infinity Series Column: Gemini 5 μm NX-C18 110 Å, 250×21.2 mm; eluent A: 0.1% TFA in $H_2O$, eluent B: 0.1% TFA in $CH_3CN$; gradient: 10-100%; flow: 20 mL/min; injection volume 0.5-2 mL; temperature: 23° C.; UV scan: 254 and 220 nm.

A. Synthesis of Compounds Having the Structure of Formula (I-A)

Representative Compounds having the structure of Formula (I-A) can be synthesized by using the general synthetic procedures set forth in Schemes A1-A5.

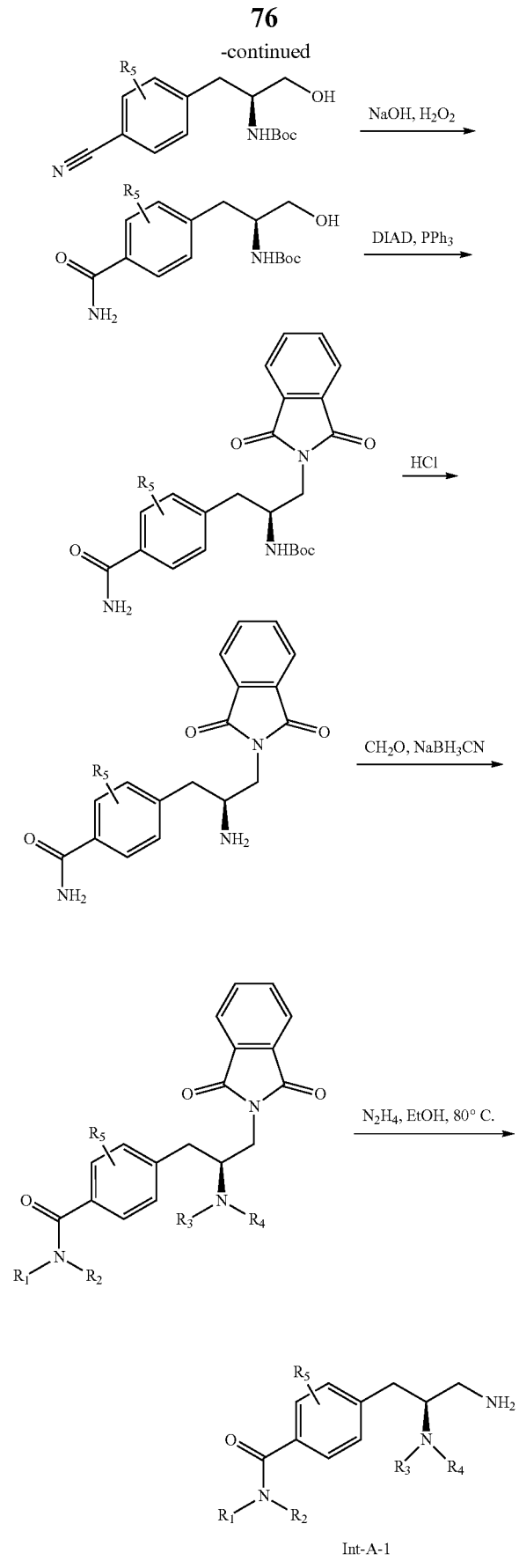

Scheme A2: Synthesis of Int-B-1
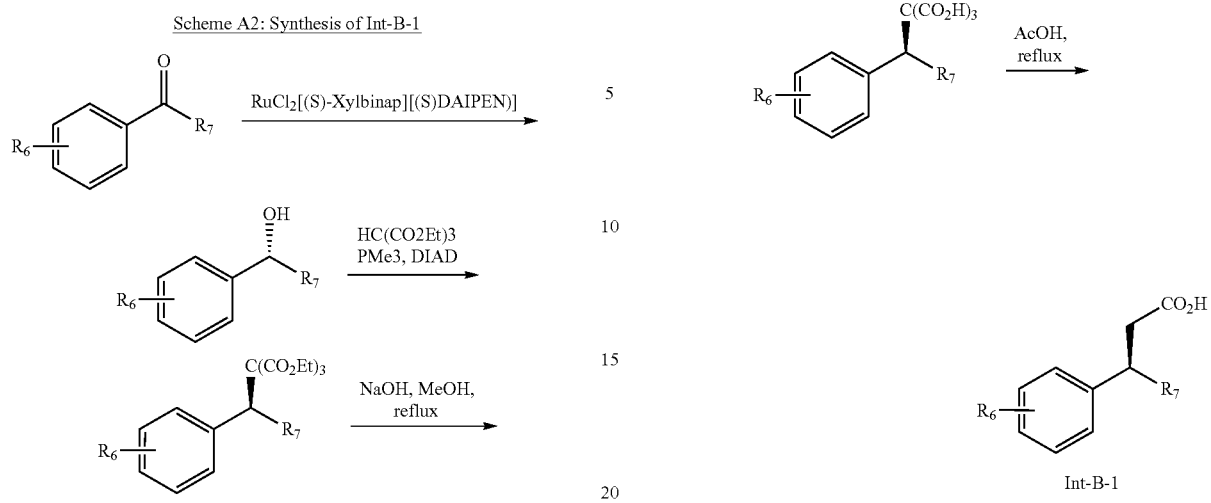
Scheme A3: Synthesis of Int-B-2
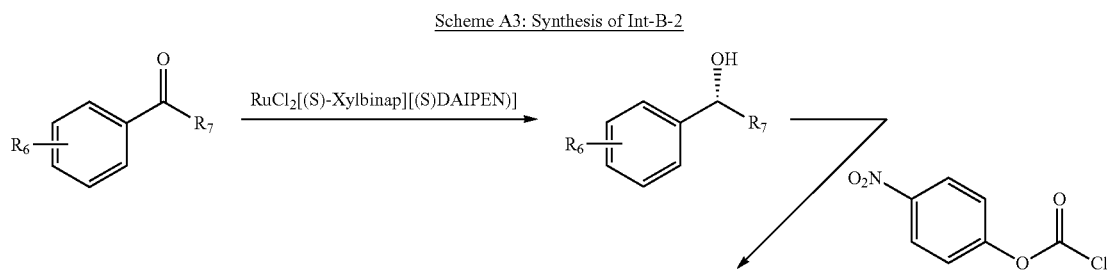
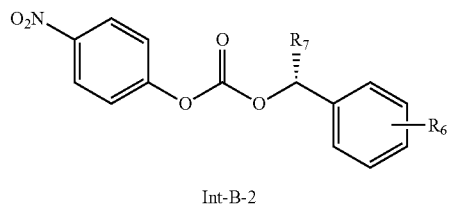
Int-B-2
Scheme A4: Synthesis of Int-B-3
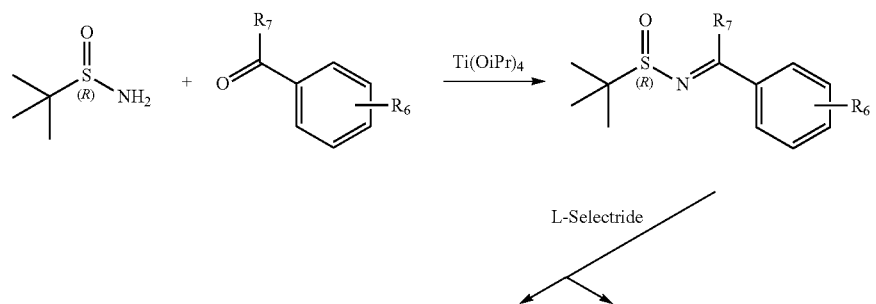

79 80
-continued
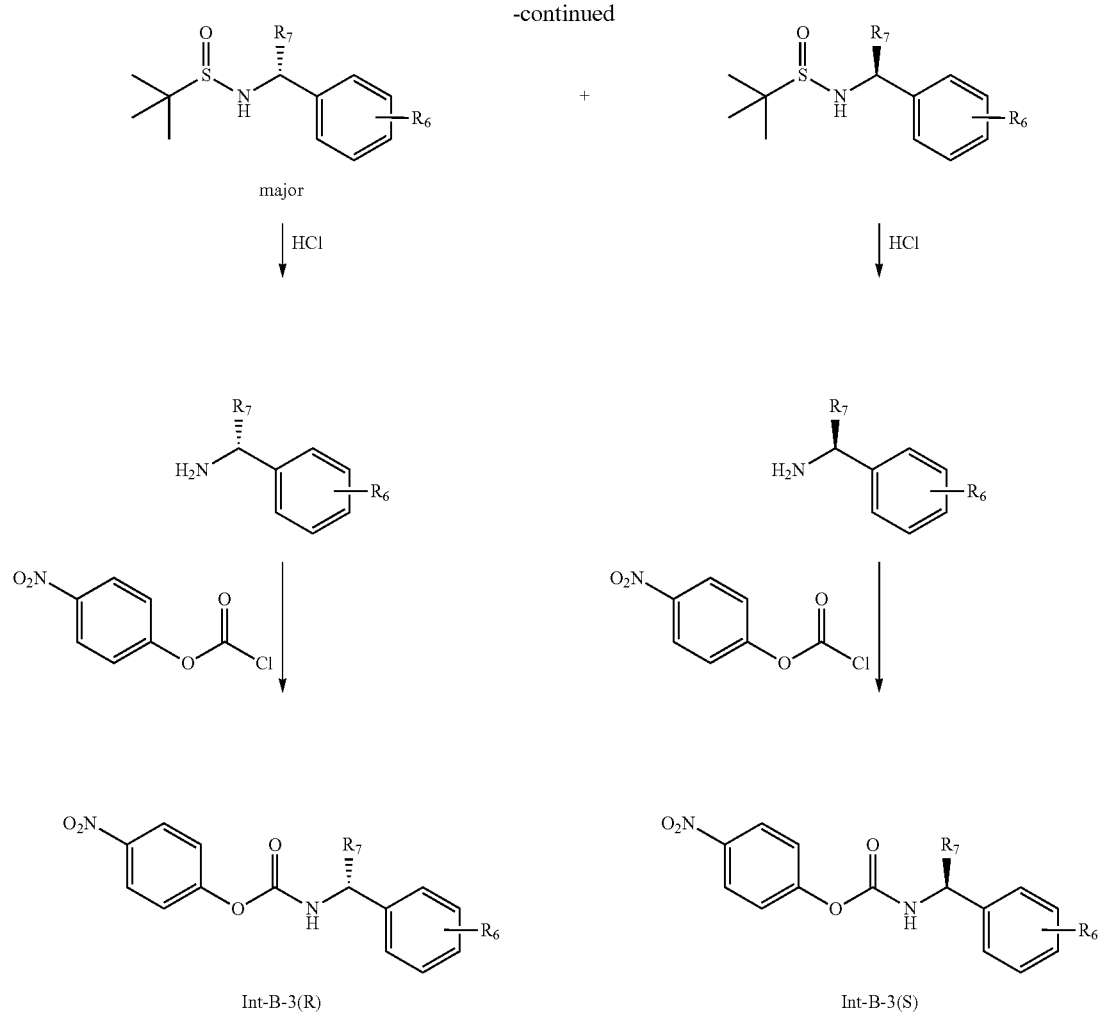
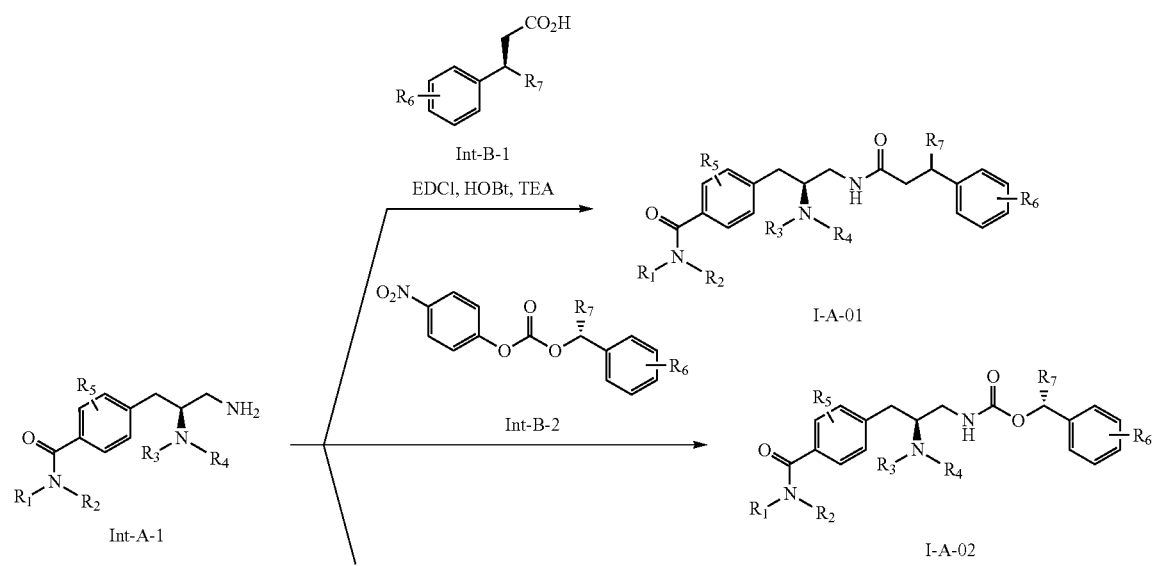
Scheme A5: Synthesis of Compounds I-A-01, I-A-02, and I-A-03

-continued

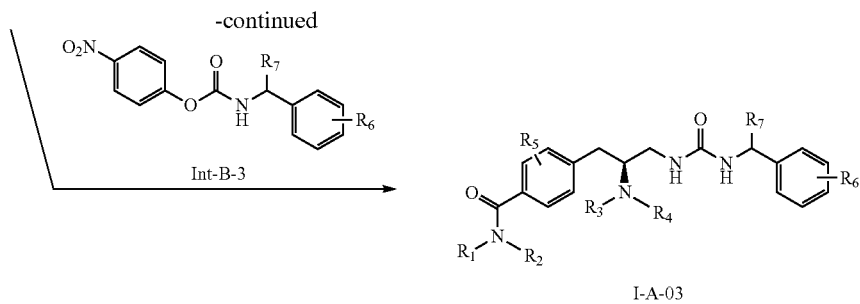

Int-B-3

I-A-03

Example A1

A-1

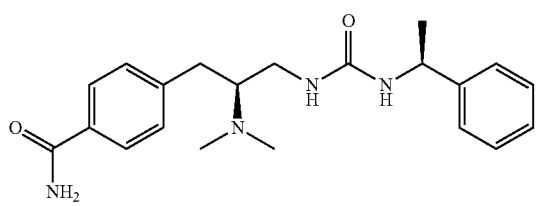

Synthesis of 4-((S)-2-(dimethylamino)-3-(3-((S)-1-phenylethyl)ureido)propyl) benzamide (Compound A-1)

Step 1: Synthesis of tert-butyl (S)-(1-amino-3-(4-bromophenyl)-1-oxopropan-2-yl)carbamate (A-1b)

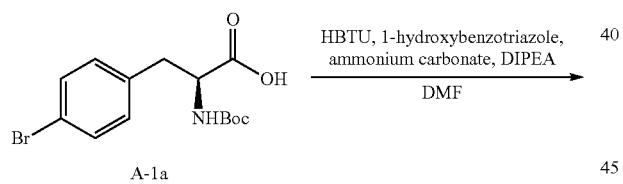

14.8 grams of the starting Boc-protected amino acid (A-1a) (1.00 equiv., 43.0 mmol), 24.5 grams of HBTU (1.50 equiv., 64.5 mmol), and 6.58 grams of 1-hydroxybenzotriazole (1.00 equiv., 43.0 mmol) were dissolved in 50 mL of DMF (6.76 volEquiv.). To this reaction mixture, 22.5 mL of N,N-diisopropylethylamine (3.00 equiv., 129 mmol) was added. Next, 20.7 grams of ammonium carbonate (5.00 Equiv., 215 mmol) was added to the reaction mixture. Finally, another 50 mL of DMF was added and the reaction mixture was allowed to continue overnight. Diethyl ether was added, and a solid formed that blocked the separatory funnel. The solution was transferred to another flask where it was concentrated, diluted with ethyl acetate (500 mL), and washed with water (5×300 mL), saturated ammonium chloride (1×300 mL), and brine (1×300 mL). The organic layer was dried over sodium sulfate and concentrated. The resulting product (A-1b) was evaluated using TLC with a mobile phase of 20:80 MeOH:DCM. This step yielded 11 g of product (74.5% yield).

Step 2: Synthesis of (S)-2-amino-3-(4-bromophenyl)propenamide (A-1c)

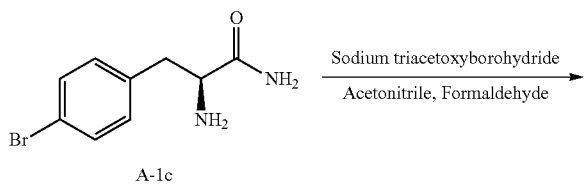

To a solution of starting material (A-1b) 11.0 grams (1.00 equiv., 32.0 mmol) in 66.0 mL of THF (6.0 volEquiv.) was added 48.1 mL of 4M HCl in dioxane (6.00 equiv., 192 mmol). Solvent was evaporated under reduced pressure and the resulting product was dissolved in ether and triturated. This reaction yielded 7 grams of product (A-1c) (89.8% yield). (M+H=243.1)

Step 3: Synthesis of (S)-3-(4-bromophenyl)-2-(dimethylamino)propenamide (A-1d)

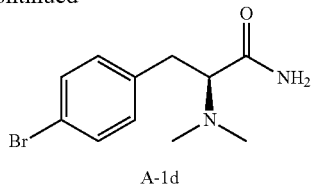

A solution of starting material (A-1c) 3.00 grams (1 equiv., 12.3 mmol) in 63.0 mL of acetonitrile (21.0 volEquiv.) was cooled to 0° C. To this reaction mixture 6.34 mL of formaldehyde (2.11 volEquiv) and 6.54 grams of sodium triacetoxyborohydride (2.5 equiv., 30.9 mmol) was added slowly. The residue was dissolved in 10 mL of isopropanol and treated with 4M HCl in dioxane. The resulting solution was then concentrated and triturated with diethyl ether. The resulting product was dried under a vacuum yielding 3.2 grams of (A-1d) as an off white solid (95.6% yield). (M+H=271.2)

Step 4: Synthesis of (S)-3-(4-bromophenyl)-N2,N2-dimethylpropane-1,2-diamine Dihydrochloride (A-1f)

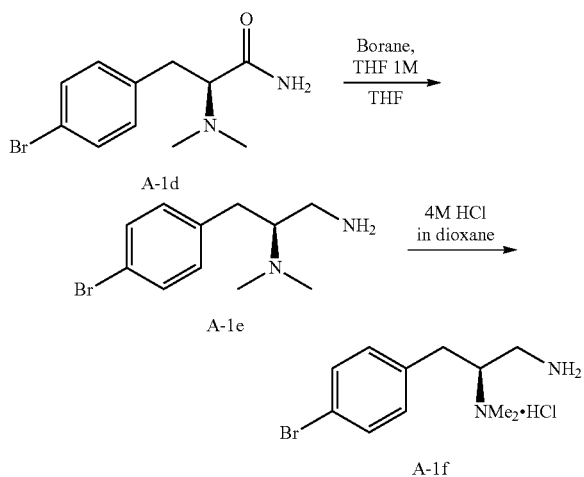

To a solution of starting material (A-1d) 3.10 grams (1.00 equiv., 11.4 mmol) in 28.0 mL of THF (9.03 vol. equiv.) was added 68.6 mL of 1M borane in THF (6.00 equiv., 68.6 mmol). After the reaction reached completion it was quenched with 50 mL of MeOH. The solvent was then removed under vacuum and the resulting residue dissolved in isopropanol. Next, 6.0 mL of 4M HCl in dioxane was added (22.8 mmol). The resulting solution was diluted with ether and a solid crashed out. The resulting solid was filtered yielding 1.8 grams of product (A-1f) (61.2% yield). (M+H=257.2)

Step 5: Synthesis of tert-butyl (S)-(3-(4-bromophenyl)-2-(dimethylamino)propyl)carbamate (A-1g)

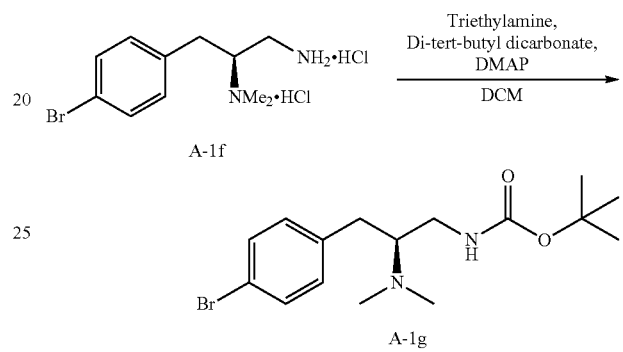

To a solution of starting material (A-1f), 2.00 grams (1.00 equiv., 6.06 mmol) in 10 mL of DCM (5.00 volEquiv.) was added 2.53 mL of Triethylamine (3.00 equiv., 18.2 mmol), 1.39 grams di-tert-butyl-dicarbonate (1.05 equiv., 6.36 mmol), and 222 mg of DMAP (0.30 equiv., 1.82 mmol). The pH of the reaction mixture was adjusted to 7 using 1M HCl. The resulting solution was extracted using DCM (3×20 mL). The organic extracts were dried over anhydrous sodium sulfate, filtered and concentrated under vacuum to give a colorless oil. The resultant crude product was purified via column chromatography eluting with 10% MeOH in DCM yielding 1.2 grams of product (A-1g) (55.4% yield). $^1$H NMR (300 MHz, CHLOROFORM-d) δ=7.39-7.36 (d, 2H), 7.01-6.98 (d, J=8.28 Hz, 2H), 2.30 (s, 6H), 1.40 (s, 9H).

Step 6: Synthesis of tert-butyl (S)-(3-(4-cyanophenyl)-2-(dimethylamino)propyl)carbamate (A-1h)

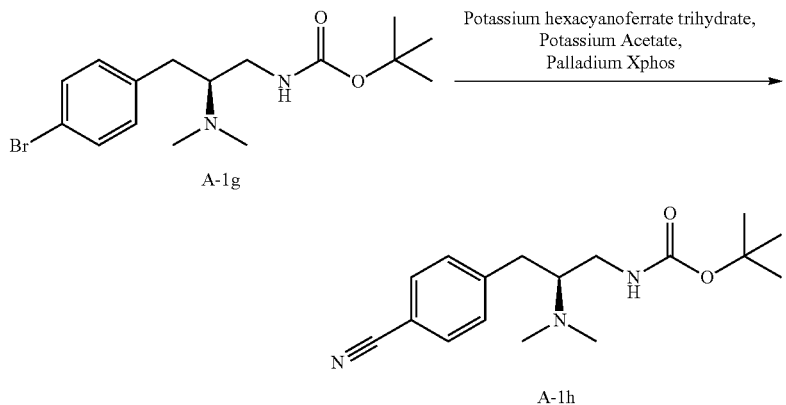

In a dry flask backfilled with Argon, 900 mg of starting material (A-1g) (1.00 equiv., 2.52 mmol), 396 mg of Palladium Xphos (0.20 equiv., 503 μmol), and 532 mg of Potassium hexacyanoferrate trihydrate (0.5 equiv., 1.26 mmol) were added. Next, 6.3 mL of dioxane was added. Then, 6.3 mL of 0.05M solution of Potassium acetate (0.125 equiv., 315 μmol) was added. The reaction mixture was then stirred at reflux for 6 hours. The reaction was then quenched with ethyl acetate and then washed with brine. The blue colored dye was discarded and the resulting product purified via column chromatography eluting with DCM:MeOH 9:1 yielding 821 mg of product (A-1h). (M+H=304.3)

Step 7: Synthesis of (S)-4-(3-amino-2-(dimethylamino)propyl)benzonitrile Dihydrochloride (A-1i)

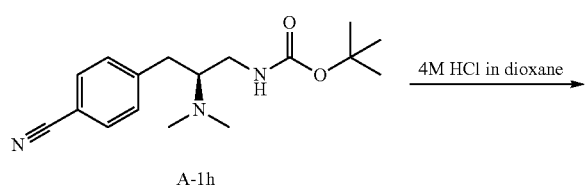

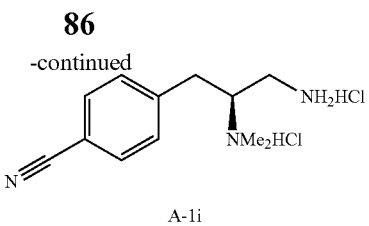

2.71 mL of 4M HCl in dioxane (4.00 equiv., 10.8 mmol) was added to 821 mg of starting material (A-1h) (1.00 equiv., 2.71 mmol). The reaction was stirred overnight. The next afternoon LCMS showed the presence of starting material in the reaction mixture (likely due to do poor stirring conditions). 1 mL of HCl in dioxane (1.48 equiv., 4.00 mmol) was added and the reaction was allowed to stir for another two hours. The reaction mixture was washed with ether and decanted three times. The solvent was then evaporated under vacuum yielding 826 mg of product. The product (A-1i) was used for the next step without further purification. (M+H=204.3)

Step 8: Synthesis of 1-((S)-3-(4-cyanophenyl)-2-(dimethylamino)propyl)-3-((S)-1-phenylethyl)urea (A-1k)

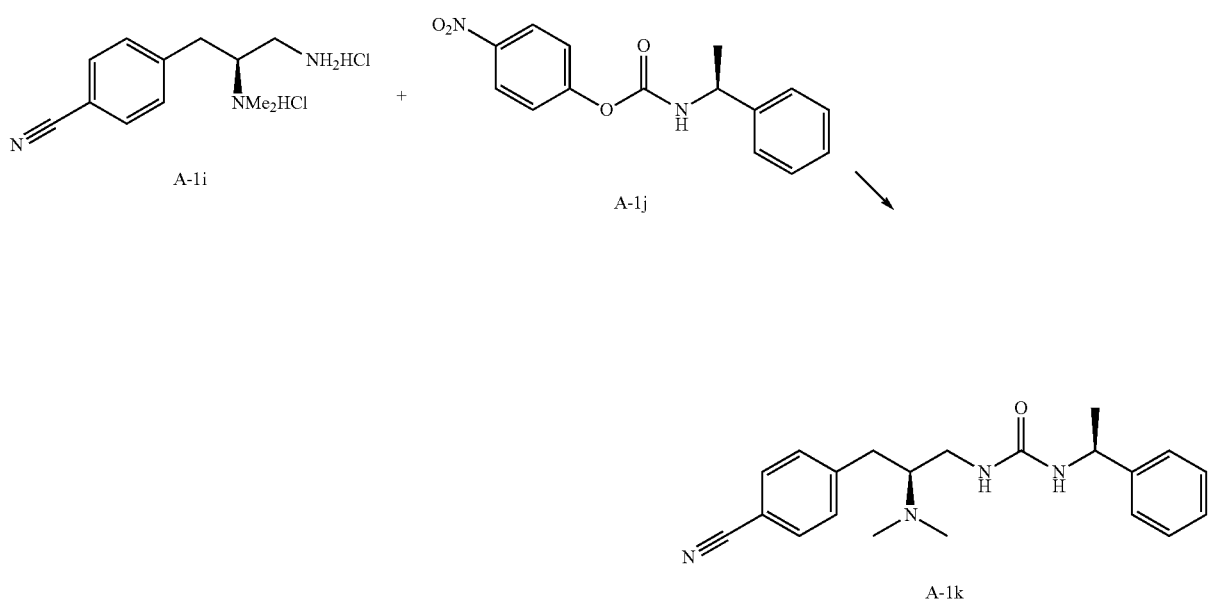

(S)-4-(3-amino-2-(dimethylamino)propyl)benzonitrile dihydrochloride (A-1i) (225 mg, 0.815 mmol, 1 eq.) was dissolved in acetonitrile (10 mL) followed by triethyl amine (0.454 mL, 3.26 mmol, 4 eq.) was added. The reaction mixture was heated at 60° C. and solution of 4-nitrophenyl (S)-(1-phenylethyl)carbamate (A-1j) (0.233 g, 0.815 mmol, 1 eq) dissolved in acetonitrile (3 mL) was added. The reaction was stirred at 60° C. for 2 h. The reaction mixture was evaporated and diluted with ethyl acetate. The solid was filtered off and the organic layer was washed with carbonate buffer (3×5 mL), brine (10 mL), dried with $Na_2SO_4$ and concentrated to get crude. The crude was purified using DCM and methanol to yield (A-1k) as a yellow solid (0.088 g, 31%, GA-00478). (M+H=351.2) $^1$H NMR (300 MHz, METHANOL-$d_4$) δ=7.60 (d, J=8.3 Hz, 2H), 7.37 (d, J=8.2 Hz, 2H), 7.32-7.25 (m, 4H), 7.23-7.16 (m, 1H), 4.73 (q, J=6.9 Hz, 1H), 3.20-2.93 (m, 3H), 2.91-2.81 (m, 1H), 2.52 (dd, J=8.7, 13.4 Hz, 1H), 2.33 (s, 6H), 1.37 (d, J=7.0 Hz, 3H).

Step 9: Synthesis of 4-((S)-2-(dimethylamino)-3-(3-((S)-1-phenylethyl)ureido) propyl)benzamide (Compound A-1)

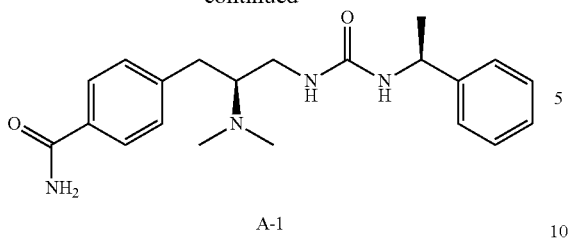

A-1

1-((S)-3-(4-cyanophenyl)-2-(dimethylamino)propyl)-3-((S)-1-phenylethyl)urea (A-1k) (0.04 g, 0.114 mmol) was dissolved in methanol/water (0.4 ml, 5:1) and cooled to 0° C. K₂CO₃ (0.0789 g, 0.571 mmol, 5 eq.) was added to the reaction mixture followed by H₂O₂ (0.089 mL, 30%, 1.14 mmol, 10 eq.) was added dropwise. The reaction mixture was stirred for 10 minutes. The reaction mixture was diluted with ethyl acetate and water. The organic layer was separated and washed with water, brine, dried over Na₂SO₄ and concentrated to get crude. The crude was purified using DCM and methanol to yield Compound A-1 (5 mg, 12%). (M+H=369.3) $^1$H NMR (300 MHz, METHANOL-d₄) δ=7.79 (d, J=8.4 Hz, 2H), 7.34-7.25 (m, 6H), 7.24-7.16 (m, 1H), 4.73 (q, J=6.9 Hz, 1H), 3.21-2.87 (m, 4H), 2.52 (dd, J=8.9, 13.0 Hz, 1H), 2.38 (s, 6H), 1.37 (d, J=7.0 Hz, 3H)

Example A2

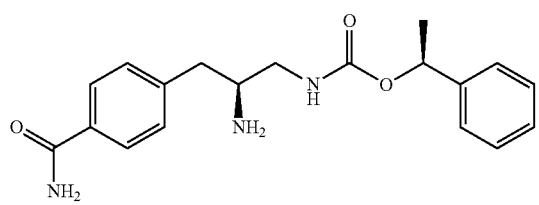

A-2

Synthesis of (S)-1-phenylethyl ((S)-2-amino-3-(4-carbamoylphenyl)propyl)carbamate (Compound A-2)

Step 1: Synthesis of tert-butyl (S)-(1-amino-3-(4-carbamoylphenyl)propan-2-yl) carbamate Intermediate (A-2g)

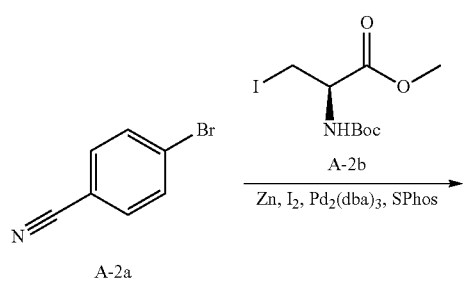

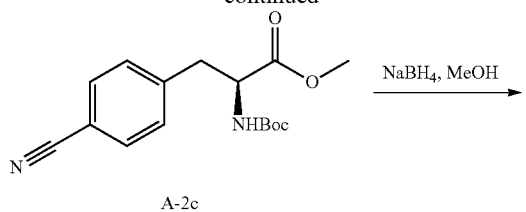

A-2c

NaBH₄, MeOH →


A-2d

NaOH, H₂O₂ →

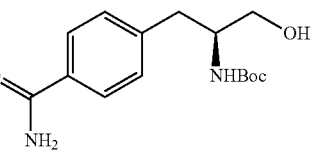

A-2e

DIAD, PPh₃, phthalimid →

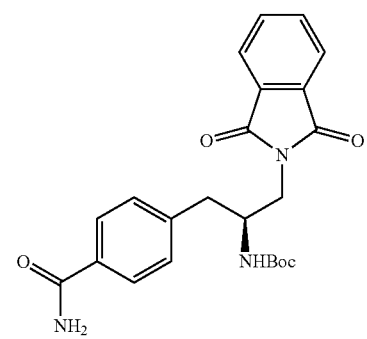

A-2f

N₂H₄, EtOH →

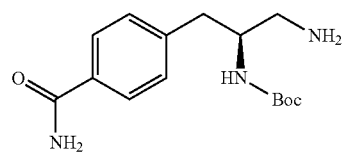

A-2g

Step 2: Synthesis of tert-butyl ((S)-1-phenylethyl) ((S)-3-(4-carbamoylphenyl)propane-1,2-diyl)dicarbamate (A-2i)

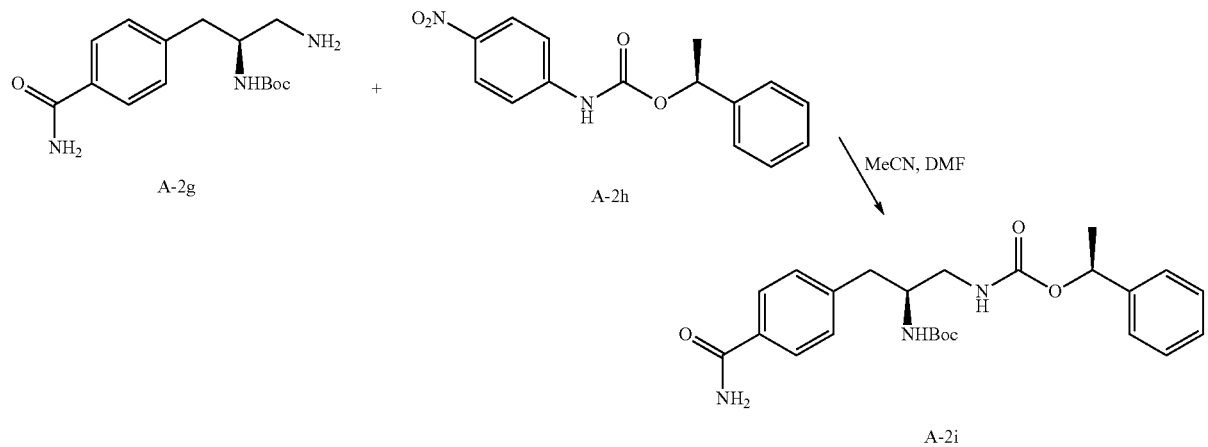

To a stirred solution of tert-butyl (S)-(1-amino-3-(4-carbamoylphenyl)propan-2-yl)carbamate (A-2g) (190 mg), in anhydrous acetonitrile (5 mL) and DMF (3 mL) was added (S)-4-nitrophenyl (1-phenylethyl) carbonate (A-2h) (200 mg) (prepared similarly by using the previous procedures: Ronald G. Sherrill, et al, J. Org. Chem. 1995, 60, 730; Miriam Crowe, et al, WO2011054844). The reaction mixture was stirred at rt overnight and then concentrated in vacuo. The residue was purified by flash column chromatography over silica gel (100% EtOAc) to afford (A-2i) as a white solid (210 mg, 73%). LC-MS: 464.2 [M+Na]$^+$; $^1$H NMR (400 MHz, CDCl$_3$) δ 7.73 (d, 2H, J=8.2 Hz), 7.40-7.25 (m, 7H), 6.06 (br s, 1H), 5.78 (q, 1H, J=6.5 Hz), 5.60 (br s, 1H), 5.03 (t, 1H, J=5.8 Hz), 4.77 (d, 1H, J=7.6 Hz), 3.90 (m, 1H), 3.23 (m, 2H), 2.87 (m, 1H), 2.79 (dd, 1H, J=13.6, 6.9 Hz), 1.53 (d, 3H, J=6.5 Hz), 1.40 (s, 9H).

Step 3: Synthesis of (S)-1-phenylethyl ((S)-2-amino-3-(4-carbamoylphenyl)propyl)carbamate (Compound A-2)

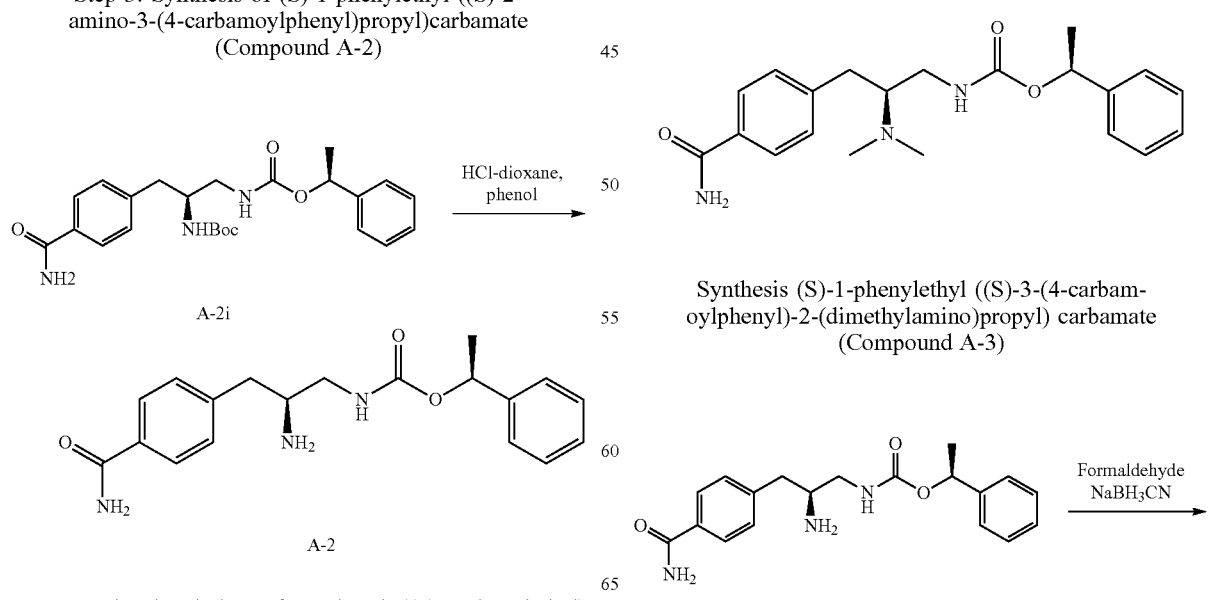

To a stirred solution of tert-butyl ((S)-1-phenylethyl) ((S)-3-(4-carbamoylphenyl)propane-1,2-diyl)dicarbamate (A-2i) (200 mg) and phenol (200 mg) in 1,4-dioxane (15 mL) was added 4N HCl solution in 1,4-dioxane (1 mL). The reaction mixture was stirred overnight and then concentrated in vacuo. The residue was treated with dichloromethane and ammonia and purified by flash column chromatography over silica gel (0-10% MeOH/CH$_2$Cl$_2$ with 5% ammonia) to afford Compound A-2 a white solid (75 mg, 48%). LC-MS: 342.2 [M+H]$^+$; $^1$H NMR (400 MHz, DMSO-d6) δ 7.90 (br s, 1H), 7.77 (d, 2H, J=8.1 Hz), 7.40-7.15 (m, 9H), 5.66 (q, 1H, J=6.6 Hz), 3.00-2.80 (m, 3H), 2.68 (dd, 1H, J=13.2, 5.0 Hz), 2.45 (dd, 1H, J=13.4, 7.3 Hz), 1.50 (br s, 2H), 1.44 (d, 3H, J=6.6 Hz).

Example A3

Synthesis (S)-1-phenylethyl ((S)-3-(4-carbamoylphenyl)-2-(dimethylamino)propyl) carbamate (Compound A-3)

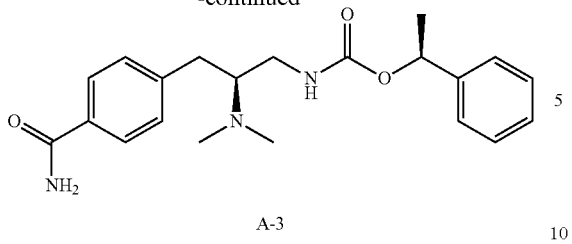

A-3

To a stirred suspension of (S)-1-phenylethyl ((S)-2-amino-3-(4-carbamoylphenyl)propyl)carbamate, Compound A-2 (40 mg, 0.12 mmol) in acetonitrile (10 mL) and water (0.5 mL) at 0° C. was added 37% aqueous solution of formaldehyde (0.047 mL, 0.6 mmol), followed by sodium cyanoborohydride (22 mg, 0.35 mmol). After 10 min, acetic acid (0.036 mL, 0.6 mmol) was added. The reaction mixture was warmed to rt and stirred for 3 h. The mixture was diluted with water and adjusted to pH 10 with aq. $Na_2CO_3$ and extracted with EtOAc. The combined organic layers were washed with brine, dried over anhydrous sodium sulfate, and concentrated. The residue was purified by flash column chromatography over silica gel (0-5% MeOH/$CH_2Cl_2$ with 5% ammonia) to afford Compound A-3, as a white foam (30 mg, 69%). LC-MS: 370.2 [M+H]$^+$; $^1$H NMR (400 MHz, DMSO-d6) δ 7.89 (br s, 1H), 7.82 and 7.76 (d, 2H, J=8.0 Hz), 7.35-7.10 (m, 8H), 6.93 and 6.65 (t, 1H, J=5.4 Hz), 5.62 (q, 1H, J=6.6 Hz), 3.06 (m, 1H), 2.95-2.70 (m, 3H), 2.47 (dd, 1H, J=15.8, 6.1 Hz), 2.22 (s, 6H), 1.41 and 1.33 (d, 3H, J=6.6 Hz).

Example A4

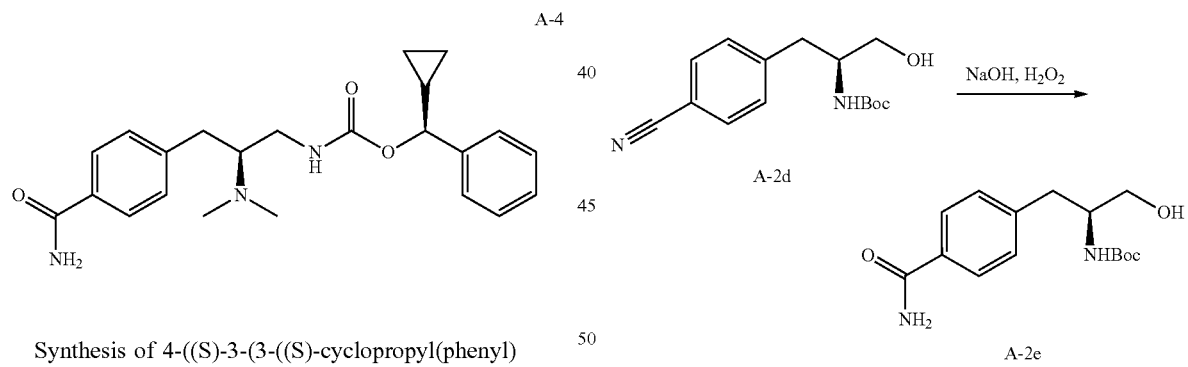

A-4

Synthesis of 4-((S)-3-(3-((S)-cyclopropyl(phenyl)methyl)ureido)-2-(dimethylamino)propyl)benzamide (Compound A-4)

Step 1: Synthesis of tert-butyl (S)-(1-(4-cyanophenyl)-3-hydroxypropan-2-yl) carbamate (A-2d)

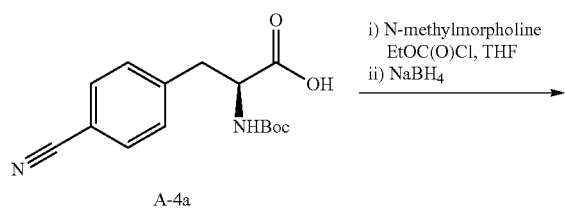

A-4a

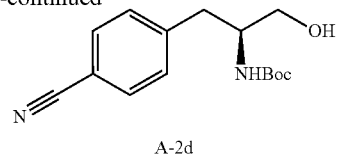

A-2d

To a stirred solution of the commercially available (S)-2-((tert-butoxycarbonyl)amino)-3-(4-cyanophenyl)propanoic acid (A-4a) (5.0 g, 17.2 mmol) in anhydrous THF (50 mL) at −10° C. under nitrogen was added N-methylmorpholine (1.89 mL, 17.2 mmol), followed by slow addition of ethyl chloroformate (1.65 mL, 17.2 mmol). After stirring at −10° C. for 10 min, the reaction mixture was warmed to rt and stirred for 1 h. The precipitates were filtered off and the filter cake was washed with THF. The filtrate was cooled to −10° C. and a solution of sodium borohydride (0.98 g, 25.9 mmol) in water (3 mL) was slowly added. After 1 h, the reaction was carefully quenched with 1N aq. HCl. The mixture was adjusted to pH 8-9 and extracted with EtOAc (3×). The combined organic layers were washed with brine, dried over anhydrous magnesium sulfate, and concentrated. The residue was purified by flash column chromatography over silica gel (0-80% EtOAc/$CH_2Cl_2$) to afford (A-2d) as a white powder (3.25 g, 68%). LC-MS: 299.2 [M+Na]$^+$; $^1$H NMR (400 MHz, CDCl$_3$) δ 7.60 (d, 2H, J=7.7 Hz), 7.35 (d, 2H, J=7.7 Hz), 4.77 (br d, 1H), 3.88 (br s, 1H), 3.68 (br d, 1H, J=10.8 Hz), 3.56 (dd, 1H, J=10.8, 4.4 Hz), 2.93 (d, 2H, J=6.7 Hz), 2.08 (br s, 1H), 1.40 (s, 9H).

Step 2: Synthesis of tert-butyl (S)-(1-(4-carbamoylphenyl)-3-hydroxypropan-2-yl)carbamate (A-2e)

To a stirred solution of tert-butyl (S)-(1-(4-cyanophenyl)-3-hydroxypropan-2-yl)carbamate (A-2d) (1.7 g, 6.2 mmol) in methanol (50 mL) was added 6N aq. NaOH (1.03 mL, 6.2 mmol), followed by 27% aq. Solution of hydrogen peroxide (2.71 mL, 21.6 mmol). The reaction mixture was stirred at 50° C. for 3 h. After cooling, the mixture was neutralized with 1N aq. HCl. Removal of methanol in vacuo and the residue was triturated with water. The solids were collected by filtration and dried to obtain (A-2e) as a white powder (1.5 g, 83%). LC-MS: 317.1 [M+Na]$^+$; $^1$H NMR (400 MHz, DMSO-d6) δ 7.89 (s, 1H), 7.77 (d, 2H, J=8.2 Hz), 7.28 (s, 1H), 7.25 (d, 2H, J=8.2 Hz), 6.65 (d, 1H, J=8.6 Hz), 4.75 (t, 1H, J=5.2 Hz), 3.35 (m, 1H), 3.26 (m, 1H), 2.87 (dd, 1H, J=13.6, 5.0 Hz), 2.59 (dd, 1H, J=13.6, 9.0 Hz), 1.30 (s, 9H).

Step 3: Synthesis of tert-butyl (S)-(1-(4-carbamoylphenyl)-3-(1,3-dioxoisoindolin-2-yl)propan-2-yl)carbamate (A-2f)

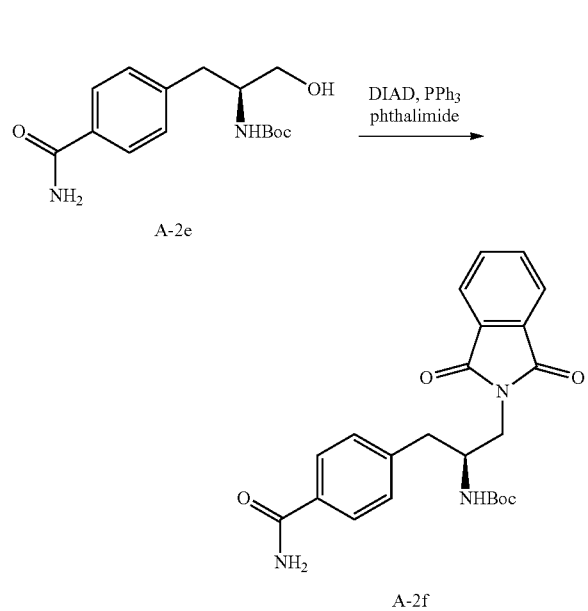

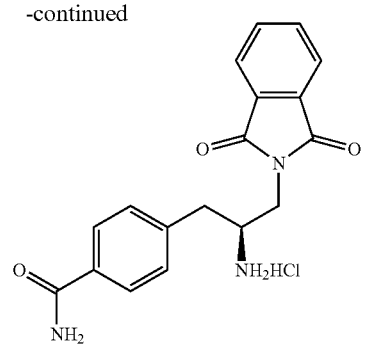

To a stirred solution of tert-butyl (S)-(1-(4-carbamoylphenyl)-3-hydroxypropan-2-yl)carbamate (A-2e) (1.0 g, 3.4 mmol), phthalimide (0.60 g, 4.1 mmol), and triphenylphosphine (1.08 g, 4.1 mmol) in anhydrous THF (40 mL) at 0° C. under nitrogen was slowly added diisopropyl azodicarboxylate (0.81 mL, 4.1 mmol) over 1 h. The reaction mixture was slowly warmed to rt and stirred overnight. The solids precipitated out were collected by filtration and washed with THF and dried to obtain (A-2f) as a white powder (1.33 g, 92%). LC-MS: 446.1 [M+Na]$^+$; $^1$H NMR (400 MHz, DMSO-d6) δ 7.90-7.75 (m, 7H), 7.31-7.27 (m, 3H), 6.89 (d, 1H, J=9.2 Hz), 4.03 (m, 1H), 3.66-3.60 (m, 2H), 2.87 (dd, 1H, J=13.8, 5.3 Hz), 2.77 (dd, 1H, J=13.8, 9.8 Hz), 1.09 and 0.96 (s, 9H).

Step 4: Synthesis of (S)-4-(2-amino-3-(1,3-dioxoisoindolin-2-yl)propyl)benzamide Hydrochloride (A-4b)

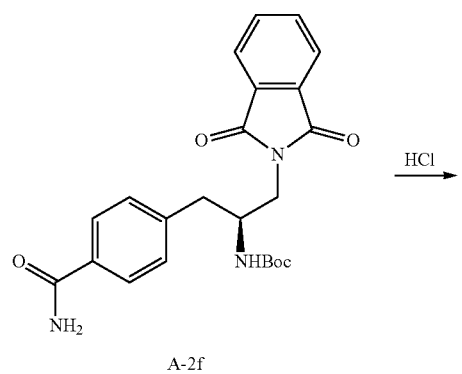

To a stirred solution of tert-butyl (S)-(1-(4-carbamoylphenyl)-3-(1,3-dioxoisoindolin-2-yl)propan-2-yl)carbamate (A-2f) (450 mg) in chloroform (20 mL) and methanol (2 mL) was added 4N HCl solution in 1,4-dioxane (2 mL). The reaction mixture was stirred at rt overnight, and then concentrated down to dryness to obtain the crude product (A-4b) as a white powder (460 mg). LC-MS: 324.1 [M+H]$^+$.

Step 5: Synthesis of (S)-4-(2-(dimethylamino)-3-(1,3-dioxoisoindolin-2-yl) propyl)benzamide (A-4c)

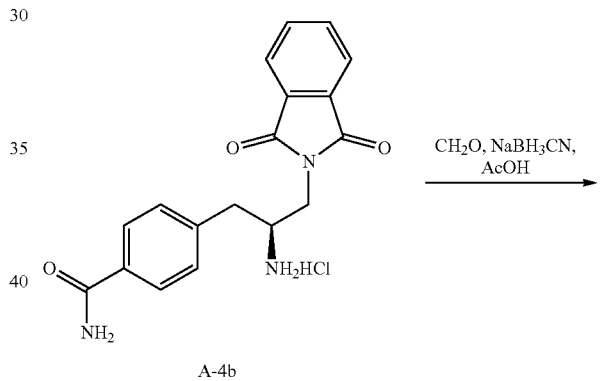

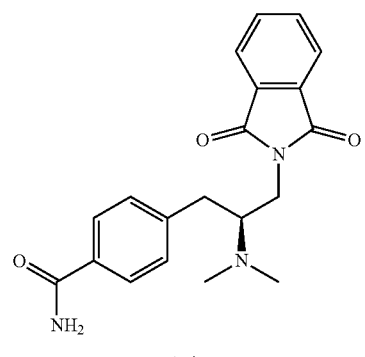

To a stirred suspension of (S)-4-(2-amino-3-(1,3-dioxoisoindolin-2-yl)propyl)benzamide hydrochloride (A-4b) (180 mg, 0.5 mmol) in acetonitrile (30 mL) and water (1 mL) at 0° C. was added 37% aqueous solution of formaldehyde (0.22 mL, 2.5 mmol), followed by sodium cyanoborohydride (90 mg, 1.5 mmol) in portions. After 10 min, acetic acid (0.143 mL, 2.5 mmol) was added. The reaction mixture was slowly warmed to rt and stirred for 3 h. The mixture was treated with water and adjusted to pH 10 with aq. Na$_2$CO$_3$ and extracted with EtOAc. The combined organic layers were washed with brine, dried over anhydrous sodium sulfate, and concentrated. The residue was purified by flash column chromatography over silica gel (0-10% MeOH/CH$_2$Cl$_2$ with 5% ammonia) to afford (A-4c) as a white solid (125 mg, 71%). LC-MS: 352.2 [M+H]$^+$; $^1$H NMR (400 MHz, DMSO-d6) δ 7.89 (br s, 1H), 7.81 (s, 4H), 7.77 (d, 2H, J=8.2 Hz), 7.31 (d, 2H, J=8.2 Hz), 7.28 (br s, 1H), 3.80 (dd, 1H, J=14.0, 9.5 Hz), 3.30 (m, 1H), 3.20 (m, 1H), 2.94 (dd, 1H, J=13.5, 4.8 Hz), 2.53 (dd, 1H, J=13.5, 9.0 Hz), 2.23 (s, 6H).

Step 6: Synthesis of (S)-4-(3-amino-2-(dimethylamino)propyl)benzamide (A-4d)

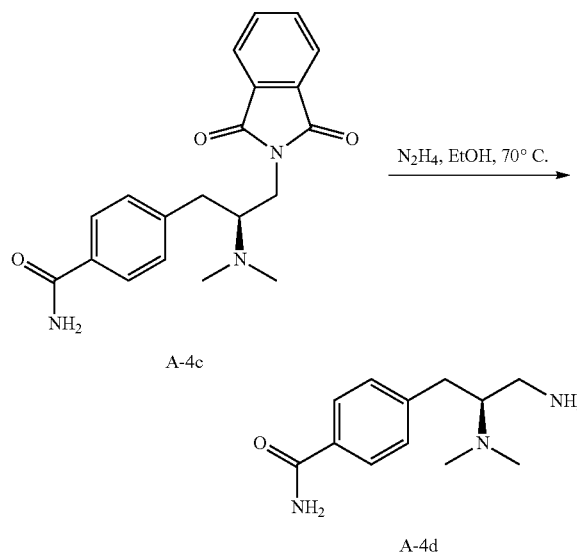

A mixture of (S)-4-(2-(dimethylamino)-3-(1,3-dioxoisoindolin-2-yl)propyl)benzamide (A-4c) (125 mg, 0.36 mmol) in ethanol (10 mL) and hydrazine monohydrate (90 mg, 1.8 mmol) was stirred at 70° C. for 3 h. The mixture was concentrated down to 2 mL and triturated with CH$_2$Cl$_2$ and filtered to remove the solids. The filtrate was concentrated and purified by flash column chromatography over silica gel (0-20% MeOH/CH$_2$Cl$_2$ with 5% ammonia) to afford (A-4d) as a white foam (75 mg, 95%). LC-MS: 222.2 [M+H]$^+$; $^1$H NMR (400 MHz, CDCl$_3$) δ 7.73 (d, 2H, J=8.1 Hz), 7.23 (d, 2H, J=8.1 Hz), 6.09 (br s, 1H), 5.65 (br s, 1H), 2.97 (dd, 1H, J=13.0, 3.0 Hz), 2.70-2.50 (m, 3H), 2.35 (s, 7H).

Step 7: Synthesis of [N,S(R)]—N-(cyclohexylphenylmethylene)-2-methyl-2-propanesulfinamide (A-4g)

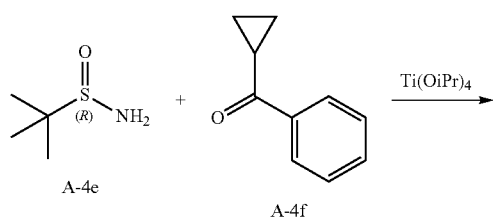

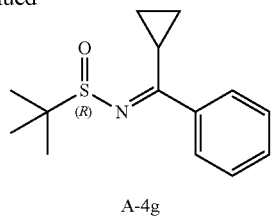

A round bottom flask was charged with titanium(IV) isopropoxide (35.2 g, 124 mmol) and anhydrous THF (100 mL). (R)-(+)-tertbutylsulfinamide (A-4e) (5 g, 41 mmol) and cyclopropyl phenyl ketone (A-4f) (6 g, 41 mmol) were added. After cooling, the reaction mixture was quenched with brine and filtered through Celite. The filter cake was washed with EtOAc and the filtrate was extracted with EtOAc. The combined organic layers were washed with brine, dried over anhydrous sodium sulfate, and concentrated. The residue was purified by flash column chromatography over silica gel (0-60% EtOAc/hexane) to afford (A-4g) as a yellow oil (4.5 g, 44%). LC-MS: 250.1 [M+H]$^+$; $^1$H NMR (400 MHz, CDCl$_3$) δ 7.50-7.40 (m, 5H), 1.25-1.00 (m, 14H).

Step 8: Synthesis of N—[(S)-cyclopropylphenylmethyl]-2-methyl-[S(R)]-2-propanesulfinamide (A-4h)

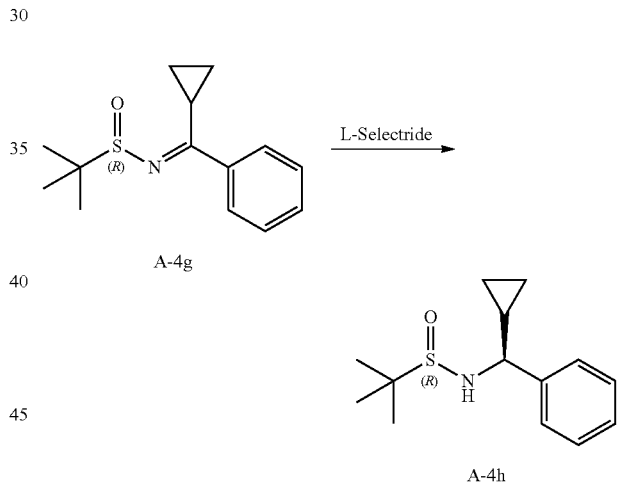

To a stirred suspension of [N(R),S(R)]—N-(cyclohexylphenylmethylene)-2-methyl-2-propanesulfinamide (A-4g) (4.5 g, 18 mmol) in anhydrous THF (50 mL) at 0° C. under nitrogen was added 1M L-Selectride solution in THF (25 mL) over 20 min. The reaction mixture was slowly warmed to rt over 3 h, and then carefully quenched with methanol. The mixture was filtered through Celite and the filtrate was concentrated. The residue was purified by flash column chromatography over silica gel (0-50% EtOAc/hexane) to isolate both diastereomers. N—[(R)-cyclopropylphenylmethyl]-2-methyl-[S(R)]-2-propanesulfinamide: colorless oil (3.0 g), LC-MS: 252.1 [M+H]$^+$; $^1$H NMR (400 MHz, CDCl$_3$) δ 7.40-7.26 (m, 5H), 3.69 (dd, 1H, J=9.2, 2.8 Hz), 3.52 (s, 1H), 1.25 (s, 9H), 1.16 (m, 1H), 0.79 (m, 1H), 0.65 (m, 1H), 0.48 (m, 1H), 0.24 (m, 1H). N—[(S)-cyclopropylphenylmethyl]-2-methyl-[S(R)]-2-propanesulfinamide (A-4h): colorless oil (0.75 g), LC-MS: 252.1 [M+H]$^+$; $^1$H NMR (400 MHz, CDCl$_3$) δ 7.36-7.26 (m, 5H), 3.59 (s, 1H), 3.56 (d, 1H, J=9.2 Hz), 1.22 (s, 9H), 1.20 (m, 1H), 0.68 (m, 1H), 0.54 (m, 1H), 0.48 (m, 1H), 0.40 (m, 1H).

Step 9: Synthesis of (S)-cyclopropyl(phenyl)methanamine Hydrochloride (A-4i)

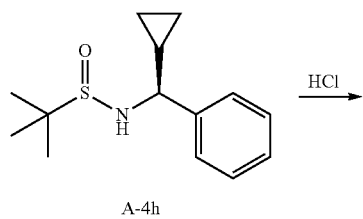

To a stirred solution of N—[(S)-cyclopropylphenylmethyl]-2-methyl-[S(R)]-2-propanesulfinamide (A-4h) (1.5 g, 6 mmol) in 1,4-dioxane (25 mL) at 0° C. was added 4M HCl solution in 1,4-dioxane (6 mL). The reaction mixture was slowly warmed to rt and stirred for 16 h. The reaction mixture was diluted with diethyl ether (30 mL) and the solids precipitated out were collected by filtration to afford (A-4i) as a white powder (1.05 g, 96%). LC-MS: 131.1 [M+H—NH$_3$]$^+$; $^1$H NMR (400 MHz, methanol-d4) δ 7.42 (m, 5H), 3.57 (d, 1H, J=10.0 Hz), 1.39 (m, 1H), 0.82 (m, 1H), 0.68-0.55 (m, 2H), 0.41 (m, 1H).

Step 10: Synthesis of 4-nitrophenyl (S)-(cyclopropyl(phenyl)methyl)carbamate (A-4k)

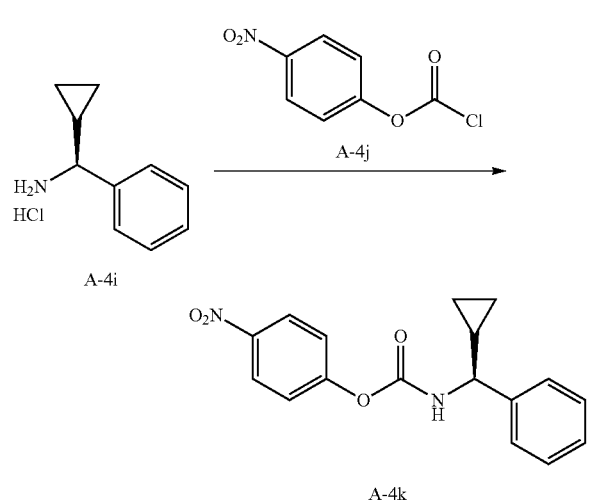

To a stirred suspension of (S)-cyclopropyl(phenyl)methanamine hydrochloride (A-4i) (1.0 g, 5.4 mmol) in anhydrous THF (30 mL) under nitrogen was added triethylamine (3 mL, 22 mmol). The solution was cooled to −40° C. and a solution of p-nitrophenol chloroformate (A-4j) (1.09 g, 5.4 mmol) in THF (5 mL) was added. The reaction mixture was slowly warmed to rt and stirred overnight. The reaction mixture was diluted with water and extracted with EtOAc. The combined organic layers were washed with 1N aq. HCl and brine, dried over anhydrous sodium sulfate, and concentrated. The residue was purified by flash column chromatography over silica gel (30-100% CH$_2$Cl$_2$/hexane) to afford (A-4k) as a white solid (1.1 g, 65%). $^1$H NMR (400 MHz, CDCl$_3$) δ 8.23 (d, 2H, J=8.8 Hz), 7.40-7.30 (m, 7H), 5.59 (d, 1H, J=7.0 Hz), 4.19 (t, 1H, J=8.4 Hz), 1.25 (m, 1H), 0.75-0.60 (m, 2H), 0.56 (m, 1H), 0.42 (m, 1H).

Step 11: Synthesis of 4-((S)-3-(3-((S)-cyclopropyl(phenyl)methyl)ureido)-2-(dimethylamino)propyl)benzamide (Compound A-4)

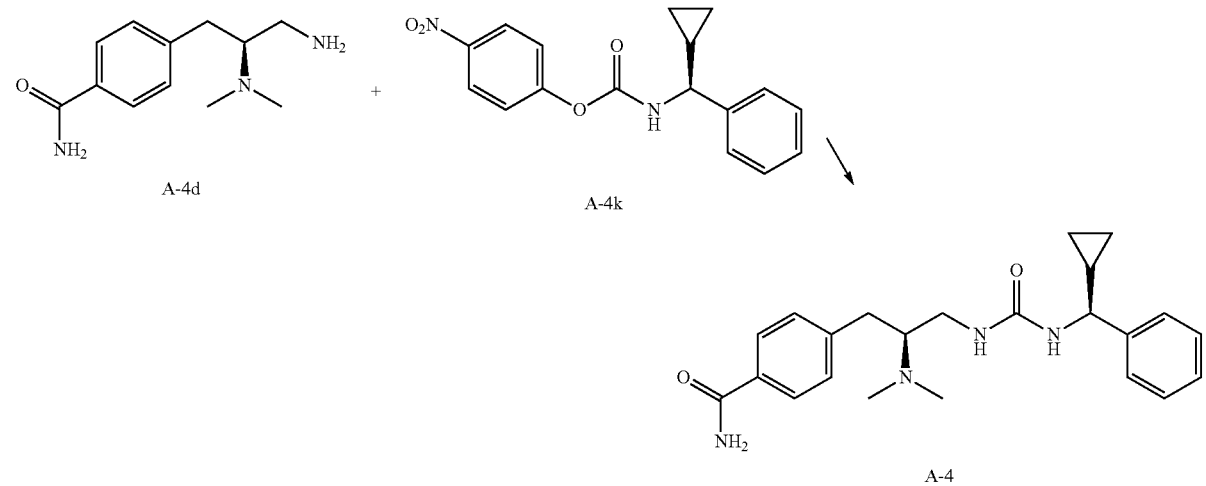

To a stirred solution of (S)-4-(3-amino-2-(dimethylamino)propyl)benzamide (A-4d) (40 mg) in anhydrous DMF (4 mL) was added 4-nitrophenyl (S)-(cyclopropyl (phenyl)methyl)carbamate (A-4k) (55 mg). The reaction mixture was stirred at rt overnight and then concentrated in vacuo. The residue was purified by flash column chromatography over silica gel (0-10% MeOH/CH$_2$Cl$_2$ with 5% ammonia) to afford Compound A-4 as a white solid (50 mg, 70%). LC-MS: 395.2 [M+H]$^+$; $^1$H NMR (400 MHz, DMSO-d6) δ 7.90 (s, 1H), 7.76 (d, 2H, J=8.0 Hz), 7.30-7.10 (m, 8H), 6.68 (d, 1H, J=7.8 Hz), 5.73 (br s, 1H), 4.09 (t, 1H, J=8.2 Hz), 3.01 (m, 1H), 2.95-2.75 (m, 2H), 2.66 (m, 1H), 2.35 (m, 1H), 2.26 (s, 6H), 1.02 (m, 1H), 0.50-0.35 (m, 2H), 0.35-0.20 (m, 2H).

Example A5

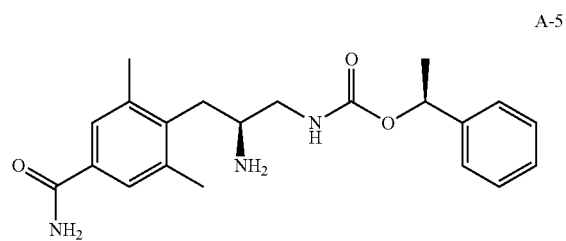 [SMILES: Cc1cc(C(N)=O)cc(C)c1C[C@H](N)CNC(=O)O[C@@H](C)c1ccccc1]

A-5

Synthesis of (S)-1-phenylethyl ((S)-2-amino-3-(4-carbamoyl-2,6-dimethylphenyl)propyl)carbamate, (Compound A-5)

Step 1: Synthesis of methyl (S)-2-((tert-butoxycarbonyl)amino)-3-(4-cyano-2,6-dimethylphenyl)propanoate (A-5b)

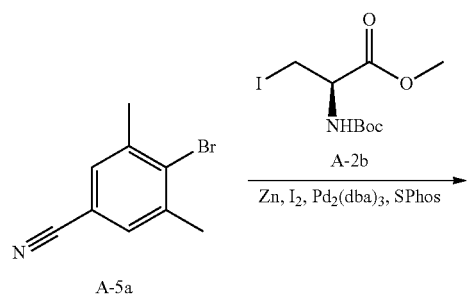

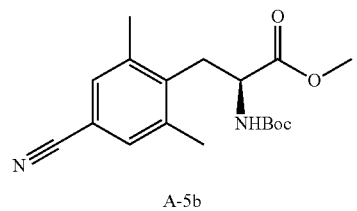

A-5b

To a stirred suspension of zinc powder (2.5 g, 38.5 mmol) in anhydrous N,N-dimethylacetamide (10 mL) under nitrogen was added iodine (200 mg). After 5 min, a solution of methyl (R)-2-((tert-butoxycarbonyl)amino)-3-iodopropanoate (A-2b) (5.0 g, 15.2 mmol) in N,N-dimethylacetamide (5 mL) was added slowly over 10 min. The mixture was stirred at rt for 30 min and then heated at 70° C. for 1 h. The mixture was cooled to rt and a suspension of 4-bromo-3,5-dimethylbenzonitrile (A-5a) (2.5 g, 12 mmol), Pd$_2$(dba)$_3$ (550 mg), and 2-dicyclohexylphosphino-2',6'-dimethoxybiphenyl (Sphos, 492 mg) in N,N-dimethylacetamide (10 mL) was added into the zinc reagent mixture. The reaction mixture was heated at 70° C. and stirred overnight. After cooling, the reaction mixture was quenched with water, diluted with EtOAc and filtered through Celite. The filter cake was washed with EtOAc and the filtrate was washed with 1N aq. HCl and brine, dried over anhydrous sodium sulfate, and concentrated. The residue was purified by flash column chromatography over silica gel (0-50% EtOAc/CH$_2$Cl$_2$) to afford (A-5b) as a white solid (1.5 g, 38%). LC-MS: 355.2 [M+Na]$^+$; $^1$H NMR (400 MHz, CDCl$_3$) δ 7.30 (s, 2H), 5.13 (d, 1H, J=8.8 Hz), 4.56 (q, 1H, J=8.0 Hz), 3.67 (s, 3H), 3.15-3.00 (m, 2H), 2.38 (s, 6H), 1.35 (s, 9H).

Step 2: Synthesis of tert-butyl (S)-(1-(4-cyano-2,6-dimethylphenyl)-3-hydroxypropan-2-yl)carbamate (A-5c)

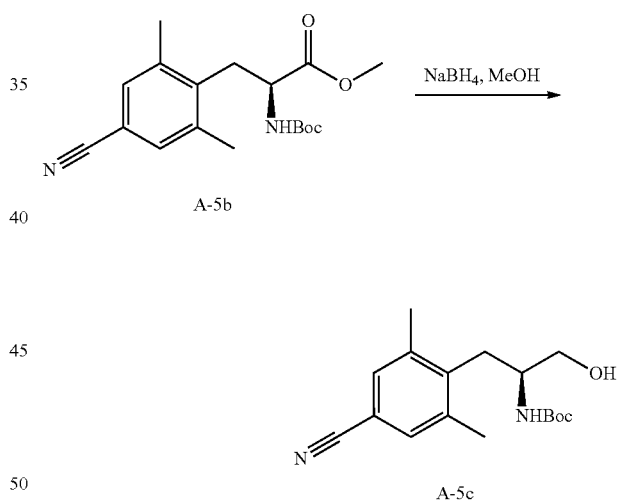

To a stirred solution of methyl (S)-2-((tert-butoxycarbonyl)amino)-3-(4-cyano-2,6-dimethylphenyl)propanoate (A-5b) (1.5 g, 4.5 mmol) in methanol (20 mL) and THF (10 mL) was added sodium borohydride in small portions with 1 h intervals until all starting material was consumed (about 800 mg NaBH$_4$ used). The reaction mixture was carefully quenched with 1N aq. HCl and adjusted to pH 5. The volatiles were removed under reduced pressure and the residue was triturated with water. The white solids precipitated out were collected by filtration, washed with water and dried to afford (A-5c) (1.0 g, 73%). LC-MS: 327.2 [M+Na]$^+$; $^1$H NMR (400 MHz, CDCl$_3$) δ 7.30 (s, 2H), 4.87 (br s, 1H), 3.90 (m, 1H), 3.70 (m, 1H), 3.55 (dt, 1H, J=10.7, 4.4 Hz), 3.05-2.85 (m, 2H), 2.41 (s, 6H), 2.09 (br s, 1H), 1.37 (s, 9H).

Step 3: Synthesis of tert-butyl (S)-(1-(4-carbamoyl-2,6-dimethylphenyl)-3-hydroxypropan-2-yl)carbamate (A-5d)

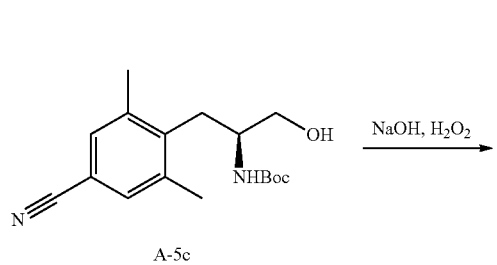

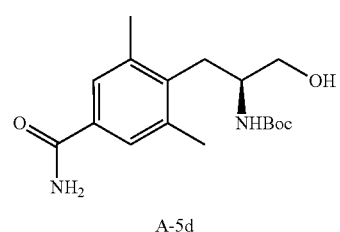

To a stirred solution of tert-butyl (S)-(1-(4-cyano-2,6-dimethylphenyl)-3-hydroxypropan-2-yl)carbamate (A-5c) (1.0 g, 3.3 mmol) in methanol (30 mL) was added 6N aq. NaOH (0.55 mL, 3.3 mmol), followed by 27% aq. Solution of hydrogen peroxide (1.45 mL, 11.5 mmol). The reaction mixture was stirred at 50° C. for 3 h. After cooling, the mixture was neutralized with 1N aq. HCl. Removal of methanol under reduced pressure and the residue was triturated with water. The solids were collected by filtration and dried to obtain (A-5d) a white powder (1.0 g, 94%). LC-MS: 345.2 [M+Na]$^+$; $^1$H NMR (400 MHz, CDCl$_3$) δ 7.45 (s, 2H), 6.20 (br s, 1H), 5.60 (br s, 1H), 4.87 (d, 1H, J=8.5 Hz), 3.88 (m, 1H), 3.69 (dd, 1H, J=10.5, 3.5 Hz), 3.55 (dd, 1H, J=10.7, 4.6 Hz), 2.95 (m, 1H), 2.43 (s, 7H), 1.38 (s, 9H).

Step 4: Synthesis of tert-butyl (S)-(1-(4-carbamoyl-2,6-dimethylphenyl)-3-(1,3-dioxoisoindolin-2-yl)propan-2-yl)carbamate (A-5e)

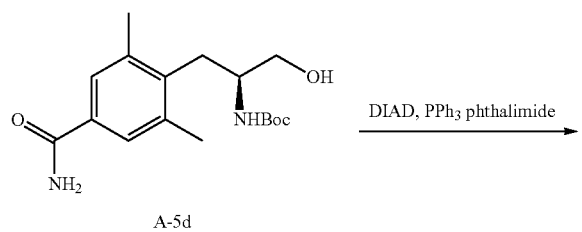

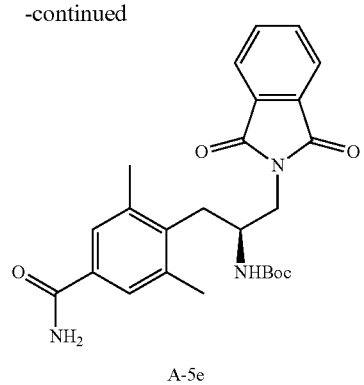

To a stirred solution of tert-butyl (S)-(1-(4-carbamoyl-2,6-dimethylphenyl)-3-hydroxypropan-2-yl)carbamate (A-5d) (1.0 g, 3.1 mmol), phthalimide (0.55 g, 3.7 mmol), and triphenylphosphine (0.98 g, 3.7 mmol) in anhydrous THF (40 mL) at 0° C. under nitrogen was added diisopropyl azodicarboxylate (0.73 mL, 3.7 mmol) over 20 min. The reaction mixture was slowly warmed to rt and stirred overnight. The mixture was concentrated and the residue was purified by flash column chromatography over silica gel (100% EtOAc) to afford (A-5e) as a white solid (1.2 g, 86%). LC-MS: 474.2 [M+Na]$^+$; $^1$H NMR (400 MHz, DMSO-d6) δ 8.00-7.75 (m, 3H), 7.65-7.50 (m, 2H), 7.50 (s, 2H), 7.21 (s, 1H), 6.94 (d, 1H, J=9.6 Hz), 4.25-4.00 (m, 1H), 3.76 (dd, 1H, J=13.5, 10.0 Hz), 3.46 (dd, 1H, J=13.5, 3.7 Hz), 2.90-2.80 (m, 2H), 2.35 (s, 6H), 1.08 and 0.88 (s, 9H).

Step 5: Synthesis of tert-butyl (S)-(1-amino-3-(4-carbamoyl-2,6-dimethylphenyl)propan-2-yl)carbamate (A-5f)

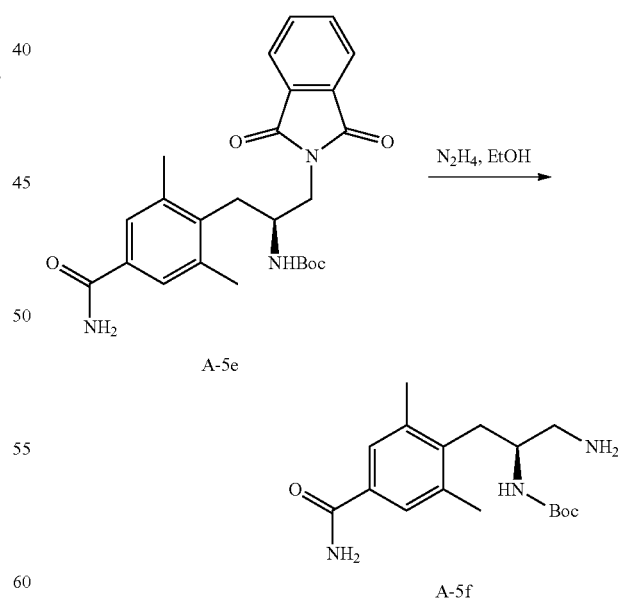

A mixture of tert-butyl (S)-(1-(4-carbamoyl-2,6-dimethylphenyl)-3-(1,3-dioxoisoindolin-2-yl)propan-2-yl)carbamate (A-5e) (600 mg, 1.33 mmol) in ethanol (10 mL) and hydrazine monohydrate (325 mg, 6.7 mmol) was stirred at 80° C. for 3 h. After cooling, the mixture was filtered to remove the solids and the filter cake was washed with ethanol. The filtrate was concentrated and purified by flash column chromatography over silica gel to afford (A-5f) a white foam (360 mg, 84%). LC-MS: 322.2 [M+H]$^+$; $^1$H NMR (400 MHz, CDCl$_3$) δ 7.45 (s, 2H), 6.07 (br s, 1H), 5.60 (br s, 1H), 4.72 (br s, 1H), 3.82 (br s, 1H), 3.00-2.60 (m, 4H), 1.35 (s, 9H).

Step 6: (S)-1-phenylethyl ((S)-2-amino-3-(4-carbamoyl-2,6-dimethylphenyl)propyl)carbamate (Compound A-5)

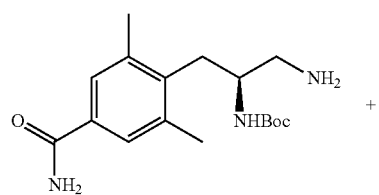

A-5f

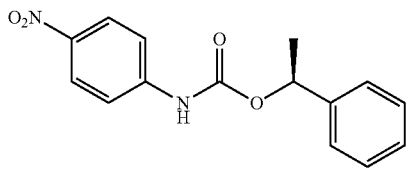

A-5g

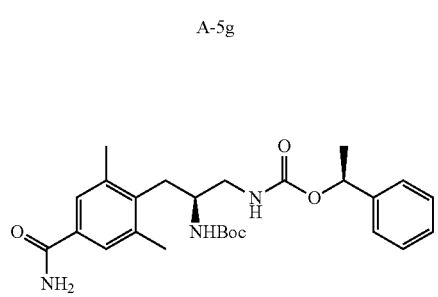

A-5h

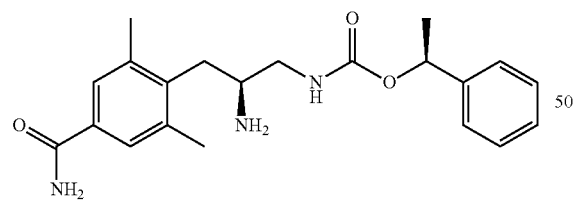

A-5

(S)-1-phenylethyl ((S)-2-amino-3-(4-carbamoyl-2,6-dimethylphenyl) propyl) carbamate (Compound A-5) was synthesized according to the procedure for Example A2 using tert-butyl (S)-(1-amino-3-(4-carbamoyl-2,6-dimethylphenyl)propan-2-yl)carbamate (A-5f) as the starting material. LC-MS: 370.2 [M+H]$^+$; $^1$H NMR (400 MHz, DMSO-d6) δ 7.80 (s, 1H), 7.53 and 7.48 (s, 2H), 7.40-6.90 (m, 7H), 5.67 (q, 1H, J=6.5 Hz), 3.10-2.80 (m, 3H), 2.66 (dd, 1H, J=13.6, 4.2 Hz), 2.52 (m, 1H), 2.30 (s, 6H), 1.40 (br s, 2H), 1.44 and 1.35 (d, 3H, J=6.5 Hz).

Example A6

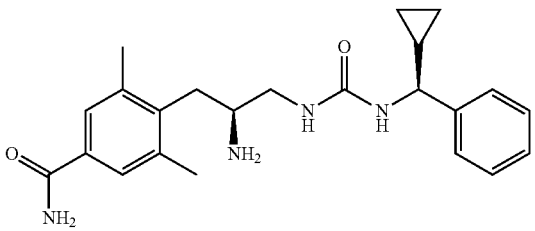

A-6

Synthesis of 4-((S)-2-amino-3-(3-((S)-cyclopropyl(phenyl)methyl)ureido)propyl)-3,5-dimethylbenzamide (Compound A-6)

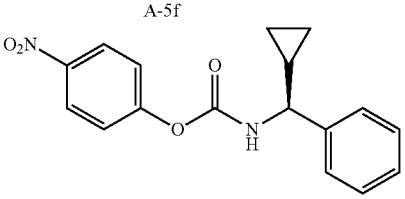

A-5f

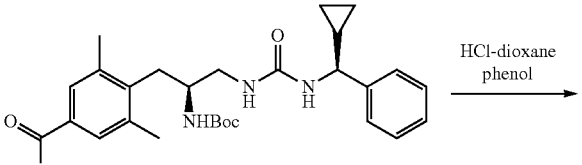

A-4k

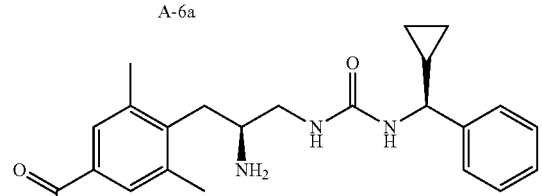

A-6a 4-((S)-2-amino-3-(3-((S)-cyclopropyl(phenyl)methyl)ureido)propyl)-3,5-dimethylbenzamide (Compound A-6) was synthesized according to the procedure for Example A2 using tert-butyl (S)-(1-amino-3-(4-carbamoyl-2,6-dimethylphenyl)propan-2-yl)carbamate (A-5f) and 4-nitrophenyl (S)-(cyclopropyl(phenyl)methyl)carbamate (A-4k) as the starting materials. LC-MS: 395.2 [M+H]$^+$; $^1$H NMR (400 MHz, DMSO-d6) δ 7.80 (s, 1H), 7.48 (s, 2H), 7.30-7.25 (m, 4H), 7.22-7.15 (m, 2H), 6.56 (d, 1H, J=8.5 Hz), 5.99 (t, 1H, J=5.6 Hz), 4.14 (t, 1H, J=8.2 Hz), 3.05-2.75 (m, 3H), 2.68 (dd, 1H, J=13.5, 5.0 Hz), 2.55 (dd, 1H, J=13.5, 7.8 Hz), 2.30 (s, 6H), 1.50 (br s, 2H), 1.04 (m, 1H), 0.50-0.38 (m, 2H), 0.35-0.25 (m, 2H).

Example A7

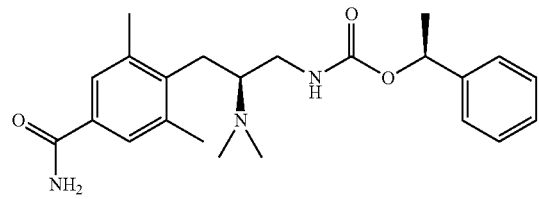

A-7

Synthesis of (S)-1-phenylethyl ((S)-3-(4-carbamoyl-2,6-dimethylphenyl)-2-(dimethylamino)propyl)carbamate (Compound A-7)

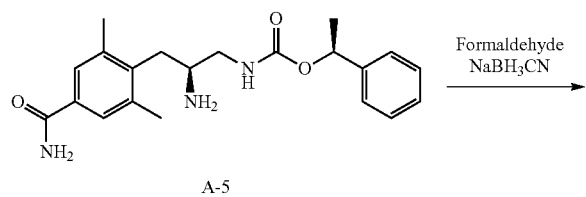

(S)-1-phenylethyl ((S)-3-(4-carbamoyl-2,6-dimethylphenyl)-2-(dimethylamino)propyl)carbamate (Compound A-7) was synthesized according to the procedure for Example A3 using (S)-1-phenylethyl ((S)-2-amino-3-(4-carbamoyl-2,6-dimethylphenyl)propyl)carbamate (Compound A-5) as the starting material. LC-MS: 398.2 [M+H]$^+$; $^1$H NMR (400 MHz, DMSO-d6) δ 7.84 and 7.79 (s, 1H), 7.56 and 7.51 (s, 2H), 7.35-7.15 and 7.02 (m, 6H), 6.91 and 6.67 (t, 1H, J=5.2 Hz), 5.62 (q, 1H, J=6.5 Hz), 3.15 (m, 1H), 2.85-2.65 (m, 3H), 2.29 (s, 12H), 1.41 and 1.29 (d, 3H, J=6.5 Hz).

Example A8

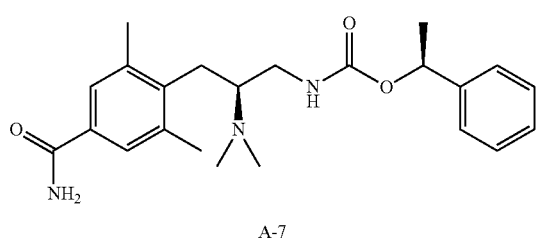

A-8

Synthesis of 4-((S)-2-(dimethylamino)-3-((S)-3-phenylbutanamido)propyl)-3,5-dimethylbenzamide (Compound A-8)

Step 1: Synthesis of triethyl (R)-2-phenylpropane-1,1,1-tricarboxylate (A-8b)

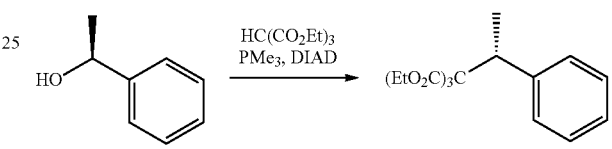

To a solution of 1.48 mL of the alcohol (A-8a) (1.00 equiv., 12 mmol) and 5.21 mL of triethyl methanetricarboxylate (2.00 equiv., 24.1 mmol) in 45.0 mL of anhydrous toluene at room temperature, 24.1 mL of 1M trimethyl phosphine solution in toluene (1M, 2.00 equiv., 24.1 mmol) was added. The resulting solution was cooled to −78° C. DIAD (4.74 mL, 2.00 equiv., 24.1 mmol) was added slowly at such a rate to maintain the temperature of the reaction at −75° C. to −77° C. The reaction was then stirred at −78° C. for 0.5 hours and warmed to room temperature for 1-3 hours and was allowed to run overnight. Solvent was concentrated in vacuo to get crude. The crude was purified by column chromatography using hexane and ethyl acetate to yield compound (A-8b) as a clear oil (3.7 g, 91.4%). $^1$H NMR (300 MHz, CHLOROFORM-d) δ=7.35-7.32 (m, 2H), 7.20-7.12 (m, 3H), 4.13-4.03 (m, 6H), 3.81-3.74 (q, J=7.18, 1H), 1.44-1.41 (d, J=7.23, 3H), 1.13-1.09, (t, J=7.14, 9H).

Step 2: Synthesis of (S)-3-phenylbutanoic Acid (A-8d)

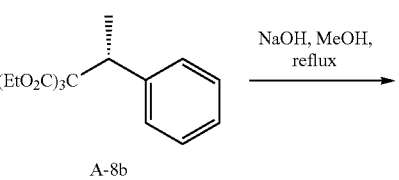

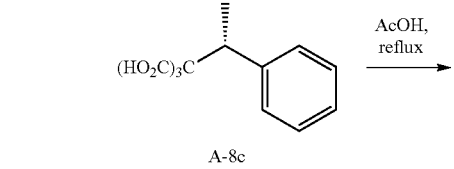

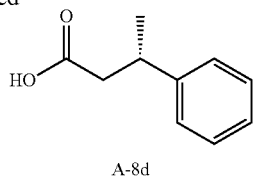

A-8d

To triethyl (R)-2-phenylpropane-1,1,1-tricarboxylate (A-8b) (3.7 g, 1.00 equiv., 11.1 mmol) 11.2 mL of MeOH was added followed by 20.1 ml of 3.3 N NaOH in water (6.00 equiv., 66.4 mmol). The resulting mixture was heated to reflux and the reaction was allowed to continue overnight. Reaction was tracked using HPLC. When no starting material remained, heating was removed and the reaction was allowed to reach room temperature. Volatiles were removed in vacuo and the crude tris acid (A-8c) was taken up in 66.4 mL of acetic acid (105 equiv., 1.16 mol) and heated to reflux. The reflux was allowed to continue overnight. The solvent was then concentrated in vacuo. The resultant crude acid was dissolved in water, and extracted with ethyl acetate. The combined extracts were washed with water and then dried using sodium sulfate and concentrated in vacuo to give product. The product was then purified via column chromatography, eluting with ethyl acetate/hexanes yielding compound (A-8d) as a clear oil (1.16 g, 63.9% over 2 steps). $^1$H NMR (400 MHz, CHLOROFORM-d) δ=7.38-7.31 (m, 2H), 7.29-7.22 (m, 3H), 3.31 (sxt, J=7.2 Hz, 1H), 2.75-2.68 (m, 1H), 2.65-2.57 (m, 1H), 1.36 (d, J=7.1 Hz, 3H)

Step 3: Synthesis of (S)-4-(3-amino-2-(dimethylamino)propyl)-3,5-dimethylbenzamide (A-8e)

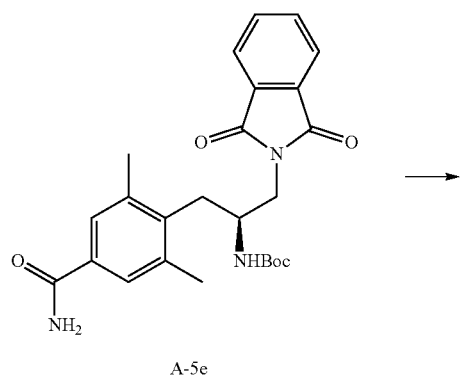

A-5e

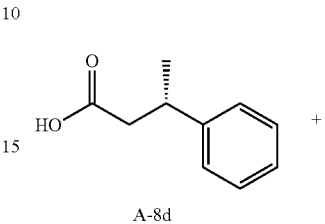

A-8e (S)-4-(3-amino-2-(dimethylamino)propyl)-3,5-dimethylbenzamide (A-8e) was synthesized according to the procedure of Example A4 using tert-butyl (S)-(1-(4-carbamoyl-2,6-dimethylphenyl)-3-(1,3-dioxoisoindolin-2-yl)propan-2-yl)carbamate (A-5e) as the starting material. LC-MS: 250.2 [M+H]$^+$; $^1$H NMR (400 MHz, CDCl$_3$) δ 7.43 (s, 2H), 6.00 (br s, 1H), 5.50 (br s, 1H), 2.91 (dd, 1H, J=13.2, 2.5 Hz), 2.78-2.65 (m, 2H), 2.63-2.50 (m, 1H), 2.43 (s, 6H), 2.37 (s, 6H), 2.35 (m, 1H).

Step 4: Synthesis of 4-((S)-2-(dimethylamino)-3-((S)-3-phenylbutanamido)propyl)-3,5-dimethylbenzamide (Compound A-8)

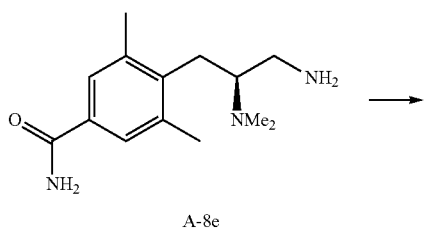

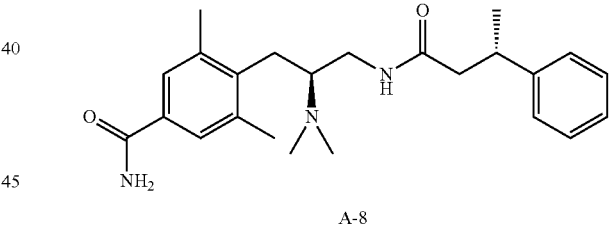

A-8

To a stirred solution of (S)-3-phenylbutanoic acid (A-8d) (16 mg, 0.1 mmol), hydroxybenzotriazole (13 mg, 0.1 mmol), and 1-ethyl-3-(3-dimethylaminopropyl)carbodiimide hydrochloride (30 mg, 0.15 mmol) in anhydrous DMF (2 mL) under nitrogen was added (S)-4-(3-amino-2-(dimethylamino)propyl)-3,5-dimethylbenzamide (A-8e) (25 mg, 0.1 mmol), followed by triethylamine (0.028 mL, 0.2 mmol). The reaction mixture was stirred at rt for 3 h and then diluted with water and extracted with EtOAc. The combined organic layers were washed with aq. NaHCO$_3$ and brine, dried over anhydrous sodium sulfate, and concentrated. The residue was purified by flash column chromatography over silica gel (0-5% MeOH/CH$_2$Cl$_2$ with 5% ammonia) to afford Compound A-8 as a white foam (37 mg, 92%). LC-MS: 396.3 [M+H]$^+$; $^1$H NMR (400 MHz, DMSO-d6) δ 7.81 (s, 1H), 7.53 (t, 1H, J=5.3 Hz), 7.48 (s, 2H), 7.30-7.10 (m, 6H), 3.15-3.05 (m, 2H), 2.95-2.65 (m, 3H), 2.35-2.20 (m, 14H), 1.13 (d, 3H, J=7.0 Hz).

Example A9

Synthesis of 4-((S)-3-(3-((S)-cyclopropyl(phenyl)methyl)ureido)-2-(dimethylamino)propyl)-3,5-dimethylbenzamide (Compound A-9)

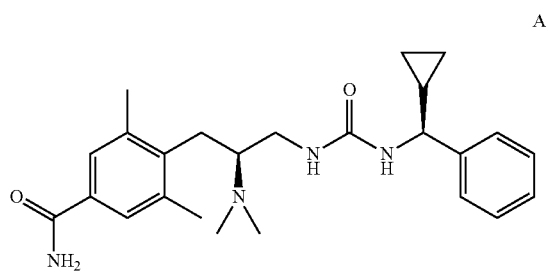

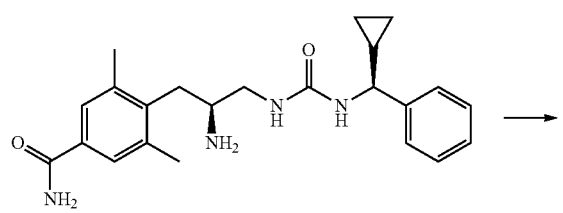

4-((S)-3-(3-((S)-cyclopropyl(phenyl)methyl)ureido)-2-(dimethylamino)propyl)-3,5-dimethylbenzamide (Compound A-9) was synthesized according to the procedure for Example A3 using 4-((S)-2-amino-3-(3-((S)-cyclopropyl(phenyl)methyl)ureido)propyl)-3,5-dimethylbenzamide (Compound A-6) as the starting material. LC-MS: 423.3 [M+H]$^+$; $^1$H NMR (400 MHz, DMSO-d6) δ 7.79 (s, 1H), 7.47 (s, 2H), 7.30-7.15 (m, 6H), 6.69 (d, 1H, J=8.4 Hz), 5.72 (m, 1H), 4.06 (t, 1H, J=8.1 Hz), 2.95-2.80 (m, 3H), 2.66 (m, 1H), 2.33 (s, 6H), 2.30 (s, 6H), 0.99 (m, 1H), 0.50-0.35 (m, 2H), 0.31-0.20 (m, 2H).

Example A10

Synthesis of 4-((S)-2-(dimethylamino)-3-((R)-3-phenylbutanamido)propyl)benzamide (Compound A-10)

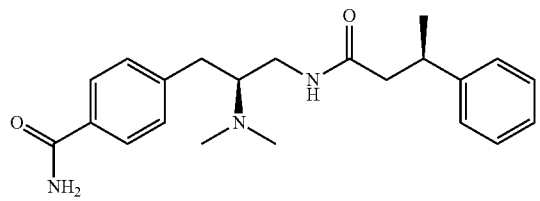

Step 1: Synthesis of triethyl (S)-2-phenylpropane-1,1,1-tricarboxylate (A-10b)

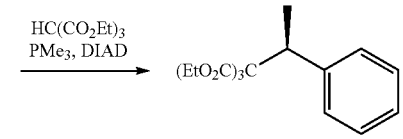

To a solution of 1.00 mL of the alcohol (A-10a) (1.00 equiv., 7.94 mmol) and 3.44 mL of triethyl methanetricarboxylate (2.00 equiv., 15.9 mmol) in 30.0 mL of anhydrous toluene at room temperature, 15.9 mL of 1M trimethyl phosphine solution in toluene (1M, 2.00 equiv., 15.9 mmol) was added. The resulting solution was cooled to −78° C. DIAD (3.13 mL, 2.00 equiv., 15.9 mmol) was added slowly at such a rate to maintain the temperature of the reaction at −75° C. to −77° C. The reaction was then stirred at −78° C. for 0.5 hours and warmed to room temperature for 1-3 hours and was allowed to run overnight. Solvent was concentrated in vacuo to get crude. The crude was purified by column chromatography using hexane and ethyl acetate to yield compound (A-10b) as clear oil (2.46 g, 92.1%). $^1$H NMR (600 MHz, CHLOROFORM-d) δ=4.45-7.43 (d, 2H), 7.30-7.20 (m, 3H), 4.22-4.13 (m, 6H), 1.23-1.19 (t, J=7.2 Hz, 9H).

Step 2: Synthesis of (R)-3-phenylbutanoic Acid (A-10d)

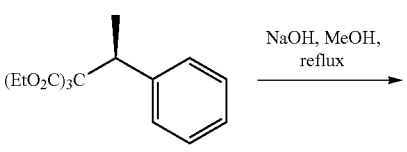

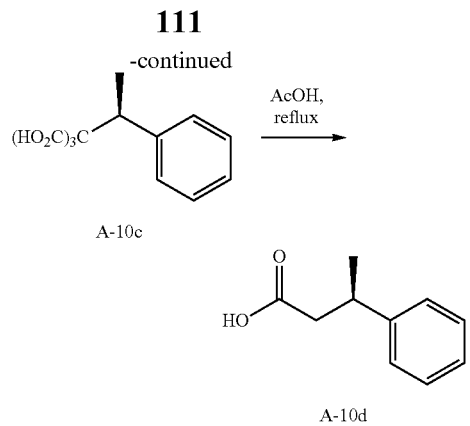

To triethyl (S)-2-phenylpropane-1,1,1-tricarboxylate (A-10b) (1.00 equiv., 2.97 mmol) 3.00 mL of MeOH was added followed by 5.41 ml of 3.3 N NaOH in water (6.00 equiv., 17.8 mmol). The resulting mixture was heated to reflux and the reaction was allowed to continue overnight. Reaction was tracked using HPLC. When no starting material remained, heating was removed and the reaction was allowed to reach room temperature. Volatiles were removed in vacuo and the crude tris acid (A-10c) was taken up in 17.9 mL of acetic acid (105 equiv., 312 mmol) and heated to reflux. The reflux was allowed to continue overnight. The solvent was then concentrated in vacuo. The resultant crude acid was dissolved in water, and extracted with ethyl acetate. The combined extracts were washed with water and then dried using sodium sulfate and concentrated in vacuo to give product. The product was then purified via column chromatography, eluting with ethyl acetate/hexanes yielding compound (A-10d) as clear oil (240 mg, 49.2% over 2 steps). $^1$H NMR (600 MHz, CHLOROFORM-d) δ=7.34-7.30 (m, 2H), 7.26-7.20 (m, 3H), 3.29 (sxt, J=7.2 Hz, 1H), 2.71-2.66 (m, 1H), 2.62-2.57 (m, 1H), 1.34 (d, J=7.0 Hz, 3H)

Step 3: Synthesis of (R)—N—((S)-3-(4-cyanophenyl)-2-(dimethylamino)propyl)-3-phenylbutanamide (A-10e)

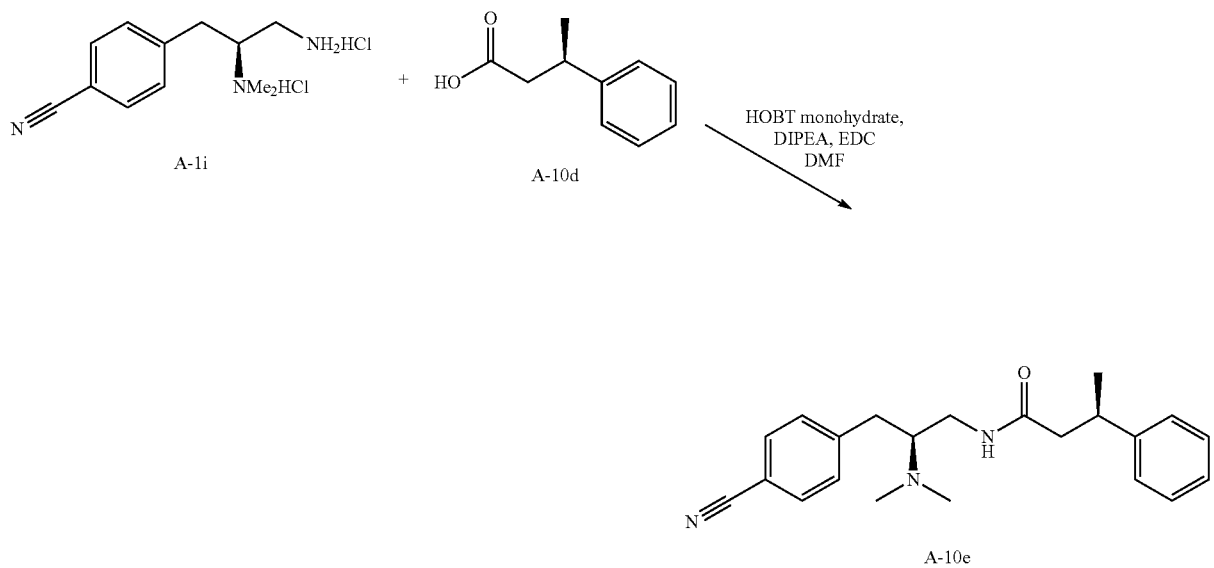

To 160 mg of the amine HCl (A-1i) (1.00 equiv., 579 μmol), 133 mg of HOBT monohydrate (1.50 equiv., 869 μmol) was added followed by the addition of 800 μL of DMF (5.00 volEquiv.). Next, 349 μL of DIPEA (3.50 equiv., 2.03 mmol) was added and the reaction mixture was cooled to 0° C. In a separate vial, 800 μL of DMF (5.00 volEquiv.) was added to 95.4 mg of acid (A-10d) (1.00 equiv 581 μmol) and then transferred to the reaction mixture at 0° C. Finally, 167 mg of EDC (1.5 equiv., 869 μmol) was added and allowed to stir at 0° C. for 5 minutes, after which it was allowed to stir at rt. After 3 hours, the reaction was quenched by adding water and stirred for 10 minutes. The white solid was extracted using ethyl acetate. The combined organic layers were washed with sat. NaHCO$_3$ twice, then with water, and brine. The solvent was then evaporated. The resultant product (A-10e) was flashed in 9:0.5:0.2 DCM/MeOH/NH$_3$ in MeOH giving 156.5 mg of product (77.3% yield).

Step 4: Synthesis of ((R)-2-(dimethylamino)-3-((S)-3-phenylbutanamido)propyl) benzamide (Compound A-10)

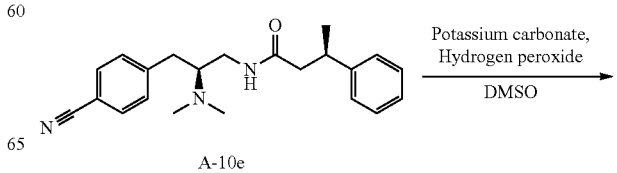

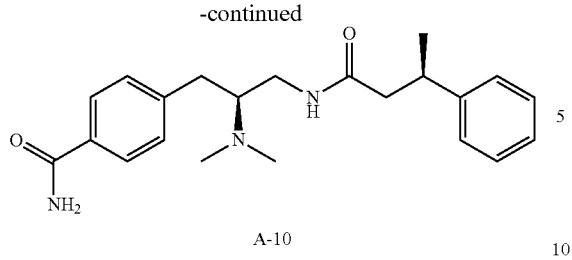

A-10

54.8 mg of starting material (A-10e) (1.00 equiv., 157 μmol) was added to a vial and dissolved in 165 μL of DMSO (3.01 volEquiv.). Next, 80.2 mg of potassium carbonate (3.00 equiv., 470 μmol) was added to the reaction mixture. Finally, 28.0 microliters hydrogen peroxide (30% aqueous, 1.75 equiv., 274 μmol) was added dropwise to the reaction mixture. The reaction was then stirred and monitored via LCMS. After 50 minutes another 1.75 equivalents of hydrogen peroxide were added to push the reaction forward, and the reaction mixture was monitored via LCMS. After 20 minutes the reaction was quenched using 0.5 mL of water, and 0.5 mL of 10% w/w aqueous sodium thiosulfate. The product was then extracted using ethyl acetate (1 mL×3) and the aqueous layer was tested via LCMS and TLC for presence of product. The organic layer was then dried using NaSO4 and concentrated in vacuo yielding 24.4 mg of product, Compound A-10 (42.3% yield). An NMR sample was taken in CDCl$_3$. The CDCl$_3$ peak covered part of the spectra so another NMR sample was prepared in deuterated methanol. (M+H=368.4) $^1$H NMR (400 MHz, METHANOL-d4) δ=7.8-7.78 (d, J=8.28 Hz, 2H), 7.26-7.18 (m, 6H), 7.14-7.10 (m, 1H), 2.27 (s, 6H), 1.25-1.24 (d, 3H).

Example A11

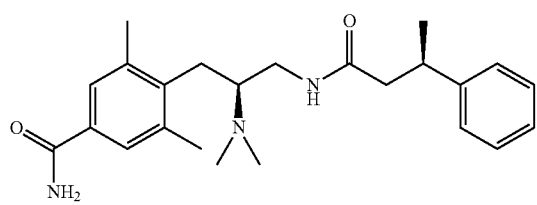

A-11

Synthesis of 4-((S)-2-(dimethylamino)-3-((R)-3-phenylbutanamido)propyl)-3,5-dimethylbenzamide (Compound A-11)

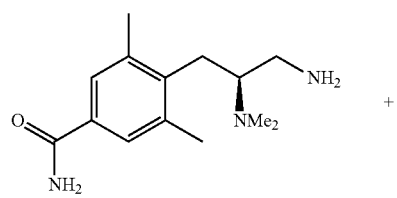

A-8f

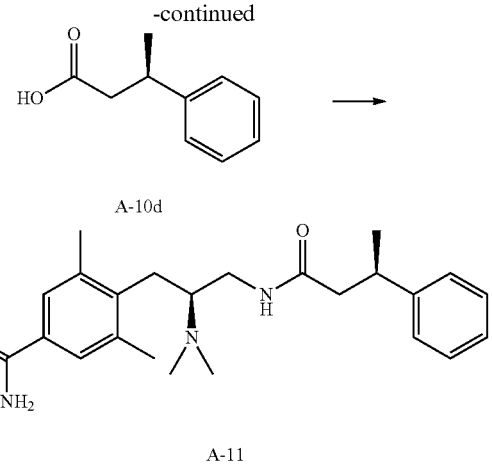

A-10d

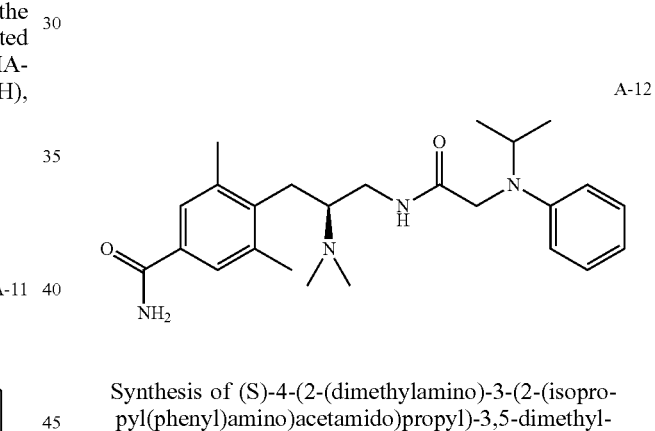

A-11

4-((S)-2-(dimethylamino)-3-((R)-3-phenylbutanamido)propyl)-3,5-dimethylbenzamide (Compound A-11) was synthesized according to the procedure for Example A8 using (R)-3-phenylbutanoic acid (A-10d) as the starting material. LC-MS: 396.3 [M+H]$^+$; $^1$H NMR (400 MHz, DMSO-d6) δ 7.81 (s, 1H), 7.47 (m, 3H), 7.30-7.10 (m, 6H), 3.15-3.05 (m, 2H), 2.90-2.75 (m, 2H), 2.65 (m, 1H), 2.35-2.20 (m, 14H), 1.14 (d, 3H, J=7.0 Hz).

Example A12

A-12

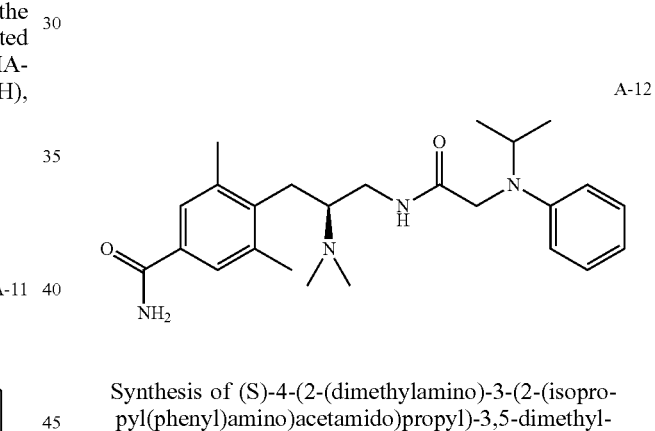

Synthesis of (S)-4-(2-(dimethylamino)-3-(2-(isopropyl(phenyl)amino)acetamido)propyl)-3,5-dimethylbenzamide (Compound A-12)

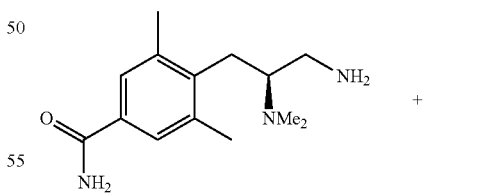

A-8f

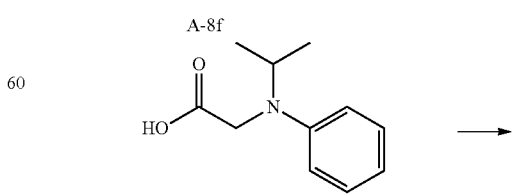

A-12a

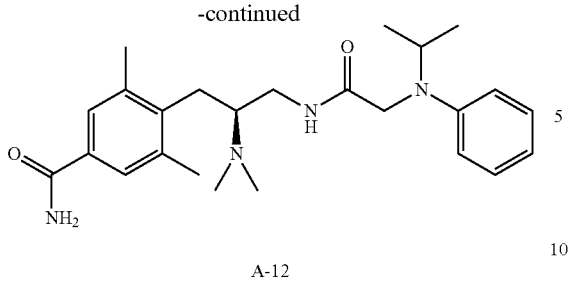

A-12

(S)-4-(2-(dimethylamino)-3-(2-(isopropyl(phenyl)amino) acetamido) propyl)-3,5-dimethylbenzamide (Compound A-12) was synthesized according to the procedure for Example A8 using N-isopropyl-N-phenylglycine (A-12a) (Rheem A. Totah, et al. J. Am. Chem. Soc. 2001, 123, 10107) as the starting material. LC-MS: 425.3 [M+H]$^+$; $^1$H NMR (400 MHz, DMSO-d6) δ 7.81 (s, 1H), 7.48 (s, 2H), 7.40 (t, 1H, J=5.2 Hz), 7.20 (s, 1H), 7.15 (t, 2H, J=8.0 Hz), 6.70-6.60 (m, 3H), 4.10 (m, 1H), 3.57 (s, 2H), 3.13 (m, 1H), 2.92-2.75 (m, 2H), 2.68 (m, 1H), 2.28 (s, 6H), 2.22 (s, 6H), 1.08 (t, 6H, J=5.6 Hz).

Example A13

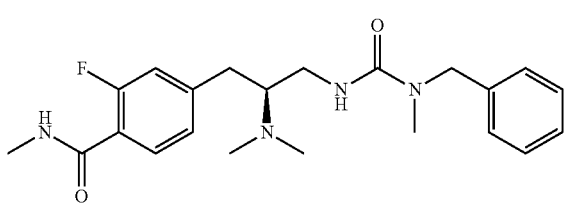

A-13

Synthesis of (S)-4-(3-(3-benzyl-3-methylureido)-2-(dimethylamino)propyl)-2-fluoro-N-methylbenzamide (Compound A-13)

To a stirred solution of (S)-4-(3-amino-2-(dimethylamino)propyl)-2-fluoro-N-methylbenzamide (Int-4F) (50.6 mg, 0.20 mmol, 1 equiv) in dry DMF (2 mL) was added CDI (35 mg, 0.22 mmol, 1.1 equiv). After stirring at RT for 4 h under nitrogen, DIPEA (70 μL, 0.4 mmol, 2 equiv) and N-methyl-1-phenylmethanamine (31 μL, 0.24 mmol, 1.2 equiv) were added and continued to stir overnight. The solution was concentrated under vacuum and the residue was purified by flash column chromatography over silica gel (0-25% MeOH in CH$_2$Cl$_2$ with 1% NH$_4$OH) to afford a white solid (47.1 mg, 59% yield). $^1$H NMR (400 MHz, CDCl$_3$) δ 8.06 (t, J=7.95 Hz, 1H) 7.76 (s, 2H) 7.32-7.52 (m, 6H) 7.14-7.18 (m, 1H) 7.00-7.09 (m, 1H), 5.54 (br d, J=6.60 Hz, 1H), 4.62 (d, J=2.45 Hz, 2H), 3.46 (ddd, J=12.66, 7.40, 4.65 Hz, 1H), 3.19 (d, J=4.65 Hz, 3H), 3.08-3.14 (m, 2H), 3.04-3.08 (m, 3H), 2.89-2.98 (m, 1H), 2.38-2.53 (m, 7H). LCMS: 401.3 [M]$^+$.

Example A14

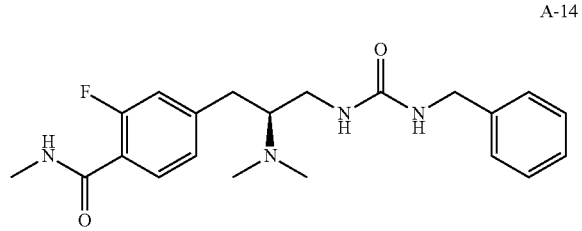 [SMILES: CNC(=O)c1ccc(C[C@@H](CNC(=O)NCc2ccccc2)N(C)C)cc1F]

A-14

Synthesis of (S)-4-(3-(3-benzylureido)-2-(dimethylamino)propyl)-2-fluoro-N-methylbenzamide (Compound A-14)

To a stirred solution of (S)-4-(3-amino-2-(dimethylamino)propyl)-2-fluoro-N-methylbenzamide (Int-4F) (50.6 mg, 0.20 mmol, 1 equiv) in dry DMF (2 mL) was added CDI (35 mg, 0.22 mmol, 1.1 equiv). After stirring at RT for 4 h under nitrogen, DIPEA (70 μL, 0.4 mmol, 2 equiv) and N-methyl-1-phenylmethanamine (31 μL, 0.24 mmol, 1.2 equiv) were added and continued to stir overnight. The solution was concentrated under vacuum and the residue was purified by flash column chromatography over silica gel (0-25% MeOH in CH$_2$Cl$_2$ with 1% NH$_4$OH) to afford a white solid (47.1 mg, 59% yield). $^1$H NMR (400 MHz, CDCl$_3$) δ 8.01 (t, J=8.07 Hz, 1H), 7.73-7.83 (m, 3H), 7.36-7.57 (m, 12H), 7.14-7.18 (m, 1H), 7.03-7.10 (m, 1H), 6.24 (br s, 1H), 5.86 (br d, J=5.38 Hz, 1H), 4.50 (d, J=5.62 Hz, 2H), 3.63-3.67 (m, 6H), 3.34-3.48 (m, 1H), 3.03-3.20 (m, 5H), 2.91-3.02 (m, 1H), 2.48-2.58 (m, 1H), 2.45 (s, 5H), 1.39-1.44 (m, 1H). LCMS: 401.3 [M]$^+$.

Example A15

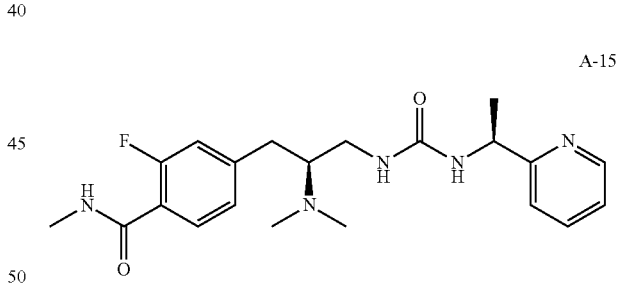

A-15

Synthesis of 4-((S)-2-(dimethylamino)-3-(3-((S)-1-(pyridin-2-yl)ethyl)ureido)propyl)-2-fluoro-N-methylbenzamide (Compound A-15)

To a stirred solution of (S)-4-(3-amino-2-(dimethylamino)propyl)-2-fluoro-N-methylbenzamide (Int-4F) (50 mg, 0.20 mmol, 1 equiv) in dry DMF (2 mL) was added CDI (35 mg, 0.22 mmol, 1.1 equiv). After stirring at RT for 4 h under nitrogen, DIPEA (70 μL, 0.4 mmol, 2 equiv) and (S)-1-(pyridin-2-yl)ethan-1-amine (29 μL, 0.24 mmol, 1.2 equiv) were added and continued to stir overnight. The solution was concentrated under vacuum and the residue was purified by flash column chromatography over silica gel (0-25% MeOH in CH$_2$Cl$_2$ with 1% NH$_4$OH) to afford a white solid (70.7 mg, 88% yield). $^1$H NMR (400 MHz, CDCl$_3$) δ 8.70 (d, J=4.88 Hz, 1H), 8.02-8.10 (m, 1H), 7.93-8.02 (m, 1H), 7.79-7.87 (m, 1H), 7.74-7.77 (m, 1H), 7.50-7.57 (m, 1H), 7.45-7.49 (m, 1H), 7.33-7.41 (m, 2H), 7.18 (dd, J=8.07, 1.47 Hz, 1H), 7.07 (dd, J=12.59, 1.10 Hz, 1H), 6.38 (br d, J=6.11 Hz, 1H), 5.78 (br d, J=5.14 Hz, 1H), 5.13 (quin, J=6.91 Hz, 1H), 3.39 (ddd, J=12.72, 7.34, 4.89 Hz, 1H), 3.08-3.24 (m, 5H), 2.92-3.04 (m, 1H), 2.50-2.61 (m, 2H), 2.43-2.50 (m, 6H), 1.60-1.67 (m, 3H). LCMS: 402.2 [M]$^+$.

Example A16

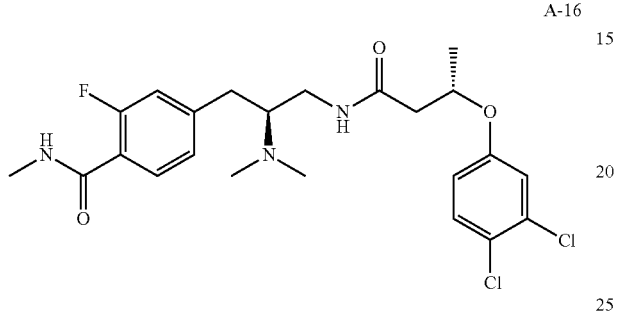

A-16

Synthesis of 4-((S)-3-((S)-3-(3,4-dichlorophenoxy)butanamido)-2-(dimethylamino)propyl)-2-fluoro-N-methylbenzamide (Compound A-16)

To a stirred solution of (S)-4-(3-amino-2-(dimethylamino)propyl)-2-fluoro-N-methylbenzamide (Int-4F) (43 mg, 0.17 mmol, 1 equiv) in dry DMF (2 mL) was added 2,5-dioxopyrrolidin-1-yl (S)-3-(3,4-dichlorophenoxy)butanoate (63.7 mg, 0.18 mmol, 1.08 equiv) under nitrogen. After 2 h, the solution was concentrated under vacuum and the residue was purified by flash column chromatography over silica gel (0-25% MeOH in CH$_2$Cl$_2$ with 1% NH$_4$OH) to afford a white solid (54.8 mg, 66% yield). $^1$H NMR (400 MHz, CDCl$_3$) δ 7.98 (t, J=8.19 Hz, 1H), 7.28 (d, J=8.80 Hz, 1H), 7.01 (s, 1H), 6.98-7.00 (m, 1H), 6.71-6.89 (m, 3H), 6.56 (br d, J=5.62 Hz, 1H), 4.70-4.78 (m, 1H), 3.34 (ddd, J=13.63, 6.91, 4.89 Hz, 1H), 2.98-3.04 (m, 3H), 2.84-2.98 (m, 2H), 2.60-2.72 (m, 1H), 2.49-2.61 (m, 1H), 2.29-2.47 (m, 2H), 2.20-2.29 (m, 7H), 1.32 (d, J=6.11 Hz, 3H). LCMS: 484.2 [M]$^+$.

Example A17

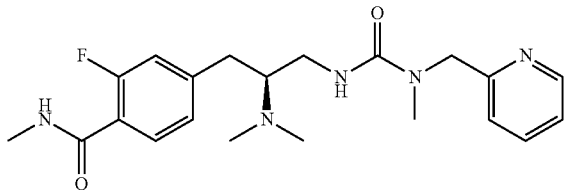

A-17

Synthesis of (S)-4-(2-(dimethylamino)-3-(3-methyl-3-(pyridin-2-ylmethyl)ureido)propyl)-2-fluoro-N-methylbenzamide (Compound A-17)

To a stirred solution of (S)-4-(3-amino-2-(dimethylamino)propyl)-2-fluoro-N-methylbenzamide (Int-4F) (42.5 mg, 0.17 mmol, 1 equiv) in dry DMF (2 mL) was added CDI (30 mg, 0.19 mmol, 1.1 equiv). After stirring at RT for 4 h under nitrogen, DIPEA (59 μL, 0.34 mmol, 2 equiv) and N-methyl-1-(pyridin-2-yl)methanamine (25 μL, 0.2 mmol, 1.2 equiv) were added and continued to stir overnight. The solution was concentrated under vacuum and the residue was purified by flash column chromatography over silica gel (0-15% MeOH in CH$_2$Cl$_2$ with 1% NH$_4$OH) to afford a white solid (18.7 mg, 27% yield). $^1$H NMR (400 MHz, CDCl$_3$) δ 8.52 (d, J=4.98 Hz, 1H), 8.00 (t, J=8.19 Hz, 1H), 7.66 (td, J=7.64, 1.83 Hz, 1H), 7.24 (d, J=7.83 Hz, 1H), 7.18 (ddd, J=7.58, 4.89, 1.22 Hz, 1H), 7.06 (dd, J=8.07, 1.47 Hz, 1H), 6.94 (dd, J=12.96, 1.47 Hz, 1H), 6.73 (br d, J=7.83 Hz, 1H), 5.72 (br s, 1H), 4.46-4.57 (m, 2H), 3.34 (ddd, J=13.21, 6.85, 4.89 Hz, 1H), 2.84-3.07 (m, 9H), 2.37-2.50 (m, 1H), 2.30-2.36 (m, 6H), 1.87-2.13 (m, 2H). LCMS: 402.2 [M]$^+$.

Example A18

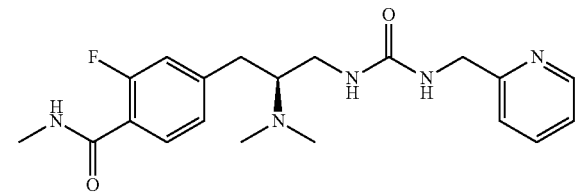

A-18

Synthesis of (S)-4-(2-(dimethylamino)-3-(3-(pyridin-2-ylmethyl)ureido)propyl)-2-fluoro-N-methylbenzamide (Compound A-18)

To a stirred solution of (S)-4-(3-amino-2-(dimethylamino)propyl)-2-fluoro-N-methylbenzamide (Int-4F) (42.5 mg, 0.17 mmol, 1 equiv) in dry DMF (2 mL) was added CDI (30 mg, 0.19 mmol, 1.1 equiv). After stirring at RT for 4 h under nitrogen, DIPEA (59 μL, 0.34 mmol, 2 equiv) and pyridin-2-ylmethanamine (21 μL, 0.2 mmol, 1.2 equiv) were added and continued to stir overnight. The solution was concentrated under vacuum and the residue was purified by flash column chromatography over silica gel (0-15% MeOH in CH$_2$Cl$_2$ with 1% NH$_4$OH) to afford a white solid (70.7 mg, 88% yield). $^1$H NMR (400 MHz, CDCl$_3$) δ 8.49 (d, J=5.13 Hz, 1H), 7.97 (t, J=8.19 Hz, 1H), 7.64 (td, J=7.64, 1.83 Hz, 1H), 7.25-7.29 (m, 2H), 7.17 (t, J=6.22 Hz, 1H), 7.04 (d, J=8.14 Hz, 1H), 6.91 (dd, J=12.96, 1.47 Hz, 1H), 6.78 (br dd, J=11.86, 5.26 Hz, 1H), 5.69 (br s, 1H), 5.38 (br d, J=5.62 Hz, 1H), 4.45 (d, J=5.38 Hz, 2H), 3.22-3.30 (m, 1H), 2.92-3.03 (m, 5H), 2.73-2.88 (m, 1H), 2.38 (dd, J=13.33, 9.66 Hz, 1H), 2.28-2.33 (m, 6H), 2.10-2.21 (m, 3H). LCMS: 388.2 [M]$^+$.

Example A19

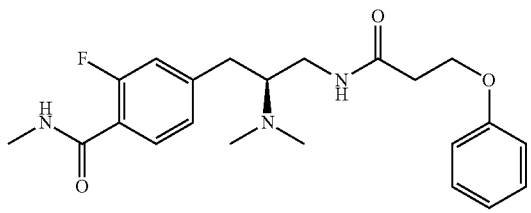

A-19

Synthesis of (S)-4-(2-(dimethylamino)-3-(3-phenoxypropanamido)propyl)-2-fluoro-N-methylbenzamide (Compound A-19)

To a stirred solution of (S)-4-(3-amino-2-(dimethylamino)propyl)-2-fluoro-N-methylbenzamide (Int-4F) (21 mg, 0.08 mmol, 1 equiv) in dry DMF (1 mL) was added EDCI (25 mg, 0.13 mmol, 1.5 equiv), HOBt (18 mg, 0.13 mmol, 1.5 equiv), 3-phenoxypropanoic acid (15 mg, 0.9 mmol, 1.1 equiv), and DIPEA (89 µL, 0.5 mmol, 6 equiv). After 6 h, the solution was diluted with water and extracted with EtOAc. The combined organic layers were washed with aq. NaHCO$_3$ and brine, dried over anhydrous sodium sulfate, and concentrated. The residue was purified by flash column chromatography over silica gel (0-15% MeOH in CH$_2$Cl$_2$) to afford a white solid (7.5 mg, 24% yield). $^1$H NMR (400 MHz, CDCl$_3$) δ 7.96-8.02 (m, 1H), 7.23-7.28 (m, 5H), 6.84-7.04 (m, 5H), 6.62-6.75 (m, 2H), 4.16-4.23 (m, 2H), 3.33-3.42 (m, 1H), 2.87-3.07 (m, 5H), 2.67-2.82 (m, 1H), 2.61 (t, J=5.87 Hz, 2H), 2.26-2.36 (m, 8H), 1.75-1.93 (m, 5H). LCMS: 402.2 [M]$^+$.

Example A20

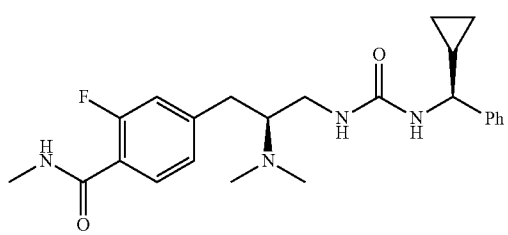

A-20

Synthesis of 4-((S)-3-(3-((S)-cyclopropyl(phenyl)methyl)ureido)-2-(dimethylamino)propyl)-2-fluoro-N-methylbenzamide (Compound A-20)

To a stirred solution of 4-((S)-2-amino-3-(3-((S)-cyclopropyl(phenyl)methyl)ureido)propyl)-2-fluoro-N-methylbenzamide (76 mg, 0.19 mmol, 1 equiv) in 9:1 CH$_3$CN:H$_2$O at 0° C. was added NaCNBH$_4$ (60 mg, 0.95 mmol, 5 equiv) and 37% formaldehyde (21 µL, 0.57 mmol, 3 equiv). After 10 min, HOAc (55 ul, 0.95 mmol, 5 equiv) was added and the solution was allowed to warm to rt for 4 h. Ethyl acetate (10 mL) was added and the solution was washed with aq. NaHCO$_3$ and brine, dried over anhydrous sodium sulfate, and concentrated. The residue was purified by flash column chromatography over silica gel (0-15% MeOH in CH$_2$Cl$_2$) to afford a white solid (45 mg, 58% yield). $^1$H NMR (400 MHz, CDCl$_3$) δ 7.26 (d, J=4.40 Hz, 4H). 6.91-7.01 (m, 1H). 6.79-6.91 (m, 1H). 6.50-6.76 (m, 1H). 3.86-3.98 (m, 1H). 3.08-3.18 (m, 1H). 2.85-3.00 (m, 6H). 2.26-2.34 (m, 5H). 1.11-1.17 (m, 2H). 0.99-1.09 (m, 1H). 0.37-0.56 (m, 2H). 0.21-0.37 (m, 2H). LCMS: 427.2 [M]$^+$.

Example A21

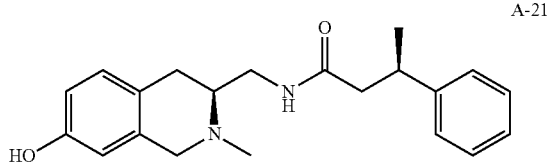 [SMILES: C[C@H](CC(=O)NC[C@@H]1Cc2ccc(O)cc2CN1C)c1ccccc1]

A-21

Synthesis of (R)—N—(((S)-7-hydroxy-2-methyl-1,2,3,4-tetrahydroisoquinolin-3-yl)methyl)-3-phenylbutanamide (Compound A-21)

To a stirred solution of (S)-3-(aminomethyl)-2-methyl-1,2,3,4-tetrahydroisoquinolin-7-ol (50 mg, 0.52 mmol, 1 equiv) in dry DMF (3 mL) was added EDCI (100 mg, 1.04 mmol, 2 equiv), HOBt (70 mg, 1.04 mmol, 2 equiv), (R)-3-phenylbutanoic acid (47 mg, 0.57 mmol, 1.1 equiv), and DIPEA (226 µL, 2.6 mmol, 5 equiv). After 3 h, the solution was diluted with water and extracted with EtOAc. The combined organic layers were washed with aq. NaHCO$_3$ and brine, dried over anhydrous sodium sulfate, and concentrated. The residue was purified by flash column chromatography over silica gel (0-10% MeOH in CH$_2$Cl$_2$) to afford a white solid (8.1 mg, 5% yield). $^1$H NMR (400 MHz, CDCl$_3$) δ 7.15-7.30 (m, 6H), 6.86 (d, J=8.31 Hz, 1H), 6.60 (br d, J=7.83 Hz, 1H), 6.40 (s, 1H), 6.03 (br s, 1H), 3.59-3.69 (m, 1H), 3.44-3.57 (m, 2H), 3.19-3.38 (m, 3H), 2.39-2.66 (m, 5H), 2.20 (s, 3H), 1.28 (d, J=6.85 Hz, 3H), 1.21 (t, J=6.97 Hz, 2H). LCMS: 339.2 [M]$^+$.

Example A22

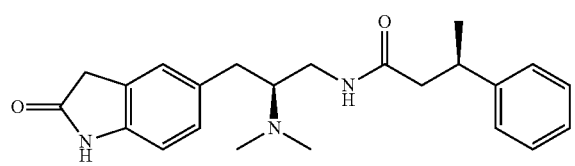

A-22

Synthesis of (R)—N—((S)-2-(dimethylamino)-3-(2-oxoindolin-5-yl)propyl)-3-phenylbutanamide (Compound A-22)

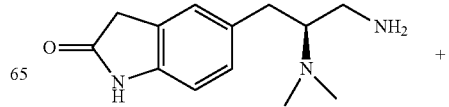

-continued

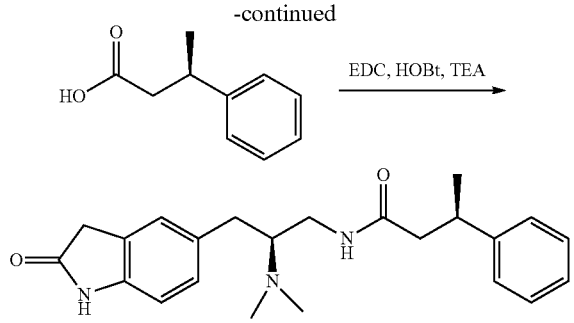

(R)—N—((S)-2-(dimethylamino)-3-(2-oxoindolin-5-yl) propyl)-3-phenylbutanamide was synthesized according to the general procedure using (S)-5-(3-amino-2-(dimethylamino)propyl)indolin-2-one and (R)-3-phenylbutanoic acid as the starting materials. LC-MS: 380.2 [M+H]$^+$; $^1$H NMR (400 MHz, DMSO-d6) δ 10.25 (s, 1H), 7.44 (m, 1H), 7.30-7.10 (m, 5H), 6.98 (s, 1H), 6.93 (d, 1H, J=7.9 Hz), 6.69 (d, 1H, J=7.9 Hz), 3.42 (s, 2H), 3.15-2.90 (m, 3H), 2.65 (dd, 1H, J=13.4, 5.5 Hz), 2.55 (m, 1H), 2.40-2.20 (m, 3H), 2.20 (s, 6H), 1.15 (d, 3H, J=6.9 Hz).

Example A23

A-23

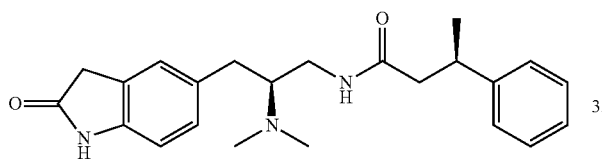

Synthesis of (S)—N—((S)-2-(dimethylamino)-3-(2-oxoindolin-5-yl)propyl)-3-phenylbutanamide (Compound A-23)

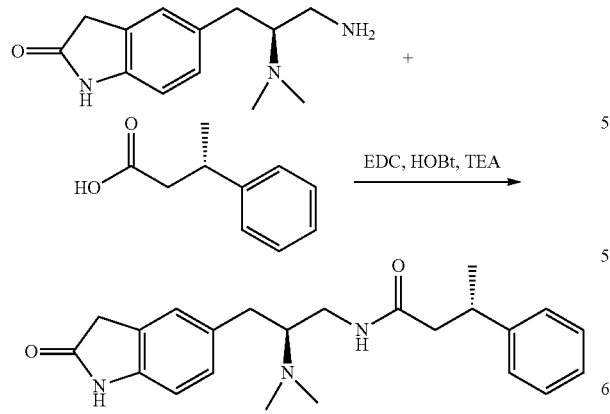

(S)—N—((S)-2-(dimethylamino)-3-(2-oxoindolin-5-yl) propyl)-3-phenylbutanamide was synthesized according to the general procedure using (S)-5-(3-amino-2-(dimethylamino)propyl)indolin-2-one and (S)-3-phenylbutanoic acid as the starting materials. LC-MS: 380.2 [M+H]$^+$; $^1$H NMR (400 MHz, DMSO-d6) δ 10.25 (s, 1H), 7.46 (br t, 1H), 7.30-7.15 (m, 5H), 6.97 (s, 1H), 6.92 (d, 1H, J=8.0 Hz), 6.69 (d, 1H, J=7.9 Hz), 3.42 (s, 2H), 3.12 (m, 1H), 3.05-2.90 (m, 2H), 2.70-2.55 (m, 2H), 2.40-2.22 (m, 3H), 2.19 (s, 6H), 1.14 (d, 3H, J=6.9 Hz).

B. Synthesis of Compounds Having the Structure of Formula (I-B)

Representative Compounds having the structure of Formula (I-B) can be synthesized by using the general synthetic procedures set forth in Schemes B1-B3.

Scheme B1

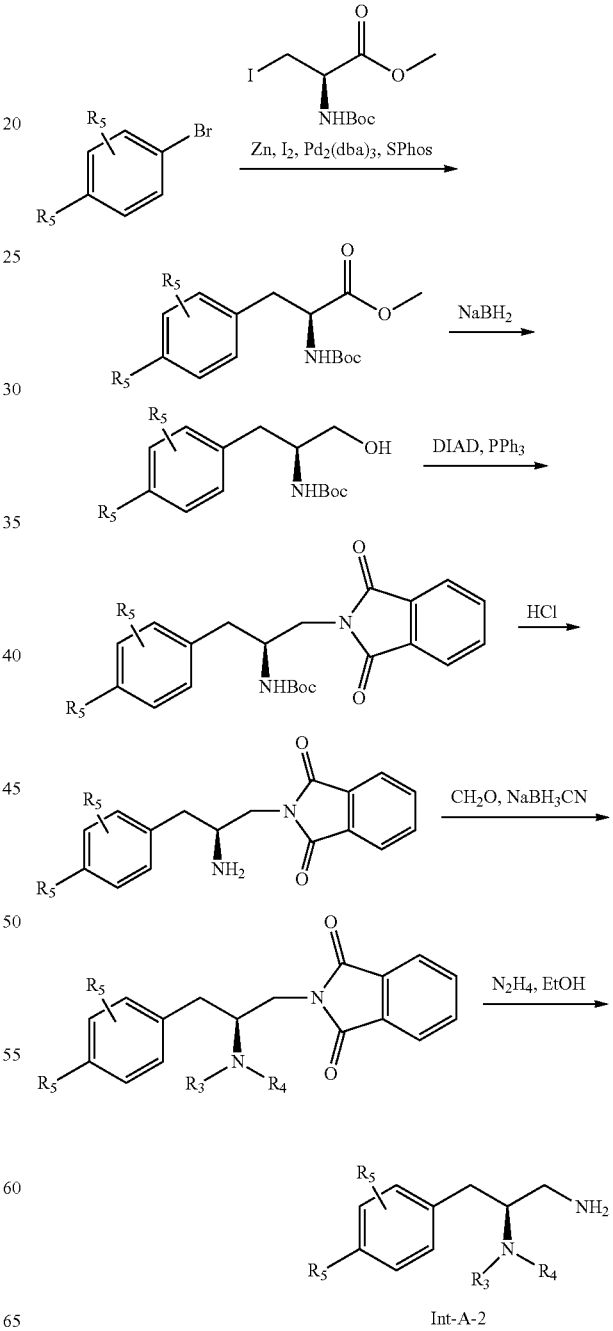

Int-A-2

Scheme B2

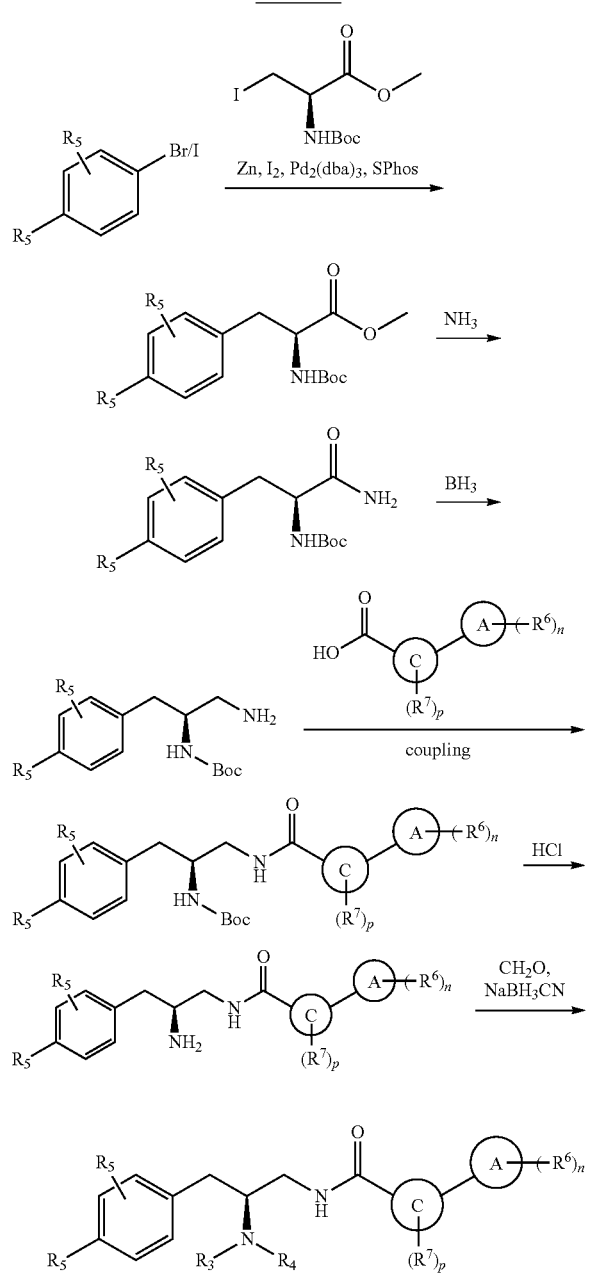

Scheme B3

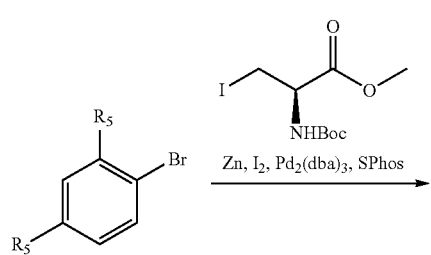

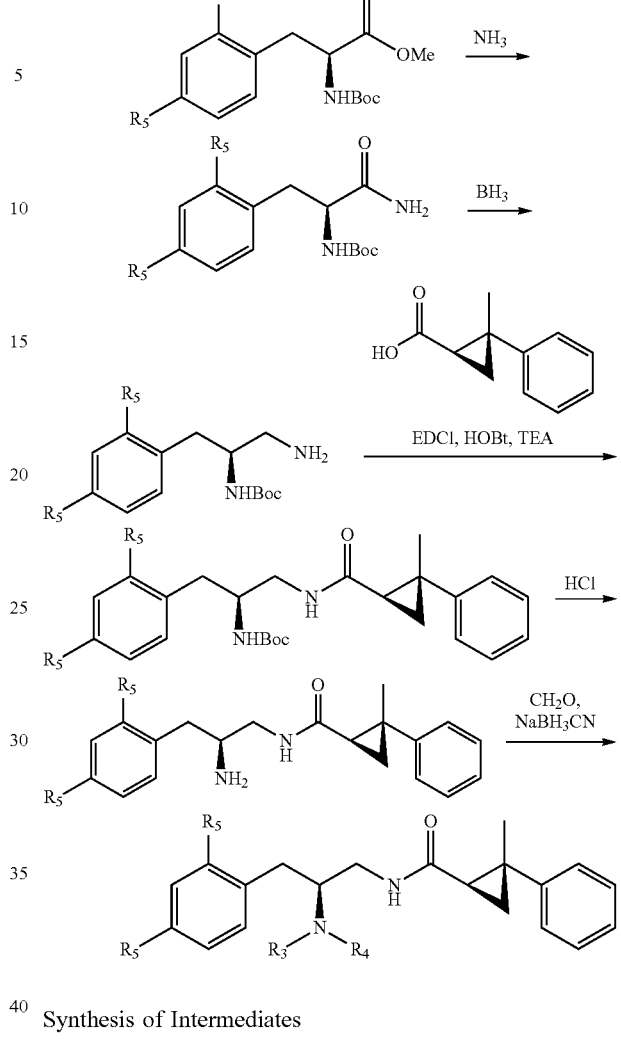

Synthesis of Intermediates

Synthesis of (S)-3-(3-fluorophenyl)-N2,N2-dimethylpropane-1,2-diamine Dihydrochloride (Int-5)

Step 1: Synthesis of (S)-2-((tert-butoxycarbonyl)amino)-3-(3-fluorophenyl)propanoic Acid (Int-1)

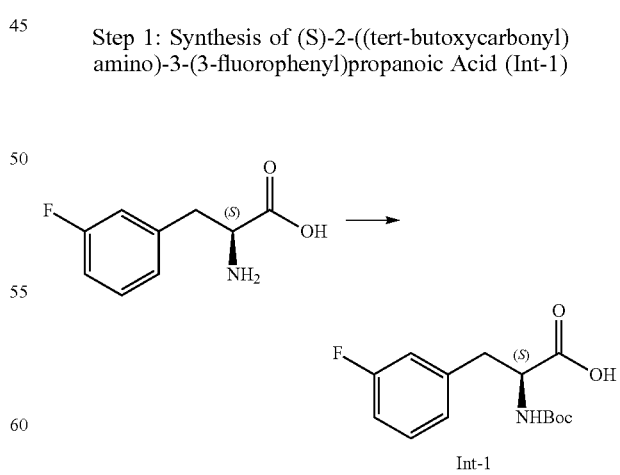

3-Fluoro-L-Phenylalanine (1 g, 5.46 mmol, Combi-blocks, Cat #SS-0819, Lot #L78093) was dissolved in THF (15 mL) and water (15 mL) and the pH of the solution was adjusted to 9 using saturated sodium bicarbonate solution.

Di-tert-butyl-dicarbonate (1.31 g, 6 mmol) was added to the solution slowly and was stirred overnight. After completion of the reaction, the pH of the solution was adjusted to 4 using 0.1 M HCl and the aqueous layer was extracted with ethyl acetate. Combined organic layers were washed with water (×2) followed by brine, dried using sodium sulfate, filtered and concentrated under reduced pressure to afford 1.5 g (97% yield) off-white solid of the title product (Int-1). LCMS (+ESI) M+H+(−Boc)=184.1.

Step 2: Synthesis of tert-butyl (S)-(1-amino-3-(3-fluorophenyl)-1-oxopropan-2-yl)carbamate (Int-2)

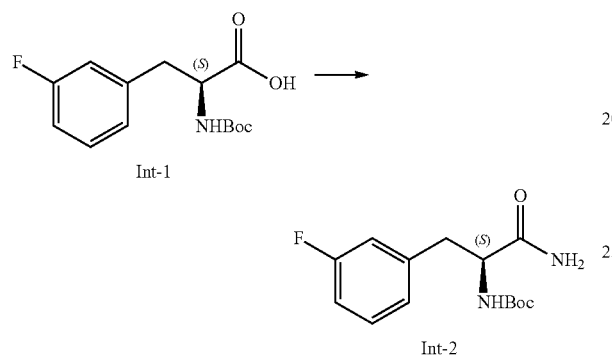

To a solution of Int-1 (1.5 g, 5.29 mmol) and DMF (15 mL), DIPEA (2.77 mL, 15.9 mmol), HATU (3.02 g, 7.94 mmol), HOBt monohydrate (715 mg, 5.29 mmol) and ammonium carbonate (4.19 g, 52.9 mmol) were added and was allowed to stir at room temperature overnight. After completion of the reaction, the mixture was diluted with ether and the organic layer was washed with water (×2) followed by brine, dried using sodium sulfate, filtered and concentrated under reduced pressure to afford 1.1 g (74% yield) an off-white solid of Int-2. LCMS (+ESI) M+H+(−Boc)=183.1. 1H NMR (400 MHz, CHLOROFORM-d) δ=7.30-7.26 (m, 1H), 7.02 (d, J=7.8 Hz, 1H), 6.98-6.91 (m, 2H), 6.02 (br s, 1H), 5.60 (br s, 1H), 5.11 (br d, J=8.0 Hz, 1H), 4.39 (br d, J=6.0 Hz, 1H), 3.07 (m, 2H), 1.41 (s, 9H).

Step 3: Synthesis of (S)-2-amino-3-(3-fluorophenyl) propenamide Hydrochloride (Int-3)

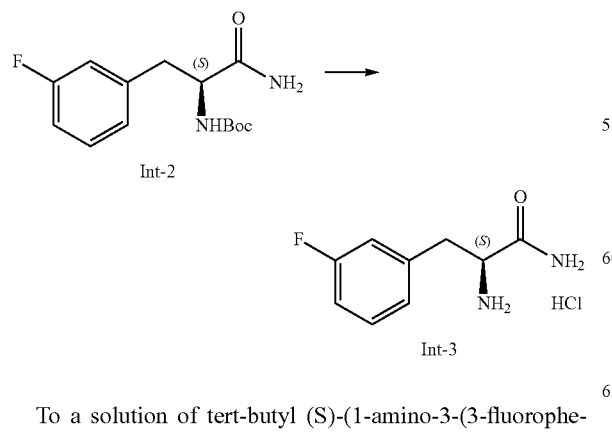

To a solution of tert-butyl (S)-(1-amino-3-(3-fluorophenyl)-1-oxopropan-2-yl)carbamate (Int-2) (1.1 g, 3.9 mmol) and THF (5.5 mL), 4 M HCl in dioxane (3.9 mL, 15.6 mmol) was added and was allowed to stir until no starting material was observed (by TLC). After completion of the reaction, the solvent was evaporated under reduced pressure. Obtained solid was re-dissolved in ether and was evaporated under reduced pressure (this step was repeated two more times). Obtained solid was dried under high vacuum to afford 710 mg (99% yield) of the title product (Int-3). LCMS (+ESI) M+H+=183.1.

Step 4: Synthesis of (S)-2-(dimethyl amino)-3-(3-fluorophenyl) propanamide Hydrochloride (Int-4)

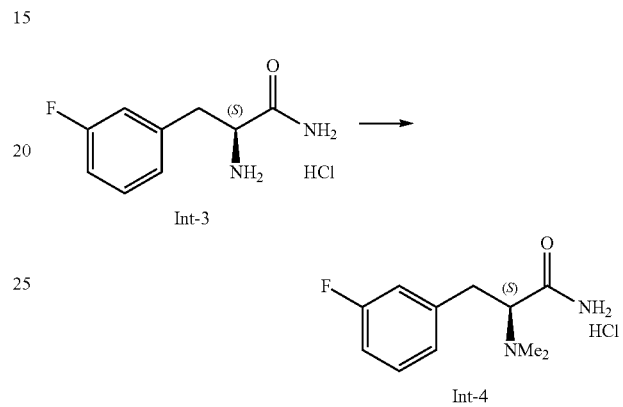

To a solution of (S)-2-amino-3-(3-fluorophenyl)propenamide hydrochloride (Int-3) (710 mg, 3.8 mmol) and 9:1 acetonitrile and water (9.9 mL), formaldehyde (13.3 M, 2.93 mL, 39 mmol) was added and was cooled to 0° C. Sodium triacetoxyborohydride (2.06 g, 9.74 mmol) was added portion wise and was stirred for 15 minutes. The completion of the reaction was monitored by LCMS. After completion of the reaction, the mixture was quenched with saturated sodium bicarbonate solution (11.5 mL) and the pH of the solution was adjusted to 8 using 5% sodium carbonate solution. The aqueous layer was extracted with 1:3 isopropanol and ethyl acetate (×4). Combined organic layers were washed with brine, dried using sodium sulfate, filtered and concentrated under reduced pressure. The crude material was re-dissolved in isopropanol and was treated with 37% HCl (12 M, 0.3 mL). The solution was partially concentrated and was precipitated using ethyl ether. The solid was filtered and washed with ether, dried under high vacuum to afford 960 mg (99% yield) of the title product (Int-4). LCMS (+ESI) M+H+=211.2.

Step 5: Synthesis of (S)-3-(3-fluorophenyl)-N2,N2-dimethylpropane-1,2-diamine Dihydrochloride (Int-5)

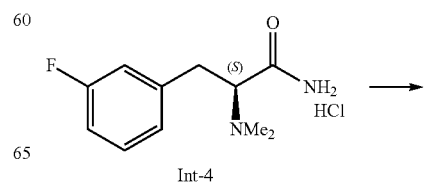

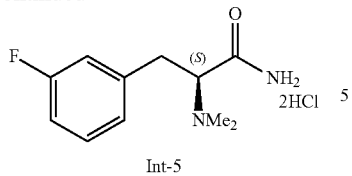

Int-5

(S)-2-(dimethylamino)-3-(3-fluorophenyl)propanamide hydrochloride (Int-4) (960 mg, 3.89 mmol) was dissolved in THF (14.4 mL) and was cooled to 0° C. Borane tetrahydrofuran (0.9 M, 26 mL, 23.3 mmol) was added to the solution slowly dropwise. After warming to room temperature, the mixture was refluxed (60° C.) for 20 hours. After completion of the reaction, the mixture was cooled and quenched using methanol and the solvent was evaporated under reduced pressure. The residue was re-dissolved in methanol and was evaporated under reduced pressure and this step was repeated two more times. Obtained oil was re-dissolved in isopropanol and 2 N HCl in ether was added followed by dilution with ether. The slurry was sonicated and was filtered to afford 530 mg (51% yield) of pale-yellow solid of the title product (Int-5). LCMS (+ESI) M+H+=197.2.

Synthesis of (S)-4-(3-amino-2-(dimethylamino)propyl)phenol Dihydrochloride (Int-7)

Step 1: Synthesis of (S)-2-(dimethylamino)-3-(4-hydroxyphenyl) propanamide Hydrochloride (Int-6)

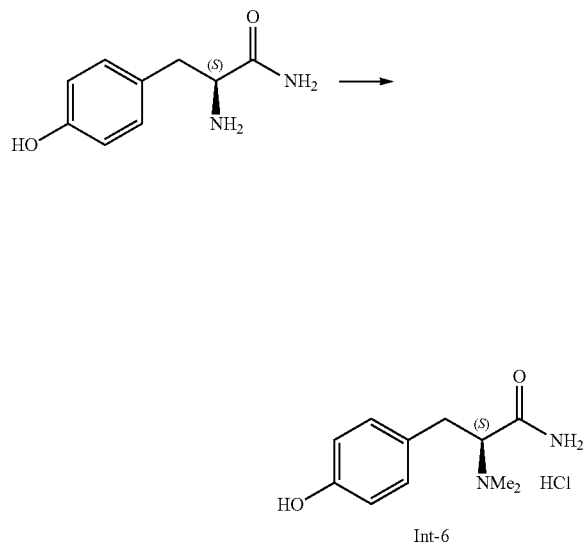

Int-6

(S)-2-(dimethylamino)-3-(4-hydroxyphenyl)propanamide hydrochloride (Int-6) was prepared by the same procedure as for Int-4, starting with L-tyrosinamide (Cat #SS-8156, Lot #L79234), for 95% yield. LCMS (+ESI) M+H+=209.2. $^1$H NMR (400 MHz, DMSO-d$_6$) δ=11.02 (br s, 1H), 9.42 (br s, 1H), 7.90 (s, 1H), 7.60 (s, 1H), 7.11-6.93 (m, 2H), 6.78-6.60 (m, 2H), 3.95 (br d, J=10.2 Hz, 1H), 3.17 (dd, J=4.1, 13.1 Hz, 1H), 2.94 (dd, J=10.8, 12.9 Hz, 1H), 2.79 (s, 6H).

Step 2: Synthesis of (S)-4-(3-amino-2-(dimethylamino)propyl)phenol Dihydrochloride (Int-7)

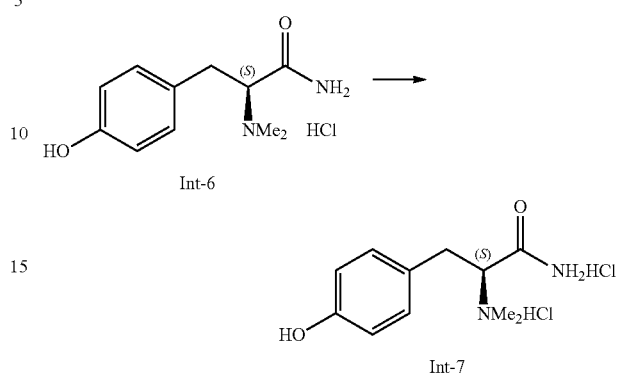

Int-6

Int-7

(S)-4-(3-amino-2-(dimethylamino)propyl)phenol dihydrochloride (Int-7) was prepared by the same procedure as for Int-5, using Int-6, for 86% yield. LCMS (+ESI) M+H+=195.2. $^1$H NMR (400 MHz, DMSO-d6) δ=11.14-10.93 (br s, 1H), 9.62-9.28 (br m, 1H), 8.50 (br s, 2H), 7.18-7.09 (m, 2H), 6.81-6.72 (m, 2H), 3.82-3.73 (m, 1H), 3.47-3.34 (m, 1H), 3.14 (br dd, J=3.3, 13.6 Hz, 1H), 2.96-2.74 (m, 6H), 2.73-2.55 (m, 2H).

Synthesis of (S)-4-(3-amino-2-(dimethylamino)propyl)benzamide (Int-13)

Step 1: Synthesis of tert-butyl (S)-(1-(4-cyanophenyl)-3-hydroxypropan-2-yl)carbamate (Int-8)

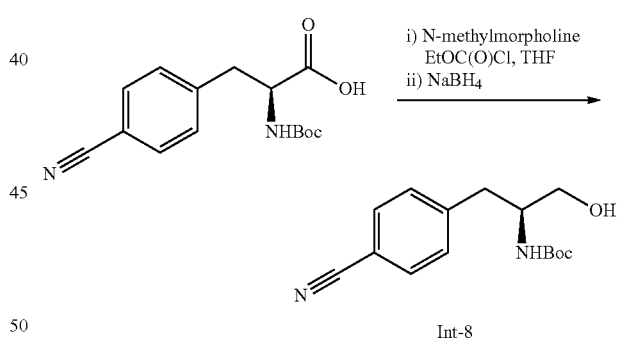

Int-8

To a stirred solution of the commercially available (S)-2-((tert-butoxycarbonyl)amino)-3-(4-cyanophenyl)propanoic acid (5.0 g, 17.2 mmol) in anhydrous THF (50 mL) at −10° C. under nitrogen was added N-methylmorpholine (1.89 mL, 17.2 mmol), followed by slow addition of ethyl chloroformate (1.65 mL, 17.2 mmol). After stirring at −10° C. for 10 min, the reaction mixture was warmed to rt and stirred for 1 h. The precipitates were filtered off and the filter cake was washed with THF. The filtrate was cooled to −10° C. and a solution of sodium borohydride (0.98 g, 25.9 mmol) in water (3 mL) was slowly added. After 1 h, the reaction was carefully quenched with 1N aq. HCl. The mixture was adjusted to pH 8-9 and extracted with EtOAc (3×). The combined organic layers were washed with brine, dried over anhydrous magnesium sulfate, and concentrated. The residue was purified by flash column chromatography over silica gel (0-80% EtOAc/CH₂Cl₂) to afford the title compound (Int-8) as a white powder (3.25 g, 68%). LC-MS: 299.2 [M+Na]⁺; ¹H NMR (400 MHz, CDCl₃) δ 7.60 (d, 2H, J=7.7 Hz), 7.35 (d, 2H, J=7.7 Hz), 4.77 (br d, 1H), 3.88 (br s, 1H), 3.68 (br d, 1H, J=10.8 Hz), 3.56 (dd, 1H, J=10.8, 4.4 Hz), 2.93 (d, 2H, J=6.7 Hz), 2.08 (br s, 1H), 1.40 (s, 9H).

Step 2: Synthesis of tert-butyl (S)-(1-(4-carbamoylphenyl)-3-hydroxypropan-2-yl)carbamate (Int-9)

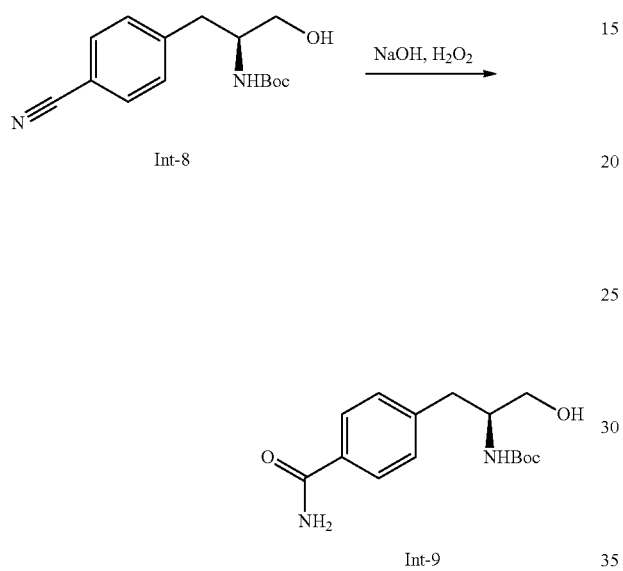

To a stirred solution of tert-butyl (S)-(1-(4-cyanophenyl)-3-hydroxypropan-2-yl)carbamate (Int-8) (1.7 g, 6.2 mmol) in methanol (50 mL) was added 6N aq. NaOH (1.03 mL, 6.2 mmol), followed by 27% aq. Solution of hydrogen peroxide (2.71 mL, 21.6 mmol). The reaction mixture was stirred at 50° C. for 3 h. After cooling, the mixture was neutralized with 1N aq. HCl. Removal of methanol in vacuo and the residue was triturated with water. The solids were collected by filtration and dried to obtain (Int-9) as a white powder (1.5 g, 83%). LC-MS: 317.1 [M+Na]⁺; ¹H NMR (400 MHz, DMSO-d6) δ 7.89 (s, 1H), 7.77 (d, 2H, J=8.2 Hz), 7.28 (s, 1H), 7.25 (d, 2H, J=8.2 Hz), 6.65 (d, 1H, J=8.6 Hz), 4.75 (t, 1H, J=5.2 Hz), 3.35 (m, 1H), 3.26 (m, 1H), 2.87 (dd, 1H, J=13.6, 5.0 Hz), 2.59 (dd, 1H, J=13.6, 9.0 Hz), 1.30 (s, 9H).

Step 3: Synthesis of tert-butyl (S)-(1-(4-carbamoylphenyl)-3-(1,3-dioxoisoindolin-2-yl)propan-2-yl)carbamate (Int-10)

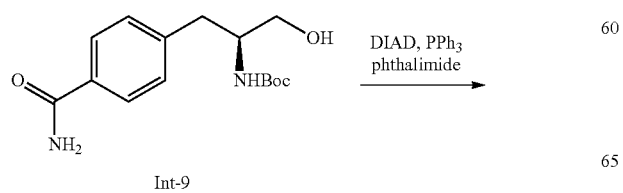

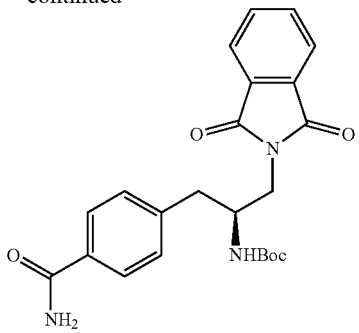

To a stirred solution of tert-butyl (S)-(1-(4-carbamoylphenyl)-3-hydroxypropan-2-yl)carbamate (Int-9) (1.0 g, 3.4 mmol), phthalimide (0.60 g, 4.1 mmol), and triphenylphosphine (1.08 g, 4.1 mmol) in anhydrous THF (40 mL) at 0° C. under nitrogen was slowly added diisopropyl azodicarboxylate (0.81 mL, 4.1 mmol) over 1 h. The reaction mixture was slowly warmed to rt and stirred overnight. The solids precipitated out were collected by filtration and washed with THF and dried to obtain the title compound (Int-10) as a white powder (1.33 g, 92%). LC-MS: 446.1 [M+Na]⁺; ¹H NMR (400 MHz, DMSO-d6) δ 7.90-7.75 (m, 7H), 7.31-7.27 (m, 3H), 6.89 (d, 1H, J=9.2 Hz), 4.03 (m, 1H), 3.66-3.60 (m, 2H), 2.87 (dd, 1H, J=13.8, 5.3 Hz), 2.77 (dd, 1H, J=13.8, 9.8 Hz), 1.09 and 0.96 (s, 9H).

Step 4: Synthesis of (S)-4-(2-amino-3-(1,3-dioxoisoindolin-2-yl)propyl)benzamide Hydrochloride (Int-11)

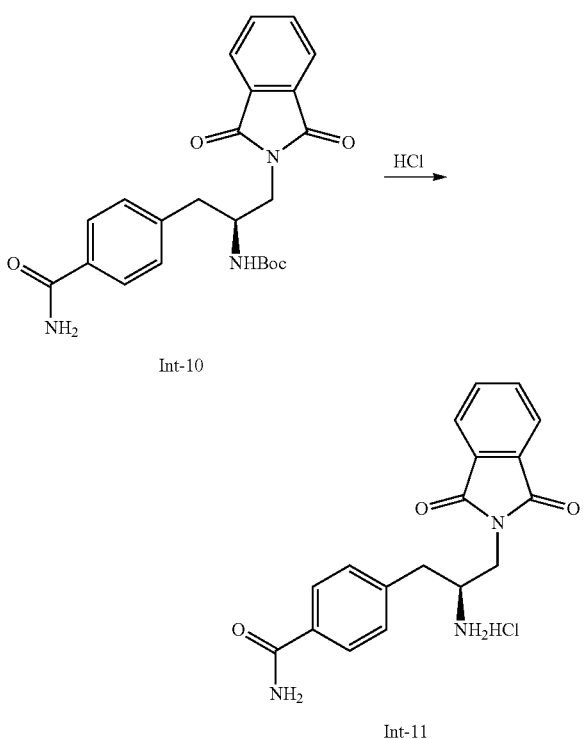

To a stirred solution of tert-butyl (S)-(1-(4-carbamoylphenyl)-3-(1,3-dioxoisoindolin-2-yl)propan-2-yl)carbamate (Int-10) (450 mg) in chloroform (20 mL) and methanol (2 mL) was added 4N HCl solution in 1,4-dioxane (2 mL). The reaction mixture was stirred at rt overnight, and then concentrated down to dryness to obtain the crude product (Int-11) as a white powder (460 mg). LC-MS: 324.1 [M+H]$^+$.

Step 5: Synthesis of (S)-4-(2-(dimethylamino)-3-(1,3-dioxoisoindolin-2-yl)propyl)benzamide (Int-12)

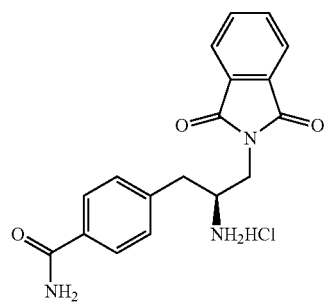

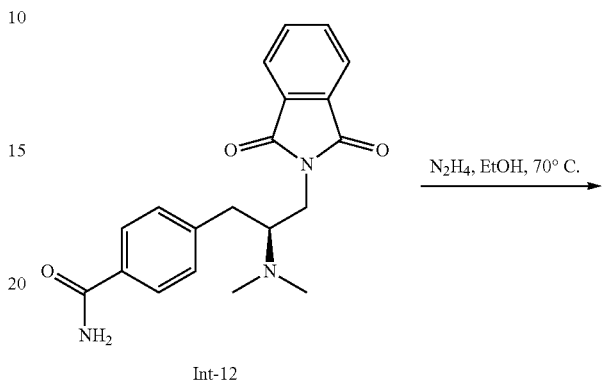

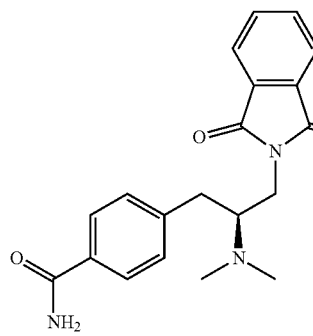

To a stirred suspension of (S)-4-(2-amino-3-(1,3-dioxoisoindolin-2-yl)propyl)benzamide hydrochloride (Int-11) (180 mg, 0.5 mmol) in acetonitrile (30 mL) and water (1 mL) at 0° C. was added 37% aqueous solution of formaldehyde (0.22 mL, 2.5 mmol), followed by sodium cyanoborohydride (90 mg, 1.5 mmol) in portions. After 10 min, acetic acid (0.143 mL, 2.5 mmol) was added. The reaction mixture was slowly warmed to rt and stirred for 3 h. The mixture was treated with water and adjusted to pH 10 with aq. Na$_2$CO$_3$ and extracted with EtOAc. The combined organic layers were washed with brine, dried over anhydrous sodium sulfate, and concentrated. The residue was purified by flash column chromatography over silica gel (0-10% MeOH/CH$_2$Cl$_2$ with 5% ammonia) to afford the title compound (Int-12) as a white solid (125 mg, 71%). LC-MS: 352.2 [M+H]$^+$; $^1$H NMR (400 MHz, DMSO-d6) δ 7.89 (br s, 1H), 7.81 (s, 4H), 7.77 (d, 2H, J=8.2 Hz), 7.31 (d, 2H, J=8.2 Hz), 7.28 (br s, 1H), 3.80 (dd, 1H, J=14.0, 9.5 Hz), 3.30 (m, 1H), 3.20 (m, 1H), 2.94 (dd, 1H, J=13.5, 4.8 Hz), 2.53 (dd, 1H, J=13.5, 9.0 Hz), 2.23 (s, 6H).

Step 6: Synthesis of (S)-4-(3-amino-2-(dimethylamino)propyl) benzamide (Int-13)

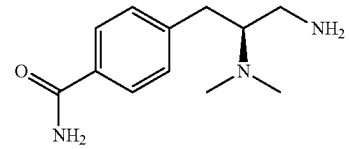

A mixture of (S)-4-(2-(dimethylamino)-3-(1,3-dioxoisoindolin-2-yl)propyl)benzamide (Int-12) (125 mg, 0.36 mmol) in ethanol (10 mL) and hydrazine monohydrate (90 mg, 1.8 mmol) was stirred at 70° C. for 3 h. The mixture was concentrated down to 2 mL and triturated with CH$_2$Cl$_2$ and filtered to remove the solids. The filtrate was concentrated and purified by flash column chromatography over silica gel (0-20% MeOH/CH$_2$Cl$_2$ with 5% ammonia) to afford the title compound (Int-13) as a white foam (75 mg, 95%). LC-MS: 222.2 [M+H]$^+$; $^1$H NMR (400 MHz, CDCl$_3$) δ 7.73 (d, 2H, J=8.1 Hz), 7.23 (d, 2H, J=8.1 Hz), 6.09 (br s, 1H), 5.65 (br s, 1H), 2.97 (dd, 1H, J=13.0, 3.0 Hz), 2.70-2.50 (m, 3H), 2.35 (s, 7H).

Synthesis of Phenylcyclopropane Carboxylic Acids (1R,2S)-2-methyl-2-phenylcyclopropane-1-carboxylic acid (Int-22), (1S,2R)-2-methyl-2-phenylcyclopropane-1-carboxylic acid (Int-23), (1R,2R)-2-methyl-2-phenylcyclopropane-1-carboxylic acid (Int-24), (1S,2S)-2-methyl-2-phenylcyclopropane-1-carboxylic acid (Int-25).

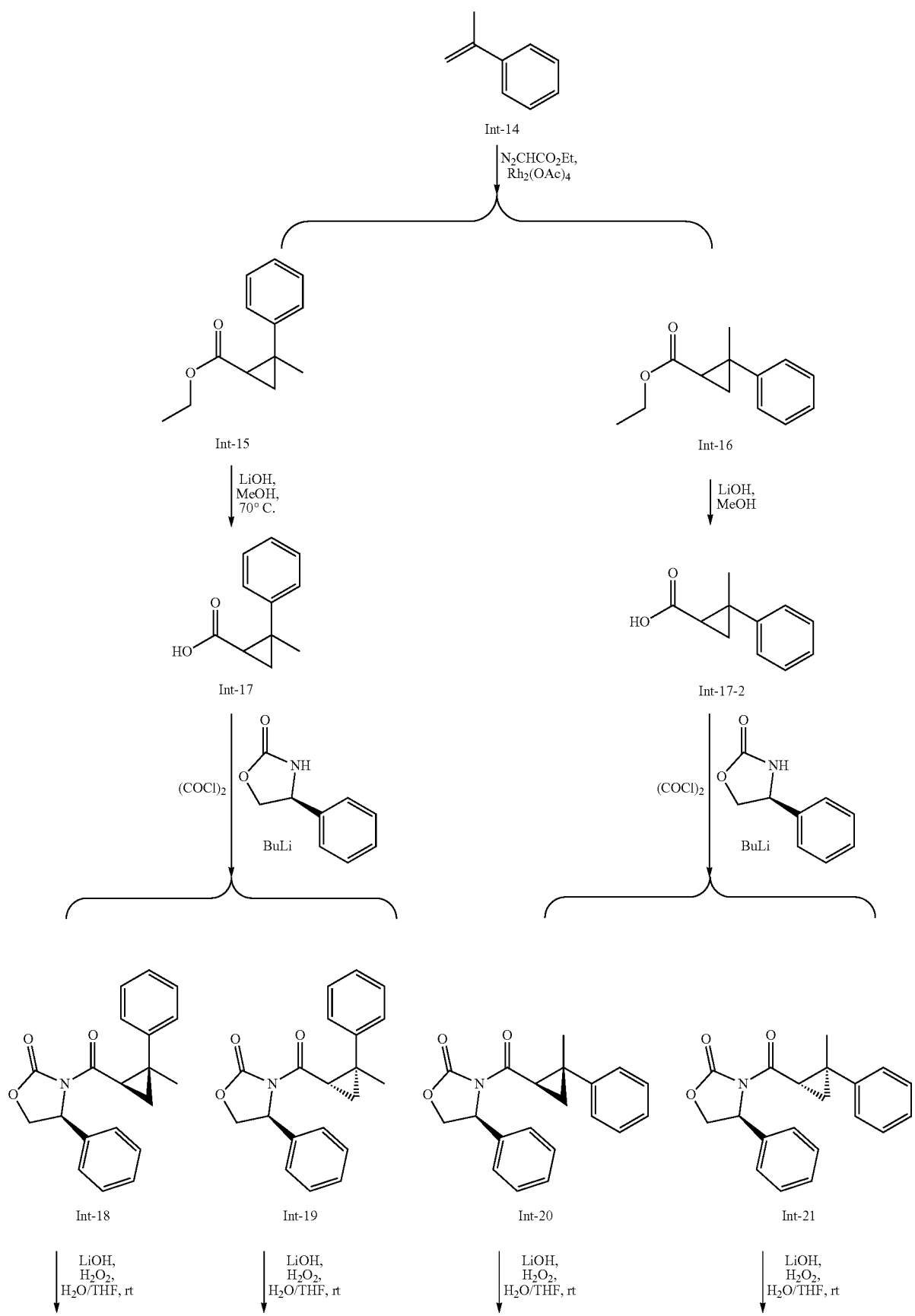

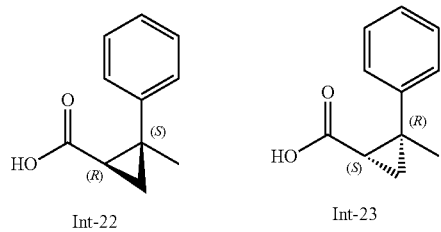
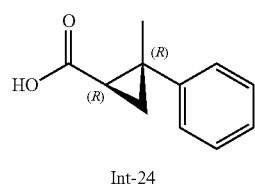
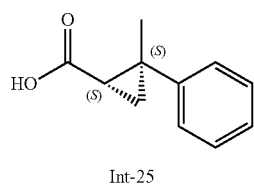

Int-22     Int-23     Int-24     Int-25

Synthesis of cis-ethyl 2-methyl-2-phenylcyclopropane-1-carboxylate (Int-15) and trans-ethyl 2-methyl-2-phenylcyclopropane-1-carboxylate (Int-16)

Synthesis of cis-2-methyl-2-phenylcyclopropane-1-carboxylic Acid (Int-17)

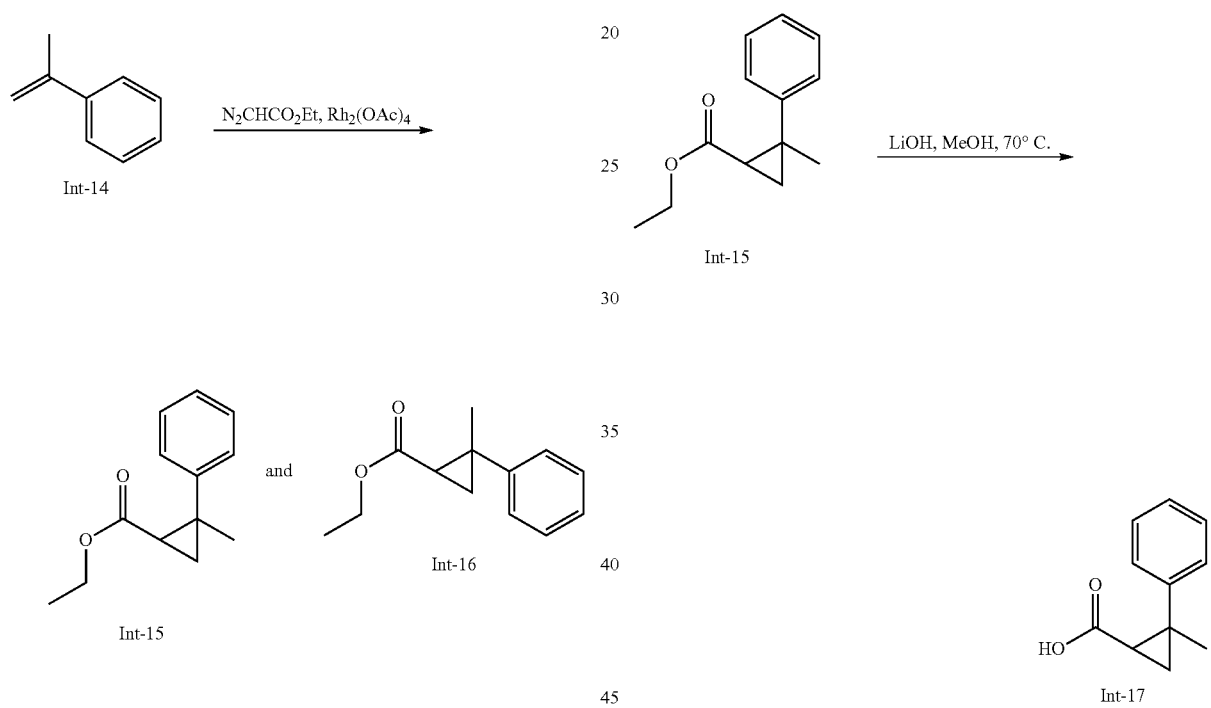

To a stirred mixture of α-methylstyrene (Int-14) (5 g, 42.4 mmol) and rhodium (II) acetate dimer (56 mg, 0.13 mmol) in dry $CH_2Cl_2$ (100 mL) was added ethyl diazoacetate (15% in toluene) (43.2 mL, 50.8 mmol, 1.0 equiv.) via additional funnel over 4 h. The resulting mixture was stirred at room temperature for overnight. Reaction mixture was concentrated under reduced pressure and purified by column chromatography on silica gel (0-5% EtOAc/hexane) to afford both the less polar trans-isomer (Int-16) (2.3 g, 27%) and the cis-isomer (Int-15) (2.2 g, 25%). Trans-isomer: colorless oil, LC-MS: 205.2 [M+H]$^+$; $^1$H NMR (400 MHz, CDCl$_3$) δ 7.34-7.28 (m, 4H), 7.21 (m, 1H), 4.23-4.16 (m, 2H), 1.96 (dd, 1H, J=8.3, 6.0 Hz), 1.53 (s, 3H), 1.47-1.39 (m, 2H), 1.30 (t, 3H, J=7.1 Hz). Cis-isomer: colorless oil, LC-MS: 205.2 [M+H]$^+$; $^1$H NMR (400 MHz, CDCl$_3$) δ 7.30-7.15 (m, 5H), 3.90-3.75 (m, 2H), 1.90 (dd, 1H, J=7.7, 5.4 Hz), 1.78 (t, 1H, J=5.0 Hz), 1.46 (s, 3H), 1.14 (dd, 1H, J=7.6, 4.6 Hz), 0.94 (t, 3H, J=7.1 Hz).

To a solution of cis-ethyl 2-methyl-2-phenylcyclopropane-1-carboxylate (Int-15) (2.5 g, 12.2 mmol, 1 equiv.) in MeOH (30 mL) and water (6 mL) was added LiOH (820 g, 34.2 mmol, 2.8 equiv.). The resulting mixture was stirred at rt overnight. Then more LiOH (820 g, 34.2 mmol, 2.8 equiv.) was added, and the reaction mixture was stirred at 50° C. for 2.5 hours. TLC and LC-MS showed that starting material was consumed. Then MeOH was carefully evaporated, and the residue was diluted with water (30 mL), followed by the addition of 1 N HCl (70 mL). Then the aqueous layer was extracted with EtOAc. The combined organic layers were dried over anhydrous Na$_2$SO$_4$. After filtration and concentration, the product was obtained as a colorless oil (Int-17) (2.15 g), which was used for the next step without further purification. $^1$H NMR (400 MHz, CDCl$_3$) δ 7.30-7.15 (m, 5H), 1.88 (dd, 1H, J=7.6, 5.6 Hz), 1.72 (t, 1H, J=5.0 Hz), 1.45 (s, 3H), 1.21 (dd, 1H, J=7.6, 4.6 Hz).

Synthesis of (S)-3-((1R,2S)-2-methyl-2-phenylcyclopropane-1-carbonyl)-4-phenyloxazolidin-2-one (Int-18) and (S)-3-((1S,2R)-2-methyl-2-phenylcyclopropane-1-carbonyl)-4-phenyloxazolidin-2-one (Int-19)

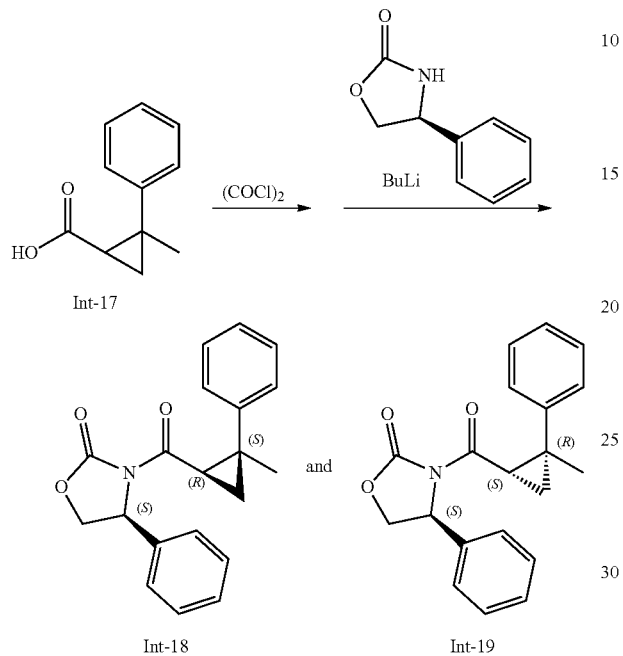

To a stirred solution of cis-2-methyl-2-phenylcyclopropane-1-carboxylic acid (Int-17) (2.15 g, 12.2 mmol, 1 equiv.) in dry CH$_2$Cl$_2$ (40 mL) at 0° C. under nitrogen were added 5 drops of dry DMF, followed by oxalyl chloride (2.07 mL, 24.1 mmol, 1.7 equiv.). The resulting mixture was stirred at 0° C. for 15 min and then stirred at rt for 2 h. The solvent was carefully evaporated to afford the desired acid chloride.

To a stirred solution of (S)-(+)-4-phenyl-2-oxazolidinone (2.31 g, 14.2 mmol, 1 equiv.) in dry THF (50 mL) at −78° C. under N2 was added n-BuLi (2.5 M in hexanes, 5.68 mL, 14.2 mmol, 1 equiv.) dropwise over 10 min. After stirring at −78° C. for 30 min, a solution of the above prepared acid chloride in THF (10 mL) was added over 15 min. Then the resulting mixture was slowly warmed rt and stirred overnight. The reaction was quenched by addition of water (20 mL) and extracted with EtOAc. The combined organic layers were dried over anhydrous MgSO$_4$. After filtration and concentration, the crude was purified by column chromatography on silica gel (0-40% EtOAc/hexane) to separate the diastereomers.

(S)-3-((1R,2S)-2-methyl-2-phenylcyclopropane-1-carbonyl)-4-phenyloxazolidin-2-one (more polar): colorless oil (Int-18), 1.8 g (45%). LC-MS: 322.2 [M+H]$^+$; $^1$H NMR (400 MHz, CDCl$_3$) δ 7.25-7.15 (m, 3H), 7.15-7.07 (m, 2H), 7.06-6.97 (m, 3H), 6.92 (d, 2H, J=7.1 Hz), 5.23 (dd, 1H, J=8.4, 2.8 Hz), 4.64 (t, 1H, J=8.6 Hz), 4.23 (dd, 1H, J=8.8, 3.0 Hz), 3.13 (t, 1H, J=6.6 Hz), 1.60 (s, 3H), 1.19 (dd, 1H, J=7.2, 4.8 Hz).

(S)-3-((1S,2R)-2-methyl-2-phenylcyclopropane-1-carbonyl)-4-phenyloxazolidin-2-one (less polar): white solid (Int-19), 1.8 g (45%). LC-MS: 322.1 [M+H]$^+$; $^1$H NMR (400 MHz, CDCl$_3$) δ 7.35-7.15 (m, 10H), 5.08 (dd, 1H, J=8.8, 4.6 Hz), 4.56 (t, 1H, J=8.8 Hz), 4.20 (dd, 1H, J=8.8, 4.6 Hz), 3.13 (t, 1H, J=6.4 Hz), 1.98 (t, 1H, J=5.2 Hz), 1.60 (s, 3H), 1.16 (dd, 1H, J=7.3, 4.8 Hz).

Synthesis of (1R,2S)-2-methyl-2-phenylcyclopropane-1-carboxylic Acid (Int-22)

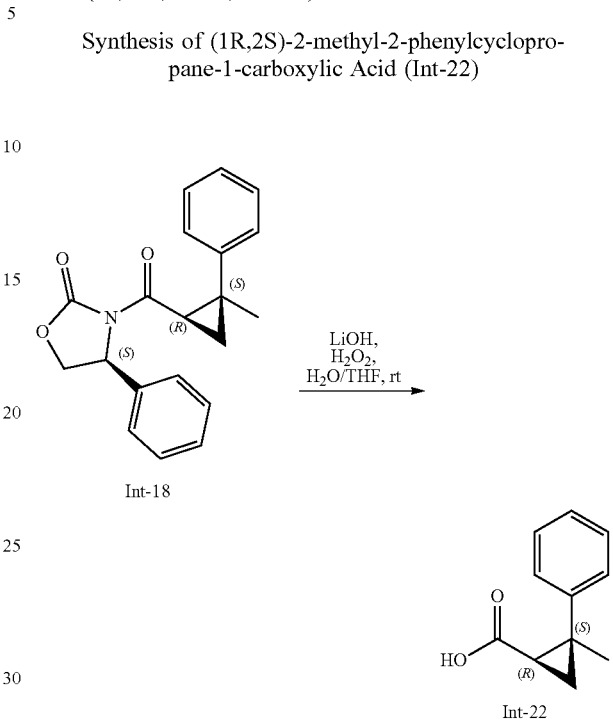

To a solution of (S)-3-((1R,2S)-2-methyl-2-phenylcyclopropane-1-carbonyl)-4-phenyloxazolidin-2-one (Int-18) (1.8 g, 5.6 mmol, 1 equiv.) in THF (20 mL) and water (18 mL) was added LiOH (451 mg, 19.6 mmol, 3.5 equiv.) and 17% H$_2$O$_2$ in water (2.5 mL, 19.6 mmol, 3.5 equiv.). After 2 h, more LiOH (451 mg) and H$_2$O$_2$ (2.5 mL) were added. The resulting mixture was stirred at rt for another 3 h. The residue was diluted with water (20 mL), followed by the addition of 1N HCl until pH 3-4. Then the aqueous layer was extracted with EtOAc. The combined organic layers were dried over anhydrous Na$_2$SO$_4$. After filtration and concentration, the crude was purified by column chromatography on silica gel (0-40% eluent EtOAc/hexane) to give the desired acid (Int-22) as a colorless oil.

Synthesis of (1S,2R)-2-methyl-2-phenylcyclopropane-1-carboxylic Acid (Int-23)

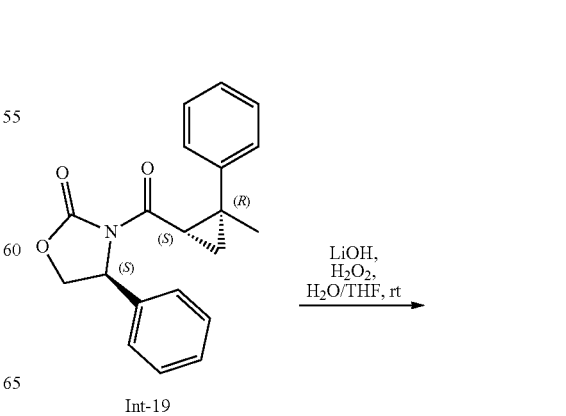

-continued

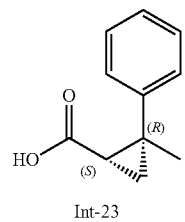

Int-23

To a solution of (S)-3-((1S,2R)-2-methyl-2-phenylcyclopropane-1-carbonyl)-4-phenyloxazolidin-2-one (Int-19) (1.8 g, 5.6 mmol, 1 equiv.) in THF (20 mL) and water (18 mL) was added LiOH (451 mg, 19.6 mmol, 3.5 equiv.) and 17% $H_2O_2$ in water (2.5 mL, 19.6 mmol, 3.5 equiv.). After 20 min, more water (8 mL) was added. The resulting mixture was stirred at rt for another 2 h (TLC and LC-MS showed that starting material was consumed). The residue was diluted with water (20 mL), followed by the addition of 1N HCl (21 mL). Then the aqueous layer was extracted with EtOAc. The combined organic layers were dried over anhydrous $Na_2SO_4$. After filtration and concentration, the crude was purified by column chromatography on silica gel (0-40% eluent EtOAc/hexane) to give the desired acid (Int-23) (540 mg, 55%) as a colorless oil.

Synthesis of trans-2-methyl-2-phenylcyclopropane-1-carboxylic Acid (Int-17-2)

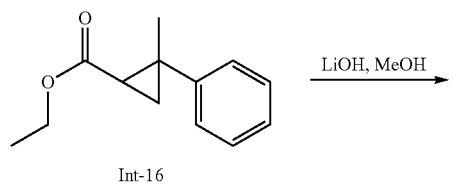

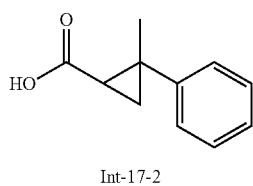

Int-17-2

To a solution of trans-ethyl 2-methyl-2-phenylcyclopropane-1-carboxylate (Int-16) (3.5 g, 17.1 mmol, 1 equiv.) in MeOH (40 mL) and water (8 mL) was added LiOH (1.02 g, 42.8 mmol, 2.5 equiv.). The resulting mixture was stirred at rt overnight. TLC and LC-MS showed that starting material has been consumed. Then MeOH was carefully evaporated. The residue was diluted with water (40 mL), acidified with 2N HCl to pH 3-4, and extracted with EtOAc. The combined organic layers were dried over anhydrous $Na_2SO_4$ and concentrated to obtain a yellowish oil (Int-17-2) (3.2 g), which was used for the next step without further purification. $^1$H NMR (400 MHz, CDCl$_3$) δ 7.35-7.15 (m, 5H), 1.99 (dd, 1H, J=8.0, 6.2 Hz), 1.59 (s, 3H), 1.55-1.45 (m, 2H).

Synthesis of (S)-3-((1R,2R)-2-methyl-2-phenylcyclopropane-1-carbonyl)-4-phenyloxazolidin-2-one (Int-20) and (S)-3-((1S,2S)-2-methyl-2-phenylcyclopropane-1-carbonyl)-4-phenyloxazolidin-2-one (Int-21)

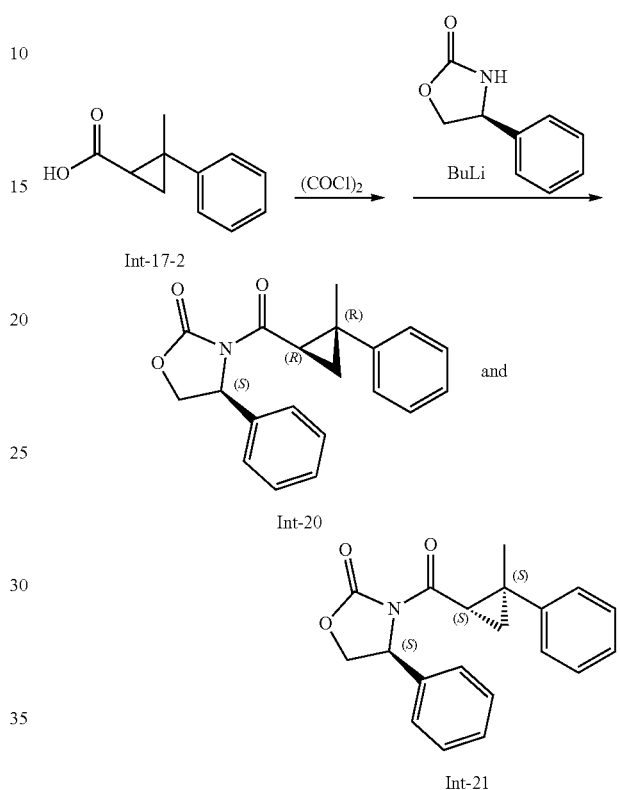

To a stirred solution of trans-2-methyl-2-phenylcyclopropane-1-carboxylic acid (Int-17-2) (2.5 g, 14.2 mmol, 1 equiv.) in dry $CH_2Cl_2$ (40 mL) at 0° C. under nitrogen were added 5 drops of dry DMF, followed by oxalyl chloride (2.07 mL, 24.1 mmol, 1.7 equiv.). The resulting mixture was stirred at 0° C. for 15 min and then stirred at rt for 2 h. The solvent was carefully evaporated to afford the desired acid chloride.

To a stirred solution of (S)-(+)-4-phenyl-2-oxazolidinone (2.31 g, 14.2 mmol, 1 equiv.) in dry THF (50 mL) at −78° C. under $N_2$ was added n-BuLi (2.5 M in hexanes, 5.68 mL, 14.2 mmol, 1 equiv.) dropwise over 10 min. After stirring at −78° C. for 30 min, a solution of the above prepared acid chloride in THF (10 mL) was added over 15 min. Then the resulting mixture was slowly warmed rt and stirred overnight. The reaction was quenched by addition of water (20 mL) and extracted with EtOAc. The combined organic layers were dried over anhydrous $MgSO_4$. After filtration and concentration, the crude was purified by column chromatography on silica gel (0-30% EtOAc/hexane) to separate the diastereomers.

(S)-3-((1R,2R)-2-methyl-2-phenylcyclopropane-1-carbonyl)-4-phenyloxazolidin-2-one (Int-20) (more polar): colorless syrup, 1.7 g (34%). LC-MS: 322.2 [M+H]$^+$; $^1$H NMR (400 MHz, CDCl$_3$) δ 7.48-7.22 (m, 10H), 5.50 (dd, 1H, J=8.6, 3.4 Hz), 4.73 (t, 1H, J=8.8 Hz), 4.29 (dd, 1H, J=8.6, 3.4 Hz), 3.47 (t, 1H, J=6.9 Hz), 1.61 (t, 1H, J=5.0 Hz), 1.37 (dd, 1H, J=7.8, 4.4 Hz), 1.17 (s, 3H).

(S)-3-((1S,2S)-2-methyl-2-phenylcyclopropane-1-carbonyl)-4-phenyloxazolidin-2-one (Int-21) (less polar): white solid, 1.7 g (34%). LC-MS: 322.1 [M+H]+; 1H NMR (400 MHz, CDCl3) δ 7.47-7.20 (m, 10H), 5.53 (dd, 1H, J=8.8, 4.4 Hz), 4.75 (t, 1H, J=8.9 Hz), 4.30 (dd, 1H, J=8.8, 4.4 Hz), 3.39 (t, 1H, J=6.9 Hz), 1.59 (t, 1H, J=5.0 Hz), 1.45 (s, 3H), 1.39 (dd, 1H, J=7.9, 4.2 Hz).

Synthesis of (1R,2R)-2-methyl-2-phenylcyclopropane-1-carboxylic Acid (Int-24)

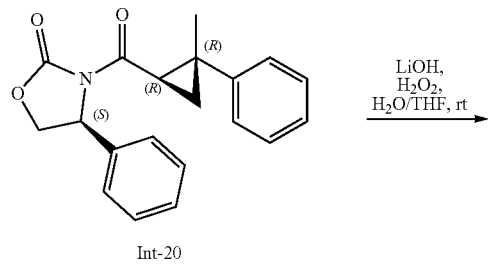

Int-20

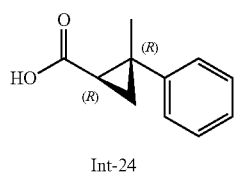

Int-24

To a solution of (S)-3-((1R,2R)-2-methyl-2-phenylcyclopropane-1-carbonyl)-4-phenyloxazolidin-2-one (Int-20) (1.7 g, 5.3 mmol, 1 equiv.) in THF (20 mL) and water (8 mL) was added LiOH (426 mg, 18.5 mmol, 3.5 equiv.) and 17% H2O2 in water (2.33 mL, 18.52 mmol, 3.5 equiv.). The resulting mixture was stirred at rt for 1 h. The residue was diluted with water (20 mL), followed by the addition of 1N HCl (20 mL). Then the aqueous layer was extracted with EtOAc. The combined organic layers were dried over anhydrous Na2SO4. After filtration and concentration, the crude was purified by column chromatography on silica gel (0-40% EtOAc/hexane) to give the desired acid (Int-24) (770 mg, 83%) as a colorless oil.

Synthesis of (1S,2S)-2-methyl-2-phenylcyclopropane-1-carboxylic Acid (Int-25)

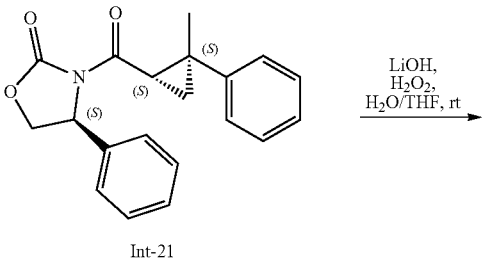

Int-21

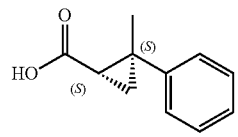

Int-25

To a solution of (S)-3-((1S,2S)-2-methyl-2-phenylcyclopropane-1-carbonyl)-4-phenyloxazolidin-2-one (Int-21) (1.7 g, 5.3 mmol, 1 equiv.) in THF (25 mL) an water (10 mL) was added LiOH (476 mg, 20.7 mmol, 3.9 equiv.) and 17% H2O2 in water (2.6 mL, 20.7 mmol, 3.9 equiv.). The resulting mixture was stirred at rt for 80 min and TLC and LC-MS showed that the reaction was complete. The residue was diluted with water (20 mL), followed by the addition of 1N HCl (23 mL). Then the aqueous layer was extracted with EtOAc. The combined organic layers were dried over anhydrous Na2SO4. After filtration and concentration, the crude was purified by column chromatography on silica gel (0-40% EtOAc/hexane) to give the desired acid (Int-25) (560 mg, 60%) as a colorless oil.

Synthesis of (1R,2R)-2-isopropyl-2-phenylcyclopropane-1-carboxylic Acid (Int-35) and (1R,2S)-2-isopropyl-2-phenylcyclopropane-1-carboxylic Acid (Int-36)

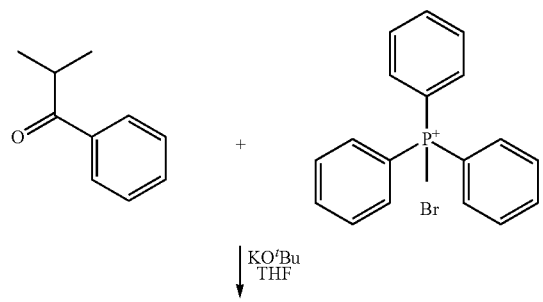

-continued
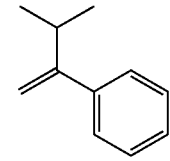
Int-26
↓ N₂CHCO₂Et, Rh₂(OAc)₄ rt
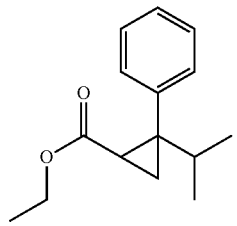
Int-27
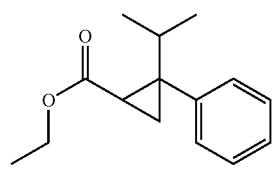
Int-28
↓ LiOH, MeOH—H₂O, 99%
↓ LiOH, MeOH ~100%
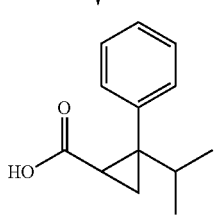
Int-29
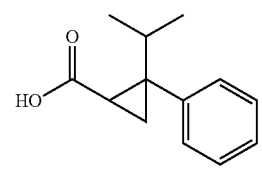
Int-30
↓ (COCl)₂
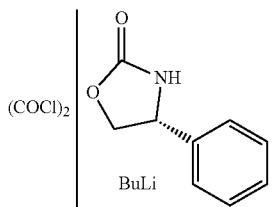
BuLi
↓ (COCl)₂
BuLi
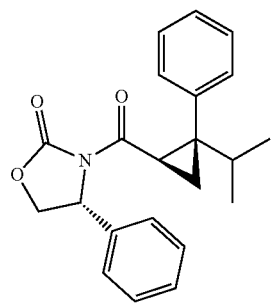
Int-31
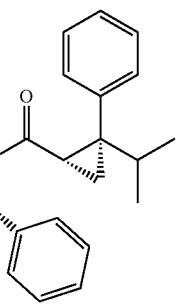
Int-32
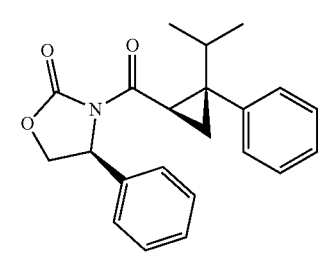
Int-33
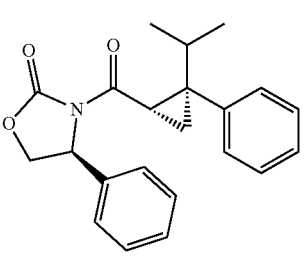
Int-34
↓ LiOH, H₂O₂, H₂O/THF, rt
↓ LiOH, H₂O₂, H₂O/THF, rt

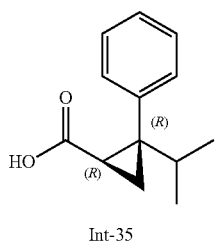

Int-35

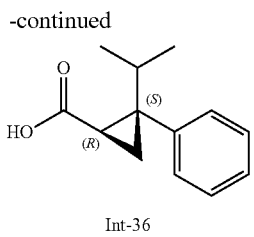

Int-36

Synthesis of 3-methyl-2-phenyl-1-butene (Int-26)

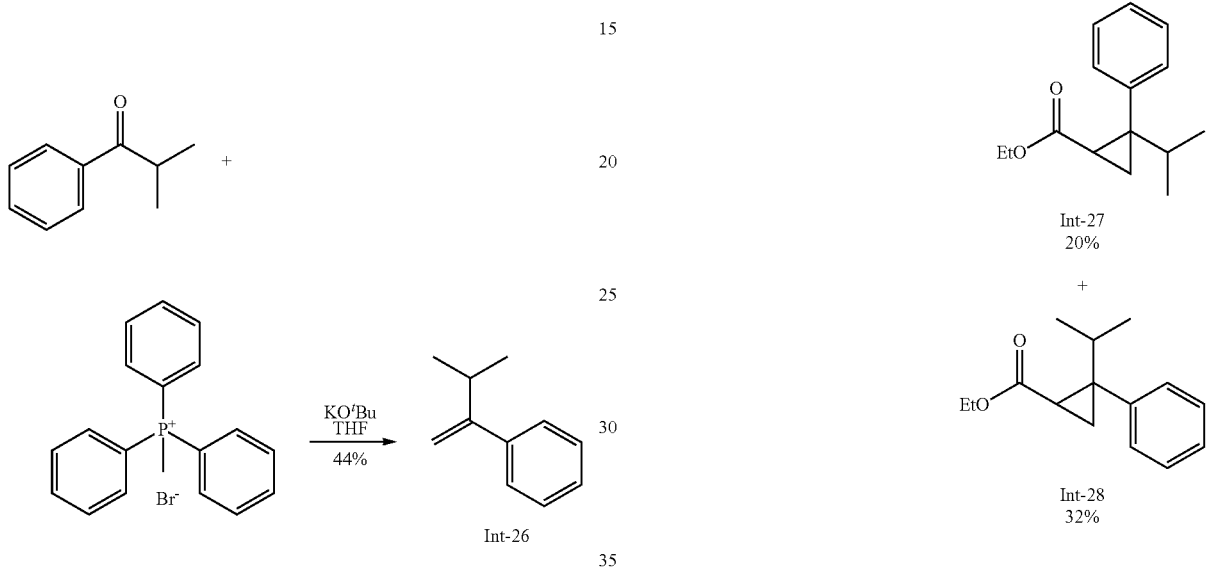

Int-27
20%

Int-28
32%

To a solution of 16 g (44.7 mmol) of methyltriphenylphosphonium bromide in 60 mL of dry THF at −78° C. was added 17.9 mL of a 2.5 M solution of n-BuLi in hexane (44.7 mmol) and the solution turned brown. After 30 min stirring at 0° C., 6.31 g (42.5 mmol) of 3-methyl-2-phenylbutanone in 30 mL of THF were added and the solution was stirred overnight. After 20 mL of water were added and the solution was extracted with $CH_2Cl_2$ (3×100 mL). The organic layer was dried over $MgSO_4$ and the solvent was evaporated. The crude product was purified by silica-gel flash chromatography (hexanes as eluent) and 2.7 g (44%) of (3-methylbut-1-en-2-yl)benzene (Int-26) were obtained as colorless oil. $^1$H-NMR (400 MHz, $CDCl_3$): δ=1.11 (d, J=7.2 Hz, 6H), 2.87 (m, 1H), 5.07 (m, 1H), 5.17 (m, 1H), 7.28-7.39 (m, 5H).

Synthesis of ethyl 2-isopropyl-2-phenylcyclopropane-1-carboxylate (Int-27) and (Int-28)

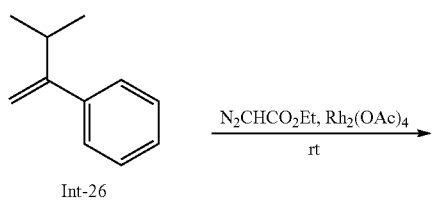

To a solution (3-methylbut-1-en-2-yl)benzene (Int-26) (6.3 g, 4.3 mmol, 1 equiv.) and rhodium (II) acetate dimer (120 mg) in dry DCM (100 mL) was added ethyl diazoacetate (15% in toluene) (37 mL, 4.3 mmol, 1 equiv.) via additional funnel over 4 h. The resulting mixture was stirred at room temperature for overnight. Reaction mixture was concentrated under reduced pressure. A mixture of racemic trans- and cis-isomers were obtained and their separation was done by column chromatography on silica gel (eluent EtOAc/Hexanes 0-10%). After purification 2.03 g of cis-isomer (Int-27) (20%) and 3.2 g of trans-isomer (Int-28) (32%) were obtained.

Cis-ethyl 2-isopropyl-2-phenylcyclopropane-1-carboxylate (Int-27): $^1$H NMR (400 MHz, $CDCl_3$, ppm) δ 7.28-7.17 (m, 5H), 3.89 (q, J=7.2 Hz, 2H), 1.91 (dd, J=6.8, 4.8 Hz, 1H), 1.63 (t, J=4.8 Hz, 1H), 1.17 (m, 1H), 1.15 (t, J=4.4 Hz, 3H), 1.01 (d, J=7.2 Hz, 3H), 0.99 (t, J=7.2 Hz, 3H), 0.86 (d, J=7.2 Hz, 3H).

Trans-ethyl 2-isopropyl-2-phenylcyclopropane-1-carboxylate (Int-28): $^1$H NMR (400 MHz, $CDCl_3$, ppm) δ 7.31-7.25 (m, 5H), 4.24 (q, J=7.2 Hz, 2H), 2.01-1.86 (m, 2H), 1.44 (t, J=4.0 Hz, 1H), 1.35 (t, J=7.2 Hz, 3H), 1.30 (t, J=4.0 Hz, 3H), 0.91 (d, J=7.2 Hz, 3H), 0.81 (d, J=7.2 Hz, 3H).

Synthesis of cis-2-isopropyl-2-phenylcyclopropane-1-carboxylic Acid (Int-29)

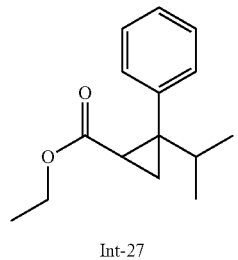

Int-27

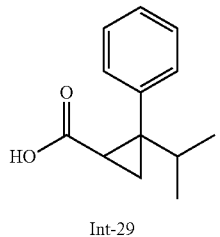

Int-29

To a solution of cis-ethyl 2-isopropyl-2-phenylcyclopropane-1-carboxylate (Int-27) (2.0 g, 8.6 mmol, 1 equiv.) in MeOH (25 mL)-water (5 mL) was added LiOH (1.03 g, 43.0 mmol, 5 equiv.). The resulting mixture was stirred at rt overnight and then stirred at 50° C. for 3 h. TLC and LC-MS showed that starting material has been consumed. After cooled to rt, MeOH was carefully evaporated. The residue was diluted with water (40 mL), followed by the addition of 1 N HCl (50 mL). Then the aqueous layer was extracted with EtOAc (100 mL×4). The combined organic layers were dried over anhydrous Na$_2$SO$_4$. After filtration and concentration, the product was obtained as a white solid (1.74 g, 99% g), which was used for the next step without further purification. $^1$H NMR (400 MHz, CDCl$_3$, ppm) δ 7.31-7.17 (m, 5H), 1.88 (t, J=4.0 Hz, 1H), 1.60 (t, J=4.8 Hz, 1H), 1.30-1.22 (m, 2H), 0.99 (t, J=6.8 Hz, 1H), 0.86 (t, J=6.8 Hz, 1H).

Synthesis of (R)-3-((1R,2R)-2-isopropyl-2-phenylcyclopropane-1-carbonyl)-4-phenyloxazolidin-2-one (Int-31) and (R)-3-((1S,2S)-2-isopropyl-2-phenylcyclopropane-1-carbonyl)-4-phenyloxazolidin-2-one (Int-32)

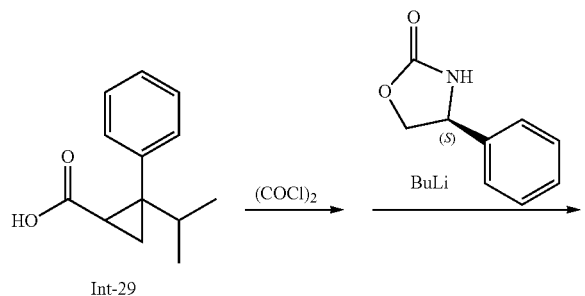

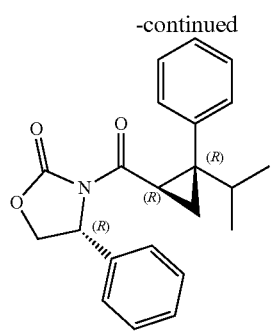

Int-31 and

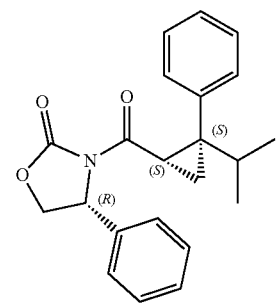

Int-32

1.74 g of cis-2-isopropyl-2-phenylcyclopropane-1-carboxylic acid (Int-29) (8.5 mmol, 1 equiv.) was dissolved in dry DCM (20 mL). The reaction mixture was cooled to 0° C. with ice-water bath. Then 5 drops of dry DMF was added, followed by the addition of (COCl)$_2$ (1.68 mL, 19.6 mmol, 2.3 equiv.). The resulting mixture was stirred at 0° C. for 15 min and then stirred at rt for 2 h. The solvent was then evaporated, then dry DCM (20 ml) was added and evaporated. To a solution of (R)-4-phenyloxazolidin-2-one (1.39 g, 8.5 mmol, 1 equiv.) in dry THF (40 ml) at −78° C. under N$_2$ was added n-BuLi (2.5 M in hexanes, 3.4 mL, 8.5 mmol, 1 equiv.) dropwise over 10 min. After stirring at −78° C. for 30 min, a THF solution of the above prepared acyl chloride (10 mL THF) was added by syringe over 15 min. Then the resulting mixture was stirred from −78° C. to rt overnight. The reaction was quenched by addition of water (20 mL), followed by extraction with EtOAc (50 mL×3). The combined organic layers were dried over anhydrous MgSO$_4$. After filtration and concentration, the crude was purified by column chromatography on silica gel (eluent EtOAc/Hexanes 0-20%).

(R)-3-((1R,2R)-2-isopropyl-2-phenylcyclopropane-1-carbonyl)-4-phenyloxazolidin-2-one (Int-31): white solid, 1.3 g (44%). $^1$H NMR (400 MHz, CDCl$_3$, ppm) δ 7.36-7.14 (m, 10H), 5.22 (dd, J=8.8, 4.4 Hz, 1H), 4.68 (t, J=8.8 Hz, 1H), 4.27 (dd, J=8.8, 4.0 Hz, 1H), 3.29 (dd, J=7.2, 5.2 Hz, 1H), 1.79 (t, J=4.8 Hz, 1H), 1.55 (m, 1H), 1.19 (t, J=4.0 Hz, 1H), 1.04 (d, J=6.8 Hz, 3H), 0.88 (d, J=6.8 Hz, 3H); LC-MS: 350.2 (M+H)$^+$.

(R)-3-((1S,2S)-2-isopropyl-2-phenylcyclopropane-1-carbonyl)-4-phenyloxazolidin-2-one (Int-32): white solid, 1.43 g (48%). $^1$H NMR (400 MHz, CDCl$_3$, ppm) δ 7.36-7.26 (m, 5H), 6.86-6.34 (m, 5H), 5.30 (dd, J=8.0, 2.8 Hz, 1H), 4.68 (t, J=8.8 Hz, 1H), 4.37 (dd, J=9.2, 2.8 Hz, 1H), 3.32 (dd, J=7.6, 5.6 Hz, 1H), 1.77 (t, J=4.8 Hz, 1H), 1.49 (m, 1H), 1.23 (t, J=4.0 Hz, 1H), 1.01 (d, J=6.8 Hz, 3H), 0.85 (d, J=6.8 Hz, 3H); LC-MS: 350.2 (M+H)$^+$.

Synthesis of (1R,2R)-2-isopropyl-2-phenylcyclopropane-1-carboxylic Acid (Int-35)

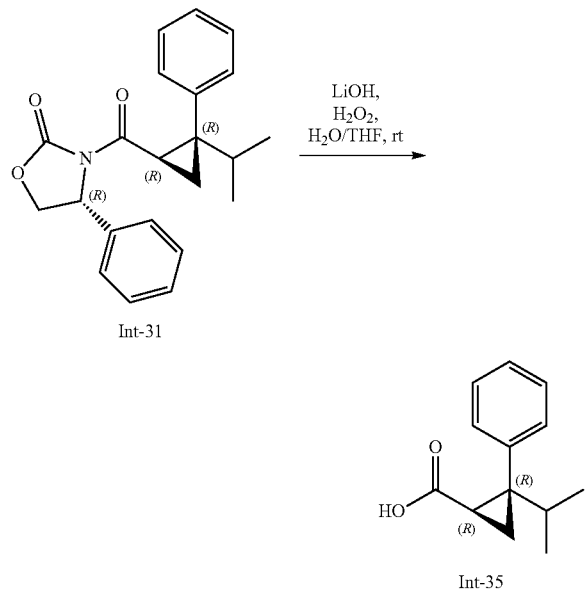

To a solution of (R)-3-((1R,2R)-2-isopropyl-2-phenylcyclopropane-1-carbonyl)-4-phenyloxazolidin-2-one (Int-31) (880 mg, 2.51 mmol, 1 equiv.) in THF (10 mL)-water (4 mL) was added 17% $H_2O_2$ in water (1.18 mL, 10.3 mmol, 4.1 equiv.) and LiOH (154 mg, 3.77 mmol, 1.5 equiv.). The resulting mixture was stirred at rt overnight (TLC and LC-MS showed that starting material has been consumed). The residue was diluted with water (20 mL), followed by the addition of 1 N NaOH (5 mL). The aqueous layer was extracted with EtOAc (80 mL×3), then treated with 1 N HCl (13 mL). Then the aqueous layer was extracted with EtOAc (70 mL×3). The combined organic layers were dried over anhydrous $Na_2SO_4$. After filtration and concentration, the product (Int-35) was obtained as a white solid (450 mg, 88%), which was used in the next step without further purification.

$^1$H NMR (400 MHz, CDCl$_3$, ppm) δ 7.31-7.17 (m, 5H), 1.88 (t, J=4.0 Hz, 1H), 1.60 (t, J=4.8 Hz, 1H), 1.30-1.22 (m, 2H), 0.99 (t, J=6.8 Hz, 1H), 0.86 (t, J=6.8 Hz, 1H).

Synthesis of trans-isopropyl-2-phenylcyclopropane-1-carboxylic Acid (Int-30)

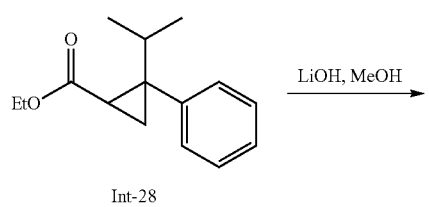

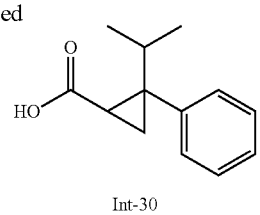

To a solution of trans-ethyl 2-isopropyl-2-phenylcyclopropane-1-carboxylate (Int-28) (3.2 g, 13.8 mmol, 1 equiv.) in MeOH (30 mL)-water (6 mL) was added LiOH (820 mg, 34.4 mmol, 2.5 equiv.). The resulting mixture was stirred at rt overnight. TLC and LC-MS showed starting material has been consumed. After cooled to rt, MeOH was carefully evaporated. The residue was diluted with water (40 mL), followed by the addition of 1 N HCl (40 mL). Then the aqueous layer was extracted with EtOAc (100 mL×3). The combined organic layers were dried over anhydrous $Na_2SO_4$. After filtration and concentration, the product (Int-30) was obtained as a white solid (2.8 g, 99% g), which was used for the next step without further purification. $^1$H NMR (400 MHz, CDCl$_3$, ppm) δ 7.41-7.21 (m, 5H), 2.17-2.00 (m, 2H), 1.49 (t, J=4.4 Hz, 1H), 1.43 (t, J=4.4 Hz, 1H), 0.93 (d, J=6.8 Hz, 3H), 0.87 (d, J=6.8 Hz, 3H).

Synthesis of (R)-3-((1R,2S)-2-isopropyl-2-phenylcyclopropane-1-carbonyl)-4-phenyloxazolidin-2-one (Int-33)

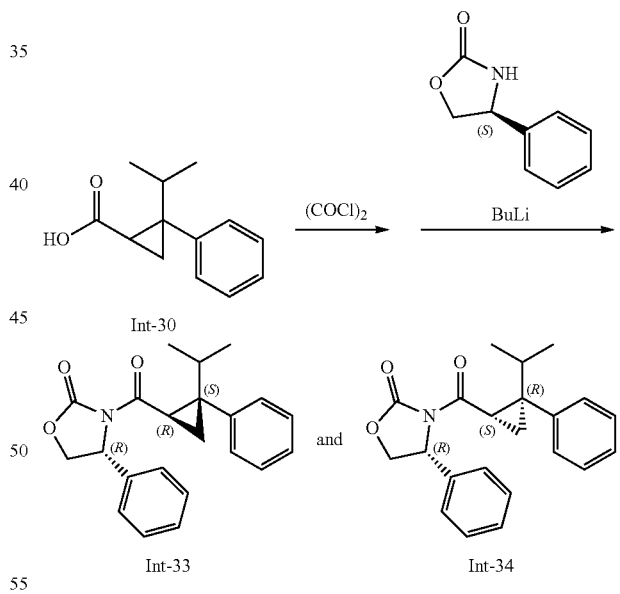

2.8 g of crude acid (Int-30) from above step (13.7 mmol, 1 equiv.) was dissolved in dry DCM (30 mL). The reaction mixture was cooled to 0° C. with ice-water bath. Then 5 drops of dry DMF was added, followed by the addition of (COCl)$_2$ (2.7 mL, 31.4 mmol, 2.3 equiv.). The resulting mixture was stirred at 0° C. for 15 min and then stirred at rt for 2 h. The solvent was then evaporated, then dry DCM (20 ml) was added and evaporated.

To a solution of (R)-4-phenyloxazolidin-2-one (2.37 g, 14.5 mmol, 1.06 equiv.) in dry THF (55 ml) at −78° C. under N$_2$ was added n-BuLi (2.5 M in hexanes, 5.5 mL, 13.4 mmol) dropwise over 10 min. After stirring at −78° C. for 30 min, a THF solution of the above prepared acyl chloride (10 mL THF) was added by syringe over 15 min. Then the resulting mixture was stirred from −78° C. to rt overnight. The reaction was quenched by addition of water (20 mL), followed by extraction with EtOAc (50 mL×3). The combined organic layers were dried over anhydrous MgSO$_4$. After filtration and concentration, the crude was purified by column chromatography on silica gel (Int-33) (eluent EtOAc/Hexanes 0-20%, less polar product). $^1$H NMR (400 MHz, CDCl$_3$, ppm) δ 7.49-7.24 (m, 10H), 5.56 (dd, J=8.8, 4.4 Hz, 1H), 4.77 (t, J=8.8 Hz, 1H), 4.34 (dd, J=8.8, 4.4 Hz, 1H), 3.34 (dd, J=7.2, 5.6 Hz, 1H), 1.90 (m, 1H), 1.63 (dd, J=5.6, 4.0 Hz, 1H), 1.36 (dd, J=7.6, 4.0 Hz, 1H), 0.90 (d, J=6.8 Hz, 3H), 0.79 (d, J=6.8 Hz, 3H); LC-MS: 350.2 (M+H)$^+$.

Synthesis of (1R,2S)-2-isopropyl-2-phenylcyclopropane-1-carboxylic Acid (Int-36)

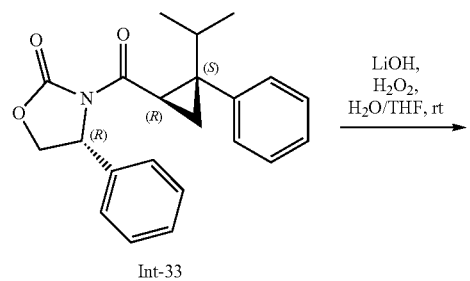

To a solution of (R)-3-((1R,2S)-2-isopropyl-2-phenylcyclopropane-1-carbonyl)-4-phenyloxazolidin-2-one (Int-33) (880 mg, 2.51 mmol, 1 equiv.) in THF (10 mL)-water (4 mL) was added 17% H$_2$O$_2$ in water (1.18 mL, 10.3 mmol, 4.1 equiv.) and LiOH (154 mg, 3.77 mmol, 1.5 equiv.). The resulting mixture was stirred at rt overnight (TLC and LC-MS showed that starting material has been consumed). The residue was diluted with water (20 mL), followed by the addition of 1 N NaOH (5 mL). The aqueous layer was extracted with EtOAc (80 mL×3), then treated with 1 N HCl (13 mL). Then the aqueous layer was extracted with EtOAc (70 mL×3). The combined organic layers were dried over anhydrous Na$_2$SO$_4$. After filtration and concentration, the product was obtained as a white solid (Int-36) (390 mg, 76%), which was used in the next step without further purification. $^1$H NMR (400 MHz, CDCl$_3$, ppm) δ 7.41-7.21 (m, 5H), 2.17-2.00 (m, 2H), 1.49 (t, J=4.4 Hz, 1H), 1.43 (t, J=4.4 Hz, 1H), 0.93 (d, J=6.8 Hz, 3H), 0.87 (d, J=6.8 Hz, 3H).

Synthesis of 5-Bromo-1-tosyl-1H-indazole (Int-37)

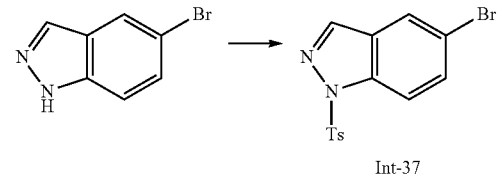 [SMILES: Brc1ccc2[nH]ncc2c1 ; Cc1ccc(S(=O)(=O)n2ncc3cc(Br)ccc32)cc1]

To a solution of 5-bromo-1H-indazole (10 g, 50.8 mmol, Combi-blocks Cat #PY-7893, Lot B16473)) and DMF (50 mL), tosyl chloride (13.5 g, 71.1 mmol) was added followed by sodium hydride (2.03 g, 50.8 mmol) and was allowed to stir at 50° C. overnight. After completion of the reaction, the mixture was poured into ice cold water and was allowed to stir for 30 minutes. The creamy white aqueous suspension was extracted with ethyl acetate, combined organic layers were washed with saturated ammonium chloride followed by brine, dried using sodium sulfate, filtered and concentrated under reduced pressure. The crude material was purified by passing through silica gel and was eluted using 100% DCM to afford 17.24 g (97%) of the title compound (Int-37) as creamy white shiny flakes. $^1$H NMR (600 MHz, CHLOROFORM-d) δ=8.14-8.09 (m, 2H), 7.88-7.83 (m, 3H), 7.65 (dd, J=1.8, 8.8 Hz, 1H), 7.29-7.24 (m, 2H), 2.37 (s, 3H).

Synthesis of methyl (S)-2-((tert-butoxycarbonyl)amino)-3-(1-tosyl-1H-indazol-5-yl)propanoate (Int-38)

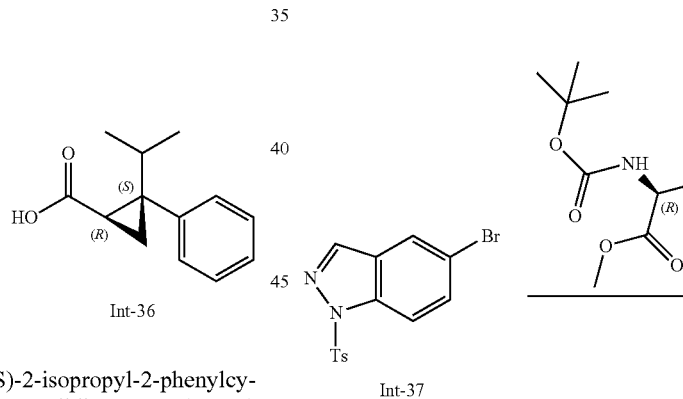

Zinc dust (14.4 g, 4.26 mmol) was suspended in anhydrous DMF (90 mL) under argon atmosphere and trimethylsilyl chloride (4.59 mL, 36.2 mmol) was added slowly and allowed to stir for 30 minutes. The solution turned yellow orange from colorless precipitate in 30 minutes. The mixture with the precipitate was allowed to settle and the solution was removed with a syringe under argon atmosphere. The now activated zinc powder was washed with DMF until no yellow-brown color was observed in the solution. Methyl (R)-2-((tert-butoxycarbonyl)amino)-3-iodopropanoate (Combiblocks, OR-1812, Batch #18260, 17 g, 51.7 mmol) dissolved in DMF (90 mL) was then added slowly to the activated zinc. The reaction is exothermic so the flask is intermittently cooled in an ice water bath. After the addition is complete the reaction was allowed to stir at room temperature for 40 minutes. The supernatant of this reaction was then added to the mixture of Int-37 (18.1 g, 51.7 mmol) in DMF (90 ml) and $2^{nd}$ Generation Xphos Precatalyst (CAS #1310584-14-5, 1.22 g, 1.55 mmol). The reaction is stirred at 50° C. overnight. Reaction was cooled to ambient temperature followed by the addition of ethyl acetate (2 L). the organic layer was washed with water (2 L), sat aq $NH_4Cl$ (300 mL), brine (300 mL), dried using $Na_2SO_4$, filtered, and concentrated to afford crude product (30 g, caramel amber residue). The crude was purified on silica gel, eluent hexanes-EtOAc to afford the title product Int-38 (6.6 g). LCMS (+ESI) M+H$^+$=474.5. $^1$H NMR (600 MHz, METHANOL-$d_4$) δ=8.27 (s, 1H), 8.10 (d, J=8.6 Hz, 1H), 7.81 (br d, J=8.3 Hz, 2H), 7.61 (s, 1H), 7.50 (br d, J=8.6 Hz, 1H), 7.31 (br d, J=8.2 Hz, 2H), 4.40 (dd, J=5.3, 9.4 Hz, 1H), 3.68 (s, 3H), 3.25 (dd, J=5.2, 13.8 Hz, 1H), 2.99 (br dd, J=9.6, 13.8 Hz, 1H), 2.34 (s, 3H), 1.32-1.22 (m, 9H).

Synthesis of tert-butyl (S)-(1-amino-1-oxo-3-(1-tosyl-1H-indazol-5-yl)propan-2-yl)carbamate (Int-39)

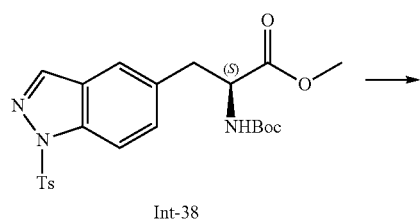

Int-38

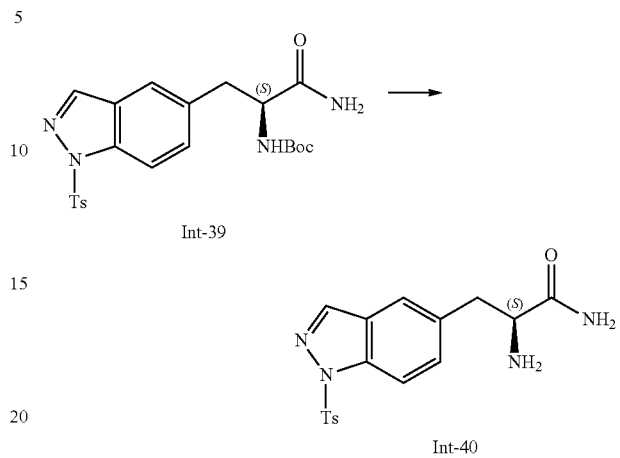

Int-39

To a solution of methyl (S)-2-((tert-butoxycarbonyl)amino)-3-(1-tosyl-1H-indazol-5-yl)propanoate (Int-38) (6.6 g, 13.9 mmol) in anhydrous methanol (1.5 mL), 7N ammonia in methanol (135 mL) was added at 0° C. and was allowed to stir over the weekend. The solvent was evaporated under reduced pressure and the crude material was purified by flash chromatography using 5% methanol/DCM as gradients to obtain 4.32 g of the title compound (Int-39). $^1$H NMR (600 MHz, METHANOL-$d_4$) δ=8.27 (s, 1H), 8.09 (br d, J=8.6 Hz, 1H), 7.81 (br d, J=8.2 Hz, 2H), 7.63 (s, 1H), 7.54 (d, J=8.6 Hz, 1H), 7.30 (d, J=8.2 Hz, 2H), 4.33 (br dd, J=5.2, 9.4 Hz, 1H), 3.25 (br dd, J=5.2, 13.8 Hz, 1H), 2.91 (br dd, J=9.6, 13.8 Hz, 1H), 2.34 (s, 3H), 1.23 (s, 9H).

Synthesis of (S)-2-amino-3-(1-tosyl-1H-indazol-5-yl)propenamide (Int-40)

To tert-butyl (S)-(1-amino-1-oxo-3-(1-tosyl-1H-indazol-5-yl)propan-2-yl)carbamate (Int-39) (4.32 g, 9.42 mmol), formic acid (14.2 mL, 377 mmol) was added and was allowed to stir at 50° C. until no starting material was observed. The solvent was evaporated under reduced pressure and the pH of the residue was adjusted between 9 and 10. The aqueous layer was extracted with ethyl acetate, washed with water, followed by brine, dried using sodium sulfate, filtered and evaporated under reduced pressure to obtain 2.76 g of title compound (Int-40). LCMS (+ESI) M+H$^+$=359.4. $^1$H NMR (600 MHz, DMSO-$d_6$) δ=8.49 (s, 1H), 8.02 (d, J=8.6 Hz, 1H), 7.80 (d, J=8.4 Hz, 2H), 7.65 (s, 1H), 7.53 (dd, J=1.5, 8.7 Hz, 1H), 7.38 (d, J=8.3 Hz, 2H), 7.31 (br s, 1H), 6.95 (br s, 1H), 3.35 (br d, J=5.0 Hz, 1H), 3.01 (dd, J=5.0, 13.5 Hz, 1H), 2.71 (dd, J=8.3, 13.5 Hz, 1H), 2.32 (s, 3H), 1.64 (br s, 2H).

Synthesis of (S)-2-(dimethylamino)-3-(1-tosyl-1H-indazol-5-yl)propanamide (Int-41)

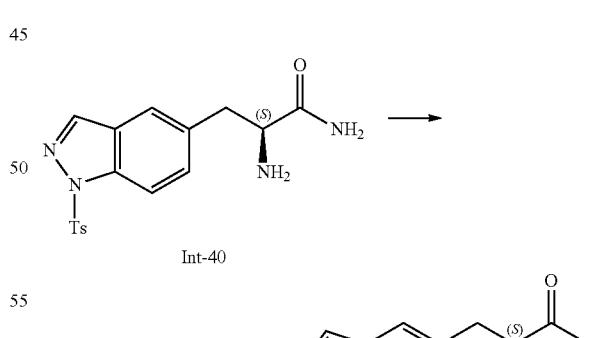

To a solution of (S)-2-amino-3-(1-tosyl-1H-indazol-5-yl)propanamide (Int-40) (2.76 g, 7.70 mmol) and methanol (27.6 mL), formaldehyde (37%, 1.15 mL, 15.4 mmol) and trimethylamine borane (2.25 g, 30.8 mmol) were added at 0°

C. and was allowed to stir at room temperature overnight. After completion of the reaction, 1.25 M HCl in methanol was added slowly with cooling and was allowed to stir for 15 minutes. The solvent was evaporated under reduced pressure and the residue was re-dissolved in methanol (this was repeated three times). To the obtained crude saturated sodium bicarbonate solution was added and was allowed to stir and the pH was adjusted to 9 and the aqueous layer was extracted with ethyl acetate. Combined organic layers were washed with brine, dried using sodium sulfate, filtered and concentrated under reduced pressure. The crude material was purified by flash chromatography using 10% methanol/DCM as gradients to afford 2 g of title compound (Int-41). LCMS (+ESI) M+H$^+$=387.4. $^1$H NMR (600 MHz, DMSO-d$_6$) δ=8.47 (s, 1H), 8.00 (d, J=8.6 Hz, 1H), 7.79 (d, J=8.3 Hz, 2H), 7.63 (s, 1H), 7.51 (dd, J=1.3, 8.6 Hz, 1H), 7.38 (d, J=8.4 Hz, 2H), 7.18 (br s, 1H), 6.87 (br s, 1H), 3.22-3.14 (m, 1H), 3.00 (dd, J=8.8, 13.4 Hz, 1H), 2.88 (dd, J=5.7, 13.5 Hz, 1H), 2.32 (s, 3H), 2.25 (s, 6H).

Synthesis of (S)-3-(1H-indazol-5-yl)-N2,N2-dimethylpropane-1,2-diamine (Int-42)

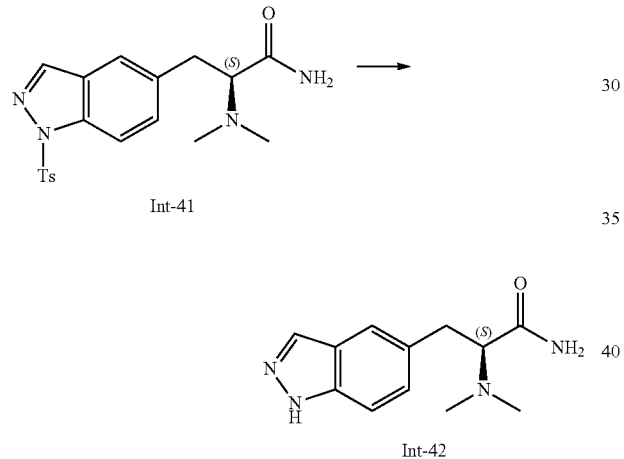

To the solution of (S)-2-(dimethylamino)-3-(1-tosyl-1H-indazol-5-yl)propanamide (Int-41) (1.94 g, 5.02 mmol) and THF (77.6 mL), LAH (1M, 25.1 mL, 25.1 mmol) was added at 0° C. and was warmed to room temperature and then was allowed to stir at 68° C. overnight. After completion of the reaction, the mixture was cooled to 0° C. and water (25 mL), 15% NaOH solution (25 mL) and water (75 mL) were added and was warmed to room temperature and later was allowed to stir at room temperature for 1 and a half hour. The solids were filtered and the cake was washed with more THF and the solvent was evaporated under reduced pressure. The crude material was purified by flash chromatography using amino column using 10% methanol/DCM as gradients to obtain 870 mg of title compound (Int-42) and 310 mg (26%) of (S)-2-(dimethylamino)-3-(1H-indazol-5-yl)propanamide at ~70% purity by $^1$H NMR. LCMS (+ESI) M+H$^+$=219.4. $^1$H NMR (600 MHz, METHANOL-d$_4$) δ=7.95 (s, 1H), 7.56 (s, 1H), 7.46 (d, J=8.5 Hz, 1H), 7.25 (d, J=8.4 Hz, 1H), 3.08-3.04 (m, 1H), 2.78-2.72 (m, 1H), 2.67-2.60 (m, 1H), 2.52 (dd, J=4.2, 13.2 Hz, 1H), 2.45 (dd, J=9.9, 13.4 Hz, 1H), 2.37 (s, 6H).

Example B1

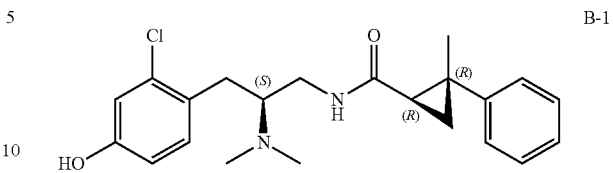

Synthesis of (1R,2R)—N—((S)-3-(2-chloro-4-hydroxyphenyl)-2-(dimethylamino)propyl)-2-methyl-2-phenylcyclopropane-1-carboxamide (Compound B-1)

Step 1: Synthesis of methyl (S)-2-((tert-butoxycarbonyl)amino)-3-(2-chloro-4-hydroxyphenyl)propanoate

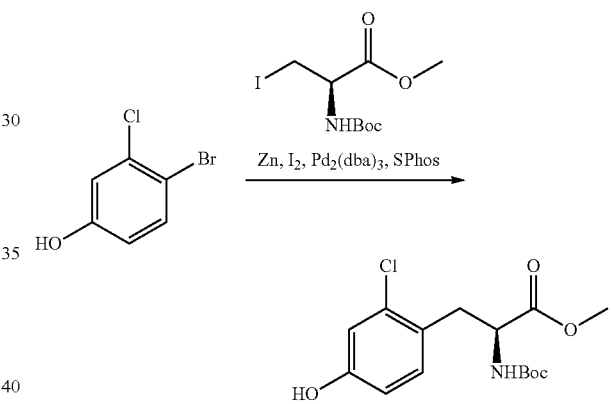

To a stirred suspension of zinc powder (2 g, 31 mmol) in anhydrous N,N-dimethylformamide (10 mL) under nitrogen was added iodine (250 mg). After 5 min, a solution of methyl (R)-2-((tert-butoxycarbonyl)amino)-3-iodopropanoate (4.0 g, 12 mmol) in N,N-dimethylformamide (10 mL) was slowly added over 10 min. Then additional iodine (250 mg) was added. The mixture was stirred at rt for 30 min. A suspension of 4-bromo-3-chlorophenol (2.0 g, 10 mmol), Pd$_2$(dba)$_3$ (230 mg, 0.25 mmol), and 2-dicyclohexylphosphino-2',6'-dimethoxybiphenyl (Sphos, 210 mg, 0.5 mmol) in N,N-dimethylformamide (10 mL) was added into the zinc reagent mixture. The reaction mixture was heated at 40° C. and stirred overnight. After cooling, the reaction mixture was quenched with water, diluted with EtOAc and filtered through Celite. The filter cake was washed with EtOAc and the filtrate was washed with brine, dried over anhydrous sodium sulfate, and concentrated. The residue was purified by flash column chromatography over silica gel (0-50% EtOAc/hexane) to afford the desired product as brown foam (2.7 g, 83%). LC-MS: 352.1 [M+Na]$^+$; $^1$H NMR (400 MHz, CDCl$_3$) (rotamers) δ 7.04 (d, 1H, J=8.3 Hz), 6.86 (s, 1H), 6.65 (d, 1H, J=7.5 Hz), 5.96 (br s, 0.2H), 5.41 (s, 0.7H), 5.07 (d, 0.8H, J=8.2 Hz), 4.83 (br s, 0.2H), 4.56 (m, 1H), 3.73 (s, 3H), 3.21 (dd, 1H, J=14.0, 6.0 Hz), 3.02 (dd, 0.8H, J=13.6, 7.6 Hz), 2.80 (m, 0.2H), 1.39 and 1.33 (s, 9H).

Step 2: Synthesis of tert-butyl (S)-(1-amino-3-(2-chloro-4-hydroxyphenyl)-1-oxopropan-2-yl)carbamate

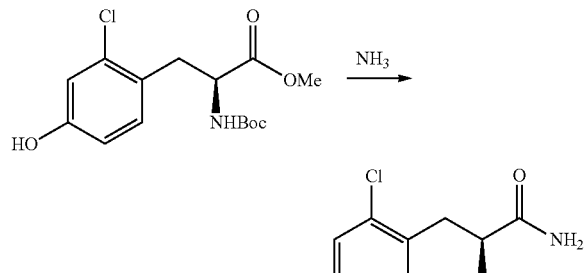

A microwave tube was charged with methyl (S)-2-((tert-butoxycarbonyl)amino)-3-(2-chloro-4-hydroxyphenyl)propanoate (2.6 g) and 7M ammonia in methanol (20 mL). The reaction was heated under microwave irradiation at 100° C. for 20 h. LC-MS indicated the reaction was complete. The reaction was concentrated down to dryness to afford the desired product as a light yellow solid (2.6 g). LC-MS: 337.1 [M+Na]$^+$.

Step 3: Synthesis of tert-butyl (S)-(1-amino-3-(2-chloro-4-hydroxyphenyl)propan-2-yl)carbamate

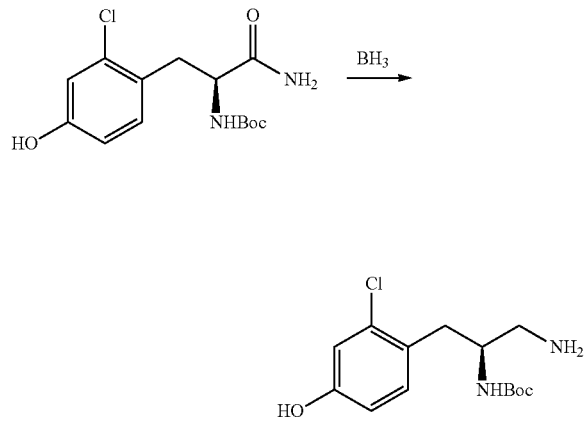

To a stirred solution of tert-butyl (S)-(1-amino-3-(2-chloro-4-hydroxyphenyl)-1-oxopropan-2-yl)carbamate (2.0 g, 6.4 mmol) in anhydrous THF (100 mL) under nitrogen was added borane-DMS complex (6.4 mL, 64 mmol). The reaction mixture was stirred overnight at room temperature and then at 60° C. for 1 h. After cooling, the reaction was carefully quenched with methanol (20 mL) and then heated at 70° C. for 1 h. The mixture was concentrated and purified by silica gel column (0-20% MeOH/CH$_2$Cl$_2$ with 5% ammonia) to recover some starting material (520 mg) and afford the desired product as a white solid (500 mg, 26%). LC-MS: 301.1 [M+H]$^+$; $^1$H NMR (400 MHz, DMSO-d6) δ 7.09 (d, 1H, J=8.2 Hz), 6.76 (s, 1H), 6.70-6.55 (m, 2H), 3.53 (m, 1H), 2.78 (dd, 1H, J=13.8, 5.2 Hz), 1.31 and 1.18 (s, 9H).

Step 4: Synthesis of tert-butyl ((S)-1-(2-chloro-4-hydroxyphenyl)-3-((1R,2R)-2-methyl-2-phenylcyclopropane-1-carboxamido)propan-2-yl)carbamate

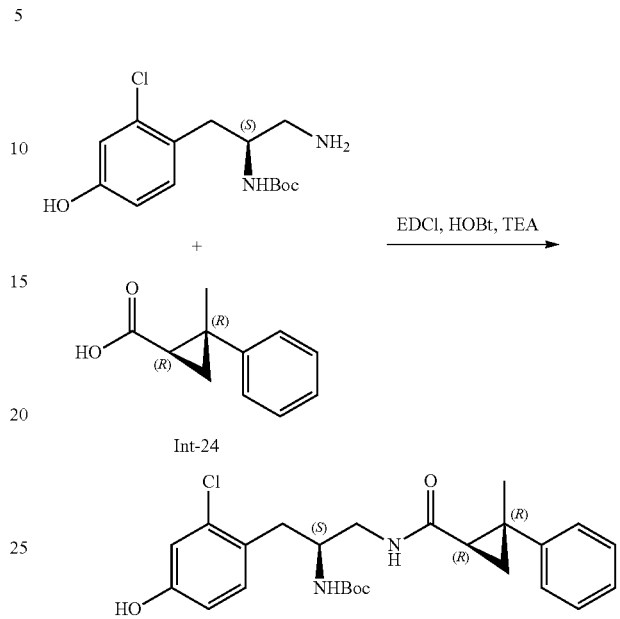

To a stirred solution of (1R,2R)-2-methyl-2-phenylcyclopropane-1-carboxylic acid (Int-24) (240 mg, 1.36 mmol) and hydroxybenzotriazole (180 mg, 1.3 mmol) in anhydrous DMF (5 mL) was added 1-ethyl-3-(3-dimethylaminopropyl)-carbodiimide hydrochloride (400 mg, 2 mmol), followed by triethylamine (0.38 mL, 2.73 mmol). The mixture was stirred under nitrogen at rt for 3 h and then slowly added into an ice-cooled solution of tert-butyl (S)-(1-amino-3-(2-chloro-4-hydroxyphenyl)propan-2-yl)carbamate (400 mg, 1.33 mmol) in anhydrous DMF (5 mL). The reaction mixture was slowly warmed to rt and stirred overnight. The mixture was diluted with water and extracted with EtOAc. The combined organic layers were washed with aq. NaHCO$_3$ and brine, dried over anhydrous sodium sulfate, and concentrated. The residue was purified by flash column chromatography over silica gel (0-80% EtOAc/hexane) to afford a white solid (420 mg, 69%). LC-MS: 481.2 [M+Na]$^+$; $^1$H NMR (400 MHz, CDCl$_3$) δ 7.46 (br s, 1H), 7.35-7.15 (m, 5H), 7.06 (br d, 1H, J=8.2 Hz), 6.89 (s, 1H), 6.68 (m, 1H), 6.46 (br s, 1H), 5.10 and 4.95 (d, 1H, J=7.6 Hz), 3.99 (m, 1H), 3.50-3.30 (m, 2H), 2.87 (m, 2H), 1.73 (t, 1H, J=7.2 Hz), 1.55-1.25 (m, 14H).

Step 5: Synthesis of (1R,2R)—N—((S)-2-amino-3-(2-chloro-4-hydroxyphenyl)propyl)-2-methyl-2-phenylcyclopropane-1-carboxamide

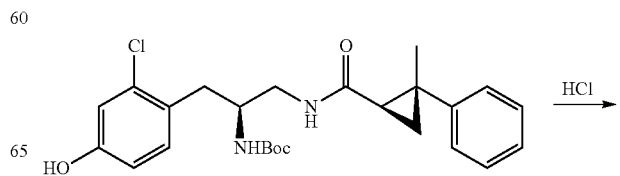

-continued

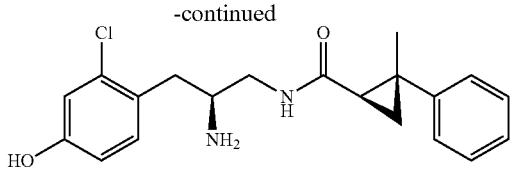

To a stirred solution of tert-butyl ((S)-1-(2-chloro-4-hydroxyphenyl)-3-(((1R,2R)-2-methyl-2-phenylcyclopropane-1-carboxamido)propan-2-yl)carbamate (420 mg) and phenol (400 mg) in 1,4-dioxane (5 mL) was added 4N HCl solution in 1,4-dioxane (2.5 mL). The reaction mixture was stirred at rt for 8 h and then concentrated in vacuo. The residue was used for next step reaction without purification.

Step 6: Synthesis of (1R,2R)—N—((S)-3-(2-chloro-4-hydroxyphenyl)-2-(dimethylamino)propyl)-2-methyl-2-phenylcyclopropane-1-carboxamide (Compound B-1)

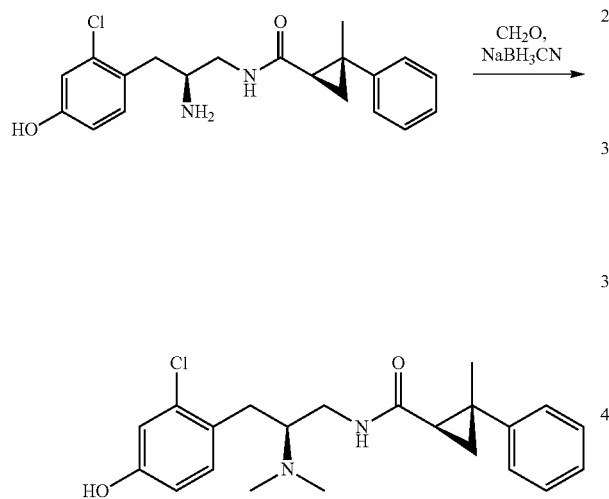

The crude (1R,2R)—N—((S)-2-amino-3-(2-chloro-4-hydroxyphenyl)-propyl)-2-methyl-2-phenylcyclopropane-1-carboxamide from above was dissolved in acetonitrile (20 mL) and water (2 mL) and cooled at 0° C. 37% aqueous solution of formaldehyde (0.40 mL) was added, followed by sodium cyanoborohydride (200 mg). After 10 min, acetic acid (0.30 mL) was added, and the reaction mixture was stirred at 0° C. for 3 h. The reaction solution was adjusted to pH 10-11 with aq. Na$_2$CO$_3$ and extracted with EtOAc. The combined organic layers were washed with brine, dried over anhydrous sodium sulfate, and concentrated. The residue was purified by flash column chromatography over silica gel (0-5% MeOH/CH$_2$Cl$_2$ with 5% ammonia) to afford the desired product as white foam (325 mg, 92% yield for 2 steps). LC-MS: 387.2 [M+H]$^+$; $^1$H NMR (400 MHz, DMSO-d6) δ 9.68 (s, 1H), 7.95 (m, 1H), 7.35-7.24 (m, 4H), 7.18 (m, 1H), 7.12 (d, 1H, J=8.4 Hz), 6.77 (s, 1H), 6.67 (d, 1H, J=8.4 Hz), 3.17 (m, 1H), 3.06 (m, 1H), 2.85-2.75 (m, 2H), 2.45 (m, 1H), 2.27 (s, 6H), 1.92 (t, 1H, J=7.2 Hz), 1.36 (s, 3H), 1.25-1.15 (m, 2H).

Example B2

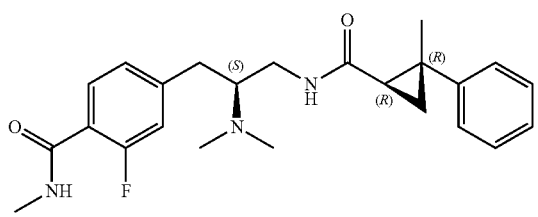

B-2

Synthesis of 4-((S)-2-(dimethylamino)-3-((1R,2R)-2-methyl-2-phenylcyclopropane-1-carboxamido)propyl)-2-fluoro-N-methylbenzamide (Compound B-2)

Step 1: Synthesis of methyl (S)-2-((tert-butoxycarbonyl)amino)-3-(3-fluoro-4-(methylcarbamoyl)phenyl)propanoate

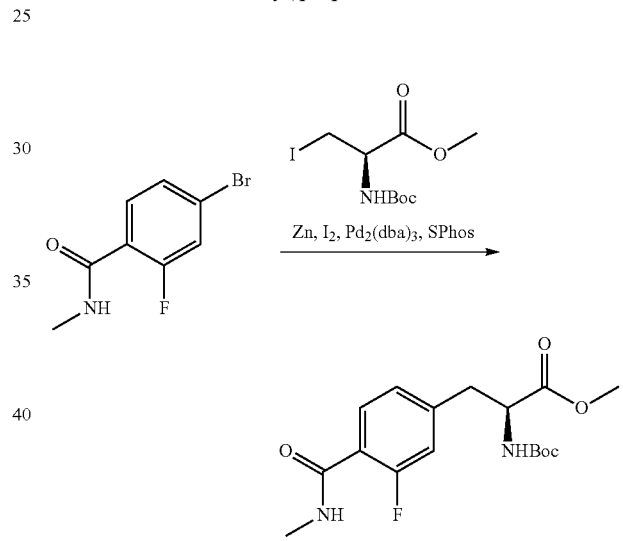

To a stirred suspension of zinc powder (2.5 g, 38.5 mmol) in anhydrous N,N-dimethylformamide (10 mL) under nitrogen was added iodine (200 mg). After 5 min, a solution of methyl (R)-2-((tert-butoxycarbonyl)amino)-3-iodopropanoate (5.0 g, 15.2 mmol) in N,N-dimethylformamide (10 mL) was added slowly over 10 min. The mixture was stirred at rt for 30 min. A suspension of 4-bromo-2-fluoro-N-methylbenzamide (2.8 g, 12 mmol), Pd$_2$(dba)$_3$ (280 mg, 0.3 mmol), and 2-dicyclohexylphosphino-2',6'-dimethoxybiphenyl (Sphos, 250 mg, 0.6 mmol) in N,N-dimethylformamide (10 mL) was added into the zinc reagent mixture. The reaction mixture was heated at 50° C. and stirred overnight. After cooling, the reaction mixture was quenched with water, diluted with EtOAc and filtered through Celite. The filter cake was washed with EtOAc and the filtrate was washed with brine, dried over anhydrous sodium sulfate, and concentrated. The residue was purified by flash column chromatography over silica gel (0-80% EtOAc/hexane) to afford the desired product as a beige solid (4.0 g, 94%). LC-MS: 377.1 [M+Na]$^+$; $^1$H NMR (400 MHz, CDCl$_3$) δ 8.04 (t, 1H, J=8.1 Hz), 7.02 (d, 1H, J=8.0 Hz), 6.91 (d, 1H, J=12.8 Hz), 6.70 (m, 1H), 5.02 (d, 1H, J=8.0 Hz), 4.60 (m, 1H), 3.73 (s, 3H), 3.18 (dd, 1H, J=13.8, 5.4 Hz), 3.07 (m, 1H), 3.03 (d, 3H, J=4.6 Hz), 1.43 (s, 9H).

Step 2: Synthesis of tert-butyl (S)-(1-(3-fluoro-4-(methylcarbamoyl)phenyl)-3-hydroxypropan-2-yl)carbamate

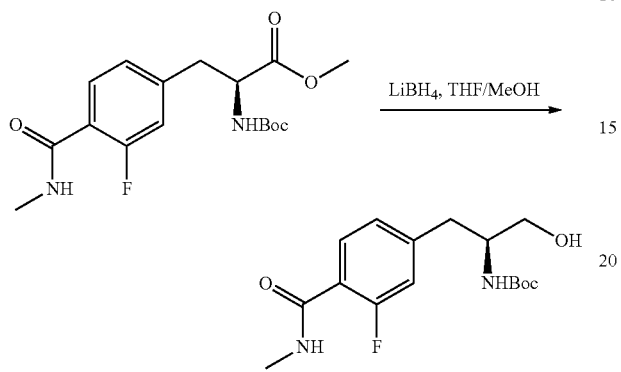

To a stirred solution of methyl (S)-2-((tert-butoxycarbonyl)amino)-3-(3-fluoro-4-(methylcarbamoyl)phenyl)propanoate (4.0 g, 11.3 mmol) in THF (80 mL) was added lithium borohydride (435 mg, 20 mmol). The reaction mixture was cooled at 0° C. and methanol (4 mL) was slowly added. The reaction mixture was slowly warmed to rt and stirred for 2 h. LC-MS indicated the completion of the reaction. The reaction was carefully quenched with methanol (10 mL) and neutralized with 2N aq. HCl. The volatiles were removed under reduced pressure and the residue was extracted with EtOAc. The organic layer was washed with brine, dried over anhydrous sodium sulfate, and concentrated to afford the desired product as a beige solid (3.8 g, 100%). LC-MS: 349.2 [M+Na]+

Step 3: Synthesis of tert-butyl (S)-(1-amino-3-(3-fluoro-4-(methylcarbamoyl)phenyl)propan-2-yl)carbamate

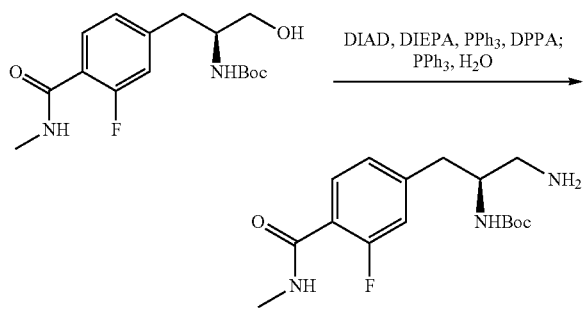

To a stirred solution of tert-butyl (S)-(1-(3-fluoro-4-(methylcarbamoyl)phenyl)-3-hydroxypropan-2-yl)carbamate (650 mg, 2.0 mmol) and triphenylphosphine (630 mg, 2.4 mmol) in anhydrous THF (20 mL) at 0° C. under nitrogen was added diisopropylethylamine (0.35 mL, 2.0 mmol), followed by slow addition of diisopropyl azodicarboxylate (0.47 mL, 2.4 mmol). The reaction mixture was slowly warmed to rt and stirred for 5 h. A second batch of triphenylphosphine (685 mg, 2.6 mmol) was added slowly over 20 min. The reaction mixture was stirred at rt for 16 h, and then water (0.36 mL, 20 mmol) was added. The reaction mixture was heated at 50° C. for 18 h and then concentrated. The residue was purified by flash column chromatography over silica gel (0-10% MeOH/CH$_2$Cl$_2$ with 5% ammonia) to afford the desired product as a white solid (270 mg, 42%). LC-MS: 326.2 [M+H]+; $^1$H NMR (400 MHz, CDCl$_3$) δ 8.03 (t, 1H, J=8.2 Hz), 7.09 (d, 1H, J=8.0 Hz), 6.98 (d, 1H, J=12.4 Hz), 6.72 (br s, 1H), 4.72 (br s, 1H), 3.79 (br s, 1H), 3.03 (d, 3H, J=4.5 Hz), 2.95-2.70 (m, 3H), 2.65 (dd, 1H, J=13.0, 6.5 Hz), 1.40 (s, 9H).

Step 4: Synthesis of tert-butyl ((S)-1-(3-fluoro-4-(methylcarbamoyl)phenyl)-3-((1R,2R)-2-methyl-2-phenylcyclopropane-1-carboxamido)propan-2-yl)carbamate

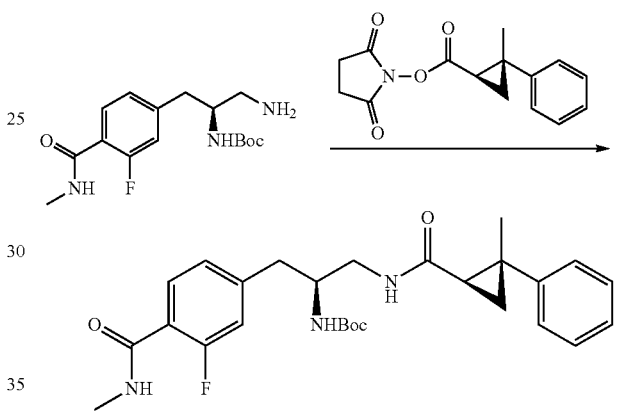

To a stirred solution of tert-butyl (S)-(1-amino-3-(3-fluoro-4-(methylcarbamoyl)phenyl)propan-2-yl)carbamate (70 mg, 0.22 mmol) in anhydrous DMF (2 mL) was added 2,5-dioxopyrrolidin-1-yl (1R,2R)-2-methyl-2-phenylcyclopropane-1-carboxylate (60 mg, 0.22 mmol). The reaction mixture was stirred overnight at rt and then concentrated in vacuo. The residue was purified by flash column chromatography over silica gel (0-100% EtOAc/hexane) to afford the desired product as a white solid (60 mg, 57%). LC-MS: 506.2 [M+Na]+; $^1$H NMR (400 MHz, CDCl$_3$) δ 8.05 (t, 1H, J=8.0 Hz), 7.35-7.15 (m, 5H), 7.11 (d, 1H, J=8.0 Hz), 7.00 (d, 1H, J=13.0 Hz), 6.71 (m, 1H), 6.10 (br s, 1H), 4.81 (br d, 1H), 3.96 (br s, 1H), 3.50-3.30 (m, 2H), 3.02 (d, 3H, J=4.8 Hz), 2.95-2.75 (m, 2H), 1.69 (dd, 1H, J=8.2, 6.0 Hz), 1.49 (s, 4H), 1.39 (s, 10H).

Step 5: Synthesis of 4-((S)-2-amino-3-((1R,2R)-2-methyl-2-phenylcyclopropane-1-carboxamido)propyl)-2-fluoro-N-methylbenzamide HCl Salt

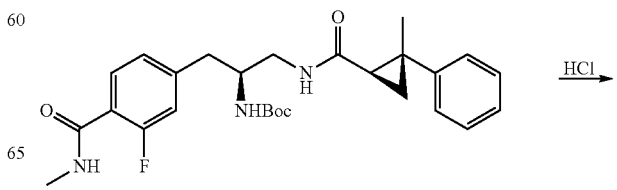

-continued

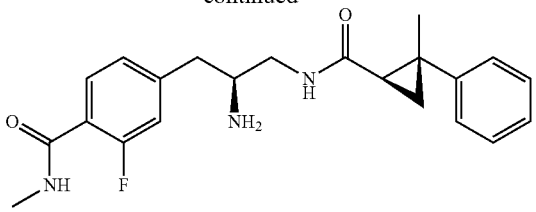

To a stirred solution of tert-butyl ((S)-1-(3-fluoro-4-(methylcarbamoyl)phenyl)-3-((1R,2R)-2-methyl-2-phenylcyclopropane-1-carboxamido)propan-2-yl)carbamate (60 mg, 0.12 mmol) and phenol (60 mg) in 1,4-dioxane (5 mL) was added 4N HCl solution in 1,4-dioxane (2 mL). The reaction mixture was stirred overnight and then concentrated in vacuo. The residue was used for next step reaction without purification.

Step 6: Synthesis of 4-((S)-2-(dimethylamino)-3-((1R,2R)-2-methyl-2-phenylcyclopropane-1-carboxamido)propyl)-2-fluoro-N-methylbenzamide (Compound B-2)

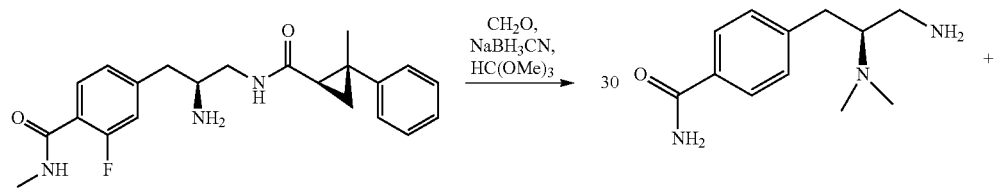

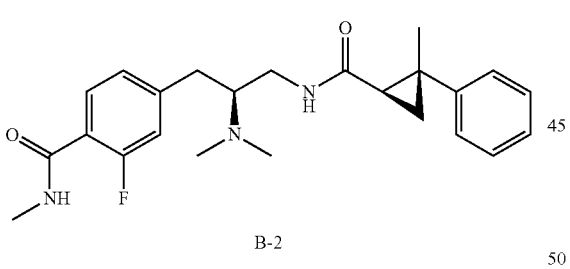

B-2

To a stirred solution of the crude 4-((S)-2-amino-3-((1R,2R)-2-methyl-2-phenylcyclopropane-1-carboxamido)propyl)-2-fluoro-N-methylbenzamide from above in acetonitrile (10 mL) and water (1 mL) was added 37% aqueous solution of formaldehyde (0.046 mL, 0.58 mmol), followed by trimethyl orthoformate (0.10 mL, 0.93 mmol). After 15 min, sodium cyanoborohydride (25 mg, 0.35 mmol) was added, and the reaction mixture was stirred at rt for 2 h. The reaction was diluted with EtOAc, washed with aq. $Na_2CO_3$ and brine, dried over anhydrous sodium sulfate, and concentrated. The residue was purified by flash column chromatography over silica gel (0-10% MeOH/$CH_2Cl_2$ with 5% ammonia) to afford the desired product as white foam (38 mg, 74% yield for 2 steps). LC-MS: 412.2 [M+H]$^+$; $^1$H NMR (400 MHz, DMSO-d6) δ 8.16 (br s, 1H), 8.02 (br t, 1H), 7.54 (t, 1H, J=7.8 Hz), 7.35-7.08 (m, 7H), 3.21 (m, 1H), 3.08 (m, 1H), 2.90-2.75 (m, 2H), 2.75 (d, 3H, J=4.2 Hz), 2.55 (m, 1H), 2.26 (s, 6H), 1.92 (t, 1H, J=7.2 Hz), 1.37 (s, 3H), 1.35-1.18 (m, 2H).

Example B3

B-3

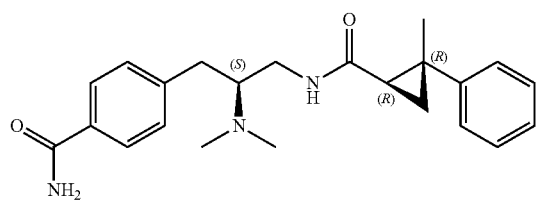

Synthesis of 4-((S)-2-(dimethylamino)-3-((1R,2R)-2-methyl-2-phenylcyclopropane-1-carboxamido)propyl)benzamide (Compound B-3)

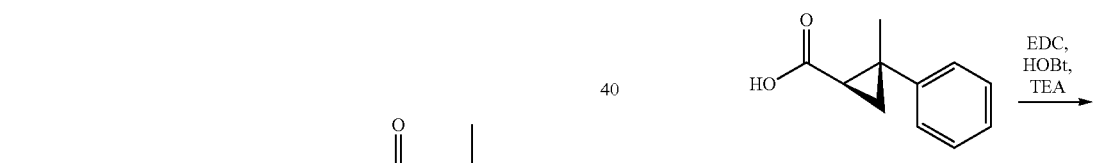

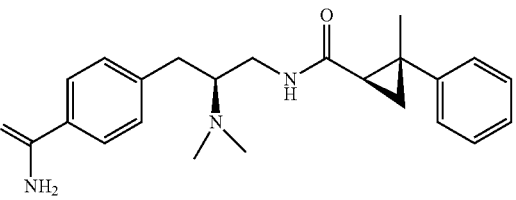

4-((S)-2-(dimethylamino)-3-((1R,2R)-2-methyl-2-phenylcyclopropane-1-carboxamido)propyl)benzamide was synthesized according to the procedure reported for Example B1 using (S)-4-(3-amino-2-(dimethylamino)propyl)benzamide and (1R,2R)-2-methyl-2-phenylcyclopropane-1-carboxylic acid (Int-24) as the starting materials. LC-MS: 380.2 [M+H]$^+$; $^1$H NMR (400 MHz, DMSO-d6) δ 7.98 (t, 1H, J=5.0 Hz), 7.90 (s, 1H), 7.78 (d, 2H, J=8.0 Hz), 7.33-7.23 (m, 7H), 7.18 (m, 1H), 3.19 (m, 1H), 3.07 (m, 1H), 2.85-2.75 (m, 2H), 2.26 (s, 6H), 1.91 (t, 1H, J=7.2 Hz), 1.36 (s, 3H), 1.28-1.18 (m, 2H).

165
Example B4

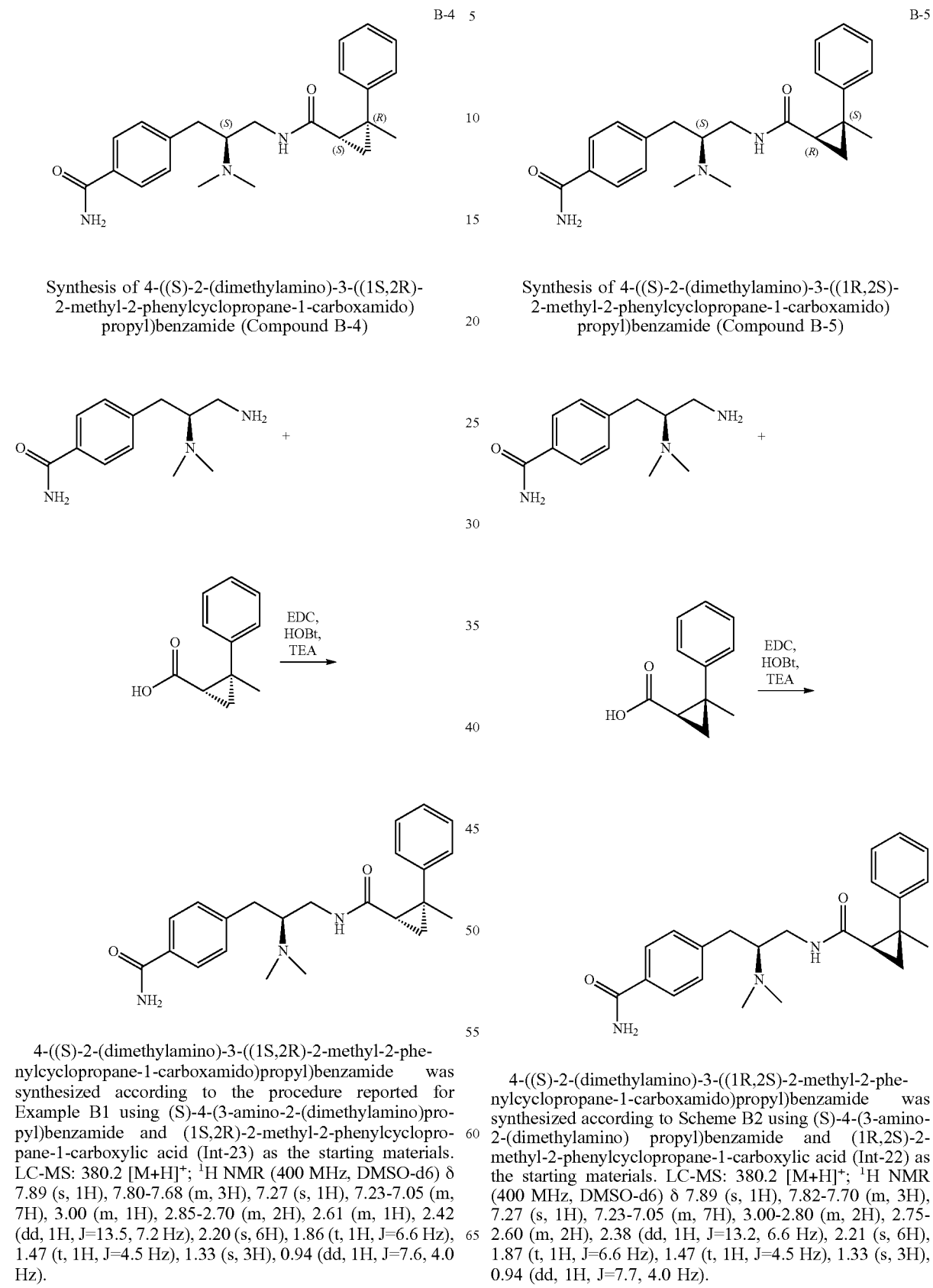

Synthesis of 4-((S)-2-(dimethylamino)-3-((1S,2R)-2-methyl-2-phenylcyclopropane-1-carboxamido)propyl)benzamide (Compound B-4)

4-((S)-2-(dimethylamino)-3-((1S,2R)-2-methyl-2-phenylcyclopropane-1-carboxamido)propyl)benzamide was synthesized according to the procedure reported for Example B1 using (S)-4-(3-amino-2-(dimethylamino)propyl)benzamide and (1S,2R)-2-methyl-2-phenylcyclopropane-1-carboxylic acid (Int-23) as the starting materials. LC-MS: 380.2 [M+H]$^+$; $^1$H NMR (400 MHz, DMSO-d6) δ 7.89 (s, 1H), 7.80-7.68 (m, 3H), 7.27 (s, 1H), 7.23-7.05 (m, 7H), 3.00 (m, 1H), 2.85-2.70 (m, 2H), 2.61 (m, 1H), 2.42 (dd, 1H, J=13.5, 7.2 Hz), 2.20 (s, 6H), 1.86 (t, 1H, J=6.6 Hz), 1.47 (t, 1H, J=4.5 Hz), 1.33 (s, 3H), 0.94 (dd, 1H, J=7.6, 4.0 Hz).

166
Example B5

Synthesis of 4-((S)-2-(dimethylamino)-3-((1R,2S)-2-methyl-2-phenylcyclopropane-1-carboxamido)propyl)benzamide (Compound B-5)

4-((S)-2-(dimethylamino)-3-((1R,2S)-2-methyl-2-phenylcyclopropane-1-carboxamido)propyl)benzamide was synthesized according to Scheme B2 using (S)-4-(3-amino-2-(dimethylamino) propyl)benzamide and (1R,2S)-2-methyl-2-phenylcyclopropane-1-carboxylic acid (Int-22) as the starting materials. LC-MS: 380.2 [M+H]$^+$; $^1$H NMR (400 MHz, DMSO-d6) δ 7.89 (s, 1H), 7.82-7.70 (m, 3H), 7.27 (s, 1H), 7.23-7.05 (m, 7H), 3.00-2.80 (m, 2H), 2.75-2.60 (m, 2H), 2.38 (dd, 1H, J=13.2, 6.6 Hz), 2.21 (s, 6H), 1.87 (t, 1H, J=6.6 Hz), 1.47 (t, 1H, J=4.5 Hz), 1.33 (s, 3H), 0.94 (dd, 1H, J=7.7, 4.0 Hz).

Example B6

Synthesis of 3-chloro-4-((S)-2-(dimethylamino)-3-((1R,2R)-2-methyl-2-phenylcyclopropane-1-carboxamido)propyl)benzamide (Compound B-6)

Example B7

Synthesis of 3-chloro-4-((S)-2-(dimethylamino)-3-((1R,2S)-2-methyl-2-phenylcyclopropane-1-carboxamido)propyl)benzamide (Compound B-7)

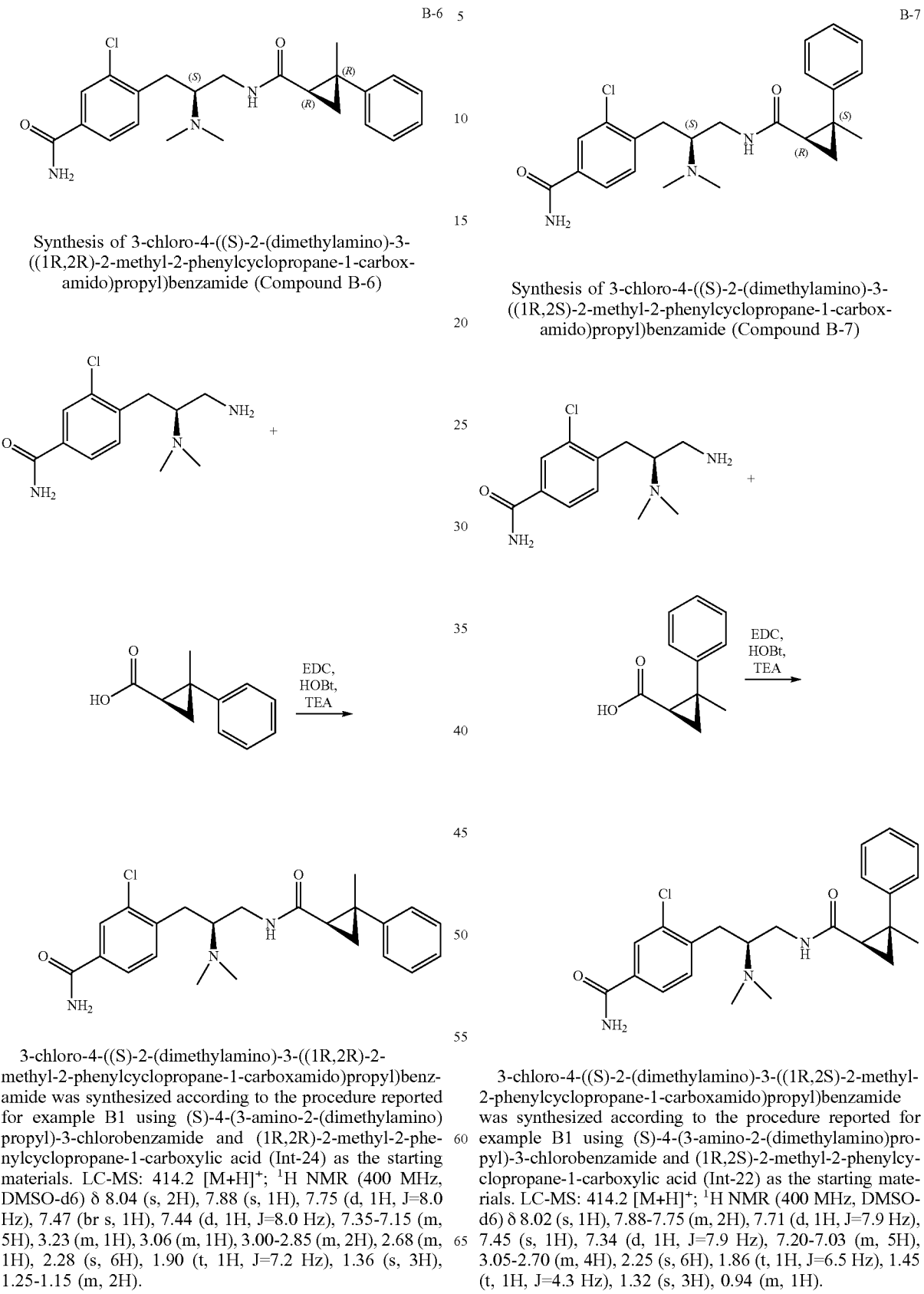

3-chloro-4-((S)-2-(dimethylamino)-3-((1R,2R)-2-methyl-2-phenylcyclopropane-1-carboxamido)propyl)benzamide was synthesized according to the procedure reported for example B1 using (S)-4-(3-amino-2-(dimethylamino)propyl)-3-chlorobenzamide and (1R,2R)-2-methyl-2-phenylcyclopropane-1-carboxylic acid (Int-24) as the starting materials. LC-MS: 414.2 [M+H]$^+$; $^1$H NMR (400 MHz, DMSO-d6) δ 8.04 (s, 2H), 7.88 (s, 1H), 7.75 (d, 1H, J=8.0 Hz), 7.47 (br s, 1H), 7.44 (d, 1H, J=8.0 Hz), 7.35-7.15 (m, 5H), 3.23 (m, 1H), 3.06 (m, 1H), 3.00-2.85 (m, 2H), 2.68 (m, 1H), 2.28 (s, 6H), 1.90 (t, 1H, J=7.2 Hz), 1.36 (s, 3H), 1.25-1.15 (m, 2H).

3-chloro-4-((S)-2-(dimethylamino)-3-((1R,2S)-2-methyl-2-phenylcyclopropane-1-carboxamido)propyl)benzamide was synthesized according to the procedure reported for example B1 using (S)-4-(3-amino-2-(dimethylamino)propyl)-3-chlorobenzamide and (1R,2S)-2-methyl-2-phenylcyclopropane-1-carboxylic acid (Int-22) as the starting materials. LC-MS: 414.2 [M+H]$^+$; $^1$H NMR (400 MHz, DMSO-d6) δ 8.02 (s, 1H), 7.88-7.75 (m, 2H), 7.71 (d, 1H, J=7.9 Hz), 7.45 (s, 1H), 7.34 (d, 1H, J=7.9 Hz), 7.20-7.03 (m, 5H), 3.05-2.70 (m, 4H), 2.25 (s, 6H), 1.86 (t, 1H, J=6.5 Hz), 1.45 (t, 1H, J=4.3 Hz), 1.32 (s, 3H), 0.94 (m, 1H).

Example B8

Synthesis of 4-((S)-2-(dimethylamino)-3-((1R,2R)-2-methyl-2-phenylcyclopropane-1-carboxamido)propyl)-3,5-dimethylbenzamide (Compound B-8)

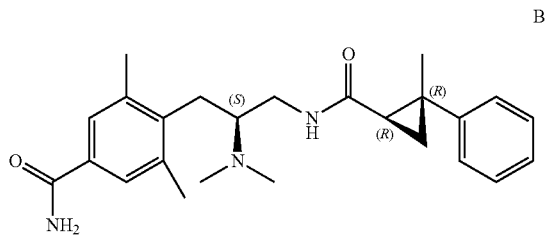

B-8

Step 1: Synthesis of methyl (S)-2-((tert-butoxycarbonyl)amino)-3-(4-cyano-2,6-dimethylphenyl)propanoate

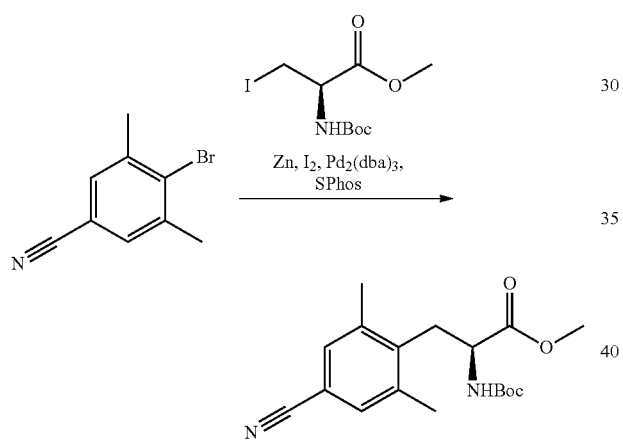

To a stirred suspension of zinc powder (2.1 g, 32.3 mmol) in anhydrous N,N-dimethylformamide (10 mL) under nitrogen was added iodine (170 mg). After 5 min, a solution of methyl (R)-2-((tert-butoxycarbonyl)amino)-3-iodopropanoate (4.2 g, 12.8 mmol) in N,N-dimethylformamide (10 mL) was added slowly over 10 min. The mixture was stirred at rt for 30 min. A suspension of 4-bromo-3,5-dimethylbenzonitrile (2.5 g, 12 mmol), Pd$_2$(dba)$_3$ (205 mg, 0.22 mmol), and 2-dicyclohexylphosphino-2',6'-dimethoxybiphenyl (Sphos, 210 mg, 0.51 mmol) in N,N-dimethylformamide (10 mL) was added into the zinc reagent mixture. The reaction mixture was heated at 50° C. and stirred overnight. After cooling, the reaction mixture was quenched with water, diluted with EtOAc and filtered through Celite. The filter cake was washed with EtOAc and the filtrate was washed with brine, dried over anhydrous sodium sulfate, and concentrated. The residue was purified by flash column chromatography over silica gel (0-20% EtOAc/CH$_2$Cl$_2$) to afford the desired product as a white solid (2.0 g, 50%). LC-MS: 355.2 [M+Na]$^+$; $^1$H NMR (400 MHz, CDCl$_3$) δ 7.30 (s, 2H), 5.13 (d, 1H, J=8.8 Hz), 4.56 (q, 1H, J=8.0 Hz), 3.67 (s, 3H), 3.15-3.00 (m, 2H), 2.38 (s, 6H), 1.35 (s, 9H).

Step 2: Synthesis of tert-butyl (S)-(1-(4-cyano-2,6-dimethylphenyl)-3-hydroxypropan-2-yl)carbamate

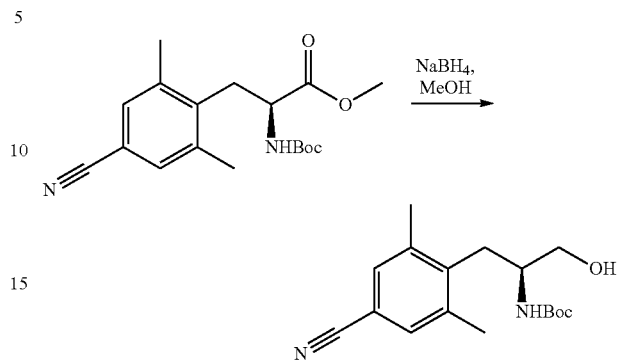

To a stirred solution of methyl (S)-2-((tert-butoxycarbonyl)amino)-3-(4-cyano-2,6-dimethylphenyl)propanoate (2.0 g, 6.0 mmol) in ethanol (50 mL) was added sodium borohydride (0.8 g, 21 mmol). The reaction mixture was heated at 50° C. for 3 h and LC-MS indicated the completion of the reaction. The reaction was carefully quenched with 2N aq. HCl and adjusted to pH 5-6. The volatiles were removed under reduced pressure and the residue was extracted with EtOAc. The organic layer was washed with brine, dried over anhydrous sodium sulfate, and concentrated. The residue was purified by flash column chromatography over silica gel (0-100% EtOAc/hexane) to afford the desired product as a white solid (1.1 g, 60%). LC-MS: 327.2 [M+Na]$^+$; $^1$H NMR (400 MHz, CDCl$_3$) δ 7.30 (s, 2H), 4.87 (br s, 1H), 3.90 (m, 1H), 3.70 (m, 1H), 3.55 (dt, 1H, J=10.7, 4.4 Hz), 3.05-2.85 (m, 2H), 2.41 (s, 6H), 2.09 (br s, 1H), 1.37 (s, 9H).

Step 3: Synthesis of tert-butyl (S)-(1-(4-carbamoyl-2,6-dimethylphenyl)-3-hydroxypropan-2-yl)carbamate

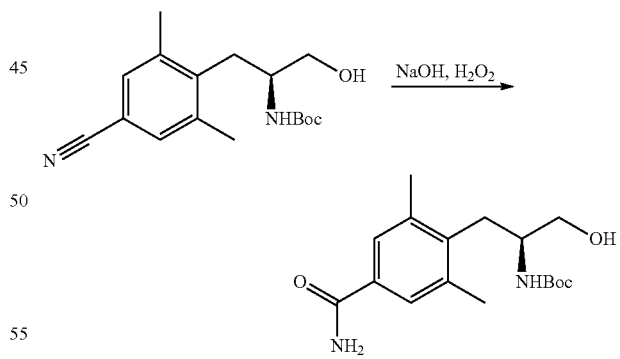

To a stirred solution of tert-butyl (S)-(1-(4-cyano-2,6-dimethylphenyl)-3-hydroxypropan-2-yl)carbamate (1.1 g, 3.6 mmol) in methanol (30 mL) was added 6N aq. NaOH (0.55 mL, 3.3 mmol), followed by 27% aq. Solution of hydrogen peroxide (1.45 mL, 11.5 mmol). The reaction mixture was stirred at 50° C. for 2 h. After cooling, the mixture was neutralized with 1N aq. HCl. Removal of methanol under reduced pressure and the residue was extracted with EtOAc. The organic layer was washed with brine, dried over anhydrous sodium sulfate, and concentrated to afford the desired product as a white solid (0.95 g, 82%). LC-MS: 345.2 [M+Na]+; 1H NMR (400 MHz, CDCl3) δ 7.45 (s, 2H), 6.20 (br s, 1H), 5.60 (br s, 1H), 4.87 (d, 1H, J=8.5 Hz), 3.88 (m, 1H), 3.69 (dd, 1H, J=10.5, 3.5 Hz), 3.55 (dd, 1H, J=10.7, 4.6 Hz), 2.95 (m, 1H), 2.43 (s, 7H), 1.38 (s, 9H).

Step 4: Synthesis of tert-butyl (S)-(1-(4-carbamoyl-2,6-dimethylphenyl)-3-(1,3-dioxoisoindolin-2-yl)propan-2-yl)carbamate

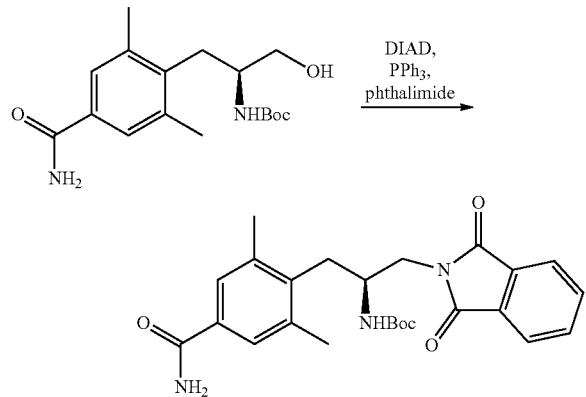

To a stirred solution of tert-butyl (S)-(1-(4-carbamoyl-2,6-dimethylphenyl)-3-hydroxypropan-2-yl)carbamate (0.95 g, 2.9 mmol), phthalimide (0.50 g, 3.4 mmol), and triphenylphosphine (0.90 g, 3.4 mmol) in anhydrous THF (50 mL) at 0° C. under nitrogen was added diisopropyl azodicarboxylate (0.70 mL, 3.4 mmol) over 20 min. The reaction mixture was slowly warmed to rt and stirred overnight. The mixture was concentrated and the residue was purified by flash column chromatography over silica gel (0-100% EtOAc/CH2Cl2) to afford the desired product as a white solid (1.15 g, 86%). LC-MS: 474.2 [M+Na]+; 1H NMR (400 MHz, DMSO-d6) δ 7.93-7.75 (m, 5H), 7.50 (s, 2H), 7.20 (s, 1H), 6.93 and 6.52 (d, 1H, J=10.0 Hz), 4.07 (m, 1H), 3.76 (t, 1H, J=12.0 Hz), 3.46 (m, 1H), 2.90-2.80 (m, 2H), 2.35 (s, 6H), 1.08 and 0.88 (s, 9H).

Step 5: Synthesis of (S)-4-(2-amino-3-(1,3-dioxoisoindolin-2-yl)propyl)-3,5-dimethylbenzamide

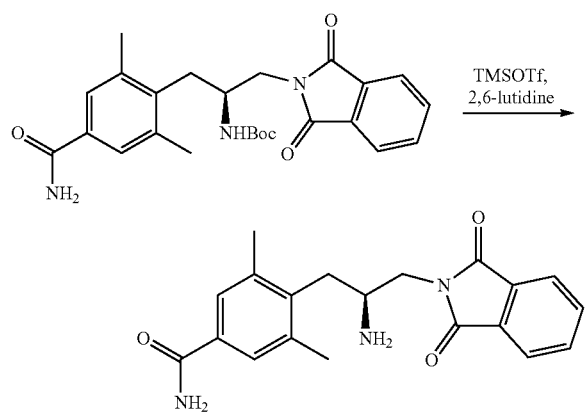

To a stirred solution of (S)-(1-(4-carbamoyl-2,6-dimethylphenyl)-3-(1,3-dioxoisoindolin-2-yl)propan-2-yl)carbamate (0.6 g, 1.3 mmol) in anhydrous CH2Cl2 (80 mL) and 2,6-lutidine (0.93 mL, 8.0 mmol) at 0° C. under nitrogen was slowly added TMSOTf (0.72 mL, 4.0 mmol). The reaction mixture was slowly warmed to rt and stirred overnight. Additional TMSOTf (0.3 mL) was added and the reaction was stirred for additional 3 h. The reaction was quenched with water, adjusted to pH 9-10 with aq. Sodium bicarbonate, and extracted with CH2Cl2 (2×). The combined organic layers were washed with brine, dried over anhydrous sodium sulfate, and concentrated. The residue was purified by flash column chromatography over silica gel (0-10% MeOH/CH2Cl2) to afford the desired product as a white foam (410 mg, 88%). LC-MS: 352.2 [M+H]+; 1H NMR (400 MHz, CDCl3) δ 7.86 (d, 2H, J=3.6 Hz), 7.74 (d, 2H, J=3.8 Hz), 7.46 (s, 2H), 6.03 (br s, 1H), 5.52 (br s, 1H), 3.75 (d, 2H, J=6.5 Hz), 3.47 (m, 1H), 2.90-2.70 (m, 2H), 2.40 (s, 6H).

Step 6: Synthesis of (S)-4-(2-(dimethylamino)-3-(1,3-dioxoisoindolin-2-yl)propyl)-3,5-dimethylbenzamide

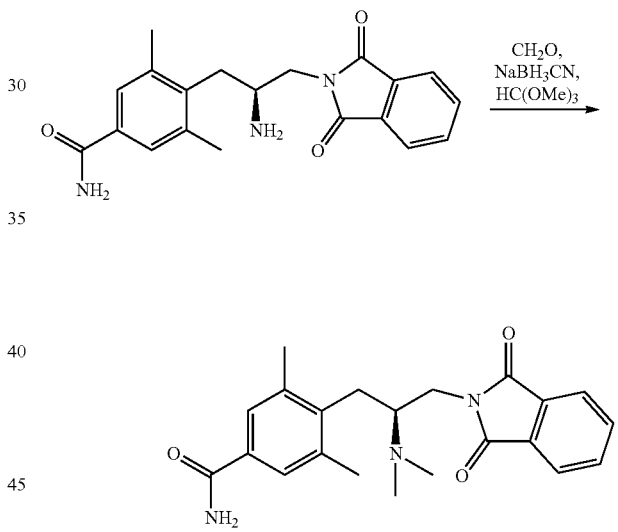

To a stirred solution of (S)-4-(2-amino-3-(1,3-dioxoisoindolin-2-yl)propyl)-3,5-dimethylbenzamide (410 mg, 1.2 mmol) in acetonitrile (10 mL) and water (1 mL) was added 37% aqueous solution of formaldehyde (0.46 mL, 5.8 mmol), followed by trimethyl orthoformate (1.0 mL, 9.3 mmol). After 15 min, sodium cyanoborohydride (225 mg, 3.5 mmol). The reaction mixture was stirred at rt for 2 h. The mixture was diluted with EtOAc, washed with aq. NaHCO3 and brine, dried over anhydrous sodium sulfate, and concentrated. The residue was purified by flash column chromatography over silica gel (0-10% MeOH/CH2Cl2) to afford the desired product as a white solid (300 mg, 68%). LC-MS: 380.2 [M+H]+; 1H NMR (400 MHz, CDCl3) δ 7.78 (dd, 2H, J=5.5, 3.0 Hz), 7.68 (dd, 2H, J=5.5, 3.0 Hz), 7.46 (s, 2H), 6.10 (br s, 1H), 5.55 (br s, 1H), 3.91 (dd, 1H, J=13.6, 10.5 Hz), 3.48 (m, 1H), 3.24 (dd, 1H, J=13.6, 4.5 Hz), 2.99 (dd, 1H, J=13.6, 4.8 Hz), 2.73 (dd, 1H, J=13.6, 10.0 Hz), 2.42 (s, 6H), 2.40 (s 6H).

Step 7: Synthesis of (S)-4-(3-amino-2-(dimethylamino)propyl)-3,5-dimethylbenzamide

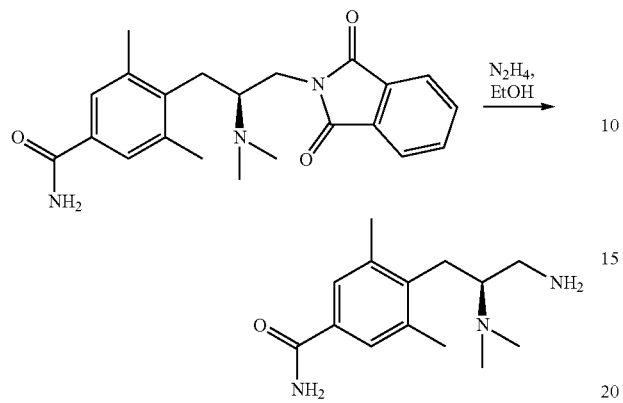

A mixture of (S)-4-(2-(dimethylamino)-3-(1,3-dioxoisoindolin-2-yl)propyl)-3,5-dimethylbenzamide (300 mg, 0.79 mmol) in ethanol (10 mL) and hydrazine monohydrate (0.20 mL, 4 mmol) was stirred at 70° C. for 5 h. After cooling, the mixture was filtered to remove the solids. The filtrate was concentrated and purified by flash column chromatography over silica gel (0-20% MeOH/CH$_2$Cl$_2$ with 5% ammonia) to afford the desired product as a white solid (175 mg, 89%). LC-MS: 250.2 [M+H]$^+$; $^1$H NMR (400 MHz, CDCl$_3$) δ 7.43 (s, 2H), 6.00 (br s, 1H), 5.50 (br s, 1H), 2.91 (dd, 1H, J=13.2, 2.5 Hz), 2.78-2.65 (m, 2H), 2.63-2.50 (m, 1H), 2.43 (s, 6H), 2.37 (s, 6H), 2.35 (m, 1H).

Step 8: Synthesis of 4-((S)-2-(dimethylamino)-3-((1R,2R)-2-methyl-2-phenylcyclopropane-1-carboxamido)propyl)-3,5-dimethylbenzamide (Compound B-8)

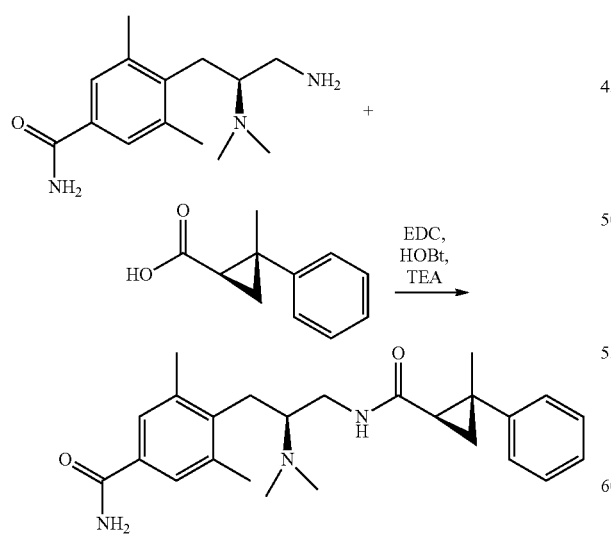

4-((S)-2-(dimethylamino)-3-((1R,2R)-2-methyl-2-phenylcyclopropane-1-carboxamido)propyl)-3,5-dimethylbenzamide was synthesized according to the procedure in Example B1 using (S)-4-(3-amino-2-(dimethylamino)propyl)-3,5-dimethylbenzamide and (1R,2R)-2-methyl-2-phenylcyclopropane-1-carboxylic acid (Int-24) as the starting materials. LC-MS: 408.3 [M+H]$^+$; $^1$H NMR (400 MHz, DMSO-d6) δ 7.99 (t, 1H, J=5.0 Hz), 7.81 (s, 1H), 7.49 (s, 2H), 7.35-7.15 (m, 6H), 3.25 (m, 1H), 2.93 (m, 1H), 2.85-2.75 (m, 2H), 2.55 (dd, 1H, J=15.2, 9.8 Hz), 2.33 and 2.32 (s, 12H), 1.89 (t, 1H, J=7.0 Hz), 1.35 (s, 3H), 1.25-1.15 (m, 2H).

Example B9

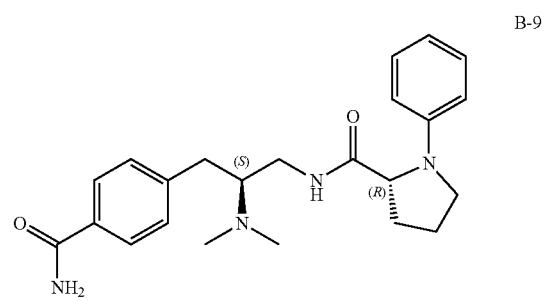

B-9

Synthesis of (R)—N—((S)-3-(4-carbamoylphenyl)-2-(dimethylamino)propyl)-1-phenylpyrrolidine-2-carboxamide (Compound B-9)

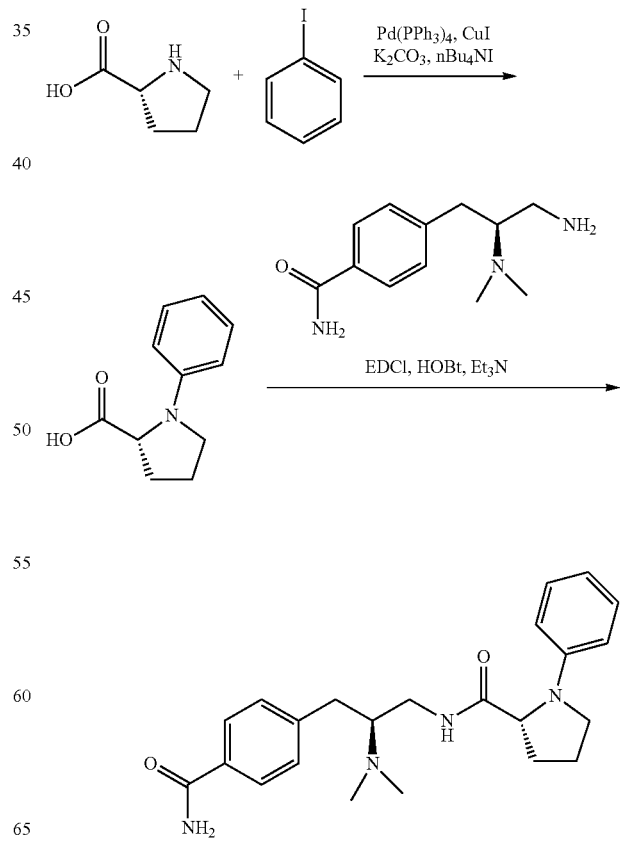

Step 1: Synthesis of phenyl-D-proline

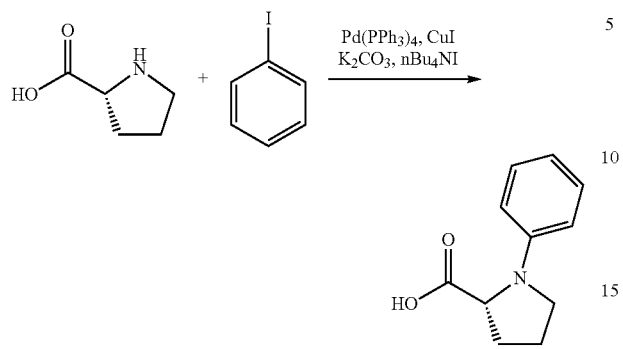

A microwave tube was charged under nitrogen with iodobenzene (810 mg, 4 mmol), D-proline (460 mg, 4 mmol), K$_2$CO$_3$ (560 mg), n-Bu$_4$NI (250 mg), CuI (40 mg), Pd(PPh$_3$)$_4$ (230 mg), TEA (1.6 mL), DMF (8 mL), and water (0.8 mL). The reaction was heated under microwave irradiation at 120° C. for 1 h. The mixture was diluted with water, adjusted to pH 2-3 with 2N aq. HCl, and extracted with EtOAc. The combined organic layers were washed with brine, dried over anhydrous sodium sulfate, and concentrated. The residue was purified by flash column chromatography over silica gel (0-100% EtOAc/hexane) to afford the desired product as a brown oil (200 mg). LC-MS: 192.1 [M+H]$^+$; $^1$H NMR (400 MHz, CDCl$_3$) δ 7.26 (t, 2H, J=7.6 Hz), 6.79 (t, 1H, J=7.5 Hz), 6.61 (d, 2H, J=8.0 Hz), 4.20 (dd, 1H, J=8.8, 2.4 Hz), 3.63 (m, 1H), 3.32 (q, 1H, J=8.0 Hz), 2.40-2.20 (m, 2H), 2.20-1.90 (m, 2H).

Step 2: Synthesis of (R)—N—((S)-3-(4-carbamoylphenyl)-2-(dimethylamino)propyl)-1-phenylpyrrolidine-2-carboxamide (Compound B-9)

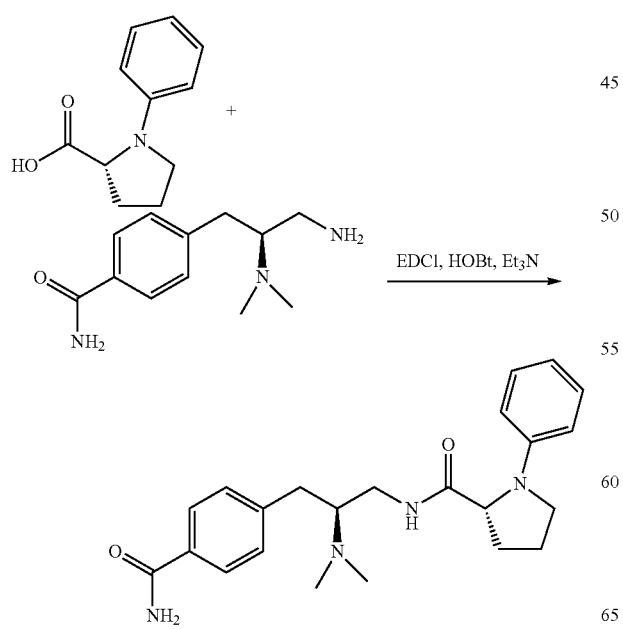

(R)—N—((S)-3-(4-carbamoylphenyl)-2-(dimethylamino)propyl)-1-phenylpyrrolidine-2-carboxamide was synthesized according to the procedure in example B1 using phenyl-D-proline and (S)-4-(3-amino-2-(dimethylamino)propyl)benzamide as the starting materials. LC-MS: 395.2 [M+H]$^+$; $^1$H NMR (400 MHz, DMSO-d6) δ 7.89 (s, 1H), 7.75 (d, 2H, J=8.0 Hz), 7.63 (t, 1H, J=5.0 Hz), 7.28 (s, 1H), 7.18 (d, 2H, J=8.0 Hz), 7.14 (t, 2H, J=7.8 Hz), 6.63 (t, 1H, J=7.2 Hz), 6.48 (d, 2H, J=8.0 Hz), 3.90 (d, 1H, J=8.8 Hz), 3.53 (m, 1H), 3.20-3.10 (m, 2H), 2.97 (m, 1H), 2.80-2.55 (m, 2H), 2.44 (dd, 1H, J=13.2, 6.8 Hz), 2.16 (s, 7H), 2.00-1.85 (m, 3H).

Example B10

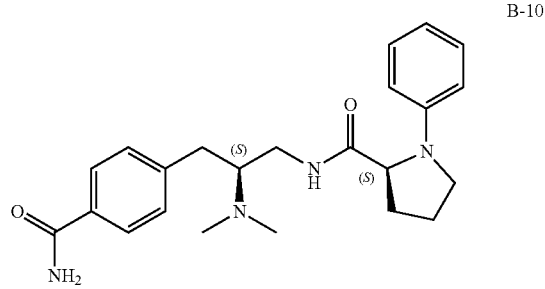

B-10

Synthesis of (S)—N—((S)-3-(4-carbamoylphenyl)-2-(dimethylamino)propyl)-1-phenylpyrrolidine-2-carboxamide (Compound B-10)

Compound B-10 was synthesized according to the procedure in Example B9 using phenyl-L-proline. LC-MS: 395.2 [M+H]$^+$; $^1$H NMR (400 MHz, DMSO-d6) δ 7.89 (s, 1H), 7.76 (d, 2H, J=8.0 Hz), 7.68 (br t, 1H), 7.28 (s, 1H), 7.21 (d, 2H, J=8.0 Hz), 7.14 (t, 2H, J=8.0 Hz), 6.62 (t, 1H, J=7.2 Hz), 6.49 (d, 2H, J=8.0 Hz), 3.90 (d, 1H, J=8.5 Hz), 3.51 (m, 1H), 3.20-3.05 (m, 2H), 2.97 (m, 1H), 2.80-2.65 (m, 2H), 2.38 (m, 1H), 2.18 (s, 7H), 1.95-1.85 (m, 3H).

Example B11

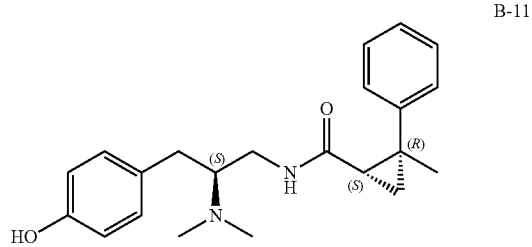

B-11

Synthesis of (1S,2R)—N—((S)-2-(dimethylamino)-3-(4-hydroxyphenyl)propyl)-2-methyl-2-phenylcyclopropane-1-carboxamide (Compound B-11)

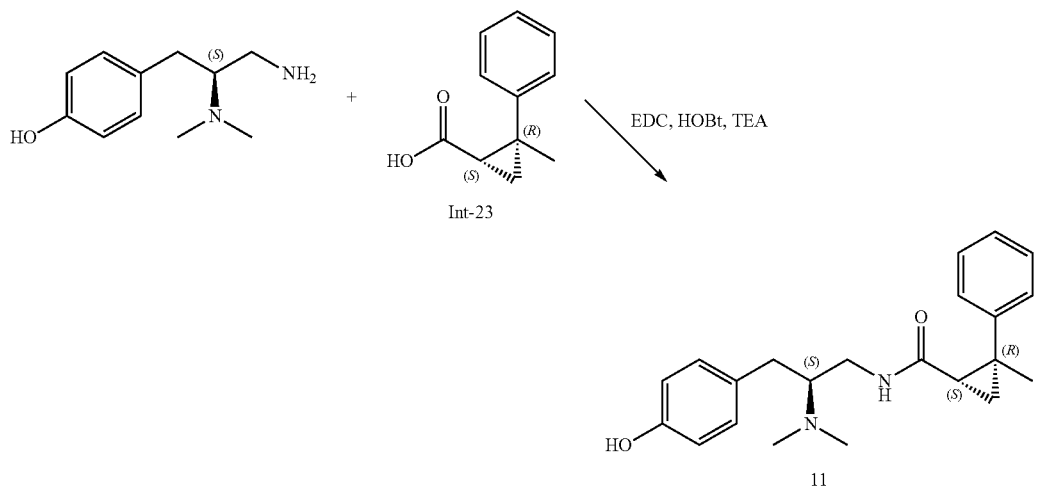

(1S,2R)—N—((S)-2-(dimethylamino)-3-(4-hydroxyphenyl)propyl)-2-methyl-2-phenylcyclopropane-1-carboxamide was synthesized according to Scheme B2 using (S)-4-(3-amino-2-(dimethylamino)propyl)phenol and (1S,2R)-2-methyl-2-phenylcyclopropane-1-carboxylic acid (Int-23) as the starting materials. LC-MS: 353.2 [M+H]$^+$; $^1$H NMR (400 MHz, DMSO-d6) δ 9.12 (s, 1H), 7.61 (t, 1H, J=5.0 Hz), 7.20-7.05 (m, 5H), 6.91 (d, 2H, J=8.4 Hz), 6.63 (d, 2H, J=8.4 Hz), 2.88 (m, 1H), 2.82 (m, 1H), 2.62 (dd, 1H, J=13.6, 5.2 Hz), 2.22 (m, 1H), 2.20 (s, 6H), 1.87 (dd, 1H, J=7.6, 5.6 Hz), 1.45 (t, 1H, J=4.8 Hz), 1.32 (s, 3H), 0.93 (dd, 1H, J=7.8, 4.0 Hz).

Example B12

B-12

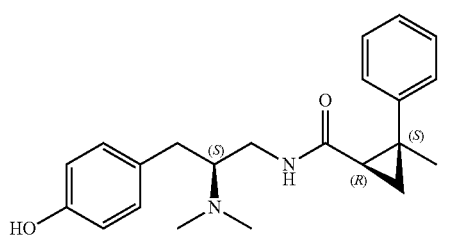

Synthesis of (1R,2S)—N—((S)-2-(dimethylamino)-3-(4-hydroxyphenyl)propyl)-2-methyl-2-phenylcyclopropane-1-carboxamide (Compound B-12)

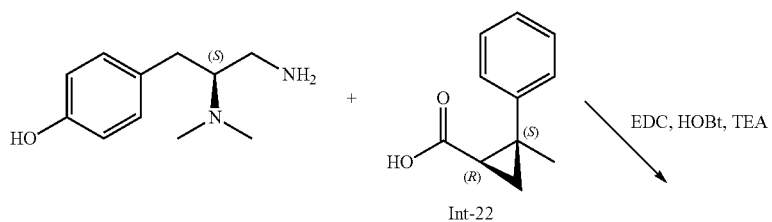

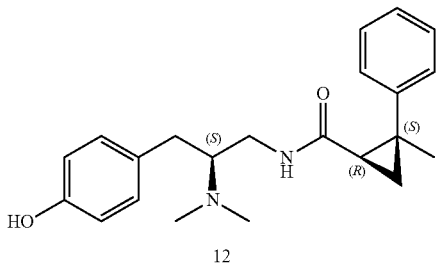

12

(1R,2S)—N—((S)-2-(dimethylamino)-3-(4-hydroxyphenyl)propyl)-2-methyl-2-phenylcyclopropane-1-carboxamide (Compound B-12) was synthesized according to the procedure for (S)-3-(3-fluorophenyl)-N2,N2-dimethylpropane-1,2-diamine dihydrochloride (Int-5) using (S)-4-(3-amino-2-(dimethylamino)propyl)phenol and (1R,2S)-2-methyl-2-phenylcyclopropane-1-carboxylic acid (Int-22) as the starting materials. LC-MS: 353.2 [M+H]⁺; ¹H NMR (400 MHz, DMSO-d6) δ 9.12 (s, 1H), 7.67 (t, 1H, J=5.0 Hz), 7.20-7.05 (m, 5H), 6.90 (d, 2H, J=8.2 Hz), 6.62 (d, 2H, J=8.2 Hz), 2.93-2.80 (m, 2H), 2.62-2.50 (m, 2H), 2.20 (s, 7H), 1.87 (dd, 1H, J=7.6, 5.6 Hz), 1.45 (t, 1H, J=4.8 Hz), 1.32 (s, 3H), 0.94 (dd, 1H, J=7.8, 4.0 Hz).

Example B13

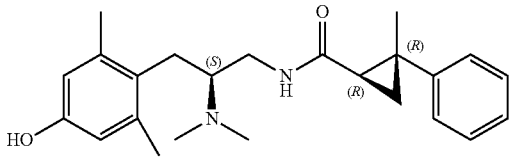

B-13

Synthesis of (1R,2R)—N—((S)-2-(dimethylamino)-3-(4-hydroxy-2,6-dimethylphenyl)propyl)-2-methyl-2-phenylcyclopropane-1-carboxamide (Compound B-13)

(1R,2R)—N—((S)-2-(dimethylamino)-3-(4-hydroxy-2,6-dimethylphenyl)-propyl)-2-methyl-2-phenyl cyclopropane-1-carboxamide (Compound B-13) was synthesized according to the procedure for (S)-3-(3-fluorophenyl)-N2,N2-dimethylpropane-1,2-diamine dihydrochloride using 4-iodo-3,5-dimethylphenol as the starting material. LC-MS: 381.3 [M+H]⁺; ¹H NMR (400 MHz, DMSO-d6) δ 8.93 (s, 1H), 7.87 (br t, 1H), 7.33-7.22 (m, 4H), 7.17 (m, 1H), 6.39 (s, 2H), 3.18 (m, 1H), 2.90 (m, 1H), 2.80-2.60 (m, 2H), 2.39 (dd, 1H, J=13.4, 8.5 Hz), 2.31 (s, 6H), 2.19 (s, 6H), 1.90 (t, 1H, J=7.2 Hz), 1.35 (s, 3H), 1.25-1.15 (m, 2H).

Example B14

B-14

Synthesis of (1R,2R)—N—((S)-3-(2,6-difluoro-4-hydroxyphenyl)-2-(dimethylamino)propyl)-2-methyl-2-phenylcyclopropane-1-carboxamide (Compound B-14)

(1R,2R)—N—((S)-3-(2,6-difluoro-4-hydroxyphenyl)-2-(dimethylamino)-propyl)-2-methyl-2-phenyl cyclopropane-1-carboxamide was synthesized according to the procedure for (S)-3-(3-fluorophenyl)-N2,N2-dimethylpropane-1,2-diamine dihydrochloride using 4-bromo-3,5-difluorophenol as the starting material. LC-MS: 389.2 [M+H]⁺; ¹H NMR (400 MHz, DMSO-d6) δ 10.15 (s, 1H), 8.02 (br s, 1H), 7.34-7.25 (m, 4H), 7.18 (m, 1H), 6.41 (d, 2H, J=8.9 Hz), 3.15 (m, 1H), 3.05 (m, 1H), 2.80-2.60 (m, 2H), 2.39 (dd, 1H, J=13.5, 7.6 Hz), 2.25 (s, 6H), 1.91 (t, 1H, J=6.9 Hz), 1.36 (s, 3H), 1.28-1.15 (m, 2H).

Example B15

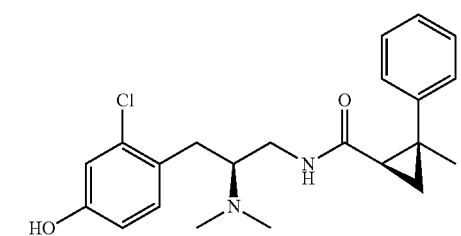

B-15

181

Synthesis of (1R,2S)—N—((S)-3-(2-chloro-4-hydroxyphenyl)-2-(dimethylamino)propyl)-2-methyl-2-phenylcyclopropane-1-carboxamide (Compound B-15)

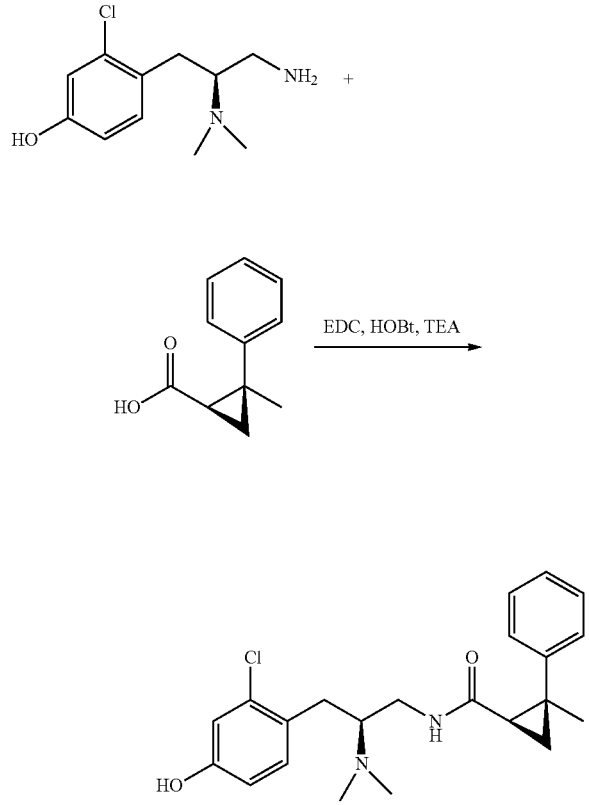

(1R,2S)—N—((S)-3-(2-chloro-4-hydroxyphenyl)-2-(dimethylamino)-propyl)-2-methyl-2-phenyl cyclopropane-1-carboxamide was synthesized according to Scheme B2 using (S)-4-(3-amino-2-(dimethylamino)propyl)-3-chlorophenol (Int-211) and (1R,2S)-2-methyl-2-phenylcyclopropane-1-carboxylic acid as the starting materials. LC-MS: 387.1 [M+H]$^+$; $^1$H NMR (400 MHz, DMSO-d6) δ 9.65 (s, 1H), 7.72 (t, 1H, J=4.8 Hz), 7.20-7.05 (m, 5H), 7.02 (d, 1H, J=8.4 Hz), 6.74 (s, 1H), 6.62 (d, 1H, J=8.4 Hz), 2.95-2.85 (m, 2H), 2.80-2.60 (m, 2H), 2.32 (dd, 1H, J=13.2, 8.2 Hz), 2.24 (s, 6H), 1.87 (t, 1H, J=6.5 Hz), 1.44 (t, 1H, J=4.5 Hz), 1.31 (s, 3H), 0.93 (dd, 1H, J=7.2, 4.0 Hz).

Example B16

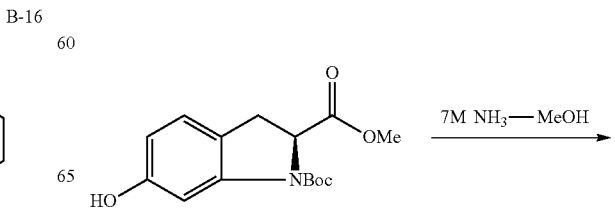

B-16

182

Synthesis of (1R,2R)—N—(((S)-6-hydroxyindolin-2-yl)methyl)-2-methyl-2-phenylcyclopropane-1-carboxamide (Compound B-16)

Step 1: Synthesis of 1-(tert-butyl) 2-methyl (S)-6-hydroxyindoline-1,2-dicarboxylate

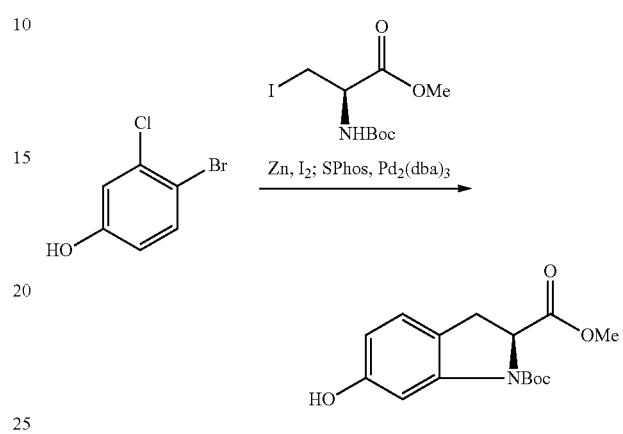

To a stirred suspension of zinc powder (3 g, 46 mmol) in anhydrous N,N-dimethylacetamide (10 mL) under nitrogen was added iodine (400 mg). After 5 min, a solution of methyl (R)-2-((tert-butoxycarbonyl)amino)-3-iodopropanoate (5.0 g, 15.2 mmol) in N,N-dimethylacetamide (10 mL) was added slowly over 10 min. The mixture was heated at 50° C. for 30 min, and then a suspension of 4-bromo-3-chlorophenol (3.0 g, 15 mmol), Pd$_2$(dba)$_3$ (750 mg), and 2-dicyclohexylphosphino-2',6'-dimethoxybiphenyl (Sphos, 675 mg) in N,N-dimethylacetamide (10 mL) was added into the zinc reagent mixture. The reaction mixture was heated at 95° C. and stirred overnight. After cooling, the reaction mixture was quenched with water, diluted with EtOAc and filtered through Celite. The filter cake was washed with EtOAc and the filtrate was washed with 1N aq. HCl and brine, dried over anhydrous sodium sulfate, and concentrated. The residue was purified by flash column chromatography over silica gel (0-50% EtOAc/hexane) to isolate 1-(tert-butyl) 2-methyl (S)-6-hydroxyindoline-1,2-dicarboxylate as a light brown solid (1.1 g, 25%) and methyl (S)-2-((tert-butoxycarbonyl)amino)-3-(2-chloro-4-hydroxyphenyl)propanoate as a light brown foam (2 g, contaminated with some des-chloro side product).

1-(tert-butyl) 2-methyl (S)-6-hydroxyindoline-1,2-dicarboxylate: LC-MS: 316.1 [M+Na]$^+$; $^1$H NMR (400 MHz, CDCl$_3$) (rotamers) δ 7.47 (s, 0.75H), 7.02 (br s, 0.25H), 6.94 (d, 1H, J=8.8 Hz), 6.45 (m, 1H), 5.14 (s, 0.75H), 5.00-4.80 (m, 1.25H), 3.75 (s, 3H), 3.43 (m, 1H), 3.02 (d, 1H, J=11.6 Hz), 1.61 and 1.49 (s, 9H).

Step 2: Synthesis of tert-butyl (S)-2-carbamoyl-6-hydroxyindoline-1-carboxylate

183

-continued

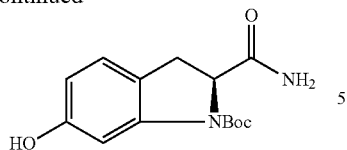

A microwave tube was charged with 1-(tert-butyl) 2-methyl (S)-6-hydroxyindoline-1,2-dicarboxylate (500 mg) and 7M ammonia in methanol (20 mL). The reaction was heated under microwave irradiation at 100° C. for 24 h. The reaction was concentrated and purified by silica gel column (0-50% EtOAc/CH$_2$Cl$_2$) to recover some starting material (250 mg) and afford the desired product as off-white foam (200 mg, 42%). LC-MS: 301.1 [M+Na]$^+$; $^1$H NMR (400 MHz, CDCl$_3$) δ 6.97 (d, 1H, J=8.0 Hz), 6.48 (d, 1H, J=8.0 Hz), 5.68 (br s, 1H), 5.46 (br s, 1H), 4.84 (br s, 1H), 3.43 (br s, 1H), 3.15 (br s, 1H), 1.55 (s, 9H).

Step 3: Synthesis of (S)-2-(aminomethyl)indolin-6-ol

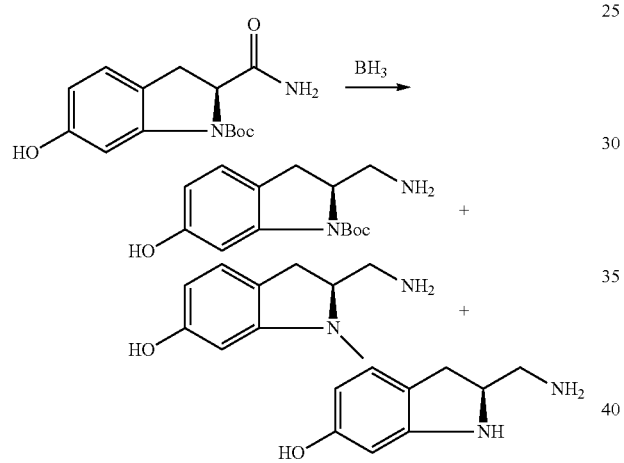

To a stirred solution of tert-butyl (S)-2-carbamoyl-6-hydroxyindoline-1-carboxylate (230 mg, 0.83 mmol) in anhydrous THF (10 mL) under nitrogen was added borane-DMS complex (2M solution in THF, 5 mL, 10 mmol). The reaction mixture was stirred at 70° C. overnight. After cooling, the reaction was carefully quenched with methanol (10 mL) and then heated at 70° C. for 2 h. The mixture was concentrated and purified by silica gel column (0-20% MeOH/CH$_2$Cl$_2$ with 5% ammonia) to isolate the products.

Step 4: Synthesis of (1R,2R)—N—(((S)-6-hydroxy-indolin-2-yl)methyl)-2-methyl-2-phenylcyclopropane-1-carboxamide (Compound B-16)

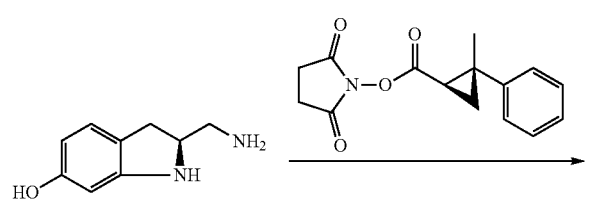

184

-continued

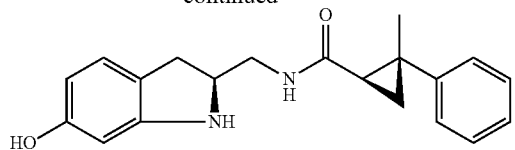

To a stirred solution of (S)-2-(aminomethyl)indolin-6-ol (15 mg) in anhydrous DMF (1 mL) was added 2,5-dioxopyrrolidin-1-yl (1R,2R)-2-methyl-2-phenylcyclopropane-1-carboxylate (20 mg). The reaction mixture was stirred overnight at rt and then concentrated in vacuo. The residue was purified by flash column chromatography over silica gel (0-5% MeOH/CH$_2$Cl$_2$ with 5% ammonia) and further purified by prep HPLC (20-100% MeCN/water-0.1% TFA) to afford the desired product (Compound B-16) as a light yellow foam (10 mg). LC-MS: 323.2 [M+H]$^+$; $^1$H NMR (400 MHz, methanol-d$_4$) δ 7.32-7.22 (m, 4H), 7.17 (m, 1H), 6.84 (d, 1H, J=8.0 Hz), 6.14 (s, 2H), 3.92 (m, 1H), 3.45-3.30 (m, 2H), 3.02 (dd, 1H, J=15.0, 9.1 Hz), 2.69 (dd, 1H, J=15.2, 6.1 Hz), 1.88 (t, 1H, J=6.8 Hz), 1.43 (s, 3H), 1.40-1.30 (m, 2H).

Example B17

B-17

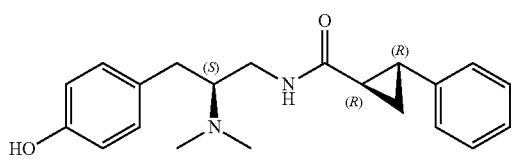

Synthesis of (1R,2R)—N—((S)-2-(dimethylamino)-3-(4-hydroxyphenyl)propyl)-2-phenylcyclopropane-1-carboxamide (Compound B-17)

(S)-4-(3-amino-2-(dimethylamino)propyl)phenol dihydrochloride salt (30 mg, 0.11 mmol), (1R,2R)-2-phenylcyclopropane-1-carboxylic acid (AstaTech, W13292, Lot #P135-06619, 19 mg, 0.11 mmol), and (benzotriazol-1-yloxy)tris-(dimethylamino)phosphonium hexafluorophosphate (BOP, 60 mg, 0.13 mmol) were suspended in DCM (3 mL), DIPEA (78 μL, 0.45 mmol) was added, and the mixture was stirred in a sealed vial overnight at ambient temperature until reaction completion (LCMS). The mixture was concentrated, chased with heptane (×3), and the residue purified by silica gel chromatography, eluent DCM-MeOH 100:0 to 90:10 to afford 34 mg (90%) of the title product as a clear oil. Analytical sample (5.2 mg) was prepared by additional chromatography, collecting fractions with >95% HPLC purity. LC-MS (ESI+), m/z 339.5 (M+H)+. $^1$H NMR (400 MHz, METHANOL-d$_4$) δ=7.26 (t, J=7.5 Hz, 2H), 7.16 (t, J=7.2 Hz, 1H), 7.10 (d, J=7.4 Hz, 2H), 7.04 (d, J=8.5 Hz, 2H), 6.72 (d, J=8.5 Hz, 2H), 3.32-3.22 (m, 2H), 2.97-2.85 (m, 2H), 2.46-2.36 (m, 7H), 2.36-2.28 (m, 1H), 1.84 (ddd, J=4.2, 5.2, 8.3 Hz, 1H), 1.45 (ddd, J=4.4, 5.1, 9.3 Hz, 1H), 1.22 (ddd, J=4.7, 6.4, 8.2 Hz, 1H).

Example B18

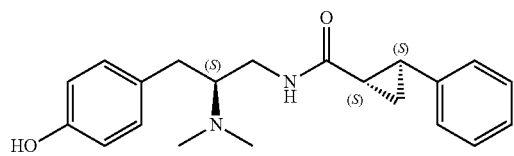

Synthesis of (1S,2S)—N—((S)-2-(dimethylamino)-3-(4-hydroxyphenyl)propyl)-2-phenylcyclopropane-1-carboxamide (Compound B-18)

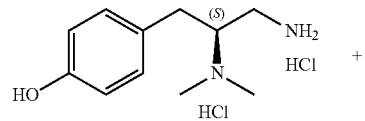

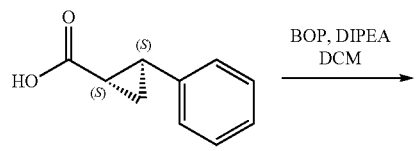

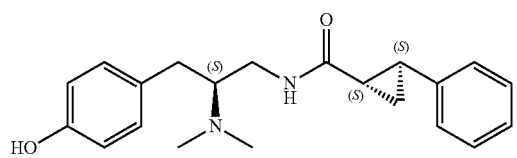

Compound B-18 was prepared according to the procedure described in Example B17, using (1S,2S)-2-phenylcyclopropane-1-carboxylic acid (AstaTech, F12973, Lot #P135-06597), in 68% yield. LC-MS (ESI+), m/z 339.5 (M+H)+. $^1$H NMR (600 MHz, METHANOL-d$_4$) δ=7.24 (t, J=7.6 Hz, 2H), 7.15 (t, J=7.3 Hz, 1H), 7.09 (dd, J=1.2, 8.4 Hz, 2H), 7.02 (d, J=8.4 Hz, 2H), 6.70 (d, J=8.4 Hz, 2H), 3.28-3.20 (m, 2H), 2.90-2.82 (m, 2H), 2.40-2.34 (m, 7H), 2.34-2.27 (m, 1H), 1.81 (ddd, J=4.3, 5.2, 8.4 Hz, 1H), 1.42 (td, J=4.7, 9.3 Hz, 1H), 1.18 (ddd, J=4.3, 6.3, 8.4 Hz, 1H).

Example B19

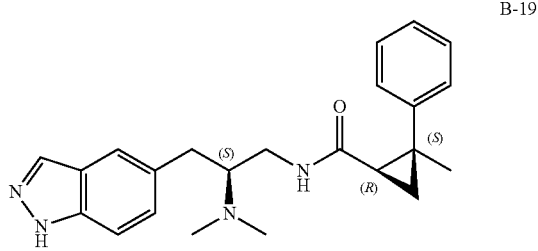

Synthesis of (1R,2S)—N—((S)-2-(dimethylamino)-3-(1H-indazol-5-yl)propyl)-2-methyl-2-phenylcyclopropane-1-carboxamide (Compound B-19))

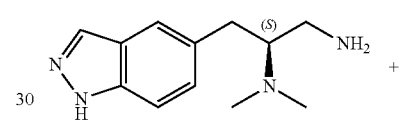

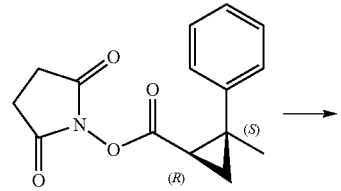

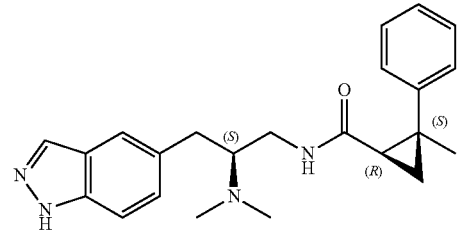

The compound was prepared by the same procedure above using (S)-3-(1H-indazol-5-yl)-N$^2$,N$^2$-dimethylpropane-1,2-diamine (nrr-249-1, 140 mg, 513 μmol), and 2,5-dioxopyrrolidin-1-yl (1R,2S)-2-methyl-2-phenylcyclopropane-1-carboxylate (PD-14-56, 147 mg, 539 μmol) to afford 138 mg (71%) of title compound. LCMS (+ESI) M+H+=377.5. $^1$H NMR (600 MHz, METHANOL-d$_4$) δ=7.95 (s, 1H), 7.52 (s, 1H), 7.45 (d, J=8.5 Hz, 1H), 7.22-7.17 (m, 3H), 7.15-7.11 (m, 2H), 7.09-7.05 (m, 1H), 3.11-3.00 (m, 2H), 2.96 (dd, J=5.0, 13.8 Hz, 1H), 2.82 (tt, J=5.4, 8.2 Hz, 1H), 2.48 (dd, J=8.8, 13.9 Hz, 1H), 2.33 (s, 6H), 1.82 (dd, J=5.5, 7.8 Hz, 1H), 1.62 (t, J=5.1 Hz, 1H), 1.40-1.36 (m, 3H), 1.00 (dd, J=4.6, 7.9 Hz, 1H).

Example B20

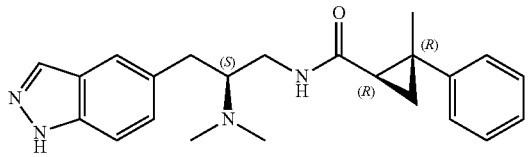

Synthesis of (1R,2R)—N—((S)-2-(dimethylamino)-3-(1H-indazol-5-yl)propyl)-2-methyl-2-phenylcyclopropane-1-carboxamide (Compound B-20)

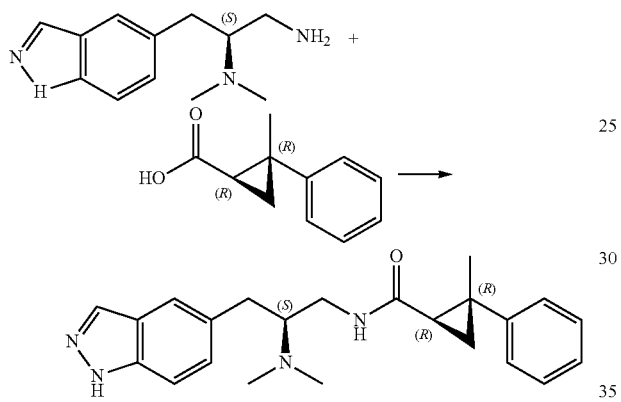

The title compound was prepared according to the procedure as above, starting with (S)-3-(1H-indazol-5-yl)-N², N²-dimethylpropane-1,2-diamine (140 mg, 641 µmol) and (1R,2R)-2-methyl-2-phenylcyclopropane-1-carboxylic acid (PD-14-51, 113 mg, 641 µmol) to afford 120 mg (50%) of title compound. LCMS (+ESI) M+H+=377.6. ¹H NMR (600 MHz, CHLOROFORM-d) δ=10.52 (br s, 1H), 7.99 (d, J=0.8 Hz, 1H), 7.53 (s, 1H), 7.36 (d, J=8.5 Hz, 1H), 7.32-7.28 (m, 2H), 7.24-7.22 (m, 2H), 7.22-7.18 (m, 1H), 7.16 (dd, J=1.5, 8.5 Hz, 1H), 6.42 (br s, 1H), 3.46 (ddd, J=4.8, 6.5, 13.7 Hz, 1H), 3.13-3.05 (m, 2H), 2.89-2.82 (m, 1H), 2.46 (dd, J=10.1, 13.4 Hz, 1H), 2.40-2.37 (m, 6H), 1.68 (dd, J=5.9, 8.4 Hz, 1H), 1.47 (s, 3H), 1.47 (m, 1H), 1.36 (dd, J=4.8, 8.5 Hz, 1H).

Example B21

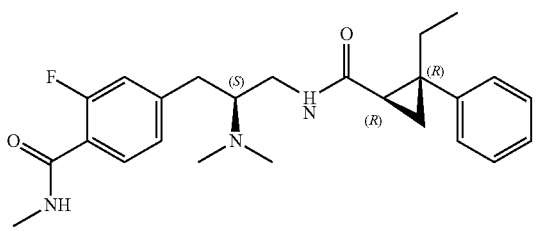

Synthesis of 4-((S)-2-(dimethylamino)-3-((1R,2R)-2-ethyl-2-phenylcyclopropane-1-carboxamido)propyl)-2-fluoro-N-methylbenzamide (Compound B-21)

2,5-dioxopyrrolidin-1-yl (1R,2R)-2-ethyl-2-phenylcyclopropane-1-carboxylate was synthesized by following the procedure used for the synthesis of Int-36 by substituting propiophenone for 3-methyl-2-phenylbutanone. To a stirred solution of (S)-4-(3-amino-2-(dimethylamino)propyl)-2-fluoro-N-methylbenzamide (Int-4F) (80 mg, 0.31 mmol) in anhydrous DMF (1 mL) was added 2,5-dioxopyrrolidin-1-yl (1R,2R)-2-ethyl-2-phenylcyclopropane-1-carboxylate (95 mg, 0.33 mmol) and diisopropylethylamine (61 µL, 0.35 mmol). The reaction mixture was stirred overnight at rt and then quenched by adding water. The product was extracted into dichloromethane, dried and then the concentrated. The residue was purified by flash column chromatography over silica gel (0-10% MeOH/CH₂Cl₂) to afford the desired product as a white solid (90 mg, 68%). LCMS (+ESI) m/z 426.2 (M+H)+. ¹H NMR (400 MHz, CDCl₃) δ ppm 8.01 (t, J=8.19 Hz, 1H) 7.16-7.31 (m, 5H) 7.06 (dd, J=8.07, 1.47 Hz, 1H) 6.93 (dd, J=12.84, 1.34 Hz, 1H) 6.63-6.78 (m, 1H) 6.36 (br d, J=5.38 Hz, 1H) 3.41 (ddd, J=13.51, 6.66, 4.77 Hz, 1H) 2.97-3.06 (m, 5H) 2.81-2.89 (m, 1H) 2.31-2.45 (m, 7H) 1.77-1.90 (m, 2H) 1.68 (dd, J=8.31, 5.87 Hz, 1H) 1.38 (dd, J=5.62, 4.65 Hz, 1H) 1.26 (dd, J=8.31, 4.40 Hz, 1H) 0.75 (t, J=7.46 Hz, 3H).

Example B22

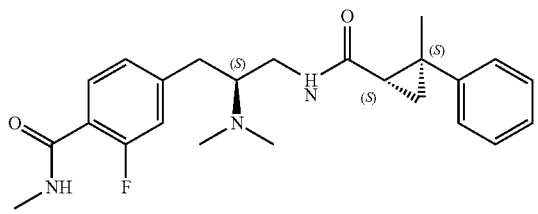

Synthesis of 4-((S)-2-(dimethylamino)-3-((1S,2S)-2-methyl-2-phenylcyclopropane-1-carboxamido)propyl)-2-fluoro-N-methylbenzamide (Compound B-22)

The title compound was prepared according to Scheme B2, starting with (S)-4-(3-amino-2-(dimethylamino)propyl)-2-fluoro-N-methylbenzamide (Int-4F) (0.079 g) and (1S,2S)-2-methyl-2-phenylcyclopropane-1-carboxylic acid (0.055) to afford the title compound (0.058 g). LCMS (+ESI) M+H+=412.2; ¹H NMR (400 MHz, METHANOL-d4) δ ppm 7.69 (t, J=7.83 Hz, 1H), 7.24-7.31 (m, 4H), 7.07-7.19 (m, 1H), 4.53 (br s, 1H), 3.30-3.33 (m, 2H), 2.94-3.04 (m, 2H), 2.91 (s, 3H), 2.54-2.65 (m, 1H), 2.37 (s, 6H), 1.82 (dd, J=8.44, 5.99 Hz, 1H), 1.42 (s, 3H), 1.34 (dd, J=5.87, 4.89 Hz, 1H), 1.27 (dd, J=8.44, 4.52 Hz, 1H).

Example B23

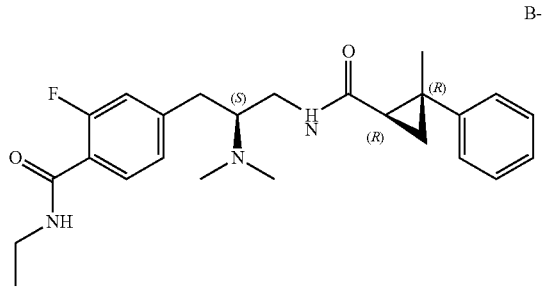

B-23

Synthesis of 4-((S)-2-(dimethylamino)-3-((1R,2R)-2-methyl-2-phenylcyclopropane-1-carboxamido)propyl)-N-ethyl-2-fluorobenzamide (Compound B-23)

The title compound was prepared according to the procedure of Example B2 above, starting with (S)-4-(3-amino-2-(dimethylamino)propyl)-N-ethyl-2-fluorobenzamide (40 mg, 0.15 mmol) and 2,5-dioxopyrrolidin-1-yl (1R,2R)-2-methyl-2-phenylcyclopropane-1-carboxylate (43 mg, 0.16 mmol) to afford the title compound (33 mg, 51%). LCMS (+ESI) m/z 426.3 (M+H)$^+$. $^1$H NMR (400 MHz CDCl$_3$) δ ppm 7.87-7.96 (m, 2H) 7.13-7.34 (m, 8H) 6.75 (dt, J=10.88, 5.56 Hz, 1H) 3.92 (br s, 1H) 3.76 (dt, J=15.04, 7.40 Hz, 1H) 3.36-3.50 (m, 4H) 2.84-2.94 (m, 7H) 1.86-2.13 (m, 2H) 1.36-1.46 (m, 4H) 1.18-1.31 (m, 5H).

Example B24

24

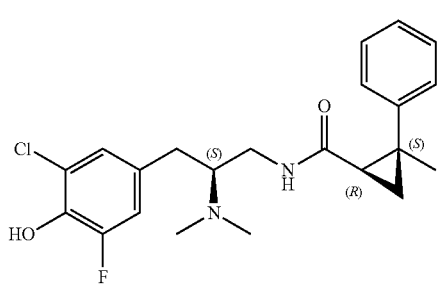

Synthesis of (1R,2S)—N—((S)-3-(3-chloro-5-fluoro-4-hydroxyphenyl)-2-(dimethylamino)propyl)-2-methyl-2-phenylcyclopropane-1-carboxamide (Compound 24)

The title compound was prepared according to the procedure of Example B1 above, starting with 4-bromo-2-chloro-6-fluorophenol to afford the title compound (0.079 g). LCMS (+ESI) m/z 405.2 (M+H+). $^1$H NMR (400 MHz, METHANOL-d4) δ ppm 7.09-7.24 (m, 5H), 6.91 (t, J=1.83 Hz, 1H), 6.82 (dd, J=11.37, 2.08 Hz, 1H), 4.53 (br s, 1H), 2.97-3.06 (m, 2H), 2.66-2.74 (m, 2H), 2.29 (s, 6H), 2.23-2.28 (m, 1H), 1.85 (dd, J=7.83, 5.62 Hz, 1H), 1.67 (t, J=5.14 Hz, 1H), 1.41 (s, 3H), 1.04 (dd, J=7.83, 4.65 Hz, 1H)

Example B25

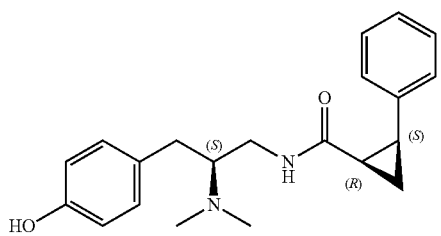

B-25

Synthesis of (1R,2S)—N—((S)-2-(dimethylamino)-3-(4-hydroxyphenyl)propyl)-2-phenylcyclopropane-1-carboxamide (Compound B-25)

The title compound was prepared according Scheme B2, starting with (S)-4-(3-amino-2-(dimethylamino)propyl)phenol (0.141 g) and (1R,2S)-2-phenylcyclopropane-1-carboxylic acid (Wuxi AppTec, LN01817094) (0.086 g) to afford the title compound (0.051 g). LCMS (+ESI) m/z 339.2 (M+H$^+$). $^1$H NMR (400 MHz, METHANOL-d4) δ ppm 7.07-7.21 (m, 5H), 6.88-6.94 (m, 2H), 6.65-6.70 (m, 2H), 2.93-3.06 (m, 2H), 2.69 (dd, J=13.82, 5.01 Hz, 1H), 2.58 (tt, J=8.22, 5.35 Hz, 1H), 2.34-2.46 (m, 1H), 2.23 (s, 6H), 2.17-2.22 (m, 1H), 1.97-2.07 (m, 1H), 1.57 (dt, J=7.09, 5.38 Hz, 1H), 1.17-1.26 (m, 1H).

Example B26

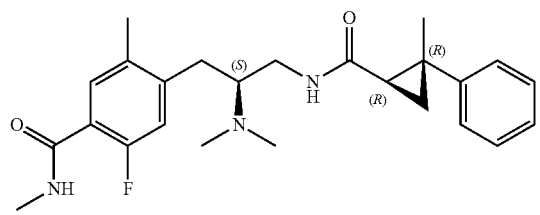

B-26

Synthesis of 4-((S)-2-(dimethylamino)-3-((1R,2R)-2-methyl-2-phenylcyclopropane-1-carboxamido)propyl)-2-fluoro-N,5-dimethylbenzamide (Compound B-26)

The title compound was prepared according to Scheme B2, starting with (S)-4-(3-amino-2-(dimethylamino)propyl)-2-fluoro-N, 5-dimethylbenzamide (0.0720 g) and 2,5-dioxopyrrolidin-1-yl (1R,2R)-2-methyl-2-phenylcyclopropane-1-carboxylate (0.0735 g) to afford the title compound (0.0980 g). LCMS (+ESI) m/z 426.2 (M+H$^+$). $^1$H NMR (400 MHz, METHANOL-d4) δ ppm 7.55 (br d, J=7.34 Hz, 1H), 7.28 (br s, 4H), 7.16 (br s, 1H), 7.05 (br d, J=12.23 Hz, 1H), 3.36 (br d, J=13.69 Hz, 1H), 3.24 (br dd, J=14.18, 4.65 Hz, 1H), 2.94-3.06 (m, 2H), 2.91 (br s, 3H), 2.61 (br dd, J=12.72, 8.80 Hz, 1H), 2.40 (s, 6H), 2.35 (s, 3H), 1.86 (br t, J=6.73 Hz, 1H), 1.41 (s, 3H), 1.34 (br d, J=4.40 Hz, 1H), 1.29 (br d, J=7.83 Hz, 1H).

Example B27

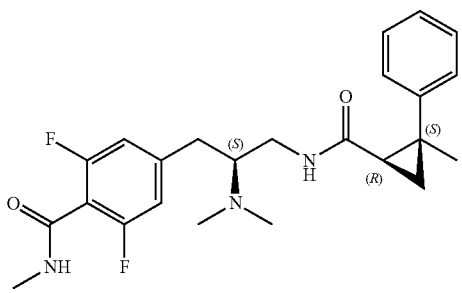

B-27

Synthesis of 4-((S)-2-(dimethylamino)-3-((1R,2S)-2-methyl-2-phenylcyclopropane-1-carboxamido)propyl)-2,6-difluoro-N-methylbenzamide (Compound B-27)

The title compound was prepared according to Scheme B2, starting with (S)-4-(3-amino-2-(dimethylamino)propyl)-2,6-difluoro-N-methylbenzamide (0.0812 g) and 2,5-dioxopyrrolidin-1-yl (1R,2S)-2-methyl-2-phenylcyclopropane-1-carboxylate (0.0818 g) to afford the title compound (0.119 g). LCMS (+ESI) m/z 430.2 (M+H+). 1H NMR (400 MHz, METHANOL-d4) δ ppm 7.07-7.27 (m, 5H), 6.83 (d, J=8.56 Hz, 2H), 4.53 (br s, 1H), 2.96-3.07 (m, 2H), 2.89 (s, 3H), 2.68-2.81 (m, 2H), 2.34-2.44 (m, 1H), 2.27 (s, 6H), 1.86 (dd, J=7.83, 5.62 Hz, 1H), 1.68 (t, J=5.01 Hz, 1H), 1.42 (s, 3H), 1.05 (dd, J=7.95, 4.77 Hz, 1H).

Example B28

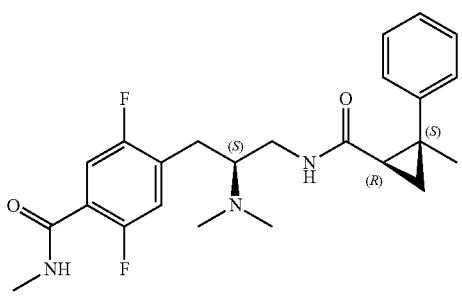

B-28

Synthesis of 4-((S)-2-(dimethylamino)-3-((1R,2S)-2-methyl-2-phenylcyclopropane-1-carboxamido)propyl)-2,5-difluoro-N-methylbenzamide (Compound B-28)

The compound was prepared by the same procedure above using (S)-4-(3-amino-2-(dimethylamino)propyl)-2,5-difluoro-N-methylbenzamide and 2,5-dioxopyrrolidin-1-yl (1R,2S)-2-methyl-2-phenylcyclopropane-1-carboxylate as starting materials. LC-MS: 430.2 [M+H]+; 1H NMR (400 MHz, DMSO-d6) δ 8.23 (br s, 1H), 7.84 (m, 1H), 7.34 (m, 1H), 7.16-7.07 (m, 6H), 3.01-2.89 (m, 2H), 2.77 (d, J=4.6 Hz, 3H), 2.68 (m, 2H), 2.52 (m, 1H), 2.21 (s, 6H), 1.87 (dd, J=7.8, 5.4 Hz, 1H), 1.51 (m, 1H), 1.34 (s, 3H), 0.96 (dd, J=7.7, 4.0 Hz, 1H).

Example B29

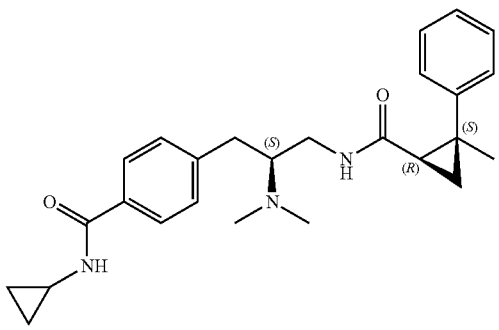

B-29

Synthesis of N-cyclopropyl-2-fluoro-4-((S)-2-(methyl(2,2,2-trifluoroethyl)amino)-3-((1R,2S)-2-methyl-2-phenylcyclopropane-1-carboxamido)propyl)benzamide (Compound B-29)

The title compound was prepared according to the procedure of Example B2 above, starting with (S)-4-(3-amino-2-(methyl(2,2,2-trifluoroethyl)amino)propyl)-N-cyclopropyl-2-fluorobenzamide (0.0273 g, 0.0786 mmole) and 2,5-dioxopyrrolidin-1-yl (1R,2S)-2-methyl-2-phenylcyclopropane-1-carboxylate (0.024 g, 0.0786 mmole) to afford the title compound (0.0111 g, 28%). LC-MS (+ESI) M+H+: 506.2. 1H NMR (400 MHz, DMSO-d6) δ ppm 8.23 (br d, J=3.18 Hz, 1H) 7.75 (t, J=5.38 Hz, 1H) 7.45 (t, J=7.83 Hz, 1H) 7.14-7.22 (m, 4H) 7.02-7.14 (m, 3H) 3.13-3.29 (m, 2H) 2.97-3.05 (m, 1H) 2.87-2.96 (m, 1H) 2.76-2.87 (m, 2H) 2.58-2.66 (m, 1H) 2.32 (s, 3H) 1.84 (dd, J=7.83, 5.62 Hz, 1H) 1.53 (t, J=4.77 Hz, 1H) 1.35 (s, 3H) 0.99 (dd, J=7.95, 4.04 Hz, 1H) 0.64-0.72 (m, 2H) 0.50-0.57 (m, 2H)

Example B30

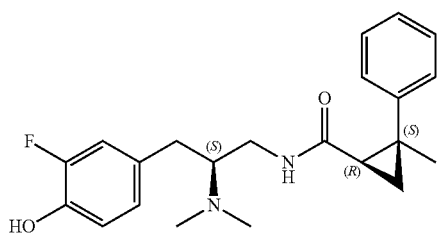

B-30

Synthesis of (1R,2S)—N—((S)-2-(dimethylamino)-3-(3-fluoro-4-hydroxyphenyl)propyl)-2-methyl-2-phenylcyclopropane-1-carboxamide (Compound B-30)

(1R,2S)—N—((S)-2-(dimethylamino)-3-(3-fluoro-4-hydroxyphenyl)-propyl)-2-methyl-2-phenylcyclopropane-1-carboxamide was synthesized according to Scheme B2 using (S)-4-(3-amino-2-(dimethylamino)propyl)-2-fluorophenol and 2,5-dioxopyrrolidin-1-yl (1R,2S)-2-methyl-2-phenylcyclopropane-1-carboxylate as the starting materials. LC-MS: 371.2 [M+1]+; 1H NMR (400 MHz, CDCl3) δ 7.04-7.21 (m, 5H), 6.47-6.64 (m, 3H), 3.58-3.42 (m, 1H), 3.11-3.18 (m, 1H), 2.56-2.76 (m, 3H), 2.21 (s, 6H), 2.06-2.12 (m, 1H), 1.69-1.73 (m, 1H), 1.56-1.60 (m, 1H), 1.35 (s, 3H), 0.99-1.03 (m, 1H).

Example B31

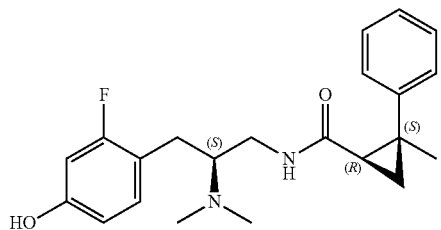

B-31

Synthesis of (1R,2S)—N—((S)-2-(dimethylamino)-3-(2-fluoro-4-hydroxyphenyl)propyl)-2-methyl-2-phenylcyclopropane-1-carboxamide (Compound B-31)

(1R,2S)—N—((S)-2-(dimethylamino)-3-(2-fluoro-4-hydroxyphenyl)-propyl)-2-methyl-2-phenylcyclopropane-1-carboxamide was synthesized according to Scheme B2 using (S)-4-(3-amino-2-(dimethylamino)propyl)-3-fluorophenol and 2,5-dioxopyrrolidin-1-yl (1R,2S)-2-methyl-2-phenylcyclopropane-1-carboxylate as the starting materials. LC-MS: 371.2 [M+1]+; 1H NMR (400 MHz, CDCl3) δ 7.27-7.31 (m, 2H), 7.12-7.24 (m, 3H), 6.76-6.84 (m, 1H), 6.28-6.46 (m, 2H), 3.23-3.40 (m, 1H), 2.98-3.07 (m, 2H), 2.89-2.92 (m, 1H), 2.56 (s, 6H), 2.32-2.41 (bs, 1H), 1.91-1.94 (m, 1H), 1.76-1.81 (m, 1H), 1.46 (s, 3H), 1.08-1.12 (m, 1H).

Example B32

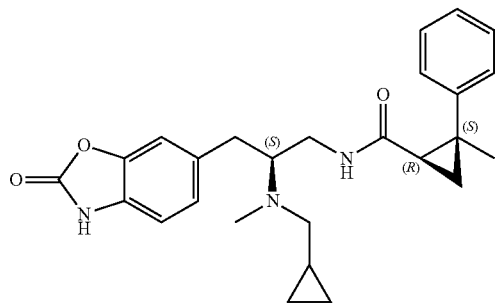

B-32

Synthesis of (1R,2S)—N—((S)-2-((cyclopropylmethyl)(methyl)amino)-3-(2-oxo-2,3-dihydrobenzo[d]oxazol-6-yl)propyl)-2-methyl-2-phenylcyclopropane-1-carboxamide (Compound B-32)

The title compound was prepared according to Scheme B2, starting with (S)-6-(3-amino-2-((cyclopropylmethyl)(methyl)amino)propyl)benzo[d]oxazol-2(3H)-one and 2,5-dioxopyrrolidin-1-yl (1R,2S)-2-methyl-2-phenylcyclopropane-1-carboxylate to provide the title compound (0.021 g). LCMS (+ESI) m/z 434.2 (M+H+). 1H NMR (400 MHz, DMSO-d6) δ ppm 11.65 (d, J=1.47 Hz, 1H), 9.73 (br s, 1H), 8.33-8.43 (m, 1H), 7.05-7.26 (m, 8H) 3.49 (m, 1H), 3.25-3.31 (m, 1H), 3.02-3.21 (m, 3H), 2.69-3.02 (m, 4H), 2.52-2.68 (m, 1H), 2.33 (dt, J=3.73, 1.93 Hz, 1H), 1.85 (td, J=8.13, 5.50 Hz, 1H), 1.56-1.61 (m, 1H), 1.37 (d, J=3.67 Hz, 3H), 1.00-1.06 (m, 1H), 0.52-0.69 (m, 2H), 0.22-0.51 (m, 2H).

Example B33

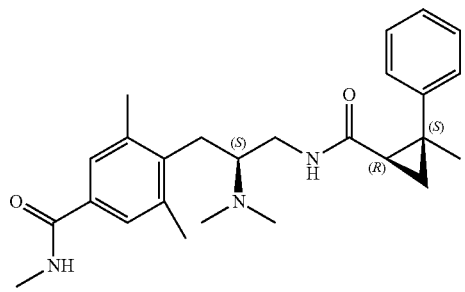

B-33

Synthesis of 4-((S)-2-(dimethylamino)-3-((1R,2S)-2-methyl-2-phenylcyclopropane-1-carboxamido)propyl)-N,3,5-trimethylbenzamide (Compound B-33)

The title compound was prepared according to the procedure of Example B2 above, starting with (S)-4-(3-amino-2-(dimethylamino)propyl)-N,3,5-trimethylbenzamide (0.100 g) and 2,5-dioxopyrrolidin-1-yl (1R,2S)-2-methyl-2-phenylcyclopropane-1-carboxylate (0.104 g) to afford the title compound (0.081 g). LC-MS (+ESI) M+H: 422.3; 1H NMR (400 MHz, DMSO-d6) δ ppm 8.25 (br d, J=4.16 Hz, 1H) 7.76 (br t, J=4.77 Hz, 1H) 7.39 (s, 2H) 7.07-7.23 (m, 5H) 2.90-2.99 (m, 1H) 2.63-2.81 (m, 6H) 2.32 (s, 6H) 2.25 (s, 6H) 1.86 (t, J=6.48 Hz, 1H) 1.43 (br t, J=3.91 Hz, 1H) 1.32 (s, 3H) 0.94 (dd, J=7.34, 3.42 Hz, 1H)

Example B34

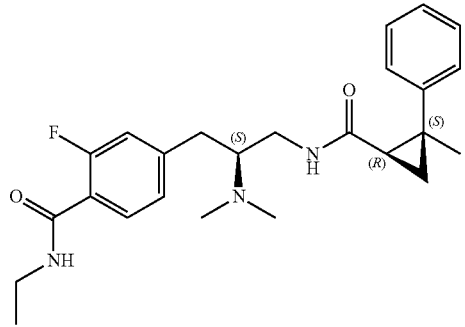

B-34

Synthesis of 4-((S)-2-(dimethylamino)-3-((1R,2S)-2-methyl-2-phenylcyclopropane-1-carboxamido)propyl)-N-ethyl-2-fluorobenzamide (Compound B-34)

The title compound was prepared according to the procedure of Example B2 above, starting with (S)-4-(3-amino-2-(dimethylamino)propyl)-N-ethyl-2-fluorobenzamide (65 mg, 0.24 mmol) and 2,5-dioxopyrrolidin-1-yl (1R,2S)-2-methyl-2-phenylcyclopropane-1-carboxylate (75 mg, 0.27 mmol) to afford the title compound (72 mg, 70%). LCMS (+ESI) m/z 426.2 (M+H)+. $^1$H NMR (400 MHz, CDCl$_3$) δ ppm 7.96 (t, J=8.19 Hz, 1H) 7.15-7.29 (m, 6H) 6.94 (d, J=7.83 Hz, 1H) 6.79 (d, J=12.72 Hz, 1H) 6.57-6.71 (m, 1H) 5.84 (br d, J=6.60 Hz, 1H) 3.46-3.55 (m, 2H) 3.09-3.19 (m, 1H) 2.79-2.87 (m, 1H) 2.53-2.66 (m, 2H) 2.09-2.24 (m, 7H) 1.70-1.78 (m, 1H) 1.54-1.66 (m, 1H) 1.43 (s, 3H) 1.25 (t, J=7.21 Hz, 3H) 1.08 (dd, J=7.95, 5.01 Hz, 1H)

Example B35

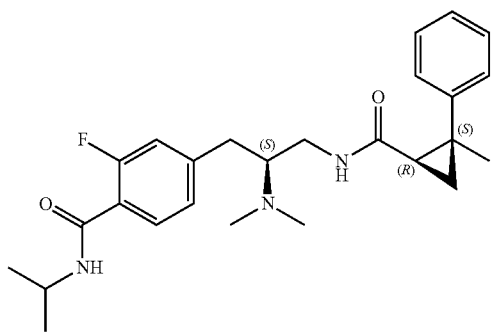

Synthesis of 4-((S)-2-(dimethylamino)-3-((1R,2S)-2-methyl-2-phenylcyclopropane-1-carboxamido)propyl)-2-fluoro-N-isopropylbenzamide (Compound B-35)

The title compound was prepared according to the procedure of Example B2 above, starting with 75 mg of (S)-4-(3-amino-2-(dimethylamino)propyl)-2-fluoro-N-isopropylbenzamide and 74 mg of 2,5-dioxopyrrolidin-1-yl (1R,2S)-2-methyl-2-phenylcyclopropane-1-carboxylate to afford the title compound (90 g). LC-MS: (+ESI) m/z 440.3 (MW+H); $^1$H NMR (400 MHz, MeOH-d$_4$) δ 7.56 (t, J=7.70 Hz, 1H), 6.98-7.24 (m, 7H), 4.14-4.22 (m, 1H), 3.04 (d, J=6.11 Hz, 2H), 2.78-2.88 (m, 2H), 2.40-2.50 (m, 1H), 2.32 (s, 6H), 1.83-1.98 (m, 1H), 1.68 (t, J=5.01 Hz, 1H), 1.41 (s, 3H), 1.24 (d, J=6.60 Hz, 6H), 1.05 (dd, J=7.70 Hz, J=4.77 Hz, 1H).

Example B36

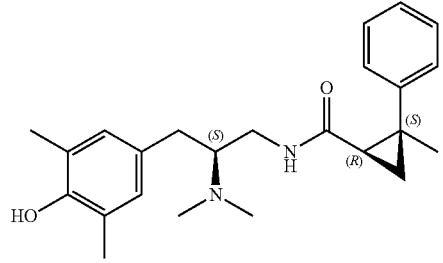

Synthesis of (1R,2S)—N—((S)-2-(dimethylamino)-3-(4-hydroxy-3,5-dimethylphenyl)propyl)-2-methyl-2-phenylcyclopropane-1-carboxamide (Compound B-36)

The title compound was prepared according to the procedure of Example B2 above, starting with 75 mg of (S)-4-(3-amino-2-(dimethylamino)propyl)-2,6-dimethylphenol and 74 mg of 2,5-dioxopyrrolidin-1-yl (1R,2S)-2-methyl-2-phenylcyclopropane-1-carboxylate to afford the title compound (46 mg). LC-MS: (+ESI) m/z 381.2 (MW+H); $^1$H NMR (400 MHz, MeOH-d$_4$) δ 7.07-7.23 (m, 5H), 6.71 (s, 1H), 3.02 (br, s, 2H), 2.70-2.78 (m, 2H), 2.35 (s, 6H), 2.20-2.30 (m, 1H), 2.17 (s, 6H), 1.80-1.85 (m, 1H), 1.65-1.70 (m, 1H), 1.65-1.70 (m, 1H), 1.40 (s, 3H), 1.02-1.07 (m, 1H).

Example B37

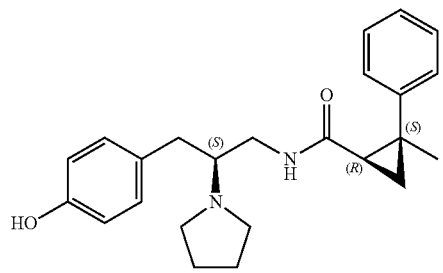

Synthesis of (1R,2S)—N—((S)-3-(4-hydroxyphenyl)-2-(pyrrolidin-1-yl)propyl)-2-methyl-2-phenylcyclopropane-1-carboxamide (Compound B-37)

(1R,2S)—N—((S)-3-(4-hydroxyphenyl)-2-(pyrrolidin-1-yl)propyl)-2-methyl-2-phenylcyclopropane-1-carboxamide was synthesized according to Scheme B2 using (S)-4-(3-amino-2-(pyrrolidin-1-yl)propyl)phenol and 2,5-dioxopyrrolidin-1-yl (1R,2S)-2-methyl-2-phenylcyclopropane-1-carboxylate as the starting materials. LC-MS: 379.2 [M+1]+; $^1$H NMR (400 MHz, CDCl$_3$) δ 7.24 (d, J=7.8 Hz, 1H), 7.16-7.19 (m, 1H), 7.08-7.12 (m, 1H), 6.71 (d, J=8.1 Hz, 2H), 6.51 (d, J=7.8 Hz, 2H), 2.85-3.0 (m, 1H), 2.45-2.70 (m, 1H), 1.72-1.81 (m, 2H), 1.46-1.62 (m, 5H), 1.57-1.42 (m, 4H), 1.18-1.20 (m, 1H), 1.02-1.06 (m, 1H).

Example B38

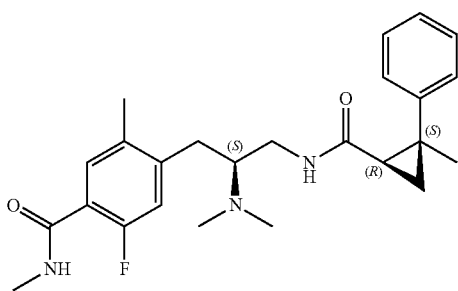

B-38

Synthesis of 4-((S)-2-(dimethylamino)-3-((1R,2S)-2-methyl-2-phenyl cyclopropane-1-carboxamido)propyl)-2-fluoro-N,5-dimethylbenzamide (Compound B-38)

The title compound was prepared according to Scheme B2, starting with (S)-4-(3-amino-2-(dimethylamino)propyl)-2-fluoro-N, 5-dimethylbenzamide (0.0900 g) and 2,5-dioxopyrrolidin-1-yl (1R,2S)-2-methyl-2-phenylcyclopropane-1-carboxylate (0.0920 g) to afford the title compound (0.0320 g). LCMS (+ESI) m/z 426.3 (M+H+). $^1$H NMR (400 MHz, METHANOL-d4) δ ppm 7.60 (d, J=7.58 Hz, 1H), 7.11-7.28 (m, 6H), 3.43-3.52 (m, 2H), 3.08-3.17 (m, 2H), 2.93 (s, 6H), 2.72-2.89 (m, 4H), 2.33 (s, 3H), 1.89 (dd, J=7.83, 5.38 Hz, 1H), 1.76 (t, J=5.01 Hz, 1H), 1.44 (s, 3H), 1.12 (dd, J=7.83, 4.65 Hz, 1H).

Example B39

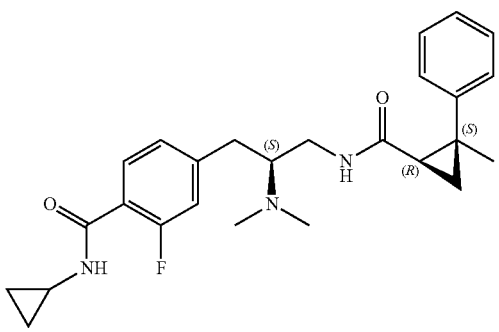

B-39

Synthesis of N-cyclopropyl-4-((S)-2-(dimethylamino)-3-((1R,2S)-2-methyl-2-phenylcyclopropane-1-carboxamido)propyl)-2-fluorobenzamide (Compound B-39)

The title compound was prepared according to the procedure of Example B2 above, starting with (S)-4-(3-amino-2-(dimethylamino)propyl)-2-fluoro-N-methylbenzamide (Int-4F) (0.07 g) and 2,5-dioxopyrrolidin-1-yl (1R,2S)-2-methyl-2-phenylcyclopropane-1-carboxylate (0.0685 g) to afford the title compound (0.0652 g). LC-MS (+ESI) M+H: 438.3; $^1$H NMR (400 MHz, DMSO-d6) δ ppm 8.30 (br d, J=3.67 Hz, 1H) 7.77-7.86 (m, 1H) 7.43 (br t, J=7.83 Hz, 1H) 7.13-7.21 (m, 4H) 7.07-7.12 (m, 1H) 6.99-7.06 (m, 2H) 2.92 (br d, J=4.16 Hz, 2H) 2.78-2.87 (m, 1H) 2.62-2.74 (m, 2H) 2.36-2.44 (m, 1H) 2.21 (br s, 6H) 1.88 (t, J=6.60 Hz, 1H) 1.49 (br t, J=4.04 Hz, 1H) 1.34 (s, 3H) 0.96 (br dd, J=7.70, 3.79 Hz, 1H) 0.68 (q, J=6.03 Hz, 2H) 0.48-0.55 (m, 2H)

Example B40

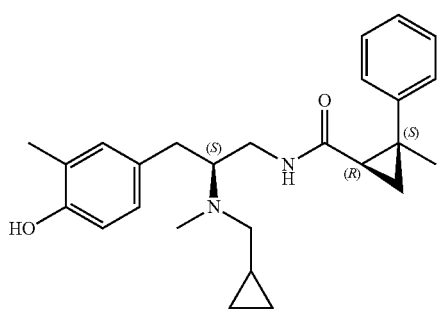

B-40

Synthesis of (1R,2S)—N—((S)-2-((cyclopropylmethyl)(methyl)amino)-3-(4-hydroxy-3-methylphenyl)propyl)-2-methyl-2-phenylcyclopropane-1-carboxamide (Compound B-40)

The title compound was prepared according to the procedure of Example B1 above, starting with 45 mg of (1R,2S)—N—((S)-2-amino-3-(4-hydroxy-3-methylphenyl)propyl)-2-methyl-2-phenylcyclopropane-1-carboxamide hydrochloride and 8.8 mg of cyclopropylaldehyde and 37% formaldehyde (20 mg) to afford the title compound (11 mg). LC-MS: (+ESI) m/z 407.3 (MW+H); $^1$H NMR (400 MHz, MeOH-d$_4$) δ 6.94-7.08 (m, 5H), 6.68 (s, 1H), 6.61 (d, J=7.83 Hz, 1H), 6.48 (d, J=8.07 Hz, 1H), 3.16 (s, 3H), 2.82-2.91 (m, 1H), 2.68-2.80 (m, 2H), 2.56 (dd, J=13.45 Hz, 3.91 Hz, 1H), 2.20-2.25 (m, 2H), 2.13 (s, 3H), 2.00-2.12 (m, 1H), 1.99 (s, 3H), 1.68 (dd, J=7.70 Hz, J=5.75 Hz, 1H), 1.38-1.50 (m, 1H), 1.25 (s, 3H), 1.14 (s, 1H), 0.81-0.97 (m, 1H), 0.60-0.78 (m, 2H), 0.34-0.43 (m, 2H), 0.05-0.03 (m, 2H).

Example B41

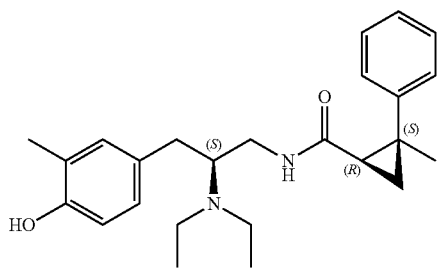

B-41

Synthesis of (1R,2S)—N—((S)-2-(diethylamino)-3-(4-hydroxy-3-methylphenyl)propyl)-2-methyl-2-phenylcyclopropane-1-carboxamide (Compound B-41)

The title compound was prepared according to the procedure of Example B1 above, starting with 45 mg of (1R,2S)—N—((S)-2-amino-3-(4-hydroxy-3-methylphenyl)propyl)-2-methyl-2-phenylcyclopropane-1-carboxamide hydrochloride and acetaldehyde (15 mg) to afford the title compound (25 mg). LC-MS: (+ESI) m/z 395.2 (MW+H); $^1$H NMR (400 MHz, MeOH-d$_4$) δ 7.08-7.25 (m, 5H), 6.83 (s, 1H), 6.76 (br d, J=8.07 Hz, 1H), 6.61-6.66 (m, 1H), 2.82-3.07 (m, 3H), 2.56-2.73 (m, 3H) 2.48 (dq, J=13.08 Hz, 6.48 Hz, 2H) 2.20-2.30 (m, 1H), 2.14 (s, 1H), 1.72-1.86 (m, 1H), 1.52-1.66 (m, 1H), 1.39 (s, 3H), 1.12-1.37 (m, 1H), 0.97-1.07 (m, 7H), 0.74-0.94 (m, 1H).

Example B42

B-42

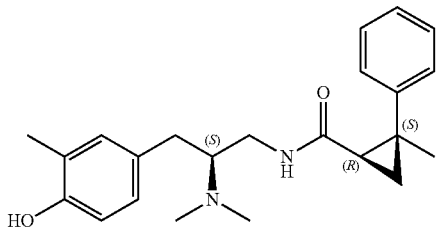

Synthesis of (1R,2S)—N—((S)-2-(dimethylamino)-3-(4-hydroxy-3-methylphenyl)propyl)-2-methyl-2-phenylcyclopropane-1-carboxamide (Compound B-42)

The title compound was prepared according to the procedure of Example B1 above, starting with 50 mg of (1R,2S)—N—((S)-2-amino-3-(4-hydroxy-3-methylphenyl)propyl)-2-methyl-2-phenylcyclopropane-1-carboxamide hydrochloride and 37% formaldehyde (46 mg) to afford the title compound (30 mg). LC-MS: (+ESI) m/z 367.2 (MW+H); $^1$H NMR (400 MHz, MeOH-d$_4$) δ 7.09-7.24 (m, 5H), 6.84 (s, 1H), 6.77 (d, J=8.07 Hz, 1H), 6.64 (d, J=8.07 Hz, 1H), 3.63 (s, 1H), 3.01 (d, J=6.36 Hz, 2H), 2.68-2.79 (m, 2H) 2.30 (s, 6H), 2.20-2.30 (m, 1H), 2.15 (s, 3H), 1.83 (dd, J=7.83 Hz, J=5.62 Hz, 1H), 1.62 (t, J=5.01 Hz, 1H), 1.39 (s, 3H), 1.15-1.34 (m, 1H), 0.96-1.14 (m, 1H), 0.83-0.94 (m, 1H).

Example B43

B-43

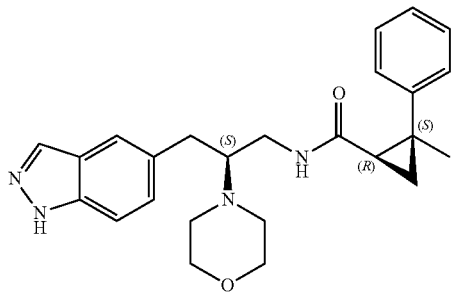

Synthesis of (1R,2S)—N—((S)-3-(2H-indazol-5-yl)-2-morpholinopropyl)-2-methyl-2-phenylcyclopropane-1-carboxamide (Compound B-43)

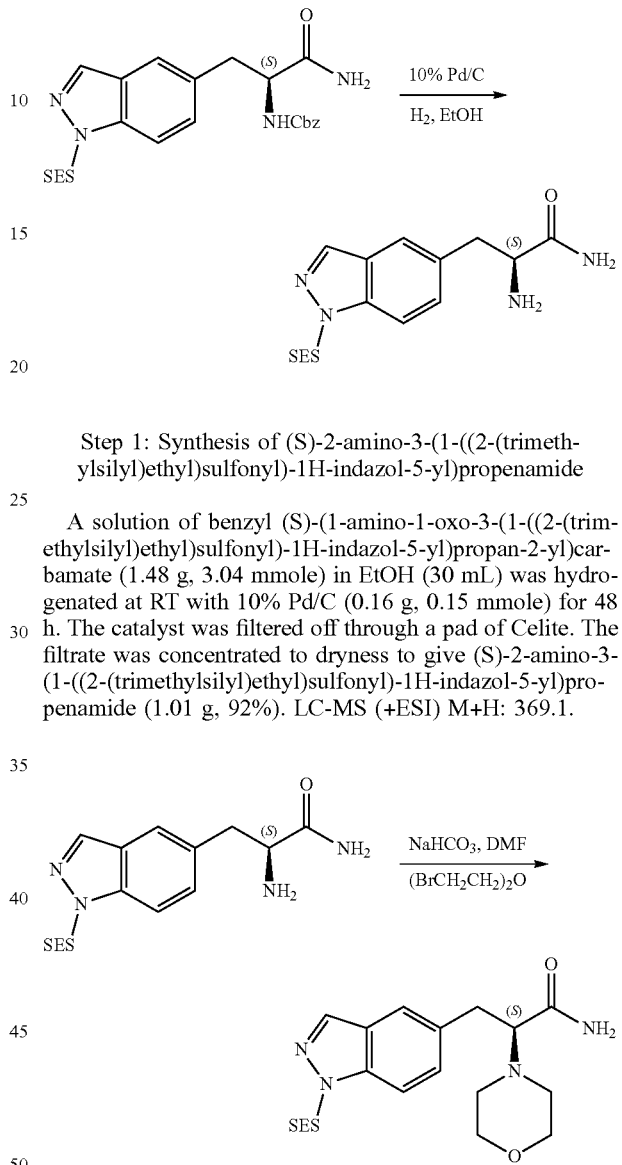

Step 1: Synthesis of (S)-2-amino-3-(1-((2-(trimethylsilyl)ethyl)sulfonyl)-1H-indazol-5-yl)propenamide A solution of benzyl (S)-(1-amino-1-oxo-3-(1-((2-(trimethylsilyl)ethyl)sulfonyl)-1H-indazol-5-yl)propan-2-yl)carbamate (1.48 g, 3.04 mmole) in EtOH (30 mL) was hydrogenated at RT with 10% Pd/C (0.16 g, 0.15 mmole) for 48 h. The catalyst was filtered off through a pad of Celite. The filtrate was concentrated to dryness to give (S)-2-amino-3-(1-((2-(trimethylsilyl)ethyl)sulfonyl)-1H-indazol-5-yl)propenamide (1.01 g, 92%). LC-MS (+ESI) M+H: 369.1.

Step 2: Synthesis of (S)-2-morpholino-3-(1-((2-(trimethylsilyl)ethyl)sulfonyl)-1H-indazol-5-yl)propenamide A mixture of (S)-2-amino-3-(1-((2-(trimethylsilyl)ethyl)sulfonyl)-1H-indazol-5-yl)propenamide (1.01 g, 2.74 mmole), NaHCO$_3$ (1.15 g, 13.7 mmole), and 1-bromo-2-(2-bromoethoxy)ethane (0.96 g, 4.11 mmole) in DMF (12 mL) was heated at 80° C. in 4 h. The reaction mixture was cooled, quenched with saturated aqueous NH$_4$Cl, extracted with EtOAc (3×). The combined extracts were dried over Na$_2$SO$_4$, concentrated, and purified by ISCO (5% MeOH/DCM) to give (S)-2-morpholino-3-(1-((2-(trimethylsilyl)ethyl)sulfonyl)-1H-indazol-5-yl)propenamide (1.2 g, 86%). LC-MS (+ESI) M+H: 439.1.

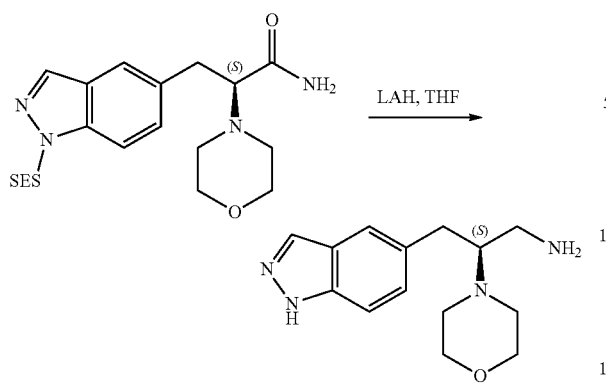

Step 3: Synthesis of (S)-3-(1H-indazol-5-yl)-2-morpholinopropan-1-amine

To a stirred solution of (S)-2-morpholino-3-(1-((2-(trimethylsilyl)ethyl)sulfonyl)-1H-indazol-5-yl)propenamide (1.4 g, 3.19 mmole) in THF (30 mL) at 0° C. was added 1M LAH (9.5 mL, 9.58 mmole) dropwise. The reaction mixture was heated to 80° C. in 16 h. The reaction mixture was cooled in an ice bath and slowly added a saturated solution of Rochelle's salt and stirred for 2 h, extracted with DCM (3×). The combined extracts were dried over Na$_2$SO$_4$, concentrated and purified by ISCO (0-25% MeOH/DCM in 1% NH$_4$OH) to give (S)-3-(1H-indazol-5-yl)-2-morpholinopropan-1-amine (0.185 g, 22%). LC-MS (+ESI) M+H: 261.1.

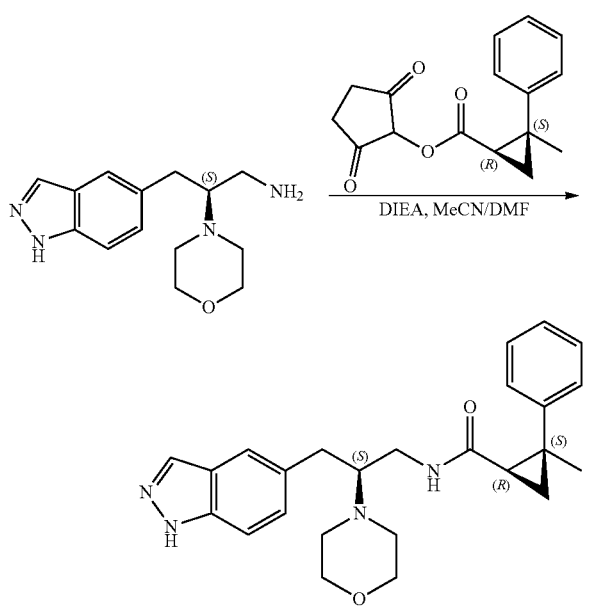

Step 4: Synthesis of (1R,2S)—N—((S)-3-(1H-indazol-5-yl)-2-morpholinopropyl)-2-methyl-2-phenylcyclopropane-1-carboxamide A mixture of (S)-3-(1H-indazol-5-yl)-2-morpholinopropan-1-amine (0.0572 g, 0.219 mmole), 2,5-dioxocyclopentyl (1R,2S)-2-methyl-2-phenylcyclopropane-1-carboxylate (0.06 g, 0.219 mmole), and DIEA (50 □mL, 0.263 mmole) in MeCN/DMF (1:1, 3 mL) was stirred at RT for 16 h. H$_2$O was added and extracted with DCM (3×). The combined extracts were dried over Na$_2$SO$_4$, concentrated and purified by ISCO (0-15% MeOH/DCM) to give the title compound (0.0478 g, 52%). LC-MS (+ESI) M+H: 419.2; $^1$H NMR (400 MHz, DMSO-d6) δ ppm 12.95 (s, 1H) 7.97 (s, 1H) 7.73 (br t, J=5.14 Hz, 1H) 7.49 (s, 1H) 7.43 (d, J=8.56 Hz, 1H) 7.04-7.21 (m, 6H) 3.54 (br d, J=4.16 Hz, 4H) 2.90-2.99 (m, 2H) 2.83 (br dd, J=13.57, 5.99 Hz, 1H) 2.63-2.70 (m, 1H) 2.43-2.49 (m, 3H) 2.41-2.49 (m, 1H) 1.88 (t, J=6.48 Hz, 1H) 1.47 (br t, J=4.40 Hz, 1H) 1.34 (s, 3H) 0.96 (dd, J=7.58, 3.91 Hz, 1H)

Example B44

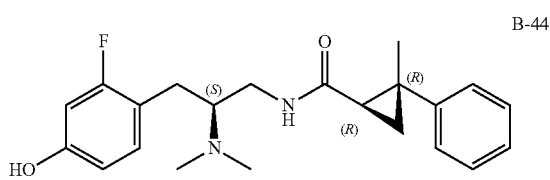

Synthesis of (1R,2R)—N—((S)-2-(dimethylamino)-3-(2-fluoro-4-hydroxyphenyl)propyl)-2-methyl-2-phenylcyclopropane-1-carboxamide (Compound B-44)

(1R,2R)—N—((S)-2-(dimethylamino)-3-(2-fluoro-4-hydroxyphenyl)-propyl)-2-methyl-2-phenylcyclopropane-1-carboxamide was synthesized according to Scheme B2 using (S)-4-(3-amino-2-(dimethylamino)propyl)-3-fluorophenol and 2,5-dioxopyrrolidin-1-yl (1R,2R)-2-methyl-2-phenylcyclopropane-1-carboxylate as the starting materials. LC-MS: 371.2 [M+1]$^+$; $^1$H NMR (400 MHz, CDCl$_3$) δ 7.17-7.25 (m, 3H), 7.11-7.15 (m, 1H), 6.84-6.95 (m, 2H), 6.49 (d, J=9.8 Hz, 2H), 3.40-3.46 (m, 1H), 3.01-3.10 (m, 1H), 2.83-2.95 (m, 2H), 2.40 (s, 6H), 2.26-2.35 (m, 1H), 1.69-1.73 (m, 1H), 1.38-1.43 (m, 4H), 1.30-1.34 (m, 1H).

Example B45

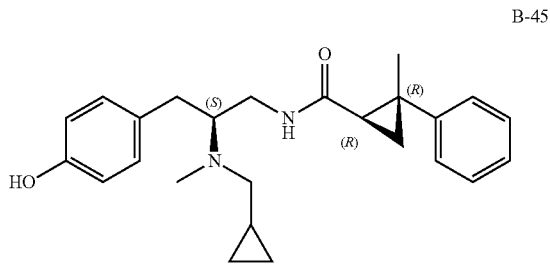

Synthesis of (1R,2R)—N—((S)-2-((cyclopropylmethyl)(methyl)amino)-3-(4-hydroxyphenyl)propyl)-2-methyl-2-phenylcyclopropane-1-carboxamide (Compound B-45)

The title compound was prepared according to the procedure of Example B1 above, starting with 31 mg of (1R,2R)—N—((S)-2-amino-3-(4-hydroxyphenyl)propyl)-

2-methyl-2-phenylcyclopropane-1-carboxamide hydrochloride and cyclopropaldehyde (6 mg) and 37% formaldehyde (19 mg) to afford the title compound (16 mg). LC-MS: (+ESI) m/z 393.3 (MW+H); $^1$H NMR (400 MHz, CDCl$_3$) δ 7.77 (br, s, 1H), 7.25-7.32 (m, 5H), 7.16-7.23 (m, 1H) 6.98 (br d, J=8.07 Hz, 2H), 6.78 (d, J=8.31 Hz, 2H), 3.52 (br d, J=14.43 Hz, 1H), 3.40 (br d, J=9.29 Hz, 1H), 3.26 (br d, J=10.03 Hz, 1H), 2.90-3.12 (m, 1H), 2.60-2.75 (m, 2H), 2.41-2.51 (m, 1H) 2.00 (s, 3H), 1.75-1.85 (m, 1H), 1.44 (s, 3H), 1.32-1.40 (m, 1H), 1.26 (br s, 1H), 1.00 (br s, 1H), 0.60-0.70 (m, 2H), 0.28 (br d, J=4.40 Hz, 2H)

Example B46

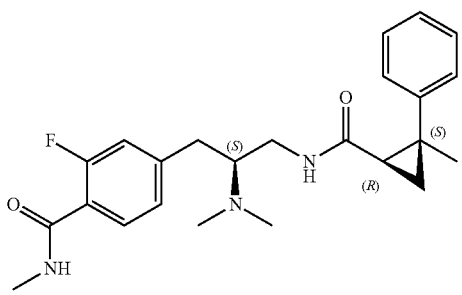

B-46

Synthesis of 4-((S)-2-(dimethylamino)-3-((1R,2S)-2-methyl-2-phenylcyclopropane-1-carboxamido)propyl)-2-fluoro-N-methylbenzamide (Compound B-46)

4-((S)-2-(dimethylamino)-3-((1R,2S)-2-methyl-2-phenylcyclopropane-1-carboxamido)propyl)-2-fluoro-N-methylbenzamide was synthesized according to Scheme B2 using (S)-4-(3-amino-2-(dimethylamino)propyl)-2-fluoro-N-methylbenzamide (Int-4F) and 2,5-dioxopyrrolidin-1-yl (1R,2S)-2-methyl-2-phenylcyclopropane-1-carboxylate as the starting materials. LC-MS: 412.2 [M+1]$^+$; $^1$H NMR (400 MHz, CDCl$_3$) δ 7.85 (t, J=8.1 Hz, 1H), 7.06-7.21 (m, 5H), 6.86 (d, J=8.1 Hz, 1H), 6.67-6.74 (m, 2H), 5.90 (bs, 1H), 3.03-3.10 (m, 1H), 2.90 (d, J=5.6 Hz, 3H), 2.76 (dd, J=13.7 Hz, 3.4 Hz, 1H) 2.47-2.60 (m, 2H), 2.08-2.15 (m, 7H), 1.65-1.70 (m, 1H), 1.50-1.54 (m, 1H), 1.35 (s, 3H), 1.00 (dd, J=8.1 Hz, 4.9 Hz, 1H).

Example B47

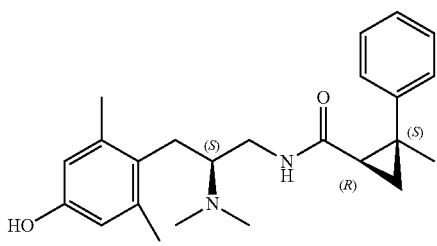

B-47

Synthesis of (1R,2S)—N—((S)-2-(dimethylamino)-3-(4-hydroxy-2,6-dimethylphenyl)propyl)-2-methyl-2-phenylcyclopropane-1-carboxamide (Compound B-47)

(1R,2S)—N—((S)-2-(dimethylamino)-3-(4-hydroxy-2,6-dimethylphenyl)-propyl)-2-methyl-2-phenylcyclopropane-1-carboxamide was synthesized according to Scheme B2 using (S)-4-(3-amino-2-(dimethylamino)propyl)-3,5-dimethylphenol (Int-1G) and 2,5-dioxopyrrolidin-1-yl (1R,2S)-2-methyl-2-phenylcyclopropane-1-carboxylate as the starting materials. LC-MS: 381.2 [M+1]$^+$; $^1$H NMR (400 MHz, CDCl$_3$) δ 7.06-7.20 (m, 5H), 6.59 (s, 1H), 6.28 (s, 2H), 2.93-2.98 (m, 1H), 2.66-2.80 (m, 2H), 2.35-2.41 (m, 1H), 2.30 (s, 3H), 2.05 (s, 3H), 1.88 (s, 1H), 1.68-1.71 (m, 1H), 1.51-1.53 (m, 1H), 1.33 (s, 3H), 0.97-1.01 (m, 1H).

Example B48

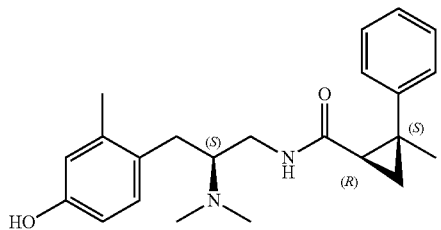

B-48

Synthesis of (1R,2S)—N—((S)-2-(dimethylamino)-3-(4-hydroxy-2-methylphenyl)propyl)-2-methyl-2-phenylcyclopropane-1-carboxamide (Compound B-48)

(1R,2S)—N—((S)-2-(dimethylamino)-3-(4-hydroxy-2-methylphenyl)-propyl)-2-methyl-2-phenylcyclopropane-1-carboxamide was synthesized according to Scheme B2 using (S)-4-(3-amino-2-(dimethylamino)propyl)-3-methylphenol and 2,5-dioxopyrrolidin-1-yl (1R,2S)-2-methyl-2-phenylcyclopropane-1-carboxylate as the starting materials. LC-MS: 367.2 [M+1]$^+$; $^1$H NMR (400 MHz, CDCl$_3$) δ 7.11-7.26 (m, 5H), 6.70 (d, J=7.8 Hz, 2H), 6.51 (s, 1H), 6.39 (d, J=7.8 Hz, 1H), 3.16-3.21 (m, 1H), 2.73-2.86 (m, 3H), 2.34 (s, 6H), 2.18-2.25 (m, 1H), 2.12 (s, 3H), 1.79-1.83 (m, 1H), 1.62-1.64 (m, 1H), 1.40 (s, 3H), 1.04-1.07 (m, 1H).

Example B49

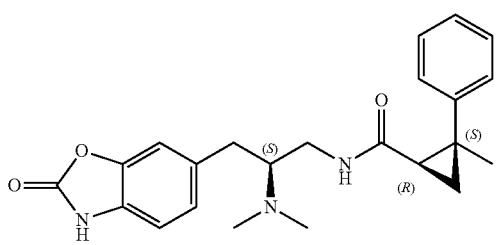

B-49

Synthesis of (1R,2S)—N—((S)-2-(dimethylamino)-3-(2-oxo-2,3-dihydrobenzo[d]oxazol-6-yl)propyl)-2-methyl-2-phenylcyclopropane-1-carboxamide (Compound B-49)

Compound B-49 was prepared by the same procedure above using (S)-6-(3-amino-2-(dimethylamino)propyl)benzo[d]oxazol-2(3H)-one and 2,5-dioxopyrrolidin-1-yl (1R,2S)-2-methyl-2-phenylcyclopropane-1-carboxylate as starting materials. LC-MS: 394.2 [M+H]+; 1H NMR (400 MHz, DMSO-d6) δ 11.5 (s, 1H), 7.95 (m, 1H), 7.30-7.15 (m, 6H), 6.98 (m, 2H), 3.17-3.14 (m, 3H), 2.77 (m, 2H), 2.26 (s, 6H), 1.91 (t, J=6.8 Hz, 1H), 1.36 (s, 3H), 1.22 (m, 2H).

Example B50

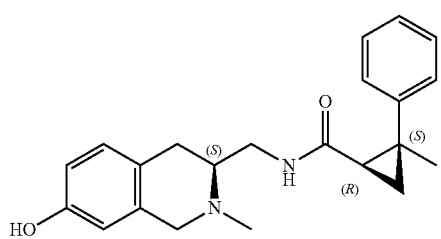

B-50

Synthesis of (1R,2S)—N—(((S)-7-hydroxy-2-methyl-1,2,3,4-tetrahydroisoquinolin-3-yl)methyl)-2-methyl-2-phenyl cyclopropane-1-carboxamide (Compound B-50)

(1R,2S)—N—(((S)-7-hydroxy-2-methyl-1,2,3,4-tetrahydroisoquinolin-3-yl)methyl)-2-methyl-2-phenyl cyclopropane-1-carboxamide was synthesized according to Scheme B2 using (S)-3-(aminomethyl)-2-methyl-1,2,3,4-tetrahydroisoquinolin-7-ol and 2,5-dioxopyrrolidin-1-yl (1R,2S)-2-methyl-2-phenylcyclopropane-1-carboxylate as the starting materials. LC-MS: 351.2 [M+1]+; 1H NMR (400 MHz, d6-DMSO) δ 9.12 (s, 1H), 7.99 (s, 1H), 7.20-7.25 (m, 4H), 7.13 (sep, J=16.4 Hz, 12.7 Hz, 8.3 Hz, 4.4 Hz, 1H), 6.80 (d, J=8.1 Hz, 1H), 6.54 (d, J=7.1 Hz, 1H), 6.42 (s, 1H), 3.57-3.67 (m, 1H), 3.44-3.55 (m, 1H), 3.05-3.14 (m, 1H), 2.90-3.01 (m, 1H), 2.23-2.43 (m, 4H), 1.87-1.91 (m, 1H), 1.51-1.55 (m, 1H), 1.36 (s, 3H), 1.09 (t, J=7.1 Hz, 1H), 0.96-0.99 (m, 1H).

Example B51

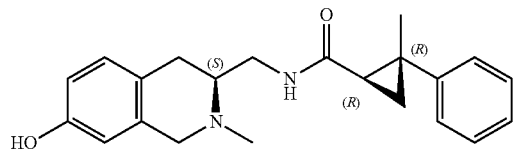

B-51

Synthesis of (1R,2R)—N—(((S)-7-hydroxy-2-methyl-1,2,3,4-tetrahydroisoquinolin-3-yl)methyl)-2-methyl-2-phenyl cyclopropane-1-carboxamide (Compound B-51)

(1R,2R)—N—(((S)-7-hydroxy-2-methyl-1,2,3,4-tetrahydroisoquinolin-3-yl)methyl)-2-methyl-2-phenyl cyclopropane-1-carboxamide was synthesized according to Scheme B2 using (S)-3-(aminomethyl)-2-methyl-1,2,3,4-tetrahydroisoquinolin-7-ol and 2,5-dioxopyrrolidin-1-yl (1R,2R)-2-methyl-2-phenylcyclopropane-1-carboxylate as the starting materials. LC-MS: 351.2 [M+1]+; 1H NMR (400 MHz, CDCl3) δ 7.25-7.30 (m, 5H), 7.17-7.22 (m, 1H), 6.86-7.0 (m, 2H), 6.62 (d, J=8.1 Hz, 1H), 6.37 (s, 1H), 3.56-3.77 (m, 4H), 2.95-2.99 (m, 1H), 2.71-2.74 (m, 2H), 2.45 (s, 3H), 2.35 (s, 1H), 1.79-1.84 (m, 1H), 1.49-1.53 (m, 4H), 1.31-1.34 (dd, J=8.3 Hz, 4.6 Hz, 1H).

Example B52

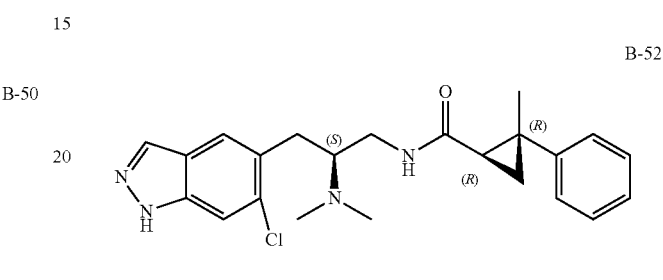

B-52

Synthesis of (1R,2R)—N—((S)-3-(6-chloro-2H-indazol-5-yl)-2-(dimethylamino)propyl)-2-methyl-2-phenylcyclopropane-1-carboxamide (Compound B-52)

The title compound was prepared according to the procedure of Example B2 above, starting with (1R,2S)—N—((S)-3-(6-chloro-1-((2-(trimethylsilyl)ethoxy)methyl)-1H-indazol-5-yl)-2-(dimethylamino)propyl)-2-methyl-2-phenylcyclopropane-1-carboxamide (0.175 g, 0.324 mmole) and 1M TBAF (3.2 mL, 3.24 mmole) to afford the title compound (0.0461 g, 35%). LC-MS (+ESI) M+H: 411.2; 1H NMR (400 MHz, DMSO-d6) δ ppm 1.11 (s, 3H) 1.18-1.23 (m, 2H) 1.34 (s, 3H) 1.91 (br t, J=6.97 Hz, 1H) 2.31 (br s, 6H) 2.67-2.73 (m, 1H) 2.87-2.96 (m, 1H) 3.00 (br dd, J=13.21, 5.62 Hz, 1H) 3.10-3.16 (m, 1H) 3.18-3.28 (m, 1H) 7.14-7.22 (m, 1H) 7.23-7.33 (m, 4H) 7.62 (s, 1H) 7.73 (s, 1H) 7.94-8.03 (m, 1H) 8.05 (s, 1H) 13.09 (s, 1H)

Example B53

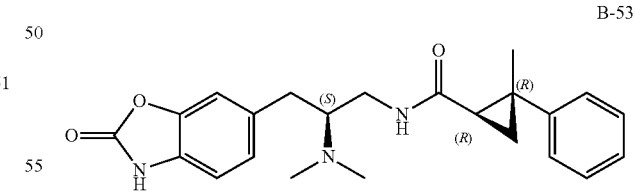

B-53

Synthesis of (1R,2R)—N—((S)-2-(dimethylamino)-3-(2-oxo-2,3-dihydrobenzo[d]oxazol-6-yl)propyl)-2-methyl-2-phenylcyclopropane-1-carboxamide (Compound B-53)

The compound was prepared by the same procedure above using (S)-6-(3-amino-2-(dimethylamino)propyl)benzo[d]oxazol-2(3H)-one and 2,5-dioxopyrrolidin-1-yl (1R,2R)-2-methyl-2-phenylcyclopropane-1-carboxylate as starting materials. LC-MS: 394.2 [M+H]+; 1H NMR (400 MHz, DMSO-d6) δ 11.5 (s, 1H), 7.74 (m, 1H), 7.15-6.88 (m, 8H), 2.88 (m, 2H), 2.67 (m, 2H), 2.33 (m, 1H), 2.21 (s, 6H), 1.86 (t, J=6.0 Hz, 1H), 1.47 (t, J=4.8 Hz, 1H), 1.33 (s, 3H), 0.94 (m, 1H).

Example B54

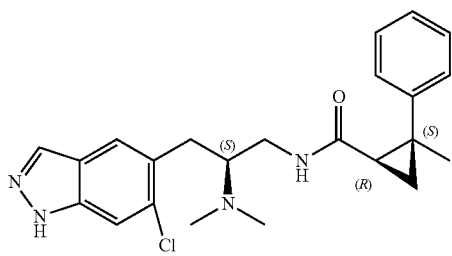

B-54

Synthesis of (1R,2S)—N—((S)-3-(6-chloro-2H-indazol-5-yl)-2-(dimethylamino)propyl)-2-methyl-2-phenylcyclopropane-1-carboxamide (Compound B-54)

The title compound was prepared according to the procedure of Example B52 above, starting with (1R,2S)—N—((S)-3-(6-chloro-1-((2-(trimethylsilyl)ethoxy)methyl)-1H-indazol-5-yl)-2-(dimethylamino)propyl)-2-methyl-2-phenylcyclopropane-1-carboxamide (0.151 g, 0.279 mmole) and 1M TBAF (1.4 mL, 1.39 mmole) to afford the title compound (0.0389 g, 34%). LC-MS (+ESI) M+H: 411.2; 1H NMR (400 MHz, DMSO-d6) δ ppm 0.93 (br dd, J=6.97, 3.55 Hz, 1H) 1.31 (s, 3H) 1.42 (br t, J=4.04 Hz, 1H) 1.83-1.90 (m, 1H) 2.29 (s, 6H) 2.34 (br s, 1H) 2.57 (br d, J=4.16 Hz, 1H) 2.68 (br d, J=0.73 Hz, 1H) 2.73-2.82 (m, 1H) 2.95 (br d, J=6.11 Hz, 3H) 7.02-7.10 (m, 1H) 7.10-7.17 (m, 4H) 7.58 (s, 1H) 7.63 (s, 1H) 7.73-7.80 (m, 1H) 8.02 (s, 1H) 13.07 (s, 1H)

Example B55

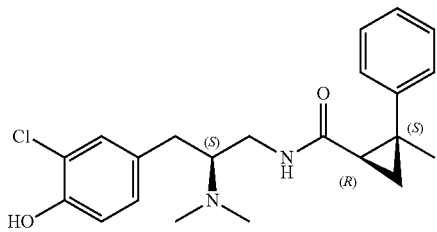

B-55

Synthesis of (1R,2S)—N—((S)-3-(3-chloro-4-hydroxyphenyl)-2-(dimethylamino)propyl)-2-methyl-2-phenylcyclopropane-1-carboxamide (Compound B-55)

(1R,2S)—N—((S)-3-(3-chloro-4-hydroxyphenyl)-2-(dimethylamino)-propyl)-2-methyl-2-phenyl cyclopropane-1-carboxamide was synthesized according to Scheme B2 using (S)-4-(3-amino-2-(dimethylamino)propyl)-2-chlorophenol (Int-311) and 2,5-dioxopyrrolidin-1-yl (1R,2R)-2-methyl-2-phenylcyclopropane-1-carboxylate as the starting materials. LC-MS: 387.2 [M+1]+; 1H NMR (400 MHz, CDCl3) δ 7.11-7.26 (m, 5H), 9.90-6.96 (m, 1H), 6.56-6.72 (m, 3H), 3.10-3.22 (m, 1H), 2.61-2.81 (m, 4H), 2.28 (s, 6H), 2.10-2.16 (m, 1H), 1.78-1.83 (m, 1H), 1.63-1.66 (m, 1H), 142 (s, 3H), 1.06-1.09 (m, 1H).

Example B56

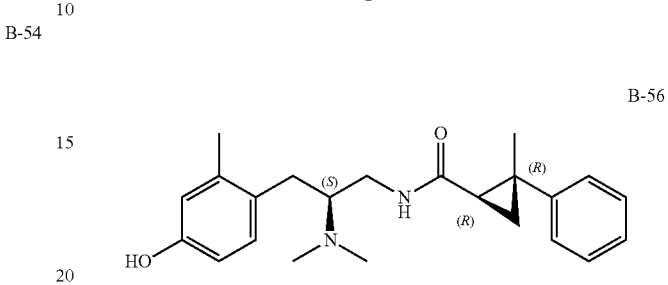

B-56

Synthesis of (1R,2R)—N—((S)-2-(dimethylamino)-3-(4-hydroxy-2-methyl phenyl)propyl)-2-methyl-2-phenylcyclopropane-1-carboxamide (Compound B-56)

The title compound was prepared according to the procedure of Example B1 above, starting with (S)-4-(3-amino-2-(dimethylamino)propyl)-3-methylphenol (229 mg) and 2,5-dioxopyrrolidin-1-yl (1R,2R)-2-methyl-2-phenylcyclopropane-1-carboxylate (301 mg) to afford the title compound (259 mg, 64%). LC-MS: (ESI+) m/z 367.2 (M+H)+. 1H NMR (400 MHz, CDCl3) δ ppm 7.27-7.32 (m, 2H) 7.17-7.25 (m, 3H) 6.93 (d, J=8.07 Hz, 1H) 6.59-6.64 (m, 2H) 6.40 (m, 1H) 3.42 (m, 1H) 3.03 (m, 1H) 2.95 (dd, J=13.45, 3.18 Hz, 1H) 2.65-2.75 (m, 1H) 2.36 (s, 6H) 2.32 (m, 1H) 2.27 (s, 3H) 1.68 (dd, J=8.56, 6.11 Hz, 1H) 1.49 (s, 3H) 1.44-1.47 (m, 1H) 1.36 (dd, J=8.31, 4.89 Hz, 1H)

Example B57

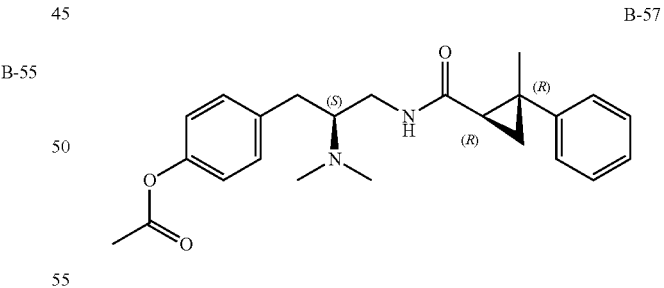

B-57

Synthesis of 4-((S)-2-(dimethylamino)-3-((1R,2R)-2-methyl-2-phenylcyclopropane-1-carboxamido)propyl)phenyl Acetate (Compound B-57)

4-((S)-2-(dimethylamino)-3-((1R,2R)-2-methyl-2-phenylcyclopropane-1-carboxamido)propyl)phenyl acetate was synthesized according to Scheme B2 using (S)-4-(3-amino-2-(dimethylamino)propyl)phenyl acetate and 2,5-dioxopyrrolidin-1-yl (1R,2R)-2-methyl-2-phenylcyclopropane-1-carboxylate as the starting materials. LC-MS: 395.2 [M+1]+; 1H NMR (400 MHz, CDCl3) δ 7.26-7.81 (m, 4H), 7.16-7.21

(m, 4H), 7.02 (d, J=8.3 Hz, 1H), 3.41-3.49 (m, 1H), 3.21-3.28 (m, 1H), 2.99-3.07 (m, 1H), 2.50-2.53 (m, 1H), 2.45 (s, 6H), 2.29 (s, 3H), 1.73-1.78 (m, 1H), 1.45-1.47 (m, 4H), 1.30-1.33 (m, 1H).

Example B58

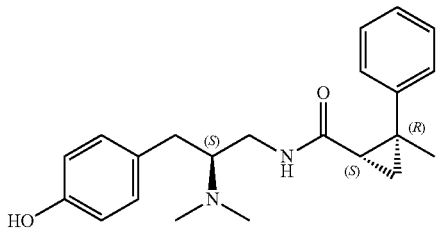

B-58

Synthesis of (1S,2R)—N—((S)-2-(dimethylamino)-3-(4-hydroxyphenyl)propyl)-2-methyl-2-phenylcyclopropane-1-carboxamide (Compound B-58)

(1S,2R)—N—((S)-2-(dimethylamino)-3-(4-hydroxyphenyl)propyl)-2-methyl-2-phenylcyclopropane-1-carboxamide was synthesized according to Scheme B2 using (S)-4-(3-amino-2-(dimethylamino)propyl)phenol and 2,5-dioxopyrrolidin-1-yl (1S,2R)-2-methyl-2-phenylcyclopropane-1-carboxylate as the starting materials. LC-MS: 353.2 [M+1]$^+$; $^1$H NMR (400 MHz, d6-DMSO) δ 9.12 (s, 1H), 7.60-7.61 (m, 1H), 7.09-7.18 (m, 5H), 6.91 (d, J=Hz, 2H), 6.63 (d, J=Hz, 2H), 2.87-2.94 (m, 1H), 2.77-2.84 (m, 1H), 2.62 (dd, J=13.7 Hz, 5.6 Hz, 1H), 2.19-2.25 (m, 7H), 1.87 (dd, J=7.8 Hz, 5.6 Hz, 1H), 1.43-1.46 (m, 1H), 1.32 (s, 3H), 0.93 (dd, J=7.8 Hz, 3.9 Hz, 1H).

Example B59

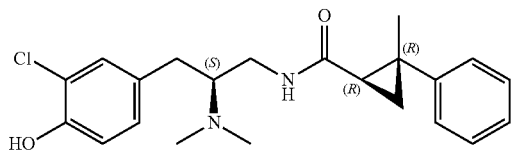

B-59

Synthesis of (1R,2R)—N—((S)-3-(3-chloro-4-hydroxyphenyl)-2-(dimethylamino)propyl)-2-methyl-2-phenylcyclopropane-1-carboxamide (Compound B-59)

(1R,2S)—N—((S)-3-(3-chloro-4-hydroxyphenyl)-2-(dimethylamino)-propyl)-2-methyl-2-phenylcyclopropane-1-carboxamide was synthesized according to Scheme B2 using (S)-4-(3-amino-2-(dimethylamino)propyl)-2-chlorophenol (Int-311) and 2,5-dioxopyrrolidin-1-yl (1R,2R)-2-methyl-2-phenylcyclopropane-1-carboxylate as the starting materials. LC-MS: 387.2 [M+1]$^+$; $^1$H NMR (400 MHz, CDCl$_3$) δ 7.19-7.30 (m, 5H), 6.84-6.91 (m, 2H), 6.67-6.71 (m, 1H), 3.40-3.57 (m, 1H), 2.73-3.09 (m, 3H), 2.25-2.40 (m, 7H), 1.71-1.74 (m, 1H), 1.46-1.52 (m, 4H), 1.39 (dd, J=8.8 Hz, 5.1 Hz, 1H).

Example B60

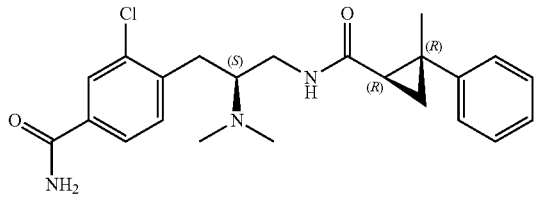

B-60

Synthesis of 3-chloro-4-((S)-2-(dimethylamino)-3-((1R,2R)-2-methyl-2-phenylcyclopropane-1-carboxamido)propyl)benzamide (Compound B-60)

3-chloro-4-((S)-2-(dimethylamino)-3-((1R,2R)-2-methyl-2-phenylcyclopropane-1-carboxamido)propyl)benzamide was synthesized according to Scheme B2 using (S)-4-(3-amino-2-(dimethylamino)propyl)-3-chlorobenzamide and 2,5-dioxopyrrolidin-1-yl (1R,2R)-2-methyl-2-phenylcyclopropane-1-carboxylate as the starting materials. LC-MS: 414.2 [M+1]$^+$; $^1$H NMR (400 MHz, CDCl$_3$) δ 7.17-7.31 (m, 5H), 6.84-6.91 (m, 2H), 6.65-6.61 (m, 1H), 3.40-3.47 (m, 1H), 2.73-3.09 (m, 3H), 2.24-2.40 (m, 7H), 1.70-1.74 (m, 1H), 1.46-1.52 (m, 4H), 1.34-1.39 (m, 1H).

Example B61

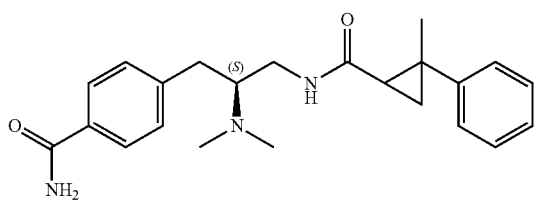

B-61

Synthesis of 4-((2 S)-2-(dimethylamino)-3-(2-methyl-2-phenylcyclopropane-1-carboxamido)propyl)benzamide (Compound B-61)

4-((2 S)-2-(dimethylamino)-3-(2-methyl-2-phenylcyclopropane-1-carboxamido)propyl)benzamide was synthesized according to Scheme B2 using (S)-4-(3-amino-2-(dimethylamino)propyl)benzamide and 2,5-dioxopyrrolidin-1-yl 2-methyl-2-phenylcyclopropane-1-carboxylate as the starting materials. LC-MS: 380.2 [M+1]$^+$.

Example B62

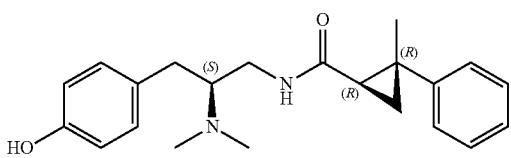

B-62

211

Synthesis of (1R,2R)—N—((S)-2-(dimethylamino)-3-(4-hydroxyphenyl)propyl)-2-methyl-2-phenylcyclopropane-1-carboxamide (Compound B-62)

(1R,2R)—N—((S)-2-(dimethylamino)-3-(4-hydroxyphenyl)propyl)-2-methyl-2-phenylcyclopropane-1-carboxamide was synthesized according to Scheme B2 using (S)-4-(3-amino-2-(dimethylamino)propyl)phenol and 2,5-dioxopyrrolidin-1-yl (1R,2R)-2-methyl-2-phenylcyclopropane-1-carboxylate as the starting materials. LC-MS: 353.2 [M+1]+; 1H NMR (400 MHz, d6-DMSO) δ 9.15 (s, 1H), 7.89-7.91 (m, 1H), 7.27-7.32 (m, 4H), 7.18-7.21 (m, 1H), 6.92 (d, J=8.3 Hz, 2H), 6.65 (d, J=8.1 Hz, 2H), 3.05-3.13 (m, 2H), 2.65-2.70 (m, 2H), 2.22-2.34 (m, 7H), 1.91-1.95 (m, 1H), 1.36 (s, 3H), 1.19-1.25 (m, 1H).

Example B63

B-63

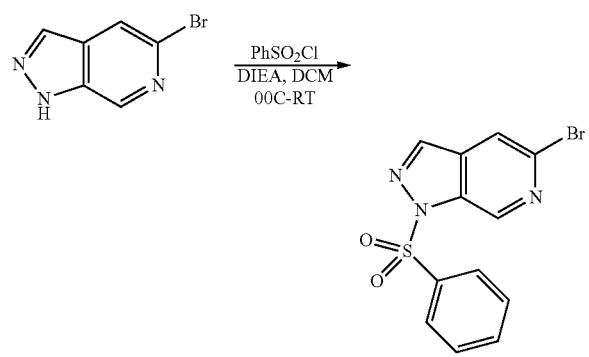

Synthesis of (1R,2R)—N—((S)-2-(dimethylamino)-3-(1H-pyrazolo[3,4-c]pyridin-5-yl)propyl)-2-methyl-2-phenylcyclopropane-1-carboxamide (Compound B-63)

Step 1: Synthesis of 5-bromo-1-(phenylsulfonyl)-1H-pyrazolo[3,4-c]pyridine

To a stirred mixture of 5-bromo-1H-pyrazolo[3,4m-c]pyridine (5 g, 25.51 mmole) and DIEA (5.4 mL, 30.61 mmole) in DCM (50 mL) at 0° C. was added benzenesulfonyl chloride (3.6 mL, 28.06 mmole). After the addition was completed, the reaction mixture was stirred for 2 h at RT. H2O was added, and the layers were separated. The organic layer was dried over $Na_2SO_4$, concentrated to give the title compound (7.5 g, 87%). LC-MS (+ESI) M+H: 338.3.

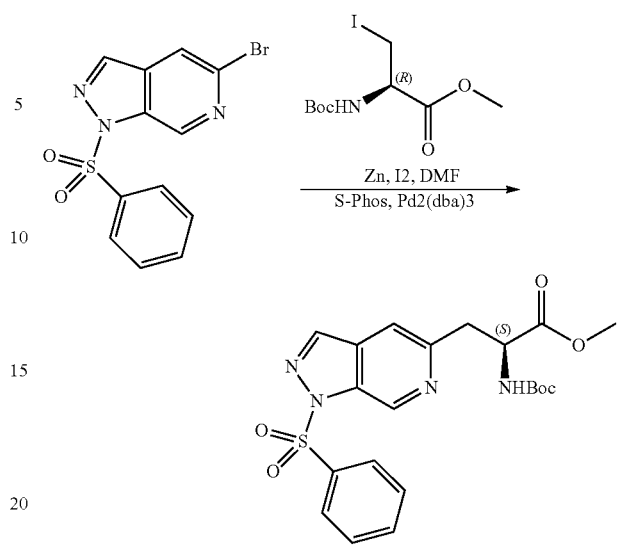

Step 2: Synthesis of methyl (S)-2-((tert-butoxycarbonyl)amino)-3-(1-(phenylsulfonyl)-1H-pyrazolo[3,4-c]pyridin-5-yl)propanoate To a stirred suspension of Zinc powder (2.3 g, 11.83 mmole) in DMF (20 mL) was added iodine (0.3 g, 1.18 mmole). After stirring for 10 minutes, methyl (R)-2-((tert-butoxycarbonyl)amino)-3-iodopropanoate (4.67 g, 14.2 mmole) was added, followed by iodine (0.3 g, 1.18 mmole). The resulting mixture was stirred for 2 h. The mixture was then added to the mixture of 5-bromo-1-(phenylsulfonyl)-1H-pyrazolo[3,4-c]pyridine (4.0 g, 11.83 mmole), S-Phos (0.24 g, 0.6 mmole), and $Pd_2(dba)_3$ (0.21 g, 0.23 mmole) in DMF (10 mL). After the addition was completed, the reaction mixture was heated to 40° C. in 16 h. The reaction mixture was cooled, diluted with EtOAc, filtered through the pad of Celite. The filtrate was concentrated to dryness, and purified by ISCO (0-50% EtOAc/Hexanes) to give the title compound (5.14 g, 94%). LC-MS (+ESI) M+H: 461.3.

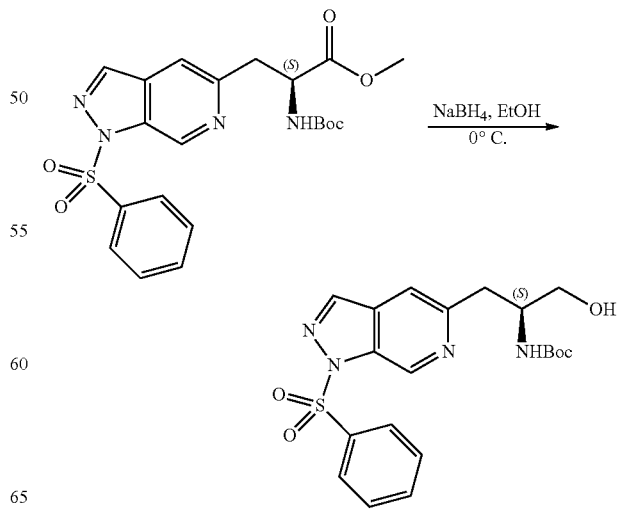

Step 3: Synthesis of tert-butyl (S)-(1-hydroxy-3-(1-(phenylsulfonyl)-1H-pyrazolo[3,4-c]pyridin-5-yl)propan-2-yl)carbamate To a stirred solution of methyl (S)-2-((tert-butoxycarbonyl)amino)-3-(1-(phenylsulfonyl)-1H-pyrazolo[3,4-c]pyridin-5-yl)propanoate (4.5 g, 9.77 mmole) in EtOH (40 mL) at 0° C. was added NaBH₄ (1.1 g, 29.31 mmole) in single portion. After the reaction was completed, the reaction was continued to stir for 4 h at 0° C., then slowly quenched with saturated aqueous NH₄Cl, diluted with H₂O, extracted with DCM (3×). The extracts were dried over Na₂SO₄, concentrated and purified by ISCO (50% EtOAc/Hexanes) to give the title compound (1.34 g, 31.7%). LC-MS (+ESI) M+H: 433.2.

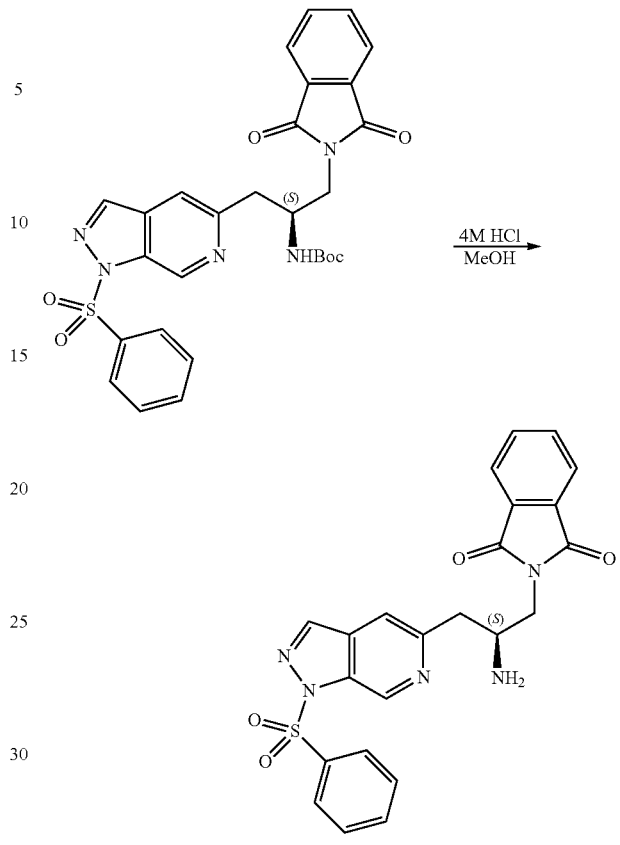

Step 4: Synthesis of tert-butyl (S)-(1-(1,3-dioxoisoindolin-2-yl)-3-(1-(phenylsulfonyl)-1H-pyrazolo[3,4-c]pyridin-5-yl)propan-2-yl)carbamate To a stirred mixture of tert-butyl (S)-(1-hydroxy-3-(1-(phenylsulfonyl)-1H-pyrazolo[3,4-c]pyridin-5-yl)propan-2-yl)carbamate (1.3 g, 3 mmole), triphenylphosphine (0.95 g, 3.6 mmole), and phthamide (0.53 g, 3.6 mmole) in THF (30 mL) at 0° C. was added DIAD (0.73 g, 3.6 mmole) dropwise. After the addition was completed, the mixture was stirred at RT for 16 h. The mixture was concentrated, and purified by ISCO (50% EtOAc/Hexanes) to give the title compound (1.15 g, 68.4%). LC-MS (+ESI) M+H: 562.2.

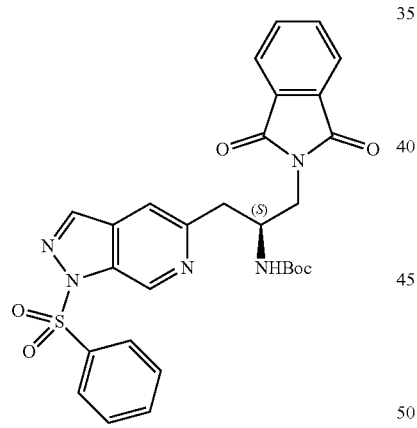

Step 5: Synthesis of (S)-2-(2-amino-3-(1-(phenylsulfonyl)-1H-pyrazolo[3,4-c]pyridin-5-yl)propyl)isoindoline-1,3-dione Hydrochloride To a stirred solution of tert-butyl (S)-(1-(1,3-dioxoisoindolin-2-yl)-3-(1-(phenylsulfonyl)-1H-pyrazolo[3,4-c]pyridin-5-yl)propan-2-yl)carbamate (1.15 g, 2.04 mmole) in MeOH (20 mL) was added 4M HCl in p-dioxane (4 mL). After the addition, the reaction mixture was stirred for 4 h at 50° C. The reaction mixture was cooled, concentrated to dryness to give the title compound (1.35 g, 100%). LC-MS (+ESI) M+H: 462.2.

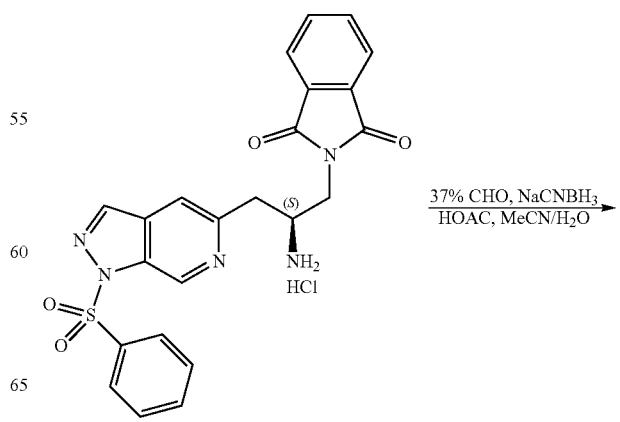

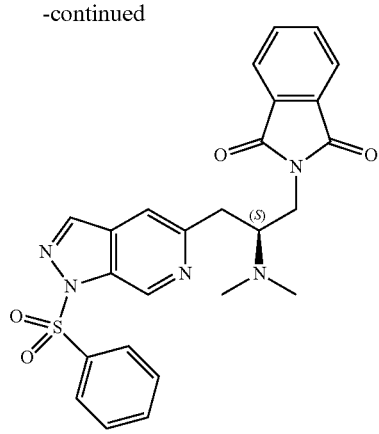

Step 6: Synthesis of (S)-2-(2-(dimethylamino)-3-(1-(phenylsulfonyl)-1H-pyrazolo[3,4-c]pyridin-5-yl)propyl)isoindoline-1,3-dione To a stirred solution of (S)-2-(2-amino-3-(1-(phenylsulfonyl)-1H-pyrazolo[3,4-c]pyridin-5-yl)propyl)isoindoline-1,3-dione hydrochloride (1.35 g, 2.52 mmole) in MeCN/H$_2$O (10/1, 22 mL) was added 37% CHO (1.02 mL, 12.6 mmole), NaCNBH$_3$ (0.5 g, 7.6 mmole). After stirring for 10 minutes, HOAc (0.73 mL, 12.6 mmole) was added. The reaction mixture was stirred for 30 minutes, DCM was added and the layers were separated. The organic layer was dried over Na$_2$SO$_4$, concentrated to give the title compound (0.95 g, 77%). LC-MS (+ESI) M+H: 490.2.

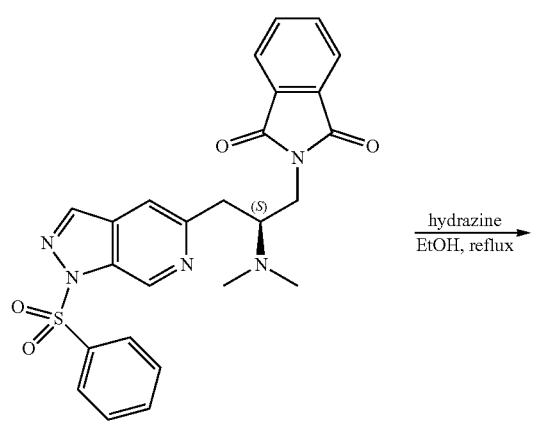

Step 7: Synthesis of (S)—N2,N2-dimethyl-3-(1-(phenylsulfonyl)-1H-pyrazolo[3,4-c]pyridin-5-yl)propane-1,2-diamine A mixture of (S)-2-(2-(dimethylamino)-3-(1-(phenylsulfonyl)-1H-pyrazolo[3,4-c]pyridin-5-yl)propyl)isoindoline-1,3-dione (0.95 g, 1.94 mmole) and hydrazine (0.8 mL, 12.6 mmole) in EtOH (30 mL) was heated to 90° C. in 2 h. The reaction mixture was cooled, the solid was filtered off, washed with EtOH. The filtrate was concentrated, and purified by ISCO (0-15% MeOH/DCM in 1% NH$_4$OH) to give the title compound (0.34 g, 50%). LC-MS (+ESI) M+H: 360.2.

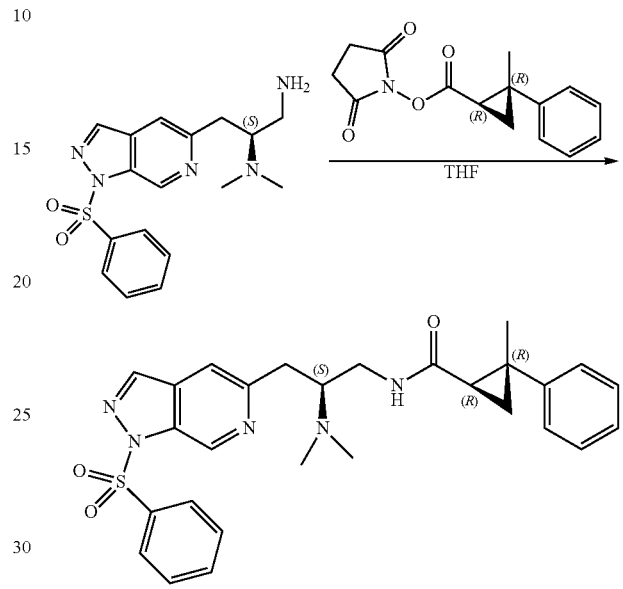

Step 8: Synthesis of (1R,2R)—N—((S)-2-(dimethylamino)-3-(1-(phenylsulfonyl)-1H-pyrazolo[3,4-c]pyridin-5-yl)propyl)-2-methyl-2-phenylcyclopropane-1-carboxamide A mixture of (S)—N2,N2-dimethyl-3-(1-(phenylsulfonyl)-1H-pyrazolo[3,4-c]pyridin-5-yl)propane-1,2-diamine (0.07 g, 0.19 mmole) and 2,5-dioxopyrrolidin-1-yl (1R,2R)-2-methyl-2-phenylcyclopropane-1-carboxylate (0.05 g, 0.19 mmole) in THF (2 mL) was stirred at RT for 16 h. The mixture was concentrated to dryness and purified by ISCO (0-15% MeOH/DCM) to give the title compound (0.1 g, 100%). LC-MS (+ESI) M+H: 518.2.

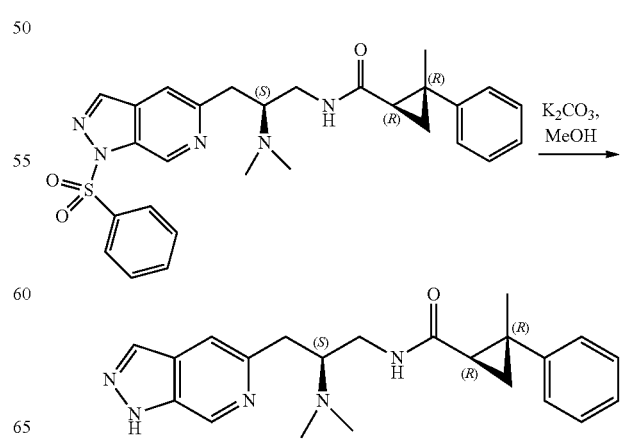

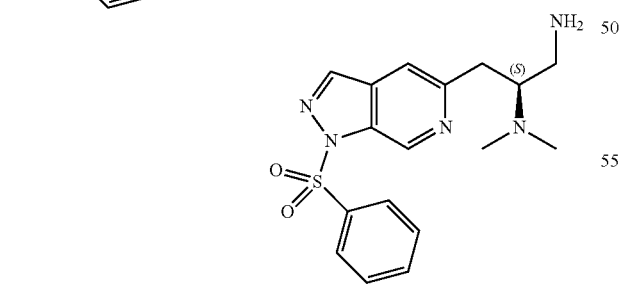

Step 9: Synthesis of (1R,2R)—N—((S)-2-(dimethylamino)-3-(1H-pyrazolo[3,4-c]pyridin-5-yl)propyl)-2-methyl-2-phenylcyclopropane-1-carboxamide (Compound 63)

A mixture of (1R,2R)—N—((S)-2-(dimethylamino)-3-(1-(phenylsulfonyl)-1H-pyrazolo[3,4-c]pyridin-5-yl)propyl)-2-methyl-2-phenylcyclopropane-1-carboxamide (0.1 g, 0.19 mmole) and $K_2CO_3$ in MeOH (3 mL) was heated to 55° C. in 1 h. The reaction mixture was cooled, concentrated. $H_2O$ was added, extracted with DCM (3×). The combined extracts were dried over $Na_2SO_4$, concentrated, and purified by preparative reverse phase HPLC. The pure fractions were concentrated to dryness to give the title compound as mono TFA salt (0.021 g, 23%). LC-MS (+ESI) M+H: 378.2. 1H NMR (400 MHz, DMSO-d6) δ ppm 13.58-13.81 (m, 1H) 9.45-9.68 (m, 1H) 9.06 (s, 1H) 8.44 (t, J=5.75 Hz, 1H) 8.25 (s, 1H) 7.79 (d, J=0.73 Hz, 1H) 7.24-7.34 (m, 4H) 7.15-7.23 (m, 1H) 3.84-3.90 (m, 2H) 3.39 (br d, J=5.62 Hz, 1H) 3.27-3.36 (m, 2H) 3.16 (dd, J=14.67, 7.83 Hz, 1H) 2.90 (s, 6H) 1.83 (t, J=7.09 Hz, 1H) 1.36 (s, 3H) 1.27 (d, J=7.09 Hz, 2H).

Example B64

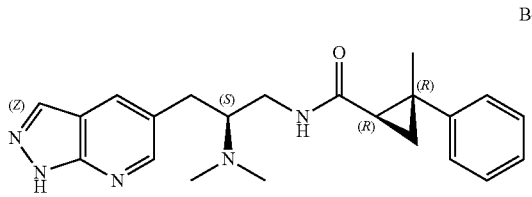

B-64

Synthesis of (1R,2R)—N—((S)-2-(dimethylamino)-3-(1H-pyrazolo[3,4-b]pyridin-5-yl)propyl)-2-methyl-2-phenylcyclopropane-1-carboxamide (Compound B-64) (RM0001450)

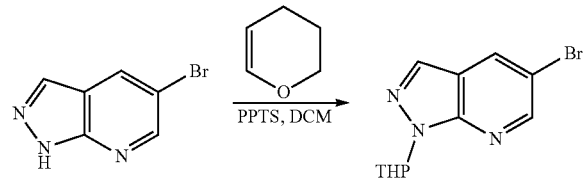

Step 1: Synthesis of 5-bromo-1-(tetrahydro-2H-pyran-2-yl)-1H-pyrazolo[3,4-b]pyridine A mixture of 5-bromo-1H-pyrazolo[3,4-b]pyridine (5 g, 25.25 mmole), DHP (4.8 g, 76 mmole), and PPTS (0.5 g, 2.5 mmole) in DCM/MeCN (1:1, 80 mL) was stirred at RT for 24 h. $H_2O$ was added, extracted with DCM (3×). The combined extracts were dried over $Na_2SO_4$, concentrated and purified by ISCO (20% EtOAc/Hexanes) to give the title compound (7.9 g, 100%). LC-MS (+ESI) M+H: 282.1.

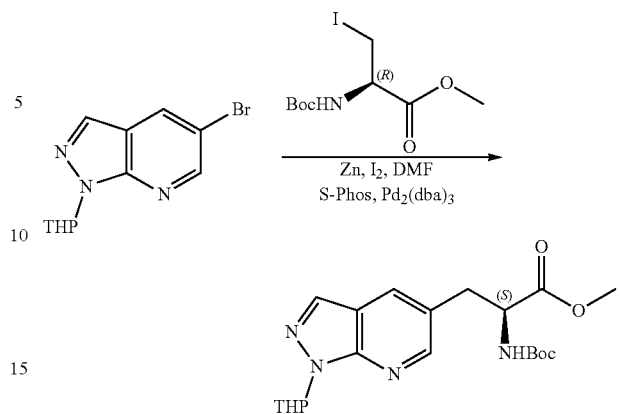

Step 2: Synthesis of methyl (2S)-2-((tert-butoxycarbonyl)amino)-3-(1-(tetrahydro-2H-pyran-2-yl)-1H-pyrazolo[3,4-b]pyridin-5-yl)propanoate To a stirred suspension of Zinc powder (2.1 g, 31.9 mmole) in DMF (20 mL) was added iodine (0.27 g, 1.06 mmole). After stirring for 10 minutes, methyl (R)-2-((tert-butoxycarbonyl)amino)-3-iodopropanoate (4.2 g, 12.76 mmole) was added, followed by iodine (0.27 g, 1.06 mmole). The resulting mixture was stirred for 2 h. The mixture was then added to the mixture of 5-bromo-1-(phenylsulfonyl)-1H-pyrazolo[3,4-c]pyridine (3.0 g, 10.63 mmole), S-Phos (0.46 g, 1.06 mmole), and $Pd_2(dba)_3$ (0.48 g, 0.53 mmole) in DMF (10 mL). After the addition was completed, the reaction mixture was heated to 50° C. in 16 h. The reaction mixture was cooled, diluted with EtOAc, filtered through the pad of Celite. The filtrate was concentrated to dryness, and purified by ISCO (0-50% EtOAc/Hexanes) to give the title compound (1.68 g, 39%). LC-MS (+ESI) M+H: 405.2.

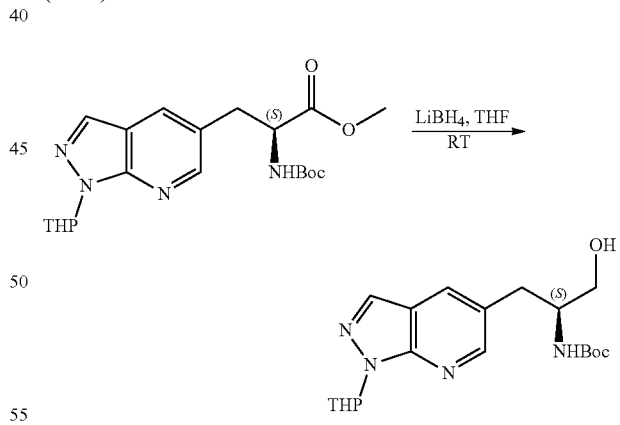

Step 3: Synthesis of tert-butyl ((2S)-1-hydroxy-3-(1-(tetrahydro-2H-pyran-2-yl)-1H-pyrazolo[3,4-b]pyridin-5-yl)propan-2-yl)carbamate To a stirred solution of methyl (2S)-2-((tert-butoxycarbonyl)amino)-3-(1-(tetrahydro-2H-pyran-2-yl)-1H-pyrazolo[3,4-b]pyridin-5-yl)propanoate (1.68 g, 4.15 mmole) in THF (20 mL) was added 4M $LiBH_4$ in THF (1.5 mL, 6.23 mmole) dropwise at RT. After the addition was completed, the reaction mixture was stirred for 2 h. The reaction mixture was cooled in an ice bath, and slowly quenched with saturated aqueous NH₄Cl, extracted with EtOAc (3×). The combined extracts were dried over Na₂SO₄, concentrated and purified by ISCO (60% EtOAc/Hexanes) to give the title compound (0.52 g, 33%). LC-MS (+ESI) M+H: 377.2.

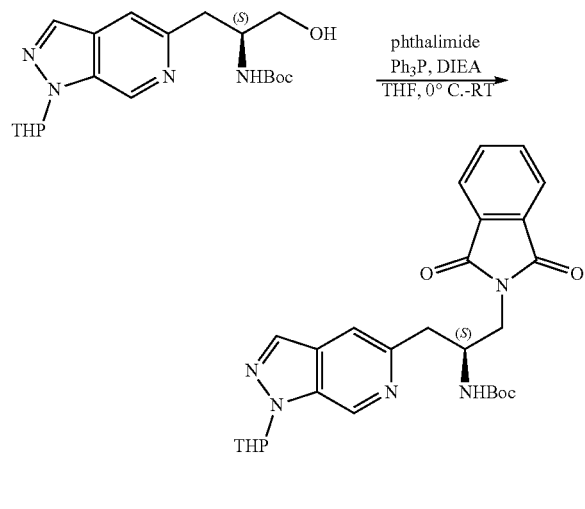

Step 4: Synthesis of tert-butyl ((2S)-1-(1,3-dioxoisoindolin-2-yl)-3-(1-(tetrahydro-2H-pyran-2-yl)-1H-pyrazolo[3,4-b]pyridin-5-yl)propan-2-yl)carbamate To a stirred mixture of tert-butyl ((2S)-1-hydroxy-3-(1-(tetrahydro-2H-pyran-2-yl)-1H-pyrazolo[3,4-b]pyridin-5-yl)propan-2-yl)carbamate (0.51 g, 1.35 mmole), triphenylphosphine (0.5 g, 1.9 mmole), and phthamide (0.3 g, 2.03 mmole) in THF (10 mL) at 0° C. was added DIAD (0.38 g, 1.9 mmole) dropwise. After the addition was completed, the mixture was stirred at RT for 16 h. The mixture was concentrated, and purified by ISCO (20-70% EtOAc/Hexanes) to give the title compound (0.68 g, 100%). LC-MS (+ESI) M+H: 506.2.

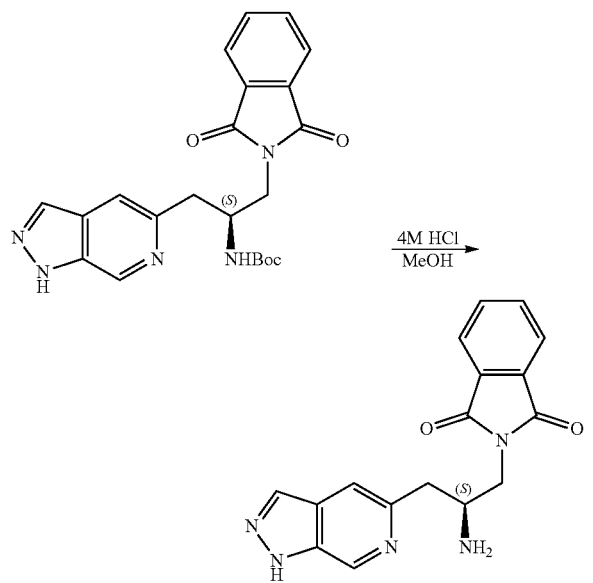

Step 5: Synthesis of (S)-2-(2-amino-3-(1H-pyrazolo[3,4-b]pyridin-5-yl)propyl)isoindoline-1,3-dione di-hydrochloride To a stirred mixture of tert-butyl ((2S)-1-(1,3-dioxoisoindolin-2-yl)-3-(1-(tetrahydro-2H-pyran-2-yl)-1H-pyrazolo[3,4-b]pyridin-5-yl)propan-2-yl)carbamate (0.68 g, 1.36 mmole) in MeOH (10 mL) was added 4M HCl in p-dioxane (3.5 mL, 13.6 mmole). After the addition was completed, the reaction mixture was stirred at RT for 16 h, concentrated to dryness. EtOAc was added, the precipitated solid was collected, washed EtOAc, dried to give the title compound (0.43 g, 80%). LC-MS (+ESI) M+H: 322.1.

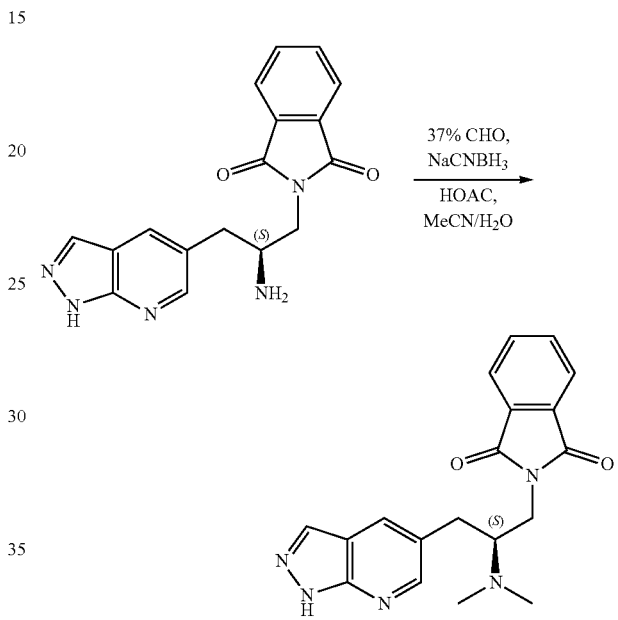

Step 6: Synthesis of (S)-2-(2-(dimethylamino)-3-(1H-pyrazolo[3,4-b]pyridin-5-yl)propyl)isoindoline-1,3-dione The title compound (0.097 g, 100%) was prepared in the same method as Step 6 of Example 63. LC-MS (+ESI) M+H: 350.1

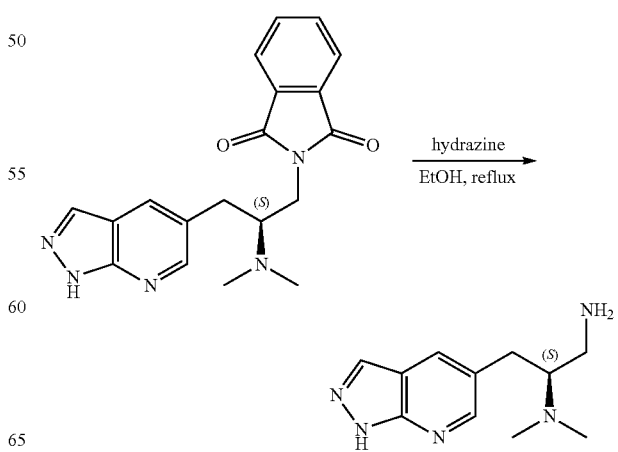

Step 7: Synthesis of (S)—N2,N2-dimethyl-3-(1H-pyrazolo[3,4-b]pyridin-5-yl)propane-1,2-diamine The title compound (0.029 g, 47%) was prepared in the same method as Step 7 of Example B63. LC-MS (+ESI) M+H: 220.2

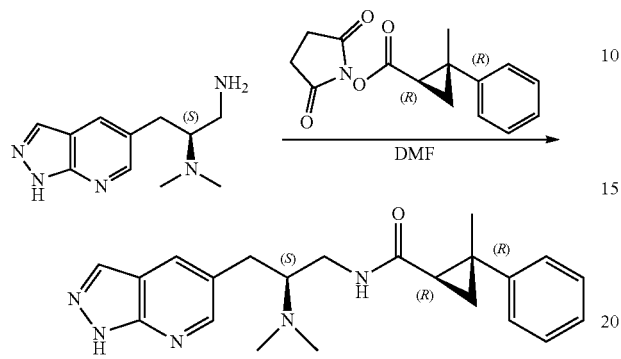

Step 8: Synthesis of (1R,2R)—N—((S)-2-(dimethylamino)-3-(1H-pyrazolo[3,4-b]pyridin-5-yl)propyl)-2-methyl-2-phenylcyclopropane-1-carboxamide (Compound B-64)

A mixture of (S)—N2,N2-dimethyl-3-(1H-pyrazolo[3,4-b]pyridin-5-yl)propane-1,2-diamine (0.029 g, 0.2 mmole) and 2,5-dioxopyrrolidin-1-yl (1R,2R)-2-methyl-2-phenyl-cyclopropane-1-carboxylate (0.038 g, 0.2 mmole) in DMF (1 mL) was stirred at RT for 1 h. The reaction mixture was concentrated to remove the excess DMF, purified by preparative reverse phase HPLC. The pure fractions were concentrated to minimal H$_2$O, neutralized by saturated aqueous NaHCO$_3$, extracted with DCM (3×). The combined extracts were dried over Na$_2$SO$_4$, concentrated, and co-evaporated with MTBE to give the title compound (0.015 g, 29%). LC-MS (+ESI) M+H: 378.2. $^1$H NMR (400 MHz, CDCl$_3$) δ ppm: 8.42 (d, J=1.96 Hz, 1H), 8.11 (d, J=1.96 Hz, 1H), 8.04 (s, 1H), 7.21-7.27 (m, 4H), 7.10-7.20 (m, 1H), 3.31-3.41 (m, 2H), 2.99-3.12 (m, 2H), 2.66-2.80 (m, 1H), 2.41 (s, 6H), 1.80 (dd, J=8.31, 5.87 Hz, 1H), 1.38 (s, 3H), 1.29-1.32 (m, 1H), 1.21-1.26 (m, 1H).

Example B65

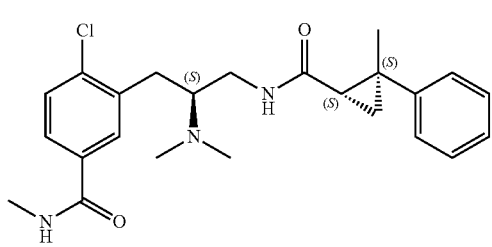

Synthesis of 4-chloro-3-((S)-2-(dimethylamino)-3-((1S,2S)-2-methyl-2-phenylcyclopropane-1-carboxamido)propyl)-N-methylbenzamide (Compound B-65)

4-chloro-3-((S)-2-(dimethylamino)-3-((1S,2S)-2-methyl-2-phenylcyclopropane-1-carboxamido)propyl)-N-methyl-benzamide is synthesized according to the general procedure using (S)-3-(3-amino-2-(dimethylamino)propyl)-4-chloro-N-methylbenzamide and 2,5-dioxopyrrolidin-1-yl (1S,2S)-2-methyl-2-phenylcyclopropane-1-carboxylate as the starting materials. 428.2 [M]$^+$.

Example B66

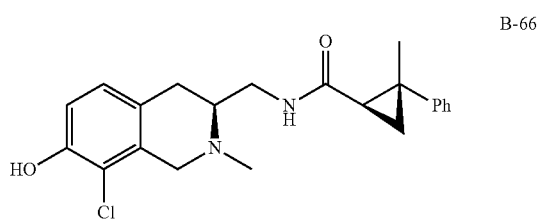 [SMILES: CN1Cc2c(ccc(O)c2Cl)C[C@H]1CNC(=O)[C@@H]1C[C@@]1(C)c1ccccc1]

Synthesis of (1R,2R)—N—(((S)-8-chloro-7-hydroxy-2-methyl-1,2,3,4-tetrahydroisoquinolin-3-yl)methyl)-2-methyl-2-phenylcyclopropane-1-carboxamide (Compound B-66)

To a stirred solution of (S)-3-(aminomethyl)-8-chloro-2-methyl-1,2,3,4-tetrahydroisoquinolin-7-ol (16.5 mg, 0.07 mmol, 1 equiv) in dry DMF (2 mL) was added 2,5-dioxopyrrolidin-1-yl (1R,2R)-2-methyl-2-phenylcyclopropane-1-carboxylate (24 mg, 0.09 mmol, 1.2 equiv). After 2 h, the solution was concentrated. The residue was purified by flash column chromatography over silica gel (0-10% MeOH in CH$_2$Cl$_2$ with 1% NH$_4$OH) to afford a white solid (15.2 mg, 56% yield). $^1$H NMR (400 MHz, CDCl$_3$) δ 8.01 (s, 1H), 7.17-7.36 (m, 6H), 6.82-6.91 (m, 2H), 6.24-6.38 (m, 1H), 3.95 (d, J=16.87 Hz, 1H), 3.60-3.72 (m, 1H), 3.36-3.57 (m, 3H), 2.83-3.05 (m, 11H), 2.65-2.78 (m, 2H), 2.36-2.49 (m, 3H), 1.75-1.78 (m, 1H), 1.34-1.61 (m, 6H). LCMS: 385.2 [M]$^+$.

Example B67

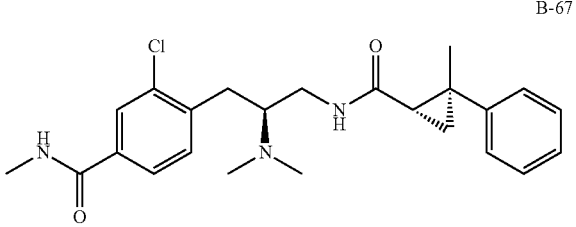 [SMILES: CNC(=O)c1ccc(C[C@@H](CNC(=O)[C@H]2C[C@]2(C)c2ccccc2)N(C)C)c(Cl)c1]

Synthesis of 3-chloro-4-((S)-2-(dimethylamino)-3-((1S,2S)-2-methyl-2-phenylcyclopropane-1-carboxamido)propyl)-N-methylbenzamide (Compound B-67)

To a stirred solution of (S)-4-(3-amino-2-(dimethylamino)propyl)-3-chloro-N-methylbenzamide (21.7 mg, 0.08 mmol, 1 equiv) in dry DMF (1 mL) was added 2,5-dioxopyrrolidin-1-yl (1S,2S)-2-methyl-2-phenylcyclopropane-1-carboxylate (24 mg, 0.09 mmol, 1.2 equiv). After 3 h, the solution was concentrated. The residue was purified by flash column chromatography over silica gel (0-10% MeOH in CH$_2$Cl$_2$ with 1% NH$_4$OH) to afford a white solid (15.2 mg, 56% yield). $^1$H NMR (400 MHz, CDCl$_3$) δ 7.77 (s, 1H), 7.53 (dd, J=7.95, 1.83 Hz, 1H), 7.18-7.35 (m, 6H), 6.89 (br d, J=4.65 Hz, 1H), 6.51 (br d, J=6.85 Hz, 1H), 3.38-3.39 (m, 1H), 3.34-3.54 (m, 1H), 3.12-3.27 (m, 1H), 2.88-3.07 (m, 6H), 2.37-2.56 (m, 6H), 1.65-1.77 (m, 1H), 1.51-1.56 (m, 2H), 1.34-1.50 (m, 3H). LCMS: 428.2 [M]$^+$.

Example B68

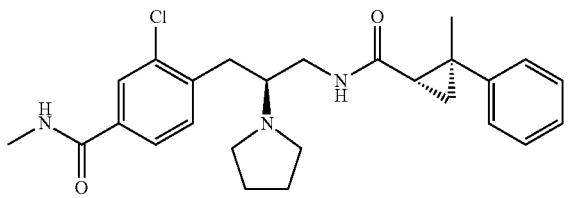

B-68

Synthesis of 3-chloro-N-methyl-4-((S)-3-((1S,2S)-2-methyl-2-phenylcyclopropane-1-carboxamido)-2-(pyrrolidin-1-yl)propyl)benzamide (Compound B-68)

To a stirred solution of (S)-4-(3-amino-2-(pyrrolidin-1-yl)propyl)-3-chloro-N-methylbenzamide (15 mg, 0.05 mmol, 1 equiv) in dry DMF (1 mL) was added 2,5-dioxopyrrolidin-1-yl (1S,2S)-2-methyl-2-phenylcyclopropane-1-carboxylate (16 mg, 0.06 mmol, 1.2 equiv). After 2 h, the solution was concentrated. The residue was purified by flash column chromatography over silica gel (0-10% MeOH in CH$_2$Cl$_2$ with 1% NH$_4$OH) to afford a white solid (15.4 mg, 67% yield). $^1$H NMR (400 MHz, CDCl$_3$) δ 7.77-7.80 (m, 1H), 7.54 (dd, J=7.83, 1.71 Hz, 1H), 7.21-7.37 (m, 8H), 6.54-6.66 (m, 1H), 6.47 (br s, 1H), 3.14-3.38 (m, 3H), 2.90-3.00 (m, 6H), 2.81 (br s, 2H), 2.62-2.78 (m, 4H), 1.84 (br s, 5H), 1.66-1.81 (m, 2H), 1.33-1.55 (m, 4H), 1.23 (t, J=7.09 Hz, 2H). LCMS: 454.2 [M]$^+$.

Example B69

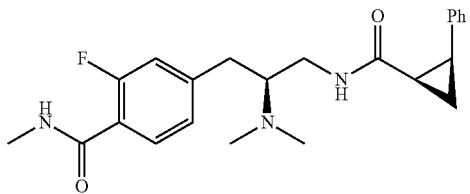

B-69

Synthesis of 4-((S)-2-(dimethylamino)-3-((1R,2S)-2-phenylcyclopropane-1-carboxamido)propyl)-2-fluoro-N-methylbenzamide (Compound B-69)

To a stirred solution of (S)-4-(3-amino-2-(dimethylamino)propyl)-2-fluoro-N-methylbenzamide (Int-4F) (27.5 mg, 0.11 mmol, 1 equiv) in dry DMF (2 mL) was added EDCI (33 mg, 0.17 mmol, 1.5 equiv), HOBt (23 mg, 0.17 mmol, 1.5 equiv), (1R,2S)-2-phenylcyclopropane-1-carboxylic acid (20 mg, 0.12 mmol, 1.1 equiv), and DIPEA (115 μL, 0.66 mmol, 6 equiv). After 4 h, the solution was diluted with water and extracted with EtOAc. The combined organic layers were washed with aq. NaHCO$_3$ and brine, dried over anhydrous sodium sulfate, and concentrated. The residue was purified by flash column chromatography over silica gel (0-15% MeOH in CH$_2$Cl$_2$) to afford a white solid (9.9 mg, 23% yield). $^1$H NMR (400 MHz, CDCl$_3$) δ 7.84-7.95 (m, 1H), 7.21 (s, 1H), 7.06-7.17 (m, 4H), 6.86 (d, J=7.83 Hz, 1H), 6.72 (br d, J=12.96 Hz, 1H), 3.01-3.17 (m, 1H), 2.88-3.00 (m, 3H), 2.64-2.85 (m, 2H), 2.40-2.48 (m, 1H), 2.32-2.39 (m, 1H), 2.31-2.39 (m, 1H), 2.14-2.25 (m, 5H), 1.84-1.93 (m, 3H), 1.51-1.63 (m, 1H). LCMS: 398.2 [M]$^+$.

Example B70

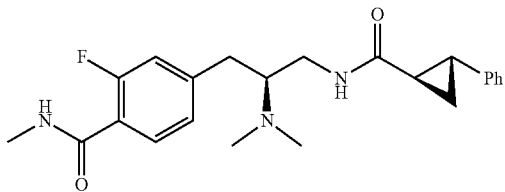

B-70

Synthesis of 4-((S)-2-(dimethylamino)-3-((1R,2R)-2-phenylcyclopropane-1-carboxamido)propyl)-2-fluoro-N-methylbenzamide (Compound B-70)

To a stirred solution of (S)-4-(3-amino-2-(dimethylamino)propyl)-2-fluoro-N-methylbenzamide (Int-4F) (57 mg, 0.23 mmol, 1 equiv) in dry DMF (2 mL) was added EDCI (67 mg, 0.35 mmol, 1.5 equiv), HOBt (47 mg, 0.35 mmol, 1.5 equiv), (1R,2R)-2-phenylcyclopropane-1-carboxylic acid (40 mg, 0.25 mmol, 1.1 equiv), and DIPEA (240 μL, 1.38 mmol, 6 equiv). After 4 h, the solution was diluted with water and extracted with EtOAc. The combined organic layers were washed with aq. NaHCO$_3$ and brine, dried over anhydrous sodium sulfate, and concentrated. The residue was purified by flash column chromatography over silica gel (0-15% MeOH in CH$_2$Cl$_2$) to afford a white solid (11.7 mg, 13% yield). $^1$H NMR (400 MHz, CDCl$_3$) δ 7.94 (td, J=8.13, 2.08 Hz, 1H), 7.06-7.21 (m, 4H), 6.93-7.02 (m, 3H), 6.84 (d, J=12.72 Hz, 1H), 6.62 (br d, J=6.36 Hz, 1H), 6.41 (br s, 1H), 3.26-3.43 (m, 1H), 2.73-2.97 (m, 6H), 2.24-2.39 (m, 8H), 1.86-1.90 (m, 1H), 1.45-1.60 (m, 2H), 1.02-1.28 (m, 1H). LCMS: 398.3 [M]$^+$.

Example B71

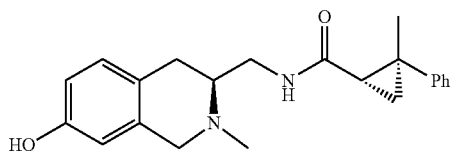

B-71

Synthesis of (1S,2S)—N—(((S)-7-hydroxy-2-methyl-1,2,3,4-tetrahydroisoquinolin-3-yl)methyl)-2-methyl-2-phenylcyclopropane-1-carboxamide (Compound B-71)

To a stirred solution of (S)-3-(aminomethyl)-2-methyl-1,2,3,4-tetrahydroisoquinolin-7-ol (22 mg, 0.12 mmol, 1 equiv) in dry DMF (1 mL) was added 2,5-dioxopyrrolidin-1-yl (1S,2S)-2-methyl-2-phenylcyclopropane-1-carboxylate (35 mg, 1.3 mmol, 1.09 equiv). After 2 h, the solution diluted in EtOAc, washed with water, separated, and dried over MgSO$_4$. The residue was purified by flash column chromatography over silica gel (0-100% EtOAc in hexanes then 0-10% MeOH in CH$_2$Cl$_2$ with 1% NH$_4$OH) to afford a white solid (28.4 mg, 68% yield). $^1$H NMR (400 MHz, CDCl$_3$) δ 7.07-7.23 (m, 6H), 6.81 (d, J=8.31 Hz, 2H), 6.57 (dd, J=8.31, 2.45 Hz, 1H), 6.32 (d, J=2.20 Hz, 1H), 3.70 (q, J=15.73 Hz, 2H), 3.56 (dt, J=14.31, 5.07 Hz, 1H), 2.97-3.06 (m, 1H), 2.57-2.74 (m, 2H), 2.40 (s, 3H), 1.68-1.83 (m, 2H), 1.31-1.45 (m, 4H), 1.26 (dd, J=8.31, 4.65 Hz, 1H). LCMS: 351.2 [M]$^+$.

Example B72

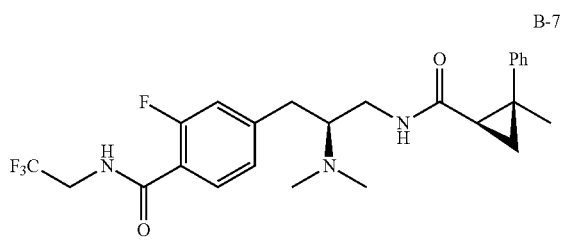

B-72

Synthesis of 4-((S)-2-(dimethylamino)-3-((1R,2S)-2-methyl-2-phenylcyclopropane-1-carboxamido)propyl)-2-fluoro-N-(2,2,2-trifluoroethyl)benzamide (Compound B-72)

To a stirred solution of (S)-4-(3-amino-2-(dimethylamino)propyl)-2-fluoro-N-(2,2,2-trifluoroethyl)benzamide (117.2 mg, 0.26 mmol, 1 equiv) in 9:1 CH$_3$CN:H$_2$O (2 mL) at 0° C. was added NaCNBH$_4$ (82 mg, 1.3 mmol, 5 equiv) and 37% formaldehyde (75 µL, 0.78 mmol, 3 equiv). After 10 min, HOAc (75 ul, 1.3 mmol, 5 equiv) was added and the solution was allowed to warm to rt for 4 h. Ethyl acetate (10 mL) was added and the solution was washed with aq. NaHCO$_3$ and brine, dried over anhydrous sodium sulfate, and concentrated. The residue was purified by flash column chromatography over silica gel (0-15% MeOH in CH$_2$Cl$_2$) to afford a white solid (32.3 mg, 56% yield). $^1$H NMR (400 MHz, CDCl$_3$) δ 7.67 (t, J=7.83 Hz, 1H), 7.02-7.29 (m, 7H), 4.09 (q, J=9.29 Hz, 2H), 3.01-3.13 (m, 2H), 2.86-3.00 (m, 2H), 2.47-2.59 (m, 1H), 2.34-2.47 (m, 6H), 1.78-1.89 (m, 1H), 1.62-1.75 (m, 1H), 1.37-1.46 (m, 3H), 0.99-1.11 (m, 1H). LCMS: 480.2 [M]$^+$.

C. Synthesis of Compounds Having the Structure of Formula (I-C)

Representative Compounds having the structure of Formula (I-C) can be synthesized by using the general synthetic procedures set forth in Schemes C1.

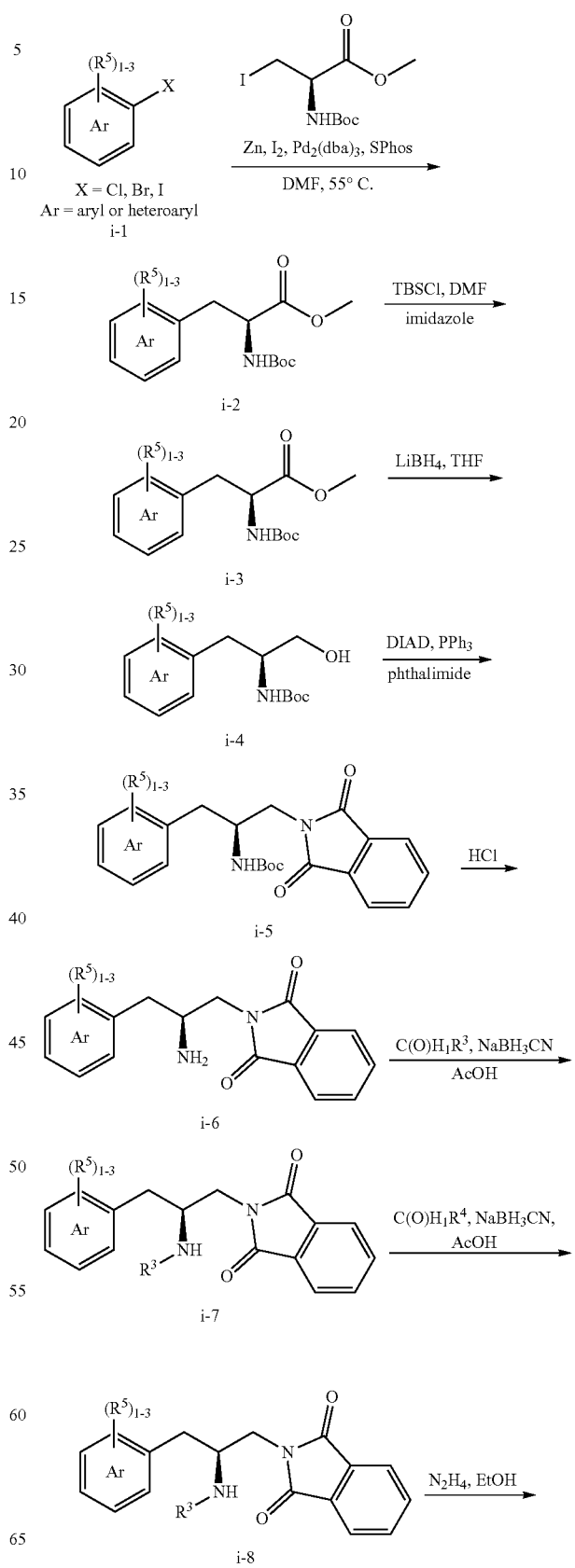

Scheme C1

227

-continued

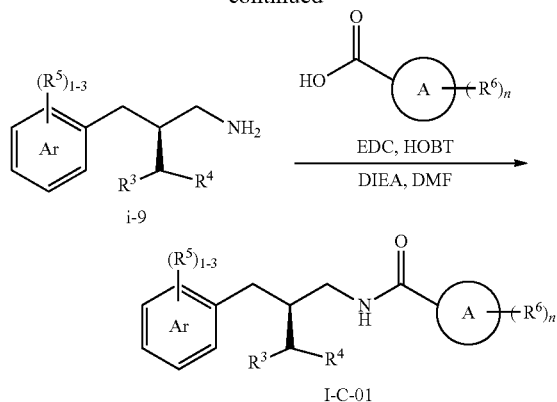

Synthesis of Intermediates

Synthesis of (S)-4-(3-amino-2-(dimethylamino) propyl)-3,5-dimethylphenol (Int-1G)

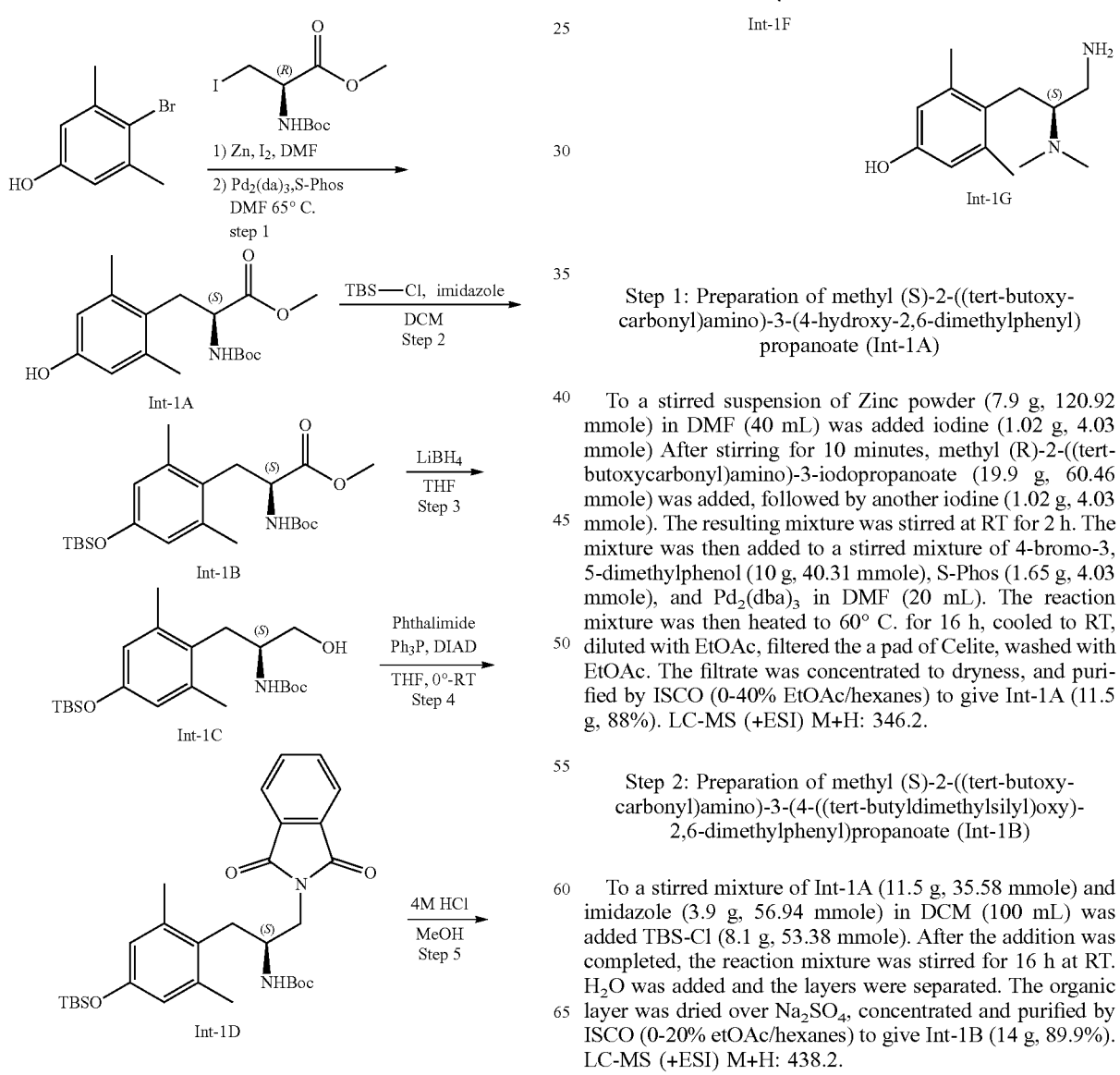

228

-continued

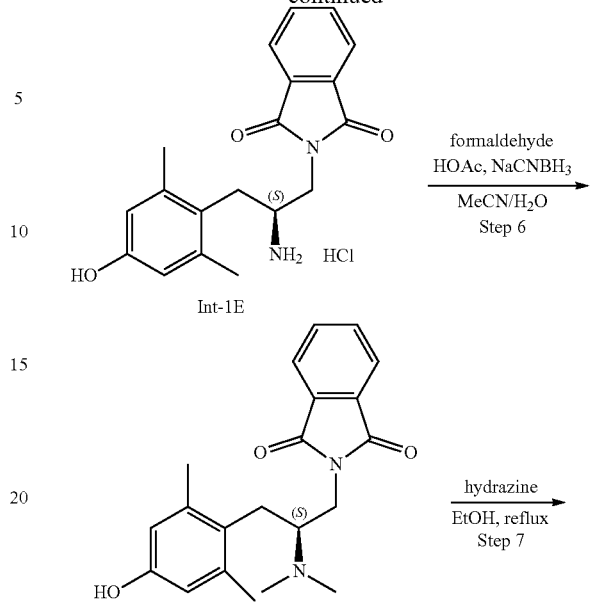

Step 1: Preparation of methyl (S)-2-((tert-butoxycarbonyl)amino)-3-(4-hydroxy-2,6-dimethylphenyl) propanoate (Int-1A)

To a stirred suspension of Zinc powder (7.9 g, 120.92 mmole) in DMF (40 mL) was added iodine (1.02 g, 4.03 mmole) After stirring for 10 minutes, methyl (R)-2-((tert-butoxycarbonyl)amino)-3-iodopropanoate (19.9 g, 60.46 mmole) was added, followed by another iodine (1.02 g, 4.03 mmole). The resulting mixture was stirred at RT for 2 h. The mixture was then added to a stirred mixture of 4-bromo-3,5-dimethylphenol (10 g, 40.31 mmole), S-Phos (1.65 g, 4.03 mmole), and $Pd_2(dba)_3$ in DMF (20 mL). The reaction mixture was then heated to 60° C. for 16 h, cooled to RT, diluted with EtOAc, filtered the a pad of Celite, washed with EtOAc. The filtrate was concentrated to dryness, and purified by ISCO (0-40% EtOAc/hexanes) to give Int-1A (11.5 g, 88%). LC-MS (+ESI) M+H: 346.2.

Step 2: Preparation of methyl (S)-2-((tert-butoxycarbonyl)amino)-3-(4-((tert-butyldimethylsilyl)oxy)-2,6-dimethylphenyl)propanoate (Int-1B)

To a stirred mixture of Int-1A (11.5 g, 35.58 mmole) and imidazole (3.9 g, 56.94 mmole) in DCM (100 mL) was added TBS-Cl (8.1 g, 53.38 mmole). After the addition was completed, the reaction mixture was stirred for 16 h at RT. $H_2O$ was added and the layers were separated. The organic layer was dried over $Na_2SO_4$, concentrated and purified by ISCO (0-20% etOAc/hexanes) to give Int-1B (14 g, 89.9%). LC-MS (+ESI) M+H: 438.2.

Step 3: Preparation of tert-butyl (S)-(1-(4-((tert-butyldimethylsilyl)oxy)-2,6-dimethylphenyl)-3-hydroxypropan-2-yl)carbamate (Int-1C)

To a stirred solution of Int-1B (14 g, 31.99 mmole) in THF (100 mL) was added 4M LiBH$_4$ in THF (12 mL, 47.98 mmole) dropwise. After the addition was completed, the reaction mixture was stirred for 16 h. The mixture was cooled in an ice bath and slowly quenched with saturated aqueous NH$_4$Cl. The mixture was diluted with H$_2$O, extracted with EtOAc (3×). The combined extracts were dried over Na$_2$SO$_4$, concentrated to dryness to give Int-1C (13.2 g, 95.6%). LC-MS (+ESI) M+Na: 432.1.

Step 4: Preparation of tert-butyl (S)-(1-(4-((tert-butyldimethylsilyl)oxy)-2,6-dimethylphenyl)-3-(1,3-dioxoisoindolin-2-yl)propan-2-yl)carbamate (Int-1D)

To a stirred mixture of Int-1C (13.2 g, 30.55 mmole), phthalimide (5.4 g, 36.66 mmole), and PPh$_3$ (9.62 g, 36.66 mmole) in THF at 0° C. was added DIAD (7.41 g, 36.66 mmole) dropwise. After the addition was completed, the reaction mixture was stirred at RT for 16 h. The mixture was concentrated to dryness, and purified by ISCO (0-40% EtOAc/Hexanes) to give Int-1D (14.5 g, 88.1%). LC-MS (+ESI) M+Na: 561.2.

Step 5: Preparation of (S)-2-(2-amino-3-(4-hydroxy-2,6-dimethylphenyl)propyl)isoindoline-1,3-dione Hydrochloride (Int-1E)

To a stirred solution of Int-1D (14.5 g, 26.91 mmole) in methanol (150 mL) at 0° C. was added 4M HCl (34 mL 269.1 mmole). The reaction mixture was stirred at 80° C. for 1 h, cooled to RT, concentrated to dryness, triturated in EtOAc, the solid (9.3 g, 96%) was collected by filtration, washed with EtOAc, dried and used in the next step. LC-MS (+ESI) M+H: 325.1.

Step 6: Preparation of (S)-2-(2-(dimethylamino)-3-(4-hydroxy-2,6-dimethylphenyl)propyl) isoindoline-1,3-dione (Int-1F)

To a stirred solution of Int-1E (9.5 g, 26.33 mmole) in MeCN/H$_2$O (10:1, 220 mL) was added 37% formaldehyde (12.6 mL, 157.96 mmole). The mixture was stirred for 30 minutes, then NaCNBH$_3$ (4.96 g, 78.98 mmole) was added. The reaction mixture was stirred for 30 minutes, slowly quenched with saturated aqueous NH$_4$Cl, extracted with EtOAc (3×). The combined extracts were dried over Na$_2$SO$_4$, concentrated and purified by ISCO (0-10% MeOH/DCM) to give Int-1F (9.08, 100%). LC-MS (+ESI) M+H: 353.2.

Step 7: Preparation of (S)-4-(3-amino-2-(dimethylamino)propyl)-3,5-dimethylphenol (Int-1G)

To a stirred solution of Int-1F (9.08 g, 25.75 mmole) in EtOH (100 mL) was added hydrazine (8.3 mL, 128.76 mmole). The reaction mixture was stirred at 90° C. for 2 h, cooled to RT, filtered off the solid, washed with EtOH. The filtrate was concentrated to dryness, and purified by ISCO (15% MeOH/DCM in 1% NH$_4$OH) to give Int-1G (3.0 g, 52.2%). LC-MS (+ESI) M+H: 223.1.

Synthesis of (S)-4-(3-Amino-2-(dimethylamino)propyl)-3-chlorophenol (Int-2H)

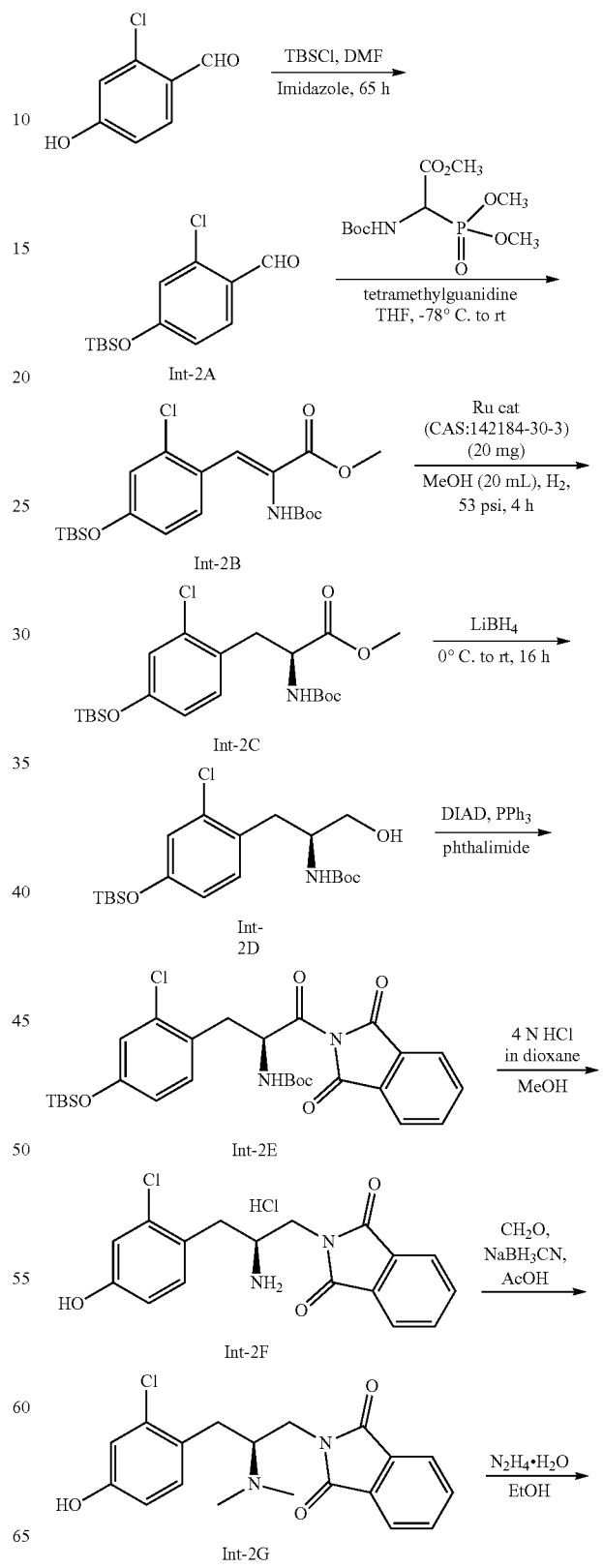

-continued

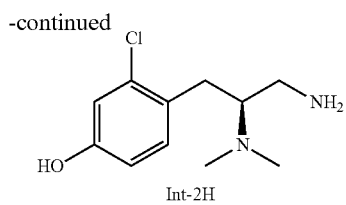
Int-2H

Step 1: Synthesis of 4-{[tert-Butyl(dimethyl)silyl]oxy}-2-chlorobenzaldehyde (Int-2A)

A solution of 2-chloro-4-hydroxybenzaldehyde (5.0 g, 32 mmol), tert-butyl(dimethyl)silyl chloride (5.3 g, 35 mmol), imidazole (2.9 g, 45 mmol) and N,N-dimethylaminopyridine (10 mg) in N,N-dimethylformamide (40 mL) was stirred at room temperature for 65 hours. The solvent was removed in vacuo and the residue was partitioned between ethyl acetate (200 mL) and water (100 mL). The organic phase was separated, washed with brine (3×50 mL), dried over sodium sulfate and concentrated in vacuo. Purification by ISCO, eluting with ethyl acetate-Hexanes (0-15%), afforded the title compound as a colorless oil (3.3 g, 39%), also recovered starting material (~3 g). $^1$H-NMR (400 MHz, CDCl$_3$) δ: 0.27 (s, 6H), 1.0 (s, 9H), 6.80 (dd, J=2.0, 8.4 Hz, 1H), 6.87 (d, J=2.4 Hz, 1H), 7.85 (d, J=8.4 Hz, 1H), 10.34 (1H, s).

Step 2: Synthesis of methyl (Z)-2-((tert-butoxycarbonyl)amino)-3-(4-((tert-butyldimethylsilyl)oxy)-2-chlorophenyl)acrylate (Int-2B)

1.76 ml (14 mmol) of N,N,N,N-tetramethylguanidine was dropwise added to a solution of 3.3 g (12.2 mmol) of Int-2A and 4 g (13.4 mmol) of methyl [(tert-butoxycarbonyl)amino](dimethoxyphosphoryl)acetate in 45 ml of anhydrous tetrahydrofuran at −78° C. over 20 min. After stirring for 1 h at −78° C., the reaction mixture was warmed to RT overnight. The mixture is mixed with 40 ml of water and 200 ml of ethyl acetate. The aqueous layer was further extracted with ethyl acetate twice (2×40 mL). The combined organic phase was washed with water (30 mL), dried over sodium sulfate and concentrated. The crude product is purified by ISCO eluting with ethyl acetate-Hexanes (0-100%) to provide the desired product as a colorless oil (4.26 g, 79%), LC-MS 464.2 (M+Na). $^1$H-NMR (400 MHz, CDCl$_3$): δ=0.23 (s, 6H), 0.99 (s, 9H), 1.37 (s, 9H), 3.87 (s, 3H), 6.67-6.76 (m, 1H), 6.91 (m, 1H), 7.41 (s, 1H), 7.55-7.58 m, 1H). By-product (methyl (Z)-2-((tert-butoxycarbonyl)amino)-3-(2-chloro-4-hydroxyphenyl)acrylate) (more polar) (0.75 g, 18%): LC-MS 350.1 (M+Na). $^1$H-NMR (400 MHz, CDCl$_3$): δ 1.42 (s, 9H), 3.89 (s, 3H), 6.64-6.66 (m, 1H), 6.84 (brs, 1H), 7.51 (s, 1H), 7.55-7.57 (m, 1H).

Step 3: Synthesis of methyl (S)-2-((tert-butoxycarbonyl)amino)-3-(4-((tert-butyldimethylsilyl)oxy)-2-chlorophenyl)propanoate (Int-2C)

A mixture of methyl Int-2B (4.26 g, 9.6 mmol) and (+)-1,2-bis[(2S,5 S)-2,5-diethylphospholano]benzene(cyclooctadiene)-rhodium(I) trifluoromethanesulfonate ([Rh(COD){(S,S)-Et-DuPHOS}] TfO—, 20 mg) in dry methanol (20 mL) was degassed for 4 times and then placed under 53 psi of hydrogen and stirred for 4 h at rt. The solution was concentrated under reduced pressure, and the residue was purified by ISCO eluting with ethyl acetate-Hexanes (0-100%) to provide the desired product as a colorless oil (4.27 g, ~100%). LC-MS 466.2 (M+Na). $^1$H-NMR (400 MHz, CDCl$_3$): δ=0.20 (s, 6H), 0.98 (s, 9H), 1.40 (s, 9H), 2.97-3.09 (m, 1H), 3.14-3.25 (m, 1H), 3.71 (s, 3H), 4.53-4.64 (m, 1H), 5.02-5.10 (m, 1H), 6.66-6.69 (m, 1H), 6.87 (m, 1H), 6.97-7.02 (m, 1H).

Step 4: Synthesis of tert-butyl (S)-(1-(4-((tert-butyldimethylsilyl)oxy)-2-chlorophenyl)-3-hydroxypropan-2-yl)carbamate (Int-2D)

To a solution of Int-2C (4.1 g, 9.2 mmol) in dry THF (50 mL) was added 4 M LiBH$_4$ in THF solution (4.6 mL, 18.4 mmol) at 0° C. over 10 min, the mixture was then stirred at 0° C. for 1 h. Then the reaction mixture was stirred at rt overnight (the reaction progress was monitored by TLC or LC-MS). Then it was cooled to 0° C., water (5 mL) and then saturated NH$_4$Cl sol. (10 mL) were added dropwise (slow addition is necessary). Then water (50 mL) and ethyl acetate (200 mL) were added, the aqueous layer was separated and extracted further with ethyl acetate (100 mL). The combined organic layers were washed with water (40 mL), and then dried over anhydrous Na$_2$SO$_4$. After filtration and concentration, the crude product was put in lyophilization overnight and used in the next step without further purification.

Step 5: Synthesis of tert-butyl (S)-(1-(4-((tert-butyldimethylsilyl)oxy)-2-chlorophenyl)-3-(1,3-dioxoisoindolin-2-yl)propan-2-yl)carbamate (Int-2E)

To a mixture of Int-2D (crude, 3.84 g, 9.23 mmol), triphenylphosphine (2.54 g, 9.69 mmol, 1.05 eq), and phthalimide (1.43 g, 9.69 mmol) in anhydrous THF at 0° C. under nitrogen, was injected DIAD (1.91 mL, 9.69 mmol) dropwise. The reaction mixture was then stirred from 0° C. to room temperature overnight. The crude reaction mixture was mixed with silica gel (40 g), concentrated to dryness on rota vapor, purified on 120 g silica gel column, eluted with 0-30% EtOAc/hexanes to provide the desired product. 4.15 g white solid, 82%. LCMS (+ESI) M+Na$^+$=567.2. $^1$H NMR (400 MHz, CHLOROFORM-d) δ ppm 7.85 (dd, J=5.26, 3.06 Hz, 2H) 7.68-7.75 (m, 2H) 7.15 (br d, J=8.31 Hz, 1H) 6.87 (d, J=2.45 Hz, 1H) 6.71 (dd, J=8.31, 2.20 Hz, 1H) 4.68 (br d, J=9.54 Hz, 1H) 4.31 (br d, J=8.07 Hz, 1H) 3.72-3.80 (m, 2H) 2.88-2.99 (m, 2H) 1.20 (s, 9H) 0.98 (s, 9H) 0.20 (s, 6H).

Step 6: Synthesis of (S)-2-(2-amino-3-(2-chloro-4-hydroxyphenyl)propyl)isoindoline-1,3-dione Hydrochloride (Int-2F)

To a solution of Int-2E (3.00 g, 5.50 mmol) in MeOH (45 mL), was added 4N HCl in dioxane (13.8 mL). The mixture was heated at 70° C. for an hour. The solvents were evaporated on rota vapor. The solid residue was treated with ethyl acetate, filtered, rinsed with ethyl acetate and dried in vacuo to provide the desired product. 1.75 g white solid, 87%. LCMS (+ESI) M+H$^+$=331.1. $^1$H NMR (400 MHz, MeOH-d$_4$) δ ppm 7.84-7.88 (m, 2H) 7.90-7.93 (m, 2H) 7.25 (d, J=8.56 Hz, 1H) 6.90 (d, J=2.45 Hz, 1H) 6.76 (dd, J=8.44, 2.57 Hz, 1H) 4.93-4.97 (m, 1H) 3.85-4.00 (m, 3H) 3.00-3.15 (m, 2H).

Step 7: Synthesis of (S)-2-(3-(4-((tert-butyldimethylsilyl)oxy)-2-chlorophenyl)-2-(dimethylamino)propyl)isoindoline-1,3-dione (Int-2G)

To a suspension of Int-2F (1.75 g, 4.80 mmol) in CH$_3$CN (30 mL) and water (3 mL), was added 37% formaldehyde (0.98 g, 12.0 mmol), sodium cyanoborohydride (0.90 g, 14.4 mmol) and HOAc (0.86 mL). The mixture was stirred at room temperature for an hour. The reaction mixture was then partitioned between ethyl acetate (100 mL) and saturated sodium bicarbonate (100 mL). Separated layers, extracted aqueous was extracted with more ethyl acetate (50 mL). The combined organic layers were dried over MgSO$_4$, filtered and concentrated on rota vapor. The crude material was purified on 80 g silica gel column, eluted with 0-10% MeOH/DCM to provide the desired product, 1.35 g white solid, 78%. LCMS (+ESI) M+H$^+$=359.1. $^1$H NMR (400 MHz, MeOH-d$_4$) δ ppm 7.72-7.82 (m, 4H) 7.09-7.15 (m, 1H) 6.74-6.79 (m, 1H) 6.59-6.66 (m, 1H) 3.82-3.95 (m, 1H) 3.43-3.51 (m, 2H) 3.32 (s, 1H) 3.02 (br dd, J=13.57, 4.04 Hz, 1H) 2.56 (br dd, J=13.82, 8.93, 1H) 2.35 (s, 6H).

Step 8: Synthesis of (S)-4-(3-amino-2-(dimethyl-amino)propyl)-3-chlorophenol (Int-2H)

To a solution of Int-2G (1.35 g, 3.76 mmol) in 95% ethanol (30 mL), was added hydrazine hydrate (80%) (750 mg, 19 mmol). The mixture was heated at 70° C. for 2 hours. The crude reaction mixture was diluted with MeOH and mixed with silica gel (~20 g), concentrated to dryness on rota vapor, and then purified on 24 g silica gel column, eluted with 0-15% MeOH in DCM with 1% NH$_4$OH to provide the desired product, 634 mg white solid, 74%. LCMS (+ESI) M+H$^+$=229.1. $^1$H NMR (400 MHz, DMSO-d$_6$) δ ppm 7.07 (d, J=8.56 Hz, 1H) 6.77 (d, J=2.45 Hz, 1H) 6.67 (dd, J=8.31, 2.45 Hz, 1H) 2.83 (dd, J=13.33, 3.79 Hz, 1H) 2.52-2.61 (m, 2H) 2.29-2.38 (m, 2H) 2.27 (s, 6H).

Synthesis of (S)-4-(3-amino-2-(dimethylamino)propyl)-2-chlorophenol (Int-3H)

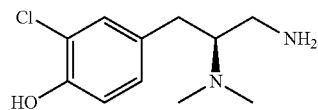

Int-3H

Int-3H was prepared in the same method as that used for making Int-2H by using appropriate intermediates.

Synthesis of (S)-4-(3-amino-2-(dimethylamino)propyl)-2-fluoro-N-methylbenzamide (Int-4F)

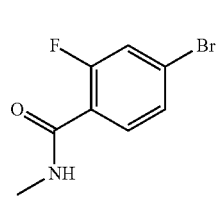

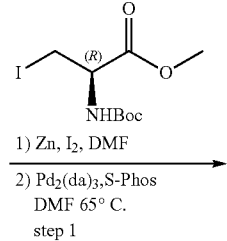

1) Zn, I$_2$, DMF
2) Pd$_2$(da)$_3$, S-Phos DMF 65° C.
step 1

-continued

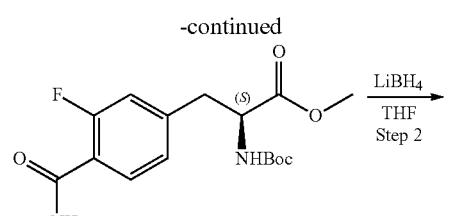

LiBH$_4$
THF
Step 2

Int-4A

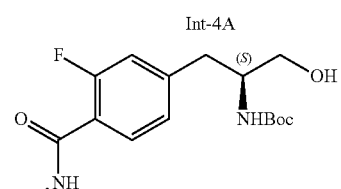

Phthalimide
Ph$_3$P, DIAD
THF, 0°-RT
Step 3

Int-4B

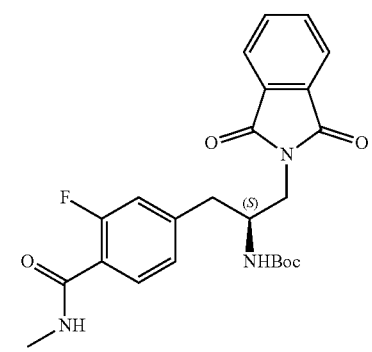

4M HCl
MeOH
Step 4

Int-4C

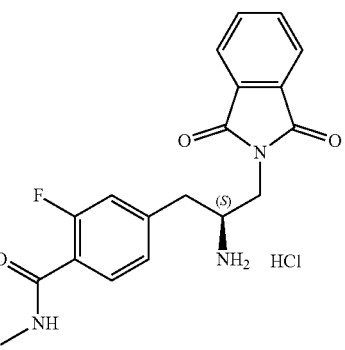

formaldehyde
HOAc, NaCNBH$_3$
MeCN/H$_2$O
Step 5

Int-4D

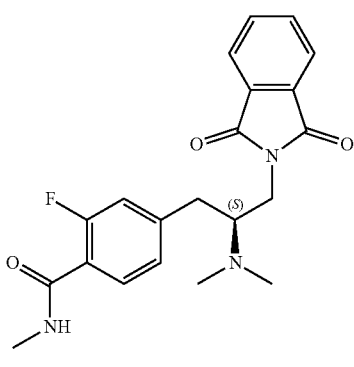

hydrazine
EtOH, reflux
Step 6

Int-4E

-continued

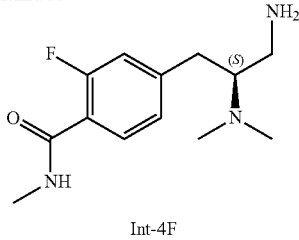

Int-4F

Step 1: Synthesis of methyl (S)-2-((tert-butoxycarbonyl)amino)-3-(3-fluoro-4-(methylcarbamoyl)phenyl)propanoate (Int-4A)

To a suspension of zinc (2.97 g, 45.2 mmol) in DMF (15 mL) under nitrogen atmosphere, was injected a solution of iodine (230 mg, 0.906 mmol) in DMF (2 mL). The mixture was stirred at room temperature for 5 minutes. A solution of methyl (R)-2-((tert-butoxycarbonyl)amino)-3-iodopropanoate (4.46 g, 13.5 mmol) in DMF (10 mL) was injected followed by another portion of iodine (230 mg, 0.906 mmol) in DMF (2 mL), stirred for 30 minutes. A mixture of N-methyl 4-bromo-2-fluorobenzamide (3.00 g, 12.9 mmol), Pd$_2$(dba)$_3$ (591 mg, 0.646 mmol) and Sphos (564 mg, 1.29 mmol) in DMF (15 mL) was injected. The reaction was then heated at 55° C. overnight. The reaction was cooled down to room temperature, quenched with water (50 mL), filtered through a celite pad, rinsed with ethyl acetate (300 mL), extracted with water (3×200 mL) followed by brine (200 mL). The organic layer was separated, dried over MgSO$_4$, filtered and concentrated on rota-vapor. The residue was purified on 220 g silica gel column eluting with gradient of 0-100% EtOAc/Hexanes to provide the desired product as a white solid (3.65 g, 80%). LCMS (+ESI) M+Na$^+$=377.1. $^1$H NMR (400 MHz, DMSO-d6) δ ppm 8.13 (br s, 1H) 7.55 (t, J=7.83 Hz, 1H) 7.33 (br d, J=8.07 Hz, 1H) 7.11-7.22 (m, 2H) 4.17-4.29 (m, 1H) 3.64 (s, 3H) 3.07 (br dd, J=13.69, 4.89 Hz, 1H) 2.90 (dd, J=13.69, 10.52 Hz, 1H) 2.77 (d, J=4.65 Hz, 3H) 1.33 (s, 9H)

Step 2: Synthesis of tert-Butyl (S)-(1-(3-fluoro-4-(methylcarbamoyl)phenyl)-3-hydroxypropan-2-yl)carbamate (Int-4B)

To a solution of Int-4A (3.63 g, 10.2 mmol) in THF (100 mL) at 0° C., lithium boron hydride in THF (4.0 N, 10 mL) was injected dropwise. The reaction mixture was then stirred from 0° C. to room temperature overnight. The crude reaction mixture was cooled with ice-water bath, quenched carefully with saturated NH$_4$Cl$_{(aq)}$, extracted with ethyl acetate. The organic layer was separated, dried over MgSO$_4$, filtered and concentrated on rota-vapor. The residue was purified on 40 g silica gel column eluting with gradient of 0-100% EtOAc/Hexanes to provide the desired product as a white solid (3.10 g, 92%). LCMS (+ESI) M+Na$^+$=349.1. $^1$H NMR (400 MHz, CHLOROFORM-d) δ ppm 8.04 (t, J=8.07 Hz, 1H) 7.12 (dd, J=7.95, 1.59 Hz, 1H) 7.01 (d, J=12.96 Hz, 1H) 6.71 (br s, 1H) 4.75 (br s, 1H) 3.81-3.90 (m, 1H) 3.64-3.71 (m, 1H) 3.57 (dt, J=10.58, 5.10 Hz, 1H) 3.03 (dd, J=4.77, 0.86 Hz, 3H) 2.90 (d, J=7.34 Hz, 2H) 2.14 (br s, 1H) 1.41 (s, 9H)

Step 3: Synthesis of tert-Butyl (S)-(1-(1,3-dioxoisoindolin-2-yl)-3-(3-fluoro-4-(methylcarbamoyl)phenyl)propan-2-yl)carbamate (Int-4C)

To a mixture of Int-4B (3.08 g, 9.44 mmol), triphenylphosphine (2.63 g, 9.91 mmol), and phthalimide (1.46 g, 9.91 mmol) in anhydrous THF at 0° C. under nitrogen, was injected DIAD (1.95 mL, 9.91 mmol) dropwise. The reaction mixture was then stirred from 0° C. to room temperature overnight. The precipitate was filtered, rinsed with THF and dried in vacuo to provide the desired product as a white solid (4.00 g, 93%). LCMS (+ESI) M+Na$^+$=478.2. $^1$H NMR (400 MHz, DMSO-d6) δ ppm 8.11-8.19 (m, 1H) 7.79-7.92 (m, 4H) 7.51-7.57 (m, 1H) 7.15 (d, J=4.65 Hz, 1H) 7.12 (s, 1H) 6.91 (d, J=9.29 Hz, 1H) 4.00 (br d, J=5.14 Hz, 1H) 3.59-3.69 (m, 2H) 3.32-3.35 (m, 1H) 2.89 (dd, J=13.94, 4.65 Hz, 1H) 2.75 (d, J=4.65 Hz, 3H) 1.10 (s, 9H)

Step 4: Synthesis of (S)-4-(2-amino-3-(1,3-dioxoisoindolin-2-yl)propyl)-2-fluoro-N-methylbenzamide Hydrochloride (Int-4D)

To a suspension of Int-4C (3.99 g, 8.76 mmol) in MeOH (20 mL) and dioxane (20 mL), was added 4N HCl in dioxane (22 mL). The mixture was stirred at room temperature overnight. The solvents were evaporated on rota vapor. The solid residue was triturated with ethyl acetate, filtered, rinsed with ethyl acetate and dried in vacuo to provide the desired product as a white solid (2.98 g, 87%). LCMS (+ESI) M+H$^+$=356.1. $^1$H NMR (400 MHz, DMSO-d6) δ ppm 8.27 (br s, 2H) 8.19 (br dd, J=4.16, 2.93 Hz, 1H) 7.83-7.90 (m, 4H) 7.61 (t, J=7.83 Hz, 1H) 7.31 (d, J=11.74 Hz, 1H) 7.25 (dd, J=8.07, 1.22 Hz, 1H) 3.80-3.88 (m, 1H) 3.70-3.80 (m, 1H) 3.65 (dd, J=14.06, 3.79 Hz, 1H) 3.13 (dd, J=14.06, 5.26 Hz, 1H) 2.96 (dd, J=14.18, 8.31 Hz, 1H) 2.77 (d, J=4.65 Hz, 3H)

Step 5: Synthesis of (S)-4-(2-(dimethylamino)-3-(1,3-dioxoisoindolin-2-yl)propyl)-2-fluoro-N-methylbenzamide (Int-4E)

To a suspension of Int-4D (1.62 g, 4.13 mmol) in CH$_3$CN (35 mL) and water (3.5 mL), was added 37% formaldehyde (1.99 g, 24.8 mmol), sodium cyanoborohydride (1.05 g, 16.5 mmol). The mixture was stirred at room temperature for an hour. The reaction mixture was then partitioned between ethyl acetate (100 mL) and saturated sodium bicarbonate (100 mL). Separated layers, the aqueous was extracted with more ethyl acetate (50 mL). The combined organic layers were dried over MgSO$_4$, filtered and concentrated on rotavapor. The crude material was purified on 40 g silica gel column eluting with gradient of 0-100% EtOAc/Hexanes to provide the desired product as a white solid (1.39 g, 88%). LCMS (+ESI) M+H$^+$=384.2.

Step 6: Synthesis of (S)-4-(3-amino-2-(dimethylamino)propyl)-2-fluoro-N-methylbenzamide (Int-4F)

To a solution of Int-4E (1.38 g, 3.60 mmol) in 95% ethanol (30 mL), was added hydrazine hydrate (80%) (1.05 g, 26.6 mmol). The mixture was heated at 70° C. for 3 hours. The crude reaction mixture was diluted with MeOH and mixed with silica gel (20 g), concentrated on rota vapor, and then purified on 24 g silica gel column eluting with gradient of 0-10% MeOH in DCM with 1% NH$_4$OH to provide the desired product as a white solid (0.716 g, 79%). LCMS (+ESI) M+H$^+$=254.2. $^1$H NMR (400 MHz, CHLOROFORM-d) δ ppm 8.01 (t, J=8.19 Hz, 1H) 7.05 (dd, J=7.95, 1.59 Hz, 1H) 6.91 (dd, J=13.08, 1.35 Hz, 1H) 6.70 (br s, 1H) 3.02 (dd, J=4.77, 0.86 Hz, 3H) 2.93 (dd, J=13.45, 3.42 Hz, 1H) 2.59-2.69 (m, 2H) 2.49-2.57 (m, 1H) 2.30-2.37 (m, 7H).

Synthesis of (S)-4-(3-amino-2-((cyclopropylmethyl)(methyl)amino)propyl)-2-fluoro-N-methylbenzamide (Int-4H)

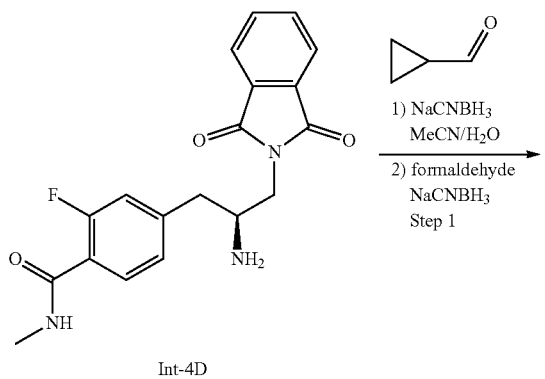

Step 1: (S)-4-(2-((cyclopropylmethyl)(methyl)amino)-3-(1,3-dioxoisoindolin-2-yl)propyl)-2-fluoro-N-methylbenzamide (Int-4G)

To a suspension of Int-4D (228 mg, 0.582 mmol) in CH₃CN (5 mL) and water (0.5 mL), was added cyclopropanecarbaldehyde (0.035 mL, 0.582 mmol). After stirred for 15 minutes at room temperature, sodium cyanoborohydride (146 mg, 2.33 mmol) was added and continued to stir for an additional hour. 37% formaldehyde (236 g, 2.91 mmol) was then added and the reaction was stirred at room temperature for 30 minutes. The reaction mixture was then partitioned between ethyl acetate (30 mL) and saturated sodium bicarbonate (30 mL). Separated layers, the aqueous was extracted with more ethyl acetate (30 mL). The combined organic layers were dried over MgSO₄, filtered and concentrated on rota-vapor. The crude material was purified on 12 g silica gel column eluting with gradient of 0-100% EtOAc/Hexanes to provide the desired product as a white solid (128 mg, 52%). LCMS (+ESI) M+H⁺=424.2, M+Na⁺=446.2.

Step 2: (S)-4-(3-amino-2-((cyclopropylmethyl)(methyl)amino)propyl)-2-fluoro-N-methylbenzamide (Int-4H)

To a solution of Int-4G (116 mg, 0.274 mmol) in 95% ethanol (30 mL), was added hydrazine hydrate (80%) (0.080 g, 2.03 mmol). The mixture was heated at 75° C. for 3 hours. The crude reaction mixture was diluted with MeOH and mixed with silica gel (4 g), concentrated on rota vapor, and then purified on 4 g silica gel column eluting with gradient of 0-10% MeOH in DCM with 1% NH₄OH to provide the desired product as an off-white solid (55 mg, 69%). LCMS (+ESI) M+H⁺=294.2.

Synthesis of (S)-4-(3-amino-2-(dimethylamino)propyl)-N,3,5-trimethylbenzamide (Int-5H)

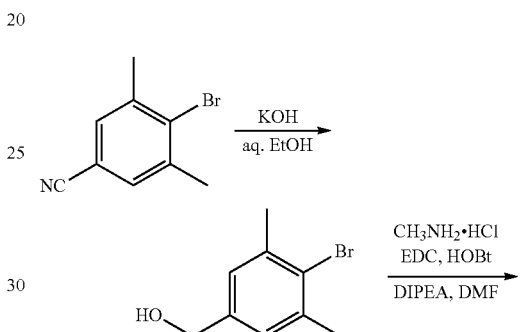

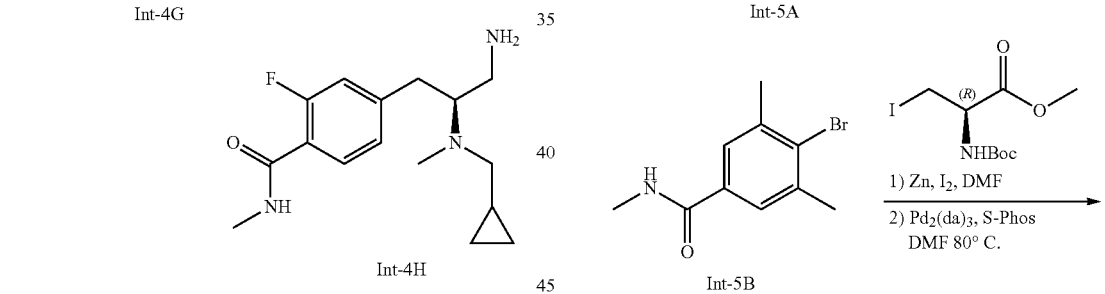

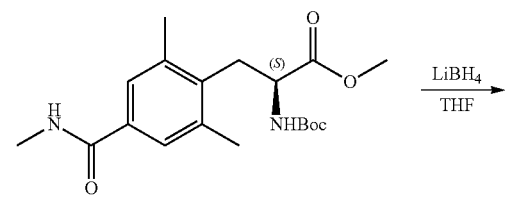

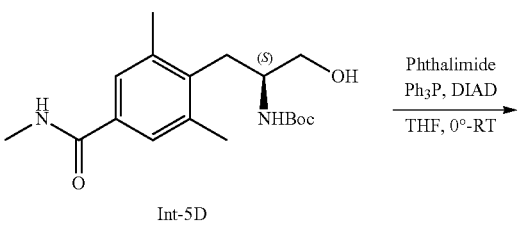

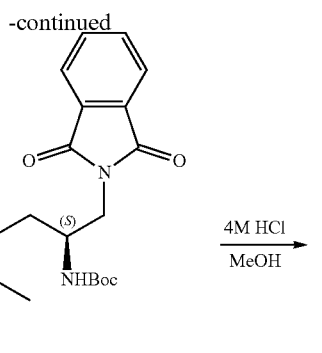

Int-5E

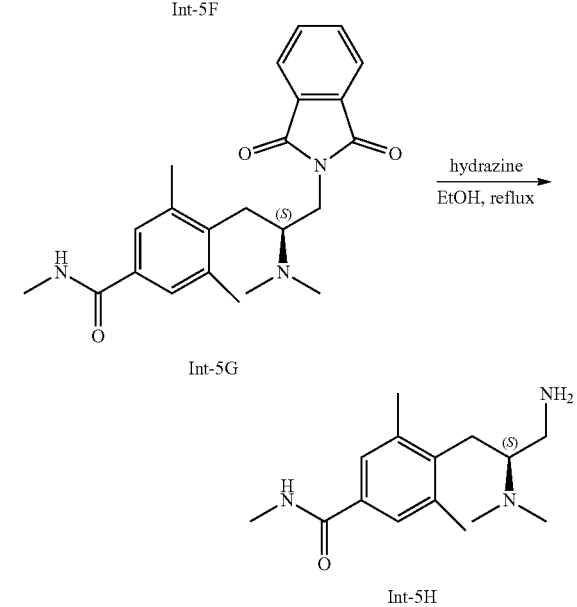

Int-5F

Int-5G

Int-5H

Step 1: Synthesis of 4-Bromo-3,5-dimethylbenzoic Acid (Int-5A)

4-Bromo-3,5-dimethylbenzonitrile (10 g, 48 mmol) was taken in ethanol (50 ml) and a solution of potassium hydroxide (13 g in 15 ml water) was added to it. The solution was heated to reflux for 22 hours. After cooling in an ice-bath, it was quenched by slowly adding 2.5 M sulfuric acid solution. The precipitated solids were collected by filtration and washed with water. After air-drying, the solids were taken up in toluene and solvent was removed to get dry powder. This was dried under vacuum to give the product as a light brown powder (10.7 g, 98%). $^1$H NMR (400 MHz, CHLOROFORM-d) δ ppm 7.82 (s, 2H) 2.46-2.52 (m, 6H).

Step 2: Synthesis of 4-Bromo-N,3,5-trimethylbenzamide (Int-5B)

Int-5A (10.7 g, 46.7 mmol) was taken in dimethylformamide (150 ml) with methylamine hydrochloride (3.5 g, 51.4 mmol), N-(3-dimethylaminopropyl)-N'-ethylcarbodiimide hydrochloride (9.9 g, 51.4 mmol) and hydroxybenzotriazole (6.9 g, 51.4 mmol). The solution was cooled in an ice-bath and diisopropylethylamine (18 ml, 100 mmol) was added. After completion of the reaction, it was diluted with ethyl acetate and washed with dilute sodium bicarbonate solution. The organic layer was dried and then concentrated. The residue was purified on Combiflash using hexanes/ethyl acetate gradient to give the product (8.7 g, 77%) as a pale white powder. $^1$H NMR (400 MHz, CHLOROFORM-d) δ ppm 7.42-7.48 (m, 2H) 6.37 (br s, 1H) 2.97-3.02 (m, 3H), 2.34-2.48 (m, 6H).

Step 3: Synthesis of Methyl (S)-2-((tert-butoxycarbonyl)amino)-3-(2,6-dimethyl-4-(methylcarbamoyl)phenyl)propanoate (Int-5C)

To a stirred suspension of Zinc powder (9.4 g, 143 mmol) in dimethylformamide (50 mL) was added iodine (1.1 g, 4.3 mmol) After stirring for 10 minutes, methyl (R)-2-((tert-butoxycarbonyl)amino)-3-iodopropanoate (17.1 g, 52 mmol) was added, followed by iodine (1.1 g, 4.3 mmol). The resulting mixture was stirred at RT for 1 h. The mixture was then added to a stirred mixture of Int-5B (10.5 g, 43 mmol), S-Phos (1.8 g, 4.3 mmole), and Pd$_2$(dba)$_3$ (2.0 g, 2.2 mmol) in DMF (20 mL) and then heated to 80° C. for 16 h. After cooling to room temperature, the suspension was diluted with ethyl acetate and filtered through packed celite. The filtrate was washed with water and the organic layer was dried and concentrated to half its original volume. The precipitated solids were collected by filtration to give the product as a white powder (6.1 g, 40%). The filtrate was concentrated, and the residue was purified on Combiflash using hexanes/ethyl acetate gradient to give additional product (6.0 g, 38%). Total yield (12.1 g, 78%). $^1$H NMR (400 MHz, CHLOROFORM-d) δ ppm 7.33 (s, 2H) 6.00-6.16 (m, 1H) 5.05 (br d, J=8.80 Hz, 1H) 4.46 (q, J=8.07 Hz, 1H) 3.56 (s, 3H), 3.02-3.04 (m, 2H), 2.91 (d, J=8.80 Hz, 3H) 2.30 (s, 6H), 1.29 (s, 9H)

Step 4: Synthesis of tert-Butyl (S)-(1-(2,6-dimethyl-4-(methylcarbamoyl)phenyl)-3-hydroxypropan-2-yl)carbamate (Int-5D)

Int-5C (6.1 g, 16.7 mmol) was taken in tetrahydrofuran (80 ml) and cooled in an ice-bath. A solution of lithium borohydride (8.4 ml, 4 M in THF, 33.5 mmol) was added slowly to it. The solution was brought to room temperature and then heated to reflux. After completion of reaction, it was cooled in an ice-bath and quenched by adding saturated ammonium chloride solution and then extracted with ethyl acetate. The organic layer was dried, concentrated and the residue was purified on Combiflash using dichloromethane/methanol gradient to give the product (4.6 g, 82%) as a white powder. $^1$H NMR (400 MHz, CHLOROFORM-d) δ ppm 7.30-7.37 (m, 2H), 6.07 (br s, 1H) 4.83 (br s, 1H) 3.79 (br s, 1H) 3.57-3.62 (m, 1H) 3.42-3.50 (m, 1H) 2.79-2.97 (m, 6H) 2.28-2.35 (m, 6H) 1.31 (br s, 9H).

Step 5: Synthesis of tert-butyl (S)-(1-(2,6-dimethyl-4-(methylcarbamoyl)phenyl)-3-(1,3-dioxoisoindolin-2-yl)propan-2-yl)carbamate (Int-5E)

Int-5D (4.6 g, 13.7 mmol) was dissolved in tetrahydrofuran (75 ml) and then phthalimide (2.4 g, 16.4 mmol) and triphenylphosphine (4.3 g, 16.4 mmol) were added. The flask was flushed with nitrogen and cooled in an ice-bath. Diisopropylazodicarboxylate (3.3 ml, 17.1 mmol) was added dropwise and the solution was stirred at room temperature. After completion of the reaction, the solution was concentrated and the residue was taken up in ethyl acetate. The precipitated solids were collected by filtration to give the product as a white powder (5.3 g, 84%). $^1$H NMR (400 MHz, DMSO-d6) δ ppm 8.29 (br d, J=4.65 Hz, 1H) 7.78-7.90 (m, 4H) 7.43-7.49 (m, 2H) 6.93 (d, J=9.54 Hz, 1H) 3.95-4.19 (m, 1H) 3.76 (dd, J=13.57, 9.90 Hz, 1H) 3.40-3.52 (m, 1H) 2.82-2.90 (m, 2H), 2.75 (d, J=9.54 Hz, 3H), 2.32-2.38 (br, 6H) 1.08 (s, 7H) 0.88 (s, 2H).

Step 6: Synthesis of (S)-4-(2-amino-3-(1,3-dioxoisoindolin-2-yl)propyl)-N,3,5-trimethylbenzamide Hydrochloride (Int-5F)

Int-5E (5.3 g, 11.5 mmol) was taken in ethanol (50 ml) and solution of HCl in 1,4-dioxane (12 ml, 57 mmol, 4 M solution) was added to it. After completion of the reaction, the solution was partially concentrated and then diluted with ethyl acetate. The precipitated solids were collected by filtration to give the product as a white powder (5.0 g, 100%). $^1$H NMR (400 MHz, DMSO-d6) δ ppm 8.33-8.51 (m, 4H) 7.80-7.88 (m, 4H) 7.50-7.65 (m, 2H) 3.88-3.96 (m, 1H) 3.21-3.35 (m, 2H) 3.06-3.17 (m, 1H) 2.76 (d, J=4.16 Hz, 3H) 2.30-2.43 (m, 6H). LC-MS (+ESI) M+H: 366

Step 7: Synthesis of (R)-4-(2-(dimethylamino)-3-(1,3-dioxo-2,3-dihydro-1H-inden-2-yl)propyl)-N,3,5-trimethylbenzamide (Int-5G)

Int-5F (2.0 g, 4.98 mmol) was taken in acetonitrile (10 ml) with water (2 ml) and heated to 50 C to get a clear solution. It was then cooled to room temperature and a solution of formaldehyde (2.4 ml, 25 mmol) was added to it. After 15 mins, sodium cyanoborohydride (0.4 g, 12 mmol) was added to it. After a further 15 mins, formaldehyde (0.4 ml, 5 mmol) was added followed by sodium cyanoborohydride (0.1 g, 3 mmol). After 1 hr the reaction was complete, and it was quenched by adding saturated ammonium chloride solution. It was extracted with dichloromethane, dried, and concentrated. The residue was purified on Combiflash using dichloromethane/methanol gradient to give the product (1.15 g, 59%). $^1$H NMR (400 MHz, CHLOROFORM-d) δ ppm 7.71 (dd, J=5.26, 3.06 Hz, 2H) 7.61 (dd, J=5.50, 3.06 Hz, 2H) 7.33 (s, 2H) 5.91-6.10 (m, 1H) 3.80-3.85 (m, 1H), 3.30-3.41 (m, 1H), 3.20-3.30 (m, 1H) 2.80-2.90 (m, 4H overlap) 2.60-2.75 (m, 1H) 2.28-2.36 (m, 12H). LC-MS (+ESI) M+H: 394

Step 8: Synthesis of (S)-4-(3-amino-2-(dimethylamino)propyl)-N,3,5-trimethylbenzamide (Int-5H)

Int-5G (1.6 g, 4.1 mmol) was taken in ethanol (40 ml) and then hydrazine solution (1.3 ml, 20 mmol, 50% solution) was added to it. The solution was heated to reflux for 3 hours during which time a thick white precipitate formed. After cooling to room temperature, the solution was diluted with ethyl acetate and the precipitated solids were removed by filtration. The filtrate was concentrated and then purified on Combiflash using dichloromethane/methanol/ammonium hydroxide gradient to give the product as a white powder (0.75 g, 70%). $^1$H NMR (400 MHz, CHLOROFORM-d) δ ppm 7.35-7.42 (m, 2H) 6.30-6.45 (br 1H) 2.99-3.05 (m, 3H), 2.88-2.96 (m, 2H) 2.85 (br, 2H) 2.67-2.70 (m, 1H) 2.54-2.60 (m, 1H) 2.43 (br, 6H), 2.35 (br, 6H). LC-MS (+ESI) M+H: 264

Synthesis of (S)—N2,N2-dimethyl-3-(1-tosyl-1H-indazol-5-yl)propane-1,2-diamine (Int-6G)

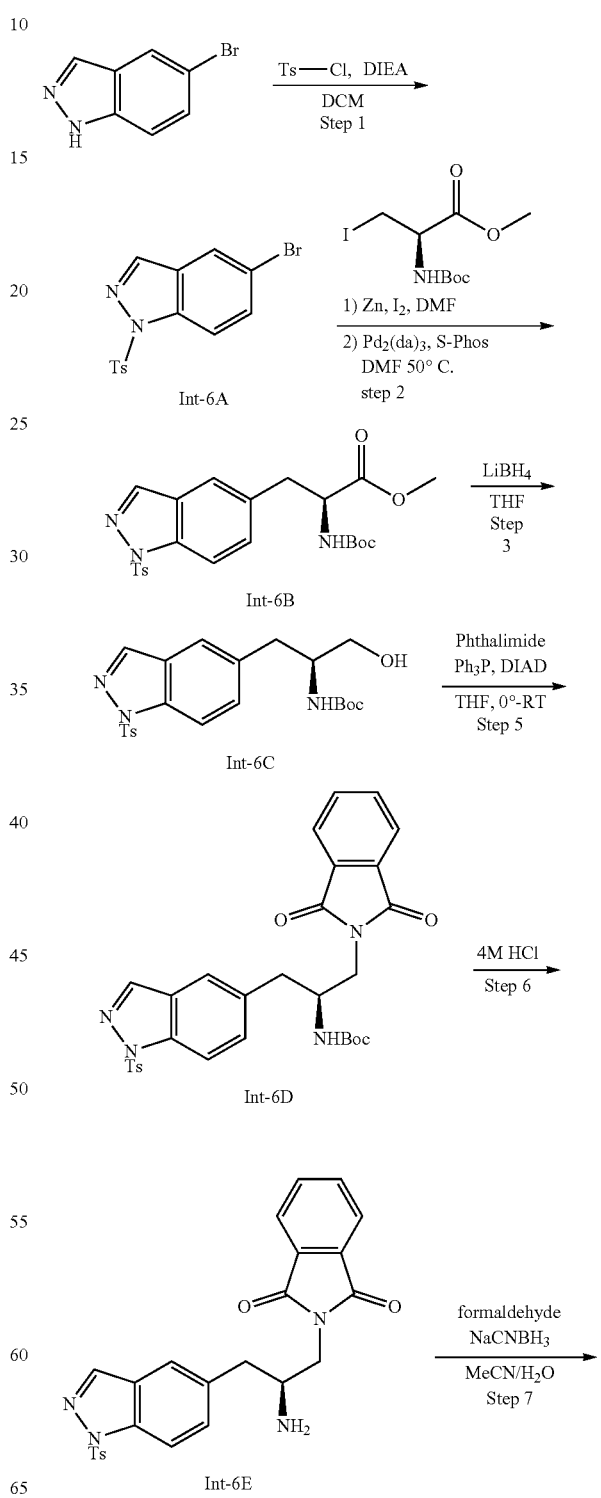

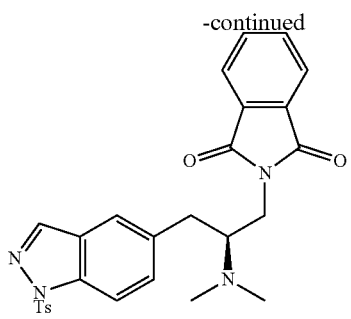

Int-6F

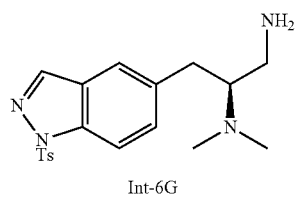 [SMILES: Cc1ccc(S(=O)(=O)n2ncc3cc(C[C@@H](CN)N(C)C)ccc32)cc1]

Int-6G

Step 1: Synthesis of 5-bromo-1-tosyl-1H-indazole (Int-6A)

To a stirred mixture of 5-bromo-1H-indazole (6.75 g, 34.25 mmole) and DIEA (7.3 mL, 41.11 mmole) in DCM (80 mL) at 0° C. was added Ts-Cl (6.85 g, 35.97 mmole). After the addition was completed, the reaction mixture was stirred for 16 h at RT. $H_2O$ was added, layers were separated. The aqueous layer was extracted with DCM (2×). The combined extracts were dried over $Na_2SO_4$, concentrated and purified by ISCO (0-30% EtOAc/Hexanes) to give Int-6A (10.35 g, 76%). LC-MS (+ESI) M+H: 399.1.

Step 2: Synthesis of methyl (S)-2-((tert-butoxycarbonyl)amino)-3-(1-tosyl-1H-indazol-5-yl)propanoate (Int-6B)

To a stirred suspension of zinc powder (0.94 g, 14.31 mmole) in DMF (10 mL) was added iodine (0.12 g, 0.48 mmole). After stirring for 10 minutes, methyl (R)-2-((tert-butoxycarbonyl)amino)-3-iodopropanoate (1.88 g, 5.72 mmole), followed by iodine (0.12 g, 0.48 mmole). The resulting mixture was stirred for 2 h. The mixture was then added to a stirred mixture of Int-6A (1.9 g, 4.77 mmole), S-Phos (0.10 g, 0.24 mmole), and $Pd_2(dba)_3$ in DMF (10 mL). The reaction mixture was heated to 60° C. in 16 h, cooled to RT, diluted with EtOAc, filtered through a pad of Celite. The filtrate was concentrated and purified by ISCO (0-60% EtOAc/Hexanes) to give Int-6B (1.21 g, 53.5%). LC-MS (+ESI) M+H: 399.1.

Step 3: Synthesis of tert-butyl (S)-(1-hydroxy-3-(1-tosyl-1H-indazol-5-yl)propan-2-yl)carbamate (Int-6C)

To a stirred solution of Int-6B (6.6 g, 14.04 mmole) in THF (60 mL) at 0° C. was added 4M $LiBH_4$ (5.3 mL, 21.06 mmole) dropwise. After the addition was completed, the reaction mixture was stirred at RT for 16 h at RT, cooled in an ice bath, slowly quenched by saturated aqueous $NH_4Cl$, stirred for 15 minutes, extracted with EtOAc (3×). The combined extracts were dried over Na2SO4, concentrated and purified by ISCO (45% EtOAc/Hexanes) to give Int-6C (2.6 g, 42%). LC-MS (+ESI) M+H: 446.2.

Step 4: Synthesis of tert-butyl (S)-(1-(1,3-dioxoisoindolin-2-yl)-3-(1-tosyl-1H-indazol-5-yl)propan-2-yl)carbamate (Int-6D)

To a stirred mixture of Int-6C (2.6 g, 5.84 mmole), $PPh_3$ (1.84 g, 7.01 mmole), and phthalimide (1.03 g, 7.01 mmole) in THF (40 mL) at 0° C. was added DIAD (1.42 g, 7.01 mmole) dropwise. After the addition was completed, the reaction mixture was stirred for 16 h at RT. The mixture was concentrated to dryness and purified by ISCO (0-50% EtOAC/Hexanes) to give Int-6D (3.1 g, 92.5%). LC-MS (+ESI) M+H: 575.2.

Step 5: Synthesis of (S)-2-(2-amino-3-(1-tosyl-1H-indazol-5-yl)propyl)isoindoline-1,3-dione Hydrochloride (Int-6E)

To a stirred solution of Int-6D (2.1 g, 3.65 mmole) in MeOH (30 mL) at 0° C. was added 4M HCl (9.6 mL, 18.28 mmole) in p-dioxane. The mixture was stirred at RT for 3 h, concentrated to dryness, triturated in EtOAc. The solid was collected, washed with EtOAc, dried to give Int-6E (1.95 g, 100%). LC-MS (+ESI) M+H: 475.2.

Step 6: Synthesis of (S)-2-(2-(dimethylamino)-3-(1-tosyl-1H-indazol-5-yl)propyl)isoindoline-1,3-dione (Int-6F)

To a stirred solution of Int-6E (1.95 g, 3.82 mmole) in $MeCN/H_2O$ (10:1, 44 mL) was added 37% formaldehyde (1.55 g, 19.09 mmole). After stirring for 30 minutes, $NaCNBH_3$ (0.72 g, 11.45 mmole). The reaction mixture was stirred for 30 minutes, quenched by saturated aqueous $NH_4Cl$, stirred for 10 minutes, extracted with DCM (3×). The combined extracts were dried over $Na_2SO_4$, concentrated to give Int-6F (2.0 g, 100%). LC-MS (+ESI) M+H: 503.2.

Step 7: Synthesis of (S)—N2,N2-dimethyl-3-(1-tosyl-1H-indazol-5-yl)propane-1,2-diamine (Int-6G)

A mixture of Int-6F (2.0 g, 3.98 mmole) and hydrazine (1.3 mL, 19.89 mmole) in EtOH (40 mL) was heated to 90° C. in 2 h. The reaction mixture was cooled, and the solid was filtered off, washed with EtOAc (3×). The filtrate was concentrated and purified by ISCO (0-25% MeOH/DCM in 1% $NH_4OH$) to give Int-6G (0.4 g, 27%). LC-MS (+ESI) M+H: 373.2.

Synthesis of (S)-3-(4-((tert-butyldimethylsilyl)oxy)phenyl)-$N^2,N^2$,2-trimethylpropane-1,2-diamine (Int-7H)

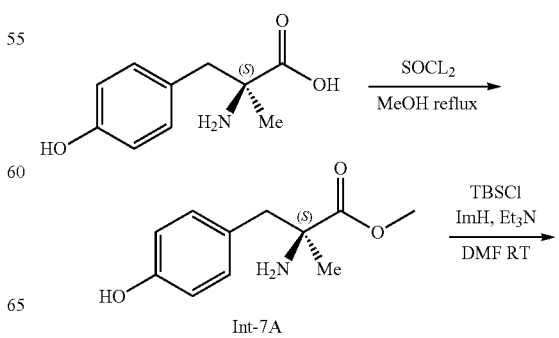

Int-7A

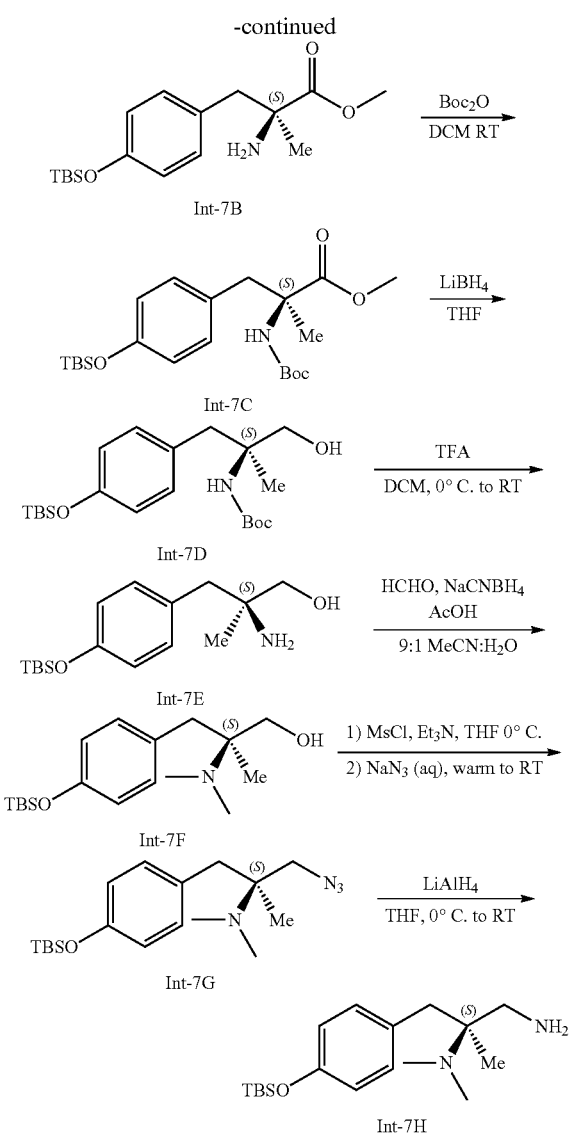

Step 1: Synthesis of methyl (S)-2-amino-3-(4-hydroxyphenyl)-2-methylpropanoate (Int-7A)

To a dry 100 mL round-bottom flask purged with N₂ is added methanol (20 mL) followed by thionyl chloride (1.45 mL, 20 mmol) dropwise at room temperature over 5 minutes. The solution is allowed to stir at room temperature for 10 additional minutes, after which time solid α-methyl-L-tyrosine (1.03 g, 5.27 mmol) is added. The mixture is heated to reflux for 24 hours, after which time LC-MS analysis indicates greater than 90% conversion to the methyl ester. The homogeneous orange reaction mixture is cooled to room temperature and the methanol is removed by rotary evaporation. Diethyl ether (5 mL) is added, causing a precipitate to form. The solid is collected by filtration, washed with ether and pump-dried to provide the product HCl salt as a beige solid, 1.48 g, which is carried forward without further purification. LC-MS: 210.1 m/z [M+H]+; ¹H NMR (400 MHz, d6-DMSO) δ ppm 8.53 (br s, 3H) 6.94-6.98 (m, 2H) 6.71-6.75 (m, 2H) 3.73 (s, 3H) 3.02 (s, 2H) 1.48 (s, 3H);

Step 2: Synthesis of methyl (S)-2-amino-3-(4-((tert-butyldimethylsilyl)oxy)phenyl)-2-methylpropanoate (Int-7B)

To a scintillation vial containing crude Int-7A (1.48 g, assumed 5.1 mmol) is added dimethylformamide (5 mL) followed by imidazole (1.2 g, 17.5 mmol), triethylamine (1.4 mL, 10 mmol), and lastly tert-butyldimethylsilyl chloride (900 mg, 6 mmol). The brown heterogeneous mixture is left to stir at room temperature and monitored by LC-MS. Additional portions of imidazole, triethylamine and tert-butyldimethylsilyl chloride are added as necessary until complete conversion to the TBS protected phenol is observed by LC-MS. After 4 hours, the reaction is worked up by addition of saturated aqueous NaHCO₃ (50 mL) and extracted 3 times with 10% methanol in ethyl acetate. The combined organic layers are washed with brine, dried over MgSO₄, filtered and concentrated by rotary evaporation to provide the crude desired product as a tan oil, 3.94 g. The crude product is contaminated with DMF, TBSOH and imidazole, and is carried forward without purification. LC-MS: 324.2 m/z [M+H]+; ¹H NMR (400 MHz, CDCl₃) δ ppm 6.98-7.02 (m, 2H) 6.73-6.77 (m, 2H) 3.69 (s, 3H) 3.06 (d, J=13.21 Hz, 1H) 2.73 (d, J=13.45 Hz, 1H) 1.38 (s, 3H) 0.98 (s, 9H) 0.19 (s, 6H).

Step 3: Synthesis of methyl (S)-2-((tert-butoxycarbonyl)amino)-3-(4-((tert-butyldimethylsilyl)oxy)phenyl)-2-methylpropanoate (Int-7C)

To a 100 mL round-bottom flask is added di-tert-butyl dicarbonate (1.5 g, 7 mmol) followed by dichloromethane (10 mL). The crude Int-7B (3.94 g, assume 5.1 mmol) is added as a solution in 15 mL dichloromethane. The reaction is stirred at room temperature for 5 days, with additional portions of di-tert-butyl dicarbonate added as necessary to push the reaction to completion. After 5 days LC-MS analysis indicates complete conversion of the starting material to the desired product. The reaction mixture is worked up by the addition of water (50 mL) and is extracted 3 times with ethyl acetate. The combined organic layers are washed with brine, dried over MgSO₄, filtered and concentrated by rotary evaporation to provide the desired crude product as a pale orange oil, 5.19 g. The crude product is contaminated with imidazole and TBSOH, and is carried forward without further purification. LC-MS: 324.2 m/z [M-Boc+H]+, 446.2 m/z [M+Na]+; ¹H NMR (400 MHz, CDCl₃) δ ppm 6.93 (d, J=8.31 Hz, 2H) 6.74 (d, J=8.31 Hz, 2H) 5.1 (br s, 1H) 3.74 (s, 3H) 3.3 (br s, 1H) 3.08-3.15 (m, 1H) 1.63 (s, 9H) 1.56 (s, 3H) 0.98 (s, 9H) 0.19 (s, 6H).

Step 4: Synthesis of tert-butyl (S)-(1-(4-((tert-butyldimethylsilyl)oxy)phenyl)-3-hydroxy-2-methylpropan-2-yl)carbamate (Int-7D)

To a 250 mL round-bottom flask containing substrate Int-7C (5.19 g, assume 5.1 mmol) is added THF (25 mL). The solution is brought to 0° C. using an ice bath, and a solution of LiBH₄ (4N in THF, 4 mL, 16 mmol) is added dropwise over 5 minutes. The reaction is allowed to warm to room temperature with stirring over 4 hours. Additional LiBH₄ (1.5 mL, 6 mmol) is added and the reaction is stirred at room temperature for an additional 16 hours, after which time LC-MS analysis indicates complete conversion to the desired alcohol product. The reaction is worked up by slowly, carefully pouring into 30 mL saturated aqueous NH₄Cl, and is extracted 3 times with ethyl acetate. The combined organic layers are washed with brine, dried over MgSO$_4$, filtered and concentrated by rotary evaporation to provide a pale yellow oil. The product is purified by column chromatography (0 to 50% ethyl acetate in hexanes) to provide the product as a colorless oil which solidifies into a white solid at room temperature, 1.74 g (4.4 mmol, 86% yield over 4 steps from α-methyl-L-tyrosine). LC-MS: 296.2 m/z [M-Boc+H]$^+$, 418.2 m/z [M+Na]$^+$; $^1$H NMR (400 MHz, CDCl$_3$) δ ppm 7.04 (d, J=8.31 Hz, 2H) 6.78 (d, J=8.31 Hz, 2H) 4.48 (br s, 1H) 4.24 (br s, 1H) 3.61-3.72 (m, 2H) 3.08 (br d, J=13.94 Hz, 1H) 2.75 (d, J=13.69 Hz, 1H) 1.47 (s, 9H) 1.06 (s, 3H) 0.99 (s, 9H) 0.20 (s, 6H).

Step 5: Synthesis of (S)-2-amino-3-(4-((tert-butyldimethylsilyl)oxy)phenyl)-2-methylpropan-1-ol (Int-7E)

To a 100 mL round-bottom flask, open to air, is added substrate Int-7D (1.04 g, 2.6 mmol). Then, dichloromethane (15 mL) is added and the colorless homogeneous solution is brought to 0° C. using an ice bath. Trifluoroacetic acid (1.4 mL, 5 mmol) is added dropwise over 5 minutes. The ice bath is removed and the solution is allowed to warm to room temperature overnight with stirring (16 hours), after which time LC-MS analysis indicates complete conversion of starting material to a mixture of the desired product and its trifluoroacetate ester (LC-MS: 392.2 m/z [M+H]$^+$) with no concomitant loss of the TBS group and only trace (<2%) isobutylene incorporation. The reaction is worked up by rotary evaporation and pump-dried to remove all volatiles to afford the product as a pale pink oil, 1.63 g. The crude product is contaminated with trifluoroacetic acid, as well as its labile trifluoroacetate ester, but is carried forward without further purification. Characterization of desired free alcohol product: LC-MS: 296.2 m/z [M+H]+; $^1$H NMR (400 MHz, CDCl$_3$) δ ppm 7.04 (d, J=8.31 Hz, 2H) 6.78 (d, J=8.31 Hz, 2H) 4.34-4.43 (m, 2H) 3.64-3.76 (m, 1H) 2.96-3.08 (m, 1H) 2.92 (s, 1H) 0.99 (overlapping s, 12H) 0.20 (s, 6H).

Step 6: Synthesis of (S)-3-(4-((tert-butyldimethylsilyl)oxy)phenyl)-2-(dimethylamino)-2-methylpropan-1-ol (Int-7F)

To a 100 mL round-bottom flask is added the crude primary amine substrate Int-7E (1.63 g, assume 2.5 mmol), followed by acetonitrile (15 mL) and water (1.5 mL). The colorless homogeneous solution is cooled to 0° C. in an ice bath. To the reaction mixture is added 37% aqueous formaldehyde (0.60 mL, 8 mmol) followed by sodium cyanoborohydride (943 mg, 15 mmol), and the reaction is stirred at 0° C. for 10 minutes. Then, acetic acid (0.86 mL, 15 mmol) is added. Additional portions of formaldehyde and sodium cyanoborohydride are added to push the reaction to completion, and additional water is added to maintain a homogeneous solution. The reaction is stirred for 2 hours after which time LC-MS analysis indicates complete conversion to the desired product, along with trace undesired TBS deprotection. The reaction is worked up by addition of 50 mL saturated aqueous NaHCO$_3$, and extracted 3 times with 10% methanol in ethyl acetate. The combined organic layers are washed with brine, dried over MgSO$_4$, filtered and concentrated by rotary evaporation. The residue obtained is purified by column chromatography (0 to 15% methanol with 1% NH$_4$OH in DCM) using an Evaporative Light Scattering Detector (ELSD) for peak visualization to afford the desired compound as a colorless oil (715 mg, 88% yield over 2 steps from Boc-protected amine). LC-MS: 324.3 m/z [M+H]+; $^1$H NMR (400 MHz, CDCl$_3$) δ ppm 7.07-7.12 (m, 2H) 6.80-6.84 (m, 2H) 4.39 (s, 1H) 3.63-3.67 (m, 1H) 3.52-3.59 (m, 1H) 3.12 (d, J=12.96 Hz, 1H) 2.94 (s, 6H) 2.83 (d, J=12.96 Hz, 1H) 1.25 (s, 3H) 0.99 (s, 9H) 0.21 (s, 6H).

Step 7: Synthesis of (S)-1-azido-3-(4-((tert-butyldimethylsilyl)oxy)phenyl)-N,N,2-trimethylpropan-2-amine (Int-7G)

To a scintillation vial containing amino alcohol substrate Int-7F (559 mg, 1.73 mmol) is added THF (10 mL), followed by triethylamine (1.4 mL, 10 mmol). The homogeneous mixture is cooled to 0° C. using an ice bath. Methanesulfonyl chloride (0.31 mL, 4 mmol) is added dropwise over 5 minutes, resulting in a yellow heterogeneous suspension. The intermediate mesylate formed (LC-MS 496.2 m/z [M+Na]$^+$) is highly reactive and can easily hydrolyze back to the starting alcohol or undergo substitution to form a vicinal aminochloride (LC-MS 342.2, 344.2 m/z [M+H]$^+$) if allowed to warm to room temperature. After 10 minutes of stirring at 0° C., an aqueous solution of sodium azide (650 mg, 10 mmol/5 mL water) is added portionwise over 30 seconds, and the biphasic clear yellow mixture is allowed to warm to room temperature with vigorous stirring for 15 minutes. The reaction is quickly worked up by pouring into 20 mL saturated aqueous NaHCO$_3$ and extracted 3 times with ethyl acetate. The combined organic layers are washed with brine, dried over MgSO$_4$, filtered and concentrated by rotary evaporation to provide the crude product as a pale yellow oil (650 mg), which is taken forward without further purification. LC-MS: 349.3 m/z [M+H]$^+$; $^1$H NMR (400 MHz, CDCl$_3$) δ ppm 7.05-7.13 (m, 2H) 6.79-6.88 (m, 2H) 2.80-3.02 (m, 4H) 2.72 (br s, 6H) 1.41 (s, 3H) 0.98 (s, 9H) 0.20 (s, 6H).

Step 8. Synthesis of (S)-3-(4-((tert-butyldimethylsilyl)oxy)phenyl)-N$^2$,N$^2$,2-trimethylpropane-1,2-diamine (Int-7H)

To the crude amino azide substrate Int-7G (650 mg, assume 1.73 mmol) in a 250 mL round-bottom flask is added THF (10 mL), and the solution is cooled to 0° C. in an ice bath. Lithium aluminum hydride (1M/THF, 4 mL, 4 mmol) is added dropwise over 5 minutes, the ice bath is removed and the pale yellow homogeneous solution is allowed to warm to room temperature with stirring. Additional lithium aluminum hydride is added as necessary to push the reaction to completion. After 2 hours, LC-MS analysis indicates complete conversion of the azide. The reaction is worked up by addition of 50 mL 1M potassium sodium tartrate and 50 mL ethyl acetate. A 1-inch bar-shaped stirbar is used to vigorously stir the biphasic mixture for 24 hours at room temperature until both the organic and aqueous layers are clear. 50 mL saturated aqueous NaHCO$_3$ is added, and the aqueous layer is extracted 3 times with ethyl acetate. The combined organic layers are washed with brine, dried over MgSO$_4$, filtered and concentrated by rotary evaporation. The residue obtained is purified by column chromatography (0 to 10% methanol in DCM) using an Evaporative Light Scattering Detector (ELSD) for peak visualization to afford the desired vicinal diamine as a colorless oil (331 mg, 1.02 mmol, 59% yield over 2 steps from the amino alcohol). LC-MS: 323.3 m/z [M+H]$^+$; $^1$H NMR (400 MHz, CDCl$_3$) δ ppm 6.98-7.11 (m, 2H) 6.78-6.90 (m, 2H) 3.97 (br s, 2H) 2.89 (s, 6H) 2.77-2.83 (m, 1H) 2.69-2.75 (m, 1H) 1.28 (s, 3H) 0.99 (s, 9H) 0.22 (s, 6H).

Example C1

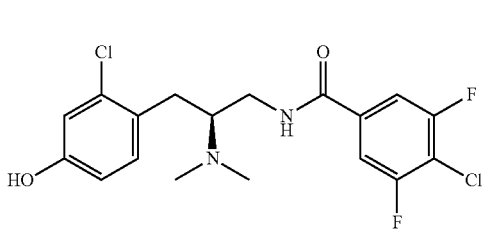

C-1

Synthesis of (S)-4-chloro-N-(3-(2-chloro-4-hydroxyphenyl)-2-(dimethylamino)propyl)-3,5-difluorobenzamide (Compound C-1)

The title compound was prepared according to Scheme C1, starting with Int-2H (intermediate 2H, 30.9 mg, 0.135 mmol), 4-chloro-3,5-difluorobenzoic acid (31.2 mg, 0.162 mmol) to afford 33.0 mg (61%) of title compound. LCMS (+ESI) M+H+=403.1, 405.1. $^1$H NMR (400 MHz, METHANOL-d4) δ ppm 7.52 (d, J=8.30 Hz, 2H) 7.14 (d, J=8.31 Hz, 1H) 6.80 (d, J=2.45 Hz, 1H) 6.67 (dd, J=8.31, 2.69 Hz, 1H) 3.46-3.56 (m, 1H) 3.36-3.42 (m, 1H) 3.15-3.23 (m, 1H) 3.07 (dd, J=13.57, 4.28 Hz, 1H) 2.61 (dd, J=13.69, 9.54 Hz, 1H) 2.44 (s, 6H).

Example C2

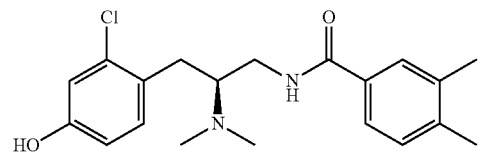

C-2

Synthesis of (S)—N-(3-(2-Chloro-4-hydroxyphenyl)-2-(dimethylamino)propyl)-3,4-dimethylbenzenamide (Compound C-2)

Int-2H (intermediate 2H, 30 mg, 0.13 mmol) in DMF (1 mL) was added 3,4-dimethyl benzoic acid (22 mg, 0.14 mmol), EDC (28 mg, 0.14 mmol), HOBT (9 mg, 0.07 mmol) and IPEA (50 mg, 0.39 mmol). The mixture was stirred at ambient temperature for 2 hours. Water and EtOAc were added. The organic layer was washed with water (×3) and concentrated. The residue was chromatographed (Silica gel, DCM/10% MeOH in DCM=9:1 to 0:1) to afford the title compound as a white solid, 27 mg (58%). LCMS (+ESI) M+H+=361. $^1$H NMR (400 MHz, Methanol-d$_4$) δ 7.50 (d, J=1.96 Hz, 1H), 7.46 (dd, J=7.83, 1.96 Hz, 1H), 7.19 (d, J=8.07, 1 Hz), 7.15 (d, J=8.31 Hz, 1H), 6.81 (d, J=2.45 Hz, 1H), 6.69 (dd, J=8.44 2.57 Hz, 1H), 3.50-3.40 (m, 2H), 3.21-3.13 (m, 1H), 3.07 (d, J=13.69, 4.65 Hz, 1H), 2.64 (dd, J=13.57, 9.42 Hz, 1H), 2.45 (s, 6H), 2.31 (s, 6H).

Example C3

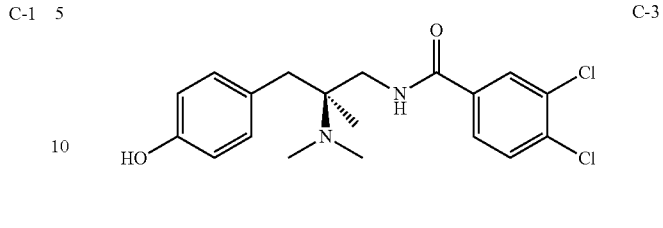

C-3

Synthesis of (S)-3,4-dichloro-N-(2-(dimethylamino)-3-(4-hydroxyphenyl)-2-methylpropyl)benzamide (Compound C-3)

To a 1-dram vial is added Int-711 (31.7 mg, 0.098 mmol), followed by DMF (0.5 mL) and DIEA (0.07 mL, 0.4 mmol). To this solution is added 3,4-dichlorobenzoic acid (26.7 mg, 0.14 mmol) as a solution in DMF (0.5 mL), and the colorless homogeneous solution is cooled to 0° C. in an ice bath. Lastly, solid HATU (76 mg, 0.2 mmol) is added to the solution all at once. The ice bath is removed and the yellow homogeneous solution is allowed to warm to room temperature over the course of 2 hours, after which time LC-MS analysis indicates complete amide-bond formation to form the intermediate (S)—N-(3-(4-((tert-butyldimethylsilyl)oxy)phenyl)-2-(dimethylamino)-2-methylpropyl)-3,4-dichlorobenzamide, which is not directly isolated (LC-MS: 495.2, 497.2, 499.2 m/z [M+H]+). To the reaction mixture is added 2 mL 1M NaOH and 2 mL methanol, and the reaction is stirred vigorously for 48 hours at room temperature, after which time LC-MS analysis indicates complete phenolic TBS deprotection to the desired final product. The reaction is worked up by addition of 50 mL saturated aqueous NaHCO$_3$. The aqueous layers are extracted 3 times with ethyl acetate, the combined organic layers washed once with brine, then dried over MgSO$_4$, filtered, and the solvent removed by rotary evaporation. The oily residue obtained is purified by column chromatography (0 to 15% methanol with 1% NH$_4$OH in DCM) using an Evaporative Light Scattering Detector (ELSD) for peak visualization to afford the desired compound as a colorless oil, 20.7 mg (0.054 mmol, 55% yield over 2 steps from primary amine). LC-MS: 381.1, 383.1, 385.1 m/z [M+H]+; $^1$H NMR (400 MHz, CDCl$_3$) δ ppm 7.79 (t, J=1.22 Hz, 1H) 7.48 (d, J=0.98 Hz, 2H) 6.99-7.04 (m, 2H) 6.71-6.75 (m, 2H) 6.66 (s, 1H) 3.21 (d, J=13.45 Hz, 1H) 3.03-3.09 (m, 1H) 3.00 (d, J=13.94 Hz, 1H) 2.54 (br d, J=12.72 Hz, 1H) 2.45 (s, 6H) 1.44 (s, 3H).

Example C4

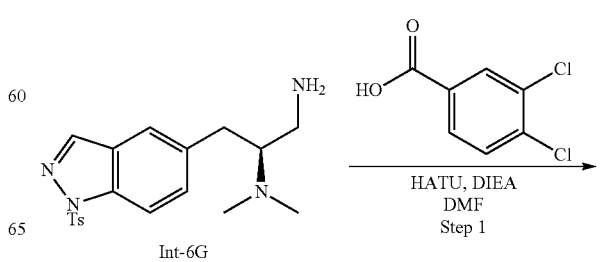

Int-6G    HATU, DIEA
DMF
Step 1

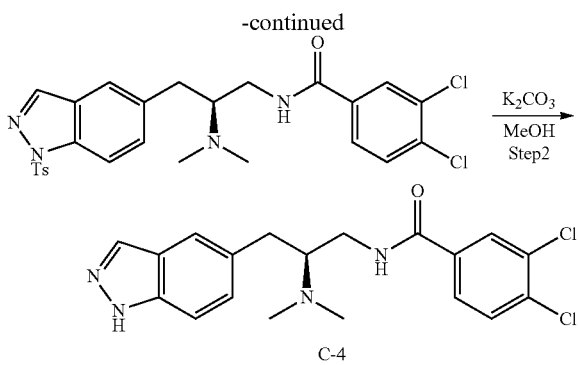

C-4

Synthesis of (S)-3,4-dichloro-N-(2-(dimethyl-amino)-3-(1H-indazol-5-yl)propyl)benzamide (Compound C-4)

Step 1: Preparation of (S)-3,4-dichloro-N-(2-(dimethylamino)-3-(1-tosyl-1H-indazol-5-yl)propyl)benzamide A mixture of Int-6G (0.13 g, 0.35 mmole), 3,4-dichlorobenzoic acid 0.067 g, 0.35 mmole), HOBT (0.03 g, 0.18 mmole), EDC (0.08 g, 0.42 mmole), and DIEA (0.12 g, 0.87 mmole) in DMF (2 mL) was stirred at RT for 16 h. H$_2$O was added, and the solid was collected, washed with H$_2$O, dried and purified by ISCO (0-10% MeOH/DCM) to give (S)-3,4-dichloro-N-(2-(dimethylamino)-3-(1-tosyl-1H-indazol-5-yl)propyl)benzamide (0.08 g, 42%). LC-MS (+ESI) M+H: 545.1.

Step 2: Preparation of (S)-3,4-dichloro-N-(2-(dimethylamino)-3-(1H-indazol-5-yl)propyl)benzamide (Compound C-4)

A mixture of (S)-3,4-dichloro-N-(2-(dimethylamino)-3-(1-tosyl-1H-indazol-5-yl)propyl)benzamide (0.08 g, 0.14 mmole) and K$_2$CO$_3$ (0.1 g, 0.71 mmole) in MeOH (5 mL) was stirred at 70° C. in 2 h. The reaction mixture was cooled, concentrated, taken up in H$_2$O, the solid was collected, dried and purified by ISCO (0-10% MeOH/DCM) to give (S)-3,4-dichloro-N-(2-(dimethylamino)-3-(1H-indazol-5-yl)propyl)benzamide (0.01 g, 20%). $^1$H NMR (400 MHz, DMSO-d6): δ ppm 12.93 (s, 1H), 8.38 (t, J=5.38 Hz, 1H), 7.91-8.00 (m, 2H), 7.68-7.79 (m, 2H), 7.56 (s, 1H), 7.44 (d, J=8.56 Hz, 1H), 7.14-7.25 (m, 1H), 3.44 (ddd, J=13.57, 7.83, 5.75 Hz, 1H), 3.19 (dt, J=13.63, 5.53 Hz, 1H), 2.97-3.03 (m, 1H), 2.89-2.96 (m, 1H), 2.57 (dd, J=13.82, 7.95 Hz, 1H), 2.30 (s, 6H). LC-MS (+ESI) M+H: 391.1.

Example C5

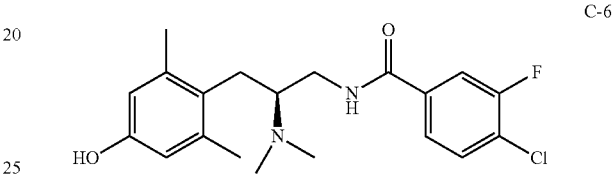

C-5

Synthesis of (S)-3-chloro-N-(2-(dimethylamino)-3-(4-hydroxy-2,6-dimethylphenyl)propyl)-4-methoxybenzamide (Compound C-5)

(S)-3-Chloro-N-(2-(dimethylamino)-3-(4-hydroxy-2,6-dimethylphenyl)propyl)-4-methoxybenzamide was synthesized according to Scheme C1 using Int-1G and 3-chloro-4-methoxybenzoic acid as the starting materials (68% yield). LC-MS: 391.2 [M+1]$^+$; $^1$H NMR (400 MHz, DMSO-d$_6$) δ 8.86 (s, 1H), 8.05 (m, 1H), 7.78-7.75 (m, 1H), 7.78-7.75 (m, 2H), 7.21-7.19 (m, 1H), 6.40 (s, 2H), 3.900 (s, 3H), 3.49-3.39 (m, 1H), 3.02-2.93 (m, 2H), 2.71-2.61 (m, 1H), 2.48-2.39 (m, 1H), 2.33 (s, 6H), 2.20 (s, 6H).

Example C6

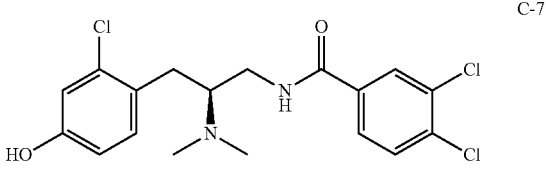 [SMILES: CN(C)[C@H](CNC(=O)c1ccc(Cl)c(Cl)c1)Cc1ccc(O)cc1Cl]

C-6

Synthesis of (S)-4-chloro-N-(2-(dimethylamino)-3-(4-hydroxy-2,6-dimethylphenyl)propyl)-3-fluorobenzamide (Compound C-6)

(S)-4-Chloro-N-(2-(dimethylamino)-3-(4-hydroxy-2,6-dimethylphenyl)propyl)-3-fluorobenzamide was synthesized according to Scheme C1 using Int-1G and 4-chloro-3-fluorobenzoic acid as the starting materials (68% yield). LC-MS: 379.2 [M+1]$^+$; $^1$H NMR (400 MHz, DMSO-d$_6$) δ 8.88 (s, 1H), 8.23 (m, 1H), 7.78-7.75 (m, 1H), 7.71-7.64 (m, 2H), 6.40 (s, 2H), 3.47-3.38 (m, 1H), 3.01-2.90 (m, 2H), 2.72-2.63 (m, 1H), 2.48-2.39 (m, 1H), 2.33 (s, 6H), 2.20 (s, 6H).

Example C7

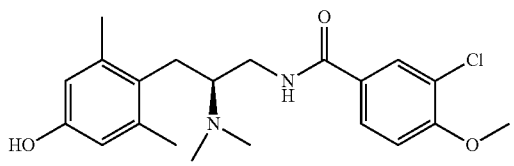

C-7

Synthesis of (S)-3,4-Dichloro-N-(3-(2-chloro-4-hydroxyphenyl)-2-(dimethylamino)propyl)benzamide (Compound C-7)

Int-2H (intermediate 2H, 30 mg, 0.13 mmol) in DMF (1 mL) was added 3,4-dichlorobenzoic acid (25 mg, 0.13 mmol), EDC (27 mg, 0.14 mmol), HOBT (8 mg, 0.06 mmol) and IPEA (42 mg, 0.33 mmol). The mixture was stirred at ambient temperature for 2 hours. Water and EtOAc were added. The organic layer was washed with water (×3) and concentrated. The residue was chromatographed (Silica gel, DCM/10% MeOH in DCM=5:1 to 0:1) to afford the title compound as a white solid, 28 mg (54%). LCMS (+ESI)

M+H+=402. ¹H NMR (400 MHz, Methanol-d₄) δ 7.91 (d, J=1.71 Hz, 1H), 7.67-7.58 (m, 2H), 7.14 (d, J=8.31 Hz, 1H), 6.81 (d, J=2.45 Hz, 1H), 6.68 (dd, J=8.31, 2.45 Hz, 1H), 3.54-3.47 (m, 1H), 3.42-3.37 (m, 1H), 3.23-3.15 (m, 1H), 3.07 (dd, J=13.69, 4.40 Hz, 1H), 2.62 (dd, J=13.69, 9.54 Hz, 1H), 2.44 (s, 6H).

Example C8

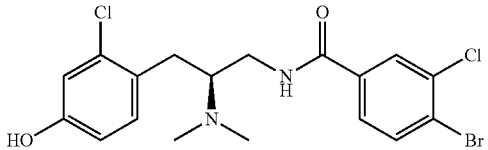

C-8

Synthesis of (S)-4-bromo-3-chloro-N-(3-(2-chloro-4-hydroxyphenyl)-2-(dimethylamino)propyl)benzamide (Compound C-8)

The title compound was prepared according to Scheme C1, starting with Int-2H (intermediate 2H, 136 mg, 0.595 mmol) and 4-bromo-3-chlorobenzoic acid (154 mg, 0.655 mmol) to afford 110 mg (42%) of title compound. LCMS (+ESI) M+H⁺=445.0, 447.0, 449.0. ¹H NMR (400 MHz, DMSO-d6) δ ppm 9.55 (br s, 1H) 8.29 (t, J=5.38 Hz, 1H) 7.92 (d, J=1.96 Hz, 1H) 7.80 (d, J=8.31 Hz, 1H) 7.60 (dd, J=8.31, 1.96 Hz, 1H) 7.07 (d, J=8.31 Hz, 1H) 6.70 (d, J=2.45 Hz, 1H) 6.60 (dd, J=8.31, 2.45 Hz, 1H) 3.37 (ddd, J=13.63, 8.13, 5.87 Hz, 1H) 3.04 (dt, J=13.57, 5.44 Hz, 1H) 2.87-2.96 (m, 1H) 2.76 (dd, J=13.82, 5.75 Hz, 1H) 2.41-2.48 (m, 1H) 2.22 (s, 6H).

Examples C10-C18

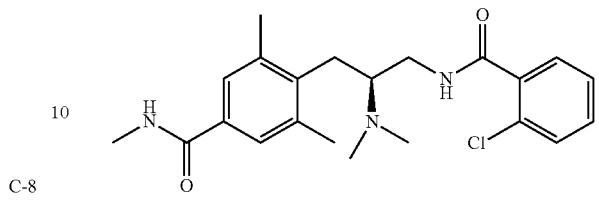

C-10

Synthesis of (S)-4-(3-(2-Chlorobenzamido)-2-(dimethylamino)propyl)-N,3,5-trimethylbenzamide (Compound C-10)

Int-5H (60 mg, 0.23 mmol) was dissolved in DMF (1 ml) with 2-chlorobenzoic acid (30 mg, 0.27 mmol) and HATU (105 mg, 0.27 mmol) was added. Diisopropylethylamine (48 mL, 0.30 mmol) was then added and the solution was stirred at room temperature. After completion of the reaction, the reaction mixture was concentrated and purified by reverse phase chromatography using a gradient of water/acetonitrile in 0.1% TFA. The solution of the product was neutralized by adding aqueous NaOH solution. The product was extracted into dichloromethane, filtered through magnesium sulfate and then concentrated to give the product as a white powder (33 mg). ¹H NMR (400 MHz, CHLOROFORM-d) δ ppm 7.87 (br s, 1H) 7.31-7.44 (m, 5H) 7.23-7.29 (m, 2H) 6.47 (br s, 1H) 5.41 (br s, 2H) 3.89-3.96 (m, 1H) 3.79-3.87 (m, 1H) 3.42 (ddd, J=14.80, 4.89, 3.30 Hz, 1H) 3.14-3.20 (m, 1H) 2.96-3.09 (m, 10H) 2.37-2.41 (m, 6H). MS: ESI 402 [M+H]+.

The Compounds of Table 4 were prepared in the same method as described in Example C10 by using appropriate reagents.

TABLE 4

| Comp. No. | Yield/Analytical Data |
|---|---|
| C-11 | 0.113 g, 18.5%; ¹H NMR (400 MHz, DMSO-d6 ): δ ppm 8.28 (br dd, J = 8.31, 3.67 Hz, 2H), 7.79 (d, J = 8.56 Hz, 2H), 7.53 (d, J = 8.80 Hz, 2H), 7.45 (s, 2H), 3.52 (br dd, J = 4.77, 1.59 Hz, 1H), 3.01 (dt, J = 14.12, 5.04 Hz, 2H), 2.81-2.91 (m, 1H), 2.75 (d, J = 4.40 Hz, 3H), 2.57-2.66 (m, 1H), 2.33 (s, 12H). LC-MS (+ESI) M + H: 402.2. |
| C-12 | 0.008 g, 12.1%; ¹H NMR (400 MHz, DMSO-d6 ): δ ppm 8.47 (t, J = 5.01 Hz, 1H), 8.22-8.33 (m, 1H), 7.73-7.82 (m, 3H), 7.45 (s, 2H), 3.46-3.58 (m, 1H), 2.96-3.05 (m, 2H), 2.83-2.92 (m, 1H), 2.75 (d, J = 4.65 Hz, 3H), 2.56-2.66 (m, 1H), 2.34 (s, 6H), 2.33 (s, 6H). LC-MS (+ESI) M + H: 436.1. |
| C-13 | 17 mg, 33%); LCMS (+ESI) M + H⁺ = 420.2. ¹H NMR (400 MHz, METHANOL-d4) δ ppm 7.51-7.66 (m, 5 H) 3.89-4.07 (m, 2 H) 3.75 (d, J = 4.89 Hz, 1 H) 3.16-3.28 (m, 5 H) 3.12 (s, 3 H) 2.92 (s, 3 H) 2.51 (s, 6 H) |
| C-14 | 7 mg, 13%; LCMS (+ESI) M + H⁺ = 420.2. ¹H NMR (400 MHz, METHANOL-d4) δ ppm 7.79 (dd, J = 7.09, 2.20 Hz, 1 H) 7.63 (ddd, J = 8.68, 4.52, 2.20 Hz, 1 H) 7.45 (s, 2 H) 7.21 (t, J = 8.80 Hz, 1 H) 3.80-3.91 (m, 2 H) 3.22-3.26 (m, 1 H) 3.08-3.18 (m, 2 H) 3.07 (s, 3 H) 3.00 (s, 3 H) 2.80 (s, 3 H) 2.39 (s, 6 H) 1.19 (s, 1 H). |
| C-15 | 0.009 g, 21.5%; ¹H NMR (400 MHz, MeOH-d4): δ ppm 7.46 (s, 2H), 7.23 (s, 1H), 7.16 (d, J = 0.98 Hz, 2H), 3.46-3.58 (m, 1H), 3.11-3.24 (m, 2H), 3.04 (dd, J = 13.69, 4.16 Hz, 1H), 2.89 (s, 3H), 2.78-2.86 (m, 1H), 2.49 (s, 6H), 2.43 (s, 6H), 2.33 (s, 3H). LC-MS (+ESI) M + H: 416.2. |
| C-16 | 0.005 g, 8.5%; ¹H NMR (400 MHz, DMSO-d6): δ ppm 9.80-9.94 (m, 1H), 8.49-8.62 (m, 1H), 8.26-8.39 (m, 1H), 7.67 (d, J = 1.71 Hz, 1H), 7.54 (s, 2H), 7.42-7.50 (m, 2H), 4.02-4.16 (m, 1H), 3.67-3.81 (m, 2H), 3.21 (br d, J = 1.22 Hz, 1H), |

| Comp. No. | Yield/Analytical Data |
|---|---|
|  | 3.03-3.07 (m, 1H), 3.01 (br d, J = 4.65 Hz, 3H), 2.94 (br d, J = 4.65 Hz, 3H), 2.76 (d, J = 4.65 Hz, 3H), 2.41 (s, 6H). LC-MS (+ESI) M + H: 436.1. |
| C-17 | 0.005 g, 12.6%; <br> $^1$H NMR (400 MHz, DMSO-d6): δ ppm 8.16-8.29 (m, 1H), 7.95-8.05 (m, 1H), 7.75 (d, J = 8.80 Hz, 2H), 7.44 (s, 2H), 6.97 (d, J = 8.80 Hz, 2H), 3.80 (s, 3H), 3.43-3.55 (m, 1H), 2.95-3.06 (m, 2H), 2.81-2.90 (m, 1H), 2.61-2.69 (m, 1H), 2.35 (br s, 6H), 2.33 (s, 6H). LC-MS (+ESI) M + H: 398.3. |
| C-18 | 0.0173 g, 38.4%; <br> $^1$H NMR (400 MHz, DMSO-d6): δ ppm 8.16-8.31 (m, 1H), 7.74 (br t, J = 5.14 Hz, 1H), 7.46 (s, 2H), 7.15 (d, J = 7.58 Hz, 1H), 6.95-7.06 (m, 2H), 3.36-3.46 (m, 1H), 2.94-3.02 (m, 2H), 2.86 (dd, J = 13.57, 5.26 Hz, 1H), 2.76 (d, J = 4.65 Hz, 3H), 2.63 (dd, J = 13.69, 7.83 Hz, 1H), 2.35 (s, 12H), 2.28 (d, J = 5.38 Hz, 6H). LC-MS (+ESI) M + H: 396.2. |

Example C19

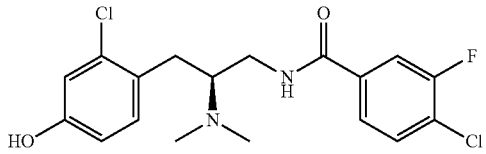

Synthesis of (S)-4-chloro-N-(3-(2-chloro-4-hydroxyphenyl)-2-(dimethylamino)propyl)-3-fluorobenzamide (Compound C-19)

The title compound was prepared according to Scheme C1, starting with Int-2H (intermediate 2H, 102 mg, 0.445 mmol) and 4-chloro-3-fluorobenzoic acid (85.5 mg, 0.490 mmol) to afford 115 mg (67%) of title compound. LCMS (+ESI) M+H$^+$=385.1, 387.1. $^1$H NMR (400 MHz, METHANOL-d4) δ ppm 7.63 (d, J=9.97 Hz, 1H) 7.53-7.58 (m, 2H) 7.14 (d, J=8.56 Hz, 1H) 6.80 (d, J=2.45 Hz, 1H) 6.68 (dd, J=8.44, 2.57 Hz, 1H) 3.47-3.54 (m, 1H) 3.36-3.43 (m, 1H) 3.18 (tt, J=9.08, 4.86 Hz, 1H) 3.07 (dd, J=13.69, 4.40 Hz, 1H) 2.62 (dd, J=13.69, 9.29 Hz, 1H) 2.44 (s, 6H).

Examples C20-C22

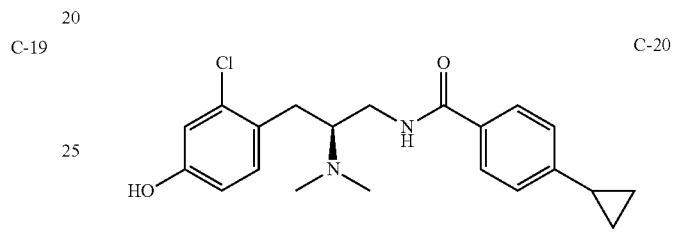

Synthesis of (S)—N-(3-(2-Chloro-4-hydroxyphenyl)-2-(di-methylamino)propyl)-4-cyclopropylbenzamide (Compound C-20)

Int-2H (intermediate 2H, 25 mg, 0.11 mmol) in DMF (1 mL) was added 4-cyclopropylbenzoic acid (18 mg, 0.11 mmol), EDC (23 mg, 0.12 mmol), HOBT (8 mg, 0.06 mmol) and IPEA (36 mg, 0.28 mmol). The mixture was stirred at ambient temperature for 2 hours. Water and EtOAc were added. The organic layer was washed with water (×3) and concentrated. The residue was chromatographed (Silica gel, DCM/10% MeOH in DCM=5:1 to 0:1) to afford the title compound as a white solid, 16 mg (39%). LCMS (+ESI) M+H+=373. $^1$H NMR (400 MHz, Methanol-d$_4$) δ 7.65-7.63 (m, 2H), 7.16-7.11 (m, 3H), 6.81 (d, J=2.69 Hz, 1H), 6.69 (dd, J=13.69, 2.69 Hz, 1H), 3.52-3.35 (m, 2H), 3.20-3.16 (m, 1H), 3.07 (dd, J=13.57, 4.52 Hz, 1H), 2.63 (dd, J=13.69, 9.29 Hz, 1H), 2.45 (s, 6H), 2.00-1.92 (m, 1H), 1.09-0.99 (m, 2H), 0.78-0.73 (m, 2H).

The Compounds of Table 5 were prepared in the same method as described in Example C20 by using appropriate reagents.

TABLE 5

| Comp. No. | Yield/Analytical Data |
|---|---|
| C-21 | White solid, 15 mg (40%). LCMS (+ESI) M + H+ = 368. $^1$H NMR (400 MHz, Methanol-d4) δ 7.75-7.71 (m, 2 H), 7.47-7.43 (m, 2 H) 7.15 (d, J = 8.31 Hz, 1 H), 6.81 (d, J = 2.45 Hz, 1 H), 6.68 (dd, J = 8.44, 2.57 Hz, 1 H), 3.53 (dd, J = 13.94, 8.56 Hz, 1 H), 3.39 (dd, J = 13.94, 5.38 Hz, 1 H), 3.20 (dt, J = 8.4, 4.55 Hz, 1 H), 3.08 (dd, J = 13.57, 4.52 Hz, 1 H), 2.63 (dd, J = 13.57, 9.42 Hz, 1 H), 2.46 (s, 6 H). |
| C-22 | white solid (22.5 mg, 54%). LCMS (+ESI) M + H$^+$ = 367.1, 369.1. $^1$H NMR (400 MHz, METHANOL-d4) δ ppm 7.77 (t, J = 1.83 Hz, 1 H) 7.66 (dt, J = 7.76, 1.38 Hz, 1 H) 7.53 (ddd, J = 8.07, 2.08, 1.10 Hz, 1 H) 7.43 (t, J = 7.95 Hz, 1 H) 7.15 (d, J = 8.31 Hz, 1 H) 6.81 (d, J = 2.45 Hz, 1 H) 6.68 (dd, J = 8.31, 2.45 Hz, 1 H) 3.46-3.54 (m, 1 H) 3.37-3.44 (m, 1 H) 3.15-3.23 (m, 1 H) 3.07 (dd, J = 13.69, 4.65 Hz, 1 H) 2.63 (dd, J = 13.57, 9.42 Hz, 1 H) 2.45 (s, 6 H) |

Example C23

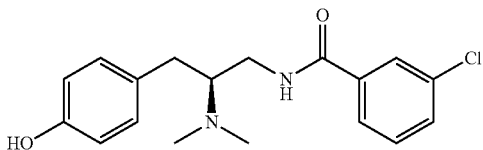

(S)-3-chloro-N-(2-(dimethylamino)-3-(4-hydroxyphenyl)propyl)benzamide (Compound C-23)

To a stirred solution of (S)-4-(3-amino-2-(dimethylamino)propyl)phenol (21 mg, 0.08 mmol, 1 equiv) in dry DMF (3 mL) was added EDCI (92 mg, 0.48 mmol, 1.5 equiv), HOBt (65 mg, 0.48 mmol, 1.5 equiv), 3-chlorobenzoic acid (55 mg, 0.35 mmol, 1.1 equiv), and DIPEA (340 µL, 1.92 mmol, 6 equiv). After 2 h, the solution was diluted with water and extracted with EtOAc. The combined organic layers were washed with aq. NaHCO$_3$ and brine, dried over anhydrous sodium sulfate, and concentrated. The residue was purified by flash column chromatography over silica gel (0-15% MeOH in CH$_2$Cl$_2$) to afford a white solid (26 mg, 26% yield). $^1$H NMR (400 MHz, CDCl$_3$) δ 7.70-7.74 (m, 1H), 7.56-7.62 (m, 1H), 7.40-7.47 (m, 2H), 6.97 (d, J=8.31 Hz, 2H), 6.68-6.78 (m, 3H), 3.52-3.63 (m, 1H), 3.15-3.30 (m, 1H), 2.85-3.03 (m, 3H), 2.45 (s, 5H), 2.27-2.40 (m, 3H), 1.96 (s, 2H). LCMS: 332.2 [M]$^+$.

Examples C24-C31

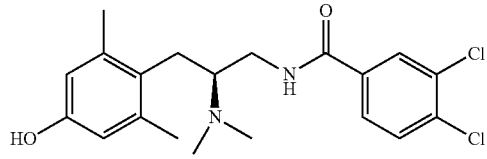

Synthesis of (S)-3,4-dichloro-N-(2-(dimethylamino)-3-(4-hydroxy-2,6-dimethylphenyl)propyl)benzamide (Compound C-24

Compound C-16 was synthesized according to Scheme C1 using Int-1G and 3,4-dichlorobenzoic acid as the starting materials (78% yield). LC-MS: 395.2 [M+1]$^+$; $^1$H NMR (400 MHz, DMSO-d$_6$) δ 8.92 (s, 1H), 8.32 (m, 1H), 8.01 (m, 1H), 7.74-7.72 (m, 2H), 6.39 (s, 2H), 3.40-3.55 (m, 1H), 3.02-2.85 (m, 2H), 2.75-2.63 (m, 1H), 2.47-2.37 (m, 1H), 2.32 (s, 6H), 2.18 (s, 6H).

The Compounds of Table 6 were prepared in the same method as described in Example C24 by using appropriate reagents.

TABLE 6

| Comp. No. | Yield/Analytical Data |
| --- | --- |
| C-25 | 89% yield; LC-MS: 361.2 [M + 1]$^+$; $^1$H NMR (400 MHz, DMSO-d$_6$) δ 8.92 (s, 1H), 8.24 (m, 1H), 7.82 (s, 1H), 7.78-7.73 (m, 1H), 7.57-7.46 (m, 2H), 6.40 (s, 2H), 3.52-3.47 (m, 1H), 3.01-2.88 (m, 2H), 2.73-2.64 (m, 1H), 2.47-2.37 (m, 1H), 2.33 (s, 6H), 2.20 (s, 6H) |
| C-26 | 56% yield; LC-MS: 429.2 [M + 1]$^+$; $^1$H NMR (400 MHz, DMSO-d$_6$) δ 8.93 (s, 1H), 8.48 (m, 1H), 8.05(s, 1H), 7.96-7.90 (m, 2H), 6.40 (s, 2H), 3.51-3.39 (m, 1H), 3.02-2.91 (m, 2H), 2.76-2.68 (m, 1H), 2.49-2.38 (m, 1H), 2.34 (s, 6H), 2.20 (s, 6H) |
| C-27 | 0.019 g, 19.6%; $^1$H NMR (400 MHz, DMSO-d6 ) δ ppm 8.89 (br s, 1H), 8.08 (dd, J = 9.66, 1.83 Hz, 2H), 7.98-8.05 (m, 1H), 7.76 (dd, J = 8.56, 1.71 Hz, 1H), 7.64 (d, J = 8.80 Hz, 1H), 7.05 (dd, J = 2.20, 0.73 Hz, 1H), 6.42 (s, 2H), 3.39-3.56 (m, 1 H), 3.28 (br s, 1H), 3.00-3.10 (m, 1H), 2.86-2.99 (m, 1H), 2.66-2.80 (m, 1H), 2.28-2.46 (m, 6H), 2.22 (s, 6H). LC-MS (+ESI) M + H: 429.2. |
| C-28 | white solid, 29 mg (70%). LCMS (+ESI) M + H+ = 355. $^1$H NMR (400 MHz, Methanol-d$_4$) δ 7.45 (d, J = 1.96 Hz, 1 H), 7.41 (dd, J = 7.70, 2.08 Hz, 1 H), 7.18 (d, J = 7.58 Hz, 1 H), 6.49 (s, 2 H), 3.55 (dd, J = 13.69, 8.56 Hz, 1 H), 3.25 (dd, J = 13.57, 5.26 Hz, 1 H), 3.16-3.07 (m, 1 H), 2.93 (dd, J = 13.94, 4.40 Hz, 1 H), 2.73 (dd, J = 13.94, 10.52, 1 H), 2.50 (s, 6H), 2.31-2.30 (m, 12 H) |
| C-29 | 7 mg (13%) of title compound. LCMS (+ESI) M + H$^+$ = 397.2, 399.2. $^1$H NMR (400 MHz, METHANOL-d4) δ ppm 7.48 (d, J = 8.46 Hz, 2 H) 6.47 (s, 2 H) 4.84-4.89 (m, 1 H) 3.56 (dd, J = 13.69, 9.05 Hz, 1 H) 3.20-3.26 (m, 1 H) 3.15 (ddt, J = 10.58, 9.23, 4.52, 4.52 Hz, 1 H) 2.93 (dd, J = 14.06, 4.03 Hz, 1 H) 2.65-2.74 (m, 1 H) 2.49 (s, 6 H) 2.31 (s, 6 H) |
| C-30 | white powder (55 mg, 60%). 1H NMR (400 MHz, CHLOROFORM-d) δ ppm 7.53-7.70 (m, 3 H) 7.19 (br s, 1 H) 6.53 (s, 2 H) 3.43-3.52 (m, 1 H) 3.22 (br t, J = 11.74 Hz, 1 H) 2.85-3.05 (m, 2 H) 2.56-2.74 (m, 1 H) 2.50 (br s, 6H) 2.23 (br s, 6H) MS: ESI 413 [M + H]+ |
| C-31 | (0.062 g, 74.5%); $^1$H NMR (400 MHz, DMSO-d6): δ ppm 8.89 (br s, 1H), 8.08 (dd, J = 9.66, 1.83 Hz, 2H), 7.98-8.05 (m, 1H), 7.76 (dd, J = 8.56, 1.71 Hz, 1H), 7.64 (d, J = 8.80 Hz, 1H), 7.05 (dd, J = 2.20, 0.73 Hz, 1H), 6.42 (s, 2H), 3.39-3.56 (m, 1H), 3.28 (br s, 1H), 3.00-3.10 (m, 1H), 2.86-2.99 (m, 1H), 2.66-2.80 (m, 1H), 2.28-2.46 (m, 6H), 2.22 (s, 6H). LC-MS (+ESI) M + H: 367.1. |

Examples C32-C35

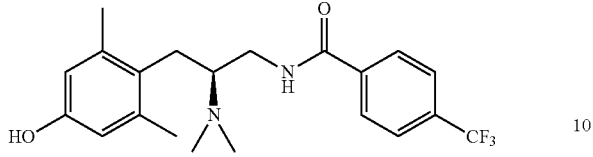

C-32

Synthesis of (S)—N-(2-(dimethylamino)-3-(4-hydroxy-2,6-dimethylphenyl)propyl)-4-(trifluoromethyl)benzamide (Compound C-32)

To a 1-dram vial is added amine substrate Int-1G (36.2 mg, 0.16 mmol), DMF (0.5 mL) and DIEA (0.1 mL, 0.57 mmol). To the amine solution is added 4-trifluoromethylbenzoic acid (34.1 mg, 0.18 mmol) as a solution in DMF (0.5 mL). The homogeneous solution is cooled to 0° C. using an ice bath. Lastly, HATU (114 mg, 0.3 mmol) is added as a solid all at once. The ice bath is removed and the solution is allowed to warm to room temperature with stirring for 1 hour, after which time LC-MS analysis indicates complete conversion to the desired product. The reaction is worked up by addition of saturated aqueous $NaHCO_3$ (20 mL) and is extracted 3 times with ethyl acetate. The combined organic layers are washed with brine, dried over $MgSO_4$, filtered and concentrated by rotary evaporation. The obtained residue is purified by column chromatography (0 to 15% methanol with 1% $NH_4OH$ in DCM) using an Evaporative Light Scattering Detector (ELSD) for peak visualization to afford the desired compound as a colorless oil (15.1 mg, 24% yield). LC-MS: 395.2 m/z [M+H]+; $^1$H NMR (400 MHz, $CDCl_3$) δ ppm 7.85 (br d, J=8.31 Hz, 2H) 7.66 (d, J=8.31 Hz, 2H) 6.52 (s, 2H) 3.44-3.56 (m, 1H) 3.23-3.35 (m, 1H) 3.00-3.15 (br s, 1H) 2.94 (dd, J=13.69, 3.42 Hz, 1H) 2.67 (br dd, J=13.45, 11.49 Hz, 1H) 2.55 (s, 6H) 2.29 (s, 6H).

The Compounds of Table 7 were prepared in the same method as described in Example C32 by using appropriate reagents.

TABLE 7

| Comp. No. | Yield/Analytical Data |
| --- | --- |
| C-33 | white solid (55.0 mg, 97% yield). LC-MS: 377.3 m/z [M + H]+; $^1$H NMR (400 MHz, d6-DMSO) δ ppm 9.08 (br s, 1 H) 8.37 (s, 1 H) 7.96-8.03 (m, 3 H) 7.86-7.90 (m, 1 H) 7.58-7.65 (m, 3 H) 6.48 (s, 2 H) 3.44-3.95 (br m, 2 H) 3.08-3.15 (m, 1 H) 2.82-2.91 (m, 1 H) 2.41 (br s, 6H) 2.27 (s, 6 H) |
| C-34 | colorless oil (52.4 mg, 93% yield). LC-MS: 378.3 m/z [M + H]+; $^1$H NMR (400 MHz, d6-DMSO) δ ppm 9.15 (br s, 2 H) 8.55 (d, J = 5.38 Hz, 2 H) 8.05 (br d, J = 8.31 Hz, 2 H) 7.82 (t, J = 7.34 Hz, 1 H) 7.73 (br d, J = 7.09 Hz, 1 H) 6.46 (br s, 2 H) 3.71-4.02 (m, 1 H) 3.17-3.27 (m, 1 H) 2.70-3.10 (br m, 2 H) 2.40 (br s, 6 H) 2.26 (s, 6 H) |
| C-35 | colorless oil (46.0 mg, 81% yield). LC-MS: 378.2 m/z [M + H]+; $^1$H NMR (400 MHz, d6-DMSO) δ ppm 9.37 (s, 1 H) 8.93 (br s, 1 H) 8.65 (br s, 1 H) 8.51 (s, 1 H) 8.20 (dd, J = 18.10, 8.31 Hz, 2 H) 7.76-7.91 (m, 2 H) 6.44 (s, 2 H) 3.18-3.36 (m, 2 H) 2.86-3.00 (m, 1 H) 2.72-2.86 (m, 1 H) 2.43 (br s, 6 H) 2.24 (s, 6 H) |

Example C36

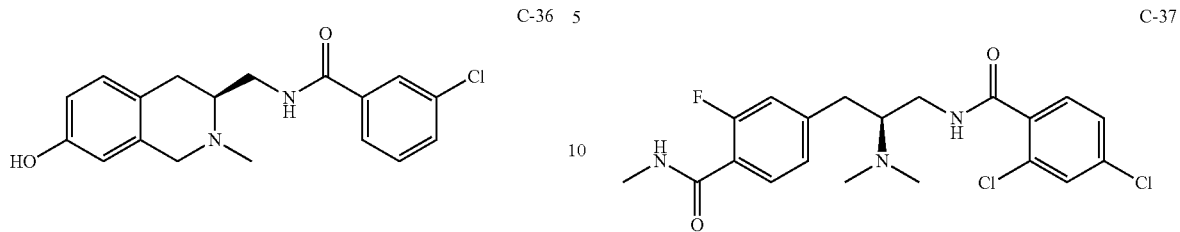

(S)-3-chloro-N-((7-hydroxy-2-methyl-1,2,3,4-tetrahydroisoquinolin-3-yl)methyl)benzamide (Compound C-36)

To a stirred solution of (S)-3-(aminomethyl)-2-methyl-1,2,3,4-tetrahydroisoquinolin-7-ol (21 mg, 0.11 mmol, 1 equiv) in dry DMF (1 mL) was added EDCI (32 mg, 0.17 mmol, 1.5 equiv), HOBt (23 mg, 0.17 mmol, 1.5 equiv), 3-chlorobenzoic acid (19 mg, 0.12 mmol, 1.1 equiv), and DIPEA (115 µL, 0.66 mmol, 6 equiv). After 4 h, the solution was diluted with water and extracted with EtOAc. The combined organic layers were washed with aq. NaHCO$_3$ and brine, dried over anhydrous sodium sulfate, and concentrated. The residue was purified by flash column chromatography over silica gel (0-15% MeOH in CH$_2$Cl$_2$) to afford a white solid (21.5 mg, 59% yield). $^1$H NMR (400 MHz, CDCl$_3$) δ 7.73 (s, 1H), 7.62 (d, J=7.58 Hz, 1H), 7.25-7.44 (m, 2H), 7.17-7.24 (m, 3H), 6.86 (d, J=8.31 Hz, 1H), 6.64 (dd, J=8.19, 1.83 Hz, 1H), 6.30 (br s, 1H), 3.63-3.85 (m, 3H), 3.48-3.63 (m, 1H), 3.11 (br s, 2H), 2.61-2.85 (m, 3H), 2.47 (s, 3H). LCMS: 331.1 [M]$^+$.

Examples C37-C40

(S)-2,4-dichloro-N-(2-(dimethylamino)-3-(3-fluoro-4-(methylcarbamoyl)phenyl)propyl) benzamide (Compound C-37)

To a stirred mixture Int-4F (0.09 g, 0.36 mmole) and DIEA (0.055 g, 0.43 mmole) in DCM at 0° C. was added 2,4-dichlorobenzoyl chloride (0.082 g, 0.39 mmole). After the addition was completed, the reaction mixture was stirred at 0° C. for 2 h. H$_2$O was added, extracted with DCM (3×). The combined extracts were dried over Na$_2$SO$_4$, concentrated and purified by ISCO (0-10% MeOH/DCM in 1% NH$_4$OH) to give (S)-2,4-dichloro-N-(2-(dimethylamino)-3-(3-fluoro-4-(methylcarbamoyl)phenyl) propyl) benzamide (0.133 g, 88.5%). $^1$H NMR (400 MHz, DMSO-d6): δ ppm 8.31 (t, J=5.50 Hz, 1H), 8.06-8.19 (m, 1H), 7.67 (d, J=1.96 Hz, 1H), 7.55 (t, J=7.95 Hz, 1H), 7.46-7.50 (m, 1H), 7.39 (d, J=8.31 Hz, 1H), 7.11-7.19 (m, 2H), 3.32-3.41 (m, 1H), 3.14-3.23 (m, 1H), 2.95 (quin, J=6.79 Hz, 1H), 2.79-2.88 (m, 1H), 2.77 (d, J=4.65 Hz, 3H), 2.61-2.69 (m, 1H), 2.28 (s, 6H). LC-MS (+ESI) M+H: 426.1.

The Compounds of Table 8 were prepared in the same method as described in Example C37 by using appropriate reagents.

TABLE 8

| Comp. No. | Yield/Analytical Data |
|---|---|
| C-38 | 58.0 mg (73%); LCMS (+ESI) M + H$^+$ = 466.2, M + Na$^+$ = 488.2. $^1$H NMR (400 MHz, METHANOL-d4) δ ppm 7.68 (s, 1 H) 7.51 (t, J = 7.95 Hz, 1 H) 7.41-7.47 (m, 2 H) 7.01 (dd, J = 7.95, 1.34 Hz, 1 H) 6.92-6.98 (m, 1 H) 3.18-3.37 (m, 3 H) 2.87 (dd, J = 13.82, 4.77 Hz, 1 H) 2.76 (s, 3 H) 2.49 (dd, J = 13.69, 8.56 Hz, 1 H) 2.23-2.41 (m, 5 H) 0.71 (dt, J = 12.11, 5.93 Hz, 1 H) 0.30-0.40 (m, 2 H) −0.01 (br d, J = 4.89 Hz, 2 H) |
| C-39 | white solid, 78 mg (76%). LCMS (+ESI) M + H+ = 426. $^1$H NMR (400 MHz, Chloroform-d) δ 8.04 (t, J = 8.07 Hz, 1 H), 7.80 (d, J = 1.96 Hz, 1 H), 7.55-7.47 (m, 2 H), 7.08 (dd, J = 7.95, 1.59 Hz, 1 H), 6.94 (dd, J = 12.72, 1.47 Hz, 1 H), 6.84 (br, s, 1 H), 6.65 (br, s, 1 H), 3.56 (ddd, J = 13.69, 6.85, 4.65 Hz, 1 H), 3.12-3.02 (m, 2 H), 3.03-3.00 (m, 3 H), 2.95-2.85 (m, 1 H), 2.48-2.40 (m, 1 H), 2.38 (s, 6 H) |
| C-40 | $^1$H NMR (400 MHz, DMSO-d6): δ ppm 8.05-8.18 (m, 1H), 7.87 (br t, J = 5.50 Hz, 1H), 7.55 (t, J = 7.95 Hz, 1H), 7.09-7.22 (m, 3H), 6.98-7.07 (m, 2H), 3.33-3.40 (m, 1H) 3.10-3.19 (m, 1H), 2.93-3.01 (m, 1H), 2.81-2.88 (m, 1H), 2.77 (d, J = 4.65 Hz, 3H), 2.61 (dd, J = 13.82, 6.97 Hz, 1H), 2.29 (s, 3H) 2.28 (s, 9H). LC-MS (+ESI) M + H: 386.2. |

Example C41

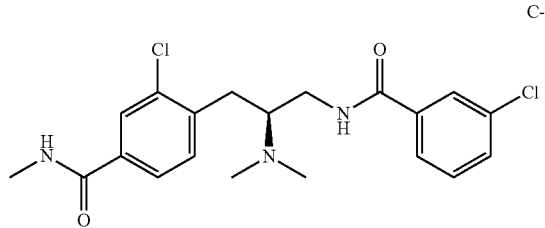

C-41

Synthesis of (S)-3-chloro-4-(3-(3-chlorobenzamido)-2-(dimethylamino)propyl)-N-methylbenzamide (Compound C-41)

The title compound was prepared according to the procedure as Example C17 starting with (S)-4-(3-amino-2-(dimethylamino)propyl)-3-chloro-N-methylbenzamide (42.3 mg, 0.157 mmol), 3-chlorobenzoic acid (29.5 mg, 0.188 mmol) to afford 46.0 mg (72%) of title compound. LCMS (+ESI) M+H$^+$=408.1, 410.1. $^1$H NMR (400 MHz, METHANOL-d4) δ ppm 7.84 (d, J=1.71 Hz, 1H) 7.73 (t, J=1.83 Hz, 1H) 7.68 (dd, J=7.95, 1.83 Hz, 1H) 7.65 (dt, J=7.83, 1.34 Hz, 1H) 7.50-7.55 (m, 1H) 7.39-7.48 (m, 2H) 3.50-3.57 (m, 1H) 3.38-3.45 (m, 1H) 3.25-3.31 (m, 1H) 3.19 (dd, J=13.45, 4.89 Hz, 1H) 2.91 (s, 3H) 2.82 (dd, J=13.45, 8.80 Hz, 1H) 2.46 (s, 6H).

Examples C42-C46

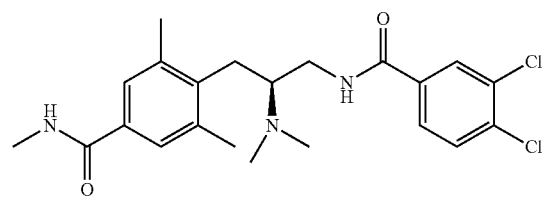

C-42

Synthesis of (S)-4-(3-(3,4-Dichlorobenzamido)-2-(dimethylamino)propyl)-N,3,5-trimethylbenzamide Hydrochloride (Compound C-42)

Int-5H (crude, 25 mg, 0.095 mmol) in DMF (1 mL) was added 3,4-dichlorobenzoic acid (22 mg, 0.11 mmol), HATU (43 mg, 0.11 mmol) and IPEA (25 mg, 0.19 mmol). The mixture was stirred at ambient temperature for 3 hours. Water and EtOAc were added. The organic layer was washed with water (×3) and concentrated. The residue was chromatographed (Silica gel, DCM/10% MeOH in DCM=9:1 to 0:1). The oil was added 2 N HCl (0.1 mL) in diethyl ether to afford the title compound as a salt, 2.8 mg (76%). LCMS (+ESI) M+H+=436. $^1$H NMR (400 MHz, methanol-d4) δ 7.96 (d, J=1.96 Hz, 1H), 7.73-7.60 (m, 4H), 4.08-3.96 (m, 2H), 3.40-3.23 (m, 3H), 3.22 (s, 3H), 3.16 (s, 3H), 2.96 (s, 3H), 2.55 (s, 6H).

The Compounds of Table 9 were prepared in the same method as described in Example C42 by using appropriate reagents.

TABLE 9

| Comp. No. | Yield/Analytical Data |
|---|---|
| C-43 | white solid, 2.1 mg (76%). LCMS (+ESI) M + H+ = 408. $^1$H NMR (400 MHz, chloroform-d) δ 7.41-7.26 (m, 4 H), 7.21-7.13 (m, 1 H), 6.92 (d, J = 7.83 Hz, 1 H), 6.70 (br, d, J = 6.11 Hz, 1 H), 6.12 (br, s, 1 H), 3.43 (ddd, J = 13.45, 6.97, 4.52 Hz, 1 H), 3.24-3.14 (m, 1 H), 3.03-2.90 (m, 5 H), 2.70 (dd, J = 13.08, 10.88 Hz, 1 H), 2.41 (s, 6 H), 2.39 (s, 6 H), 2.22-2.12 (m, 1 H), 1.03-0.81 (m, 4 H) |
| C-44 | LC-MS: 402.2 [M + 1]$^+$; $^1$H NMR (400 MHz, DMSO-d$_6$) δ 7.58 (m, 1H), 7.49 (m, 1H), 7.34-7.25 (m, 4H), 3.49-3.43 (m, 1H), 3.18-3.11 (m, 2H), 2.95-2.83 (m, 1H), 2.77 (s, 3H), 2.74-2.69 (m, 1H), 2.56 (s, 6H), 2.44 (s, 6H) |
| C-45 | (0.017 g, 41.4%). $^1$H NMR (400 MHz, DMSO-d6): δ ppm 8.21-8.28 (m, 1H), 8.12-8.21 (m, 1H), 7.75-7.80 (m, 2H), 7.49-7.54 (m, 1H), 7.41-7.47 (m, 4H), 3.62 (m, 1H) 3.31 (s, 6H), 2.99-3.08 (m, 1H), 2.84-2.94 (m, 1H), 2.76 (d, J = 4.65 Hz, 3H), 2.61-2.72 (m, 1 H), 2.53 (br d, J = 1.71 Hz, 1H), 2.35 (s, 6H). LC-MS (+ESI) M + H: 368.2 |
| C-46 | LC-MS: 369.2 [M + 1]$^+$; $^1$H NMR (400 MHz, DMSO-d$_6$) δ 8.58 (m, 1H), 8.03-8.00 (m, 1H), 7.96-7.91 (m, 2H), 7.52-7.47 (m, 3H), 3.55-3.31 (m, 3H), 3.26-2.21 (m, 1H), 3.18-3.09 (m, 1H), 2.90 (s, 3H), 2.88-2.87 (m, 1H), 2.56 (s, 6H), 2.44 (s, 6H) |

Examples C47-C49

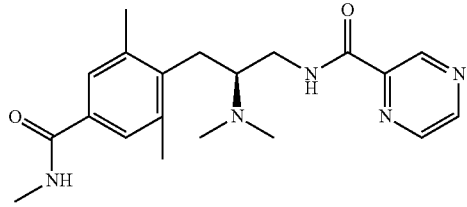

Synthesis of (S)—N-(3-(2,6-dimethyl-4-(methylcarbamoyl)phenyl)-2-(dimethylamino)propyl)pyrazine-2-carboxamide (Compound C-47)

Int-5H (40 mg, 0.15 mmol) was taken in dimethylformamide (0.6 ml) with pyrazine-2-carboxylic acid (22 mg, 0.18 mmol) and HATU (70 mg, 0.18 mmol) was added. Diisopropylethylamine (32 mL, 0.19 mmol) was then added and the solution was stirred at room temperature. After completion of the reaction, the reaction mixture was concentrated and the residue was purified by reverse phase chromatography using a gradient of water/acetonitrile in 0.1% TFA. The solution of the product was neutralized by adding aqueous NaOH solution. The product was extracted into dichloromethane, filtered through magnesium sulfate and then concentrated to give the product as a white powder (12 mg). $^1$H NMR (400 MHz, METHANOL-d4) δ ppm 9.05 (s, 1H) 8.59-8.71 (m, 1H) 8.43-8.53 (m, 1H) 7.74-8.11 (m, 1H) 7.36-7.46 (m, 2H) 3.83-4.01 (m, 2H) 3.44-3.69 (m, 1H) 3.21-3.35 (m, 1H) 2.90-3.19 (m, 6H), 2.76 (br s, 3H) 2.28-2.40 (m, 6H). MS ESI 370 [M+H].

The Compounds of Table 10 were prepared in the same method as described in Example C47 by using appropriate reagents.

Examples C50-C52

Synthesis of (S)-2,4-dichloro-N-(2-(dimethylamino)-3-(1H-indazol-5-yl)propyl) benzamide (Compound C-50)

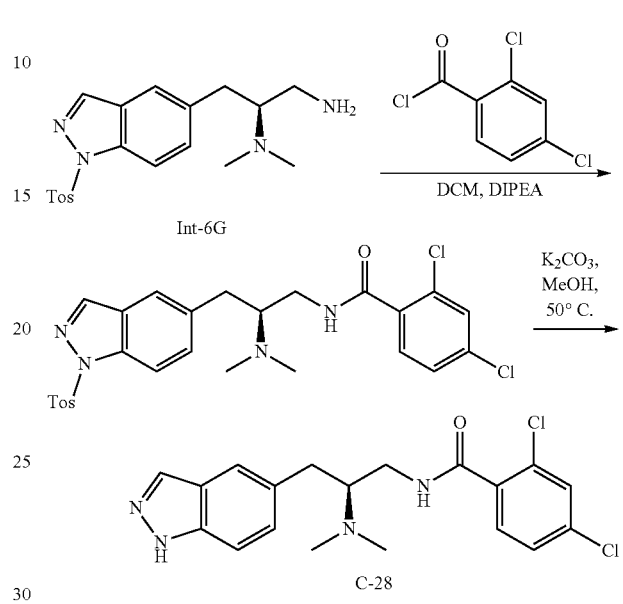

To a solution of Int-6G (200 mg, 0.54 mmol) in dry DCM (4 mL) was added DIPEA (0.32 mL, 1.88 mmol). The mixture was cooled to 0° C. and a solution of 2,4-dichlorobenzoyl chloride (16 mg, 0.69 mmol) in dry DCM (2 mL) was added dropwise over 5 min. The mixture was stirred from 0° C. to room temperature overnight. The crude mixture was diluted with ethyl acetate and washed with sat. NaHCO$_3$ solution and water. The organic layer was dried over anhydrous MgSO$_4$. After filtration and concentration, the crude material was purified on 12 g silica gel column, eluted with 10% MeOH in DCM: DCM (0-25%) to provide the desired intermediate (about 193 mg), which was not pure and used directly in the next step. LC-MS: 545.1 [M+1]$^+$.

The above intermediate was dissolved in methanol (7 mL), then potassium carbonate (400 mg, 2.89 mmol) was added. The resulting mixture was stirred at 55° C. for 2 h.

TABLE 10

| Comp. No. | Yield/Analytical Data |
|---|---|
| C-48 | (0.003 g, 6.8%). $^1$H NMR (400 MHz, MeOH-d4): δ ppm 8.47 (d, J = 1.96 Hz, 1H), 8.06 (d, J = 1.96 Hz, 1H), 7.46 (s, 2H), 3.50-3.65 (m, 1H), 3.23-3.27 (m, 1H,) 3.25 (br d, J = 5.14 Hz, 1H), 3.05-3.14 (m, 1H), 2.89-2.95 (m, 1H), 2.88 (s, 3H), 2.59 (br s, 6H), 2.43 (s, 6H). LC-MS (+ESI) M + H: 438.3 |
| C-49 | white powder (12 mg). $^1$H NMR (400 MHz, DMSO-d6)δ ppm 8.65-8.74 (br s, 1H) 8.24-8.32 (m, 2 H) 7.50-7.56 (m, 3 H) 3.62-3.70 (br s, 1 H) 3.10-3.20 (m, 2 H) 2.82-3.30 (m 3 H), 2.76-2.78 (s, 6 H) 2.52-2.54 (m, 3 H) 2.40 (s, 6 H) 2.27-2.37 (m, 3 H) |

The mixture was cooled to room temperature and diluted with ethyl acetate and water, the aqueous later was extracted with ethyl acetate twice. The combined organic layers were dried over anhydrous $Na_2SO_4$, filtered and concentrated. The crude material was purified on 80 g silica gel column, eluted with 10% MeOH in DCM: DCM (0-40%) to provide the desired product as a white solid. (42 mg, 20% for two steps). LC-MS: 391.1 [M+1]$^+$; $^1$H NMR (400 MHz, MeOD-d$_6$) δ 7.98 (s, 1H), 7.66 (s, 1H), 7.51-7.32 (m, 2H), 7.30-7.24 (m, 2H), 7.22 (m, 1H), 3.53-3.41 (m, 2H), 3.16-3.13 (m, 2H), 2.75-2.68 (m, 1H), 2.46 (s, 6H).

The Compounds of Table 11 were prepared in the same method as described in Example C50 by using appropriate reagents.

TABLE 11

| Comp. No. | Yield/Analytical Data |
| --- | --- |
| C-51 | (0.025 g, 42.2%); $^1$H NMR (400 MHz, DMSO-d6): δ ppm 12.92 (s, 1H), 7.98 (s, 1H), 7.75 (t, J = 5.38 Hz, 1H), 7.57 (s, 1H), 7.46 (d, J = 8.56 Hz, 1H), 7.22 (dd, J = 8.56, 1.47 Hz, 1H), 7.13 (d, J = 7.83 Hz, 1H), 6.92-7.04 (m, 2H), 3.32-3.39 (m, 1H), 3.13-3.22 (m, 1H), 2.87-3.00 (m, 2H), 2.56-2.65 (m, 1H), 2.30 (s, 6 H), 2.28 (d, J = 3.42 Hz, 6H). LC-MS (+ESI) M + H: 351.2. |
| C-52 | (0.011 g, 30%); 1H NMR (400 MHz, DMSO-d6): δ ppm 12.92 (s, 1H), 8.32 (br dd, J = 6.85, 3.67 Hz, 1H), 8.23 (d, J = 1.71 Hz, 1H), 7.96 (s, 1H), 7.56 (s, 1H), 7.47-7.52 (m, 1H), 7.44 (d, J = 8.56 Hz, 1H), 7.20 (dd, J = 8.56, 1.47 Hz, 1H), 3.27 (br s, 1H), 3.11-3.20 (m, 1H), 2.99 (dt, J = 8.80, 4.40 Hz, 1H), 2.85-2.94 (m, 1H), 2.51-2.55 (m, 1H), 2.47 (s, 3H), 2.33 (s, 6H), 2.28 (s, 3H). LC-MS (+ESI) M + H: 352.2. |

Examples C53-C54

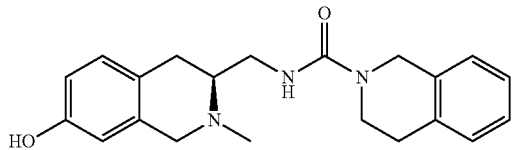

C-53

Synthesis of (S)—N-((7-hydroxy-2-methyl-1,2,3,4-tetrahydroisoquinolin-3-yl)methyl)-3,4-dihydroiso-quinoline-2(1H)-carboxamide (Compound C-53)

To a stirred solution of (S)-3-(aminomethyl)-2-methyl-1,2,3,4-tetrahydroisoquinolin-7-ol (75 mg, 0.39 mmol, 1 equiv) in dry DMF (2 mL) was added CDI (70 mg, 0.43 mmol, 1.1 equiv) under nitrogen. After 3.5 h, DIPEA (136 uL, 0.78 mmol, 2 equiv) and 1,2,3,4-tetrahydroisoquinoline (59 uL, 0.47 mmol, 1.2 equiv) were added and allowed to stir overnight. The solution was then concentrated under vacuum and the residue was purified by flash column chromatography over silica gel (0-15% MeOH in $CH_2Cl_2$ with 1% $NH_4OH$) to afford a white solid (78.8 mg, 57% yield). $^1$H NMR (400 MHz, CDCl$_3$) δ 9.17 (br s, 2H), 7.65 (s, 1H), 7.01-7.19 (m, 5H), 6.87 (d, J=8.31 Hz, 1H), 6.68 (dd, J=8.19, 2.57 Hz, 1H), 6.51 (d, J=2.45 Hz, 1H), 5.51 (t, J=4.65 Hz, 1H), 4.45-4.54 (m, 1H), 3.37-3.77 (m, 5H), 2.91-3.00 (m, 1H), 2.81 (t, J=5.87 Hz, 2H), 2.66-2.74 (m, 1H), 2.41 (s, 2H). LCMS: 352.2 [M]$^+$.

The Compounds of Table 12 were prepared in the same method as described in Example C53 by using appropriate reagents.

TABLE 12

| Comp. No. | Yield/Analytical Data |
| --- | --- |
| C-54 | white solid (19.9 mg, 50% yield). $^1$H NMR (400 MHz, CDCl$_3$) δ 7.85 (d, J = 2.20 Hz, 1 H), 7.59 (dd, J = 8.31, 1.96 Hz, 1 H), 7.47 (d, J = 8.31 Hz, 1 H), 6.87-6.95 (m, 2 H), 6.59 (dd, J = 8.19, 2.57 Hz, 1 H), 6.45 (d, J = 2.45 Hz, 1 H), 3.65-3.80 (m, 3 H), 3.46-3.54 (m, 3 H), 2.96-3.03 (m, 1 H), 2.67-2.81 (m, 2 H), 2.43 (s, 3 H). LCMS: 365.1 [M] |

Example C55

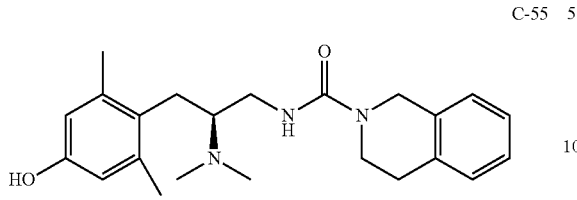

Synthesis of (S)—N-(2-(dimethylamino)-3-(4-hydroxy-2,6-dimethylphenyl)propyl)-3,4-dihydroisoquinoline-2(1H)-carboxamide (Compound C-55)

To a stirred solution of Int-1G (62.7 mg, 0.28 mmol, 1 equiv) in dry DMF (4 mL) was added CDI (47 mg, 0.29 mmol, 1.04 equiv) under nitrogen. After 3.5 h, DIPEA (100 uL, 0.56 mmol, 2 equiv) and 1,2,3,4-tetrahydroisoquinoline (42 uL, 0.34 mmol, 1.2 equiv) were added and allowed to stir overnight. The solution was then concentrated under vacuum and the residue was purified by flash column chromatography over silica gel (0-15% MeOH in CH$_2$Cl$_2$ with 1% NH$_4$OH) to afford a light yellow solid (53.0 mg, 50% yield). $^1$H NMR (400 MHz, CDCl$_3$) δ 7.66-7.85 (m, 1H), 7.26-7.39 (m, 4H), 6.75 (s, 2H), 5.58 (dd, J=5.62, 2.69 Hz, 1H), 4.57-4.67 (m, 2H), 3.67-3.74 (m, 2H), 3.33-3.47 (m, 2H), 2.97-3.11 (m, 4H), 2.71-2.86 (m, 1H), 2.55-2.67 (m, 6H), 2.35-2.49 (m, 6H). LCMS: 382.3 [M]$^+$.

Example C56

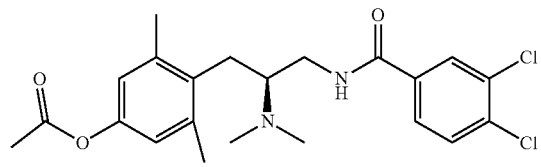

(S)-4-(3-(3,4-dichlorobenzamido)-2-(dimethylamino)propyl)-3,5-dimethylphenyl Acetate (Compound C-56)

To a stirred solution of (S)-3,4-dichloro-N-(2-(dimethylamino)-3-(4-hydroxy-2,6-dimethylphenyl)propyl)benzamide (Compound C-24) (200 mg, 0.46 mmol, 1 equiv) in dry THF (10 mL) was added NAHCO$_3$ (80 mg, 0.92 mmol, 2 equiv) and acetic anhydride (219 μL, 2.32 mmol, 5 equiv). After 18 h, the solution was filtered, rinsed with ethyl acetate, and concentrated. The residue was purified by flash column chromatography over silica gel (0-10% MeOH in CH$_2$Cl$_2$ with 1% NH$_4$OH) to afford a white solid (178 mg, 89% yield). $^1$H NMR (400 MHz, CDCl$_3$) δ 10.13 (br s, 1H), 7.85 (d, J=2.20 Hz, 1H), 7.66 (br t, J=4.40 Hz, 1H), 7.55 (dd, J=8.31, 2.20 Hz, 1H), 7.44 (d, J=8.31 Hz, 1H), 6.77 (s, 2H), 3.26-3.51 (m, 4H), 2.91-3.03 (m, 1H), 2.76 (dd, J=13.69, 11.49 Hz, 1H), 2.60 (s, 6H), 2.22-2.45 (m, 9H), 1.87-2.04 (m, 3H). LCMS: 437.1 [M].

Example C57

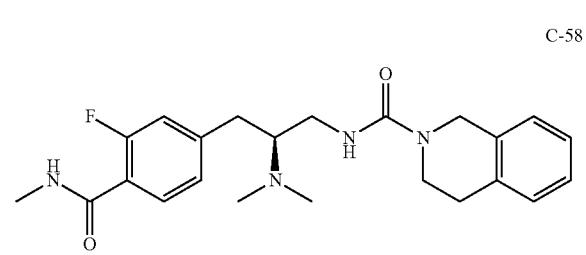 [SMILES: CNC(=O)c1ccc(C[C@@H](CNC(=O)N2CCc3ccccc3C2)N(C)C)cc1F]

(S)-4,5-dichloro-N-(2-(dimethylamino)-3-(4-hydroxy-2,6-dimethylphenyl)propyl)-2-fluorobenzamide (Compound C-57)

To a stirred solution of (Int-1G) (26 mg, 0.12 mmol, 1 equiv) in dry DMF (2 mL) was added EDCI (35 mg, 0.18 mmol, 1.5 equiv), HOBt (24 mg, 0.18 mmol, 1.5 equiv), 4,5-dichloro-2-fluorobenzoic acid (27 mg, 0.13 mmol, 1.1 equiv), and DIPEA (126 μL, 0.72 mmol, 6 equiv). After 4 h, the solution was diluted with water and extracted with EtOAc. The combined organic layers were washed with aq. NaHCO$_3$ and brine, dried over anhydrous sodium sulfate, and concentrated. The residue was purified by flash column chromatography over silica gel (0-15% MeOH in CH$_2$Cl$_2$ with 1% NH$_4$OH) to afford a white solid (22.5 mg, 45% yield). $^1$H NMR (400 MHz, CDCl$_3$) δ 8.08 (d, J=7.34 Hz, 1H), 7.45-7.62 (m, 1H), 7.21-7.27 (m, 1H), 6.48 (s, 2H), 3.42-3.50 (m, 1H), 3.12-3.24 (m, 1H), 2.83-2.96 (m, 2H), 2.53-2.65 (m, 1H), 2.35-2.47 (m, 6H), 2.22-2.30 (m, 6H). LCMS: 413.1 [M].

Example C58

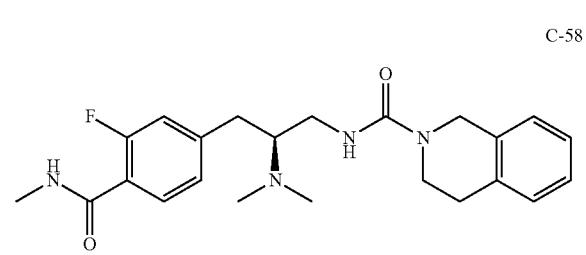 [SMILES: CNC(=O)c1ccc(C[C@@H](CNC(=O)N2CCc3ccccc3C2)N(C)C)cc1F]

(S)—N-(2-(dimethylamino)-3-(3-fluoro-4-(methylcarbamoyl)phenyl)propyl)-3,4-dihydroisoquinoline-2(1H)-carboxamide (Compound C-58)

To a stirred solution of Int-4F (50 mg, 0.2 mmol, 1 equiv) in dry DMF (2 mL) was added CDI (33 mg, 0.2 mmol, 1.1 equiv). After stirring at RT for 4 h under nitrogen, DIPEA (70 μL, 0.4 mmol, 2 equiv) and 1,2,3,4-tetrahydroisoquinoline (30 μL, 0.24 mmol, 1.2 equiv) were added and continued to stir overnight. The solution was concentrated under vacuum and the residue was purified by flash column chromatography over silica gel (0-15% MeOH in CH$_2$Cl$_2$ with 1% NH$_4$OH) to afford a white solid (26.1 mg, 32% yield). $^1$H NMR (400 MHz, CDCl$_3$) δ 7.99 (t, J=8.19 Hz, 1H), 6.99-7.20 (m, 6H), 6.93 (dd, J=12.84, 1.59 Hz, 1H), 6.69 (br dd, J=11.49, 4.65 Hz, 1H), 5.30 (br d, J=6.11 Hz, 1H), 4.47 (s, 2H), 3.47-3.60 (m, 2H), 3.37 (ddd, J=13.14, 7.03, 4.77 Hz, 1H), 2.81-3.06 (m, 9H), 2.39-2.47 (m, 1H), 2.32-2.39 (m, 6H). LCMS: 413.3 [M]⁺.

Example C59

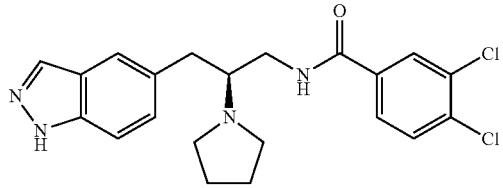

C-59

(S)—N-(3-(1H-indazol-5-yl)-2-(pyrrolidin-1-yl)propyl)-3,4-dichlorobenzamide (Compound C-59)

To a stirring solution of (S)-3,4-dichloro-N-(2-(pyrrolidin-1-yl)-3-(1-tosyl-1H-indazol-5-yl)propyl)benzamide (74.4 mg, 0.13 mmol, 1 equiv) in dry MeOH (3 mL) was added $K_2CO_3$ (90 mg, 0.65 mmol, 5 equiv) and heated to 70° C. After 3 h, the solution was filtered, washed with MeOH, and concentrated. The residue was purified by flash column chromatography over silica gel (0-15% MeOH in $CH_2Cl_2$ with 1% $NH_4OH$) to afford a white solid (46 mg, 85% yield). ¹H NMR (400 MHz, CDCl₃) δ 10.76 (br s, 1H), 7.99 (d, J=0.98 Hz, 1H), 7.76 (d, J=1.47 Hz, 1H), 7.54 (s, 1H), 7.35-7.49 (m, 3H), 7.17 (dd, J=8.56, 1.47 Hz, 1H), 6.85-6.97 (m, 1H), 3.41-3.47 (m, 2H), 3.18 (dd, J=13.45, 3.42 Hz, 1H), 2.86-2.96 (m, 1H), 2.67-2.85 (m, 5H), 1.86 (br s, 5H). LCMS: 417.1 [M].

Example C60

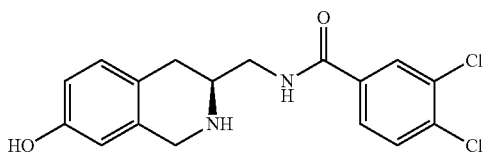

C-60

(S)-3,4-dichloro-N-((7-hydroxy-1,2,3,4-tetrahydroisoquinolin-3-yl)methyl)benzamide (Compound C-60)

To a stirring solution of tert-butyl (S)-3-((3,4-dichlorobenzamido)methyl)-7-hydroxy-3,4-dihydroisoquinoline-2(1H)-carboxylate (1.106 g, 2.45 mmol, 1 equiv) in dry dioxane (5 mL) was added 4M HCl in dioxanes (3 mL, 12.3 mmol, 5 equiv). After 4 h, the solution was filtered, washed with MeOH, and dried under vacuum. A small aliquot of the precipitate was purified by flash column chromatography over silica gel (0-25% MeOH in $CH_2Cl_2$ with 1% $NH_4OH$) to afford 15 mg of a white solid. ¹H NMR (400 MHz, CDCl₃) δ 8.11 (d, J=2.20 Hz, 1H), 7.85 (dd, J=8.44, 2.08 Hz, 1H), 7.68 (d, J=8.31 Hz, 1H), 7.47-7.55 (m, 1H), 7.07 (d, J=8.31 Hz, 1H), 6.73 (dd, J=8.56, 2.45 Hz, 1H), 6.62 (d, J=2.45 Hz, 1H), 4.24-4.34 (m, 2H), 3.63-3.83 (m, 3H), 3.34-3.37 (m, 1H), 2.99-3.07 (m, 1H), 2.86-2.96 (m, 1H). LCMS: 351.1 [M].

Example C61

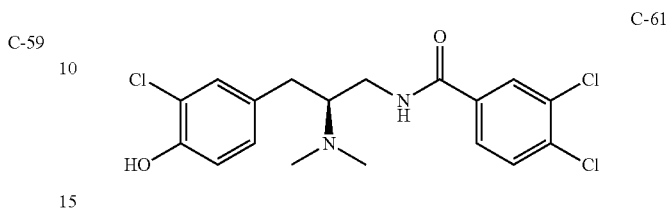

C-61

Synthesis of (S)-3,4-dichloro-N-(3-(3-chloro-4-hydroxyphenyl)-2-(dimethylamino)propyl)benzamide (Compound C-61)

The title compound was prepared in a manner similar to Example C8, starting with (S)-4-(3-amino-2-(dimethylamino)propyl)-2-chlorophenol (Int-3H, 53.8 mg, 0.235 mmol), 3,4-dichlorobenzoic acid (44.9 mg, 0.235 mmol) to afford 51.3 mg (55%) of title compound. LCMS (+ESI) M+H⁺=401.1, 403.1. ¹H NMR (400 MHz, DMSO-d6) δ ppm 9.82 (s, 1H) 8.35 (t, J=5.50 Hz, 1H) 8.01 (d, J=1.71 Hz, 1H) 7.71-7.78 (m, 2H) 7.17 (d, J=1.96 Hz, 1H) 6.97 (dd, J=8.31, 1.96 Hz, 1H) 6.85 (d, J=8.07 Hz, 1H) 3.39 (ddd, J=13.45, 7.83, 5.62 Hz, 1H) 3.12-3.20 (m, 1H) 2.84-2.97 (m, 1H) 2.69-2.75 (m, 1H) 2.39 (dd, J=13.94, 7.83 Hz, 1H) 2.27 (s, 6H).

Examples C62-C64

Synthesis of (S)-3,4-dichloro-N-(2-((cyclopropylmethyl)(methyl)amino)-3-(1H-indazol-5-yl)propyl)benzamide (Compound C-62)

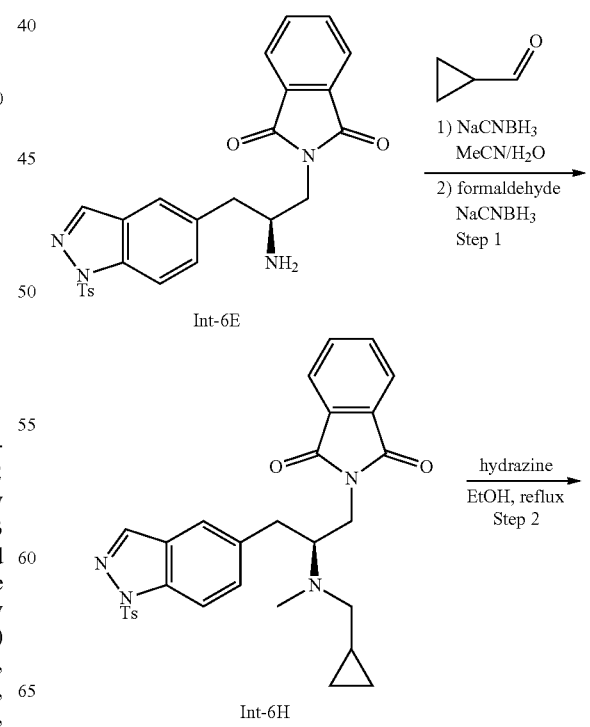

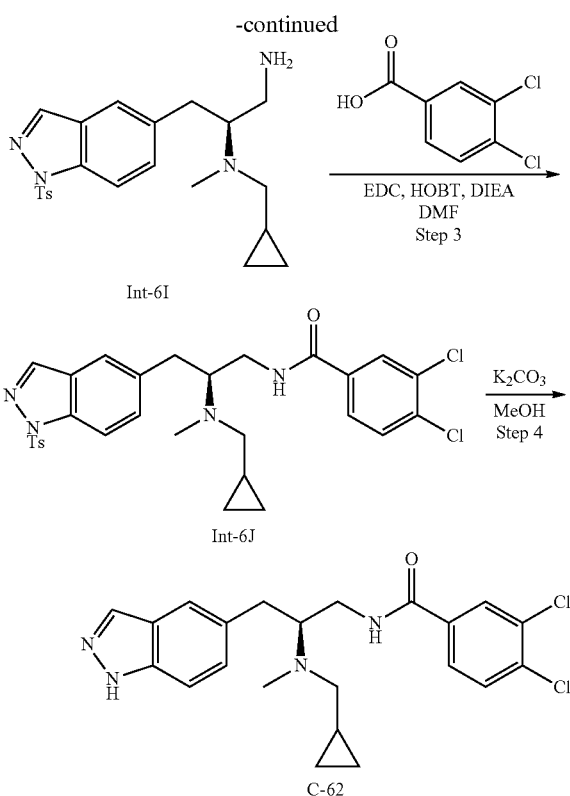

Step 1: Preparation of (S)-2-(2-((cyclopropylmethyl)(methyl)amino)-3-(1-tosyl-1H-indazol-5-yl)propyl)isoindoline-1,3-dione (Int-6H)

To a stirred mixture of Int-6E (0.3 g, 0.59 mmole), in MeCN/H2O (4:1, 10 mL) was added cyclopropanecarbaldehyde (0.045 g, 0.65 mmole). The stirring was continued for 30 minutes, NaCNBH3 (0.055 g, 0.88 mmole) was added and stirred for 30 minutes. 37% formaldehyde (0.14 g, 1.76 mmole) and continued to stir for 15 minutes, NaCNBH3 (0.055 g, 0.88 mmole) was finally added. The reaction mixture was stirred for 1 h, saturated aqueous NH4Cl was added, extracted with DCM (3×). The combined extracts were dried over Na2SO4, concentrated and purified by ISCO (0-10% MeOH/DCM) to give (S)-2-(2-((cyclopropylmethyl) (methyl)amino)-3-(1-tosyl-1H-indazol-5-yl)propyl) isoindoline-1,3-dione (0.26 g, 80.2%). LC-MS (+ESI) M+H: 543.2.

Step 2: Preparation of (S)—N2-(cyclopropylmethyl)-N2-methyl-3-(1-tosyl-1H-indazol-5-yl)propane-1,2-diamine (Int-6I)

To a stirred mixture of Int-6H (0.25 g, 0.46 mmole) in EtOH (5 mL) was added hydrazine (0.074 g, 2.31 mmole). The reaction mixture was heated to 90° C. for 2 h, cooled to RT, and the solid was filtered off, washed with EtOAc. The filtrate was concentrated and purified by ISCO (0-15% MeOH/DCM in 1% NH4OH) to give Int-6I (0.16 g, 83.7%). LC-MS (+ESI) M+H: 413.2.

Step 3: Preparation of (S)-3,4-dichloro-N-(2-((cyclopropylmethyl) (methyl)amino)-3-(1-tosyl-1H-indazol-5-yl)propyl)benzamide (Int-6J)

A mixture of Int-6I (0.16 g, 0.38 mmole), 3,4-dichlorobenzoic acid (0.09 g, 0.38 mmole), HOBT (0.03 g, 0.2 mmole), EDC (0.08 g, 0.46 mmole), and DIEA (0.13 g, 0.96 mmole) in DMF (3 mL) was stirred for 16 h. H2O was added and the solid was collected, washed with H2O, dried and purified by ISCO (50% EtOAc/DCM) to give Int-6J (0.18 g, 81.1%). LC-MS (+ESI) M+H: 585.2.

Step 4: Synthesis of (S)-3,4-dichloro-N-(2-((cyclopropylmethyl)(methyl)amino)-3-(1H-indazol-5-yl) propyl) benzamide (Compound C-62)

A mixture of Int-6J (0.18 g, 0.31 mmole) and K2CO3 (0.22 g, 1.56 mmole) in MeOH (5 mL) was heated to 70° C. in 2 h. The mixture was cooled to RT, H2O was added, adjusted pH=6-7 with 5N HCl, extracted with DCM (3×). The extracts were dried over Na2SO4, concentrated, and purified by ISCO (0-15% MeOH/DCM in 1% NH4OH) to give Compound C-65 (0.054 g, 39.7%). $^1$H NMR (400 MHz, DMSO-d6): δ ppm 12.92 (s, 1H), 8.32 (t, J=5.14 Hz, 1H), 7.95 (dt, J=5.01, 1.04 Hz, 2H), 7.72 (d, J=1.22 Hz, 2H), 7.55 (s, 1H), 7.43 (d, J=8.56 Hz, 1H), 7.21 (dd, J=8.56, 1.47 Hz, 1H), 3.37-3.46 (m, 1H), 3.12-3.22 (m, 2H), 2.90 (dd, J=13.94, 4.89 Hz, 1H), 2.58 (dd, J=13.57, 7.46 Hz, 1H), 2.39 (t, J=6.60 Hz, 2H), 2.35 (s, 3H), 0.68-0.79 (m, 1H), 0.38 (dd, J=7.70, 5.75 Hz, 2H), 0.04 (br d, J=1.96 Hz, 2H). LC-MS (+ESI) M+H: 431.2.

The Compounds of Table 13 were prepared in the same method as described in Example C62 by using appropriate reagents.

TABLE 13

| Comp. No. | Yield/Analytical Data |
|---|---|
| C-63 | (0.034 g, 71%); $^1$H NMR (400 MHz, DMSO-d6): δ ppm 12.95 (s, 1 H), 8.44 (t, J = 5.26 Hz, 1H), 7.92-8.00 (m, 2H), 7.73 (s, 2H), 7.61 (s, 1H), 7.45 (d, J = 8.31 Hz, 1H,) 7.25 (d, J = 8.56 Hz, 1H), 3.39-3.48 (m, 1H), 3.23-3.32 (m, 2H), 3.19 (dt, J = 14.73, 5.35 Hz, 2H), 2.86-2.94 (m, 1H), 2.73 (dd, J = 13.82, 7.46 Hz, 1H), 2.47 (s, 3H). LC-MS (+ESI) M + H: 459.1. |
| C-64 | (60 mg, 48%). 1H NMR (400 MHz, CHLOROFORM-d) δ ppm 10.78 (br s, 1 H) 8.02 (s, 1 H) 7.85 (br s, 1 H) 7.44-7.60 (m, 3 H) 7.29-7.43 (m, 1 H) 7.11-7.28 (m, 2 H) 3.62 (br s, 1 H) 3.16 (br d, J = 13.45 Hz, 3 H) 2.81 (br s, 2 H) 2.58 (br s, 3H) 1.17 (br s, 6 H) LC-MS (+ESI) M + H: 420. |

Example C65

Synthesis of (S)-4-chloro-N-(2-(dimethylamino)-3-(2H-indazol-5-yl)propyl)-3-fluorobenzamide (Compound C-65)

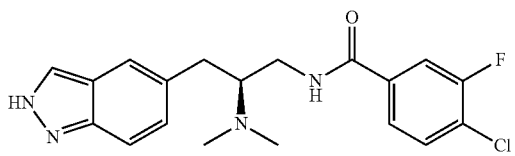

C-65

The title compound was prepared in the same method as described in previous examples. $^1$H NMR (400 MHz, CHLOROFORM-d) δ ppm 10.5 (br s, 1H) 7.99 (d, J=0.98 Hz, 1H) 7.54 (s, 1H) 7.49 (dd, J=10.03, 1.22 Hz, 1H) 7.37-7.42 (m, 3H) 7.17 (dd, J=8.56, 1.71 Hz, 1H) 6.98 (br d, J=5.62 Hz, 1H) 3.59 (ddd, J=13.69, 6.73, 4.77 Hz, 1H) 3.12-3.20 (m, 2H) 2.90-2.98 (m, 1H) 2.38-2.54 (m, 7H)

Example C66

Synthesis of (S)—N-(2-(dimethylamino)-3-(4-hydroxyphenyl)propyl)-[1,1'-biphenyl]-2-carboxamide (Compound C-66)

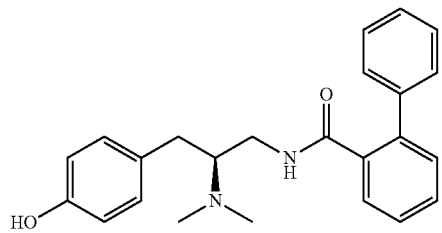

C-66

The title compound was prepared in the same method as described in previous examples. $^1$H NMR (400 MHz, CHLOROFORM-d) δ ppm 7.70 (d, J=8.0 Hz, 1H) 7.46-7.50 (m, 1H) 7.35-7.45 (m, 7H), 6.89 (d, J=8.0 Hz, 2H) 6.79 (d, J=8.0 Hz, 2H) 6.20 (d, J=6.0 Hz, 1H) 3.38-3.44 (m, 1H) 2.70-2.76 (m, 1H) 2.03-2.14 (m, 2H) 1.97 (s, 6H)

Example C67

Synthesis of (S)—N-(3-(4-carbamoylphenyl)-2-(dimethylamino)propyl)-2,4-dimethylbenzamide (Compound C-67)

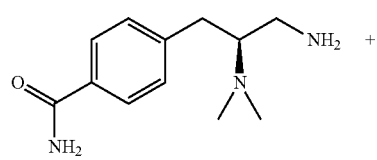

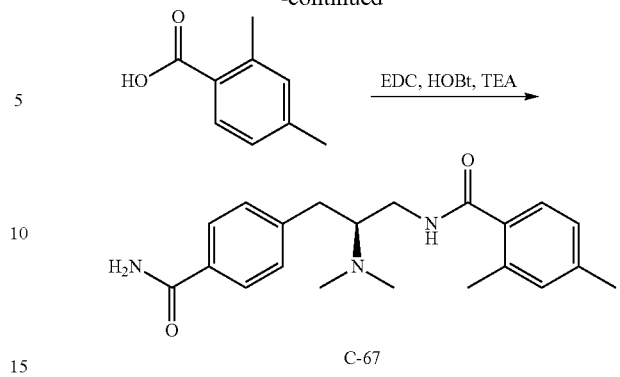

C-67

(S)—N-(3-(4-carbamoyl phenyl)-2-(dimethylamino)propyl)-2,4-dimethylbenzamide was synthesized according to the general procedure using (S)-4-(3-amino-2-(dimethylamino)propyl)benzamide and 2,4-dimethylbenzoic acid as the starting materials. LC-MS: 354.2 [M+H]$^+$; $^1$H NMR (400 MHz, DMSO-d6) δ 7.91 (br s, 1H), 7.87 (br t, 1H, J=4.8 Hz), 7.79 (d, 2H, J=7.8 Hz), 7.30 (d, 3H, J=7.8 Hz), 7.14 (d, 1H, J=7.6 Hz), 7.06-6.97 (m, 2H), 3.13 (m, 1H), 2.95 (m, 1H), 2.85 (dd, 1H, J=13.6, 6.4 Hz), 2.58 (dd, 1H, J=13.6, 7.2 Hz), 2.28 (s, 12H).

Example C68

Synthesis of (S)-4-(2-(dimethylamino)-3-(2-methoxybenzamido)propyl)-N,3,5-trimethylbenzamide (Compound C-68)

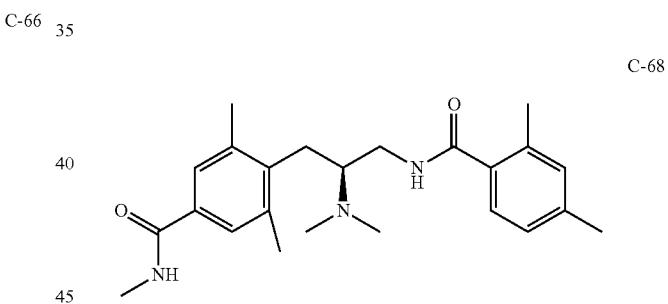

C-68

The title compound was prepared in the same method as described in previous examples. $^1$H NMR (400 MHz, DMSO-d6): δ ppm 8.33 (br t, J=4.52 Hz, 1H), 8.17 (q, J=4.48 Hz, 1H), 7.73 (dd, J=7.83, 1.71 Hz, 1H), 7.35-7.43 (m, 3H), 7.06 (d, J=7.83 Hz, 1H), 6.94 (td, J=7.46, 0.98 Hz, 1H), 3.82 (s, 3H), 3.08-3.15 (m, 2H), 2.78-2.88 (m, 2H), 2.67 (d, J=4.40 Hz, 3H), 2.54-2.61 (m, 1H), 2.34 (s, 6H), 2.28 (s, 6H). LC-MS (+ESI) M+H: 398.2.

Example D1

In Vitro Activity

MOR Agonist and Antagonist Assays

MOR cAMP Agonist Assay

The ability of test compounds to activate the mu opioid receptor (MOR) assay was evaluated at Multispan Inc. (26219 Eden Landing Road, Hayward, Calif. 94545) in stably transfected cell CHO cell expressing the mOR receptor (CHO-K1 Multispan Inc., Cat #C1350-1a) by measuring cAMP levels in cells treated with the test compounds using a commercial kit (cAMP Hi-Range Kit; Cisbio, Cat #62AM6PEC). The activity of test compounds is recorded in Table 14, below, as their $EC_{50}$, the concentration the test compound, which induces a response halfway between the baseline and its maximal response. With respect to MOR activity, "+++" denotes an $EC_{50}$ less than 100 nM; "++" denotes an $EC_{50}$ from 100 nM to 1,000 nM; and "+" denotes an $EC_{50}$ greater than 1,000 nM.

MOR cAMP Antagonist Assay

The ability of test compounds to antagonize or inhibit the mu opioid receptor (MOR) assay was evaluated at Multispan Inc. (26219 Eden Landing Road, Hayward, Calif. 94545) in stably transfected cell CHO cell expressing the mOR receptor (CHO-K1 Multispan Inc., Cat #C1350-1a) by measuring cAMP levels in cells treated with the test compounds using a commercial kit (cAMP Hi-Range Kit; Cisbio, Cat #62AM6PEC) after activation of the receptor with the mOR agonist DAMGO at the $EC_{80}$. The activity of test compounds is recorded in Table 14, below, as their $IC_{50}$, the concentration the test compound, which induces a response halfway between the baseline and its maximal response. With respect to MOR activity, "+++" denotes an $IC_{50}$ less than 100 nM; "++" denotes an $IC_{50}$ from 100 nM to 1,000 nM; and "+" denotes an $IC_{50}$ greater than 1,000 nM.

MOR GTPγS Agonist Assay

The ability of test compounds to activate the mu opioid receptor (MOR) assay was evaluated at Multispan Inc. (26219 Eden Landing Road, Hayward, Calif. 94545) in stably transfected cell CHO cell expressing the MOR receptor (CHO-K1 Multispan Inc., Cat #C1350-1a). Membranes obtained from the stable cell lines over-expressing MOR were subjected to GTPγS assay using SPA beads (Perkin Elmer, Cat #RPNQ0001). The activity of test compounds is recorded in Table 14, below, as their $EC_{50}$, the concentration the test compound, which induces a response halfway between the baseline and its maximal response. With respect to MOR activity, "+++" denotes an $EC_{50}$ less than 100 nM; "++" denotes an $EC_{50}$ from 100 nM to 1,000 nM; and "+" denotes an $EC_{50}$ greater than 1,000 nM.

KOR cAMP Antagonist Assay

The ability of compounds to inhibit the kappa opioid receptor (KOR) was evaluated at Multispan Inc. (26219 Eden Landing Road, Hayward, Calif. 94545) in stably transfected cell CHO cell expressing the kOR receptor (CHO-K1 Multispan Inc., Cat #C1352-1a) by measuring cAMP levels after activation of the kOR receptor with dynorphin B in cells treated with the compound. cAMP levels were measured with a commercial kit (cAMP Hi-Range Kit; Cisbio, Cat #62AM6PEC). The activity of test compounds is recorded in Table 14, below, as the $IC_{50}$, the concentration at which test compounds inhibit 50% of the activation induced by dynorphin B. With respect to KOR activity, "+++" denotes an $IC_{50}$ less than 100 nM; "++" denotes an $IC_{50}$ from 100 nM to 1,000 nM; and "+" denotes an $IC_{50}$ greater than 1,000 nM.

TABLE 14

Activity of Representative Compounds

| Compound No. | mOR cAMP $EC_{50}$ | MOR GTPγS $EC_{50}$ | MOR cAMP $IC_{50}$ | kOR cAMP $IC_{50}$ |
|---|---|---|---|---|
| A-1 | + | --- | --- | ++ |
| A-2 | + | --- | --- | + |
| A-3 | +++ | --- | --- | + |
| A-4 | +++ | --- | --- | +++ |
| A-5 | ++ | --- | --- | +++ |
| A-6 | ++ | --- | --- | ++ |
| A-7 | + | --- | --- | ++ |
| A-8 | + | --- | --- | + |
| A-9 | + | --- | --- | + |
| A-10 | + | --- | --- | ++ |
| A-11 | + | --- | --- | ++ |
| A-22 | --- | +++ | +++ | --- |
| A-23 | --- | +++ | +++ | --- |
| B-1 | +++ | --- | --- | +++ |
| B-2 | +++ | --- | --- | + |
| B-3 | +++ | --- | --- | + |
| B-4 | +++ | --- | --- | ++ |
| B-5 | +++ | --- | --- | +++ |
| B-6 | +++ | --- | --- | ++ |
| B-7 | +++ | --- | --- | +++ |
| B-8 | +++ | --- | --- | ++ |
| B-9 | ++ | --- | --- | + |
| B-10 | ++ | --- | --- | ++ |
| B-11 | ++ | --- | --- | + |
| B-12 | + | --- | --- | +++ |
| B-13 | +++ | --- | --- | +++ |
| B-14 | +++ | --- | --- | + |
| B-15 | + | --- | --- | + |
| B-16 | + | --- | --- | + |
| B-17 | +++ | --- | --- | ++ |
| B-18 | --- | --- | --- | ++ |
| B-19 | +++ | --- | --- | + |
| B-20 | +++ | --- | --- | + |
| B-21 | +++ | --- | --- | --- |
| B-22 | +++ | --- | --- | --- |
| B-23 | +++ | --- | --- | --- |
| B-24 | --- | --- | --- | ++ |
| B-25 | ++ | --- | --- | --- |
| B-26 | +++ | --- | --- | --- |
| B-27 | +++ | --- | --- | --- |
| B-28 | +++ | --- | --- | --- |
| B-29 | +++ | --- | --- | --- |
| B-30 | --- | --- | +++ | +++ |
| B-31 | +++ | --- | +++ | +++ |
| B-32 | ++ | --- | --- | --- |
| B-33 | --- | --- | --- | --- |
| B-34 | +++ | --- | --- | --- |
| B-35 | --- | --- | --- | --- |
| B-36 | --- | --- | +++ | +++ |
| B-37 | --- | --- | --- | --- |
| B-38 | --- | --- | --- | --- |
| B-39 | +++ | --- | --- | + |
| B-40 | +++ | --- | --- | + |
| B-41 | +++ | --- | ++ | ++ |
| B-42 | +++ | --- | +++ | ++ |
| B-43 | + | --- | --- | + |
| B-44 | --- | --- | --- | + |
| B-45 | --- | --- | --- | --- |
| B-46 | +++ | --- | --- | + |
| B-47 | +++ | --- | +++ | --- |
| B-48 | + | --- | +++ | +++ |
| B-49 | +++ | --- | --- | + |
| B-50 | +++ | --- | --- | --- |
| B-51 | +++ | --- | --- | --- |
| B-52 | +++ | --- | --- | --- |
| B-53 | +++ | --- | --- | --- |
| B-54 | +++ | --- | --- | ++ |
| B-55 | --- | --- | +++ | +++ |
| B-56 | +++ | --- | --- | +++ |
| B-57 | --- | --- | --- | --- |
| B-58 | ++ | --- | --- | + |
| B-59 | +++ | --- | --- | --- |
| B-60 | +++ | --- | --- | +++ |
| B-61 | +++ | --- | --- | + |
| B-62 | +++ | --- | --- | ++ |
| C-1 | --- | --- | +++ | --- |
| C-2 | --- | --- | +++ | --- |
| C-3 | --- | + | --- | --- |
| C-4 | --- | +++ | --- | --- |

TABLE 14-continued

Activity of Representative Compounds

| Compound No. | mOR cAMP $EC_{50}$ | MOR GTPγS $EC_{50}$ | MOR cAMP $IC_{50}$ | kOR cAMP $IC_{50}$ |
|---|---|---|---|---|
| C-5 | --- | +++ | --- | --- |
| C-6 | --- | +++ | --- | --- |
| C-7 | --- | --- | +++ | --- |
| C-8 | --- | --- | +++ | --- |
| C-9 | --- | | | |
| C-10 | --- | ++ | --- | --- |
| C-11 | --- | +++ | --- | --- |
| C-12 | --- | +++ | --- | --- |
| C-13 | --- | +++ | --- | --- |
| C-14 | --- | +++ | --- | --- |
| C-15 | --- | +++ | --- | --- |
| C-16 | --- | +++ | --- | --- |
| C-17 | --- | +++ | --- | --- |
| C-18 | --- | +++ | --- | --- |
| C-19 | --- | ++ | --- | --- |
| C-20 | --- | + | --- | --- |
| C-21 | --- | + | --- | --- |
| C-22 | --- | +++ | + | ++ |
| C-23 | --- | ++ | --- | --- |
| C-24 | --- | +++ | +++ | +++ |
| C-25 | --- | +++ | --- | --- |
| C-26 | --- | +++ | +++ | --- |
| C-27 | --- | +++ | +++ | --- |
| C-28 | --- | +++ | +++ | --- |
| C-29 | --- | +++ | --- | --- |
| C-30 | --- | +++ | +++ | --- |
| C-31 | --- | +++ | +++ | --- |
| C-32 | --- | +++ | ++ | --- |
| C-33 | --- | +++ | +++ | --- |
| C-34 | --- | +++ | +++ | --- |
| C-35 | --- | +++ | +++ | --- |
| C-36 | --- | +++ | --- | --- |
| C-35 | --- | +++ | --- | --- |
| C-38 | --- | +++ | --- | --- |
| C-39 | --- | +++ | +++ | --- |
| C-40 | --- | +++ | +++ | + |
| C-41 | --- | +++ | --- | --- |
| C-42 | --- | +++ | --- | --- |
| C-43 | --- | +++ | --- | --- |
| C-44 | --- | +++ | --- | --- |
| C-45 | --- | +++ | --- | + |
| C-46 | --- | + | --- | --- |
| C-47 | --- | + | --- | --- |
| C-48 | --- | ++ | --- | --- |
| C-49 | --- | ++ | --- | --- |
| C-50 | --- | ++ | --- | --- |
| C-51 | --- | ++ | --- | --- |
| C-52 | --- | + | --- | --- |
| C-53 | --- | +++ | --- | --- |
| C-54 | --- | +++ | +++ | --- |
| C-55 | --- | + | --- | --- |
| C-56 | --- | --- | +++ | --- |
| C-57 | --- | +++ | +++ | --- |
| C-58 | --- | +++ | --- | --- |
| C-59 | --- | ++ | +++ | --- |
| C-60 | --- | +++ | +++ | --- |
| C-61 | --- | +++ | +++ | --- |
| C-62 | --- | ++ | --- | --- |
| C-63 | --- | + | --- | --- |
| C-64 | --- | +++ | +++ | --- |
| C-65 | --- | +++ | --- | --- |
| C-66 | --- | + | + | ++ |
| C-67 | --- | +++ | --- | + |
| C-68 | --- | +++ | --- | --- |

Example D2

In Vivo Activity

Hot Plate Assay

Male Sprague-Dawley rats weighing 275-300 grams were used in the study, n=8-10 per group. Animals are injected SC with 0.9% normal saline solution. At 15, 45, and 80 min after the injection, animals were placed onto a hotplate set to 52 degrees centigrade, and baseline latency is recorded (baseline latency=average time to $2^{nd}$ withdrawal response consisting of either a lick of a rear paw, shaking a rear paw, backwards walking or jumping). A day later animals were injected SC with test compounds either in vehicle solution, or with a mix of compounds in solution. Next the test latency was recorded (test latency=time to withdrawal on the hotplate measured at 15, 45, 80, 120, 180 and 240 min using the procedure described). Times were then converted to % maximum possible effect (% MPE)=(test_latecy−baseline_latency)/(30 sec−baseline_latency); where 30 sec is the cutoff where the animal is removed if no response ifs observed as it is the time point at which injury is expected to occur.

FIG. 1 shows that MOR agonist Compound B-56 is analgesic in the hotplate test as it increased the time to exhibit a withdrawal response in the hotplate test. This is indicative of central activation of MORs as peripheral MOR agonists have been shown to have limited efficacy in this test (Emerich, D. F., et al., Brain Research, 1998, 801 (1-2):259-266). Further, MOR antagonists Compound B-15 blocks in vivo the analgesic activity of the agonist Compound B-56, when co-dosed, but has no effect on its own (see FIG. 1).

Respiratory Depression Assay

Figure 2:
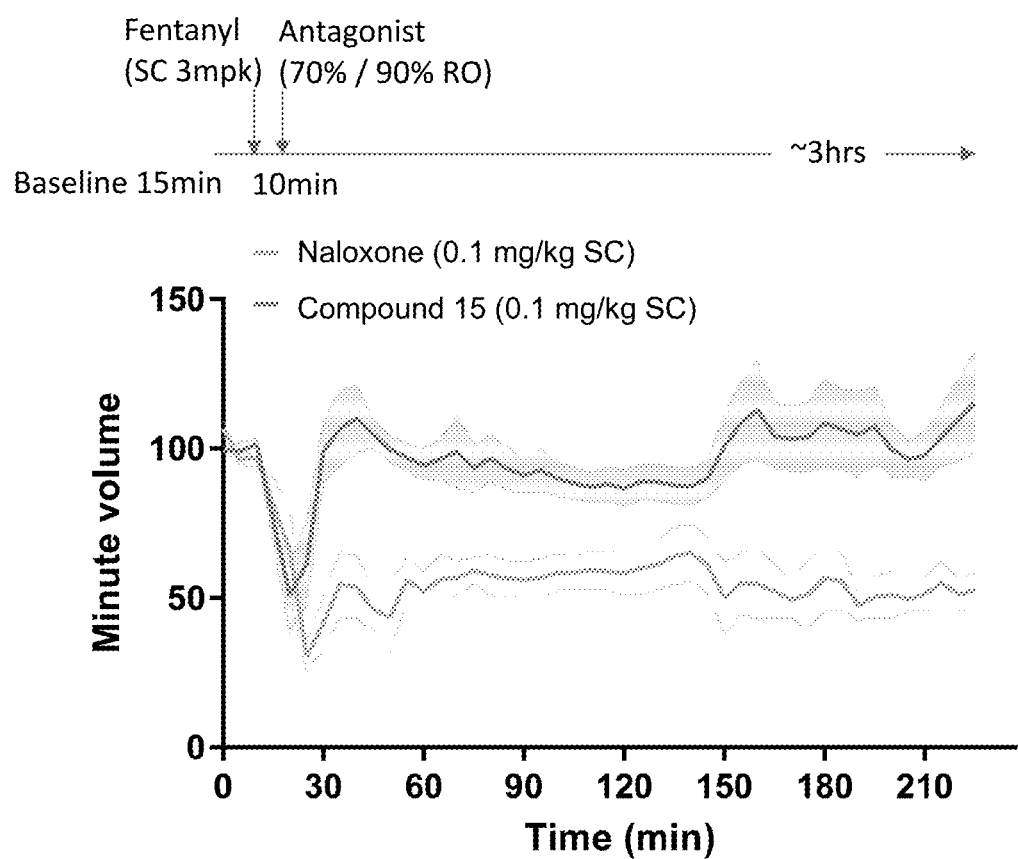
FIG. 2 illustrates that MOR antagonist Compound B-15 blocks in vivo the respiratory depression of the MOR agonist fentanyl.

Male Sprague-Dawley rats weighing 275-300 grams were used in this study, n=4-6 per group. The animals were placed into a whole body unrestrained plethysmograph, and baseline breathing was recorded for 15 minutes. Next, animals were injected SC with fentanyl (3 mg/kg SC), and breathing was monitored for 10-12 min. Next animals were injected with test compound, either naloxone (0.1 mg/kg SC) or Compound B-15 (30 mg/kg SC), and breathing was recorded for up to 4 hrs. Post-hoc an experimenter blinded to the treatment conditions analyzed the trace as previously described (Laferriere, A., et al., Developmental Brain Research, 2005, 156(2):210-217) and minute volume (MV=tidal volume×breaths per minute) was calculated for each animal. Data is presented in FIG. 2 as a % of the average of the baseline period (post drug MV/average baseline MV).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

The invention claimed is:

1. A compound having the structure of Formula (I):

Formula (I)

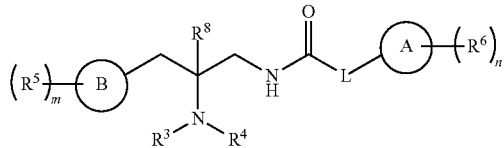

or an isomer, racemate, or isotope, or pharmaceutically acceptable salt thereof, wherein:

ring A is carbocycle or heterocycle;
ring B is carbocycle or heterocycle;
L is a ring C;
ring C is a $C_3$-$C_7$ cycloalkyl or 3-7 membered heterocycloalkyl, substituted with 0-5 $R^7$;
$R^1$ and $R^2$ are each independently H, $(C_1$-$C_6)$alkyl, or $C_3$-$C_7$ cycloalkyl substituted with 0-5 halo;
$R^3$ and $R^4$ are each independently H, $(C_1$-$C_6)$alkyl, $(C_1$-$C_6)$haloalkyl, carbocycle, or carbocyclealkyl;
each $R^5$ is independently —C(O)NR$^1$R$^2$, —NR$^1$C(O)R$^2$, —OC(O)R$^1$, —C(O)OR$^1$, —S(O)$_t$NR$^1$R$^2$, —NR$^1$S(O)$_t$R$^2$, —OH, —CN, halo, oxo, $(C_1$-$C_6)$alkyl, $(C_1$-$C_6)$haloalkyl, $(C_1$-$C_6)$alkoxy, or carbocycle; or $R^3$ and one $R^5$, together with the atoms to which they are connected, form a 5-7 membered heterocycle;
each $R^6$ is independently —C(O)NR$^1$R$^2$, —NR$^1$C(O)R$^2$, —OC(O)R$^1$, —C(O)OR$^1$, —S(O)$_t$NR$^1$R$^2$, —NR$^1$S(O)$_t$R$^2$, —OH, —CN, halo, oxo, $(C_1$-$C_6)$alkyl, $(C_1$-$C_6)$haloalkyl, $(C_1$-$C_6)$alkoxy, or carbocycle;
each $R^7$ is independently —C(O)NR$^1$R$^2$, —NR$^1$C(O)R$^2$, —OC(O)R$^1$, —C(O)OR$^1$, —S(O)$_t$NR$^1$R$^2$, —NR$^1$S(O)$_t$R$^2$, —OH, 13 CN, halo, oxo, $(C_1$-$C_6)$alkyl, $(C_1$-$C_6)$haloalkyl, $(C_1$-$C_6)$alkoxy, or carbocycle;
$R^8$ is H or $(C_1$-$C_6)$alkyl;
m is 1-5;
n is 0-5; and
t is 0.

2. The compound of claim 1, or an isomer, racemate, or isotope, or pharmaceutically acceptable salt thereof, wherein:
ring A is phenyl, pyridinyl, or pyrazinyl;
ring C is a $C_3$-$C_7$ cycloalkyl or 3-7 membered heterocycloalkyl, substituted with 0-5 $R^7$;
$R^1$ and $R^2$ are each, independently, H, methyl, ethyl, isopropyl or cyclopropyl, substituted with 0-3 halo;
$R^3$ and $R^4$ are each, independently, H, $(C_1$-$C_6)$alkyl, $(C_1$-$C_6)$haloalkyl, or cyclopropylmethyl;
each $R^5$ is independently —C(O)NR$^1$R$^2$, —OH, halo, $(C_1$-$C_6)$alkyl, $(C_1$-$C_6)$haloalkyl, $(C_1$-$C_6)$alkoxy, or carbocycle; or $R^3$ and one $R^5$, together with the atoms to which they are connected, form a 5-7 membered heterocycle;
each $R^6$ is independently halo, $(C_1$-$C_6)$alkyl, $(C_1$-$C_6)$haloalkyl, $(C_1$-$C_6)$alkoxy, or carbocycle;
each $R^7$ is independently halo, $(C_1$-$C_6)$alkyl, $(C_1$-$C_6)$haloalkyl, $(C_1$-$C_6)$alkoxy, or carbocycle;
$R^8$ is H;
m is 1-3; and
n is 0-3.

3. The compound of claim 2, or a isomer, racemate, or isotope, or pharmaceutically acceptable salt thereof, wherein ring A is phenyl.

4. The compound of claim 3, or an pharmaceutically acceptable isomer, racemate, or isotope, or pharmaceutically acceptable salt thereof, wherein ring B is phenyl, indazolyl, 2,3-dihydrobenzoxazolyl, benzoxazolonyl, or pyrazolopyridinyl.

5. The compound of claim 4, or an isomer, racemate, or isotope, or pharmaceutically acceptable salt thereof, wherein ring B is phenyl.

6. The compound of claim 2, or an isomer, racemate, or isotope, or pharmaceutically acceptable salt thereof, wherein ring C is cyclopropyl or pyrrolidinyl, and wherein cyclopropyl and pyrrolidinyl are substituted with 0-5 $R^7$.

7. The compound of claim 6, or an isomer, racemate, or isotope, or pharmaceutically acceptable salt thereof, wherein at least one $R^7$ is methyl, ethyl, isopropyl, or cyclopropyl.

8. The compound of claim 7, or an isomer, racemate, or isotope, or pharmaceutically acceptable salt thereof, wherein ring C is cyclopropyl substituted with 0-2 $R^7$.

9. The compound of claim 8, or an isomer, racemate, or isotope, or pharmaceutically acceptable salt thereof, wherein ring C is cyclopropyl substituted with 1 $R^7$ and $R^7$ is methyl.

10. The compound of claim 8, or an isomer, racemate, or isotope, or pharmaceutically acceptable salt thereof, wherein ring C is cyclopropyl substituted with 0 $R^7$.

11. The compound of claim 2, or an isomer, racemate, or isotope, or pharmaceutically acceptable salt thereof, wherein $R^3$ and $R^4$ are each, independently, H, methyl, ethyl, or cyclopropylmethyl.

12. The compound of claim 11, or an isomer, racemate, or isotope, or pharmaceutically acceptable salt thereof, wherein $R^3$ and $R^4$ are each methyl.

13. The compound of claim 2, or an isomer, racemate, or isotope, or pharmaceutically acceptable salt thereof, wherein each $R^5$ is independently —C(O)NR$^1$R$^2$, —OH, halo, or $(C_1$-$C_6)$alkyl.

14. The compound of claim 2, or an isomer, racemate, or isotope, or pharmaceutically acceptable salt thereof, wherein $R^3$ and one $R^5$, together with the atoms to which they are connected, form a 5-7 membered heterocycle.

15. The compound of claim 2, or an isomer, racemate, or isotope, or pharmaceutically acceptable salt thereof, wherein each $R^6$ is independently is halo, methyl, methoxy, or cyclopropyl.

16. The compound of claim 2, or an isomer, racemate, or isotope, or pharmaceutically acceptable salt thereof, wherein n is 0.

17. The compound of claim 2, or an, racemate, or isotope, or pharmaceutically acceptable salt thereof, wherein $R^8$ is H.

18. The compound of claim 1, or an racemate, or isotope, or pharmaceutically acceptable salt thereof, selected from

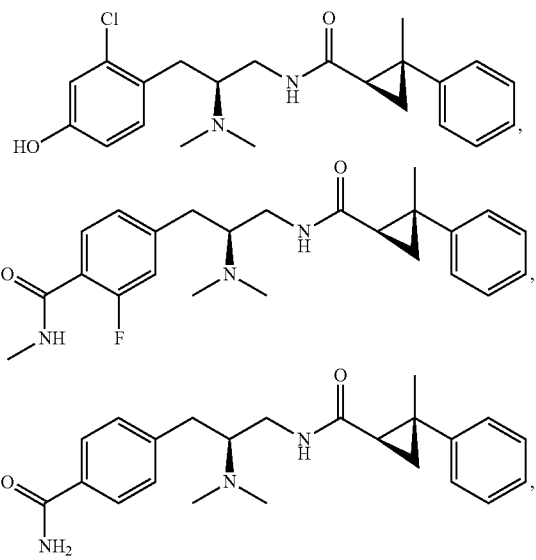

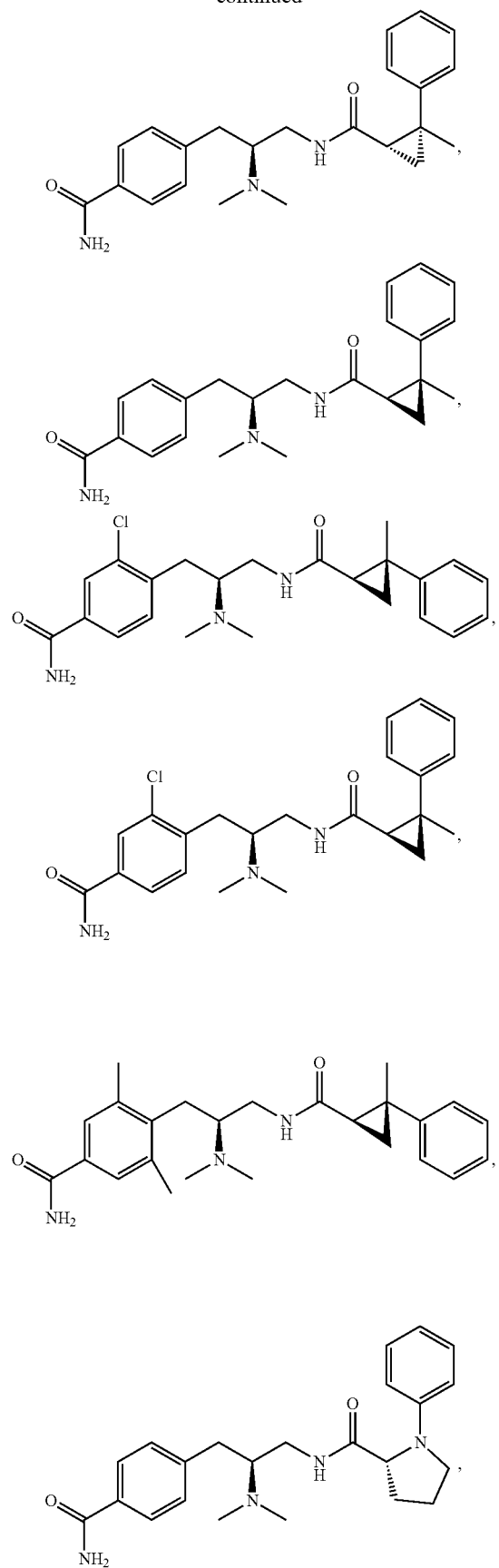
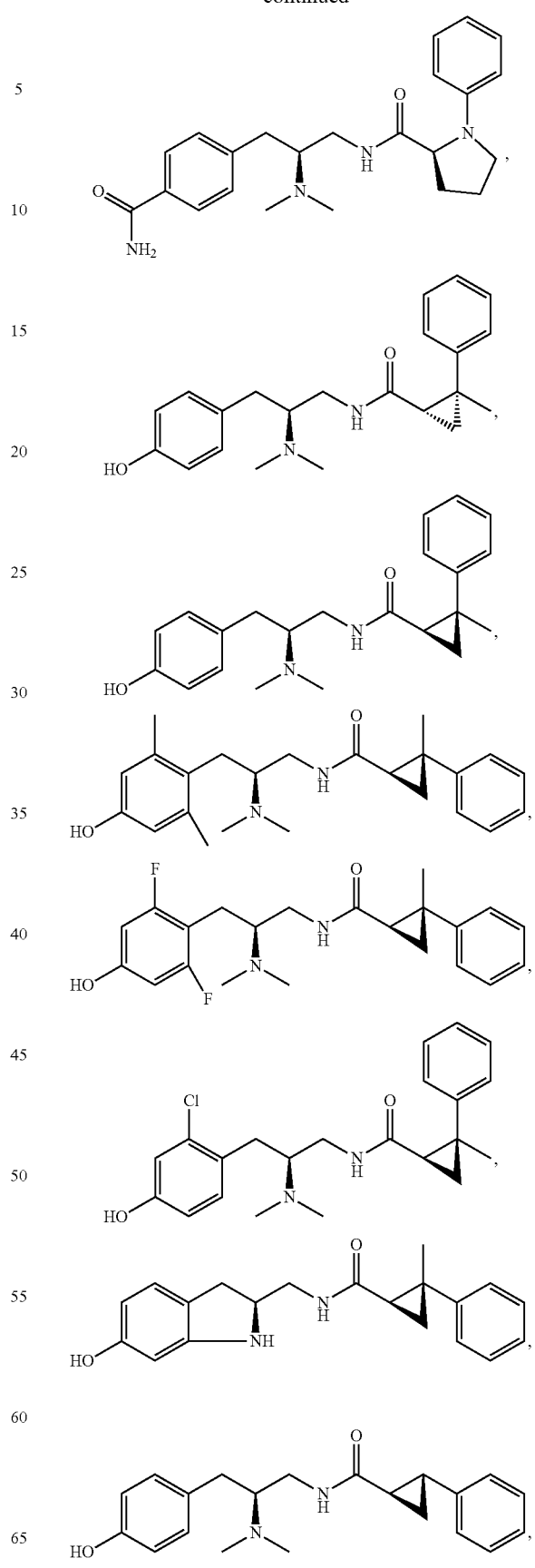

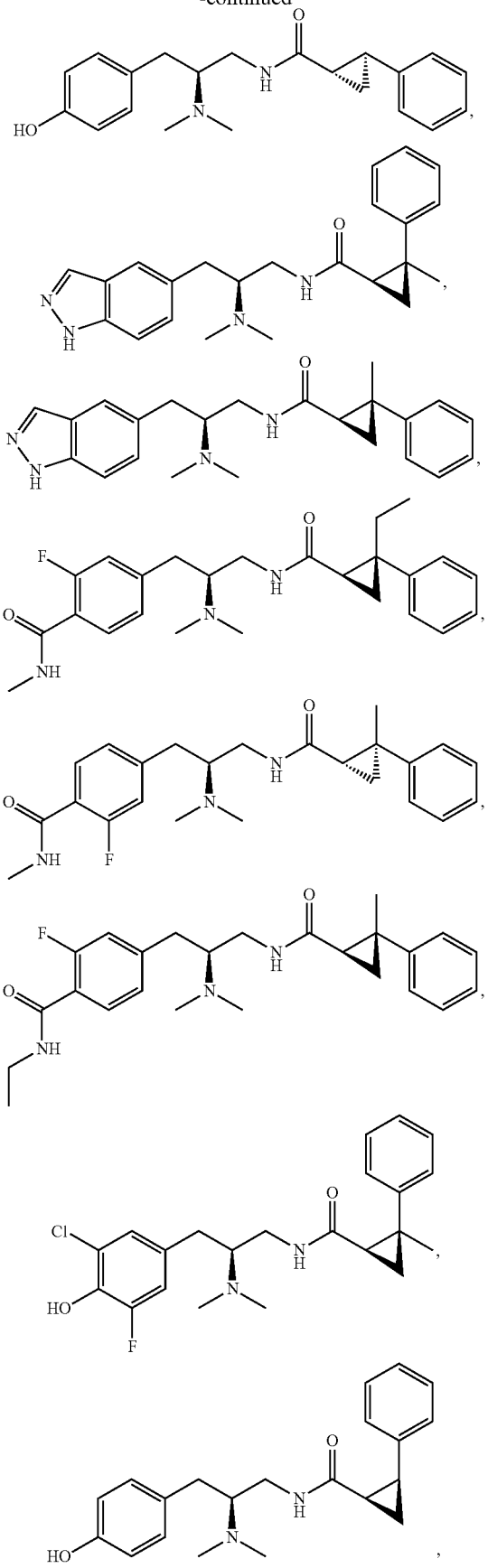
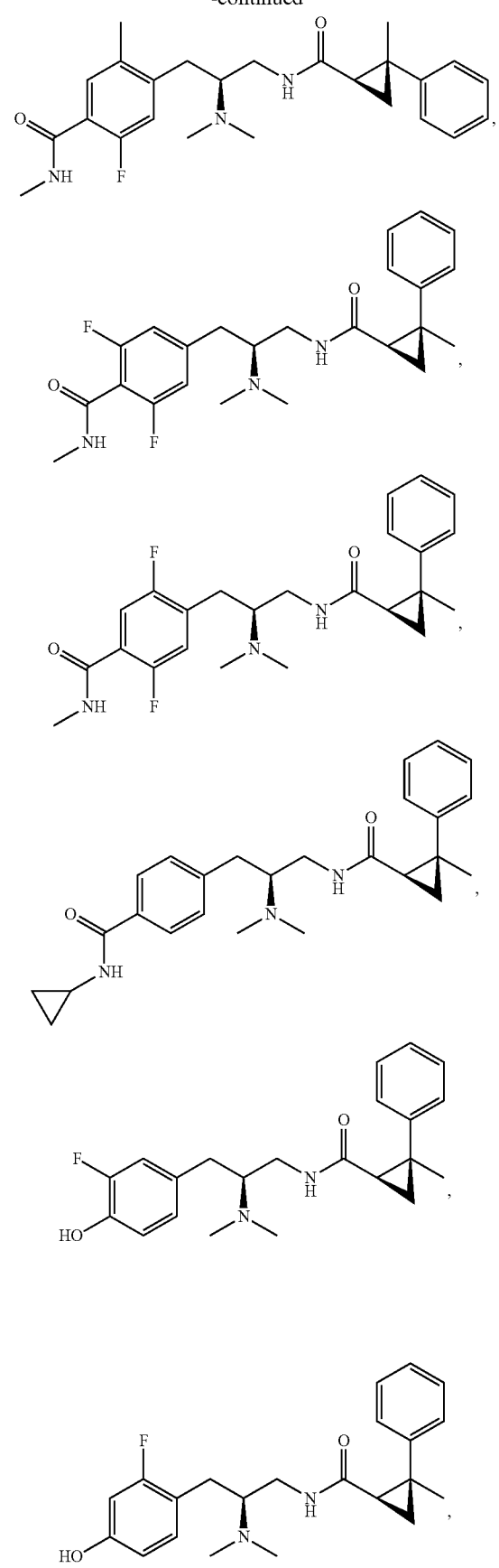

287
-continued
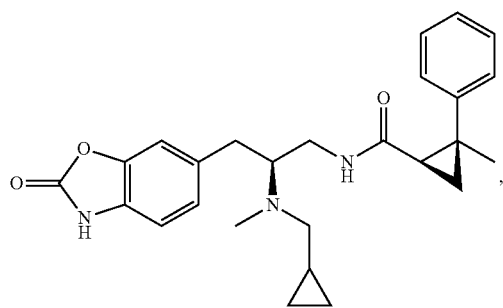
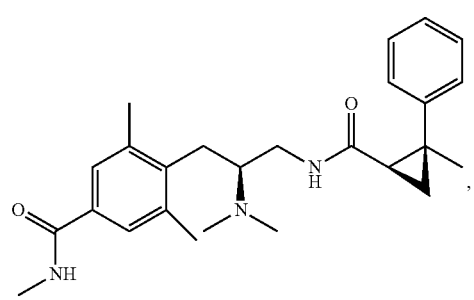
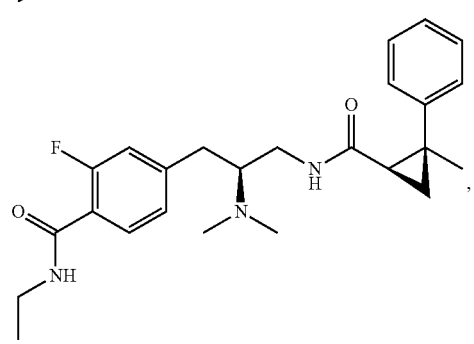
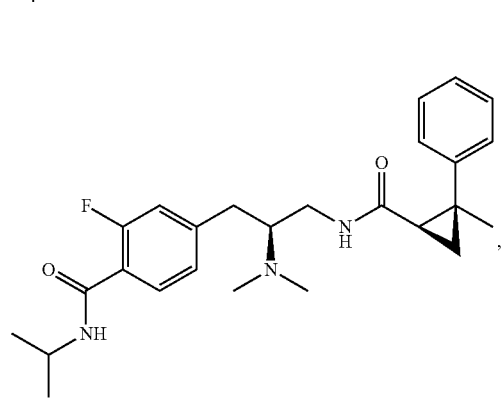
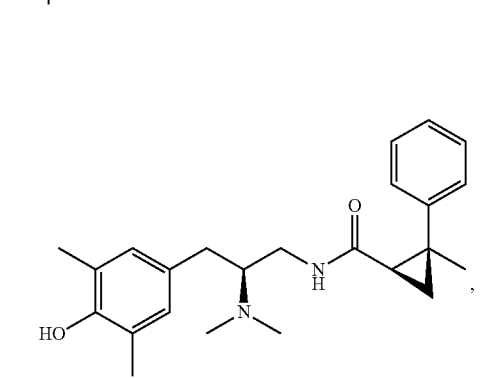
288
-continued
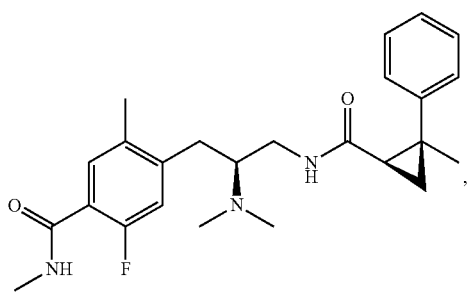
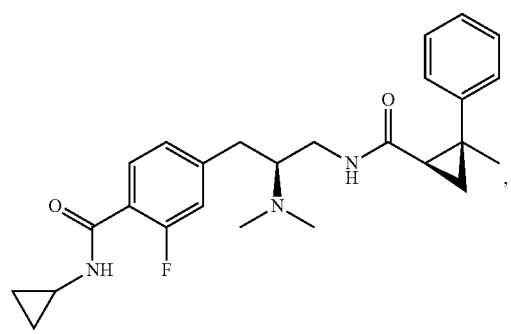
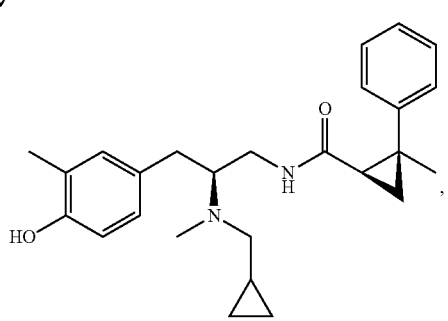
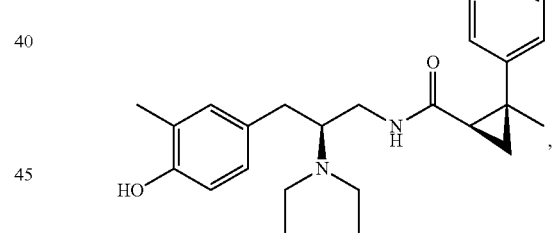
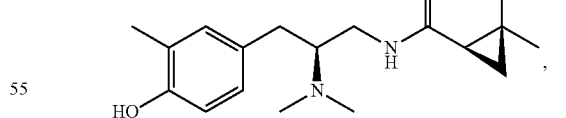
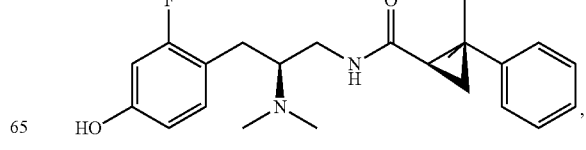

289
-continued
290
-continued
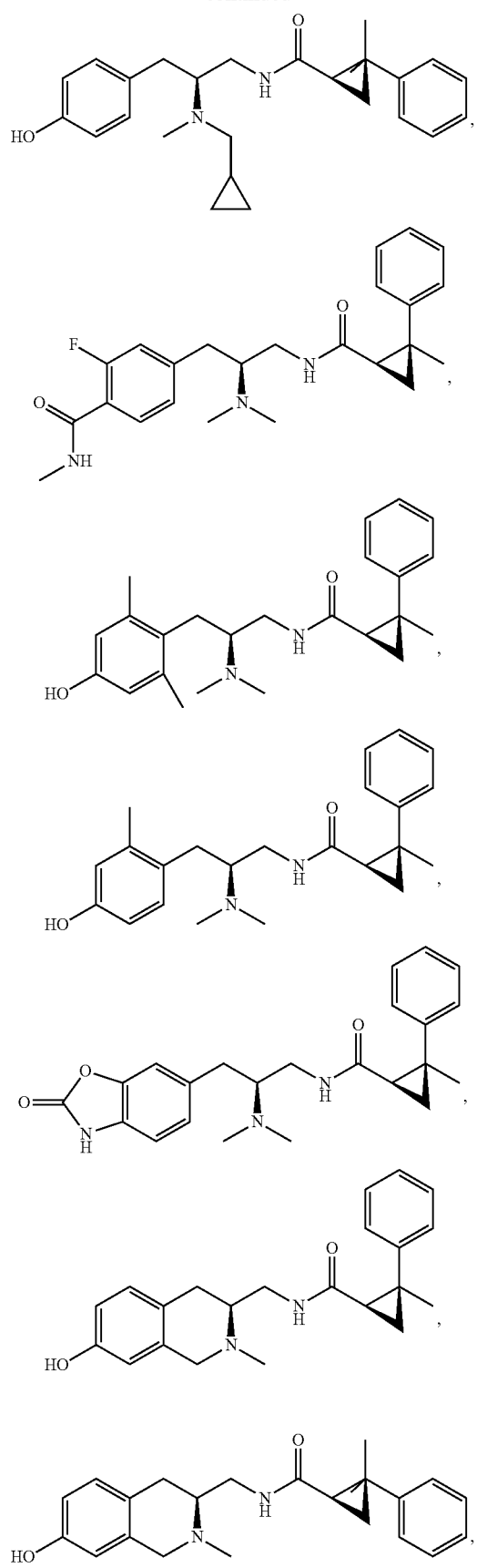
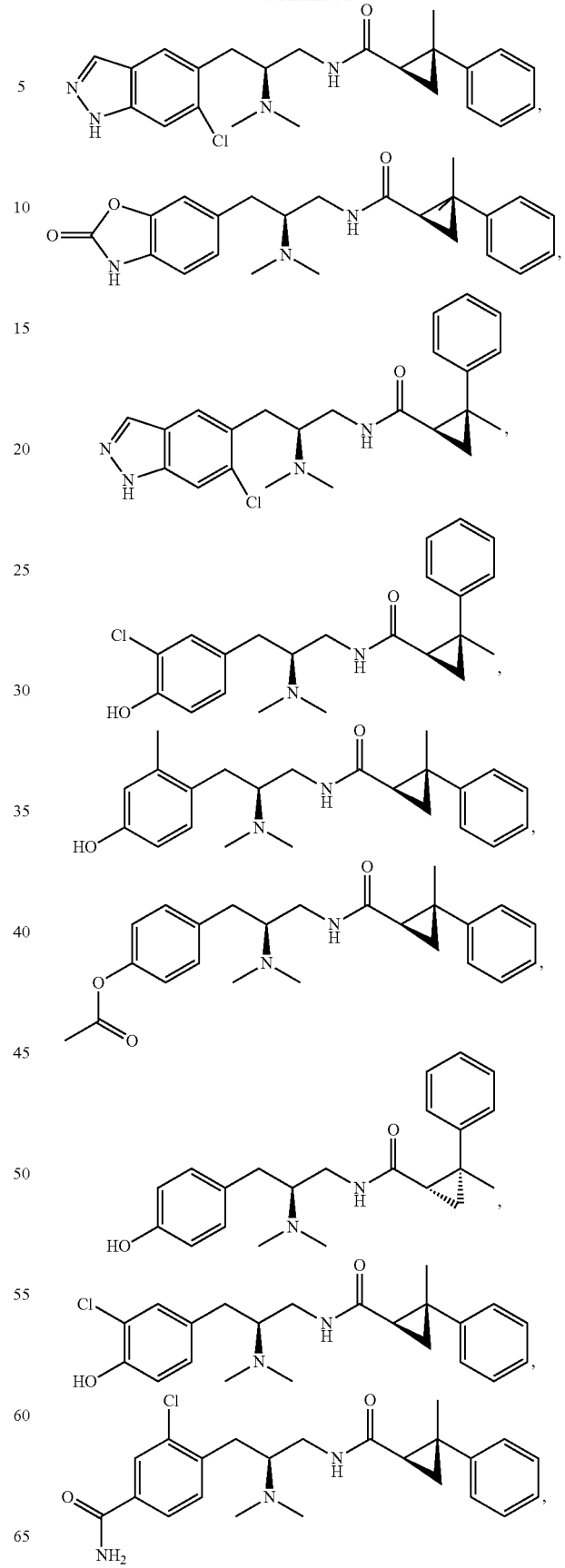

-continued

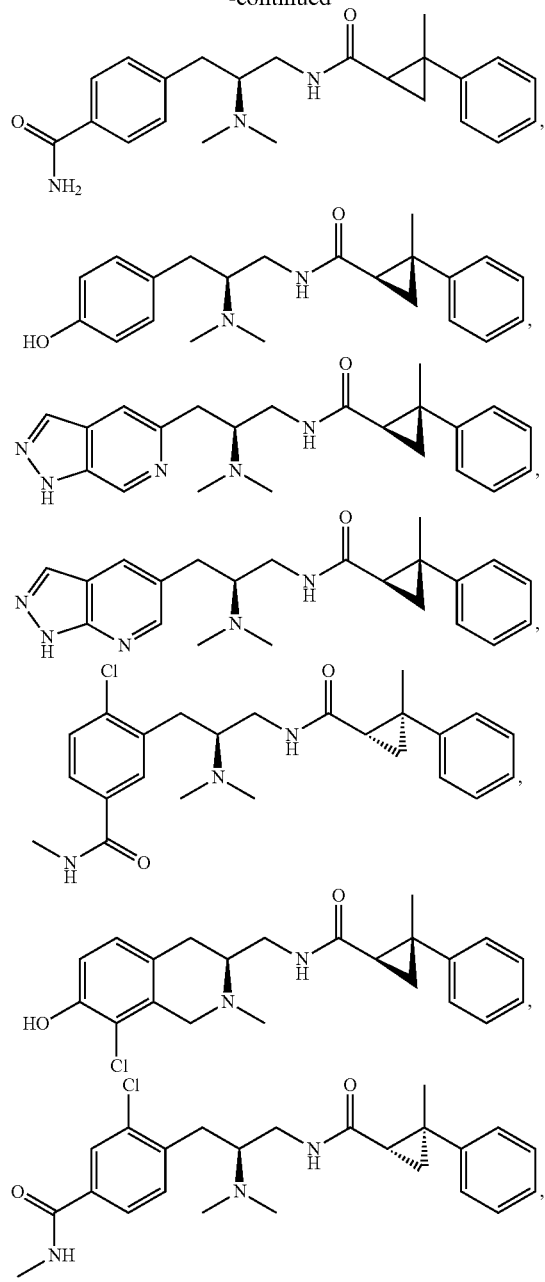

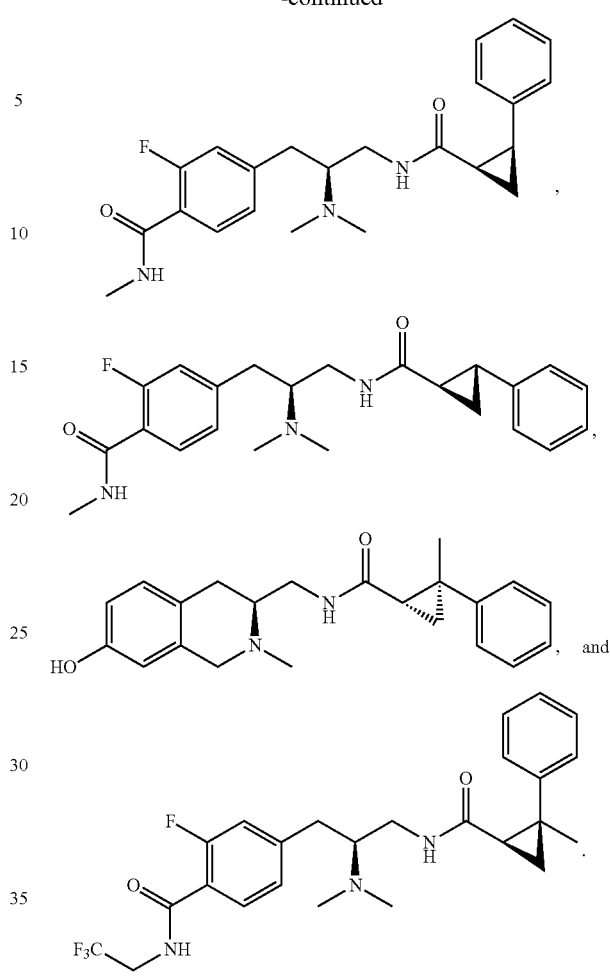

19. A pharmaceutical composition comprising a compound of claim 1, or an isomer, racemate, or isotope, or pharmaceutically acceptable salt thereof, and a pharmaceutically acceptable carrier, diluent, or excipient.

20. A method of treating pain, comprising administering to a subject in need thereof an effective amount of a compound of claim 1, or an isomer, racemate, or isotope, or pharmaceutically acceptable salt thereof.

* * * * *